US009453794B2

(12) United States Patent
Gulati et al.

(10) Patent No.: US 9,453,794 B2
(45) Date of Patent: Sep. 27, 2016

(54) SYSTEMS AND METHODS FOR BLOOD GLUCOSE AND OTHER ANALYTE DETECTION AND MEASUREMENT USING COLLISION COMPUTING

(71) Applicant: Zyomed Corp., Altadena, CA (US)

(72) Inventors: Sandeep Gulati, La Canada Flintridge, CA (US); Timothy L. Ruchti, Gurnee, IL (US); William Van Antwerp, Valencia, CA (US); John L. Smith, Portland, OR (US)

(73) Assignee: Zyomed Corp., Altadena, CA (US)

( * ) Notice: Subject to any disclaimer, the term of this patent is extended or adjusted under 35 U.S.C. 154(b) by 0 days.

(21) Appl. No.: 15/081,430

(22) Filed: Mar. 25, 2016

(65) Prior Publication Data

US 2016/0231235 A1    Aug. 11, 2016

Related U.S. Application Data

(63) Continuation of application No. 14/869,550, filed on Sep. 29, 2015.

(60) Provisional application No. 62/057,496, filed on Sep. 30, 2014, provisional application No. 62/057,103, filed on Sep. 29, 2014.

(51) Int. Cl.
*G01J 5/02* (2006.01)
*G01N 21/359* (2014.01)
(Continued)

(52) U.S. Cl.
CPC .......... *G01N 21/359* (2013.01); *A61B 5/1455* (2013.01); *A61B 5/14532* (2013.01);
(Continued)

(58) Field of Classification Search
CPC ............. G01N 21/359; G01N 33/491; G01N 2201/1228; G01N 2201/1232; G01N 2201/129
See application file for complete search history.

(56) References Cited

U.S. PATENT DOCUMENTS 3,638,640 A    2/1972   Shaw
3,761,921 A    9/1973   Adler et al.
(Continued)

FOREIGN PATENT DOCUMENTS

CA    2337097 A1    1/2000
CA    2454894 A1    7/2004
(Continued)

OTHER PUBLICATIONS

Amerov AK et al., 'Method and Device for Non-Invasive Blood Glucose Measurement,' Proc SPIE 3599, Optical Diagnostics of Biological Fluids IV, May 17, 1999, San Jose, California, USA, 3599:33-42.
(Continued)

*Primary Examiner* — Kiho Kim
(74) *Attorney, Agent, or Firm* — Goodwin Procter LLP

(57) ABSTRACT

In a noninvasive system for detection/measurement of glucose and other analytes in a medium such as tissue, illumination is directed to the medium and corresponding radiation from the medium is collected. Spectral energy changes associated with fragment(s)/feature(s) obtained from the collected radiation are determined using collision computing. Such spectral energy changes generally represent analyte concentration. The illumination is controlled to target a particular volume of the medium and/or such that the spectral energy changes become directionally monotonic with respect to analyte concentration. The illumination parameters include: intensity, wavelength, bandwidth, focal length, and/or duration of illumination, location and/or a size of an illuminated spot on the medium surface, depth at which the illumination can reach below the medium surface, spacing between the illuminated spot and a spot on the medium surface from which radiation is collected, and angle of the illumination relative to the medium surface.

30 Claims, 207 Drawing Sheets

(51) Int. Cl.
*G01N 33/483* (2006.01)
*A61B 5/1455* (2006.01)
*A61B 5/145* (2006.01)

(52) U.S. Cl.
CPC ..... *G01N33/4833* (2013.01); *G01N 2201/062* (2013.01); *G01N 2201/067* (2013.01); *G01N 2201/0612* (2013.01); *G01N 2201/12* (2013.01)

(56) References Cited

U.S. PATENT DOCUMENTS

| | | |
|---|---|---|
| 3,807,839 A | 4/1974 | Sugarman et al. |
| 3,814,510 A | 6/1974 | Adler et al. |
| 3,958,560 A | 5/1976 | March |
| 3,963,019 A | 6/1976 | Quandt |
| 4,012,128 A | 3/1977 | Regan |
| 4,014,321 A | 3/1977 | March |
| 4,017,192 A | 4/1977 | Rosenthal |
| 4,071,020 A | 1/1978 | Pugliese |
| 4,127,110 A | 11/1978 | Bullara |
| 4,167,331 A | 9/1979 | Nielsen |
| 4,169,976 A | 10/1979 | Cirri |
| 4,223,680 A | 9/1980 | Jobsis |
| 4,260,467 A | 4/1981 | Smith et al. |
| 4,278,887 A | 7/1981 | Lipshutz et al. |
| 4,305,398 A | 12/1981 | Sawa |
| 4,324,460 A | 4/1982 | Daley |
| 4,350,163 A | 9/1982 | Ford, Jr. et al. |
| 4,427,889 A | 1/1984 | Muller |
| 4,570,638 A | 2/1986 | Stoddart et al. |
| 4,597,392 A | 7/1986 | Opitz et al. |
| 4,655,225 A | 4/1987 | Dahne et al. |
| 4,725,147 A | 2/1988 | Stoddart |
| 4,746,508 A | 5/1988 | Carey et al. |
| 4,750,830 A | 6/1988 | Lee |
| 4,789,234 A | 12/1988 | Ginsburg et al. |
| 4,817,623 A | 4/1989 | Stoddart et al. |
| 4,832,480 A | 5/1989 | Kornacker et al. |
| 4,863,265 A | 9/1989 | Flower et al. |
| 4,882,492 A | 11/1989 | Schlager |
| 4,901,728 A | 2/1990 | Hutchison |
| 4,975,581 A | 12/1990 | Robinson et al. |
| 4,997,281 A | 3/1991 | Stark |
| 5,005,577 A | 4/1991 | Frenkel |
| 5,009,230 A | 4/1991 | Hutchinson |
| 5,028,787 A | 7/1991 | Rosenthal et al. |
| 5,057,695 A | 10/1991 | Hirao et al. |
| 5,065,767 A | 11/1991 | Maddess |
| 5,070,874 A | 12/1991 | Barnes et al. |
| 5,077,476 A | 12/1991 | Rosenthal |
| 5,086,229 A | 2/1992 | Rosenthal et al. |
| 5,204,532 A | 4/1993 | Rosenthal |
| 5,209,231 A | 5/1993 | Cote et al. |
| 5,219,400 A | 6/1993 | Jacot et al. |
| 5,222,496 A | 6/1993 | Clarke et al. |
| 5,223,865 A | 6/1993 | Shirao et al. |
| 5,229,841 A | 7/1993 | Taranowski et al. |
| 5,237,178 A | 8/1993 | Rosenthal et al. |
| 5,243,983 A | 9/1993 | Tarr et al. |
| 5,297,554 A | 3/1994 | Glynn et al. |
| 5,315,329 A | 5/1994 | McAdams |
| 5,318,022 A | 6/1994 | Taboada et al. |
| 5,324,979 A | 6/1994 | Rosenthal |
| 5,370,114 A | 12/1994 | Wong et al. |
| 5,398,681 A | 3/1995 | Kupershmidt |
| 5,424,545 A | 6/1995 | Block et al. |
| 5,433,197 A | 7/1995 | Stark |
| 5,435,309 A | 7/1995 | Thomas et al. |
| 5,448,992 A | 9/1995 | Kupershmidt |
| 5,459,317 A | 10/1995 | Small et al. |
| 5,460,177 A | 10/1995 | Purdy et al. |
| 5,477,327 A | 12/1995 | Bergman |
| 5,485,230 A | 1/1996 | Zimmerman |
| 5,492,118 A | 2/1996 | Gratton et al. |
| 5,494,032 A | 2/1996 | Robinson et al. |
| 5,515,847 A | 5/1996 | Braig et al. |
| 5,531,878 A | 7/1996 | Vadgama et al. |
| 5,533,509 A | 7/1996 | Koashi et al. |
| 5,535,743 A | 7/1996 | Backhaus et al. |
| 5,551,422 A | 9/1996 | Simonsen et al. |
| 5,553,615 A * | 9/1996 | Carim ............... A61B 5/14535 356/39 |
| 5,553,617 A | 9/1996 | Barkenhagen |
| 5,560,356 A | 10/1996 | Peyman |
| 5,582,168 A | 12/1996 | Samuels et al. |
| 5,601,079 A | 2/1997 | Wong et al. |
| 5,615,672 A | 4/1997 | Braig et al. |
| 5,636,633 A | 6/1997 | Messerschmidt et al. |
| 5,655,530 A | 8/1997 | Messerschmidt |
| 5,657,754 A | 8/1997 | Rosencwaig |
| 5,666,956 A | 9/1997 | Buchert |
| 5,671,301 A | 9/1997 | Kupershmidt |
| 5,676,143 A | 10/1997 | Simonsen et al. |
| 5,685,300 A | 11/1997 | Kuenstner |
| 5,710,630 A | 1/1998 | Essenpreis et al. |
| 5,713,353 A | 2/1998 | Castano |
| 5,747,806 A | 5/1998 | Khalil et al. |
| 5,750,994 A | 5/1998 | Schlager |
| 5,788,632 A | 8/1998 | Pezzaniti et al. |
| 5,817,181 A | 10/1998 | Okamura et al. |
| 5,820,557 A | 10/1998 | Hattori et al. |
| 5,823,951 A | 10/1998 | Messerschmidt |
| 5,823,966 A | 10/1998 | Buchert |
| 5,835,215 A | 11/1998 | Toida et al. |
| 5,890,489 A | 4/1999 | Elden |
| 5,896,198 A | 4/1999 | Chou et al. |
| 5,900,632 A | 5/1999 | Sterling et al. |
| 5,913,833 A | 6/1999 | Elstrom et al. |
| 5,935,062 A | 8/1999 | Messerschmidt et al. |
| 5,945,676 A | 8/1999 | Khalil et al. |
| 5,957,841 A | 9/1999 | Maruo et al. |
| 5,969,815 A | 10/1999 | Toida et al. |
| 5,971,922 A | 10/1999 | Arita et al. |
| 6,002,953 A | 12/1999 | Block |
| 6,026,314 A | 2/2000 | Amerov et al. |
| 6,040,578 A | 3/2000 | Malin et al. |
| 6,061,581 A | 5/2000 | Alam et al. |
| 6,061,582 A | 5/2000 | Small et al. |
| 6,064,898 A | 5/2000 | Aldrich |
| 6,066,847 A | 5/2000 | Rosenthal |
| 6,072,180 A | 6/2000 | Kramer et al. |
| 6,073,037 A | 6/2000 | Alam et al. |
| 6,088,087 A | 7/2000 | Graves et al. |
| 6,097,975 A | 8/2000 | Petrovsky et al. |
| 6,106,553 A | 8/2000 | Feingold |
| 6,113,537 A | 9/2000 | Castano |
| 6,113,541 A | 9/2000 | Dias et al. |
| 6,115,673 A | 9/2000 | Malin et al. |
| 6,120,460 A | 9/2000 | Abreu |
| 6,152,875 A | 11/2000 | Hakamata |
| 6,152,876 A | 11/2000 | Robinson et al. |
| 6,163,154 A | 12/2000 | Anderson et al. |
| 6,167,290 A | 12/2000 | Yang et al. |
| 6,172,743 B1 | 1/2001 | Kley et al. |
| 6,181,957 B1 | 1/2001 | Lambert et al. |
| 6,188,477 B1 | 2/2001 | Pu et al. |
| 6,188,705 B1 | 2/2001 | Krainak et al. |
| 6,212,424 B1 | 4/2001 | Robinson |
| 6,213,943 B1 | 4/2001 | Abreu |
| 6,226,089 B1 | 5/2001 | Hakamata |
| 6,230,034 B1 | 5/2001 | Messerschmidt et al. |
| 6,236,047 B1 | 5/2001 | Malin et al. |
| 6,240,306 B1 | 5/2001 | Rohrscheib et al. |
| 6,246,893 B1 | 6/2001 | Gobeli |
| 6,251,114 B1 | 6/2001 | Farmer et al. |
| 6,278,889 B1 | 8/2001 | Robinson |
| 6,280,381 B1 | 8/2001 | Malin et al. |
| 6,305,804 B1 | 10/2001 | Rice et al. |
| 6,312,393 B1 | 11/2001 | Abreu |
| 6,327,037 B1 | 12/2001 | Chou et al. |
| 6,353,226 B1 | 3/2002 | Khalil et al. |
| 6,370,407 B1 | 4/2002 | Kroeger et al. |
| 6,387,059 B1 | 5/2002 | Marchitto et al. |

(56) References Cited

U.S. PATENT DOCUMENTS

| | | |
|---|---|---|
| 6,387,126 B1 | 5/2002 | Cumming |
| 6,400,972 B1 | 6/2002 | Fine |
| 6,404,985 B1 | 6/2002 | Ohtsuka |
| 6,405,065 B1 | 6/2002 | Malin et al. |
| 6,411,373 B1 | 6/2002 | Garside et al. |
| 6,415,167 B1 | 7/2002 | Blank et al. |
| 6,423,001 B1 | 7/2002 | Abreu |
| 6,424,848 B1 | 7/2002 | Berman et al. |
| 6,424,849 B1 | 7/2002 | Berman et al. |
| 6,424,850 B1 | 7/2002 | Lambert et al. |
| 6,440,676 B1 | 8/2002 | Kroes et al. |
| 6,442,408 B1 | 8/2002 | Wenzel et al. |
| 6,442,410 B1 | 8/2002 | Steffes |
| 6,443,893 B1 | 9/2002 | Schnakenberg et al. |
| 6,445,938 B1 | 9/2002 | Berman et al. |
| 6,456,870 B1 | 9/2002 | Rennert et al. |
| 6,461,870 B2 | 10/2002 | Yatscoff et al. |
| 6,468,802 B1 | 10/2002 | Yatscoff et al. |
| 6,475,159 B1 | 11/2002 | Casscells et al. |
| 6,475,800 B1 | 11/2002 | Hazen et al. |
| 6,477,394 B2 | 11/2002 | Rice et al. |
| 6,478,423 B1 | 11/2002 | Turner et al. |
| 6,485,703 B1 | 11/2002 | Cote et al. |
| 6,487,429 B2 | 11/2002 | Hockersmith et al. |
| 6,493,566 B1 | 12/2002 | Ruchti et al. |
| 6,494,576 B1 | 12/2002 | L'Esperance, Jr. |
| 6,501,982 B1 | 12/2002 | Ruchti et al. |
| 6,503,198 B1 | 1/2003 | Aronowtiz et al. |
| 6,503,231 B1 | 1/2003 | Prausnitz et al. |
| 6,504,614 B1 | 1/2003 | Messerschmidt et al. |
| 6,508,785 B1 | 1/2003 | Eppstein |
| 6,512,936 B1 | 1/2003 | Monfre et al. |
| 6,512,937 B2 | 1/2003 | Blank et al. |
| 6,515,131 B2 | 2/2003 | Babich et al. |
| 6,517,482 B1 | 2/2003 | Elden et al. |
| 6,521,211 B1 | 2/2003 | Unger et al. |
| 6,522,903 B1 | 2/2003 | Berman et al. |
| 6,527,716 B1 | 3/2003 | Eppstein |
| 6,528,039 B2 | 3/2003 | Unger |
| 6,534,012 B1 | 3/2003 | Hazen et al. |
| 6,537,207 B1 | 3/2003 | Rice et al. |
| 6,542,762 B1 | 4/2003 | Alam et al. |
| 6,544,193 B2 | 4/2003 | Abreu |
| 6,551,576 B1 | 4/2003 | Unger et al. |
| 6,556,850 B1 | 4/2003 | Braig et al. |
| 6,560,478 B1 | 5/2003 | Alfano et al. |
| 6,565,532 B1 | 5/2003 | Yuzhakov et al. |
| 6,571,117 B1 | 5/2003 | Marbach |
| 6,574,425 B1 | 6/2003 | Weiss et al. |
| 6,574,490 B2 | 6/2003 | Abbink et al. |
| 6,574,501 B2 | 6/2003 | Lambert et al. |
| 6,576,220 B2 | 6/2003 | Unger |
| 6,577,885 B1 | 6/2003 | Braig et al. |
| 6,580,934 B1 | 6/2003 | Braig et al. |
| 6,587,196 B1 | 7/2003 | Stippick et al. |
| 6,587,199 B1 | 7/2003 | Luu |
| 6,587,702 B1 | 7/2003 | Ruchti et al. |
| 6,587,704 B1 | 7/2003 | Fine et al. |
| 6,593,753 B2 | 7/2003 | Scott et al. |
| 6,594,513 B1 | 7/2003 | Jobsis et al. |
| 6,594,518 B1 | 7/2003 | Benaron et al. |
| 6,595,929 B2 | 7/2003 | Stivoric et al. |
| 6,596,257 B2 | 7/2003 | Bryan |
| 6,599,750 B2 | 7/2003 | Yatscoff et al. |
| 6,602,715 B2 | 8/2003 | Yatscoff et al. |
| 6,605,038 B1 | 8/2003 | Teller et al. |
| 6,615,064 B1 | 9/2003 | Aldrich |
| 6,618,614 B1 | 9/2003 | Chance |
| 6,622,032 B1 | 9/2003 | Robinson et al. |
| 6,622,033 B2 | 9/2003 | Messerschmidt et al. |
| 6,630,833 B2 | 10/2003 | Scott |
| 6,636,759 B2 | 10/2003 | Robinson |
| 6,640,117 B2 | 10/2003 | Makarewicz et al. |
| 6,650,915 B2 | 11/2003 | Routt et al. |
| 6,654,125 B2 | 11/2003 | Maynard et al. |
| 6,668,181 B2 | 12/2003 | Wenzel et al. |
| 6,671,542 B2 | 12/2003 | Rennert et al. |
| 6,675,029 B2 | 1/2004 | Monfre et al. |
| 6,675,030 B2 | 1/2004 | Ciurczak et al. |
| 6,681,127 B2 | 1/2004 | March |
| 6,681,128 B2 | 1/2004 | Steuer et al. |
| 6,684,099 B2 | 1/2004 | Ridder et al. |
| 6,694,159 B2 | 2/2004 | Hall et al. |
| 6,697,654 B2 | 2/2004 | Lorenz et al. |
| 6,699,667 B2 | 3/2004 | Keen |
| 6,701,169 B1 | 3/2004 | Denninghoff |
| 6,704,588 B2 | 3/2004 | Ansari et al. |
| 6,704,662 B2 | 3/2004 | Gulati |
| 6,712,764 B2 | 3/2004 | Jeffries et al. |
| 6,718,189 B2 | 4/2004 | Rohrscheib et al. |
| 6,721,582 B2 | 4/2004 | Trepagnier et al. |
| 6,721,583 B1 | 4/2004 | Durkin et al. |
| 6,725,073 B1 | 4/2004 | Motamedi et al. |
| 6,728,560 B2 | 4/2004 | Kollias et al. |
| 6,738,652 B2 | 5/2004 | Mattu et al. |
| 6,743,211 B1 | 6/2004 | Prausnitz et al. |
| 6,747,276 B1 | 6/2004 | Watanabe |
| 6,748,259 B1 | 6/2004 | Benaron et al. |
| 6,757,554 B2 | 6/2004 | Rubinstein et al. |
| 6,773,696 B2 | 8/2004 | Unger |
| 6,773,922 B2 | 8/2004 | Jeng et al. |
| 6,777,240 B2 | 8/2004 | Hazen et al. |
| 6,781,690 B2 | 8/2004 | Armstrong et al. |
| 6,788,965 B2 | 9/2004 | Ruchti et al. |
| 6,790,652 B1 | 9/2004 | Terry et al. |
| 6,801,316 B2 | 10/2004 | Guthermann |
| 6,816,241 B2 | 11/2004 | Grubisic |
| 6,839,584 B2 | 1/2005 | Makarewicz et al. |
| 6,841,389 B2 | 1/2005 | Novikov et al. |
| 6,853,854 B1 | 2/2005 | Proniewicz et al. |
| 6,862,091 B2 | 3/2005 | Johnson |
| 6,864,978 B1 | 3/2005 | Hazen et al. |
| 6,865,408 B1 | 3/2005 | Abbink et al. |
| 6,871,169 B1 | 3/2005 | Hazen et al. |
| 6,876,931 B2 | 4/2005 | Lorenz et al. |
| 6,885,882 B2 | 4/2005 | Cote et al. |
| 6,889,069 B2 | 5/2005 | Routt et al. |
| 6,895,264 B2 | 5/2005 | Rice et al. |
| 6,944,487 B2 | 9/2005 | Maynard et al. |
| 6,949,070 B2 | 9/2005 | Ishler |
| 6,952,266 B2 | 10/2005 | Abbink |
| 6,954,661 B2 | 10/2005 | Cho et al. |
| 6,954,662 B2 | 10/2005 | Freger et al. |
| 6,956,649 B2 | 10/2005 | Acosta et al. |
| 6,958,039 B2 | 10/2005 | Burd et al. |
| 6,968,221 B2 | 11/2005 | Rosenthal |
| 6,983,176 B2 | 1/2006 | Gardner et al. |
| 6,989,901 B2 | 1/2006 | Abbink |
| 6,990,364 B2 | 1/2006 | Ruchti et al. |
| 6,994,691 B2 | 2/2006 | Ejlersen |
| 6,996,428 B2 | 2/2006 | Kislov et al. |
| 6,998,247 B2 | 2/2006 | Monfre et al. |
| 7,009,180 B2 | 3/2006 | Sterling et al. |
| 7,010,336 B2 | 3/2006 | Lorenz et al. |
| 7,015,782 B2 | 3/2006 | Kincaid et al. |
| 7,016,021 B2 | 3/2006 | Nakajima et al. |
| 7,016,713 B2 | 3/2006 | Gardner et al. |
| 7,027,848 B2 | 4/2006 | Robinson et al. |
| 7,033,406 B2 | 4/2006 | Weir et al. |
| 7,038,774 B2 | 5/2006 | Hazen et al. |
| 7,039,446 B2 | 5/2006 | Ruchti et al. |
| 7,039,448 B2 | 5/2006 | Schlegel et al. |
| 7,043,288 B2 | 5/2006 | Davis, III et al. |
| 7,052,472 B1 | 5/2006 | Miller et al. |
| 7,071,594 B1 | 7/2006 | Yan et al. |
| D526,719 S | 8/2006 | Richie, Jr. et al. |
| 7,092,832 B2 | 8/2006 | Brown |
| D529,616 S | 10/2006 | Deros et al. |
| 7,133,710 B2 | 11/2006 | Acosta et al. |
| 7,133,717 B2 | 11/2006 | Coston et al. |
| 7,147,153 B2 | 12/2006 | Rowe et al. |
| 7,161,679 B2 | 1/2007 | Messerschmidt et al. |
| 7,183,102 B2 | 2/2007 | Monfre et al. |
| 7,206,623 B2 | 4/2007 | Blank et al. |

(56) References Cited

U.S. PATENT DOCUMENTS

| | | |
|---|---|---|
| 7,221,169 B2 | 5/2007 | Jean et al. |
| 7,228,159 B2 | 6/2007 | Petersson et al. |
| 7,233,816 B2 | 6/2007 | Blank et al. |
| 7,299,080 B2 | 11/2007 | Acosta et al. |
| 7,307,734 B2 | 12/2007 | Dogariu |
| 7,308,293 B2 | 12/2007 | Gerlitz |
| 7,317,938 B2 | 1/2008 | Lorenz et al. |
| 7,330,746 B2 | 2/2008 | Demuth et al. |
| 7,333,841 B2 | 2/2008 | Maruo et al. |
| 7,333,843 B2 | 2/2008 | Monfre et al. |
| 7,353,055 B2 | 4/2008 | Hogan |
| 7,356,364 B1 | 4/2008 | Bullock et al. |
| 7,383,069 B2 | 6/2008 | Ruchti et al. |
| 7,388,669 B2 | 6/2008 | Abbink |
| 7,395,158 B2 | 7/2008 | Monfre et al. |
| 7,417,730 B2 | 8/2008 | Duan et al. |
| 7,436,511 B2 | 10/2008 | Ruchti et al. |
| 7,440,786 B2 | 10/2008 | Hockersmith et al. |
| 7,488,930 B2 | 2/2009 | Ajgaonkar et al. |
| 7,505,801 B2 | 3/2009 | Monfre et al. |
| 7,508,524 B2 | 3/2009 | Mahadevan-Jansen et al. |
| 7,509,153 B2 | 3/2009 | Blank et al. |
| 7,519,406 B2 | 4/2009 | Blank et al. |
| 7,526,329 B2 | 4/2009 | Hogan et al. |
| 7,534,208 B2 | 5/2009 | Caduff et al. |
| 7,536,213 B2 | 5/2009 | Lipson et al. |
| 7,567,876 B2 | 7/2009 | Gulati |
| 7,571,056 B2 | 8/2009 | Ben-Menahem et al. |
| 7,593,230 B2 | 9/2009 | Abul-Haj et al. |
| 7,606,608 B2 | 10/2009 | Blank et al. |
| 7,620,212 B1 | 11/2009 | Allen et al. |
| 7,620,674 B2 | 11/2009 | Ruchti et al. |
| 7,623,906 B2 | 11/2009 | Robinson et al. |
| 7,640,140 B2 | 12/2009 | Ruchti et al. |
| 7,697,966 B2 | 4/2010 | Monfre et al. |
| 7,698,105 B2 | 4/2010 | Ruchti et al. |
| RE41,333 E | 5/2010 | Blank et al. |
| 7,729,734 B2 | 6/2010 | Mandelis et al. |
| 7,738,085 B2 | 6/2010 | Braig et al. |
| 7,742,166 B2 | 6/2010 | Lipson et al. |
| 7,751,192 B2 | 7/2010 | Abul-Haj et al. |
| 7,783,332 B2 | 8/2010 | Laufer et al. |
| 7,787,924 B2 | 8/2010 | Acosta et al. |
| 7,872,734 B2 | 1/2011 | Braig et al. |
| 7,892,943 B2 | 2/2011 | Violette |
| 7,914,460 B2 | 3/2011 | Melker et al. |
| 7,973,925 B2 | 7/2011 | Lipson et al. |
| 8,022,366 B2 | 9/2011 | Hartley |
| 8,027,033 B2 | 9/2011 | Lipson et al. |
| 8,078,244 B2 | 12/2011 | Melman et al. |
| 8,082,015 B2 | 12/2011 | Yodh et al. |
| 8,102,531 B2 | 1/2012 | Abbink et al. |
| 8,135,450 B2 | 3/2012 | Esenaliev et al. |
| 8,160,666 B2 | 4/2012 | Rebec et al. |
| 8,170,326 B2 | 5/2012 | Gulati et al. |
| 8,175,666 B2 | 5/2012 | Harjunmaa et al. |
| 8,180,419 B2 | 5/2012 | Debreczeny et al. |
| 8,180,422 B2 | 5/2012 | Rebec |
| 8,200,307 B2 | 6/2012 | Caduff et al. |
| 8,200,347 B2 | 6/2012 | El-Rifai et al. |
| 8,203,704 B2 | 6/2012 | Merritt et al. |
| 8,235,897 B2 | 8/2012 | Gal et al. |
| 8,310,681 B2 | 11/2012 | Hogan |
| 8,315,681 B2 | 11/2012 | Kanayama et al. |
| 8,340,738 B2 | 12/2012 | Xu |
| 8,355,125 B2 | 1/2013 | Lipson et al. |
| 8,358,410 B2 | 1/2013 | Hallstein et al. |
| 8,364,218 B2 | 1/2013 | Gerlitz |
| 8,374,665 B2 | 2/2013 | Lamego |
| 8,380,268 B2 | 2/2013 | Georgakoudi et al. |
| 8,401,604 B2 | 3/2013 | Gerlitz |
| 8,411,265 B2 | 4/2013 | Lipson et al. |
| 8,420,404 B2 | 4/2013 | Diebold et al. |
| 8,442,363 B2 | 5/2013 | Hallstein et al. |
| 8,452,360 B2 | 5/2013 | Mandelis et al. |
| 8,486,125 B2 | 7/2013 | Lytle et al. |
| 8,504,128 B2 | 8/2013 | Blank et al. |
| 8,541,743 B2 | 9/2013 | Hartley |
| 8,548,549 B2 | 10/2013 | Schurman et al. |
| 8,552,359 B2 | 10/2013 | Xu |
| 8,570,528 B2 | 10/2013 | Hogan |
| 8,571,617 B2 | 10/2013 | Reichgott et al. |
| 8,577,432 B2 | 11/2013 | Hogan et al. |
| 8,608,310 B2 | 12/2013 | Otis et al. |
| 8,639,306 B2 | 1/2014 | Cornsweet |
| 8,670,642 B2 | 3/2014 | Islam |
| 8,718,738 B2 | 5/2014 | Blank et al. |
| 8,730,468 B2 | 5/2014 | Messerchmidt |
| 8,743,355 B2 | 6/2014 | Korman |
| 8,803,366 B2 | 8/2014 | Proud |
| 8,843,186 B2 | 9/2014 | Halaka |
| 8,903,466 B2 | 12/2014 | Gerlitz |
| 8,972,880 B2 | 3/2015 | Lin et al. |
| 9,005,914 B2 | 4/2015 | Altschul et al. |
| 9,008,745 B2 | 4/2015 | Pushpala et al. |
| 9,026,188 B2 | 5/2015 | Taylor et al. |
| 9,037,206 B2 | 5/2015 | Grata et al. |
| 9,055,902 B2 | 6/2015 | Liu |
| 9,078,606 B1 | 7/2015 | Bharj |
| 9,078,617 B2 | 7/2015 | Pintel et al. |
| 9,078,626 B2 | 7/2015 | Brister et al. |
| 9,101,308 B2 | 8/2015 | Korman |
| 9,125,625 B2 | 9/2015 | Wang et al. |
| 9,131,885 B2 | 9/2015 | Simpson et al. |
| 9,134,231 B2 | 9/2015 | Wang |
| 9,158,133 B1 | 10/2015 | Pletcher et al. |
| 9,164,167 B2 | 10/2015 | Hyde et al. |
| 9,170,225 B2 | 10/2015 | Dutta et al. |
| 9,174,009 B2 | 11/2015 | Peatfield et al. |
| 9,179,856 B2 | 11/2015 | Caduff et al. |
| 9,182,368 B2 | 11/2015 | Pushpala et al. |
| 9,198,580 B2 | 12/2015 | Naganuma et al. |
| 9,201,038 B2 | 12/2015 | Macfie et al. |
| 9,217,706 B2 | 12/2015 | Mucci et al. |
| 9,220,412 B2 | 12/2015 | Cuccia |
| 9,220,437 B2 | 12/2015 | Dhurandhar et al. |
| 9,237,864 B2 | 1/2016 | Simpson et al. |
| 9,237,865 B2 | 1/2016 | Wang et al. |
| 9,243,276 B2 | 1/2016 | Malecha |
| 9,244,036 B2 | 1/2016 | Colas |
| 9,247,905 B2 | 2/2016 | Caduff et al. |
| 9,270,503 B2 | 2/2016 | Fleming et al. |
| 9,277,866 B2 | 3/2016 | Cuccia |
| 9,282,895 B2 | 3/2016 | Wenzel et al. |
| 9,282,900 B2 | 3/2016 | Irisawa |
| 9,285,314 B2 | 3/2016 | Pacifici et al. |
| 9,289,167 B2 | 3/2016 | Diab et al. |
| 9,289,954 B2 | 3/2016 | Linhardt et al. |
| 9,294,074 B2 | 3/2016 | Brockway |
| 9,295,419 B2 | 3/2016 | Weiss et al. |
| 9,307,901 B1 | 4/2016 | Linhardt et al. |
| 9,307,935 B2 | 4/2016 | Pluta et al. |
| 9,314,953 B2 | 4/2016 | Lauer et al. |
| 9,320,460 B2 | 4/2016 | Liu et al. |
| 9,323,073 B2 | 4/2016 | Pugh et al. |
| 9,332,936 B2 | 5/2016 | Nishida et al. |
| 9,345,426 B2 | 5/2016 | Colvin, Jr. et al. |
| 9,345,431 B2 | 5/2016 | Tseng et al. |
| 9,351,671 B2 | 5/2016 | Ruchti et al. |
| 9,351,672 B2 | 5/2016 | Ruchti et al. |
| 2001/0031914 A1 | 10/2001 | Gobeli et al. |
| 2001/0034500 A1 | 10/2001 | March |
| 2001/0046510 A1 | 11/2001 | Mullen |
| 2002/0005725 A1 | 1/2002 | Scott |
| 2002/0007113 A1 | 1/2002 | March et al. |
| 2002/0041166 A1 | 4/2002 | Grubisic |
| 2002/0042558 A1 | 4/2002 | Mendelson |
| 2002/0049374 A1 | 4/2002 | Abreu |
| 2002/0049389 A1 | 4/2002 | Abreu |
| 2002/0072658 A1 | 6/2002 | Rice et al. |
| 2002/0084417 A1 | 7/2002 | Khalil et al. |
| 2002/0123677 A1 | 9/2002 | Miki et al. |
| 2002/0133065 A1 | 9/2002 | Lucassen et al. |
| 2002/0133080 A1 | 9/2002 | Apruzzese et al. |

(56) References Cited

U.S. PATENT DOCUMENTS

| | | |
|---|---|---|
| 2002/0138049 A1 | 9/2002 | Allen et al. |
| 2002/0138855 A1 | 9/2002 | Zhang et al. |
| 2002/0150896 A1 | 10/2002 | Polonsky et al. |
| 2002/0151773 A1 | 10/2002 | Berman et al. |
| 2002/0151774 A1 | 10/2002 | Soller et al. |
| 2002/0151816 A1 | 10/2002 | Rich et al. |
| 2002/0155600 A1 | 10/2002 | Kopelman et al. |
| 2002/0159952 A1 | 10/2002 | Unger |
| 2002/0161289 A1 | 10/2002 | Hopkins et al. |
| 2002/0172936 A1 | 11/2002 | Canter et al. |
| 2002/0190211 A1 | 12/2002 | Watanabe |
| 2002/0192637 A1 | 12/2002 | Parsons et al. |
| 2002/0192657 A1 | 12/2002 | Erwin et al. |
| 2003/0004419 A1 | 1/2003 | Treado et al. |
| 2003/0004423 A1 | 1/2003 | Lavie et al. |
| 2003/0013947 A1 | 1/2003 | Frattarola |
| 2003/0018272 A1 | 1/2003 | Treado et al. |
| 2003/0021857 A1 | 1/2003 | Tanaka et al. |
| 2003/0023151 A1 | 1/2003 | Khalil et al. |
| 2003/0027240 A1 | 2/2003 | Asher et al. |
| 2003/0032064 A1 | 2/2003 | Soller et al. |
| 2003/0032885 A1 | 2/2003 | Rubinstein et al. |
| 2003/0040009 A1 | 2/2003 | Denny et al. |
| 2003/0040511 A1 | 2/2003 | Lai |
| 2003/0040664 A1 | 2/2003 | Thennadil et al. |
| 2003/0044993 A1 | 3/2003 | Yatscoff et al. |
| 2003/0045783 A1 | 3/2003 | March et al. |
| 2003/0048432 A1 | 3/2003 | Jeng et al. |
| 2003/0049853 A1 | 3/2003 | Yatscoff et al. |
| 2003/0050544 A1 | 3/2003 | Routt et al. |
| 2003/0053951 A1 | 3/2003 | Tartaglia et al. |
| 2003/0054428 A1 | 3/2003 | Monfre et al. |
| 2003/0060693 A1 | 3/2003 | Monfre et al. |
| 2003/0065305 A1 | 4/2003 | Higuchi et al. |
| 2003/0069489 A1 | 4/2003 | Abreu |
| 2003/0076508 A1 | 4/2003 | Cornsweet |
| 2003/0078499 A1 | 4/2003 | Eppstein |
| 2003/0078504 A1 | 4/2003 | Rowe |
| 2003/0083582 A1 | 5/2003 | Hirsh |
| 2003/0092982 A1 | 5/2003 | Eppstein |
| 2003/0104393 A1 | 6/2003 | Sharp et al. |
| 2003/0105391 A1 | 6/2003 | Berman et al. |
| 2003/0109998 A1 | 6/2003 | Lorenz et al. |
| 2003/0112444 A1 | 6/2003 | Yang et al. |
| 2003/0114735 A1 | 6/2003 | Silver et al. |
| 2003/0117629 A1 | 6/2003 | Messerschmidt et al. |
| 2003/0135166 A1 | 7/2003 | Gonnelli |
| 2003/0135167 A1 | 7/2003 | Gonnelli |
| 2003/0135201 A1 | 7/2003 | Gonnelli |
| 2003/0137669 A1 | 7/2003 | Rollins et al. |
| 2003/0139687 A1 | 7/2003 | Abreu |
| 2003/0167033 A1 | 9/2003 | Chen et al. |
| 2003/0170747 A1 | 9/2003 | Janigro et al. |
| 2003/0175764 A1 | 9/2003 | Francis et al. |
| 2003/0175992 A1 | 9/2003 | Toranto et al. |
| 2003/0175993 A1 | 9/2003 | Toranto et al. |
| 2003/0176775 A1 | 9/2003 | Berman |
| 2003/0176777 A1 | 9/2003 | Muller-Dethlefs |
| 2003/0191377 A1 | 10/2003 | Robinson et al. |
| 2003/0198996 A1 | 10/2003 | Surber et al. |
| 2003/0199742 A1 | 10/2003 | Braig et al. |
| 2003/0202937 A1 | 10/2003 | Sabbadini et al. |
| 2003/0208113 A1 | 11/2003 | Mault et al. |
| 2003/0211086 A1 | 11/2003 | Berkley et al. |
| 2003/0211599 A1 | 11/2003 | Sabbadini et al. |
| 2003/0211625 A1 | 11/2003 | Cohan et al. |
| 2003/0214655 A1 | 11/2003 | Weiss et al. |
| 2003/0216627 A1 | 11/2003 | Lorenz et al. |
| 2003/0224369 A1 | 12/2003 | Surber et al. |
| 2003/0225318 A1 | 12/2003 | Montegrande et al. |
| 2003/0225321 A1 | 12/2003 | Cote et al. |
| 2003/0225360 A1 | 12/2003 | Eppstein et al. |
| 2003/0233250 A1 | 12/2003 | Joffe et al. |
| 2003/0235318 A1 | 12/2003 | Bharitkar et al. |
| 2004/0012789 A1 | 1/2004 | Guthermann |
| 2004/0023317 A1 | 2/2004 | Motamedi et al. |
| 2004/0024553 A1 | 2/2004 | Monfre et al. |
| 2004/0029205 A1 | 2/2004 | Small et al. |
| 2004/0033575 A1 | 2/2004 | Van Duijn et al. |
| 2004/0034291 A1 | 2/2004 | Braig et al. |
| 2004/0038412 A1 | 2/2004 | Yatscoff et al. |
| 2004/0039269 A1 | 2/2004 | Ward et al. |
| 2004/0039271 A1 | 2/2004 | Blank et al. |
| 2004/0039297 A1 | 2/2004 | Abreu |
| 2004/0039298 A1 | 2/2004 | Abreu |
| 2004/0039342 A1 | 2/2004 | Eppstein et al. |
| 2004/0039343 A1 | 2/2004 | Eppstein et al. |
| 2004/0044197 A1 | 3/2004 | Pandey et al. |
| 2004/0052730 A1 | 3/2004 | Hochman |
| 2004/0059207 A1 | 3/2004 | March |
| 2004/0059212 A1 | 3/2004 | Abreu |
| 2004/0063216 A1 | 4/2004 | Lubocki |
| 2004/0071675 A1 | 4/2004 | Mazarakis et al. |
| 2004/0075812 A1 | 4/2004 | Kardon et al. |
| 2004/0078219 A1 | 4/2004 | Kaylor et al. |
| 2004/0087841 A1 | 5/2004 | Braig et al. |
| 2004/0087842 A1 | 5/2004 | Lakowicz et al. |
| 2004/0087843 A1 | 5/2004 | Rice et al. |
| 2004/0092825 A1 | 5/2004 | Madar et al. |
| 2004/0097802 A1 | 5/2004 | Cohen |
| 2004/0100376 A1 | 5/2004 | Lye et al. |
| 2004/0106904 A1 | 6/2004 | Gonnelli et al. |
| 2004/0111018 A1 | 6/2004 | Isenberg et al. |
| 2004/0120557 A1 | 6/2004 | Sabol et al. |
| 2004/0122706 A1 | 6/2004 | Walker et al. |
| 2004/0122707 A1 | 6/2004 | Sabol et al. |
| 2004/0122708 A1 | 6/2004 | Avinash et al. |
| 2004/0122709 A1 | 6/2004 | Avinash et al. |
| 2004/0122719 A1 | 6/2004 | Sabol et al. |
| 2004/0122787 A1 | 6/2004 | Avinash et al. |
| 2004/0122790 A1 | 6/2004 | Walker et al. |
| 2004/0127777 A1 | 7/2004 | Ruchti et al. |
| 2004/0127778 A1 | 7/2004 | Lambert et al. |
| 2004/0128088 A1 | 7/2004 | Laletin et al. |
| 2004/0132109 A1 | 7/2004 | Enari et al. |
| 2004/0133093 A1 | 7/2004 | Glynn |
| 2004/0138539 A1 | 7/2004 | Jay et al. |
| 2004/0142403 A1 | 7/2004 | Hetzel et al. |
| 2004/0142496 A1 | 7/2004 | Nicholson et al. |
| 2004/0147820 A1 | 7/2004 | Routt et al. |
| 2004/0152963 A1 | 8/2004 | March |
| 2004/0157319 A1 | 8/2004 | Keen |
| 2004/0162470 A1 | 8/2004 | Tu |
| 2004/0167459 A1 | 8/2004 | Higuchi et al. |
| 2004/0180379 A1 | 9/2004 | Van Duyne et al. |
| 2004/0181172 A1 | 9/2004 | Carney et al. |
| 2004/0186363 A1 | 9/2004 | Smit et al. |
| 2004/0197846 A1 | 10/2004 | Hockersmith et al. |
| 2004/0197927 A1 | 10/2004 | Jeng et al. |
| 2004/0220457 A1 | 11/2004 | Burd et al. |
| 2004/0220458 A1 | 11/2004 | Burd et al. |
| 2004/0254438 A1 | 12/2004 | Chuck et al. |
| 2005/0010090 A1 | 1/2005 | Acosta et al. |
| 2005/0010091 A1 | 1/2005 | Woods et al. |
| 2005/0054907 A1 | 3/2005 | Page et al. |
| 2005/0054908 A1 | 3/2005 | Blank et al. |
| 2005/0065416 A1 | 3/2005 | Subotics |
| 2005/0070772 A1 | 3/2005 | Cornsweet |
| 2005/0085701 A1 | 4/2005 | Burd et al. |
| 2005/0119541 A1 | 6/2005 | Lorenz et al. |
| 2005/0124869 A1 | 6/2005 | Hefti et al. |
| 2005/0245796 A1 | 11/2005 | Woods et al. |
| 2005/0261560 A1 | 11/2005 | Ridder et al. |
| 2005/0267342 A1 | 12/2005 | Blank et al. |
| 2005/0267343 A1 | 12/2005 | Woods et al. |
| 2005/0267344 A1 | 12/2005 | Woods et al. |
| 2006/0020184 A1 | 1/2006 | Woods et al. |
| 2006/0063983 A1 | 3/2006 | Yamakoshi |
| 2006/0116562 A1 | 6/2006 | Acosta et al. |
| 2006/0157640 A1 | 7/2006 | Perlman et al. |
| 2006/0173254 A1 | 8/2006 | Acosta et al. |
| 2006/0173255 A1 | 8/2006 | Acosta et al. |
| 2006/0183983 A1 | 8/2006 | Acosta et al. |
| 2006/0183986 A1 | 8/2006 | Rice et al. |

(56) References Cited

U.S. PATENT DOCUMENTS

| | | |
|---|---|---|
| 2006/0195023 A1 | 8/2006 | Acosta et al. |
| 2006/0200013 A1 | 9/2006 | Smith et al. |
| 2006/0200017 A1 | 9/2006 | Monfre et al. |
| 2006/0206018 A1 | 9/2006 | Abul-Haj et al. |
| 2006/0211927 A1 | 9/2006 | Acosta et al. |
| 2006/0217602 A1 | 9/2006 | Abul-Haj et al. |
| 2006/0234386 A1 | 10/2006 | Burns et al. |
| 2006/0281982 A1 | 12/2006 | Grata et al. |
| 2007/0032717 A1 | 2/2007 | Brister et al. |
| 2007/0149868 A1 | 6/2007 | Blank et al. |
| 2007/0179367 A1 | 8/2007 | Ruchti et al. |
| 2007/0225675 A1 | 9/2007 | Robinson et al. |
| 2007/0240497 A1 | 10/2007 | Robinson et al. |
| 2007/0244381 A1 | 10/2007 | Robinson et al. |
| 2007/0244382 A1 | 10/2007 | Robinson et al. |
| 2007/0255141 A1 | 11/2007 | Esenaliev et al. |
| 2007/0278389 A1 | 12/2007 | Ajgaonkar et al. |
| 2007/0279628 A1 | 12/2007 | Lipson |
| 2008/0027297 A1* | 1/2008 | Yamakoshi ........ A61B 5/14532 600/316 |
| 2008/0086038 A1 | 4/2008 | Thornton |
| 2008/0111971 A1 | 5/2008 | Gerlitz |
| 2008/0221410 A1 | 9/2008 | Campbell et al. |
| 2008/0232653 A1 | 9/2008 | Rowe |
| 2008/0249387 A1 | 10/2008 | Hogan |
| 2008/0291394 A1 | 11/2008 | Ishak |
| 2008/0319286 A1 | 12/2008 | Ridder et al. |
| 2008/0319299 A1 | 12/2008 | Stippick et al. |
| 2009/0003764 A1 | 1/2009 | Ridder et al. |
| 2009/0018415 A1 | 1/2009 | Robinson et al. |
| 2009/0036759 A1 | 2/2009 | Ault et al. |
| 2009/0054753 A1 | 2/2009 | Robinson et al. |
| 2009/0088615 A1 | 4/2009 | Robinson et al. |
| 2009/0098587 A1 | 4/2009 | Hetzel et al. |
| 2009/0156915 A1 | 6/2009 | Cross |
| 2009/0185191 A1 | 7/2009 | Boppart et al. |
| 2009/0225277 A1 | 9/2009 | Gil |
| 2009/0247840 A1 | 10/2009 | Blank et al. |
| 2009/0270700 A1 | 10/2009 | Van Herpen et al. |
| 2009/0270756 A1 | 10/2009 | Gamache et al. |
| 2009/0284748 A1 | 11/2009 | Melman et al. |
| 2010/0010325 A1 | 1/2010 | Ridder et al. |
| 2010/0011471 A1 | 1/2010 | Jesse et al. |
| 2010/0016689 A1 | 1/2010 | Kanayama et al. |
| 2010/0049016 A1 | 2/2010 | Aronowitz et al. |
| 2010/0072386 A1 | 3/2010 | Harra et al. |
| 2010/0094113 A1 | 4/2010 | Robinson et al. |
| 2010/0113899 A1 | 5/2010 | Robinson et al. |
| 2010/0113901 A1 | 5/2010 | Zhang et al. |
| 2010/0160747 A1 | 6/2010 | Robinson et al. |
| 2010/0168535 A1 | 7/2010 | Robinson et al. |
| 2010/0170807 A1 | 7/2010 | Diebold et al. |
| 2010/0179403 A1 | 7/2010 | Martinsen et al. |
| 2010/0252721 A1 | 10/2010 | Xu |
| 2010/0256920 A1 | 10/2010 | Amano et al. |
| 2010/0312314 A1 | 12/2010 | Ice et al. |
| 2010/0324398 A1 | 12/2010 | Tzyy-Ping |
| 2011/0077496 A1 | 3/2011 | Chaiken |
| 2011/0115894 A1 | 5/2011 | Burnett |
| 2011/0172504 A1 | 7/2011 | Wegerich |
| 2011/0184260 A1 | 7/2011 | Robinson et al. |
| 2011/0194183 A1 | 8/2011 | Lipson et al. |
| 2011/0319742 A1 | 12/2011 | Mir et al. |
| 2012/0059232 A1 | 3/2012 | Gross et al. |
| 2012/0101351 A1 | 4/2012 | Caduff et al. |
| 2012/0129269 A1 | 5/2012 | Choi et al. |
| 2012/0130215 A1 | 5/2012 | Fine et al. |
| 2012/0150000 A1 | 6/2012 | Al-Shamma'a et al. |
| 2012/0162549 A1 | 6/2012 | Gao et al. |
| 2012/0165626 A1 | 6/2012 | Irina et al. |
| 2012/0191001 A1 | 7/2012 | Segman |
| 2012/0195864 A1 | 8/2012 | Simpson et al. |
| 2012/0203085 A1 | 8/2012 | Rebec |
| 2012/0238844 A1 | 9/2012 | Grata et al. |
| 2012/0323097 A9 | 12/2012 | Chowdhury |
| 2013/0006070 A1 | 1/2013 | Xu |
| 2013/0006071 A1 | 1/2013 | Xu |
| 2013/0006072 A1 | 1/2013 | Xu |
| 2013/0006073 A1 | 1/2013 | Xu |
| 2013/0008803 A1 | 1/2013 | Meyerhoff et al. |
| 2013/0018238 A1 | 1/2013 | Patti et al. |
| 2013/0037421 A1 | 2/2013 | Cardosi et al. |
| 2013/0075614 A1 | 3/2013 | Hartley |
| 2013/0095540 A1 | 4/2013 | Burgard et al. |
| 2013/0117377 A1 | 5/2013 | Miller |
| 2013/0125027 A1 | 5/2013 | Abovitz |
| 2013/0178723 A1 | 7/2013 | Wang |
| 2013/0204152 A1 | 8/2013 | Roth et al. |
| 2013/0211204 A1 | 8/2013 | Caduff et al. |
| 2013/0231539 A1 | 9/2013 | Gerlitz |
| 2013/0245405 A1 | 9/2013 | Xu |
| 2014/0003762 A1 | 1/2014 | Macnamara |
| 2014/0058226 A1 | 2/2014 | Chernobrod et al. |
| 2014/0081105 A1 | 3/2014 | Hanssen et al. |
| 2014/0104596 A1 | 4/2014 | Korman |
| 2014/0177023 A1 | 6/2014 | Gao et al. |
| 2014/0188092 A1 | 7/2014 | Islam |
| 2014/0188094 A1 | 7/2014 | Islam |
| 2014/0236021 A1 | 8/2014 | Islam |
| 2014/0249389 A1 | 9/2014 | Ward et al. |
| 2014/0250430 A1 | 9/2014 | Proud |
| 2014/0293467 A1 | 10/2014 | Palikaras et al. |
| 2015/0011849 A1 | 1/2015 | Ruchti et al. |
| 2015/0011850 A1 | 1/2015 | Ruchti et al. |
| 2015/0013429 A1 | 1/2015 | Atkin et al. |
| 2015/0015888 A1 | 1/2015 | Gulati et al. |
| 2015/0018642 A1 | 1/2015 | Gulati et al. |
| 2015/0018644 A1 | 1/2015 | Gulati et al. |
| 2015/0018646 A1 | 1/2015 | Gulati et al. |
| 2015/0030574 A1 | 1/2015 | Simpson et al. |
| 2015/0031969 A1 | 1/2015 | Khair |
| 2015/0041656 A1 | 2/2015 | Novotny et al. |
| 2015/0045636 A1 | 2/2015 | Novotny et al. |
| 2015/0045664 A1 | 2/2015 | Saha et al. |
| 2015/0073242 A1 | 3/2015 | Sokolov et al. |
| 2015/0097549 A1 | 4/2015 | Welsh et al. |
| 2015/0112167 A1 | 4/2015 | Conrad et al. |
| 2015/0126830 A1 | 5/2015 | Schurman et al. |
| 2015/0141763 A1 | 5/2015 | Roth et al. |
| 2015/0173474 A1 | 6/2015 | Barrows et al. |
| 2015/0177224 A1 | 6/2015 | Priefer et al. |
| 2015/0196233 A1 | 7/2015 | Gerlitz |
| 2015/0241378 A1 | 8/2015 | Liu et al. |
| 2015/0250408 A1 | 9/2015 | Senyange et al. |
| 2015/0257689 A1 | 9/2015 | Al-Ali et al. |
| 2015/0260650 A1 | 9/2015 | Ashrafi et al. |
| 2015/0265182 A1 | 9/2015 | Jain et al. |
| 2015/0268415 A1 | 9/2015 | Schowengerdt et al. |
| 2015/0276723 A1 | 10/2015 | Nagalla et al. |
| 2015/0297123 A1 | 10/2015 | Khokhoev et al. |
| 2015/0301020 A1 | 10/2015 | Sen et al. |
| 2015/0305658 A1 | 10/2015 | Islam |
| 2015/0338338 A1 | 11/2015 | Messerschmidt et al. |
| 2015/0342509 A1 | 12/2015 | Peeters et al. |
| 2015/0346090 A1 | 12/2015 | Xu et al. |
| 2015/0359522 A1 | 12/2015 | Recht et al. |
| 2015/0366490 A1 | 12/2015 | Gerlitz et al. |
| 2015/0374905 A1 | 12/2015 | Yodfat et al. |
| 2016/0007891 A1 | 1/2016 | Aberg et al. |
| 2016/0009771 A1 | 1/2016 | Miyawaki et al. |
| 2016/0011290 A1 | 1/2016 | Iannello |
| 2016/0015301 A1 | 1/2016 | Elliott et al. |
| 2016/0022180 A1 | 1/2016 | Joseph et al. |
| 2016/0022221 A1 | 1/2016 | Ou et al. |
| 2016/0025624 A1 | 1/2016 | Mucci et al. |
| 2016/0033406 A1 | 2/2016 | Ashrafi et al. |
| 2016/0040306 A1 | 2/2016 | Solis Herrera |
| 2016/0045143 A1 | 2/2016 | Lee et al. |
| 2016/0051171 A1 | 2/2016 | Pikov et al. |
| 2016/0061660 A1 | 3/2016 | Kim |
| 2016/0069804 A1 | 3/2016 | Ashrafi et al. |
| 2016/0073886 A1 | 3/2016 | Connor |
| 2016/0077037 A1 | 3/2016 | Cha et al. |
| 2016/0081552 A1 | 3/2016 | Wojtczuk et al. |

(56) References Cited

U.S. PATENT DOCUMENTS

| | | |
|---|---|---|
| 2016/0091496 A1 | 3/2016 | Xu et al. |
| 2016/0095533 A1 | 4/2016 | Shang |
| 2016/0095540 A1 | 4/2016 | Shang |
| 2016/0097712 A1 | 4/2016 | Shimizu et al. |
| 2016/0097716 A1 | 4/2016 | Gulati et al. |
| 2016/0097734 A1 | 4/2016 | Zhang et al. |
| 2016/0103063 A1 | 4/2016 | Kurasawa et al. |
| 2016/0116739 A1 | 4/2016 | TeKolste et al. |
| 2016/0128612 A1 | 5/2016 | Cho et al. |
| 2016/0131523 A1 | 5/2016 | Cho et al. |
| 2016/0139041 A1 | 5/2016 | Gulati et al. |
| 2016/0139042 A1 | 5/2016 | Gulati et al. |
| 2016/0139043 A1 | 5/2016 | Gulati et al. |
| 2016/0139045 A1 | 5/2016 | Gulati et al. |
| 2016/0143564 A1 | 5/2016 | Klein et al. |
| 2016/0151002 A1 | 6/2016 | Ruchti et al. |
| 2016/0166187 A1 | 6/2016 | Pluta et al. |

FOREIGN PATENT DOCUMENTS

| | | |
|---|---|---|
| CN | 103860180 A | 6/2014 |
| DE | 4243142 A1 | 6/1994 |
| EP | 0160768 A1 | 11/1985 |
| EP | 0236023 A2 | 9/1987 |
| EP | 0589191 A1 | 3/1994 |
| EP | 0603658 A1 | 6/1994 |
| EP | 0663591 A1 | 7/1995 |
| EP | 0670143 A1 | 9/1995 |
| EP | 0686372 A1 | 12/1995 |
| EP | 0792619 A1 | 9/1997 |
| EP | 0807812 A1 | 11/1997 |
| EP | 0967477 A1 | 12/1999 |
| EP | 0967478 A1 | 12/1999 |
| EP | 1184662 A1 | 3/2002 |
| EP | 1314400 A2 | 5/2003 |
| EP | 1437086 A1 | 7/2004 |
| EP | 1563788 A2 | 8/2005 |
| EP | 2544124 A1 | 1/2013 |
| EP | 2883493 A2 | 6/2015 |
| GB | 2407378 A | 4/2005 |
| TW | 445373 B | 7/2001 |
| WO | WO-8911825 A1 | 12/1989 |
| WO | WO-9004353 A2 | 5/1990 |
| WO | WO-9012534 A1 | 11/1990 |
| WO | WO-9115991 A1 | 10/1991 |
| WO | WO-9115992 A1 | 10/1991 |
| WO | WO-9117765 A1 | 11/1991 |
| WO | WO-9207511 A1 | 5/1992 |
| WO | WO-9210131 A1 | 6/1992 |
| WO | WO-9301745 A1 | 2/1993 |
| WO | WO-9307801 A1 | 4/1993 |
| WO | WO-9317621 A1 | 9/1993 |
| WO | WO-9402837 A1 | 2/1994 |
| WO | WO-9413199 A1 | 6/1994 |
| WO | WO-9416614 A1 | 8/1994 |
| WO | WO-9423643 A1 | 10/1994 |
| WO | WO-9503542 A1 | 2/1995 |
| WO | WO-9519562 A1 | 7/1995 |
| WO | WO-9530368 A1 | 11/1995 |
| WO | WO-9628720 A1 | 9/1996 |
| WO | WO-9636275 A1 | 11/1996 |
| WO | WO-9702781 A1 | 1/1997 |
| WO | WO-9704832 A1 | 2/1997 |
| WO | WO-9715229 A1 | 5/1997 |
| WO | WO-9734521 A1 | 9/1997 |
| WO | WO-9739686 A1 | 10/1997 |
| WO | WO-9743947 A1 | 11/1997 |
| WO | WO-9800057 A1 | 1/1998 |
| WO | WO-9803847 A2 | 1/1998 |
| WO | WO-9804190 A2 | 2/1998 |
| WO | WO-9829134 A2 | 7/1998 |
| WO | WO-9840723 A1 | 9/1998 |
| WO | WO-9902651 A1 | 1/1999 |
| WO | WO-9904043 A1 | 1/1999 |
| WO | WO-9905966 A1 | 2/1999 |
| WO | WO-9913336 A1 | 3/1999 |
| WO | WO-9935496 A1 | 7/1999 |
| WO | WO-9940724 A1 | 8/1999 |
| WO | WO-9956616 A1 | 11/1999 |
| WO | WO-0000215 A1 | 1/2000 |
| WO | WO-0000824 A1 | 1/2000 |
| WO | WO-0001294 A1 | 1/2000 |
| WO | WO-0002479 A1 | 1/2000 |
| WO | WO-0003727 A1 | 1/2000 |
| WO | WO-0005581 A1 | 2/2000 |
| WO | WO-0006143 A1 | 2/2000 |
| WO | WO-0006774 A1 | 2/2000 |
| WO | WO-0016692 A1 | 3/2000 |
| WO | WO-0028090 A2 | 5/2000 |
| WO | WO-0028317 A2 | 5/2000 |
| WO | WO-0038653 A1 | 7/2000 |
| WO | WO-0060350 A2 | 10/2000 |
| WO | WO-0101852 A1 | 1/2001 |
| WO | WO-0106918 A1 | 2/2001 |
| WO | WO-0113783 A1 | 3/2001 |
| WO | WO-0122061 A1 | 3/2001 |
| WO | WO-0122741 A2 | 3/2001 |
| WO | WO-0122869 A1 | 4/2001 |
| WO | WO-0122871 A1 | 4/2001 |
| WO | WO-0137722 A1 | 5/2001 |
| WO | WO-0146456 A2 | 6/2001 |
| WO | WO-0178589 A1 | 10/2001 |
| WO | WO-0179818 A2 | 10/2001 |
| WO | WO-0186474 A1 | 11/2001 |
| WO | WO-0196872 A2 | 12/2001 |
| WO | WO-0196986 A2 | 12/2001 |
| WO | WO-0226119 A2 | 4/2002 |
| WO | WO-0230506 A2 | 4/2002 |
| WO | WO-02057759 A1 | 7/2002 |
| WO | WO-02059600 A2 | 8/2002 |
| WO | WO-02059615 A2 | 8/2002 |
| WO | WO-02060321 A2 | 8/2002 |
| WO | WO-02064015 A2 | 8/2002 |
| WO | WO-02064193 A2 | 8/2002 |
| WO | WO-02065090 A2 | 8/2002 |
| WO | WO-02069789 A1 | 9/2002 |
| WO | WO-02069791 A1 | 9/2002 |
| WO | WO-02069796 A2 | 9/2002 |
| WO | WO-02071932 A1 | 9/2002 |
| WO | WO-02078538 A2 | 10/2002 |
| WO | WO-02080778 A1 | 10/2002 |
| WO | WO-02085195 A2 | 10/2002 |
| WO | WO-02086478 A2 | 10/2002 |
| WO | WO-02086500 A2 | 10/2002 |
| WO | WO-02086501 A2 | 10/2002 |
| WO | WO-02087429 A1 | 11/2002 |
| WO | WO-02094085 A2 | 11/2002 |
| WO | WO-02099452 A1 | 12/2002 |
| WO | WO-03008647 A2 | 1/2003 |
| WO | WO-03010510 A2 | 2/2003 |
| WO | WO-03012405 A2 | 2/2003 |
| WO | WO-03012486 A2 | 2/2003 |
| WO | WO-03015005 A2 | 2/2003 |
| WO | WO-03017048 A2 | 2/2003 |
| WO | WO-03023352 A2 | 3/2003 |
| WO | WO-03023397 A1 | 3/2003 |
| WO | WO-03025562 A3 | 3/2003 |
| WO | WO-03026732 A2 | 4/2003 |
| WO | WO-03026733 A2 | 4/2003 |
| WO | WO-03037174 A1 | 5/2003 |
| WO | WO-03037181 A2 | 5/2003 |
| WO | WO-03039367 A1 | 5/2003 |
| WO | WO-03039483 A2 | 5/2003 |
| WO | WO-03048998 A2 | 6/2003 |
| WO | WO-03052345 A1 | 6/2003 |
| WO | WO-03054792 A2 | 7/2003 |
| WO | WO-03061696 A2 | 7/2003 |
| WO | WO-03063699 A1 | 8/2003 |
| WO | WO-03071391 A2 | 8/2003 |
| WO | WO-03075961 A2 | 9/2003 |
| WO | WO-03076883 A2 | 9/2003 |
| WO | WO-03076893 A2 | 9/2003 |
| WO | WO-03077971 A2 | 9/2003 |
| WO | WO-03087759 A2 | 10/2003 |

(56) References Cited

FOREIGN PATENT DOCUMENTS

| | | |
|---|---|---|
| WO | WO-03087775 A2 | 10/2003 |
| WO | WO-03089013 A1 | 10/2003 |
| WO | WO-03097096 A1 | 11/2003 |
| WO | WO-03103771 A1 | 12/2003 |
| WO | WO-2004010138 A1 | 1/2004 |
| WO | WO-2004015388 A2 | 2/2004 |
| WO | WO-2004019172 A2 | 3/2004 |
| WO | WO-2004032715 A2 | 4/2004 |
| WO | WO-2004033021 A1 | 4/2004 |
| WO | WO-2004034221 A2 | 4/2004 |
| WO | WO-2004043230 A2 | 5/2004 |
| WO | WO-2004047630 A1 | 6/2004 |
| WO | WO-2004047870 A1 | 6/2004 |
| WO | WO-2004052228 A2 | 6/2004 |
| WO | WO-2004052644 A2 | 6/2004 |
| WO | WO-2004056278 A2 | 7/2004 |
| WO | WO-2004057285 A1 | 7/2004 |
| WO | WO-2004060154 A1 | 7/2004 |
| WO | WO-2004061742 A2 | 7/2004 |
| WO | WO-2004061743 A2 | 7/2004 |
| WO | WO-2004061744 A2 | 7/2004 |
| WO | WO-2004062480 A2 | 7/2004 |
| WO | WO-2004071287 A1 | 8/2004 |
| WO | WO-2004071290 A1 | 8/2004 |
| WO | WO-2004077012 A2 | 9/2004 |
| WO | WO-2004080281 A2 | 9/2004 |
| WO | WO-2004080297 A1 | 9/2004 |
| WO | WO-2004080483 A1 | 9/2004 |
| WO | WO-2004081524 A2 | 9/2004 |
| WO | WO-2004090786 A2 | 10/2004 |
| WO | WO-2004099824 A2 | 11/2004 |
| WO | WO-2004105595 A1 | 12/2004 |
| WO | WO-2004112599 A1 | 12/2004 |
| WO | WO-2004112601 A1 | 12/2004 |
| WO | WO-2005015184 A1 | 2/2005 |
| WO | WO-2005015237 A1 | 2/2005 |
| WO | WO-2005044099 A1 | 5/2005 |
| WO | WO-2005058152 A1 | 6/2005 |
| WO | WO-2005072605 A1 | 8/2005 |
| WO | WO-2005080966 A1 | 9/2005 |
| WO | WO-2006005653 A1 | 1/2006 |
| WO | WO-2006086566 A2 | 8/2006 |
| WO | WO-2006086579 A2 | 8/2006 |
| WO | WO-2006116637 A2 | 11/2006 |
| WO | WO-2007065653 A1 | 6/2007 |
| WO | WO-2009154798 A2 | 12/2009 |
| WO | WO-2010062495 A2 | 6/2010 |
| WO | WO-2010096081 A1 | 8/2010 |
| WO | WO-2010144313 A2 | 12/2010 |
| WO | WO-2012087319 A2 | 6/2012 |
| WO | WO-2012134515 A1 | 10/2012 |
| WO | WO-2013013605 A1 | 1/2013 |
| WO | WO-2013016573 A1 | 1/2013 |
| WO | WO-2013118115 A1 | 8/2013 |
| WO | WO-2013125987 A1 | 8/2013 |
| WO | WO-2013132252 A1 | 9/2013 |
| WO | WO-2014020611 A1 | 2/2014 |
| WO | WO-2014072823 A2 | 5/2014 |
| WO | WO-2014105520 A1 | 7/2014 |
| WO | WO-2014105521 A1 | 7/2014 |
| WO | WO-2014110492 A2 | 7/2014 |
| WO | WO-2014118601 A1 | 8/2014 |
| WO | WO-2014118745 A1 | 8/2014 |
| WO | WO-2014125492 A1 | 8/2014 |
| WO | WO-2014127127 A1 | 8/2014 |
| WO | WO-2014137919 A1 | 9/2014 |
| WO | WO-2014150447 A1 | 9/2014 |
| WO | WO-2014151293 A1 | 9/2014 |
| WO | WO-2014160210 A1 | 10/2014 |
| WO | WO-2014181319 A1 | 11/2014 |
| WO | WO-2014206549 A1 | 12/2014 |
| WO | WO-2015128657 A1 | 9/2015 |
| WO | WO-2015138688 A1 | 9/2015 |
| WO | WO-2015138690 A2 | 9/2015 |
| WO | WO-2015154105 A1 | 10/2015 |
| WO | WO-2015164452 A1 | 10/2015 |
| WO | WO-2015164578 A2 | 10/2015 |
| WO | WO-2015176004 A1 | 11/2015 |
| WO | WO-2015199940 A1 | 12/2015 |
| WO | WO-2015200031 A1 | 12/2015 |
| WO | WO-2016027202 A2 | 2/2016 |
| WO | WO-2016042343 A1 | 3/2016 |
| WO | WO-2016048624 A1 | 3/2016 |
| WO | WO-201605407 A1 | 4/2016 |
| WO | WO-2016068589 A1 | 5/2016 |
| WO | WO-2016073945 A1 | 5/2016 |
| WO | WO-2016077633 A1 | 5/2016 |
| WO | WO-2016080911 A1 | 5/2016 |

OTHER PUBLICATIONS

Arnold MA and Small GW, 'Determination of Physiological Levels of Glucose in an Aqueous Matrix with Digitally Filtered Fourier Transform Near-Infrared Spectra,' Anal Chem, Jul. 15, 1990, 62(14):1457-64.

Bykov AV et al., 'Monte Carlo Simulation of Light Propagation in Human Tissue and Noninvasive Glucose Sensing,' Chapter 3, Handbook of Optical Sensing of Glucose in Biological Fluids and Tissues, (1st Ed, 2008), VV Tuchin (ed), CRC Press Taylor & Francis Group LLC, Boca Raton, Florida, USA (Publ), pp. 65-95, ISBN: 978-1-58488-974-8 DOI: 10.1201/978584889755.

Chaiken J et al., 'Analyzing Near-Infrared Scattering From Human Skin to Monitor Changes in Hematocrit,' J Biomed Opt, Sep. 16, 2011, 16(9):097005-(1-18).

Delpy DT et al., 'Estimation of Optical Pathlength Through Tissue From Direct Time of Flight Measurement,' Phys Med Biol, Dec. 1988, 33(12):1433-42.

Durduran T et al., 'Diffuse Optics for Tissue Monitoring and Tomography,' Rep Prog Phys, Jul. 2010, 73(7):076701-(1-43).

Farrell TJ et al., 'A Diffusion Theory Model of Spatially Resolved, Steady-State Diffuse Reflectance for the Noninvasive Determination of Tissue Optical Properties in vivo,' Med Phys, Jul.-Aug. 1992, 19(4):879-88.

Flock ST et al., 'Monte Carlo Modeling of Light Propagation in Highly Scattering Tissues-II: Comparison with Measurements in Phantoms,' IEEE Trans Biomed Eng, Dec. 1989, 36(12):1169-73.

Haaland DM et al., 'Reagentless Near-Infrared Determination of Glucose in Whole Blood Using Multivariate Calibration,' Appl Spectrosc, Oct. 1992, 46(10):1575-8.

Hazen KH et al., 'Temperature-Insensitive Near-Infrared Spectroscopic Measurement of Glucose in Aqueous Solutions,' Appl Spectrosc, Apr. 1994, 48(4):477-83.

Kirillin MY et al., 'Application of Time Gating in the Measurement of Glucose Level in a Three-Layer Biotissue Model by Using Ultrashort Laser Pulses,' Quantum Electron+, Feb. 22, 2008, 38(5):486-90.

Larsson M et al., 'In vivo Determination of Local Skin Optical Properties and Photon Path Length by Use of Spatially Resolved Diffuse Reflectance with Applications in Laser Doppler Flowmetry,' Appl Opt, Jan. 1, 2003, 42(1):124-34.

Liu R et al., 'Next Step of Non-Invasive Glucose Monitor by NIR Technique From the Well Controlled Measuring Condition and Results,' Opt Quant Electron, Dec. 2005 Jan. 20, 2006 (ePub), 37(13):1305-17.

Marquardt LA et al., 'Near-Infrared Spectroscopic Measurement of Glucose in a Protein Matrix,' Anal Chem, Nov. 15, 1993, 65(22):3271-8.

Nagali V and Hanson RK, 'Design of a Diode-Laser Sensor to Monitor Water Vapor in High-Pressure Combustion Gases,' Appl Optics, Dec. 20, 1997, 36(36):9518-27.

Nayar SK and Mitsunaga T, 'High Dynamic Range Imaging: Spatially Varying Pixel Exposures,' Cvpr 2000: IEEE Conference on Computer Vision and Pattern Recognition, 2000 Proceedings, Jun. 13-15, 2000, Hilton Head Island, South Carolina, 1(2000):472-9.

Noda I, 'Recent Advancement in the Field of Two-Dimensional Correlation Spectroscopy,' J Mol Struct, Jul. 30, 2008, 883-884:2-26.

(56) References Cited

OTHER PUBLICATIONS

Ruchti TL et al., 'Longitudinal Evaluation of Alternate-Site Glucose Lag in Insulin Requiring Diabetics,' 2004, Sensys Medical, Chandler, AZ (Publ), (1 page) (Poster).

Small GW et al., 'Strategies for Coupling Digital Filtering with Partial Least-Squares Regression: Application to the Determination of Glucose in Plasma by Fourier Transform Near-Infrared Spectroscopy,' Anal Chem, Nov. 15, 1993, 65(22):3279-89.

Tearney GJ et al., 'Scanning Single-Mode Fiber Optic Catheter-Endoscope for Optical Coherence Tomography,' Opt Lett, Apr. 1, 1996, 21(7):543-5.

Thennadil SN et al., 'Comparison of Glucose Concentration in Interstitial Fluid, and Capillary and Venous Blood During Rapid Changes in Blood Glucose Levels,' Diabetes Technol Ther, Sep.-Nov. 2001, 3(3):357-65.

Thilwind RE et al., 'Improved Depth Resolution in Near-Infrared Diffuse Reflectance Spectroscopy Using Obliquely Oriented Fibers,' J Biomed Opt, Mar.-Apr. 2009, 14(2):024026-(1-9).

Xu K et al., 'The Interface Between Probe and Skin in Non-Invasive Glucose Sensing,' Proc SPIE 5068, Fall Meeting 2002 Optical Technologies in Biophysics Medicine, Oct. 14, 2003, Saratov, Russia, 5068(2003):104-11.

Yen S-J et al., 'Calculated Calibration Models for Glucose in Cutaneous Tissue from Temperature Modulation of Localized Reflectance Measurements,' Proc SPIE 5771, Fall Meeting 2004 Optical Technologies in Biophysics and Medicine, Aug. 5, 2005, Saratov, Russia, 5771:166-73.

Rand D and Steiglitz K, 'Computing with Solitons,' Dissertation for the Degree of Doctor of Philosophy, Jul. 1, 2007, Princeton University, Princeton, New Jersey (Publ), pp. 1-44, <http://www.cs.princeton.edu/~ken/EncycArticle070207.pdf>, (Thesis).

Jakubowski MH, 'Computing with Solitons in Bulk Media,' Dissertation for the Degree of Doctor of Philosophy, Jan. 1999, Princeton University, Princeton, New Jersey (Publ), pp. iii-141, https://www.cs.princeton.edu/~ken/mvl.ps , (Thesis).

A Adamatzky, 'Chapter 14: New Media for Collision-Based Computing,' Collision-Based Computing, (1st Edition, 2002), A Adamatzky (Ed.), Springer-Verlag, London, GB (Publ), ISBN: 1-85233-540-8, pp. 411-442.

A Adamatzky, Preface and Index, Collision-Based Computing, (1st Edition, 2002), A Adamatzky (Ed.), Springer-Verlag, London, GB (Publ), ISBN: 1-85233-540-8, pp. I-XXIII and 542-549.

A Wuensche, 'Chapter 13: Finding Gliders in Cellular Automata,' Collision-Based Computing, (1st Edition, 2002), A Adamatzky (Ed.), Springer-Verlag, London, GB (Publ), ISBN: 1-85233-540-8, pp. 381-410.

Agrawal RP et al., 'Noninvasive Method for Glucose Level Estimation by Saliva,' J Diabetes Metab, 2013, 4(5):2-5.

Ahmad M et al, 'Non-invasive Blood Glucose Monitoring Using Near-Infrared Spectroscopy,' EDN, Oct. 16, 2013, pp. 1-9, <http://www.edn.com/design/medical/4422840/Non-invasive-blood-glucose-monitoring-using-near-infrared-spectroscopy>.

Alexeev VL et al., 'Photonic Crystal Glucose-Sensing Material for Noninvasive Monitoring of Glucose in Tear Fluid,' Clin Chem, 2004, 50(12):2353-60.

Allen J, 'Photoplethysmography and its Application in Clinical Physiological Measurement,' Physiol Meas, Mar. 2007, Feb. 20, 2007 (ePub), 28(3):R1-39.

Amato, I, 'Race Quickens for Non-Stick Blood Monitoring Technology,' Science, Nov. 6, 1992, 258(5084):892-3.

Amerov Ak et al., 'Scattering and Absorption Effects in the Determination of Glucose in Whole Blood by Near-Infrared Spectroscopy,' Anal Chem, Jul. 15, 2005, 77(14):4587-94.

Amir O et al., 'Continuous Noninvasive Glucose Monitoring Technology Based on "Occlusion Spectroscopy",' J Diabetes Sci Technol, Jul. 2007, 1(4):463-9.

Amirlak B, 'Skin Anatomy,' Medscape Ref, Feb. 27, 2013, pp. 1/6-6/6, http://emedicine.medscape.com/article/1294744-overview#aw2aab6b7 <http://emedicine.medscape.com/article/1294744-overview>.

Anderson RR and Parrish JA, 'The Optics of Human Skin,' J Invest Dermatol, Jul. 1981, 77(1):13-9.

Anonymous, 'Clinical Evaluation of the Glucall™ Continual & Non-Invasive Glucose Monitor,' available no later than Jan. 27, 2012, K.M.H. Co, Ltd (Publ), Gyeonggi-do, Korea pp. 1-14, <http://kmholding.en.eC51.com/>.

Anonymous, 'Non-Invasive Breath-Based Glucometer Technology to Provide Breakthrough in Diabetes Testing and Self-Management,' Positive°ID Press Release, available no later than May 30, 2014, pp. 1-16, <http://psidcorp.com>.

Anonymous, 'Non-invasive Device Could End Daily Finger Pricking for People with Diabetes,' Health and Ageing News, Jul. 14, 2015, University of Leeds, Leeds UK (Publ), pp. 1/6-6/6 (Brochure).

Anonymous, 'Prospective Noninvasive Glucose Measurement Using a Wearable Raman Spectrometer,' C8 MediSensors, 2011 DTM Poster, 2011 (Brochure).

Anonymous, 'The Mosquito,' E-Mosquito, no Publication Date Available, Download Date of May 9, 2015, pp. 1/4-4/4 <http://www.m-pharm.ca/index.php/mosquito> (Brochure).

Anonymous, 'Xhale's Non-Invasive Breath-Based Blood Glucose Monitor Executive Summary,' available no later than Jun. 24, 2011, Xhale, Inc. (Publ), Gainesville, FL, pp. 1-2 (Brochure).

Anonymous, DIRAmed LLC Corporate Overview, available no later than Mar. 22, 2014, DIRAmed LLC, Columbus, OH, pp. 1-2, <http://10tv.solutionsbyweb/TechColumbus/files/diramedoverview.pdf> (Powerpoint).

Anonymous, GluCall Brochure, available no later than Jan. 27, 2012, pp. 1-8 (Brochure).

Anonymous, Glucosense Brochure, 2015, pp. 1-8, <http://www/glucosense.net/>.

Anonymous, Health-Chem Diagnostics, LLC. TD Glucose Monitoring System Brochure, available no later than Mar. 15, 2011, Health-Chem Diagnostics, LLC, Pompano Beach, FL, pp. 1-3.

Anonymous, Prediktor Company Presentation for Medical Investors, available no later than Oct. 15, 2013, pp. 1-24 (Powerpoint).

Anonymous, Sensys Medical, Inc. Corporate Presentation, May 16, 2007, Sensys Medical, Inc. (Publ), pp. 1-7, 9-40 (Powerpoint).

Anumula H et al., 'Development of a Noninvasive Corneal Birefringence Compensated Glucose Sensing Polarimeter,' Proceedings of the SPIE, 2003, 4958:303-12.

Applegate RA and Lakshminarayanan V, 'Parametric Representation of Stiles-Crawford Functions: Normal Variation of Peak Location and Directionality,' J Opt Soc Am A, Jul. 1993, 10(7):1611-23.

Arnold MA et al., 'Phantom Glucose Calibration Models from Simulated Noninvasive Human Near-Infrared Spectra,' Anal Chem, May 1, 1998, 70(9):1773-81.

Arnold MA et al., 'Selectivity Assessment of Noninvasive Glucose Measurements Based on Analysis of Multivariate Calibration Vectors,' J Diabetes Sci Technol, Jul. 2007, 1(4):454-62.

Arshovsky, VY, 'Like Night and Day: Rods and Cones Have Different Pigment Regeneration Pathways,' Neuron, Sep. 26, 2002, 36(1):1-3.

Asher, SA, 'Supplemental Review of Tear Glucose Sensing Literature,' Clin Chem, 2006, pp. 1-3, clinchem.2006.078543-1.doc.

Ashok V and Kumar N, Determination of Blood Glucose Concentration by Using Wavelet Transform and Neural Networks, Iran J Med Sci, Mar. 2013, 38(1):51-6.

Aydin S, 'A Comparison of Ghrelin, Glucose, Alpha-amylase and Protein Levels in Saliva from Diabetes,' J Biochem Molec Biol, Jan. 2007, 40(1):29-35.

Baca JT et al., 'Mass Spectral Determination of Fasting Tear Glucose Concentrations in Nondiabetic Volunteers,' Clin Chem, May 10, 2007, 53(7):1370-2.

Badugu R et al., Ophthalmic Glucose Monitoring Using Disposable Contact Lenses—A Review, J Fluorescence, Sep. 2004, 14(5):617-33.

Badugu R et al., 'A Glucose Sensing Contact Lens: A New Approach to Non-invasive Continuous Physiological Glucose Monitoring,' Proc. SPIE 5317, Optical Fibers and Sensors for Medical Applications IV, 234, Jun. 10, 200 doi: 10.1117/12.530060.

Badugu R et al., 'A Glucose-Sensing Contact Lens: From Bench Top to Patient,' Curr Opin Biotechnol, Feb. 2005, 16(1):100-7.

(56) References Cited

OTHER PUBLICATIONS

Bandodkar AJ et al., 'Tattoo-Based Noninvasive Glucose Monitoring: A Proof-of-Concept Study,' Anal Chem, Dec. 12, 2014 ePub, 87(1):394-8.
Barbur JL et al., 'A Comparative Study of Stimulus-specific Pupil Responses in the Domestic Fowl (*Gallus gallus domesticus*) and the Human,' Vision Res, 2002, 42(2):249-55.
Barman I et al., 'An Accurate Spectroscopic Calibration for Non-invasive Glucose Monitoring by Modeling the Physiological Glucose Dynamics,' Anal Chem, Jul. 15, 2010, 82(14):6104-14.
Bashkatov, AN et al., 'Optical Properties of the Subcutaneous Adipose Tissue in the Spectral Range 400-2500 nm,' Opt Spectrosc, 2005, 99(5):836-42.
Basu A et al., 'Time Lag of Glucose from Intravascular to Interstitial Compartment in Humans,' Diabetes, Dec. 2013, 62(12):4083-7.
Bhatnagar PL et al., 'A Model for Collision Processes in Gases. I. Small Amplitude Processes in Charged and Neutral One-Component Systems,' Physical Rev, May 1, 1954, 94(3):511-25.
Bishop DK et al., 'A Disposable Tear Glucose Biosensor—Part 1: Design and Concept Testing,' J Diabetes Sci Technol, Mar. 2010, 4(2):299-306.
Branco G, 'The Development and Evaluation of Head Probes for Optical Imaging of the Infant Head,' Thesis Submitted for the Degree of Doctor of Philosophy, Jan. 2007, J Hebden and DT Delpy (Sup), Department of Medical Physics and Bioengineering, University College of London (UCL) (Publ), pp. i-v, viii and 6-36 (Thesis) Upload split between two.
Brubaker RF, 'The Flow of Aqueous Humor in the Human Eye,' Trans Am Ophthalmol Soc, 1982, 80:391-474.
Burns SA et al., 'A Psychophysical Technique for Measuring Cone Photopigment Beaching,' Invest Ophthalmol Vision Sci, 1987, 28:711-7.
Camou S et al., 'CW-Photoacoustic-Based Protocol for the Non-Invasive Detection of Aqueous Glucose at Low MG/DL Concentration Levels,' 15th International Conference on Miniaturized Systems for Chemistry and Life Sciences, Oct. 2, 2011, Seattle, Washington, pp. 1992-1994 (Poster).
Carlson RE, 'Development of an Implantable Glucose Sensor,' Receptors LLS, available no later than Feb. 13, 2010, Receptors LLC (Publ), pp. 1-10 <http://www.receptosllc.com/uploads/RFID_Glucose_Sensor_White_Paper.pdf> (Summary).
Cengiz E and Tamborlane WV, 'A Tale of Two Compartments: Interstitial Versus Blood Glucose Monitoring,' Diabetes Tech Thera, Jun. 2009, 11(Suppl. 1):S11-S16.
Chance B. et al., 'Comparison of Time-resolved and Unresolved Measurements of Deoxyhemoglobin in Brain,' Proc Natl Acad Sci USA, 1988, 85:4971-5.
Chuang H et al., 'Pilot Studies of Transdermal Continuous Glucose Measurement in Outpatient Diabetic Patients and in Patients During and After Cardiac Surgery,' J Diabetes Sci Technol, 2008, 2(4):595-602.
Chuang H et al., 'Transdermal Glucose Monitoring Enabled by Prelude™ SkinPrep System,' ATTD Integrity Poster, 2010 (Poster).
Claussen JC et al., 'Nanostructuring Platinum Nanoparticles on Multilayered Graphene Petal Nanosheets for Electrochemical Biosensing,' Adv Funct Mater, Aug. 21, 2012, 22(16):3399-405.
Cohan PS, 'Will Grove Instruments Bloodless Glucose Tester Hit the Market by 2016?' Telegram.com Worcester Massachusetts, Jul. 29, 2013, p. 1, <http://www.telegram.com/article/20130729/COLUMN70/307299996>.
Daae LNW et al., 'Determination of Glucose in Human Vitreous Humor—Various Analytical Methods Give Different Results,' Z Rechtsmedizin, 1978, 80(4):287-91.
Das, A et al., 'Geneo—A Non-Invasive Portable Glucose Monitor Using Near-Infrared Spectroscopy,' NJIT and Albert Dorman Honors College, available no later than Aug. 30, 2011, pp. 1-14 (Powerpoint).
Daum KM and Hill RM, 'Human Tear Glucose,' Invest Ophthalmol Vis Sci, Apr. 1982, 22(4):509-14.

DeLint PJ et al., 'Slow Optical Changes in Human Photoreceptors Induced by Light,' Invest Ophthalmol Vis Sci, Jan. 2000, 41(1):282-9.
DiMattio J, 'Onset of Changes in Glucose Transport Across Ocular Barriers in Streptozotocin-Induced Diabetes,' Invest Ophthalmol Vis Sci, Jul. 1984, 25(7):820-6.
Domschke A et al., 'Initial Clinical Testing of a Holographic Non-Invasive Contact Lens Glucose Sensor,' Diabetes Technol Ther, Feb. 2006, 8(1):89-93.
E Fredkin and T Toffoli, 'Chapter 3: Conservative Logic,' Collision-Based Computing, (1st Edition, 2002), A Adamatzky (Ed.), Springer-Verlag, London, GB (Publ), ISBN: 1-85233-540-8, pp. 47-81.
E Petraglio et al., 'Chapter 16: Arithmetic Operations with Self-Replicating Loops,' Collision-Based Computing, (1st Edition, 2002), A Adamatzky (Ed.), Springer-Verlag, London, GB (Publ), ISBN: 1-85233-540-8, pp. 469-490.
E Fredkin and T Toffoli, Chapter 2: 'Design Principles for Achieving High-Performance Submicron Digital Technologies,' Collision-Based Computing, (1st Edition, 2002), A Adamatzky (Ed.), Springer-Verlag, London, GB (Publ), ISBN: 1-85233-540-8, pp. 27-46.
Elkady, A et al., 'Microwave Power Absorption in Human Body for Non-invasive Glucose Monitoring,' Prog Electromag Res Sym Proc, Aug. 12-15, 2013, Stockholm, Sweden, pp. 109-113.
Elsner AE et al., 'Cone Photopigment Bleaching Abnormalities in Diabetes,' Invest Ophthalmol Vis Sci, 1987, 28(4):718-24.
Enejder AMK, et al., 'Raman Spectroscopy for Noninvasive Glucose Measurements,' J Biomedical Opt, May 2005, 10(3):031114-1-03114-9.
English LB, 'In Pursuit of an Ideal—A Perspective on Non-invasive Continuous Glucose Monitoring,' Euro Endocrinol, 2012, 8(1):18-21.
Ferrari M. e al., 'Continuous Non-invasive Monitoring of Human Brain by Near-infrared Spectroscopy,' Adv Exp Med Biol, 1985, 191:873-82.
Ferrari M. et al., "Determination of Cerebral Venous Hemoglobin Saturation by Derivative Near Infrared Spectroscopy", 1989, Adv Exp Med Biol, 1989, 248:47-53.
Ferraty F and Vieu P, 'The Functional Nonparametric Model and Application to Spectrometric Data,' Computation Statistics, Nov. 2002, 17(4):545-64.
Fogh-Andersen N. et al., 'Composition of Interstitial Fluid,' Clin Chem, 1995, 41(10):1522-5.
Fritsch T et al., 'Is Exhaled Carbon Monoxide Level Associate with Blood Glucose Level? A Comparison of Two Breath Analyzing Methods,' J Biomed Opt, Jun. 5, 2008, 13(3):034012.
Futterman S et al., 'Metabolism of Glucose and Reduction of Retinaldehyde in Retinal Photoreceptors,' J Neurochem, 1970, 17(2):149-56.
Gabbay RA and Sivarajah S, 'Optical Coherence Tomography-Based Continuous Noninvasive Glucose Monitoring in Patients with Diabetes,' Diabetes Technol Therapeut, 2008, 10(3):188-93.
Gal A et al., 'A Non-Invasive SMBG Device for Home Use,' Feb. 2010, Integrity Applications, ATTD (Pub), Basel, CH (Poster).
Gal A et al., 'Calibration Schemes of a Truly Non-Invasive Glucose Monitor for Variety of Diabetics,' 14th Annual Diabetes Technology Meeting (DTM), Oct. 31-Nov. 2, 2013, San Francisco, California, USA, Integrity Applications, Ashkelon, Israel (Publ), (1 page) (Poster).
Gal A et al., 'Validity of GlucoTrack®, A Non-Invasive Glucose Monitor for a Variety of People with Diabetes,' Diabetes UK Professional Conference, Mar. 13-15, 2013, Manchester, United Kingdom, Integrity Applications, Ashkelon, Israel (Publ), (1 page) (Poster).
Goebel F-D et al., 'Short-term Changes of Glycosylated Haemoglobins During Glucose Administration in Health and Diabetic Subjects,' Res Exp Med (Berl), Jun. 1981, 179(2):133-40.
Groendaal W et al., 'Quantifying the Composition of Human Skin for Glucose Sensor Development,' J Diabetes Sci Technol, Sep. 2010, 4(5):1032-40.
Guilbault GG and Palleschi G, 'Non-invasive Biosensors in Clinical Analysis,' Biosens Bioelectron, 1995, 10(3-4):379-92.

(56) References Cited

OTHER PUBLICATIONS

Guittet M et al., 'Blood Glucose Monitoring Without Finger Pricking,' 2009, Glucowatch, www.glucosewatch.co.uk <http://www.glucosewatch.co.uk> (Brochure).
Gutman S et al., 'Regulatory Aspects of Noninvasive Glucose Measurements,' Diabetes Technol Ther, 2002, 4(6):779-81.
H Martens and T Naes, Multivariate Calibration, (1st Ed, 1989), John Wiley and Sons, New York, NY (Publ), pp. 1-419. ISBN 978-0-4719-3047-1.
Harman-Boehm I et al., 'Noninvasive Glucose Monitoring: A Novel Approach,' J Diabetes Sci Technol, Mar. 2009, 3(2):253-60.
Harman-Boehm I et al., 'Noninvasive Glucose Monitoring: Increasing Accuracy by Combination of Multi-Technology and Multi-Sensors,' J Diabetes Sci Technol, May 1, 2010, 4(3):583-95.
Haus HA and Ippen EP, 'Group Velocity of Solitons,' Optics Letters, 2001, 26(21):1654-6.
Hazeki O. et al. 'Near-infrared Spectrophotometric Monitoring of Haemoglobin and Cytochrame a,a4 In Situ,' Adv Exp Med Biol, 1987, 215:283-9.
Hazen KH et al., 'Measurement of Glucose and Other Analytes in Undiluted Human Serum with Near-Infrared Transmission Spectroscopy,' *Analyt Chimica Acta*, 1998, 371:255-67.
Hazen KH et al., 'Measurement of Glucose in Water with First-Overtone Near-Infrared Spectra,' Appl Spectrosc, Dec. 1, 1998, 52(12):1597-1605.
Heinemann L, 'Noninvasive Glucose Monitoring Systems: Will We Ever Have Such Sensors for Practical Use?,' J Diabetes Sci Technol, Nov. 2007, 1(6):936-9.
Heise H. et al., 'Multivariate Determination of Glucose in Whole-Blood by Attenuated Total Reflection Infrared-Spectroscopy,' Anal Chem, 1989, 61:2009-15.
Helwig AM et al., 'Evaluation of Kromoscopy: Resolution of Glucose,' Applied Optics, 2000, 39(25):4715-20.
Higgins PJ and Bunn HF, 'Kinetic Analysis of the Nonenzymatic Glycosylation of Hemoglobin,' J Biol Chem, May 25, 1981, 256(10):5204-8.
J Durand-Lose, 'Chapter 6: Computing Inside the Billiard Ball Model,' Collision-Based Computing, (1st Edition, 2002), A Adamatzky (Ed.), Springer-Verlag, London, GB (Publ), ISBN: 1-85233-540-8, pp. 135-160.
J-P Rennard, 'Chapter 17: Implementation of Logical Functions in the Game of Life,' Collision-Based Computing, (1st Edition, 2002), A Adamatzky (Ed.), Springer-Verlag, London, GB (Publ), ISBN: 1-85233-540-8, pp. 491-512.
Jean BR et al., 'A Microwave Frequency Sensor for Non-Invasive Blood-Glucose Measurement,' SAS 2008—IEEE Sensors Applications Symposium, Feb. 12, 2008, pp. 1-4.
Jin Z et al., 'Determination of Glucose in Submicroliter Samples by CE-LIF Using Precolumn or On-Column Enzymatic Reactions,' Anal Chem, Apr. 1, 1997, 69(7):1326-31.
Jovanovic L et al., 'Human Factors Assessment for Measuring Glucose Non-Invasively,' Management of Insulin Treatment—New Technologies and Beyond, 67th Scientific Sessions of the American Diabetes Association, Jun. 22, 2007, Biodel, Inc. (Ed), Abstract No. 033-OR (Poster).
Jung Y and Hwang J, 'Near-infrared Studies of Glucose and Sucrose in Aqueous Solutions: Water Displacement Effect and Red Shift in Water Absorption form Water-solute Interaction,' Appl Spectrosc, Feb. 2013, 67(2):171-80.
K Morita et al., 'Chapter 7: Universal Computing in Reversible and Number-Conserving Two-Dimensional Cellular Spaces,' Collision-Based Computing, (1st Edition, 2002), A Adamatzky (Ed.), Springer-Verlag, London, GB (Publ), ISBN: 1-85233-540-8, pp. 161-199.
Karlovsek MZ, 'Diagnostic Values of Combined Glucose and Lactate Values in Cerebrospinal Fluid and Vitreous Humour—Our Experiences,' Forensic Sci Int'l, Oct. 20, 2004, 146(S):S19-S23.
Khalil OS, 'Non-Invasive Glucose Measurement Technologies: An Update from 1999 to the Dawn of the New Millennium,' J Diabetes Technol Ther, 2004, 6(5):660-97.
Kilp H and Heisig B, 'Glucose and Lactat-Concentration in Tears after Mechanical Alteration and Contact-Lens-Wearing,' Albrecht v Graefes Arch klin exp Ophthal., 1975, 193(4):259-67.
Klonoff DC and Braig J, 'Mid-Infrared Spectroscopy for Noninvasive Blood Glucose Monitoring,' LEOS Newsletter, Apr. 1998, 12(2):1-3.
Klonoff DC, 'Noninvasive Blood Glucose Monitoring,' Diabetes Care, Mar. 1997, 20(3):433-7.
Klonoff DC, 'The Benefits of Implanted Glucose Sensors,' J Diabetes Sci Technol, Nov. 2007, 1(6):797-800.
Knop E and Knop N, 'Anatomy and Immunology of the Ocular Surface,' Chem Immunol Allergy, 2007, 92:36-49.
Ko JB et al., 'Body Metabolism Provides a Foundation for Noninvasive Blood Glucose Monitoring,' Diabetes Care, May 2004, 27(5):1211-2.
Koh PH et al., 'Chapter 4: Fundamentals of Tissue Optics,' Methodology of Optical Topography Measurements for Functional Brain Imaging and the Development and Implementation of Functional Optical Signal Analysis Software, Sep. 2007, Department of Medical Physics and Bioengineering, University College, London GB (Publ), pp. 59-84 (Thesis).
Kottmann J et al., 'Mid-infrared Fiber-Coupled Photoacoustic Sensor for Biomedical Applications,' Sensors (Basel), Jan. 2013, 13(1):535-49.
Krishnaswamy A and Baranoski GV, 'A Study on Skin Optics,' Jan. 2004, Natural Phenomena Simulation Group, School of Computer Science, University of Waterloo, Canada, Technical Report CS-2004-01, pp. 1-17.
Krouwer JS and Cembrowski GS, 'A Review of Standards and Statistics Used to Describe Blood Glucose Monitor Performance,' J Diabetes Sci Technol, Jan. 2010, 4(1):75-83.
Kuksa V et al., 'Retinoid Cycle in the Vertebrate Retina: Experimental Approaches and Mechanisms of Isomerization,' Vision Res, Dec. 2003, 43(28):2959-81.
LA Bunimovich and MA Khlabystora, 'Chapter 15: Lorentz Lattice Gases and Many-Dimensional Turing Machines,' Collision-Based Computing, (1st Edition, 2002), A Adamatzky (Ed.), Springer-Verlag, London, GB (Publ), ISBN: 1-85233-540-8, pp. 443-467.
Lane JD et al., 'Tear Glucose Dynamics in *Diabetes mellitus*,' Curr Eye Res, Nov. 2006, 31(11):895-901.
LeBlanc JM et al., 'Evaluation of Lacrimal Fluid as an Alternative for Monitoring Glucose in Critically Ill Patients,' Intensive Care Med, Aug. 16, 2005 ePub, 31(10):1442-5.
Liakat S et al., 'Noninvasive in vivo Glucose Sensing on Human Subjects using Mid-Infrared Light,' Biomed Opt Express, Jun. 23, 2014, 5(7):2397-404.
Lin MC, Efficient Collision Detection for Animation and Robotics, Ph.D., Thesis, 1993, Univ. of California at Berkeley, pp. 1-159 (Thesis).
Lipson J et al., 'Requirements for Calibration in Noninvasive Glucose Monitoring by Raman Spectroscopy,' J Diabetes Sci Technol, Mar. 2009, 3(2):233-41.
M Delorme and J Mazoyer, 'Chapter 9: Signals on Cellular Automata,' Collision-Based Computing, (1st Edition, 2002), A Adamatzky (Ed.), Springer-Verlag, London, GB (Publ), ISBN: 1-85233-540-8, pp. 231-275.
Mahroo OAR and Lamb TD, 'Recovery of the Human Photopic Electroretinogram After Bleaching Exposures: Estimation of Pigment Regeneration Kinetics,' J Physiol, Oct. 31, 2003, 554(2):417-37.
Makaram P et al., 'Trends in Nanomaterial-Based Non-Invasive Diabetes Sensing Technologies,' Diagnostics, 2014, 4:27-46.
Malchoff CD et al, 'A Novel Noninvasive Blood Glucose Monitor,' Diabetes Care, Dec. 2002, 25(12):2268-75.
Malin SF et al., 'Development of a Noninvasive Prediction of Glucose by Near-Infrared Diffuse Reflectance Spectroscopy,' Clin Chem, 1999, 45(9):1651-8.
Malinin L, 'Development Non-Invasive Blood Glucose Monitor Based on Impedance Measurements,' Internat J Biomed Engineer Tech, 2012, 8(1):60-81.
March WF et al., 'Clinical Trial of a Noninvasive Contact Lens Glucose Sensor,' Diabetes Technol Ther, Dec. 2004, 6(6):782-9.

(56) References Cited

OTHER PUBLICATIONS

March WF et al., 'Non-invasive Glucose Monitoring of the Aqueous Humor of the Eye: Part II. Animal Studies and the Scleral Lens,' Diabetes Care, 1982, 5(3): 259-65.
Mascarenhas P. et al., 'Effect of Diabetes Mellitus Type 2 on Salivary Glucose—A Systematic Review and Meta-Analysis of Observational Studies,' PLoS One, Jul. 2014, 9(7):1-15.
Mauras N et al., 'A Randomized Clinical Trial to Assess the Efficacy and Safety of Real-Time Continuous Glucose Monitoring in the Management of Type 1 Diabetes in Young Children Aged 4 to <10 Years,' Diabetes Care, Dec. 30, 2011 ePub, 35(2):204-10.
Mazarevica G et al., 'Properties of Erythrocyte Light Refraction in Diabetic Patients,' J Biomed Opt, Apr. 1, 2002, 7(2):244-7.
McCarthy BM et al., 'An Investigation of Pulse Transit Time as a Non-Invasive Blood Pressure Measurement Method,' J Phys: Conf Ser, 2011, 307(1):1-5.
MD Westmoreland and J Krone, 'Chapter 8: Derivation Schemes in Twin Open Set Logic,' Collision-Based Computing, (1st Edition, 2002), A Adamatzky (Ed.), Springer-Verlag, London, GB (Publ), ISBN: 1-85233-540-8, pp. 201-230.
MH Jakubowski et al., 'Chapter 10: Computing with Solitons: A Review and Prospectus,' Collision-Based Computing, (1st Edition, 2002), A Adamatzky (Ed.), Springer-Verlag, London, GB (Publ), ISBN: 1-85233-540-8, pp. 277-297.
Miller J et al., 'Minimally Invasive, Direct, Real Time Measurement of Drug Concentration in the Anterior Eye,' Br J Ophthalmol, Sep. 2005, 89(9):1147-51.
Minh TDC et al., 'Noninvasive Measurement of Plasma Glucose from Exhaled Breath in Healthy and Type I Diabetic Subjects,' Am J Physiol Endocrinol Metab, Apr. 5, 2011, 300(6):E1166-E1175.
Mishra, S, 'FreedomMeditech Clearpath DS-120™,' available no later than Apr. 27, 2015, Freedom Meditech, Inc. (Publ), San Diego, CA pp. 1-26 (Powerpoint).
MJ Ablowitz, 'Chapter 10: Communications,' Nonlinear Dispersive Waves Asymptotic Analysis and Solutions, (1st Edition, 2011), Cambridge University Press, New York, NY (Publ), ISBN: 978-1-107-01254-7, pp. 261-312.
MJ Ablowitz, 'Chapter 1: Introduction,' Nonlinear Dispersive Waves Asymptotic Analysis and Solutions, (1st Edition, 2011), Cambridge University Press, New York, NY (Publ), ISBN: 978-1-107-01254-7, pp. 3-16.
MJ Ablowitz, 'Chapter 2: Linear and Nonlinear Wave Equations,' Nonlinear Dispersive Waves Asymptotic Analysis and Solutions, (1st Edition, 2011), Cambridge University Press, New York, NY (Publ), ISBN: 978-1-107-01254-7, pp. 17-42.
MJ Ablowitz, 'Chapter 5.5: Solitary Wave Solutions,' Nonlinear Dispersive Waves Asymptotic Analysis and Solutions, (1st Edition, 2011), Cambridge University Press, New York, NY (Publ), ISBN: 978-1-107-01254-7, pp. 118-128.
MJ Ablowitz, 'Chapter 6: Nonlinear Schrödinger Models and Water Waves,' Nonlinear Dispersive Waves Asymptotic Analysis and Solutions, (1st Edition, 2011), Cambridge University Press, New York, NY (Publ), ISBN: 978-1-107-01254-7, pp. 130-166.
MJ Ablowitz, 'Chapter 8.1: Traveling Wave Solutions of the KdV Equation,' through 'Chapter 8.3: The Miura Transformation and Conservation Laws for the KdV Equation,' Nonlinear Dispersive Waves Asymptotic Analysis and Solutions, (1st Edition, 2011), Cambridge University Press, New York, NY (Publ), ISBN: 978-1-107-01254-7, pp. 189-197.
MJ Ablowitz, 'Chapter 8.7: More General Classes of Nonlinear Evolution Equations,' Nonlinear Dispersive Waves Asymptotic Analysis and Solutions, (1st Edition, 2011), Cambridge University Press, New York, NY (Publ), ISBN: 978-1-107-01254-7, pp. 205-210.
Monte-Moreno E, 'Non-invasive Estimate of Blood Glucose and Blood Pressure from a Photoplethysmograph by Means of Machine Learning Techniques,' Artif Intell Med, Oct. 2011, 53(2):127-38.
Mortellaro M and DeHennis A, 'Performance Characterization of an Abiotic and Fluorescent-Based Continuous Glucose Monitoring System in Patients with Type 1 Diabetes,' Biosens Bioelectron, May 17, 2014 ePub, 61:227-31.
Moseley H, 'Mathematical Model of Diffusion in the Vitreous Humour in the Eye,' Clin Phys Physiol Meas, 1981, 2(3):175-81.
Mourant JR et al., 'Influence of the Scattering Phase Function on Light Transport Measurements in Turbid Media Performed with Small Source-Detector Separations,' Optics Lett, Apr. 1, 1996, 21(7):546-8.
Moyer J et al., 'Correlation Between Sweat Glucose and Blood Glucose in Subjects with Diabetes,' Diabetes Technol Thera, May 2012, 14(5):398-402.
N Margolus, 'Chapter 4: Physics-Like Models of Computation,' Collision-Based Computing, (1st Edition, 2002), A Adamatzky (Ed.), Springer-Verlag, London, GB (Publ), ISBN: 1-85233-540-8, pp. 83-104.
N Margolus, 'Chapter 5: Universal Cellular Automata Based on the Collisions of Soft Spheres,' Collision-Based Computing, (1st Edition, 2002), A Adamatzky (Ed.), Springer-Verlag, London, GB (Publ), ISBN: 1-85233-540-8, pp. 107-134.
Ostrander K et al., 'Non-Invasive Detection of Venous Glucose Using Fourier Transform Infrared Spectroscopy,' 2010, 2010 MIRTHE Conference, Houston, TX (Poster).
Ostroy SE et al., 'Extracellular Glucose Dependence of Rhodopsin Regeneration in the Excised Mouse Eye,' Exp Eye Res, 1992, 55(3):419-23.
Ozana N et al., 'Improved Noncontact Optical Sensor for Detection of Glucose Concentration and Indication of Dehydration Level,' Biomed Opt Express, May 22, 2014, 5(6):1926-40.
P Siwak, 'Chapter 11: Iterons of Automata,' Collision-Based Computing, (1st Edition, 2002), A Adamatzky (Ed.), Springer-Verlag, London, GB (Publ), ISBN: 1-85233-540-8, pp. 299-353.
Patel BJ et al., 'Comparison and Correlation of Glucose Levels in Serum and Saliva of Both Diabetic and Non-diabetic Patients,' J Intl Oral Health, May 2015, 7(5):70-6.
Pleitez M et al., 'Windowless Ultrasound Photoacoustic Cell for In Vivo Mid-IR Spectroscopy of Human Epidermis: Low Interference by Changes of Air Pressure, Temperature, and Humidity Caused by Skin Contact Opens the Possibility for a Non-invasive Monitoring of Glucose in the Interstitial Fluid,' Rev Sci Instrum, Aug. 2013, 84(8):084901-8.
Pleitez MA et al., 'In Vivo Noninvasive Monitoring of Glucose Concentration in Human Epidermis by Mid-Infrared Pulsed Photoacoustic Spectroscopy,' Anal Chem, Dec. 7, 2012, 85(2):1013-20.
Pleitez MA et al., 'Measuring Blood Sugar with Light,' AIP Publishing, Oct. 25, 2013, pp. 1-3, <http://publishing.aip.org/publishing/journal-highlights/measuring-blood-sugar-light>.
Pleitez MA et al., 'Photothermal Deflectometry Enhanced by Total Internal Reflection Enables Non-invasive Glucose Monitoring in Human Epidermis,' Analyst, Jan. 21, 2015, 140(2):483-8.
Poddar R et al., Non-invasive Glucose Monitoring Techniques: A Review and Current Trends, www.researchgate.net <http://www.researchgate.net>, Oct. 31, 2008, arXiv:0810.5755v1 [physics.med-ph], pp. 1-47, <http://www.researchgate.net/plublication/210255819_Non-Invasive_Glucose_Monitoring_Techniques_A_review_and_current_trends>.
R Rendell, 'Chapter 18: Turing Universality of the Game of Life,' Collision-Based Computing, (1st Edition, 2002), A Adamatzky (Ed.), Springer-Verlag, London, GB (Publ), ISBN: 1-85233-540-8, pp. 513-539.
Rabinovitch B. et al., 'Non-invasive Glucose Monitoring of the Aqueous Humor of the Eye: Part I Measurement of Very Small Optical Rotations,' Diabetes Care, May-Jun. 1982, 5(3):254-8.
Rao SS et al., 'Impaired Glucose Tolerance and Impaired Fasting Glucose,' Am Fam Physician, Apr. 15, 2004, 69(8):1961-8.
Rawer R et al., 'Polarimetric Methods for Measurement of Intra Ocular Glucose Concentration,' Biomedizinische Technik, Jan. 2002, 47(Suppl 1 Pt 1a):186-8.
Reim M. et al., 'Steady State Levels of Glucose in the Different Layers of the Cornea, Aqueous Humor, Blood and Tears In Vivo,' Ophthalmologica, 1967, 154:39-50.

(56) References Cited

OTHER PUBLICATIONS

Robinson MR et al., 'Noninvasive Glucose Monitoring in Diabetic Patients: A Preliminary Evaluation,' Clin Chem, Sep. 1992, 38(9):1618-22.
S Blair and K Wagner, 'Chapter 12: Gated Logic with Optical Solutions,' Collision-Based Computing, (1st Edition, 2002), A Adamatzky (Ed.), Springer-Verlag, London, GB (Publ), ISBN: 1-85233-540-8, pp. 355-380.
Saari JC, 'Biochemistry of Visual Pigment Regeneration,' Invest Ophthalmol Vis Sci, Feb. 2000, 41(2):337-48.
Sacks DB, 'Guidelines and Recommendations for Laboratory Analysis in the Diagnosis and Management of Diabetes Mellitus,' Diabetes Care, May 20, 2011 ePub, 34(6):e61-e99.
Schrady N., 'The View From a Distance: Advances in Optics and Electronics are Allowing Physicians to Glean Diagnostic Information Without Drawing Blood,' Forbes, Feb. 25, 1985, 135(2):142.
Scuffi C, 'Interstitium Versus Blood Equilibrium in Glucose Concentration and its Impact on Subcutaneous Continuous Glucose Monitoring Systems,' Euro Endocrin, 2014, 10(1):36-42.
Seiyama A et al., 'Simultaneous Measurement of Haemoglobin Oxygenation of Brain and Skeletal Muscle of Rat In Vivo by Near-infrared Spectroscopy,' Adv Exp Med Biol, 1987, 215:291-5.
Sen DK and Sarin GS, 'Tear Glucose Levels in Normal People and in Diabetic Patients,' Br J Ophthalmol, Sep. 1980, 64(9):693-5.
Shetty N et al., Gingival Crevicular Blood: As a Non-invasive Screening Tool for Diabetes Mellitus in Dental Clinics, J Indian Soc Peridontol, Jul. 2013, 17(4):472-7.
Shvartsman LD and Fine I, 'Optical Transmission of Blood: Effect of Erythrocyte Aggregation,' IEEE Trans Biomed Eng, Aug. 2003, 50(8):1026-33.
Sigurgeirsson H et al., 'Algorithms for Particle-Field Simulations with Collisions,' J Computational Phys., 2001, 172:766-807.
Siu VS et al., 'A "Plasmonic Cuvette": Dye Chemistry Coupled to Plasmonic Interferometry for Glucose Sensing,' Nanophotonics, 2014, 3(3):125-40.
Skladnev, VN et al., 'Clinical Evaluation of a Noninvasive Alarm System for Nocturnal Hypoglycemia,' J Diabetes Sci Technol, Jan. 2010, 4(1):67-74.
Skyler JS, 'Continuous Glucose Monitoring,' 2012, Diabetes Research Institute, University of Miami, Coral Gables, Florida, pp. 1-13 (Powerpoint).
Smith JL, 'The Pursuit of Noninvasive Glucose: Hunting the Deceitful Turkey,' 4th ed., 2011, pp. 1-129 http://www.mendosa.com/noninvasive_glucose.pdf.
So C-F et al., 'Recent Advances in Noninvasive Glucose Monitoring,' Med Devices (Auckl), Jun. 27, 2012, 5:45-52.
Spivak P, LED Photo 'Bioscience Systems Patented Technology Revolutionizes Glucose Monitoring Forever!' Jul. 8, 2014, <http://www.biosciencesystems.com/> (Website Page).
Statland BE, 'GlucoWatch® Automatic Glucose Biographer Notice of Premarket Approval,' Food and Drug Administration, Mar. 22, 2001, pp. 1-7 (Document).
Steven P and Gebert A, 'Conjunctiva-Associate Lymphoid Tissue—Current Knowledge, Animal Models and Experimental Prospects,' Ophthalmic Res, 2009, 42(1):2-8.
Szpaderska AM et al., 'Differential Injury Response in Oral Mucosal and Cutaneous Wounds,' J Dent Res, 2003, 82(8):621-6.
T Dauxois and M Peyrard, Physics of Solitons, (1st Ed, Mar. 9, 2006), Cambridge University Press, Cambridge UK (Publ), pp. 1-436, ISBN: 978-0-5211-4360-8.
T Toffoli, 'Chapter 1: Symbol Super Colliders,' Collision-Based Computing, (1st Edition, 2002), A Adamatzky (Ed.), Springer-Verlag, London, GB (Publ), ISBN: 1-85233-540-8, pp. 1-23.
Takada M. et al., 'Non-invasive Near-infrared Measurements of Human Arm Tissues In Vivo,' Adv Exp Med Biol, 1987, 215:301-4.
Tamura M. et al., 'Spectroscopic Characteristics of Rat Skeletal and Cardiac Tissues in the Visible and Near-infrared Region,' Adv Exp Med, 1987, 215:297-300.
Tamura T et al., 'Wearable Photoplethysmographic Sensors—Past and Present,' Electronics 2014, Apr. 23, 2014, (3):282-302.
Thennadil SH et al, 'Comparison of Glucose Concentration in Interstitial Fluid, and Capillary and Venous Blood During Rapid Changes in Blood Glucose Levels,' Diabetes Technol Therapeut, 2001, 3(3):357-66.
Thiese ND et al., 'Glucose PopTest: Saliva Glucose Measurements Reflect Blood Glucose Level in Diabetes Population,' ADA Poster, Pop Test LLC, Cliffside Park, New Jersey, Jun. 5, 2015 (Poster).
Thomas LW, 'The Chemical Composition of Adipose Tissue of Man and Mice,' Q J Exp Physiol Cogn Med Sci, Apr. 7, 1962, 47(2):179-88.
Tomek, A, 'VeriChip Corporation and Receptors LLC Successfully Complete Phase I Development of In Vivo Glucose Sensing RFID Microchip,' Nov. 19, 2008, Receptor LLC (Publ), Chaska, MN, pp. 1-2 (Press Release).
van Haeringen NJ and Glasius E, 'Collection Method Dependant Concentrations of Some Metabolites in Human Tear Fluid, with Special Reference to Glucose in Hyperglycaemic Conditions,' Albrecht v. Graefes Arch kiln exp Ophthal, 1977, 202:1-7.
Various, Appendix, Laboratory Medicine Practice Guidelines—Guidelines and Recommendation for Laboratory Analysis in the Diagnosis and Management of Diabetes Mellitus, (1st Edition, 2011), DB Sacks (Ed), National Academy of Clinical Biochemistry, Washington, DC (Publ), pp. 59-104.
Various, Chapters 10-13, Laboratory Medicine Practice Guidelines—Guidelines and Recommendation for Laboratory Analysis in the Diagnosis and Management of Diabetes Mellitus, (1st Edition, 2011), DB Sacks (Ed), National Academy of Clinical Biochemistry, Washington, DC (Publ), pp. 31-58.
Various, Preamble and Chapters 1-9, Laboratory Medicine Practice Guidelines—Guidelines and Recommendation for Laboratory Analysis in the Diagnosis and Management of Diabetes Mellitus, (1st Edition, 2011), DB Sacks (Ed), National Academy of Clinical Biochemistry, Washington, DC (Publ), pp. i-30.
Vashist SK et al., 'Technology Behind Commercial Devices for Blood Glucose Monitoring in Diabetes Management: A Review,' Anal Chimica Acta, Oct. 10, 2011, 703(2):124-36.
Vashist SK, 'Non-invasive Glucose Monitoring Technology in Diabetes Management: A Review,' Anal Chimica Acta, Oct. 31, 2012, 750:16-27.
Wagner J et al., 'Invasiveness as a Barrier to Self-Monitoring of Blood Glucose in Diabetes,' Diabetes Technol Ther, 2005, 7(4):612-9.
Wang F, 'Binary Phase Masking for Optical Interrogation of Matters in Turbid Media,' Opt Letters, Nov. 15, 2008, 33(22):2587-89.
Ward KJ et al., 'Post-Prandial Blood Glucose Determination by Quantitative Mid-Infrared Spectroscopy,' Applied Spectrosc, 1992, 46(6):959-65.
Waynant RW and Chenault VM, 'Overview of Non-Invasive Fluid Glucose Measurement Using Optical Techniques to Maintain Glucose Control in Diabetes Mellitus,' LEOS Newsletter, Apr. 1998, 12(2):1-6.
Whitehurst T et al., 'Four Month Data From a Clinical Study of an Implantable Fluorescence-Based Glucose Sensor,' 2013, AP-WS 2013, Senseonics, Inc. (Publ) (Poster).
Wilson C and van der Kooij F, 'NovioSense Will Improve the Glucose Management of Diabetes Patients by Removing the Painful Fingerpricks and thus to Significantly Improve the Quality of Life of People Living with Diabetes,' NovioSense Tear Glucose Sensor Brochure, 2004, Deloitte (Publ) pp. 1-4 (Brochure).
Yamaguchi M et al., 'Evaluation of Time-Course Changes of Gingival Crevicular Fluid Glucose Levels in Diabetes,' Biomed Microdevices, 2005, 7(1):53-8.
Yamaguchi M et al., 'Noninvasively Measuring Blood Glucose Using Saliva,' IEEE Eng Med Bio Mag, May/Jun. 1998, 17(3):59-63.
Yoffee L, 'Micromem Developing Magnetic, Non-invasive Glucose Sensor,' Medical Device Daily, Jan. 26, 2009, 13(15):1-2.
Zanon M et al., Non-Invasive Continuous Glucose Monitoring with Multi-Sensor Systems: A Monte Carlo-Based Methodology for Assessing Calibration Robustness, Sensors, Jun. 3, 2013, 13(6):7279-95.

(56) References Cited

OTHER PUBLICATIONS

Zhang J et al., 'Noninvasive Diagnostic Devices for Diabetes through Measuring Tear Glucose,' J Diabetes Sci Tech, Jan. 2011, 5(1):166-72.
Zhang W et al., 'Noninvasive Glucose Monitoring Using Saliva Nano-biosensor,' Sensing and Bio Sensing Res, 2015, 4:23-9.
Zhao F-Q and Keating AF, 'Functional Properties and Genomics of Glucose Transporters,' Curr Genomics, 2007, 8(2):113-28.
Zhao Z and Myllyla R, 'Photoacoustic Blood Glucose and Tissue Measurements Based on Optical Scattering Effect,' Proc SPIE 4707 Saratov Fall Meeting 2001: Optical Technologies in Biophysics and Medicine III, Jul. 16, 2002, 4707(153):1-4, <http://dx.doi.org/10.1117/12.465582>.
Zhao, Z, 'Pulsed Photoacoustic Techniques and Glucose Determination in Human Blood and Tissue,' University of Oulu, 2002, pp. 1-111 (Thesis).
Abbink R and Gardner Cgal, 'Getting Under the Skin,' SPIE's OE Magazine, Sep. 31, 2003, 1:18-20.
Adamatzky A, 'Collision-Based Computing in Belousov-Zhabotinsky Medium,' Chaos Solitons Fractals, Sep. 2004, 21(5):1259-64.
Alexeeva NV and Arnold MA, 'Impact of Tissue Heterogeneity on Noninvasive Near-Infrared Glucose Measurements in Interstitial Fluid of Rat Skin,' J Diabetes Sci Technol, Sep. 1, 2010, 4(5):1041-54.
Alexeeva NV and Arnold MA, 'Near-Infrared Microspectroscopic Analysis of Rat Skin Tissue Heterogeneity in Relation to Noninvasive Glucose Sensing,' J Diabetes Sci Technol, Mar. 2009, 3(2):219-32.
Alexeeva NV, 'Characterization of Skin Tissue Heterogeneity with Near-Infrared Microspectroscopy and its Effects on Noninvasive Measurement of Glucose,' Dissertation #2668, Dec. 2011, University of Iowa, Iowa Research Online, Iowa City, Iowa (Publ), pp. 1-313 (Thesis).
Amaral CF et al., 'Multiparameter Techniques for Non-Invasive Measurement of Blood Glucose,' Sens Actuat B: Chem, Jun. 18, 2009, Apr. 24, 2009 (ePub), 140(1):12-6.
Amerov AK et al., 'Kromoscopic Analysis in Two and Three Component Aqueous Solutions of Blood Constituents,' Proc SPIE, 2001, 4263:1-10.
Amerov AK et al., 'Molar Absorptivities of Glucose and Other Biological Molecules in Aqueous Solutions over the First Overtone and Combination Regions of the Near-Infrared Spectrum,' Appl Spectrosc, Oct. 1, 2004, 58(10):1195-1204.
Anas MN et al., 'Non-Invasive Blood Glucose Measurement—Measurement of Bioelectrical Signal,' 2012 IEEE EMBS International Conference on Biomedical Engineering and Sciences, Dec. 17-19, 2012, Langkawi, Malaysia 1:503-7.
Anonymous, 'GlucoLight Develops Automated Glucose Monitor Using MathWorks™ Tools,' Jun. 2008, The MathWorks, Inc., Natick, MA (Publ) (2 pages).
Anonymous, 'Glucolight Ensures Reliable Software for Medical Trials Using PolySpace™ Products for C/C++,' Aug. 2007, The MathWorks, Inc., Natick, MA (Publ) (2 pages).
Anonymous, 'Grove Instruments Inc. Granted Ninth U.S. And International Patent on Core Technology,' May 8, 2012, Grove Instruments, Worcester, Massachusetts (Publ), (2 pages) (Press Release).
Arnold MA and Small GW, 'Noninvasive Glucose Sensing,' Anal Chem, Sep. 1, 2005, 77(17):5429-39.
Arora R et al., 'Analytical Capabilities of Coherent Anti-Stokes Raman Scattering Microspectroscopy,' J Mod Opt, Nov. 1, 2008, 55(19-20):3237-54.
Aziz Nam et al., 'An Assessment Study of Absorption Effect: LED vs Tungsten Halogen Lamp for Noninvasive Glucose Detection,' J Innov Opt Health Sci, Nov. 19, 2014, 8(2):1550013 (5 pages).
Bai C, 'Noninvasive Near Infrared Spectroscopy on Living Tissue with Multivariate Calibration Approaches,' Dissertation #776, Dec. 2010, University of Iowa, Iowa Research Online, Iowa City, Iowa (Publ), pp. 1-208 (Thesis).

Barman I et al., 'Effect of Photobleaching on Calibration Model Development in Biological Raman Spectroscopy,' J Biomed Opt, Jan.-Feb. 2011, 16(1):011004.
Bechtel KL et al., 'Intrinsic Raman Spectroscopy for Quantitative Biological Spectroscopy Part II: Experimental Applications,' Opt Express, Aug. 18, 2008, 16(17):12737-45.
Bhandare P et al., 'Multivariate Determination of Glucose in Whole Blood Using Partial Least-Squares and Artificial Neural Networks Based on Mid-Infrared Spectroscopy,' Appl Spectrosc, Feb. 28, 1993, 47(8):1214-21.
Blank TB et al., 'The Use of Near-Infrared Diffuse Reflectance for the Non-Invasive Prediction of Blood Glucose Levels,' IEEE Laser Electro-Optics Soc Newslett, Oct. 1990, 13(5):9-12.
Brown CD, 'Noble Complexity in In-Vivo Spectroscopy,' 2002, InLight Solutions, Albuquerque, New Mexico (Publ) (37 pages) (Powerpoint Presentation).
Burmeister JJ and Arnold MA, 'Evaluation of Measurement Sites for Noninvasive Blood Glucose Sensing with Near-Infrared Transmission Spectroscopy,' Clin Chem, Sep. 1999, 45(9):1621-7.
Caduff A et al., 'Cutaneous Blood Perfusion as a Perturbing Factor for Noninvasive Glucose Monitoring,' Diabetes Technol Ther, Jan. 2010, 12(1):1-9.
Caduff A et al., 'First Human Experiments with a Novel Non-Invasive, Non-Optical Continuous Glucose Monitoring System,' Biosense Bioelectron, Nov. 30, 2003, 19(3):209-17.
Cameron BD and Li Y, 'Polarization-Based Diffuse Reflectance Imaging for Noninvasive Measurement of Glucose,' J Diabetes Sci Technol, Nov. 2007, 1(6):873-8.
Chen CS et al., 'Noninvasive Blood Glucose Monitoring Using the Optical Signal of Pulsatile Microcirculation: A Pilot Study in Subjects with Diabetes,' J Diabetes Complications, Nov.-Dec. 2008, Apr. 16, 2008 (ePub), 22(6):371-6.
Chen J et al., 'Comparison of Combination and First Overtone Spectral Regions for Near-Infrared Calibration Models for Glucose and Other Biomolecules in Aqueous Solutions,' Anal Chem, Sep. 15, 2004, 76(18):5405-13.
Chung H et al., 'Simultaneous Measurements of Glucose, Glutamine, Ammonia, Lactate, and Glutamate in Aqueous Solutions by Near-Infrared Spectroscopy,' Appl Spectrosc, Feb. 1, 1996, 50(2):270-6.
Cooley DW, 'Data Acquisition Unit for Low-Noise, Continuous Glucose Monitoring,' PhD Dissertation #2844, May 2012, University of Iowa, Iowa Research Online, Iowa City, Iowa (Publ), pp. 1-214 (Thesis).
Dauxois T and Peyrard M, 'Physics of Solitons,' 1st Ed, Mar. 9, 2006, Cambridge University Press (Publ), ISBN: 9780521143608.
do Amaral CEF and Wolf B, 'Current Development in Non-Invasive Glucose Monitoring,' Med Eng Phys, Jun. 2008, 30(5):541-9.
Dou XM et al., 'Biological Applications of Anti-Stokes Raman Spectroscopy: Quantitative Analysis of Glucose in Plasma and Serum by a Highly Sensitive Multichannel Raman Spectrometer,' Appl Spectrosc, Jun. 2, 1996, 50(10):1301-6.
Downes A and Elfick A, 'Raman Spectroscopy and Related Techniques in Biomedicine,' Sensors (Basel), 2010, 10(3):1871-89.
Ediger MN et al., 'Noninvasive Optical Screening for Diabetes,' J Diabetes Sci Technol, Jul. 2009, 3(4):776-80.
Esenaliev RO et al., 'Noninvasive Monitoring of Glucose Concentration with Optical Coherence Tomography,' Opt Lett, Jul. 1, 2001, 26(13):992-4.
Fard ST et al., 'Optical Glucose Monitoring Using Vertical Cavity Surface Emitting Lasers (VCSELs),' Proc SPIE, 2009, 7397(739704):1-11.
Fleming CM et al., 'Spectroscopy in Heterogenous Media,' 2002, InLight Solutions, Albuquerque, New Mexico (Publ) (36 pages) (Powerpoint Presentation).
Gal A et al., '6 Months Analysis of Intra and Inter-Daily Performances of a Truly Non-Invasive Glucose Monitoring Device for Home Use,' American Diabetes Association (ADA) 74th Scientific Sessions®, Jun. 13-17, 2014, San Francisco, California, USA, Integrity Applications, Ashkelon, Israel (Publ), (1 page) (Poster).

(56) References Cited

OTHER PUBLICATIONS

Gal A et al., 'A Novel Non-Invasive Glucose Monitor for Home Use: Assessing the Learning Curve of Use,' 14th Annual Diabetes Technology Meeting (DTM), Nov. 6-8, 2014, Bethesda, Maryland, USA, Integrity Applications, Ashkelon, Israel (Publ), (1 page) (Poster).

Gal A et al., 'Approaching a Truly Non-Invasive Glucose Monitor-Calibration Validity,' Poster #: A46, 12th Annual Diabetes Technology Meeting (DTM), Nov. 8-10, 2012, Bethesda, Maryland, USA, Integrity Applications, Ashkelon, Israel (Publ), (1 page) (Poster).

Gal A et al., 'Enabling Frequent Blood Glucose Monitoring at Home Using a Truly Non-Invasive Device,' 14th Annual Diabetes Technology Meeting (DTM), Nov. 6-8, 2014, Bethesda, Maryland, USA, Integrity Applications, Ashkelon, Israel (Publ), (1 page) (Poster).

Gal A et al., 'GlucoTrack®—a Truly Non-Invasive SMBG Device for Home Use,' Poster #935, The European Association for the Study of Diabetes (EASD) 45th Annual Meeting, Sep. 29-Oct. 2, 2009, Vienna, Austria, Integrity Applications, Ashkelon, Israel (Publ), (1 page) (Poster).

Gal A et al., 'Presenting a Truly Non-Invasive Glucose Monitor for Home Use,' American Diabetes Association (ADA) 73rd Scientific Sessions®, Jun. 21-25, 2013, Chicago, Illinois, USA, Integrity Applications, Ashkelon, Israel (Publ), (1 page) (Poster).

Gal A et al., 'Presenting a Truly Non-Invasive Glucose Monitor for Home Use,' Poster # 1083, The European Association for the Study of Diabetes (EASD) 49th Annual Meeting, Sep. 23-27, 2013, Barcelona, Spain, Integrity Applications, Ashkelon, Israel (Publ), (1 page) (Poster).

Gal A et al., 'Progressing Towards a Truly-Non-Invasive Glucose Monitor for Home Use,' Poster #1010, The European Association for the Study of Diabetes (EASD) 47th Annual Meeting, Sep. 12-16, 2011, Lisbon, Portugal, Integrity Applications, Ashkelon, Israel (Publ), (1 page (Poster).

Gal A et al., 'Simplifying Calibration Practice for Home Use Non-Invasive Glucose Monitoring Device: Shortening Procedure Duration,' The 9th international Conference on Advanced Technologies & Treatments for Diabetes (ATTD 2016), Feb. 3-6, 2016, Milan, Italy, Integrity Applications, Ashkelon, Israel (Publ), (1 page) (Poster).

Gal A et al., 'Suitability of GlucoTrack®, a Non-Invasive Glucose Monitor, for Variety of Diabetic Populations,' 14th Annual Diabetes Technology Meeting (DTM), Oct. 31-Nov. 2, 2013, San Francisco, California, USA, Integrity Applications, Ashkelon, Israel (Publ), (1 page) (Poster).

Gal A et al., 'Validity of GlucoTrack®, a Non-Invasive Glucose Monitor, for a Variety of Diabetics,' American Diabetes Association (ADA) 71st Scientific Sessions Meeting, Jun. 24-28, 2011, San Diego, California, USA, Integrity Applications, Ashkelon, Israel (Publ), (1 page) (Poster).

Ghosn MG et al., 'Depth-Resolved Monitoring of Glucose Diffusion in Tissues by Using Optical Coherence Tomography,' Opt Lett, Aug. 1, 2006, 31(15):2314-6.

Goodarzi M et al., 'Multivariate Calibration of NIR Spectroscopic Sensors for Continuous Glucose Monitoring,' Trends Anal Chem, Apr. 2015, 67:147-58.

Gutman SI, 'Premarket Approval Application (PMA) Supplement Gluco Watch G2 Biographer Approval Notification,' PMA Application No. P99026/S008, Aug. 26, 2002, U.S. Department of Health & Human Services, Food and Drug Administration, Rockville, Maryland (Publ) (7 pages).

Hazen KH, 'Glucose Determination in Biological Matrices Using Near-Infrared Spectroscopy,' PhD Dissertation #unknown, Aug. 1995, University of Iowa, Iowa City, Iowa (Publ), pp. 1-350 (Thesis).

Heise HM et al., 'Noninvasive Blood Glucose Sensors Based on Near-Infrared Spectroscopy,' Artif Organs, Jun. 1994, 18(6):439-47.

Heise HM et al., 'Recent Advances in Mid- and Near-Infrared Spectroscopy with Applications for Research and Teaching, Focusing on Petrochemistry and Biotechnology Relevant Products,' Eur J Phys, Nov. 2013, 34(6):S139-59.

ISA, International Search Report (Form ISA/210) for International Application No. PCT/U52015/052999 mailed Feb. 26, 2016, (9 pages).

ISA, Partial International Search (Form ISA/206) for International Application No. PCT/US2015/052999, mailed Dec. 8, 2015, (8 pages).

ISA, Written Opinion (Form ISA/237) for International Application No. PCT/US2015/052999 mailed Feb. 26, 2016, (14 pages).

Jensen PS et al., 'Influence of Temperature on Water and Aqueous Glucose Absorption Spectra in the Near- and Mid-Infrared Regions at Physiologically Relevant Temperatures,' Appl Spectrosc, Jan. 2003, 57(1):28-36.

Jiao S and Wang LV, 'Two-Dimensional Depth-Resolved Mueller Matrix of Biological Tissue Measured with Double-Beam Polarization-Sensitive Optical Coherence Tomography,' Opt Lett, Jan. 15, 2002, 27(2):101-3.

Keren S et al., 'Noninvasive Molecular Imaging of Small Living Subjects Using Raman Spectroscopy,' Proc Natl Acad Sci USA, Apr. 15, 2008, 105(15):5844-9.

Kohl M et al., 'Influence of Glucose Concentration on Light Scattering in Tissue-Simulating Phantoms,' Opt Lett, Dec. 15, 1994, 19(24):2170-2.

Kohl M et al., 'The Influence of Glucose Concentration Upon the Transport of Light in Tissue-Simulating Phantoms,' Phys Med Biol, Jul. 1995, 40(7):1267-87.

Koo T-W, 'Measurement of Glucose in Human Blood Serum Using Near-Infrared Raman Spectroscopy,' 1998 Master's Thesis #47446, Apr. 27, 1998, Massachusetts Institute of Technology Department of Mechanical Engineering, Cambridge, Massachusetts (Publ), <http://hdl.handle.net/1721.1/47446>, pp. 1-81.

Kottmann J et al., 'Glucose Sensing in Human Epidermis Using Mid-Infrared Photoacoustic Detection,' Biomed Opt Express, Apr. 1, 2012, 3(4):667-80.

Kramer KE, 'Improving the Robustness of Multivariate Calibration Models for the Determination of Glucose by Near-Infrared spectroscopy,' Dissertation #99, Dec. 2005, University of Iowa, Iowa Research Online, Iowa City, Iowa (Publ), pp. 1-304 (Thesis).

Kudo H et al., 'Soft Contact-Lens Biosensor for Real-Time Tear Sugar Monitoring at the Eye,' 2012 IEEE International Conference on Systems, Man, and Cybernetics, Oct. 14-17, 2012, Seoul, Korea, IEEE Publications, New York, New York (Publ) 1:2048-51.

Kulkarni OC et al., 'A Feasibility Study on Noninvasive Blood Glucose Measurement Using Photoacoustic Method,' 2010 4th International Conference on Bioinformatics and Biomedical Engineering (iCBBE), Jun. 18-20, 2010, Chengdu, China, IEEE Publications, New York, New York (Publ) (4 pages).

Kuranov RV et al., 'Prediction Capability of Optical Coherence Tomography for Blood Glucose Concentration Monitoring,' J Diabetes Sci Technol, Jul. 2007, 1(4):470-7.

Lambrecht A et al., 'Continuous Glucose Monitoring by Means of Fiber-Based Mid-Infrared Laser Spectroscopy,' Appl Spectrosc, May 1, 2006, 60(7):729-36.

Larin KV et al., 'Noninvasive Blood Glucose Monitoring with Optical Coherence Tomography: A Pilot Study in Human Subjects,' Diabetes Care, Dec. 2002, 25(12):2263-7.

Larin KV et al., 'Specificity of Noninvasive Blood Glucose Sensing Using Optical Coherence Tomography Technique: A Pilot Study,' Phys Med Biol, May 21, 2003, 48(10):1371-90.

Lepore M et al., 'Determination of Glucose Content by Means of Visible Micro-Raman Spectroscopy and Interval Partial Least Square Multivariate Analysis,' 2011 International Workshop of BioPhotonics, Jun. 8-10, 2011, Parma, Italy, IEEE Publications, New York, New York (Publ) (3 pages).

Li Q-B et al., 'A Non-Linear Model for Calibration of Blood Glucose Non-Invasive Measurement Using Near Infrared Spectroscopy,' Infrared Phys Techn, Sep. 2010, 53(5):410-7.

Liao Y-T et al., 'A 3-?W CMOS Glucose Sensor for Wireless Contact-Lens Tear Glucose Monitoring,' IEEE J Solid-St Circ, Jan. 2012, 47(1):335-44.

Liu L, 'Identification of a Selective Glucose Spectral Signature for Noninvasive Near Infrared Measurements with Multivariate Calibration Approaches,' PhD Dissertation #unknown, May 2006, University of Iowa, Iowa City, Iowa (Publ), pp. 1-262 (Thesis).

(56) References Cited

OTHER PUBLICATIONS

MacKenzie HA et al., 'Advances in Photoacoustic Noninvasive Glucose Testing,' Clin Chem Sep. 1999, 45(9):1587-95.
Malik BH and Cote GL, 'Real-Time, Closed-Loop Dual-Wavelength Optical Polarimetry for Glucose Monitoring,' J Biomed Opt, Jan.-Feb. 2010, 15(1):017002.
Marbach R et al., 'Noninvasive Blood Glucose Assay by Near-Infrared Diffuse Reflectance Spectroscopy of the Human Inner Lip,' Appl Spectrosc, Jul. 1, 1993, 47(7):875-81.
Marquardt LA and Arnold MA, 'Near-Infrared Spectroscopic Measurement in Glucose in a Protein Matrix,' Anal Chem, Nov. 1993, 65(2):3271-8.
Maruo K et al., 'In vivo noninvasive Measurement of Blood Glucose by Near-Infrared Diffuse-Reflectance Spectroscopy,' Appl Spectrosc, Jun. 3, 2003, 57(10):1236-44.
Maruo K et al., 'Noninvasive Blood Glucose Assay Using a Newly Developed Near-Infrared System,' IEEE J Sel Top Quantum Electron, Mar.-Apr. 2003, 9(2):322-30.
Mattu MJ and Small GW, 'Determination of Glucose in a Biological Matrix by Multivariate Analysis of Multiple Band-Pass-Filtered Fourier Transform Near-Infrared Interferograms,' Anal Chem, Nov. 15, 1997, 69(22):4695-702.
Mayzel Y et al., 'Evaluation of Performance and Efficacy of GlucoTrack®, a Truly Non-Invasive Glucose Monitor for Home-Use,' Poster # 1011, The European Association for the Study of Diabetes (EASD) 47th Annual Meeting, Sep. 12-16, 2011, Lisbon, Portugal, Integrity Applications, Ashkelon, Israel (Publ), (1 page) (Poster).
Mueller M et al., 'Data Processing for Noninvasive Continuous Glucose Monitoring with a Multisensor Device,' J Diabetes Sci Technol, May 1, 2011, 5(3):694-702.
Murthy SS et al., 'Noninvasive Transcutaneous Sampling of Glucose by Electroporation,' J Diabetes Sci Technol, Mar. 2008, 2(2):250-4.
O Lyandres et al., 'Chapter 10: Surface-Enhanced Raman Sensors for Metabolic Analytes,' Biomedical Vibrational Spectroscopy, (1st Ed, 2008), P Lasch and J Kneipp (Eds), John Wiley & Sons, Hoboken, NJ (Pub) 1:221-41 ISBN: 978-470-22945.3.
Oh J et al., 'The High Quality Spectral Fingerprint of Glucose Captured by Raman Spectroscopy in Noninvasive Glucose Measurement,' SPIE 7906, Optical Diagnostics and Sensing XI: Toward Point-of-Care Diagnostics; and Design and Performance Validation of Phantoms Used in Conjunction with Optical Measurement of Tissue III, Identifier: 79060G, Feb. 10, 2011, San Francisco, California (8 pages).
Olesberg JT et al., 'In vivo Near-Infrared Spectroscopy of Rat Skin Tissue with Varying Blood Glucose Levels,' Anal Chem, Jan. 1, 2006, 78(1):215-23.
Olesberg JT et al., 'Tunable Laser Diode System for Noninvasive Blood Glucose Measurements,' Appl Spectrosc, Dec. 1, 2005, 59(12):1480-4.
Olesberg JT, 'Applications of Long-Wavelength Sources and Detectors for Medical Monitoring,' P Electrochem Soc. State of the Art Program on Compound Semiconductors (SOTAPOCS), May 12, 2013, Electrochemical Society, Pennington, New Jersey (Publ), pp. 210-217.
Oliver NS et al., 'Glucose Sensors: A Review of Current and Emerging Technology,' Diabet Med, Mar. 2009, 26(3):197-210.
Pan S et al., 'Near-Infrared Spectroscopic Measurement of Physiological Glucose Levels in Variable Matrices of Protein and Triglycerides,' Anal Chem, Apr. 1, 1996, 68(7):1124-35.
Park E-J et al., 'Feasibility of a Closed-Loop Controlled Noninvasive Ultrasonic Glucose Sensing and Insulin Delivery System,' 2009 IEEE International Ultrasonics Symposium Proceedings, Sep. 20-23, 2009, Rome, Italy, IEEE Publications, New York, New York (Publ) 1:1749-52.
Park E-J et al., 'Noninvasive Ultrasonic Glucose Sensing with Large Pigs (~200 Pounds) Using a Lightweight Cymbal Transducer Array and Biosensors,' J Diabetes Sci Technol, May 2009, 3(3):517-23.
Pleitez M et al., 'Infrared Spectroscopic Analysis of Human Interstitial fluid in vitro and in vivo Using FT-IR Spectroscopy and Pulsed Quantum Cascade Lasers (QCL),' Poster #P 46, FTIR Spectroscopy in Microbiological and Medical Diagnostics Conference, Oct. 20-21, 2011, Berlin, Germany (Poster).
Purvinis G et al., 'Noninvasive Polarimetric-Based Glucose Monitoring: An in vivo Study,' J Diabetes Sci Technol, Mar. 1, 2011, 5(2):380-7.
Qian J, 'Glucose Monitoring in Various Matrices with Near-Infrared Spectroscopy and Chemometrics,' PhD Dissertation #4901, Aug. 2013, University of Iowa, Iowa Research Online, Iowa City, Iowa (Publ), pp. 1-195 (Thesis).
Ren M and Arnold MA, 'Comparison of Multivariate Calibration Models for Glucose, Urea, and Lactate from Near-Infrared and Raman Spectra,' Anal Bioanal Chem, Jan. 3, 2007 (ePub), 387(3):879-88.
Roth HW, 'Conjunctiva,' Contact Lens Complications, Thieme Publishing Group (Publisher), New York, NY, (2003), pp. 35-57 ISBN 3 131 27791.2.
Saptari V and Youcef-Toumi K, 'Design of a Mechanical-Tunable Filter Spectrometer for Noninvasive Glucose Measurement,' Appl Optics, May 1, 2004, 43(13):2680-8.
Saptari VA, 'A Spectroscopic System for Near Infrared Glucose Measurement,' 2004 PhD Thesis #34131, Jan. 1, 2006, Massachusetts Institute of Technology Department of Mechanical Engineering, Cambridge, Massachusetts (Publ), <http://hdl.handle.net/1721.1/34131>, pp. 1-161 (Thesis).
Saptari VA, 'Analysis, Design and Use of a Fourier-Transform Spectrometer for Near Infrared Glucose Absorption Measurement,' 1999 Master's Thesis #9348, Dec. 14, 1999, Massachusetts Institute of Technology, Cambridge, Massachusetts (Publ), <http://hdl.handle.net/1721.1/9348>, pp. 1-76 (Thesis).
Schlager KJ, 'Quarterly Progress Report No. 1: Transcutaneous Analyte Measuring Methods (TAMM Phase II),' Sep.-Nov. 1991, Biotronics Technologies, Inc., Waukesha, Wisconsin (Ed), Naval Medical Research and Development Command, Bethesda, Maryland (Publ), 1:1-28.
Shih W-C et al., 'Constrained Regularization: Hybrid Method for Multivariate Calibration,' Anal Chem, Jan. 1, 2007, 79(1):234-9.
Shih W-C, 'Non-Invasive Glucose Sensing with Raman Spectroscopy,' 2007 PhD Thesis #40362, Feb. 27, 2008, Massachusetts Institute of Technology Department of Mechanical Engineering, Cambridge, Massachusetts (Publ), <http://hdl.handle.net/1721.1/40362>, pp. 1-43 (Thesis).
Sodickson LA and Block MJ, 'Kromoscopic Analysis: A Possible Alternative to Spectroscopic Analysis for Noninvasive Measurement of Analytes in vivo,' Clin Chem, Sep. 1994, 40(9):1838-44.
Solanki J et al., 'Polarization Sensitive Optical Low-Coherence Reflectometry for Blood Glucose Monitoring in Human Subjects,' Rev Sci Imstrum, Jul. 2013, 84(7):073114.
Tamada JA et al., 'Noninvasive Glucose Monitoring: Comprehensive Clinical Results. Cygnus Research Team,' JAMA, Nov. 17, 1999, 282(19):1839-44.
Tu Q and Chang C, 'Diagnostic Applications of Raman Spectroscopy,' Nanomedicine, Jul. 2012, Oct. 22, 2011 (ePub), 8(5):545-58.
Tura A et al., 'A Low Frequency Electromagnetic Sensor for Indirect Measurement of Glucose Concentration: in vitro Experiments in Different Conductive Solutions,' Sensors (Basel), May 28, 2010 (ePub), 10(6):5346-58.
Tura A et al., 'Non-Invasive Glucose Monitoring: Assessment of Technologies and Devices According to Quantitative Criteria,' Diabetes Res Clin Pract, Jul. 2007 Dec. 1, 2006 (ePub), 77(1):16-40.
Vashist SK, 'Continuous Glucose Monitoring Systems: A Review,' Diagnostics, Dec. 2013, Oct. 21, 2013 (ePub), 3(4):385-412.
Vonach R et al., 'Application of Mid-Infrared Transmission Spectrometry to the Direct Determination of Glucose in Whole Blood,' Appl Spectrosc, Jun. 1, 1998, 52(6):820-2.
Vonach R et al., 'Application of Mid-Infrared Transmission Spectrometry to the Direct Determination of Glucose in Whole Blood,' Appl Spectrosc, Feb. 13, 1998, 52(6):820-2.
Wang X et al., 'Glucose Concentration Measured by the Hybrid Coherent Anti-Stokes Raman-Scattering Technique,' Phys Rev A, Jan. 20, 2010, 81(8):013813 (6 pages).

(56) References Cited

OTHER PUBLICATIONS

Wentholt IM et al., 'Pendra Goes Dutch: Lessons for the CE Mark in Europe,' Diabetologia, Jun. 2005 May 4, 2005 (ePub), 48(6):1055-8.
Wootten M, 'Subluminescence Diodes at 2.4 Microns from GaInAsSb/AlGaAsSb Quantum Well Heterostructures for Optical Glucose Sensing,' Master's Thesis #2427, May 2013, University of Iowa, Iowa Research Online, Iowa City, Iowa (Publ), pp. 1-33 (Thesis).
Xu K et al., 'Non-Invasive Glucose Sensing with Near-Infrared Spectroscopy Enhanced by Optical Measurement Conditions Reproduction Technique,' Optics Lasers Eng, Oct. 2005, 43(10):1096-106.
Yadav J et al., 'Prospects and Limitations of Non-Invasive Blood Glucose Monitoring Using Near-Infrared Spectroscopy,' Biomed Signal Process Control, Apr. 2015, 18:214-27.
Yamakoshi K and Yamakoshi Y, 'Pulse Glucometry: A New Approach for Noninvasive Blood Glucose Measurement Using Instantaneous Differential Near-Infrared Spectrophotometry,' J Biomed Opt, Sep.-Oct. 2006, 11(5):054028.
Yao H et al., 'A Dual Microscale Glucose Sensor on a Contact Lens, Tested in Conditions Mimicking the Eye,' MEMS 2011 Conference, Jan. 23-27, 2011, Cancun, Mexico, IEEE Publications, New York, New York (Publ) 1:25-8.
Yao H et al., 'A Soft Hydrogel Contact Lens With an Encapsulated Sensor for Tear Glucose Monitoring,' MEMS 2012 Conference, Jan. 29-Feb. 2, 2012, IEEE Publications, New York, New York (Publ) 1:769-72.
Zhang Y et al., 'Continuous Noninvasive Monitoring of Changes in Human Skin Optical Properties During Oral Intake of Different Sugars with Optical Coherence Tomography,' Biomed Opt Express, Feb. 28, 2014, 5(4):990-9.
Zhinghai H and Guangshuai Z, 'Variation of Absorption Coefficient of Glucose Water in Consideration of Water Displacement,' Adv Mater Res, 2011 (2011), 159:358-62.
Zhou Y et al., 'Noninvasive Monitoring of Glucose Concentration Using Differential Absorption Low-Coherence Interferometry Based on Rapid Scanning Optical Delay Line,' 2011 J Phys: Conf Ser, 2011, 277(012053):1-6.
Anonymous, 'Tissue Spectroscopy for Glucose Measurement,' George W. Hopkins Analytical/Medical Laboratory HP Laboratories Palo Alto (Ed), Jul. 10, 2006, Hewlett-Packard Development Company, LP (Publ), pp. 1-55 (uploaded in two parts).
Branco G, 'The Development and Evaluation of Head Probes for Optical Imaging of the Infant Head,' Thesis Submitted for the Degree of Doctor of Philosophy, Jan. 2007, J Hebden and DT Delpy (Sup), Department of Medical Physics and Bioengineering, University College of London (UCL) (Publ), pp. i-v, viii and 6-36 (Thesis) (uploaded in two parts).
Kong, C-R, 'Clinical Feasibility of Raman Spectroscopy for Quantitative Blood Glucose Measurement,' DSpace@MIT, 2011, Massachusetts Institute of Technology (Publ), pp. 1-175 <http://hdl.handle.net/1721.1/66013> (Thesis) (uploaded in three parts).
Wilson KG, 'The Renormalization Group: Critical Phenomena and the Kondo Problem,' Rev Mod Phys, Oct. 1975, 47(4):773-840 (uploaded in two parts).
Gil GA, 'Online Raman Spectroscopy for Bioprocess Monitoring,' 2005 Master's Thesis #36757, Aug. 14, 2006, Massachusetts Institute of Technology Department of Electrical Engineering and Computer Science, Cambridge, Massachusetts (Publ), <http://hdl.handle.net/1721.1/36757>, pp. 1-202( uploaded in two parts).
Arnold MA and Small GW, 'Noninvasive Glucose Sensing,' Anal Chem, Sep. 1, 2005 (Sep. 1, 2005), 77(17):5429-39.
Anonymous, The PreciSense® Solution, published as early as Mar. 14, 2008, PreciSense A/S, Denmark, (Publ), pp. 1-2 (Brochure).
Kristensen JS et al., 'Trans-Cutaneous Fluorescence Lifetime Based Continuous Glucose Reading for Long Term Interrogation,' published as early as Mar. 14, 2008, PreciSense A/S, Denmark, (Publ), pp. 1-2 (Brochure).
Yadav J et al., 'Prospects and Limitations of Non-Invasive Blood Glucose Monitoring Using Near-Infrared Spectroscopy,' Biomed Signal Process Contr, Apr. 2015 (Apr. 2015), 18:214-27.
Ricketts DS et al., 'Electrical Soliton Oscillator,' IEEE T Microw Theory, Jan. 2006 (Jan. 2006), 54(1):373-82.
U.S. Provisional Application for U.S. Appl. No. 61/047,199, in the name of Gamache RW and Pluta S, titled 'Non-Invasive Measuring and Monitoring of Physiological Characteristics Using Spectrographic Impedance,' filed on Apr. 23, 2008 (Apr. 23, 2008) (9 pages).
Filho PB, 'Tissue Characterization Using and Impedance Spectroscopy Probe,' Thesis for degree of Ph.D., Sep. 2002 (Sep. 2002), Department of Medical Physics and Engineering, University of Sheffield, Sheffield, UK (Publ), <http://www.academia.edu/6930287/Tissue_Characterisation_Using_an_Impedance_Spectroscopy-probe>, pp. 1-198 (THESIS).

\* cited by examiner

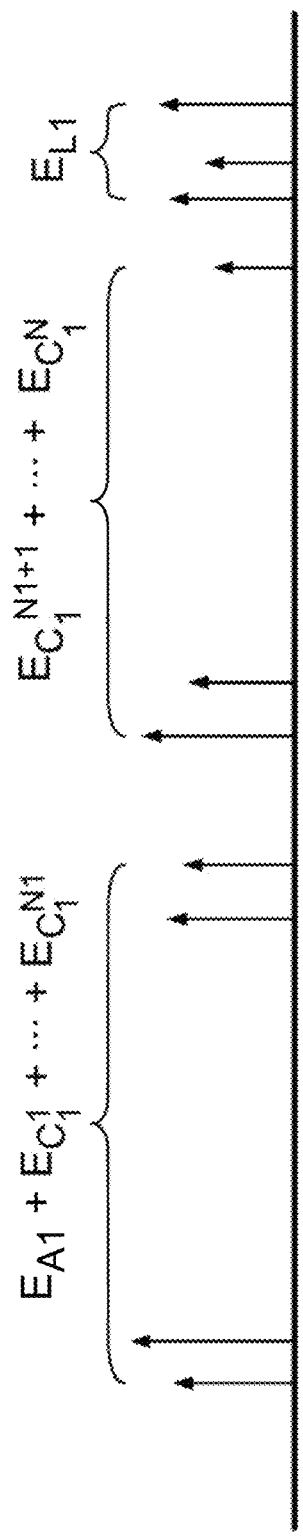

After 1st collision

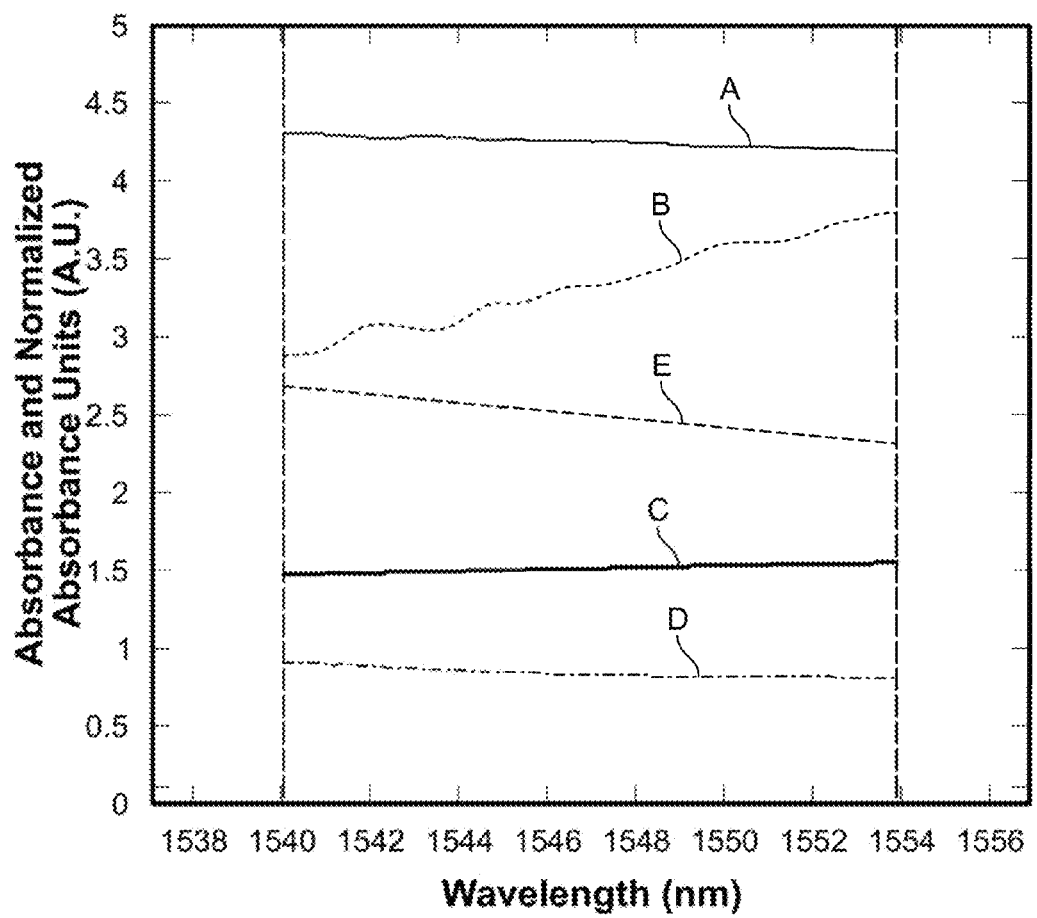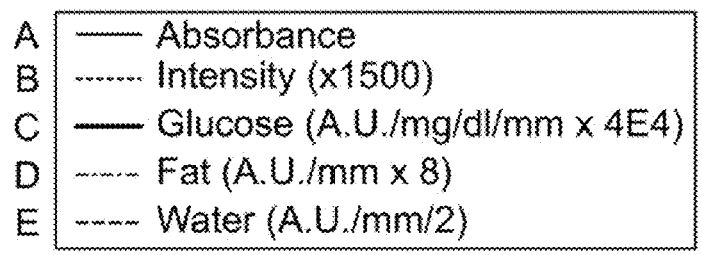
FIG. 36

| NegCon_GL | PosCon_GL | Ring 1 | Ring 2 | Ring 3 | ALL |
|---|---|---|---|---|---|
| NO-GL-1 | GL-1 | Z_kernel_E1 | Z_kernel_D1 | Z_kernel_S1 | Z_kernel_MM1 |
| NO-GL-2 | GL-2 | Z_kernel_E1 | Z_kernel_D1 | Z_kernel_S1 | Z_kernel_MM1 |
| NO-GL-3 | GL-3 | Z_kernel_E1 | Z_kernel_D1 | Z_kernel_S1 | Z_kernel_MM1 |
| NO-GL-4 | GL-4 | Z_kernel_E1 | Z_kernel_D1 | Z_kernel_S1 | Z_kernel_MM1 |
| NO-GL-5 | GL-5 | Z_kernel_E1 | Z_kernel_D1 | Z_kernel_S1 | Z_kernel_MM1 |
| NO-GL-6 | GL-6 | Z_kernel_E1 | Z_kernel_D1 | Z_kernel_S1 | Z_kernel_MM1 |
| NO-GL-1 | GL-7 | Z_kernel_E2 | Z_kernel_D2 | Z_kernel_S2 | Z_kernel_MM2 |
| NO-GL-2 | GL-8 | Z_kernel_E2 | Z_kernel_D2 | Z_kernel_S2 | Z_kernel_MM2 |
| NO-GL-3 | GL-9 | Z_kernel_E2 | Z_kernel_D2 | Z_kernel_S2 | Z_kernel_MM2 |
| NO-GL-4 | GL-10 | Z_kernel_E2 | Z_kernel_D2 | Z_kernel_S2 | Z_kernel_MM2 |
| NO-GL-5 | GL-11 | Z_kernel_E2 | Z_kernel_D2 | Z_kernel_S2 | Z_kernel_MM2 |
| NO-GL-1 | GL-12 | Z_kernel_E3 | Z_kernel_D3 | Z_kernel_S3 | Z_kernel_MM3 |
| NO-GL-2 | GL-13 | Z_kernel_E3 | Z_kernel_D3 | Z_kernel_S3 | Z_kernel_MM3 |
| NO-GL-3 | GL-14 | Z_kernel_E3 | Z_kernel_D3 | Z_kernel_S3 | Z_kernel_MM3 |
| NO-GL-4 | GL-15 | Z_kernel_E3 | Z_kernel_D3 | Z_kernel_S3 | Z_kernel_MM3 |
| NO-GL-5 | GL-16 | Z_kernel_E3 | Z_kernel_D3 | Z_kernel_S3 | Z_kernel_MM3 |
| NO-GL-6 | GL-17 | Z_kernel_E3 | Z_kernel_D3 | Z_kernel_S3 | Z_kernel_MM3 |
| NO-GL-7 | GL-18 | Z_kernel_E3 | Z_kernel_D3 | Z_kernel_S3 | Z_kernel_MM3 |
| NO-GL-8 | GL-19 | Z_kernel_E4 | Z_kernel_D4 | Z_kernel_S4 | Z_kernel_MM4 |
| NO-GL-9 | GL-20 | Z_kernel_E4 | Z_kernel_D4 | Z_kernel_S4 | Z_kernel_MM4 |
| NO-GL-10 | GL-21 | Z_kernel_E4 | Z_kernel_D4 | Z_kernel_S4 | Z_kernel_MM4 |
| NO-GL-11 | GL-22 | Z_kernel_E4 | Z_kernel_D4 | Z_kernel_S4 | Z_kernel_MM4 |

Z and CF have 10 components each. Bracket length in frequency domain is 4, facilitating collision of Z1~Z7

Z: Sorted by Amplitude

| Group | k | | | m | | | j | | | |
|---|---|---|---|---|---|---|---|---|---|---|
| Z: Amplitude_Order_Index | Z1 | Z2 | Z3 | Z4 | Z5 | Z6 | Z7 | Z8 | Z9 | Z10 |
| Z: Frequencies | 260 | 305 | 415 | 100 | 500 | 360 | 250 | 510 | 175 | 210 |
| Z: Amplitudes | 1000 | 930 | 700 | 100 | 65 | 8 | 6 | 2.3 | 1.1 | 0.4 |

| Epsilon limit | 0.0005 | 0.0005 | 0.0005 | 0.025 | 0.025 | 0.10 | 0.10 | 0.10 | 0.10 | 0.10 |
| Maximum variation | 0.13 | 0.1525 | 0.2075 | 2.5 | 12.5 | 36 | 25 | 51 | 17.5 | 21 |

CF: Sorted by Amplitude

| Group | k | | | m | | | j | | | |
|---|---|---|---|---|---|---|---|---|---|---|
| CF: Amplitude_Order_Index | CF1 | CF2 | CF3 | CF4 | CF5 | CF6 | CF7 | CF8 | CF9 | CF10 |
| CF: Frequencies | 259.88 | 304.98 | 415.175 | 100 | 500.1 | 340 | 260 | 505 | 180 | 230 |
| CF: Amplitudes | 210 | 180 | 126 | 22 | 12 | 1.6 | 1.1 | 0.5 | 0.2 | 0.07 |

Z: After scaling

| Group | k | | | m | | | j | | | |
|---|---|---|---|---|---|---|---|---|---|---|
| Z: Amplitude_Order_Index | Z1 | Z2 | Z3 | Z4 | Z5 | Z6 | Z7 | Z8 | Z9 | Z10 |
| Z: Frequencies | 260 | 305 | 415 | 100 | 500 | 360 | 250 | 510 | 175 | 210 |
| Z: Scaling Coefficient | 1.9 | 1.9 | 1.9 | 1.9 | 1.9 | 1.9 | 1.9 | 1.9 | 1.9 | 1.9 |
| Z: Scaled Amplitudes | 1900 | 1767 | 1330 | 190 | 123.5 | 15.2 | 11.4 | 4.37 | 2.09 | 0.76 |

FIG. 58A

Z and CF have 10 components each. Bracket length in frequency domain is 4, facilitating collision of Z1-Z7

| Computation Step Index | g1 | g2 | g3 | g4 | g5 | g6 | g7 | g8 | g9 | g10 |
|---|---|---|---|---|---|---|---|---|---|---|
| Collision of Z1 | | | | | | | | | | |
| Z: Amplitude_Order_Index | Z1 | | | | | | | | | |
| Z: Frequencies | 260 | | | | | | | | | |
| Z: Scaled Amplitudes | 1900 | | | | | | | | | |
| CF: Amplitude_Order_Index | CF1 | CF2 | CF3 | CF4 | | | | | | |
| CF: Frequencies | 259.88 | 304.98 | 415.175 | 100 | | | | | | |
| CF: Amplitudes | 210 | 180 | 126 | 22 | | | | | | |

To permit interactions, components frequencies must be within $\varepsilon_k$ times 260 (within 0.05% of 260). Thus max. permissible freq. difference = 0.13

| | g1 | g2 | g3 | g4 | g5 | g6 | g7 | g8 | g9 | g10 |
|---|---|---|---|---|---|---|---|---|---|---|
| Z: Amplitude_Order_Index | Z1 | | | Determined after sorting and truncation | | | | | | |
| Z: Pre-sort Index | | Z1_1 | Z1_2 | Z1_3 | | | | | | |
| Z: Frequencies | 260 | -- | -- | -- | | | | | | |
| Z: Amplitudes | 399000 | -- | -- | -- | | | | | | |

FIG. 58B

| Computation Step Index | g1 | g2 | g3 | g4 | g5 | g6 | g7 | g8 | g9 | g10 |
|---|---|---|---|---|---|---|---|---|---|---|
| Collision of Z5 | | | | | | | | | | |
| Z: Amplitude_Order_Index | | | | | Z5 | | | | | |
| Z: Frequencies | | | | | 500 | | | | | |
| Z: Scaled Amplitudes | | | | | 123.5 | | | | | |
| CF: Amplitude_Order_Index | | | | | CF5 | CF6 | CF7 | CF8 | | |
| CF: Frequencies | | | | | 500.1 | 340 | 260 | 505 | | |
| CF: Amplitudes | | | | | 12 | 1.6 | 1.1 | 0.5 | | |
| To permit interactions, components frequencies must be within $\varepsilon_\eta$ times 500 (within 2.5% of 500). Thus max. permissible freq. difference = 12.5 | | | | | | | | | | |
| New frequency is formed if component frequencies differ by more than $\varepsilon_\eta$ times 500 (i.e., by more than 0.05% of 500), which is 0.25 | | | | | | | | | | |
| Z: Amplitude_Order_Index | | | | | Z5 | Z5_1 | Z5_2 | Z5_3 | Determined after sorting and truncation | |
| Z: Pre-sort Index | | | | | 500 | -- | -- | 1005 | | |
| Z: Frequencies | | | | | 1482 | -- | -- | 61.75 | | |
| Z: Amplitudes | | | | | | | | | | |
| Z: Amplitude update via conditional co-product | | | | | Merge Z7 with Z5 | | | | | |
| Z: Updated amplitudes | | | | | 1494.54 | -- | -- | 61.75 | | |

FIG. 58C

| Computation Step Index | g1 | g2 | g3 | g4 | g5 | g6 | g7 | g8 | g9 | g10 |
|---|---|---|---|---|---|---|---|---|---|---|
| Collision of Z7 | | | | | | | | | | |
| Z: Amplitude_Order_Index | | | | | | | Z7 | | | |
| Z: Frequencies | | | | | | | 250 | | | |
| Z: Scaled Amplitudes | | | | | | | 11.4 | | | |
| CF: Amplitude_Order_Index | | | | | | | CF7 | CF8 | CF9 | CF10 |
| CF: Frequencies | | | | | | | 260 | 505 | 180 | 230 |
| CF: Amplitudes | | | | | | | 1.1 | 0.5 | 0.2 | 0.07 |
| To permit interactions, components frequencies must be within $\varepsilon_\eta$ times 250 (within 10% of 250). Thus max. permissible freq. difference = 25 | | | | | | | | | | |
| New frequency is formed if component frequencies differ by more than $\varepsilon_\eta$ times 250 (i.e., by more than 0.05% of 250), which is 0.125 | | | | | | | | | | |
| | | | | | | | | Determined after sorting and truncation | | |
| Z: Amplitude_Order_Index | | | | | | | Z7 | Z7_1 | Z7_2 | Z7_3 |
| Z: Pre-sort Index | | | | | | | 510 | -- | -- | 480 |
| Z: Frequencies | | | | | | | 12.54 | -- | -- | 0.798 |
| Z: Amplitudes | | | | | | | | | | |
| Z: Amplitudes update via conditional co-product | | | | | | | Merge with Z'5 | | | |
| Z': Updated amplitudes | | | | | | | -- | -- | -- | 0.798 |

FIG. 58D

Illustration of the Shift Operator 5

Z: Scaled and Sorted by Amplitude Group
Z: Amplitude_Order_Index
Z: Frequencies
Z: Scaled Amplitudes

| | | | k | | | | m | | | | j | | |
|---|---|---|---|---|---|---|---|---|---|---|---|---|---|
| Z1 | Z2 | Z3 | Z4 | Z5 | Z6 | Z7 | Z8 | Z9 | Z10 | Z11 | Z12 | Z13 | Z14 |
| 260 | 261 | 259 | 415 | 305 | 100 | 130 | 360 | 250 | 358 | 175 | 210 | 460 | 500 |
| 1900 | 1767 | 1630 | 1330 | 1410 | 190 | 123.5 | 15.2 | 11.4 | 4.37 | 2.09 | 0.76 | 0.52 | 0.21 |

CF: Sorted by Amplitude Group
CF: Amplitude_Order_Index
CF: Frequencies
CF: Amplitudes

| | | | k | | | | m | | | | j | | |
|---|---|---|---|---|---|---|---|---|---|---|---|---|---|
| CF1 | CF2 | CF3 | CF4 | CF5 | CF6 | CF7 | CF8 | CF9 | CF10 | CF11 | CF12 | CF13 | CF14 |
| 259.85 | 260.93 | 259.5 | 415.175 | 305.1 | 100 | 133 | 340 | 275 | 338 | 180 | 230 | 415 | 338 |
| 210 | 180 | 205 | 126 | 146 | 22 | 12 | 1.6 | 1.1 | 0.5 | 0.2 | 0.07 | 0.04 | 0.01 |

Computation index   g1   g2   g3   g4   g5   g6   g7   g8   g9   g10   g11   g12   g13   g14

Example 1: Right Shift
Frequencies of Z1, Z2, and Z3 are within a specified threshold of each other. The threshold can be $\delta_2$ or a multiple thereof.
Therefore shift δ = 2
The first collision interaction is right shifted to Z3
    Collision of Z3    Z3 : {CF1, CF2, CF3, CF4}
    Collision of Z4    Z4 : {CF2, CF3, CF4, CF5}

Collision of Z7    Z7 : {CF5, CF6, CF7, CF8}

Frequencies of Z8, Z9, and Z10 are within a specified threshold of each other. The threshold can be $\delta_1$ or a multiple thereof.
The shift δ is not readjusted
    Collision of Z8    Z8 : {CF6, CF7, CF8, CF9}
    Collision of Z9    Z9 : {CF7, CF8, CF9, CF10}
    Collision of Z10    Z9 : {CF8, CF9, CF10, CF11}

FIG. 59A

Z: Scaled and Sorted by Amplitude Group
Z: Amplitude_Order_Index

| | | | | | k | | m | | | | j | | | |
|---|---|---|---|---|---|---|---|---|---|---|---|---|---|---|
| Z: Frequencies | Z1 260 | Z2 261 | Z3 259 | Z4 415 | Z5 305 | Z6 100 | Z7 130 | Z8 360 | Z9 250 | Z10 358 | Z11 175 | Z12 210 | Z13 460 | Z14 300 |
| Z: Scaled Amplitudes | 1900 | 1767 | 1630 | 1330 | 1410 | 190 | 123.5 | 15.2 | 11.4 | 4.37 | 2.09 | 0.76 | 0.52 | 0.21 |

CF: Sorted by Amplitude Group
CF: Amplitude_Order_Index

| | | k | | | | m | | | | | j | | | |
|---|---|---|---|---|---|---|---|---|---|---|---|---|---|---|
| CF: Frequencies | CF1 259.85 | CF2 260.93 | CF3 259.5 | CF4 415.175 | CF5 305.1 | CF6 100 | CF7 133 | CF8 340 | CF9 275 | CF10 338 | CF11 180 | CF12 230 | CF13 415 | CF14 338 |
| CF: Amplitudes | 210 | 180 | 205 | 126 | 146 | 22 | 12 | 1.6 | 1.1 | 0.5 | 0.2 | 0.07 | 0.04 | 0.01 |

| Computation Index | g1 | g2 | g3 | g4 | g5 | g6 | g7 | g8 | g9 | g10 | g11 | g12 | g13 | g14 |
|---|---|---|---|---|---|---|---|---|---|---|---|---|---|---|

Example 2: Center Shift
Frequencies of Z1, Z2, and Z3 are within a specified threshold of each other. The threshold can be $\delta_2$ or a multiple thereof.
Therefore shift $\delta = 2$
The first collision interaction is center shifted to Z2, because Z2 is the central component among Z1, Z2, and Z3.
After the collision of Z2, the collision of Z4 is performed
   Collision of Z2: Z2 (CF1, CF2, CF3, CF4)
   Collision of Z4: Z4 (CF2, CF3, CF4, CF5)

Center shift for an even number of close frequency components is determined as either the component to the left of the actual center, or the component to the right of the actual center

FIG. 59B

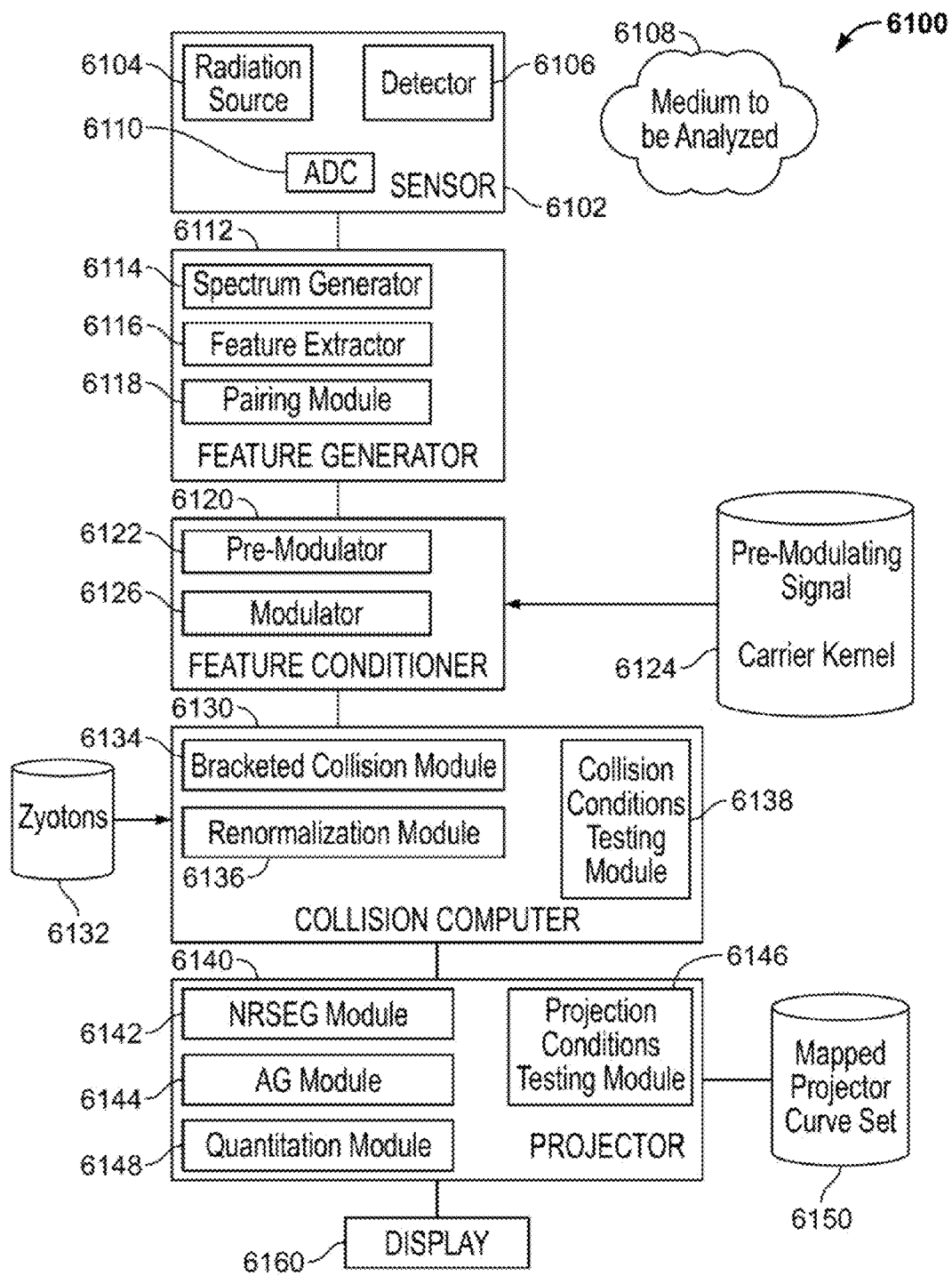
FIG. 61  Non-Invasive Measurement System

| Feature Set | | | | | | | POSCON_GL | NEGCON_GL |
|---|---|---|---|---|---|---|---|---|
| | Wavelengths, nm | | | Wavenumbers, cm⁻¹ | | | | |
| Feature ID | center | Width | Start | End | Start | End | Width | | |
| 1 | 1083.6 | 7.0 | 1080.1 | 1087.1 | 9258.4 | 9198.8 | 59.6 | | NO-GL-1 |
| 2 | 1086.6 | 7.1 | 1083.0 | 1090.1 | 9233.6 | 9173.5 | 60.1 | | NO-GL-2 |
| 3 | 1089.8 | 7.1 | 1086.2 | 1093.3 | 9206.4 | 9146.6 | 59.8 | | NO-GL-3 |
| 4 | 1093.7 | 7.1 | 1090.1 | 1097.2 | 9173.5 | 9114.1 | 59.4 | | NO-GL-4 |
| 5 | 1095.7 | 7.2 | 1092.1 | 1099.3 | 9156.7 | 9096.7 | 60.0 | | NO-GL-5 |
| 6 | 1099.6 | 7.2 | 1096.0 | 1103.2 | 9124.1 | 9064.5 | 59.5 | | NO-GL-6 |
| 7 | 1285.3 | 9.9 | 1280.3 | 1290.2 | 7810.7 | 7750.7 | 59.9 | GL-1 | |
| 8 | 1289.1 | 10.0 | 1284.1 | 1294.1 | 7787.6 | 7727.4 | 60.2 | GL-2 | |
| 9 | 1293.0 | 10.0 | 1288.0 | 1298.0 | 7764.0 | 7704.2 | 59.8 | GL-3 | |
| 10 | 1297.2 | 10.1 | 1292.1 | 1302.2 | 7739.3 | 7679.3 | 60.0 | GL-4 | |
| 11 | 1301.1 | 10.1 | 1296.0 | 1306.1 | 7716.0 | 7656.4 | 59.7 | GL-5 | |
| 12 | 1305.3 | 10.2 | 1300.2 | 1310.4 | 7691.1 | 7631.3 | 59.9 | GL-6 | |
| 13 | 1400.2 | 11.7 | 1394.3 | 1405.0 | 7172.1 | 7117.4 | 54.6 | | NO-GL-7 |
| 14 | 1403.2 | 11.8 | 1397.3 | 1409.1 | 7156.7 | 7096.7 | 59.9 | | NO-GL-8 |
| 15 | 1406.2 | 11.8 | 1400.3 | 1412.1 | 7141.3 | 7081.7 | 59.7 | | NO-GL-9 |
| 16 | 1409.3 | 11.8 | 1403.4 | 1415.2 | 7125.6 | 7066.1 | 59.4 | | NO-GL-10 |
| 17 | 1413.2 | 11.9 | 1407.2 | 1419.1 | 7106.3 | 7046.7 | 59.6 | | NO-GL-11 |
| 18 | 1547.3 | 14.3 | 1540.1 | 1554.4 | 6493.1 | 6433.4 | 59.7 | GL-7 | |
| 19 | 1550.4 | 14.3 | 1543.3 | 1557.6 | 6479.6 | 6420.1 | 59.5 | GL-8 | |
| 20 | 1554.7 | 14.5 | 1547.4 | 1561.9 | 6462.5 | 6402.5 | 60.0 | GL-9 | |
| 21 | 1557.5 | 14.5 | 1550.2 | 1564.7 | 6450.8 | 6391.0 | 59.8 | GL-10 | |
| 22 | 1562.6 | 14.6 | 1555.3 | 1569.9 | 6429.6 | 6369.8 | 59.8 | GL-11 | |
| 23 | 1638.2 | 16.1 | 1630.1 | 1646.2 | 6134.6 | 6074.6 | 60.0 | GL-12 | |
| 24 | 1641.3 | 16.1 | 1633.2 | 1649.3 | 6122.9 | 6063.2 | 59.8 | GL-13 | |
| 25 | 1646.5 | 16.2 | 1638.4 | 1654.6 | 6103.5 | 6043.8 | 59.8 | GL-14 | |
| 26 | 1652.3 | 16.3 | 1644.1 | 1660.4 | 6082.4 | 6022.6 | 59.7 | GL-15 | |
| 27 | 1658.1 | 16.5 | 1649.8 | 1666.3 | 6061.3 | 6001.3 | 60.0 | GL-16 | |
| 28 | 1663.3 | 16.5 | 1655.1 | 1671.6 | 6041.9 | 5982.3 | 59.6 | GL-17 | |
| 29 | 1668.7 | 16.6 | 1660.4 | 1677.0 | 6022.6 | 5963.0 | 59.6 | GL-18 | |
| 30 | 1673.1 | 16.7 | 1664.7 | 1681.4 | 6007.1 | 5947.4 | 59.7 | GL-19 | |
| 31 | 1676.8 | 16.8 | 1668.4 | 1685.2 | 5993.8 | 5934.0 | 59.8 | GL-20 | |
| 32 | 1678.5 | 16.9 | 1670.0 | 1686.9 | 5988.0 | 5928.0 | 60.0 | GL-21 | |
| 33 | 1682.8 | 17.0 | 1674.3 | 1691.3 | 5972.6 | 5912.6 | 60.0 | FL-22 | |
| 34 | 1689.3 | 17.1 | 1680.8 | 1697.9 | 5949.5 | 5889.6 | 59.9 | GL-23 | |

FIG. 83

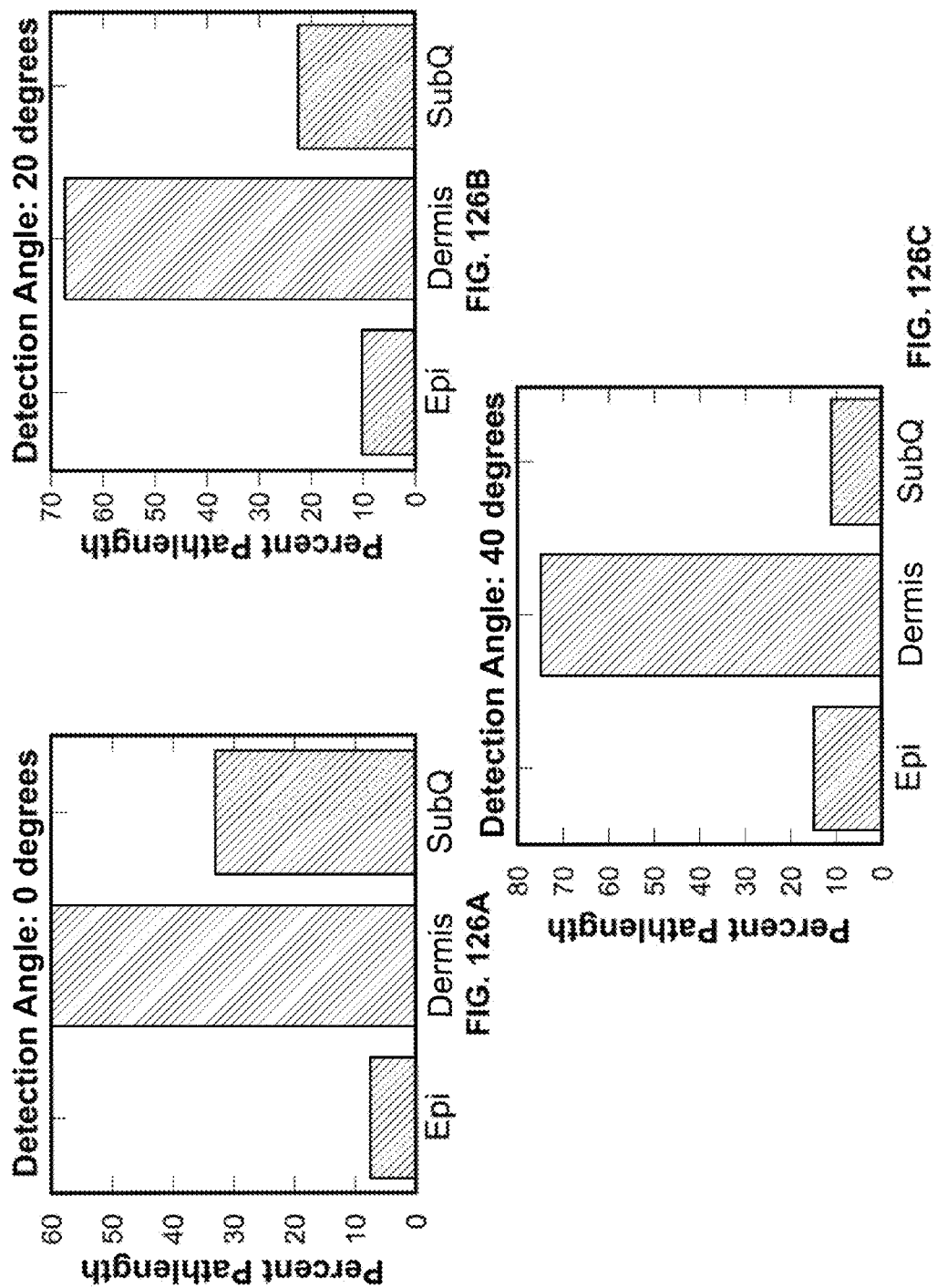

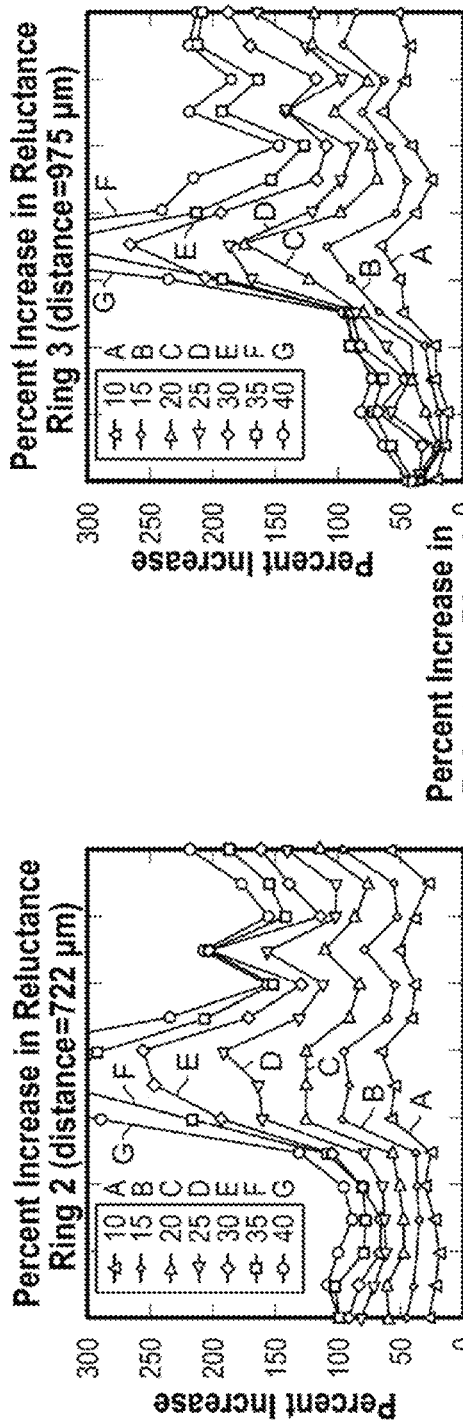
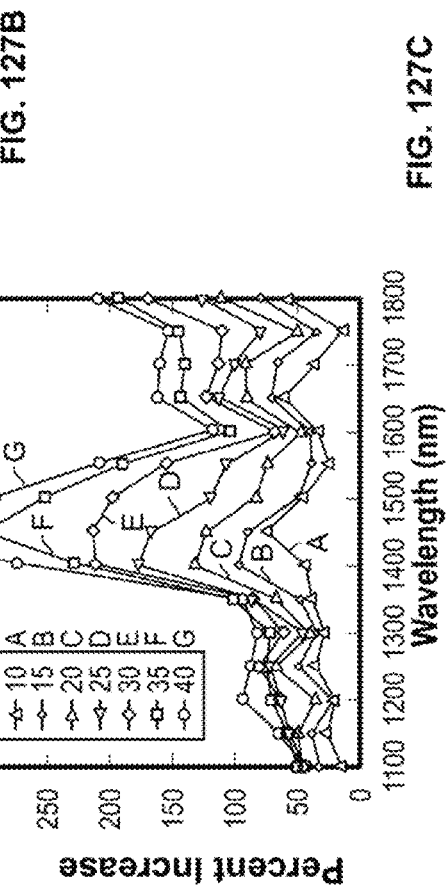
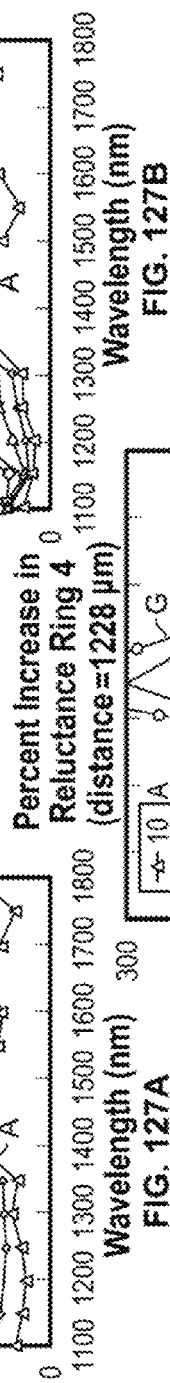
FIG. 127A
FIG. 127B
FIG. 127C

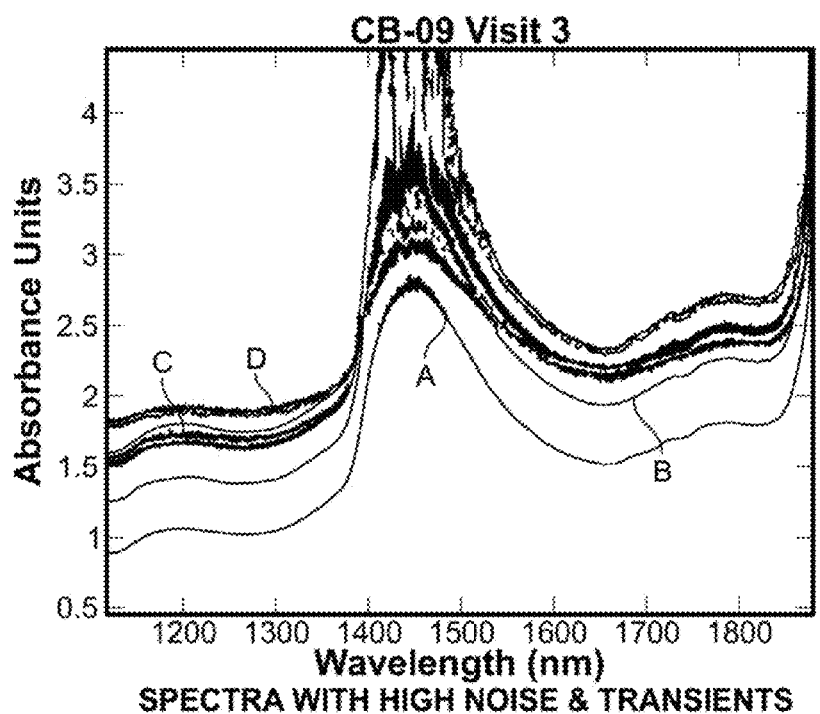
SPECTRA WITH HIGH NOISE & TRANSIENTS    FIG. 128A
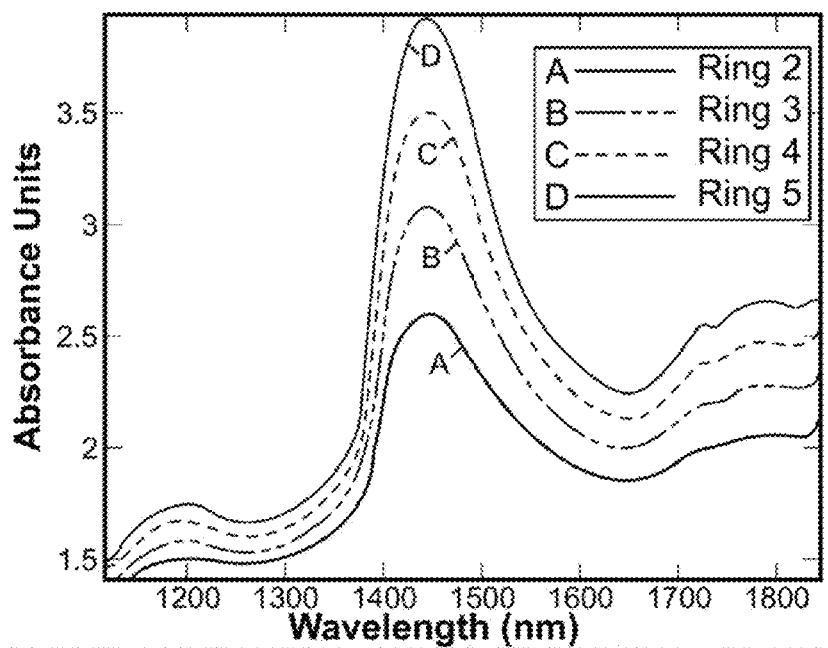
SPECTRA WITH VERY LOW NOISE & MINIMAL TRANSIENTS
FIG. 128B

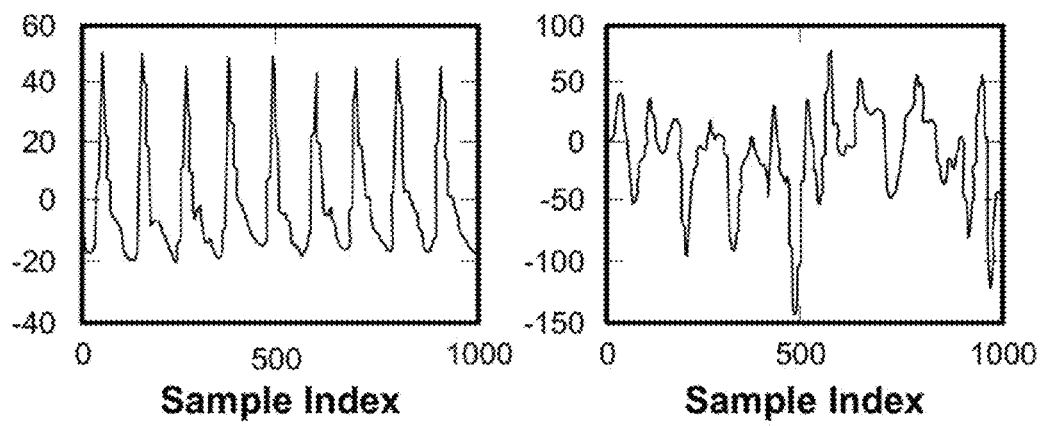
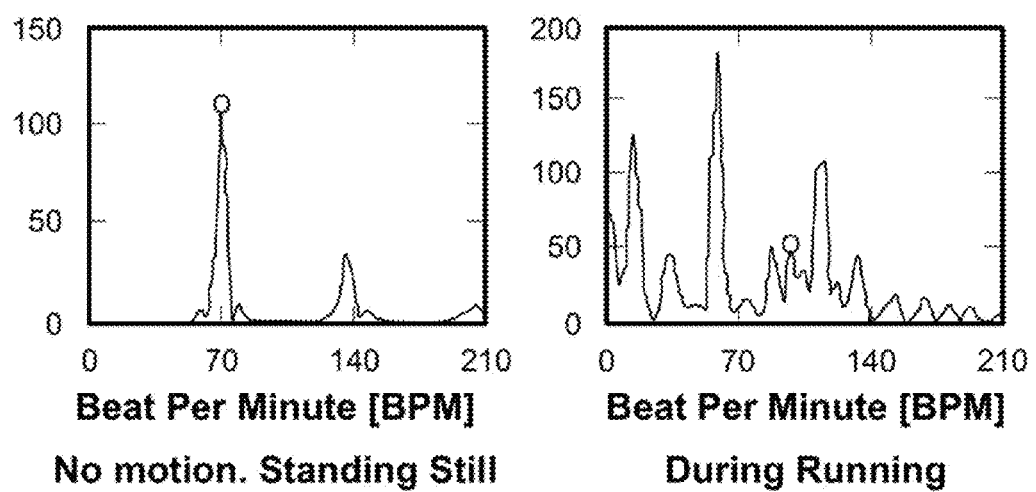
FIG. 138A
FIG. 138B and# SYSTEMS AND METHODS FOR BLOOD GLUCOSE AND OTHER ANALYTE DETECTION AND MEASUREMENT USING COLLISION COMPUTING Cross-Reference to Related Applications This application is a continuation of and claims the benefit of priority to U.S. patent application Ser. No. 14/869,550 entitled "Systems and Methods for Blood Glucose and Other Analyte Detection and Measurement Using Collision Computing," filed on Sep. 29, 2015, which claims benefit of priority to U.S. Provisional Patent Application Ser. No. 62/057,103 entitled "A System and Method for Generating Feature Sets Using Tomographic Spectroscopy, for Analyte Detection," filed on Sep. 29, 2014; and to U.S. Provisional Patent Application Ser. No. 62/057,496 entitled "Non-Invasive Glucose Monitoring," filed on Sep. 30, 2014, the contents of each of which are incorporated herein by reference in their entirety.

FIELD OF THE INVENTION

In general, this disclosure relates to a system for detecting and/or quantifying the presence of very small amounts of material, the property or concentration of a material, or changes in the amount or properties of the material, or an event or anomaly of interest and, in one example, specifically to a system that performs measurement of biochemical analytes using diffuse reflectance tomographic spectroscopy in conjunction with collision computing.

BACKGROUND

The measurement of substances at extremely low concentrations in complex samples has absorbed the efforts of chemists for centuries. Modern spectroscopic techniques, which allow measurement of substances at parts-per-million (ppm) or even parts-per-billion (ppb) concentrations, have revolutionized this field and allowed the detection and measurement of naturally-occurring materials such as hormones, contaminating substances such as mercury, and pollutants such as atmospheric sulfur dioxide at levels far below those achieved using earlier methods of analysis. The direct measurement of many important substances in human tissue, however, has not been as successfully accomplished, and many other measurements where the substance to be measured is at a low concentration cannot be made accurately in a high noise and/or high clutter environment. One particularly challenging problem concerns the management of diabetes.

Diabetes is a condition in which the body's natural control of blood sugar (glucose) has been lost. Insulin is a hormone that is secreted by the pancreas that works with the body to process blood sugar. Typically, diabetes is caused by some problem with the body's ability to create or use insulin. Diabetes occurs in different medical conditions: type 1 diabetes (previously known as "juvenile diabetes"), type 2 ("adult onset") diabetes, and gestational diabetes (a complication of pregnancy). In type 1 diabetes, the patient's pancreas is no longer able to produce insulin at normal rates, while in type 2 and gestational diabetes, a patient's cells are not able to properly utilize insulin. Some patients with type 2 or gestational diabetes can treat their conditions using diet, exercise, or a variety of pharmaceutical preparations. All patients with type 1 diabetes (and many with type 2, especially of longer duration) typically must control the disease with injections or infusions of insulin.

A body's normal creation and processing of insulin generally varies over the course of the day depending on a variety of factors, including when and what a person eats, whether that person is exercising, and the time of day. This variation in normal insulin production usually serves to maintain safe glucose levels in the body. If diabetes is left untreated, the complications that can arise can be extremely serious. In the absence of insulin, glucose in the blood can reach dangerously high levels. Extended periods of high blood glucose levels ("hyperglycemia") can lead to a condition known as ketoacidosis, which, if untreated, can be fatal. Chronic poor control of glucose levels can also cause serious long-term complications, which include eye damage (resulting in blindness), kidney damage, cardiovascular disease, loss of feeling in the extremities, and slow healing of wounds. Frequently, diabetes may require amputations of toes, feet or legs. If blood glucose levels are allowed to drop below a threshold value (generally 50-60 milligrams per deciliter), the person can be in acute danger from this "hypoglycemia," which can cause confusion, difficulty speaking, unconsciousness, and coma.

To allow better information and control, blood glucose measurement systems that can be used by individual users have been developed. These blood glucose measurement systems typically require the use of an electronic meter and disposable test strips. A test strip is inserted into the meter, and the user pricks himself or herself (usually on a finger) with a lancet to draw a small amount of blood which is applied to the test strip. The blood glucose meter, using one of a variety of analysis techniques, determines the amount of glucose in the small blood sample drawn from the user. However, because of the pain involved in lancing a body part to draw blood, the need to dispose of materials contaminated with blood, and the visibility and potential embarrassment of testing using conventional blood glucose monitoring systems, many investigators have tried to develop technologies that allow measurement of blood glucose without drawing blood or causing discomfort. These technologies have been termed "noninvasive" blood glucose measurement systems, or simply "noninvasive glucose."

For example, U.S. Pat. No. 4,655,225, issued to Dahne et al., with a filing date of Apr. 18, 1985, appears to describe a relatively simple approach to measuring glucose in tissue. This patent states at column 1, lines 8 through 18: "This determination is carried out by measuring the optical near infrared absorption of glucose in regions of the spectrum where typical glucose absorption bands exist and computing the measured values with reference values obtained from regions of the spectrum where glucose has no or little absorption and where the errors due to background absorptions by the constituents of the surrounding tissues or blood containing the glucose are of reduced significance or can be quantitatively compensated." When investigators eventually determined that no regions of the near-infrared NIR spectrum meeting these criteria could be found, they employed advanced techniques, augmented with sophisticated modifications to the instrumentation and complicated mathematical treatments. The NIR region used in these techniques is typically the region of the electromagnetic spectrum in the wavelength range of 700-2,500 nanometers The most commonly-investigated technique for noninvasive glucose over the past twenty-five years or so has been near-infrared spectroscopy (NIRS), using light that is just beyond the visible portion of the spectrum, and generally considered to be a wavelength range of about 700 nanometers to about 2,500 nanometers. When near-infrared light is applied to tissue, generally the light is both scattered by cells and structures under the skin and is absorbed by substances in the tissue, including glucose, which can be termed an "analyte" (a substance whose concentration is being determined). The amount of absorbance due to glucose in this wavelength region, however, is extremely small and, coupled with (i) the low concentration of glucose in the fluids of tissue (about 50-500 milligrams per deciliter, equivalent to about 0.05% to 0.5%), (ii) the presence of many compounds with similar chemical structures and similar absorbance patterns in the near-infrared region, and (iii) the extremely high concentration of water in tissue, makes direct measurement of an analyte in this region of the spectrum very challenging, requiring the use of sophisticated spectroscopic imaging and computational techniques.

Many patents, such as U.S. Pat. No. 5,460,177, issued to Purdy, et al. in 1995, appears to describe approaches for using light from the near-infrared portion of the spectrum to provide "expressions" or spectra that can be examined to determine the concentration of glucose without drawing a sample of blood. Commonly-employed data reduction techniques in previous investigations generally include what are known as "multivariate" techniques, such as principal component analysis ("PCA"), partial least squares ("PLS"), support vector machine ("SVM"), and multiple linear regression ("MLR"). As a group, when these approaches are applied to the measurement of chemical substances, they are often referred to as "chemometrics." These multivariate techniques may make it theoretically possible to create a correlation between measurable properties of a material like tissue, such as the amount of light absorbed or reflected as a function of wavelength (known as a "spectrum"), and the concentration of an analyte such as glucose. An example spectrum, which plots a variable related to light intensity (such as absorbance, transmittance, energy, etc.) as a function of the wavelength of light expressed in nanometers, is shown in FIG. 1.

In order to perform a multivariate analysis on a set of data, some techniques first build what is called a "model." This may be done by first creating a number of like measurements (typically termed the "calibration set" in the context of multivariate analysis), which are spectra which contain the value of a parameter related to light intensity as a function of wavelength and which have known values for the concentration of the analyte. FIG. 2, for example, depicts an absorbance spectrum for one known concentration of glucose. The overall variance in the calibration data set may be separated into "factors" which typically represent decreasing amounts of variance. This model, once created using the multivariate technique, may represent the contribution of a measurement at each wavelength to the concentration of the analyte. The values of the model at each wavelength are often termed "final regression coefficients." At some wavelengths, the value is positive, which may mean that the measurement at that wavelength contributes actual value to the calculation of the concentration, while at other wavelengths the value is negative, which may indicate an amount to be subtracted in the concentration calculation.

Once such a model, an example of which is shown in FIG. 3, has been created, a spectrum with an unknown analyte concentration can be analyzed using that model. With reference to FIG. 4, this can be done by multiplying the value of the new spectrum at each wavelength by the value of the final regression coefficient of the model at the same wavelength, and adding up all the results of those multiplications to give an estimated value of the analyte. The accuracy of this estimated concentration value usually depends on many factors—among them: the number of spectra used in the calibration set, the number of multivariate "factors" used to construct the model, the accuracy of the measurement process for the spectra, the similarity of the instrumentation used to generate the spectra, and the strength of the measured parameter. The measured parameter in the examples described above is the amount of absorbance of glucose molecules at each of the wavelengths, which is quite weak, and which is hidden under the strong absorbance of other components of tissue; the absorbance spectra of some tissue components are shown in FIG. 5, but these spectra are normalized—they are not based on a uniform scale.

Attempts at making measurements of glucose in tissue using these techniques have been made, but to the present time, these efforts have not succeeded in producing clinically accurate results. Several systems have used near-infrared spectroscopy and multivariate analysis techniques, but to date, no system for noninvasive measurement of glucose using near-infrared spectroscopy appears to have gained regulatory approval or appears to have been marketed in the U.S. In addition to multivariate and many other regression techniques, other practitioners have sought to extract a glucose signal from near-infrared tissue spectroscopy data using other methods of data reduction. Examples of these include: subtractive techniques where the spectra of interfering substances are sequentially removed from a tissue spectrum, analysis of a number of equations with several unknowns, neural networks, model trees, genetic algorithms, chaotic networks (and many related approaches that can be classified as fast learning algorithms), and an optical method known as Kromoscopy (Appl. Opt. 2000 Sep. 1: 39(25):4715-20). Many other approaches to measuring glucose in tissue have also been attempted, and a book has been written on the subject: *The Pursuit of Noninvasive Glucose: "Hunting the Deceitful Turkey"* by John L. Smith, $4^{th}$ Edition (Copyright 2015), the disclosure of which is incorporated herein by reference in its entirety. Like the multivariate techniques described above, these techniques have not succeeded in producing clinically accurate results for noninvasive measurement of glucose. A new inventive approach for the direct, noninvasive measurement of glucose in tissue, as well as other analytes of interest, is therefore required.

The term "collision" has been used in different fields and contexts. For example, in computer networking and telecommunications and during the execution of various algorithms processing data, data-packet collisions generally imply that two distinct pieces of data have the same hash value, checksum, fingerprint, or cryptographic digest. The hashing collisions typically allocate the same memory location to different data values. In the computational problem of determining the intersection of two or more computer animated objects, as encountered in simulations and/or video games, linear algebra and computational geometry methods (e.g., the axis-aligned bounding box method for an n-body collision described in Lin, Ming C (1993). "Efficient Collision Detection for Animation and Robotics (thesis)". University of California, Berkeley), collision analysis techniques may be used to determine whether two animated objects would or have collided and the time of impact, and for post-collision trajectory estimation. Computational atomic physics, which introduced a class of stochastic algorithms, such as those used in game theory, molecular dynamics, social simulations, and econometrics, is inspired by techniques used in particle-field simulations. These techniques generally involve collisions of atomic and subatomic particles (such as those described in Sigurgeirsson et al. (2001), "Algorithms for Particle-Field Simulations with Collisions", Journal of Computational Physics 172, 766-807) and algorithms used for calculating post-collision electron and positron scattering and excitation in atoms and ions, such as in non-perturbative close coupling approach.

Various methods inspired by the classical Boltzmann collision operator used in statistical physics or fluid simulations for describing the interaction between colliding particles in rarefied gas include Bobylev-Rjasanow's Integral Transform Method, Pareschi-Russo's Spectral Method, and Mouhot-Pareschi's method. These computational techniques typically exploit the fundamental properties of the Boltzmann binary collision operator (e.g., the Bhatnagar-Gross-Krook (BGK) operator described in P. L. Bhatnagar, E. P. Gross, M. Krook (1954). "A Model for Collision Processes in Gases. I. Small Amplitude Processes in Charged and Neutral One-Component Systems," Physical Review 94 (3): 511-525) that are related to conservation of mass, momentum, and energy, to infer properties of the colliding entities. While the binary collision operator and its approximation have been used in computer simulations and modeling to infer properties of colliding entities, to date these techniques generally do not take into consideration the environment of the entities, such as noise, clutter from confounders, and ultra- weak magnitudes of signals associated with entities of interest.

Computational collision techniques, such as those described in *Collision-Based Computing*, Andrew Adamatzky, (Ed.), ISBN 978-1-4471-0129-1, generally appear to describe computer implementations of various collisions described above, such collisions between particles or collisions between physical entities. With reference to FIGS. 6-8B, collisions between two traveling waveforms can occur on a space-time grid or a grid in another Cartesian coordinate system. In general, the two traveling waveforms move toward each other along a straight line connecting their centers of mass, with each point of one discretized wavefront (102 in FIG. 6) engaging in a series of collision steps with a corresponding point of the other discretized waveform (104 in FIG. 6), with the result of each step being determined by a set of rules established at the line of collision $L_C$ (100 in FIG. 6). Those rules determine the mathematical result of collision interactions and the shape of the resulting symbolic waveforms. Following completion of these partial steps in a collision between two waveforms, two resulting waveforms (106, 108 in FIGS. 7A-7F) are typically produced. The two resulting waveforms: (i) may be completely unchanged (except for a phase shift or delay) relative to the colliding waveforms, as shown in FIG. 7F), (ii) may be deformed (as shown in FIG. 8A), or (iv) either or both waveforms may be essentially completely destroyed (as shown in FIG. 8B). The nature of change in each waveform as a result of the collision (which can also be described as the degree of "elasticity" of the collision) generally depends on the composition of the waveforms, the relative energy of each waveform, and the rules established at the collision line $L_c$. A "soliton" is an example of a waveform that does do not change its properties other than a delay or phase shift during the collision process.

SUMMARY

In various embodiments, the systems and methods described herein facilitate detection and/or measurement of the presence and concentration of one or more chemical constituents of interest (generally called analytes) in a specified environment or a medium to be analyzed (e.g., turbid layers of human tissue with inhomogeneities that scatter light in random directions) in the presence of one or more confounders. This is achieved in part by employing one or more nonlinear, non-invertible computational collisions between two entities—waveforms derived from sample observations, where the samples are represented in an observation domain (also called a data-collection domain), and a purposefully constructed waveform that is typically not based on the data-collection domain—yielding waveforms that can be processed to detect analyte presence and/or measure analyte concentration in the uncharacterized samples. Various embodiments described herein provide for precise and accurate detection and/or measurement of an analyte of interest in a medium to be analyzed. Various embodiments also facilitate detection and/or measurement of events in different types of environments.

Specifically, in certain embodiments a new computational collision technique is described whereby the presence and/or concentration of clinical and chemical analytes can be determined from sensor data in the presence of high noise, background interference, and interference from other substances with similar properties as that of the analyte(s). This computational collision process can be extended to other types of data where the information sought is considered or treated as the equivalent of an analyte. Thus, detection and/or measurement of an analyte, as described herein, may include the identification, characterization, and/or measurement of any material, property, magnitude, condition, anomaly, or an event of interest. The domain from which the source data for the uncharacterized samples may originate is generally referred to as the data-collection domain.

Although collisions actually occur only within a computer, with the interaction of what are termed "frequency components," of two waveforms in the frequency domain, the collision process can be symbolically depicted as the collision between two discretized waveforms in a synthetic domain termed a "collision time domain." For completeness and clarity, that process is described below in detail and illustrated in the referenced figures.

When the waveforms to be collided are properly constructed and are made co-dependent (as described below), energy changes (e.g., changes in spectral energy due to absorption of NIR radiation by the analyte molecules in a medium in certain embodiments) as derived from data corresponding to particular materials, conditions, or events, can be transferred from one waveform to the other, and amplified in successive collisions. In various embodiments, collision computing in which two co-dependent waveforms collide, allows for drawing inferences about the underlying properties of waveforms participating in the collision, based on the energy transfer from one waveform to the other, and the energy properties of the surviving waveform. In various embodiments, collision computing facilitates an estimation of a Net Analyte Signal (NAS) from spectral or other data sources. Through a projection process, the NAS can be used to determine the presence and/or the concentration of an analyte in a medium to be analyzed.

Thus, in various embodiments, methods and systems described herein provide for detecting the presence of and for estimating concentration of analytes from sensor data, by transforming the incoming sensor data to a waveform ($\Psi_{CF}$), i.e., a mathematical representation of the sensor data in the computer memory; colliding it with another waveform in the computer memory, referred to as the Zyoton ($\Psi_Z$), which is unrelated to and independent of the data domain of the sensor; and assessing the properties of the spectral energy of a modified Zyoton ($\Psi_{Z'}$) generated after the collision. Depending on the nature of input data, characteristics of the sensor used for observing the analyte, complexity and concentration of confounders, and expected concentration of the analyte, one or more iterations of computational collisions may be performed. After each collision operation between the two waveforms, the power spectral density of the collision-modified Zyoton $\psi_{Z'}$ is estimated. Waveform collisions may be implemented in the analog or digital computing domain and in a time or frequency domain, i.e., the colliding waveforms may be expressed in the time domain or in the frequency domain. Analyte presence and concentration can be determined based on net gain or loss in the spectral energy after a selected number of collision iterations. Observability of consistent patterns in spectral energy gain or loss after each collision between the two waveforms is a prerequisite in various embodiments to concluding the integrity and consistency of the collision process. The processing unit in which the collisions are implemented is denoted as the collision computer.

Throughout this specification, data features which have been modified or conditioned by modulation (called conditioned features), as well as the Zyotons, are described as waveforms. When these waveforms collide, the collision operation takes place specifically at their wavefronts and, in that context, these waveforms may be described as wavefronts. These two terms are generally used separately to emphasize the special aspects of the collision computing process. Additionally, components of the original data that interfere with the determination of the analyte or obscure its signal are referred to as confounders and, taken as a group, are represented by the term "clutter." The collision computing process generally functions to improve the signal to clutter ratio by decreasing the impact of the confounders present in the original data.

Unlike a collision between physical particles, which can be perfectly or imperfectly elastic or inelastic depending on how the kinetic energy and momentum are conserved and whether the two particles continue to exist as two entities, and unlike a collision between two waveforms that are not specifically constructed to be co-dependent (as described below), the waveform collisions between two co-dependent waveforms described herein are interferometric, where the two distinct but co-dependent waveforms combine post-collision and the interaction is dissipative, that is, the spectral energy of the combined system is less than the pre-collision energies of two waveforms. Also, as a result of this collision, the two waveforms combine to a single waveform, called the modified Zyoton. The purposeful dissipation during collisions is causal in character and serves as a probe to characterize analytes of interest because, as described below, generally the energy associated with the analyte of interest is transferred into the modified Zyoton while the energy associated with noise and clutter may be discarded. Precisely measuring a change in the energy of the modified Zyoton relative to the energy of the original Zyoton, in spectral regions (e.g., wavelength ranges) where the energy changes are most visible, allows us to quantify concentration of analytes with accuracy and reliability. As a design principle, the two waveforms and collision operators are designed based on analysis of sensor data to intentionally maximize changes in spectral energy in the spectral regions associated with the analyte, in each collision iteration. Also, the two waveforms are designed such that the Zyoton waveform typically has higher initial spectral energy than the other waveform with which it collides.

One important aspect of various methods and systems described herein is the discovery that very small portions of data (also called spectral data features) contain analyte-specific frequency components that persist, even in the presence of overwhelming amounts of clutter, and that these frequency components can be amplified and separated from that clutter. As used herein the term "frequency components" generally refers to spatial frequencies, i.e., those components of a traveling waveform that are periodic across position in space. These frequency components (or components) can be determined by a Fourier transform of a time-domain representation of the waveform.

Collision computing described herein facilitates the amplification and separation of data. To this end, a stable waveform called a Zyoton, which generally does not change its shape and morphology when it propagates through a propagation medium, is computationally collided with another waveform called a conditioned feature derived from a spectrum to be analyzed. The nature of the Zyoton and how it changes through the collision computing process are explained in detail below. A conditioned feature is obtained by modulating a pre-selected, fixed carrier waveform referred to as a carrier kernel having particular spectral properties, with the feature data to be analyzed. In particular, the spectral properties of the Zyoton and the carrier kernel are selected such that the Zyoton and the conditioned feature are co-dependent and can extract and amplify, in substance, the energy associated with the analyte but not with the noise and/or clutter. Thus, post-collision, the modified Zyoton waveform may represent, substantially, the energy loss in the radiation energy incident upon the medium due to the absorption of such energy by the analyte of interest, if present in the medium, or the presence of one or more confounders in the medium, or both, as well as, optionally, the radiant energy lost to dissipative processes such as scattering, specifically in the spectral region chosen for the feature.

Optionally, collision computing can be applied to analyze and characterize analyte presence or concentration from the emission spectra of a medium, which includes the spectrum of frequencies of electromagnetic radiation emitted due to an atom or molecule making a transition from a high energy state to a lower energy state. The energy of the emitted photon is equal to the energy difference between the two states. The energy states of the transitions can lead to emissions over a range of frequencies yielding an emission spectrum. By observing the frequencies and amplitudes of wavelengths in an emission spectrum, e.g., as spectral energy or changes therein at different wavelength ranges, elemental or molecular composition of the sample or concentration of an analyte in complex samples can be determined.

Example sources of emitted light are described in the table below:

TABLE 1

| Name | Source | Example |
| --- | --- | --- |
| Chemiluminescence | Chemical reactions | Glow sticks |
| Triboluminescence | Friction energy | Light emission seen when pulling friction tape off the roll in the dark. |
| Bioluminescence | Biological processes | Light emission seen from fireflies and some jellyfish |
| Thermoluminescence | Heat energy | Used for archeological dating |
| Electroluminescence | Electric voltage | Source of light seen in LEDs |

TABLE 1-continued

| Name | Source | Example |
| --- | --- | --- |
| Fluorescence | Light energy | Immediate re-emission after absorption of light |
| Phosphoresence | Light energy | Delayed re-emission after absorption of light |
| Blackbody emission | All materials above 0° K | Red-hot metal; the human body at 300° K |

Collision computing treatment of spectra acquired in absorption spectroscopy or emission spectroscopy can be performed similarly as described above, to the extent of extracting spectral features from different wavelength regions, conditioning them using carrier kernel waveforms as described below, colliding them with Zyotons to estimate the absorbed or emitted energy change, and then transforming that result to conclude the presence of and/or to estimate the amount of the analyte. In part due to the shape and morphology preservation properties of the Zyoton, the collision produces a resulting waveform that can represent a change in energy substantially related only to the energy loss represented by the feature used in the collision, and not due to the collision operation itself. Moreover, the collision operator and one or more parameters thereof are selected such that the energy change represented by the feature is amplified when that change is represented in the resulting waveform. The resulting waveform (the modified Zyoton) can be collided iteratively with the same or different Zyotons, in order to further amplify the energy loss represented by the feature, without substantially introducing any noise or distortion.

Beyond the difficult problem of noninvasive glucose measurement described above, which is generally considered intractable using various known techniques, there are many other measurements of high value that cannot be performed affordably or reliably using various known analytical techniques and sensors, typically due to any of: lack of direct, unique markers or sensor signatures; an ultra-weak detected signal; overwhelming amount of interference or clutter that may obscure the signal of interest (where clutter can be described as other materials or sources of noise which may interfere with the signal in the data-collection domain. For example, in measurement of glucose in tissue, other materials in tissue that absorb in the same spectral region as the analyte, e.g., glucose, or the noise generated by the scattering of light by tissue, are generally considered to be clutter. Materials which absorb radiation in the same spectral region as the analyte are often referred to as confounders); rapidly changing background or tissue medium properties; inadequate or narrow measurement time window; or a combination of two or more of these exacerbating factors.

Nonlimiting examples of these measurement problems in various domains suitable for analysis with collision computing include:
  a. Concentration measurements of biologically important molecules, either in-vivo or in-vitro, that have a cross-product of concentration and measurable property (absorbance, emission, fluorescence, magnetic cross-section, etc.) that is below the measurement limit of various known measurement systems;
  b. Measurement of environmental toxins at concentrations below an existing detection threshold;
  c. Accurate heart-rate and metabolic state tracking during exercise and variable motion using photoplethysmograph (PPG) devices;
  d. In-vivo, early detection and continuous monitoring near-skin and deep tissue inflammation or infection e.g., detection and monitoring post-surgery, post stem-cell therapy, etc.;
  e. Direct detection of circulating tumor cells using nanoparticle tagging;
  f. Isolation and real-time detection of sophisticated cyberthreats including cyber-theft and injection of dormant, cyber viruses that can dramatically compromise privacy, information security, and infrastructure security;
  g. Real-time steganography detection in video, audio, and digital imagery;
  h. Remote identification of subsurface mineral, oil, gas, or water resources from the ground, aircraft or spacecraft, including water-table depletion mapping; and
  i. The location, mapping, and characterizing of underground activities in hidden facilities.

Accordingly, in one aspect, a method is provided for determining concentration of glucose in a tissue sample. The method may include obtaining energy absorbed by glucose from energy directed to the tissue sample, as a result of a collision between two co-dependent waveforms, and projecting the energy absorbed by glucose to a glucose concentration.

In various embodiments, the method may include: receiving a feature corresponding to a specified wavelength range of a spectral signal, where the spectral signal generally represents at least one of: (i) absorption of energy, within the specified wavelength range, and (ii) loss of energy within the specified wavelength range due to scattering. Glucose in the tissue sample, and/or one or more confounders in the tissue may absorb the energy that is represented by the received feature. The method may also include generating a conditioned feature by modulating a carrier kernel using the received feature.

The step of receiving the feature may include directing near-infrared radiation to the tissue sample, collecting radiation from the tissue sample, generating an absorption spectrum from the collected radiation, and selecting a region of the absorption spectrum bounded by the wavelength range as the feature. Collecting the radiation may include receiving diffusely reflected radiation from the tissue sample and/or receiving radiation transmitted through the tissue sample. In some instances, one of the two co-dependent waveforms comprises an original Zyoton constructed to amplify energy absorbed by the feature, and the carrier kernel is constructed such that the original Zyoton and the conditioned feature obtained by modulating the carrier kernel using the feature are co-dependent. The step of colliding the original Zyoton with the conditioned feature may include, in a first iteration, colliding the original Zyoton with the conditioned feature to obtain a modified Zyoton, and renormalizing the modified Zyoton to obtain a renormalized Zyoton.

In various embodiments, the method also includes: in each of $\mathbb{N}-1$ additional iterations, where $\mathbb{N}>1$, colliding the original Zyoton with a renormalized Zyoton from an immediately preceding iteration, to obtain a remodified Zyoton, and renormalizing the remodified Zyoton to obtain a renormalized modified Zyoton. The method may further include computing energy gain of the renormalized modified Zyoton obtained after $\mathbb{N}$ iterations relative to energy of the original Zyoton, to determine the energy absorbed by glucose. In some cases, the number of iterations $\mathbb{N}$ is selected such that accuracy of the glucose concentration measurement, as determined by Absolute Relative Deviation (ARD) relative to a glucose concentration measurement obtained using a reference method, is less than 15%.

In other cases, the number of iterations N is selected such that accuracy of a plurality of glucose concentration measurements, as determined by Mean Absolute Relative Deviation (MARD) relative to a plurality of glucose concentration measurements obtained using a reference method, is less than 15%. The conditioned feature may be derived from a glucose feature, where the glucose feature represents at least absorption of energy by glucose within a first specified wavelength range.

In various embodiments, the method includes: repeating the steps (a) through (c) with respect to another conditioned feature derived from a non-glucose feature paired with the glucose feature, forming a first feature pair. The non-glucose feature may represent absorption of energy, within a second specified wavelength range, by at least one confounder in the tissue sample. Alternatively or in addition, the non-glucose feature may represent loss of energy due to scattering within the second specified wavelength range. The method may further include: computing energy gain of the renormalized modified Zyoton corresponding to the non-glucose feature relative to energy of the original Zyoton, and computing net renormalized spectral energy gain (NRSEG) for the first feature pair based on energy gains corresponding to the glucose feature and the non-glucose feature of the first feature pair.

The method may also include normalizing the NRSEG for the first feature pair according to a weight designated to the first feature pair, to obtain a normalized NRSEG. In some instances, receiving the glucose feature and the non-glucose feature may include directing, via a source, near infra-red radiation to the tissue sample, and collecting, via a detector, radiation from the tissue sample. In various embodiments, the projecting step may include: (i) computing a number of NRSEG values for the first feature pair, where each NRSEG value corresponds to a respective illumination state of the near infra-red radiation from an illumination sequence. In general, different illumination states can target light paths of different lengths and/or at different depths through the tissue sample.

The method may further include (ii) computing a normalized absorption gradient (NAG) based on the several NRSEG values; and (iii) selecting from a number of individual projector curves one particular individual projector such that the computed NAG is within lower bound and upper bound NAG values associated with that individual projector curve. The method may also include (iv) determining glucose concentration using the selected individual projector curve and a representative energy absorption value based on a plurality of energy absorption values.

In certain embodiments, the method further includes repeating step (i) described above for each additional feature pair in a set of feature pairs that includes the first feature pair, and computing a number of NRSEG values for each additional feature pair in the set. Each NRSEG value of the various NRSEG values associated with a particular feature may correspond to a respective illumination state of the near infra-red radiation from an illumination sequence. The computing the NAG may include: for each feature pair in the set designated as acceptable: (A) computing an absorption gradient (AG), and (B) weighting the AG according to a weight associated with the corresponding acceptable feature pair. Computing the NAG may also include averaging the weighted AGs. The representative energy absorption value can be computed by: selecting a particular illumination state; for each feature pair in the set designated as acceptable, weighting an NRSEG value corresponding to the particular illumination state according to a weight associated with the corresponding acceptable feature pair; and averaging the weighted NRSEG values. The representative energy absorption value may then be set to the average of the weighted NRSEG values. In general, a set includes at least one member.

In various embodiments, the method includes, prior to computing the NAG, for the several NRSEG values corresponding to at least one feature pair in the set, computing a mean NRSEG value, and excluding an NRSEG value that is different from the mean NRSEG value by a specified threshold. The method may also include determining monotonicity of the plurality of NRSEG values corresponding to each feature pair in the set, and designating each feature pair having monotonicity as acceptable.

In some cases, determining the glucose concentration using the selected individual projector curve includes interpolation, which can include adding to a product of the representative energy absorption value and a slope of the selected individual projector curve, an intercept of the selected individual projector curve. In some cases, determining the normalized absorption gradient includes determining a slope of a regression of the plurality of NRSEG values, typically but not necessarily normalized, with respect to the illumination states, the illumination states being ordered such that successive illumination states represent monotonically changing distance between the source and at least one detector. In some cases, projecting the energy absorbed by glucose to glucose concentration includes mapping the computed NRSEG value to glucose concentration using a single projector curve. The method may also include designating the determined glucose concentration to one of a number of concentration bands. In certain instances, obtaining energy absorbed by glucose as a result of collision includes a single collision iteration. Monotonically changing distance can be monotonically increasing distance or monotonically decreasing distance.

In another aspect, a system is provided for determining concentration of glucose in a tissue sample. The system may include a first processor and a first memory in electrical communication with the first processor, the first memory including instructions which, when executed by a processing unit including at least one of the first processor and a second processor, and in electronic communication with a memory module comprising at least one of the first memory and a second memory, program the processing unit to: obtain energy absorbed by glucose from energy directed to the tissue sample as a result of collision between two co-dependent waveforms, and project the energy absorbed by glucose to a glucose concentration. In various embodiments, the instructions can program the processing unit to perform one or more of the method steps described above.

In another aspect, an article of manufacture is provided that includes a non-transitory storage medium having stored therein instructions which, when executed by a processing unit program the processing unit, which is in electronic communication with a memory module, to determine concentration of glucose in a tissue sample. The instructions may program the processing unit to: obtain energy absorbed by glucose from energy directed to the tissue sample as a result of collision between two co-dependent waveforms, and project the energy absorbed by glucose to a glucose concentration. In various embodiments, the instructions can program the processing unit to perform one or more of the method steps described above.

Performing Collision Computing

In another aspect, a method is provided for measuring a property associated with an information signal. The method may include colliding using a collision grid a first conditioned feature waveform that at least partially represents a property of the information signal with an original Zyoton, which includes a waveform that without a collision travels substantially unperturbed at a selected velocity in a substantially constant propagation medium at least over a length of a space-time grid, to obtain a first modified Zyoton, the first conditioned feature waveform and the original Zyoton being constructed to: (i) be co-dependent, and (ii) transfer the property of the information signal to the first modified Zyoton through the collision.

In various embodiments, the space-time grid includes at least one spatial dimension and a time dimension. The information signal may include one of a signal obtained from a sensor and a signal generated by data analysis. In some instances, the method further includes deriving the first conditioned feature waveform by modulating a carrier kernel using a first feature derived from the information signal. In some cases, the method includes generating the first feature by: selecting from the information signal one of: (i) a single contiguous range of wavelengths, and (ii) a combination of a plurality of discontiguous ranges of wavelengths.

In other cases, the method includes generating the first feature by: transforming the information signal into a spectral signal; and selecting from the spectral signal one of: (a) a single contiguous range of wavelengths, and (b) a combination of a plurality of discontiguous ranges of wavelengths. In some instances, modulating the carrier kernel includes frequency modulation of the carrier kernel using the first feature. In other instances, modulating the carrier kernel includes: generating an intermediate signal by modulating the first feature using a modulation signal; and modulating the carrier kernel with the intermediate signal. In other instances, modulating the carrier kernel includes interpolating the first feature to match a length of the interpolated first feature in time domain to a length of the carrier kernel in the time domain. In certain embodiments, constructing the original Zyoton and the first conditioned feature waveform to be co-dependent includes determining whether an absolute difference between a scaled velocity of the original Zyoton and a velocity of the first conditioned feature does not exceed a threshold $\kappa_{DV2}$.

In various embodiments, the method further includes adjusting at least one of: (i) the velocity of the original Zyoton, and (ii) the velocity of the first conditioned feature waveform, such that the absolute difference between the scaled velocity of the original Zyoton and the velocity of the first conditioned feature is within the threshold $\kappa_{DV2}$. In some instances, the original Zyoton includes an analyte-information-representing first group of frequency components and a non-analyte-information-representing group of frequency components, the first conditioned feature including corresponding groups of frequency components, the method further including: adjusting using a scaling vector at least one of: (i) a frequency domain amplitude of at least one component of the analyte-information-representing group of the original Zyoton, and (ii) a frequency domain amplitude of at least one component of the corresponding group of the first conditioned feature waveform, such that the absolute difference between the scaled velocity of the original Zyoton and the velocity of the first conditioned feature is within the threshold $\kappa_{DV2}$.

The method may also include renormalizing the first modified Zyoton to obtain a first renormalized Zyoton. In certain cases, the property of the information signal includes energy absorbed by at least one of an analyte and one or more confounders, the first renormalized Zyoton includes a set of analyte-information-representing components and a set of non-analyte-information-representing components, and the set of analyte-information-representing components of the first renormalized Zyoton represents the energy absorbed by at least one of the analyte and the confounder. Not all members of the set of analyte-information-representing components may represent analyte information, however. Similarly, one or more members of the set of non-analyte-information-representing components may represent analyte information.

The method may further include colliding using the collision grid the first renormalized Zyoton with the original Zyoton to obtain a second modified Zyoton, and renormalizing the second modified Zyoton to obtain a second renormalized Zyoton. The method may also include iterating the colliding and renormalizing steps (ℕ −2) times, ℕ >2, each iteration being based on a renormalized Zyoton from an immediately preceding iteration, and producing a new renormalized Zyoton, until a final renormalized Zyoton is produced after (ℕ −2) iterations. In certain cases, the at least partially represented property of the information signal includes energy absorbed by at least one of an analyte and a confounder in a wavelength range associated with a first feature corresponding to the first conditioned feature waveform, the final renormalized Zyoton includes a set of analyte-information-representing components and a set of non-analyte-information-representing components, and the set of analyte-information-representing components of the final renormalized Zyoton represents the energy absorbed by at least one of an analyte and a confounder in the wavelength range associated with the first feature.

In various embodiments, the method may further include: colliding using the collision grid a second conditioned feature waveform that at least partially represents the property of the information signal with the original Zyoton, to obtain a new first modified Zyoton, the second conditioned feature waveform and the original Zyoton being constructed to: (i) be co-dependent, and (ii) transfer the property of the information signal to the new first modified Zyoton through the collision; renormalizing the new first modified Zyoton to obtain a new first renormalized Zyoton; and iterating the colliding and renormalizing steps (ℕ −2) times, ℕ >2, each iteration being based on a new renormalized Zyoton from an immediately preceding iteration, and producing another new renormalized Zyoton, until a new final renormalized Zyoton is produced after (ℕ −2) iterations.

In such embodiments, the new final renormalized Zyoton includes a set of analyte-information-representing components and a set of non-analyte-information-representing components, and the set of analyte-information-representing components of the new final renormalized Zyoton represents the energy absorbed by at least one of an analyte and a confounder in a wavelength range associated with a second feature corresponding to the second conditioned feature waveform. The method may also include determining ℕ based on at least in part at least one of a specified signal-to-clutter ratio (SCR), a specified signal-to-noise ratio (SNR), a target precision, a target sensitivity, a target accuracy, a target stability, and an expected dynamic range of an analyte in a medium to be analyzed.

Renormalization can include downscaling, using a scaling vector, frequency domain amplitudes of a set of frequency components in an analyte-information-representing band of the first modified Zyoton to obtain the first renormalized Zyoton. The scaling vector can be a plurality of preset values, and can be determined according to frequency domain amplitudes of a set of frequency components in an analyte-information-representing band of the original Zyoton. In certain embodiments, renormalization includes truncating the first modified Zyoton by removing at least one frequency component in a non-analyte-information-representing band of the first modified Zyoton to obtain the first renormalized Zyoton, and distributing energy of the at least one removed frequency component among a set of remaining frequency components in at least one of a non-analyte-information-representing band and a transition band of the first renormalized Zyoton.

In various embodiments, the method further includes determining, prior to renormalizing, whether an absolute difference between a velocity of the original Zyoton and a velocity of the first modified Zyoton does not exceed a threshold $\kappa_{DV3}$. In some instances, the method includes determining, prior to renormalizing, whether divergence of the first modified Zyoton does not exceed a threshold $\tau$. In some instances, the method includes determining, prior to renormalizing, whether energy of the first modified Zyoton is greater than energy of the original Zyoton. In some cases, the method includes determining, after renormalizing, whether an absolute difference between a scaled velocity of the original Zyoton and a velocity of the first renormalized Zyoton does not exceed a threshold $\kappa_{DV1}$.

The property of the information signal may include at least one of: (i) a spectral energy absorbed by at least one of an analyte and one or more confounders, (ii) another property of at least one of the analyte and the confounder, and (iii) an information measure. The information signal may include a sensor signal. In some cases, the sensor signal may include one of: an intensity spectrum signal and an absorbance spectrum signal. In some cases, the sensor signal may include an emission spectrum, where the emission can be fluorescence, phosphorescence, black-body emission, etc. In some cases, the sensor signal includes at least one of a reflectance signal, and a transmission signal. In some cases, the sensor signal includes electromagnetic radiation received from a medium to be analyzed. The electromagnetic radiation may include near infra-red radiation. The collision grid may include a frequency-domain grid, and colliding may involve a first bracketed conditional interaction, in frequency domain, between a first component of the original Zyoton and a first bracket of components of the first conditional feature waveform.

In various embodiments, the first bracketed conditional interaction may include, for each component of the first conditional feature waveform in the first bracket: testing if frequencies of the component of the first conditioned feature waveform and the first component of the original Zyoton satisfy a first epsilon test; if the first epsilon test succeeds, generating a component of the first modified Zyoton, and setting an amplitude of the generated component of the first modified Zyoton as a product of amplitudes of the component of the first conditioned feature waveform and the first component of the original Zyoton; if the frequencies of the component of the first conditioned feature waveform and the first component of the original Zyoton satisfy a second epsilon test, setting a frequency of the generated component of the first modified Zyoton to a frequency of the first component of the original Zyoton; and otherwise setting the frequency of the generated component of the first modified Zyoton to a sum of frequencies of the component of the first conditioned feature waveform and the first component of the original Zyoton.

The first epsilon test may be selected based on to which group of components of the original Zyoton the first component of the original Zyoton belongs. In some cases, the first epsilon test is the second epsilon test. In certain instances, colliding may involve a second bracketed conditional interaction, in frequency domain, between a second component of the original Zyoton and a second bracket of components of the first conditional feature waveform. In such instances, the first bracketed conditional interaction may produce a first component of the modified Zyoton and the second bracketed conditional interaction may produce a second component of the modified Zyoton, and the method may further include: determining if the first and second modified Zyoton components are to be merged by testing if frequencies of the first and second modified Zyoton components satisfy a third epsilon test. The third epsilon test can be selected based on to which group of components of the modified Zyoton a larger one of the first and second components of the modified Zyoton belongs, the larger component being determined by comparing amplitudes of the first and second components of the modified Zyoton.

In various embodiments, the method may further include merging the first and second modified Zyoton components into the first modified Zyoton component by resetting an amplitude of the first modified Zyoton component to a sum of amplitudes of the first and second modified Zyoton components, and removing the second modified Zyoton component. In some such embodiments, merging the first and second modified Zyoton components into the first modified Zyoton component may further include, if a frequency of the first modified Zyoton component is smaller than a frequency of the second modified Zyoton component, setting a frequency of the first modified Zyoton component to the frequency of the second modified Zyoton component.

In other such embodiments, merging the first and second modified Zyoton components into the first modified Zyoton component may further include, if, prior to merging, the amplitude of the first modified Zyoton component is smaller than the amplitude of the second modified Zyoton component, setting a frequency of the first modified Zyoton component to the frequency of the second modified Zyoton component. The method may further include selecting a length of the first bracket of components of the first conditional feature waveform based at least in part on at least one of a specified signal-to-clutter ratio (SCR), a specified signal-to-noise ratio (SNR), a target precision, a target sensitivity, a target accuracy, a system stability, and an expected dynamic range of an analyte in a medium to be analyzed. The method may also include, prior to the first bracketed conditional interaction, at least one of: (i) shifting components of the original Zyoton according to a delay-shift parameter, (ii) scaling an amplitude of the first component of the original Zyoton according to at least one of (a) a precision of a computing device, (b) a dynamic range of a computing device, (c) a resolution of a sensor used to obtain a feature used to generate the first conditioned feature, (d) a dynamic range of the sensor, and (e) SNR of the sensor, and (iii) applying a phase rotation to the first component of the original Zyoton.

In various embodiments, the original Zyoton includes a plurality of components selected from a kernel of components of a base Zyoton generated from a family of waveforms, a number of components in the plurality being based on at least in part at least one of a specified signal-to-clutter ratio (SCR), a specified signal-to-noise ratio (SNR), a target precision, a target sensitivity, a target accuracy, a target stability, and an expected dynamic range of an analyte in a medium to be analyzed. The collision grid may include a frequency-domain grid, and a length of the original Zyoton may include a sum of: (i) a number (k) of analyte-information-representing components, (ii) a number (m) of transition components, and (iii) a number (j) of non-analyte-information-representing components of the original Zyoton.

In some embodiments, the original Zyoton is synthesized from at least one of a plurality of waveform families comprising: solitons; autosolitons; similaritons; custom solitons generated using a sine-Gordon-based equation; self-compressing similaritons; vortex-solitons; multi-color solitons; parabolic-similaritons; Ricci solitons; wavelets; curvelets; ridgelets; bions; elliptic waves comprising at least one of Jacobi elliptic functions and Weierstrass elliptic functions; and nonautonomous similinear wave equation.

In other embodiments, the original Zyoton is synthesized from at least one of a plurality of waveform generators comprising: meromorphic functions; Gamma functions; Riemann Zeta functions; regular instantons; Frobenius manifolds; harmonic oscillators; Hermite polynomials; polynomial sequences; asymptotic Hankel functions; Bessel functions; fractals; Neumann functions (spherical); poweroid coupled with sinusoidal functions; spatial random fields; cyclostationary series; random number generators; spherical harmonics; chaotic attractors; exponential attractors; multipoint Krylov-subspace projectors; Lyapunov functions; inertial manifolds of Navier-Stokes equation; evolution equation for polynomial nonlinear reaction-diffusion equation; evolution equation for Kuramoto-Savashinsky equation; evolution equation of exponential attractors; Fourier series; and Ramanuj an theta functions.

In some cases, the original Zyoton is synthesized from a random number generator having a replicability and at least one of: a periodicity of at least 1000, a correlation between a pair of generated values of at most 90%, and a spectral bandwidth of at least 100 Hz. In some cases, the original Zyoton is synthesized from a polynomial sequence, a Fourier transform of the polynomial sequence having a spectral bandwidth of at least 100 Hz. In certain instances, the original Zyoton is synthesized from a random number generator comprising at least one of: a linear congruential generator, a multiplicative congruential generator, an additive congruential generator, and a Fibonacci generator. In certain instances, the original Zyoton is synthesized from a polynomial sequence comprising at least one of an Abel polynomial sequence and a Bell polynomial sequence. In some embodiments, the original Zyoton is synthesized, at least in part, from at least one of: (i) a waveform family and (ii) a waveform generator, and the method further includes at least one of transforming and reducing a function to at least one of the waveform family and the waveform generator. In some cases, the original Zyoton is synthesized by at least one of: an addition, a multiplication, and a subtraction of at least two waveforms derived from at least two waveform families.

In another aspect, a system is provided for measuring a property associated with an information signal. The system may include a first processor and a first memory in electrical communication with the first processor, the first memory including instructions which, when executed by a processing unit including at least one of the first processor and a second processor, and in electronic communication with a memory module comprising at least one of the first memory and a second memory, program the processing unit to: collide using a collision grid a first conditioned feature waveform that at least partially represents a property of the information signal with an original Zyoton, which includes a waveform that without a collision travels substantially unperturbed at a selected velocity in a substantially constant propagation medium at least over a length of a space-time grid, to obtain a first modified Zyoton, the first conditioned feature waveform and the original Zyoton being constructed to: (i) be co-dependent, and (ii) transfer the property of the information signal to the first modified Zyoton through the collision. In various embodiments, the instructions can program the processing unit to perform one or more of the method steps described above.

In another aspect, an article of manufacture is provided that includes a non-transitory storage medium having stored therein instructions which, when executed by a processing unit program the processing unit, which is in electronic communication with a memory module, to measure a property associated with an information signal. The instructions may program the processing unit to: collide using a collision grid a first conditioned feature waveform that at least partially represents a property of the information signal with an original Zyoton, which includes a waveform that without a collision travels substantially unperturbed at a selected velocity in a substantially constant propagation medium at least over a length of a space-time grid, to obtain a first modified Zyoton, the first conditioned feature waveform and the original Zyoton being constructed to: (i) be co-dependent, and (ii) transfer the property of the information signal to the first modified Zyoton through the collision. In various embodiments, the instructions can program the processing unit to perform one or more of the method steps described above.

Zyoton and Carrier Kernel Synthesis

In another aspect, a method is provided for enabling extraction of a property of an element of a specified environment. The method may include selecting using at least one of: (i) at least one waveform family, and (ii) at least one waveform generator, a set of frequency components for an analyte-information-representing band and a set of frequency components for a non-analyte-information-representing band; and synthesizing a Zyoton by combining the set of frequency components selected for the analyte-information-representing band and the set of frequency components selected for the non-analyte-information representing band, where: at least one frequency component in the set of frequency components for the analyte-information-representing band corresponds to a property to be extracted; at least one of the frequency components for the non-analyte-information representing band does not correspond significantly to the property to be extracted; and the selected set of frequency components of the waveform family allow the Zyoton to propagate through a substantially constant propagation medium over a length of a collision grid without substantial change in morphology thereof. Not all members of the band of analyte-information-representing components may represent analyte information, however. Similarly, one or more members of the band of non-analyte-information-representing components may represent analyte information.

In some embodiments, after a collision of the Zyoton with a waveform constructed to perturb the Zyoton within specified limits, the selected set of frequency components allow: generation of a modified Zyoton via the collision; and subsequent propagation of the modified Zyoton through the substantially constant propagation medium over the length of the collision grid without substantial change in morphology of the modified Zyoton. In some cases, the at least one waveform family may include at least one of: optical solitons, autosolitons, similaritons, custom solitons generated using a sine-Gordon-based equation, self-compressing similaritons, vortex-solitons, multi-color solitons, parabolic-Similaritons, and Ricci solitons.

In some cases, the at least one waveform family includes at least one of: solitons; wavelets; curvelets; ridgelets; bions; elliptic waves comprising at least one of Jacobi elliptic functions and Weierstrass elliptic functions; and nonautonomous similinear wave equations. In some cases, the at least one waveform generator includes at least one of: meromorphic functions; Gamma functions; Riemann Zeta functions; regular instantons; Frobenius manifolds; harmonic oscillators; Hermite polynomials; polynomial sequences; asymptotic Hankel functions; Bessel functions; fractals; Neumann functions (spherical); poweroid coupled with sinusoidal functions; spatial random fields; cyclostationary series; random number generators; spherical harmonics; chaotic attractors; exponential attractors; multipoint Krylov-subspace projectors; Lyapunov functions; inertial manifolds of Navier-Stokes equation; evolution equation for polynomial nonlinear reaction-diffusion equation; evolution equation for Kuramoto-Savashinsky equation; evolution equation of exponential attractors; Fourier series; and Ramanujan theta functions.

In certain instances, the specified environment includes a medium to be analyzed; and the property to be extracted includes at least one of: presence of an analyte, absence of the analyte, a quantity of an analyte, and a rate of change of the quantity of the analyte, in the medium to be analyzed. In various embodiments, the method may further include selecting from the at least one waveform family a set of frequency components for a transition band, and synthesizing the Zyoton by combining the set of frequency components for the analyte-information-representing band, the set of frequency components for the transition band, and the set of frequency components for the non-analyte-information-representing band.

In another aspect, a system is provided for enabling extraction of a property of an element of a specified environment. The system may include a first processor and a first memory in electrical communication with the first processor, the first memory including instructions which, when executed by a processing unit including at least one of the first processor and a second processor, and in electronic communication with a memory module comprising at least one of the first memory and a second memory, program the processing unit to: select using at least one of: (i) at least one waveform family, and (ii) at least one waveform generator, a set of frequency components for an analyte-information-representing band and a set of frequency components for a non-analyte-information representing band; and synthesize a Zyoton by combining the set of frequency components selected for the analyte-information-representing band and the set of frequency components selected for the non-analyte-information-representing band.

At least one frequency component in the set of frequency components for the analyte-information-representing band corresponds to a property to be extracted; at least one of the frequency components for the non-analyte-information-representing band does not correspond significantly to the property to be extracted; and the selected set of frequency components of the waveform family allow the Zyoton to propagate through a substantially constant propagation medium over a length of a collision grid without substantial change in morphology thereof. In various embodiments, the instructions can program the processing unit to perform one or more of the method steps described above.

In another aspect, an article of manufacture is provided that includes a non-transitory storage medium having stored therein instructions which, when executed by a processing unit program the processing unit, which is in electronic communication with a memory module, to enable extraction of a property of an element of a specified environment. The instructions may program the processing unit to: select using at least one of: (i) at least one waveform family, and (ii) at least one waveform generator, a set of frequency components for an analyte-information-representing band and a set of frequency components for a non-analyte-information representing band; and synthesize a Zyoton by combining the set of frequency components selected for the analyte-information-representing band and the set of frequency components selected for the non-analyte-information-representing band.

At least one frequency component in the set of frequency components for the analyte-information-representing band corresponds to a property to be extracted; at least one of the frequency components for the non-analyte-information-representing band does not correspond significantly to the property to be extracted; and the selected set of frequency components of the waveform family allow the Zyoton to propagate through a substantially constant propagation medium over a length of a collision grid without substantial change in morphology thereof. In various embodiments, the instructions can program the processing unit to perform one or more of the method steps described above.

In another aspect, another method is provided for enabling extraction of a property of an element of a specified environment. The method may include receiving a representative spectral signal from a data-collection domain, the representative spectral signal indicating a property of the element of the specified environment; generating a Zyoton from at least one waveform family, the at least one waveform family being independent of the data-collection domain; and generating a co-dependent carrier kernel for conditioning at least one feature corresponding to the representative spectral signal. In some instances, the element of the specified environment includes an analyte, and the property of the element of the specified environment includes concentration of the analyte. In some cases, the specified environment may include at least one confounder.

In some cases, the specified environment may include a portion of skin tissue, and the analyte may include glucose. In certain embodiments, the property of the element of the specified environment that is represented by the representative spectral signal includes energy loss via at least one of: (i) absorption by the analyte, (ii) absorption by the at least one confounder, (iii) noise generated by variation in absorption by the at least one confounder, and (iv) noise generated by scattering. The at least one confounder may include a dominant confounder. The representative signal may represent information about an analyte and/or one or more confounders.

In various embodiments, the representative signal includes a first model signal, and generating the Zyoton may include: obtaining a transformed signal from the first model signal representing energy loss via absorption by the analyte; adding a noise signal to the transformed signal to obtain a second signal; determining frequency components of the second signal; using the frequency components of the second signal, determining a number of frequency components required to separate a high analyte absorption region of the transformed signal from a low analyte absorption region of the transformed signal; selecting the at least one waveform family according to a morphology of one of the first model signal, the transformed signal, and the second signal; obtaining a base Zyoton based on the at least one selected waveform family; and selecting the determined required number of frequency components of the base Zyoton as frequency components of the Zyoton.

In some instances, the noise signal corresponds to an amount of noise that is a multiple of at least one of: (i) a noise associated with the first model signal, and (ii) a noise associated with the transformed signal; and the determined required number of frequency components represents a number of frequency components (k) required to separate the high analyte absorption region of the transformed signal from the low analyte absorption region of the transformed signal in presence of the specified amount of noise. In some cases, obtaining the transformed signal may include generating a second derivative of one of: the first model signal and an interpolated first model signal.

In other cases, obtaining the transformed signal may include generating a first composite signal by combining with the first model signal a second model signal representing energy loss via absorption by at least one non-dominant confounder, where the determined required number of frequency components represents a number of frequency components (m) required to separate the high analyte absorption region of the transformed signal from the low analyte absorption region of the transformed signal in presence of the at least one non-dominant confounder.

In still other cases, obtaining the transformed signal may include generating a second composite signal by combining with the first model signal a third model signal representing energy loss via variations in absorption by a dominant confounder; where the determined required number of frequency components represents a number of frequency components (j) required to separate the high analyte absorption region of the transformed signal from the low analyte absorption region of the transformed signal in presence of the dominant confounder and the specified amount of noise.

The Zyoton may include k analyte-information-representing components, $k \geq 1$, and the method may further include: setting amplitudes of the k analyte-information-representing components within a first range of amplitudes according to an amplitude profile. The first model signal may correspond to a pure-component analyte signal, and the transformed signal can be first, second, or higher-order derivative thereof.

In various embodiments, the method may further include generating the amplitude profile by: generating a plurality of wavelength-region pairs, each pair having a high absorption representing wavelength region corresponding to a respective wavelength range of the representative spectral signal and a low absorption representing wavelength region corresponding to a different respective wavelength range of the representative spectral signal; for each pair in the plurality of wavelength-region pairs, computing a ratio of a magnitude of a region of the transformed signal corresponding to the high absorption representing wavelength region and a magnitude of a region of the transformed signal corresponding to the low absorption representing wavelength region; determining a range of the magnitude ratios; and setting the amplitude profile as a function bounded by the range of magnitude ratios, the function being one of linear, quadratic, and exponential.

In some embodiments, the Zyoton includes k analyte-information-representing components, $k \geq 1$, and j non-analyte-information representing components, $j \geq 1$, the k analyte-information-representing components having amplitudes within a first range, and the method may further includes: randomly setting amplitudes of the j non-analyte-information representing components within a second range of amplitudes, any amplitude in the second range being less than 1/100 of any amplitude in the first range. In some instances, the Zyoton further includes m transition components, $m \geq 1$, and the method further includes: randomly setting amplitudes of the m transition components within a third range of amplitudes, any amplitude in the third range being at least two times any amplitude in the second range.

Generating the co-dependent carrier kernel may include: for each of the k analyte-information-representing major components of the Zyoton, including in the carrier kernel as a corresponding analyte-information-representing major component a frequency component having a frequency within a specified threshold $\sigma$ of frequency of the corresponding analyte-information-representing k component of the Zyoton; and including in the carrier kernel as at least one non-major component, at least one of: at least one harmonic of at least one of an analyte-information-representing component, a transition component, and non-analyte-information-representing component included in the carrier kernel; and for at least one non-major component of the Zyoton, including in the carrier kernel a frequency component having a frequency within the specified threshold $\sigma$ of frequency of the corresponding non-major component of the Zyoton.

In some instances, one of: the non-major component of the Zyoton is a transition component, and the corresponding non-major component of the carrier kernel is a transition component; and the non-major component of the Zyoton is a non-analyte-information-representing j component, and the corresponding non-major component of the carrier kernel is a non-analyte-information-representing j component. In certain embodiments, the method may further include setting amplitudes of the information-representing, transition, and non-information representing frequency components of the carrier kernel according to the amplitudes of the respective analyte-information-representing, transition, and non-analyte-information-representing Zyoton components scaled by a pre-set scaling factor.

The method may also include: selecting an amplitude scaling coefficient such that: (i) a difference between a scaled velocity of the Zyoton, scaled by the amplitude scaling factor, and a velocity of the carrier kernel does not exceed a specified velocity difference threshold $\kappa^{SYN}$; and setting amplitudes of the analyte-information-representing, transition, and non-analyte-information-representing frequency components of the carrier kernel according to the amplitudes of the respective analyte-information-representing, transition, and non-analyte-information-representing Zyoton components scaled by the selected scaling factor.

In another aspect, another system is provided for enabling extraction of a property of an element of a specified environment. The system may include a first processor and a first memory in electrical communication with the first processor, the first memory including instructions which, when executed by a processing unit including at least one of the first processor and a second processor, and in electronic communication with a memory module comprising at least one of the first memory and a second memory, program the processing unit to: receive a representative spectral signal from a data-collection domain, the representative spectral signal indicating a property of the element of the specified environment; generate a Zyoton from at least one waveform family, the at least one waveform family being independent of the data-collection domain; and generate a co-dependent carrier kernel for conditioning at least one feature corresponding to the representative spectral signal. In various embodiments, the instructions can program the processing unit to perform one or more of the method steps described above.

In another aspect, another article of manufacture is provided that includes a non-transitory storage medium having stored therein instructions which, when executed by a processing unit program the processing unit, which is in electronic communication with a memory module, to enable extraction of a property of an element of a specified environment. The instructions may program the processing unit to: receive a representative spectral signal from a data-collection domain, the representative spectral signal indicating a property of the element of the specified environment; generate a Zyoton from at least one waveform family, the at least one waveform family being independent of the data-collection domain; and generate a co-dependent carrier kernel for conditioning at least one feature corresponding to the representative spectral signal. In various embodiments, the instructions can program the processing unit to perform one or more of the method steps described above.

Systems and Methods of Universal Projection

In another aspect, a method is provided for quantitating an analyte. The method may include: receiving from an uncharacterized sample an energy change value to be mapped, the energy change value corresponding to an uncharacterized sample; mapping the energy change value to be mapped to a quantity of an analyte in the uncharacterized sample, via an individual projector curve associating: (i) energy change values obtained from a synthetic reference system to analyte quantities of the reference system, and (ii) energy change values obtained from a non-synthetic reference system to the analyte quantities of the reference system.

The method may further include: computing a representative absorption gradient (AG) using a first set of energy change values corresponding to a first feature pair, each energy change value in the first set corresponding to a respective path of radiation through a medium to be analyzed; selecting the individual projector curve from a plurality of projector curves using the representative gradient value associated with the first feature pair; and determining a quantity of an analyte using the selected individual projector curve, the energy change value to be mapped being a representative energy change value associated with the first feature pair.

The energy change value to be mapped can be a net renormalized spectral energy gain, which may be optionally normalized. In some cases, the representative gradient value may include a normalized AG (NAG), and the method further includes: weighting the representative gradient associated with the first feature pair by a weight associated with the first feature pair, to obtain the NAG. Computing the representative energy change value can include weighting one energy change value from the first set of energy change values by a weight associated with the first feature pair. In certain instances, a plurality of feature pairs may include the first feature pair, and the method may further include: generating a set of acceptable feature pairs from the plurality of feature pairs; for each feature pair in the set of acceptable feature pairs computing a respective absorption gradient (AG) using a respective set of energy change values corresponding to the feature pair; computing the representative AG value as an average of the respective AGs associated with each of the acceptable feature pairs. The energy value change can be a net, renormalized spectral energy gain corresponding to a feature or a feature pair, which may be optionally normalized.

In various embodiments, generating the set of acceptable feature pairs may include testing for each feature pair in the plurality of feature pairs monotonicity of the corresponding set of energy change values across a plurality of illumination states. Computing the AG for each acceptable feature pair may include: determining a slope of a regression of the corresponding set of energy change values with respect to the illumination states, the illumination states being ordered such that successive illumination states represent monotonically changing distance between the source and at least one detector.

Prior to computing the average, the method may further include normalizing each of the AGs corresponding to the acceptable feature pairs using a weight associated with the corresponding acceptable feature pair. In some cases, computing the representative energy change value includes: for each acceptable feature pair, selecting one energy change value from the respective set of energy change values; weighting for each acceptable feature pair, the selected energy change value by a weight associated with the acceptable feature pair; and setting an average of the weighted energy change values as the representative energy change value. In some embodiments, the uncharacterized sample includes a portion of tissue; and the analyte includes glucose. In some embodiments, the energy change includes one of energy gain and energy loss.

In another aspect, a system is provided for quantitating an analyte. The system may include a first processor and a first memory in electrical communication with the first processor, the first memory including instructions which, when executed by a processing unit including at least one of the first processor and a second processor, and in electronic communication with a memory module comprising at least one of the first memory and a second memory, program the processing unit to: receive an energy change value to be mapped, the energy change value corresponding to an uncharacterized sample; and map the energy change value to be mapped to a quantity of an analyte in the uncharacterized sample, via an individual projector curve associating: (i) energy change values obtained from a synthetic reference system to analyte quantities of the reference system, and (ii) energy change values obtained from a non-synthetic reference system to the analyte quantities of the reference system. In various embodiments, the instructions can program the processing unit to perform one or more of the method steps described above.

In another aspect, an article of manufacture is provided that includes a non-transitory storage medium having stored therein instructions which, when executed by a processing unit program the processing unit, which is in electronic communication with a memory module, to quantitate an analyte. The instructions may program the processing unit to: receive an energy change value to be mapped, the energy change value corresponding to an uncharacterized sample; and map the energy change value to be mapped to a quantity of an analyte in the uncharacterized sample, via an individual projector curve associating: (i) energy change values obtained from a synthetic reference system to analyte quantities of the reference system, and (ii) energy change values obtained from a non-synthetic reference system to the analyte quantities of the reference system. In various embodiments, the instructions can program the processing unit to perform one or more of the method steps described above.

System and Method of Generating a Projector Curve Set

In another aspect, a method is provided for calibrating a measurement system for non-invasive analyte measurement. The method may include obtaining from a selected plurality of synthetic medium samples, each having a reference analyte concentration, a plurality of energy-value sets from the measurement system, each energy value in a particular energy-value set corresponding to a respective reference analyte concentration from the selected plurality of synthetic medium samples; generating a composite projector curve using the plurality of energy value sets and the plurality of reference analyte concentrations; and partitioning the composite projector curve into a set of non-overlapping individual projector curves according to a set of slopes of the composite projector curve, each individual projector curve being identified by a lower bound analyte concentration and an upper bound analyte concentration. In some instances, the plurality of energy-value sets includes a first energy-value set, each energy value in the first energy-value set corresponding to a first reference analyte concentration, and the method may further include: excluding from the first energy-value set an energy value that is different from a mean of the energy values by a specified threshold.

In various embodiments, the method may further include obtaining from representative subjects a plurality of groups of energy value vectors from the measurement system, each energy-value-vector group corresponding to a respective analyte concentration determined using a reference invasive measurement system, and each energy-value vector in a particular group corresponding to a respective feature pair; partitioning the plurality of groups of energy-value vectors into a plurality of projection sets, such that the analyte concentration corresponding to any energy-value-vector group in each projection set is within lower and upper bound analyte concentrations corresponding to a single respective individual projector curve from the set of individual projector curves; computing for each energy-value-vector group in each projection set, an average of normalized absorption gradients (NAGs), each NAG corresponding to an energy-value vector that corresponds to an acceptable feature pair; for each projector curve: designating as a lower bound NAG a minimum of averaged NAGs of all energy-value-vector groups of the corresponding projection set; and designating as an upper bound NAG a maximum of averaged NAGs of all energy-value-vector groups of the corresponding projection set. An energy-value vector may include a plurality of energy values, each energy value corresponding to an illumination state in an illumination sequence. In some instances, the partitioning step may include rejecting from a group of energy-value vectors any non-monotonic energy-value vector.

In another aspect, a system is provided for calibrating a measurement system for non-invasive analyte measurement. The system may include a first processor and a first memory in electrical communication with the first processor, the first memory including instructions which, when executed by a processing unit including at least one of the first processor and a second processor, and in electronic communication with a memory module comprising at least one of the first memory and a second memory, program the processing unit to: obtain from a selected plurality of synthetic medium samples, each having a reference analyte concentration, a plurality of energy-value sets from the measurement system, each energy value in a particular energy-value set corresponding to a respective reference analyte concentration from the selected plurality of synthetic medium samples.

The instructions may program the processing unit to generate a composite projector curve using the plurality of energy value sets and the plurality of reference analyte concentrations; and partition the composite projector curve into a set of non-overlapping individual projector curves according to a set of slopes of the composite projector curve, each individual projector curve being identified by a lower bound analyte concentration and an upper bound analyte concentration. In various embodiments, the instructions can program the processing unit to perform one or more of the method steps described above.

In another aspect, an article of manufacture is provided that includes a non-transitory storage medium having stored therein instructions which, when executed by a processing unit program the processing unit, which is in electronic communication with a memory module, to calibrate a measurement system for non-invasive analyte measurement. The instructions may program the processing unit to: obtain from a selected plurality of synthetic medium samples, each having a reference analyte concentration, a plurality of energy-value sets from the measurement system, each energy value in a particular energy-value set corresponding to a respective reference analyte concentration from the selected plurality of synthetic medium samples.

The instruction may program the processing unit to generate a composite projector curve using the plurality of energy value sets and the plurality of reference analyte concentrations; and partition the composite projector curve into a set of non-overlapping individual projector curves according to a set of slopes of the composite projector curve, each individual projector curve being identified by a lower bound analyte concentration and an upper bound analyte concentration. In various embodiments, the instructions can program the processing unit to perform one or more of the method steps described above.

In another aspect, a method is provided for computing analyte concentration in a medium. The method may include: selecting a member of a projector curve set according to a normalized absorption gradient (NAG) value, such that the NAG value is within a range of minimum and maximum NAG values associated with that member; and interpolating analyte concentration using a slope and an intercept of the selected member. The method may further include: receiving for a feature pair, a respective net renormalized spectral energy gain (NRSEG) value for each one of a plurality of illumination states; and designating the feature pair as acceptable feature pair, if the respective NRSEG values are monotonic across the illumination states, and rejecting the feature pair, otherwise.

The method may also include: receiving for a first acceptable feature pair, a respective net renormalized spectral energy gain (NRSEG) value for each one of a plurality of illumination states; computing a first absorption gradient (AG), typically but not necessarily normalized, across the illumination states using the NRSEG values associated with the first acceptable feature pair; and computing the NAG by applying to the first AG a first weight corresponding to the first acceptable feature pair. The method may also include: receiving for a second acceptable feature pair, a respective net renormalized spectral energy gain (NRSEG) value for each one of the plurality of illumination states; computing a second absorption gradient (AG) across the illumination states using the NRSEG values associated with the second acceptable feature pair; and computing the NAG by applying to the second AG a second weight corresponding to the second acceptable feature pair and averaging the first and second weighted AGs.

In another aspect, a system is provided for computing analyte concentration in a medium. The system may include a first processor and a first memory in electrical communication with the first processor, the first memory including instructions which, when executed by a processing unit including at least one of the first processor and a second processor, and in electronic communication with a memory module comprising at least one of the first memory and a second memory, program the processing unit to: select a member of a projector curve set according to a normalized absorption gradient (NAG) value, such that the NAG value is within a range of minimum and maximum NAG values associated with that member, and interpolate analyte concentration using a slope and an intercept of the selected member. In various embodiments, the instructions can program the processing unit to perform one or more of the method steps described above.

In another aspect, an article of manufacture is provided that includes a non-transitory storage medium having stored therein instructions which, when executed by a processing unit program the processing unit, which is in electronic communication with a memory module, to compute analyte concentration in a medium. The instructions may program the processing unit to: select a member of a projector curve set according to a normalized absorption gradient (NAG) value, such that the NAG value is within a range of minimum and maximum NAG values associated with that member, and interpolate analyte concentration using a slope and an intercept of the selected member. In various embodiments, the instructions can program the processing unit to perform one or more of the method steps described above.

PPG

In another aspect, a method is provided for generating features for measurement of heart beats. The method may include receiving a signal based on one of reflected and transmitted radiation from a tissue during a global time interval starting at a global start time and ending at a global end time; designating a first portion of the signal starting at the global start time and ending at a first end time less than the global end time as a first feature; designating a second portion of the signal starting at the global start time and ending at a second end time greater than the first end time as a second feature; and identifying a start of a heart-beat cycle within the first feature.

The method may further include determining that an expected end of the heart-beat cycle is absent within the first portion of the signal, designated as the first feature; and designating the first feature as a non-analyte feature. The method may also include determining that the expected end of the heat-beat cycle is present within the second portion of the signal, designated as the second feature; and designating the second feature as an analyte feature. In certain embodiments, the method may include determining a heart rate by: colliding a first conditioned feature waveform derived from the first feature with a co-dependent Zyoton to obtain a first energy change; colliding a second conditioned feature waveform derived from the second feature with a co-dependent Zyoton to obtain a second energy change; computing an end of the heart-beat cycle using the first and second energy changes; and computing the heart-rate using the start of the heart-beat cycle and the end of the heart-beat cycle.

In another aspect, a system is provided for generating features for measurement of heart beats. The system may include a first processor and a first memory in electrical communication with the first processor, the first memory including instructions which, when executed by a processing unit including at least one of the first processor and a second processor, and in electronic communication with a memory module comprising at least one of the first memory and a second memory, program the processing unit to: receive a signal based on one of reflected and transmitted radiation from a tissue during a global time interval starting at a global start time and ending at a global end time; designate a first portion of the signal starting at the global start time and ending at a first end time less than the global end time as a first feature; designate a second portion of the signal starting at the global start time and ending at a second end time greater than the first end time as a second feature; and identify a start of a heart-beat cycle within the first feature. In various embodiments, the instructions can program the processing unit to perform one or more of the method steps described above.

In another aspect, an article of manufacture is provided that includes a non-transitory storage medium having stored therein instructions which, when executed by a processing unit program the processing unit, which is in electronic communication with a memory module, to generate features for measurement of heart beats. The instructions may program the processing unit to: receive a signal based on one of reflected and transmitted radiation from a tissue during a global time interval starting at a global start time and ending at a global end time; designate a first portion of the signal starting at the global start time and ending at a first end time less than the global end time as a first feature; designate a second portion of the signal starting at the global start time and ending at a second end time greater than the first end time as a second feature; and identify a start of a heart-beat cycle within the first feature. In various embodiments, the instructions can program the processing unit to perform one or more of the method steps described above.

BRIEF DESCRIPTION OF THE FIGURES

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 10D shows frequency components from an analyte and confounders;

FIG. 36 shows the scaled intensity and absorbance spectra associated with a single feature, with scaled absorbance for glucose, fat, and water confounders overlaid on the plot;

FIG. 49 shows an example of a mapping between glucose features, non-glucose features, and Zyotons with which these features are collided after conditioning thereof, according to one embodiment;

FIG. 57 depicts the symbolic interaction of components of a Zyoton and a conditioned feature on a synthetic collision grid;

FIGS. 58A-58D are successive pages illustrating the generation of modified frequency components from the collision interactions of components of an original Zyoton and a conditioned feature;

FIGS. 59A-59B are successive pages illustrating the generation of modified frequency components from the collision interactions of components of a different original Zyoton and a conditioned feature;

FIG. 61 schematically shows an overall non-invasive measurement system using collision computing, according to one embodiment;

FIG. 83 shows glucose and non-glucose features in a tabular format;

FIG. 109 shows the mean photon path for skin with a thin dermis and a glucose level of 80 mg/dl;

FIG. 110 shows the mean photon path for skin with a thin dermis and a glucose level of 300 mg/dl;

FIG. 111 shows the mean photon path for skin with a thick dermis and a glucose level of 80 mg/dl;

FIG. 112 shows the mean photon path for skin with a thick dermis and a glucose level of 300 mg/dl;

FIG. 113 shows a photograph of the probe from FIGS. 91 and 92;

FIG. 114 is a photograph of a fabricated mask wheel which contains an optical mask that selectively passes light to individual illumination rings;

FIG. 115A shows the spectrum obtained for tissue;

FIG. 115B shows the second derivative of the spectrum in FIG. 12A;

FIG. 115C shows the second derivative spectra of protein and fat;

FIG. 116 is a schematic diagram of a dynamically-controlled illumination/detection optical system;

FIG. 117 is an illustration of an illumination/detection optical system with angular control;

FIG. 118A is an illustration of varying tissue illumination and detection areas;

Figure 68:
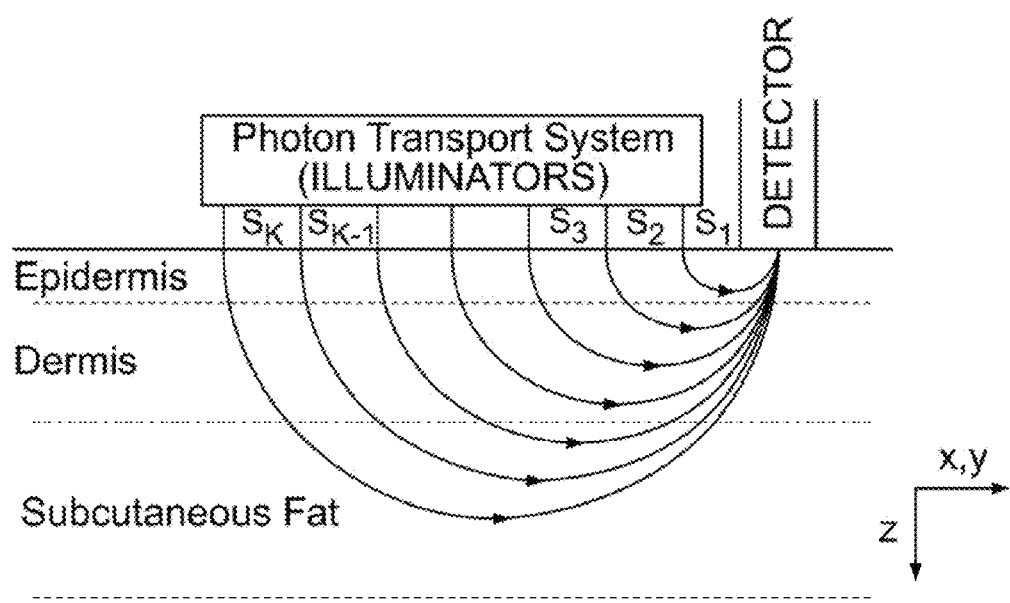
FIG. 68 schematically depicts an illumination/detection system for non-invasive glucose measurement, according to one embodiment.
Figure 118A:
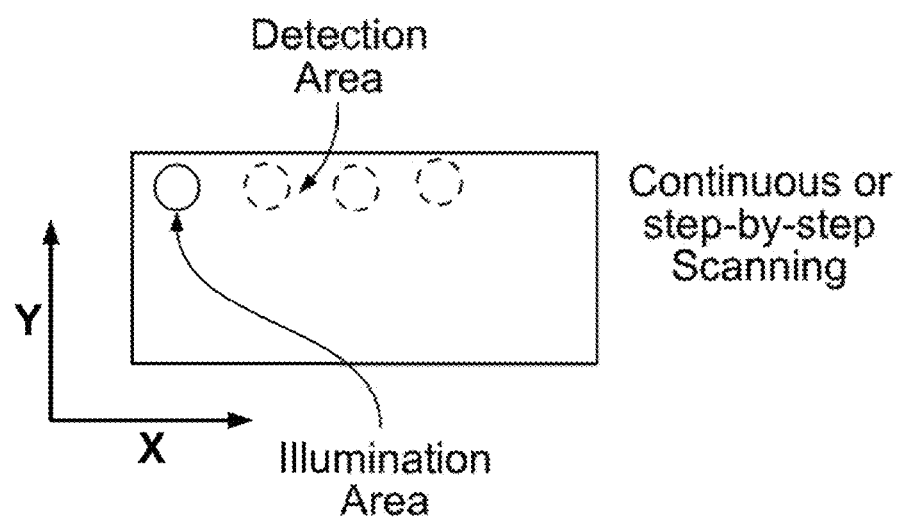
Figure 118B:
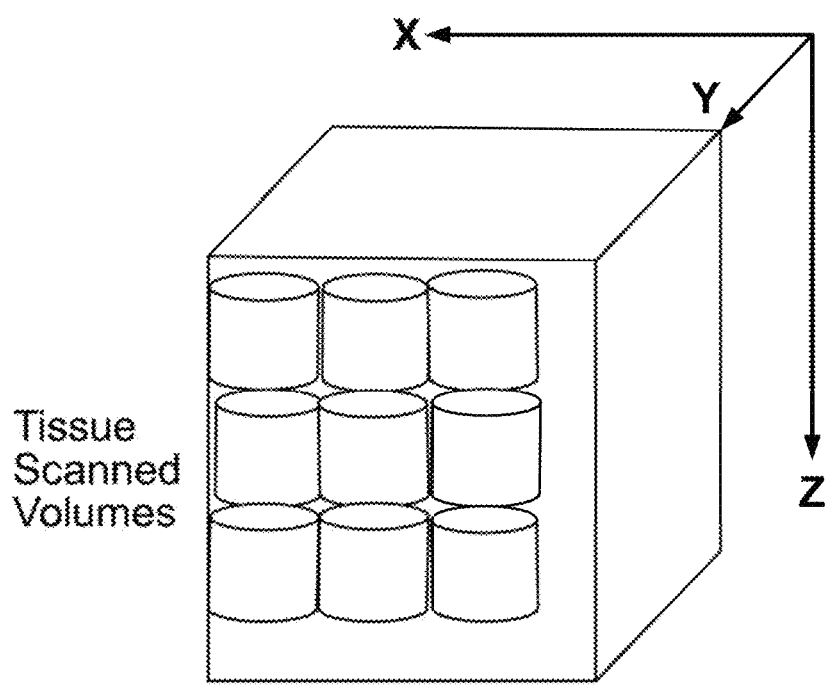
Figure 119A:
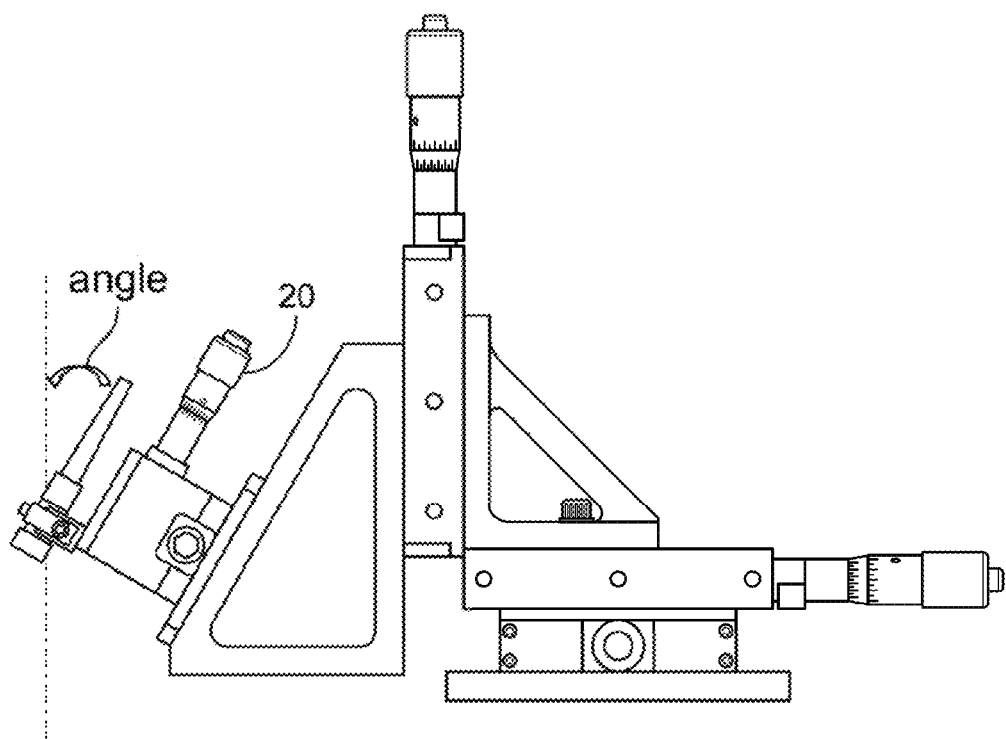
Figure 119B:
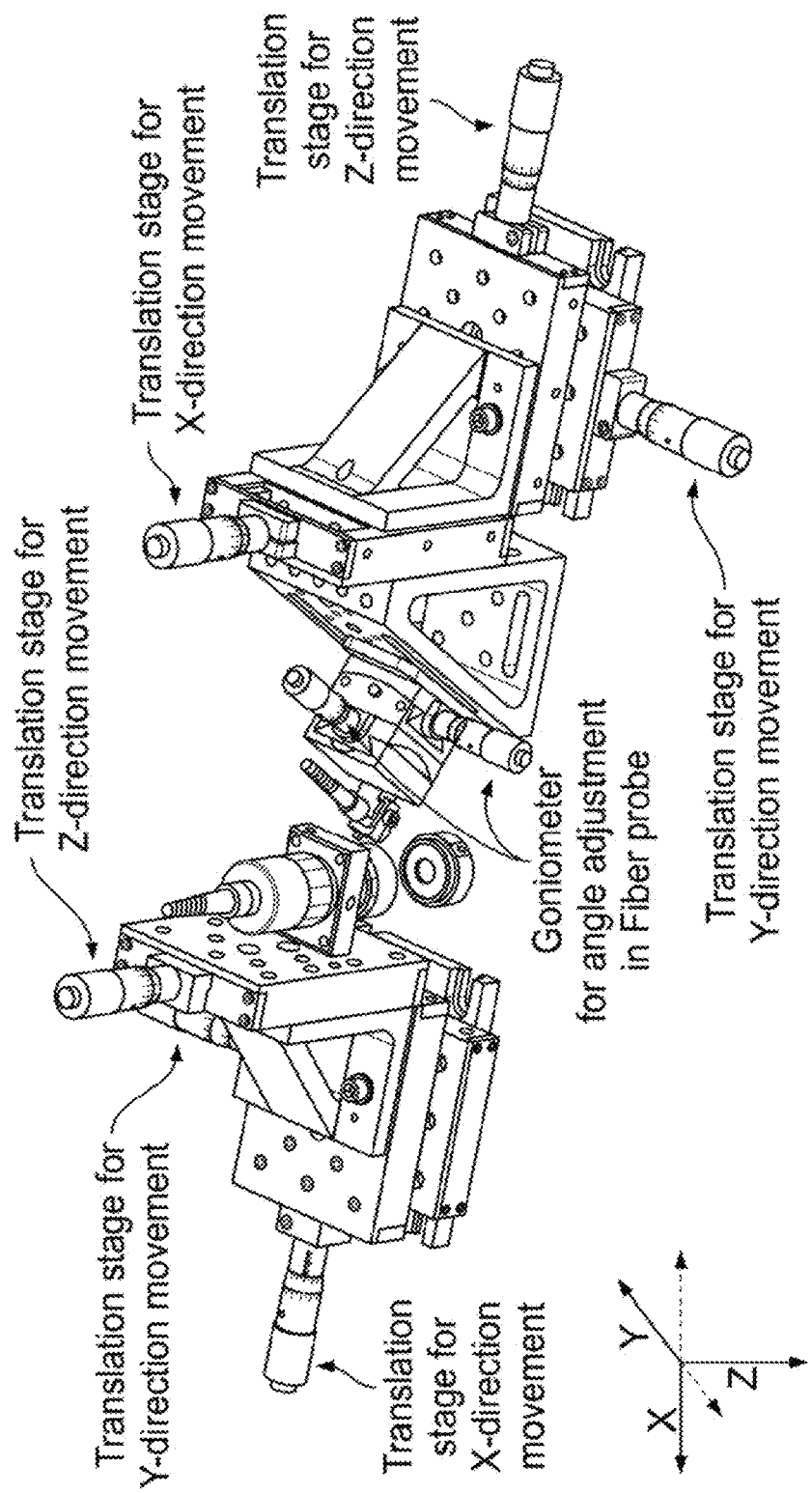
Figure 120:
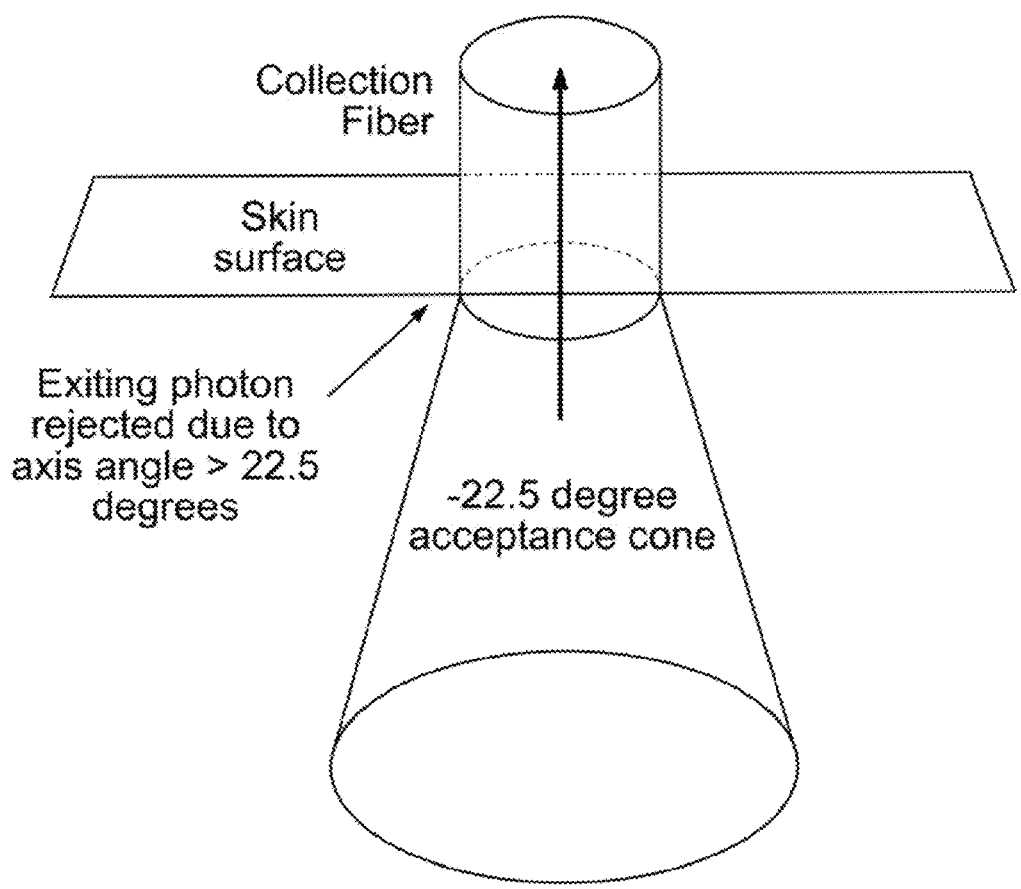
Figure 121:
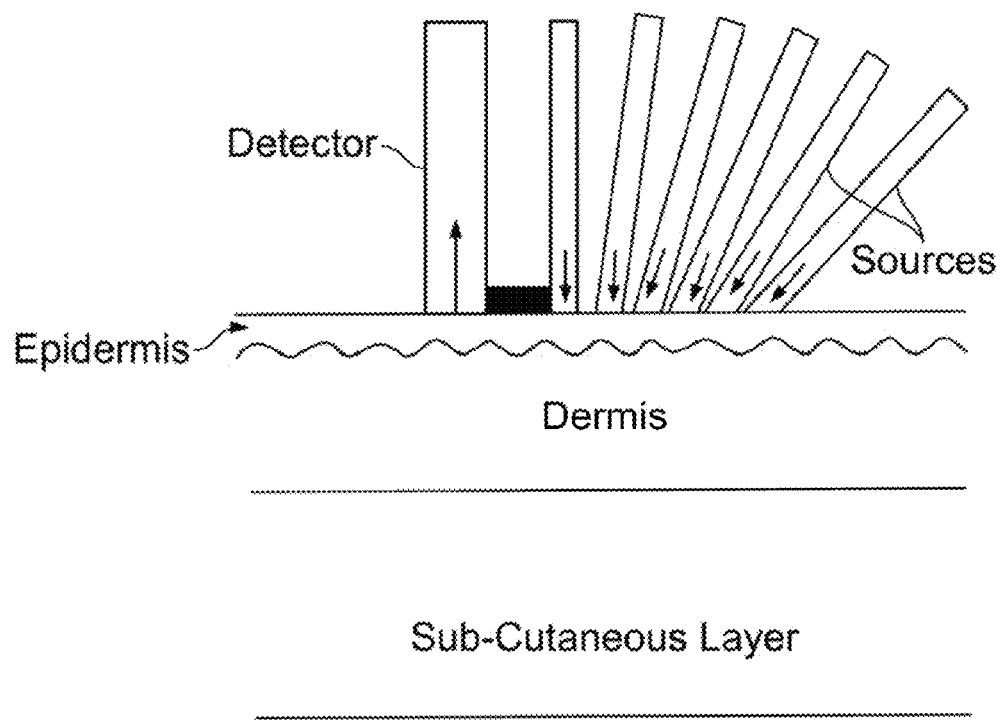
Figure 122:
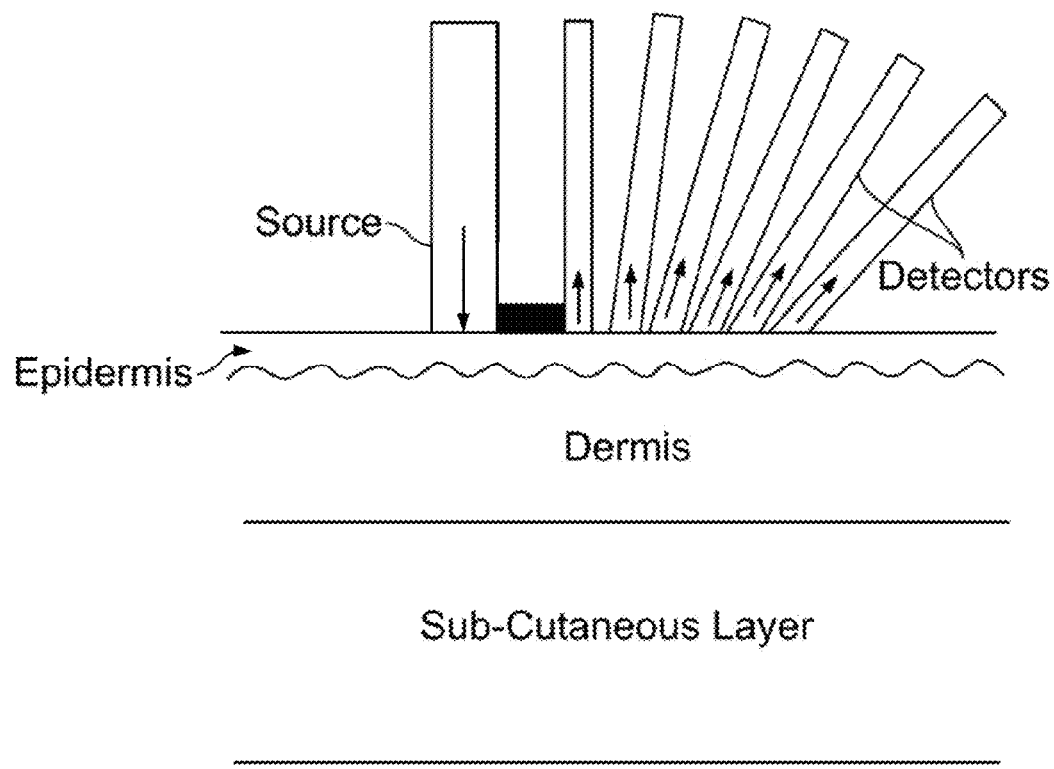
Figure 123:
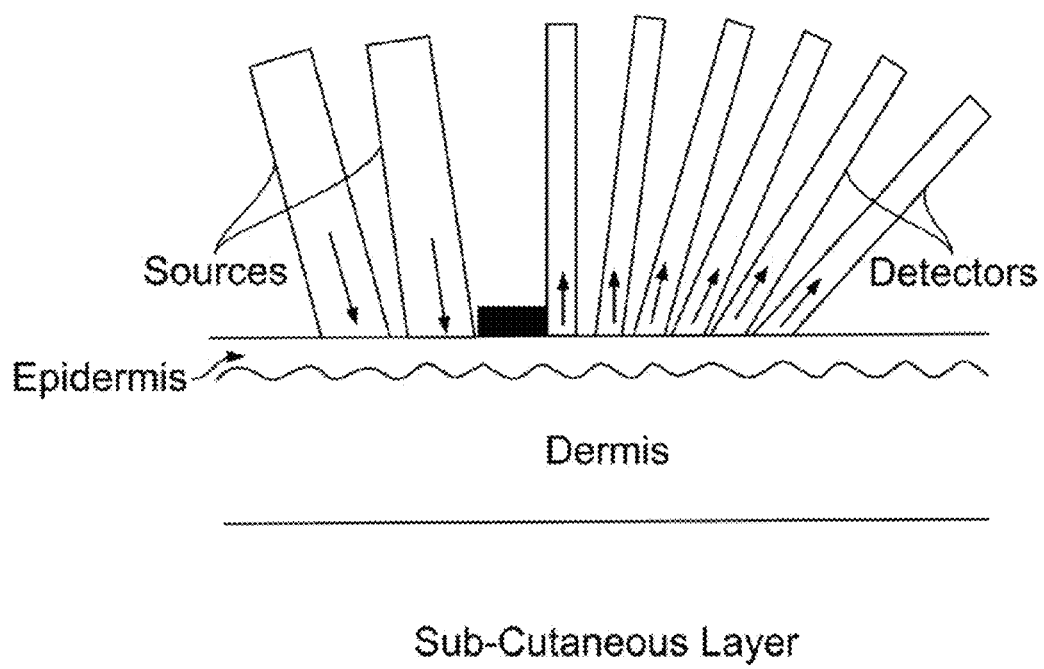
Figure 124A:
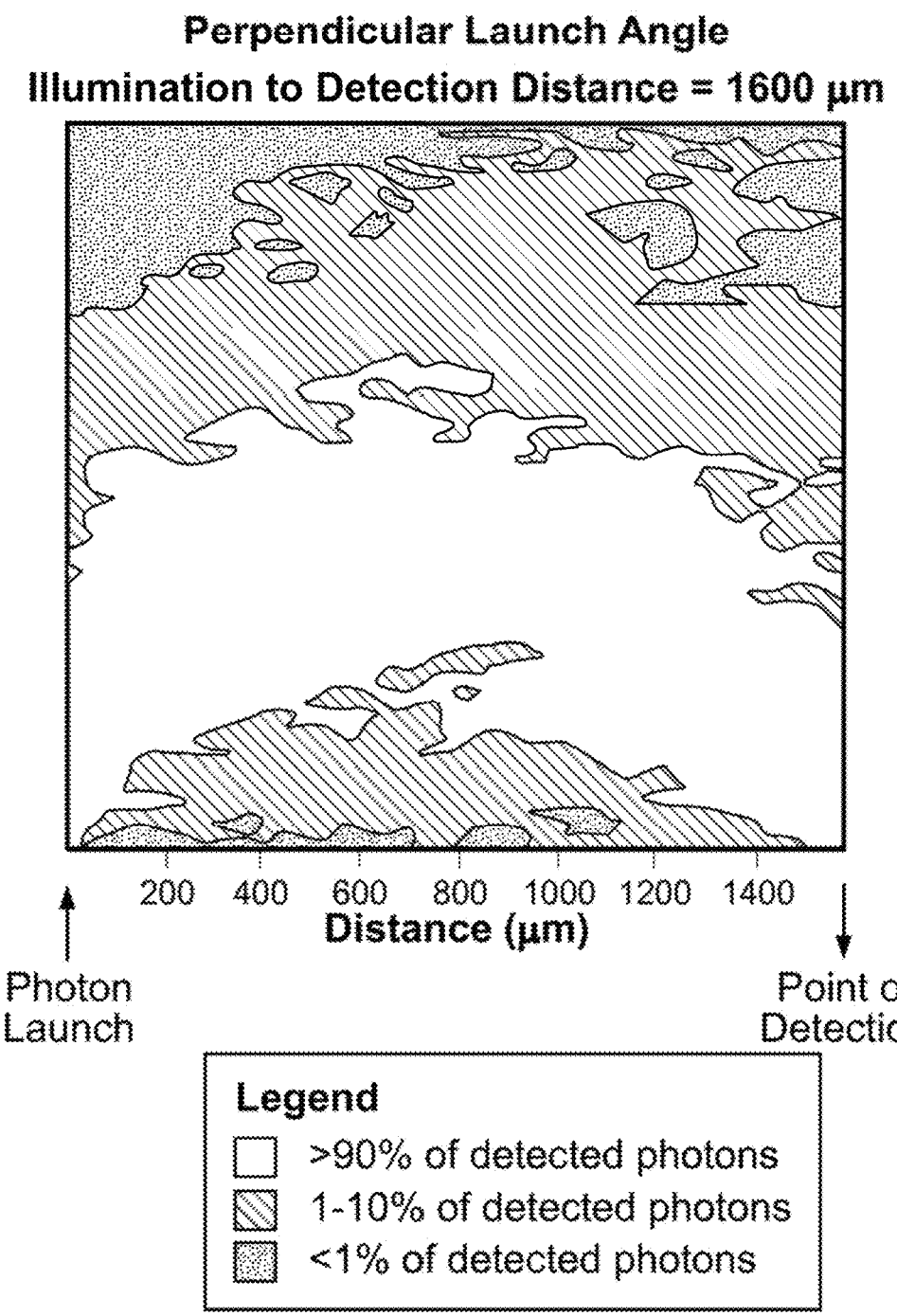
Figure 124B:
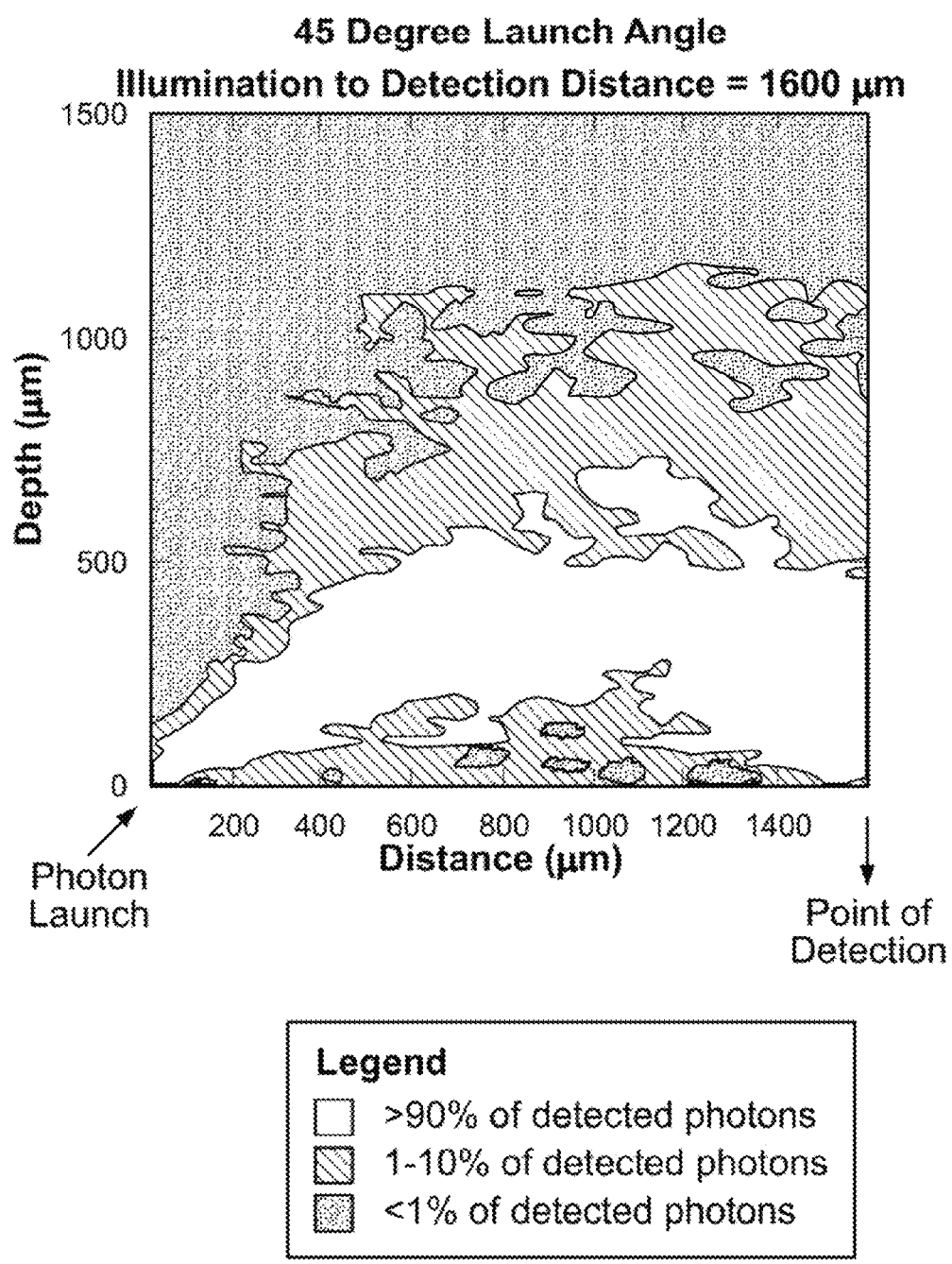
Figure 125:
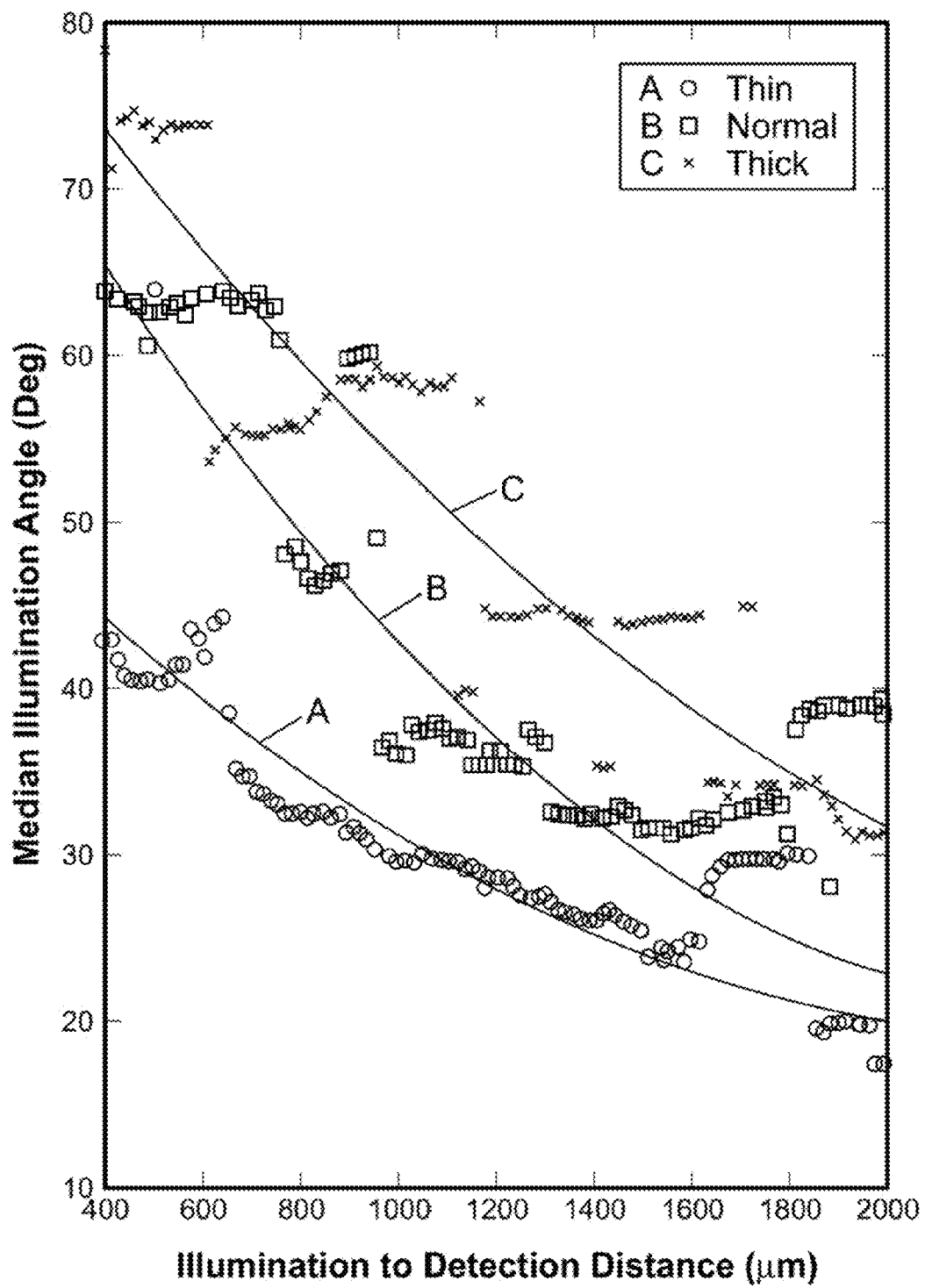
Figure 130:
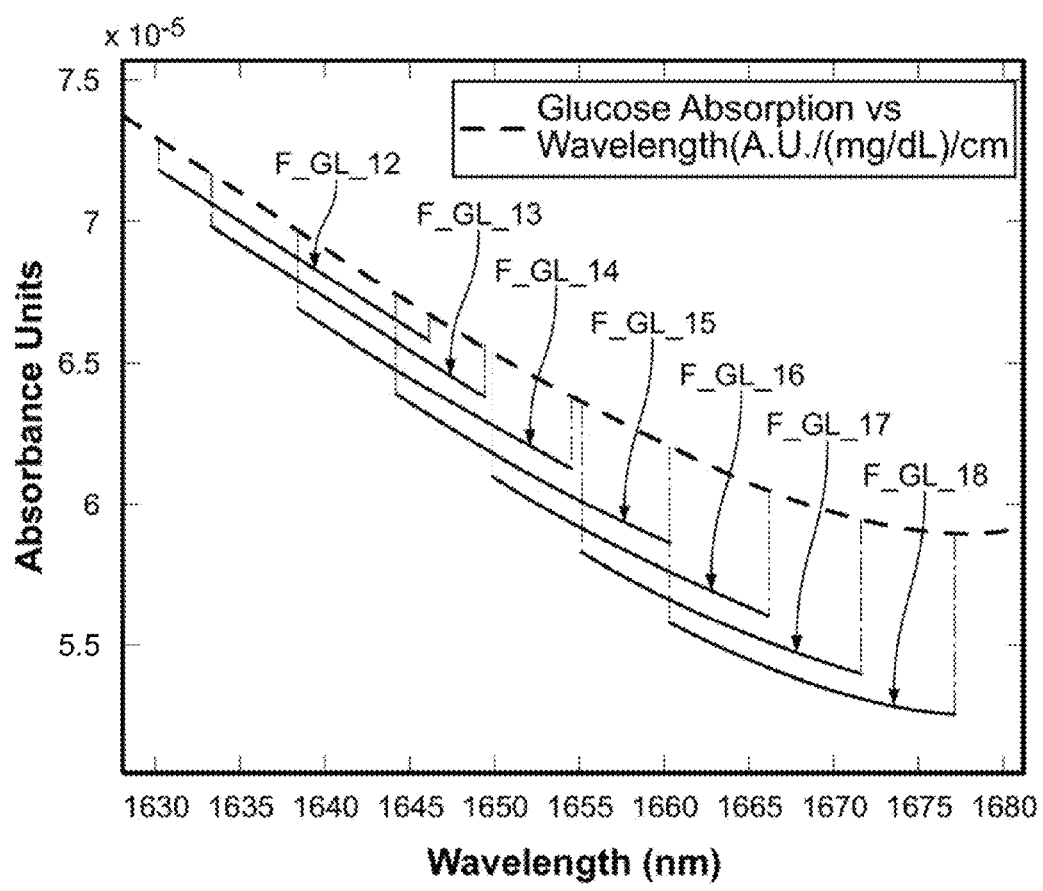
Figure 131A:
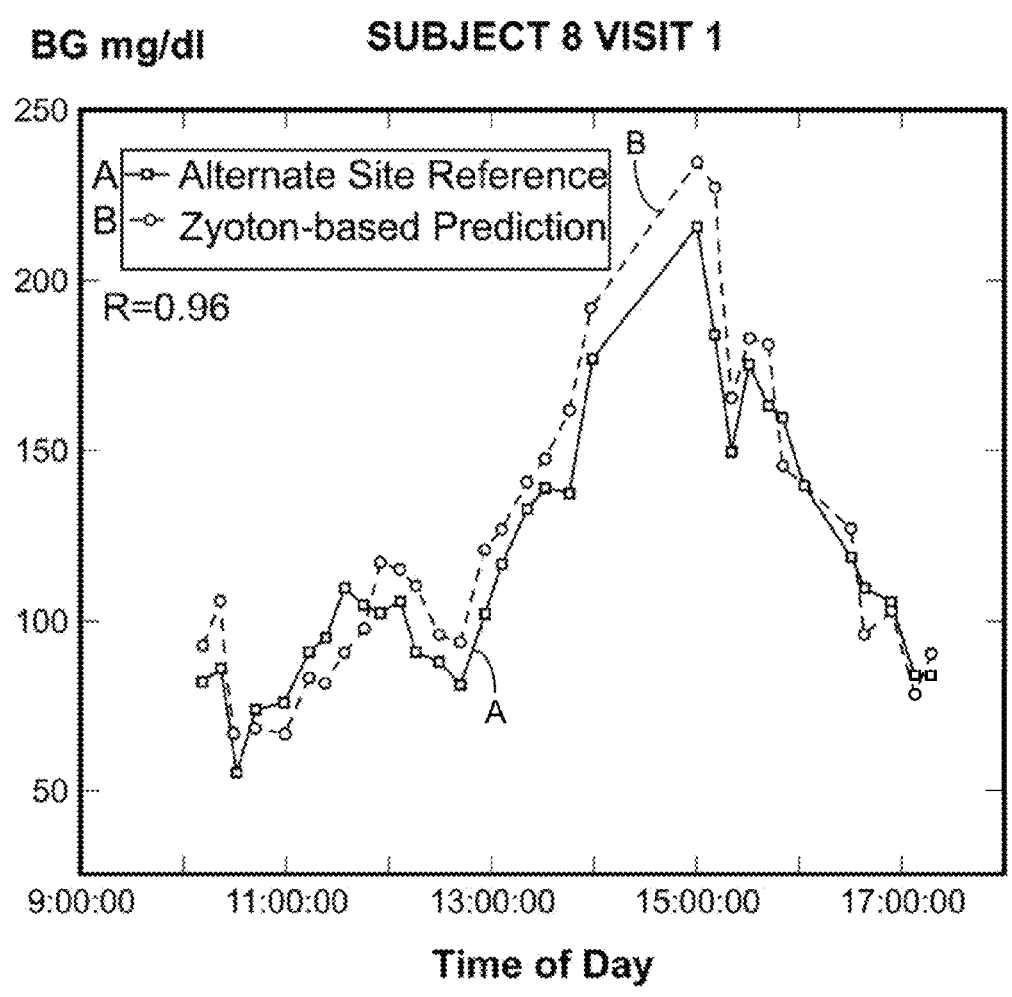
Figure 131B:
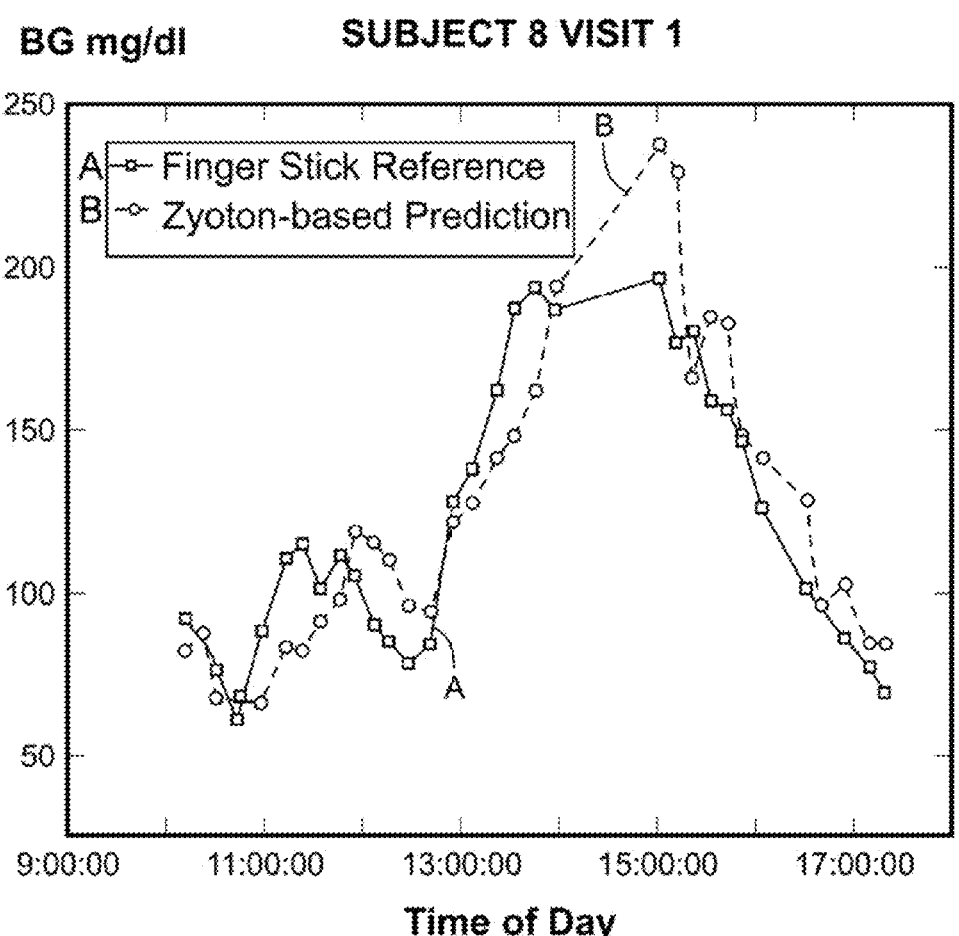
Figure 132A:
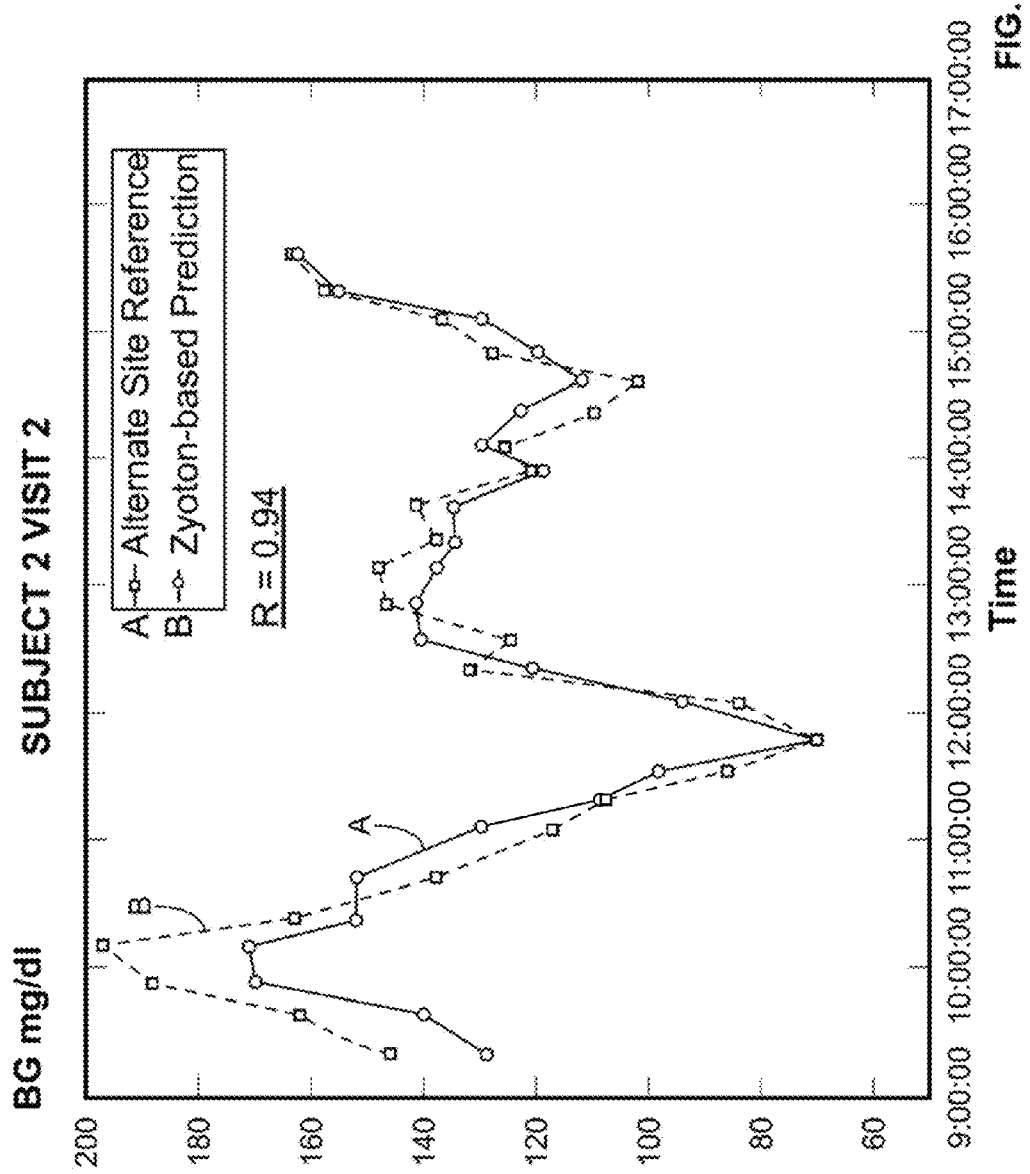
Figure 132B:
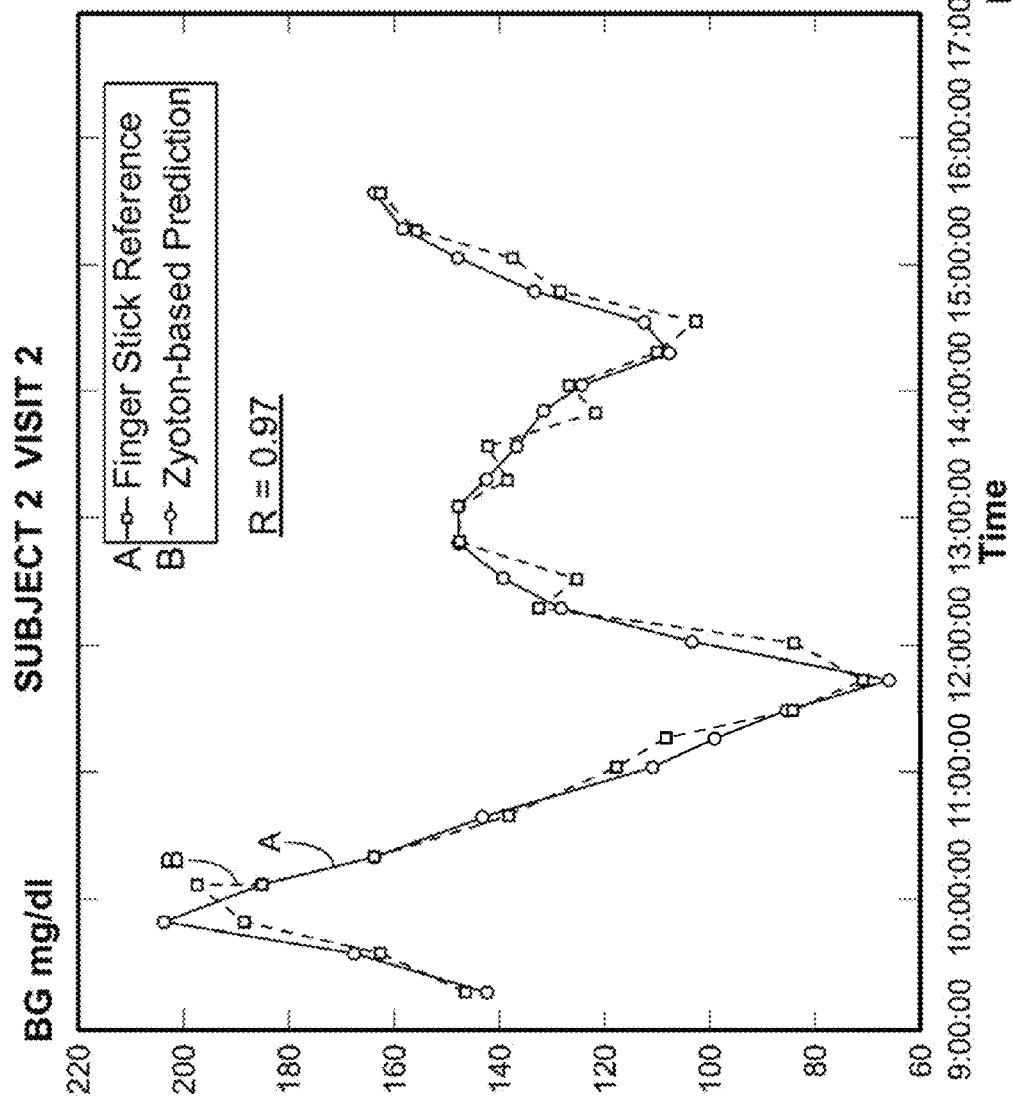
Figure 133:
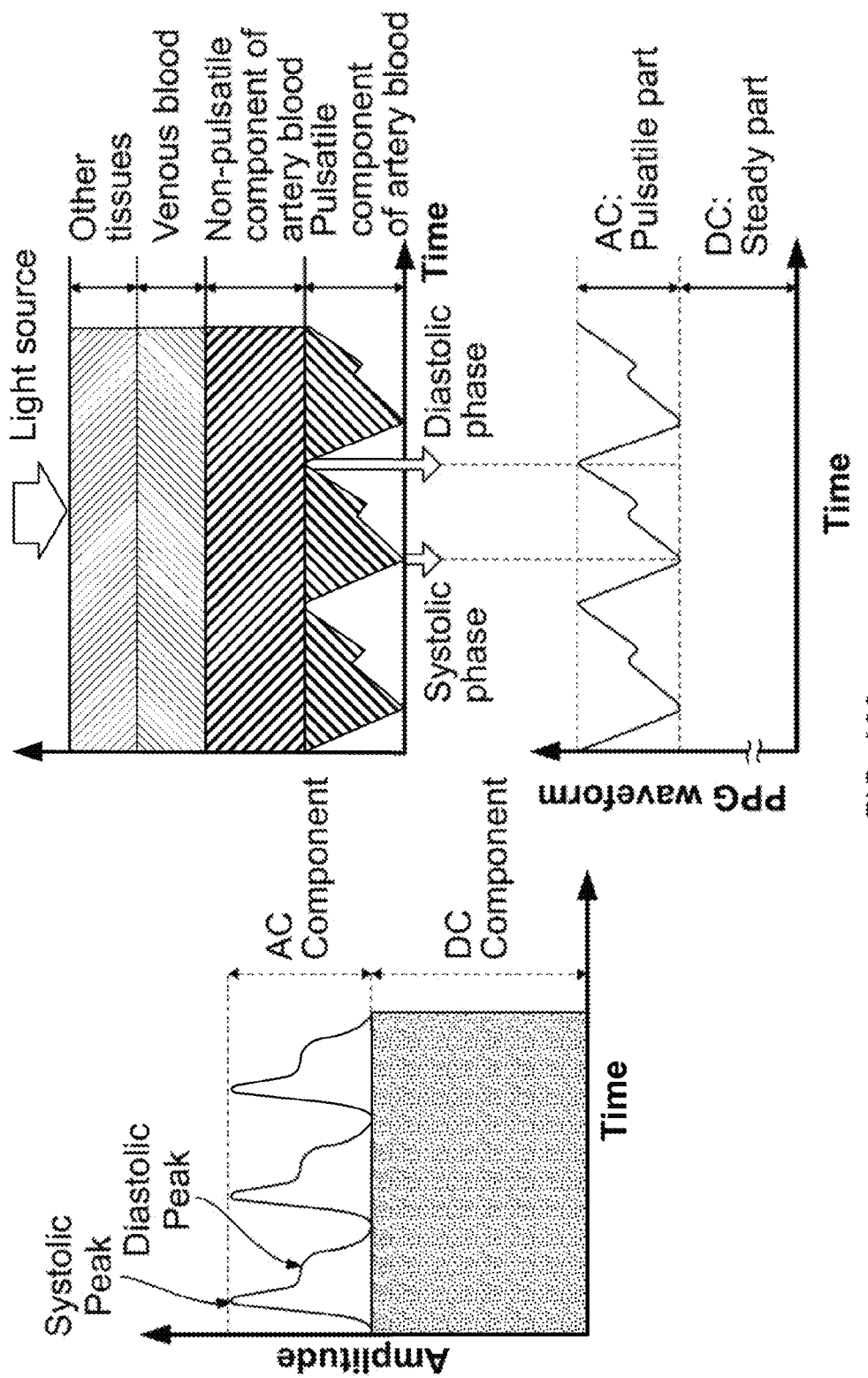
Figure 134:
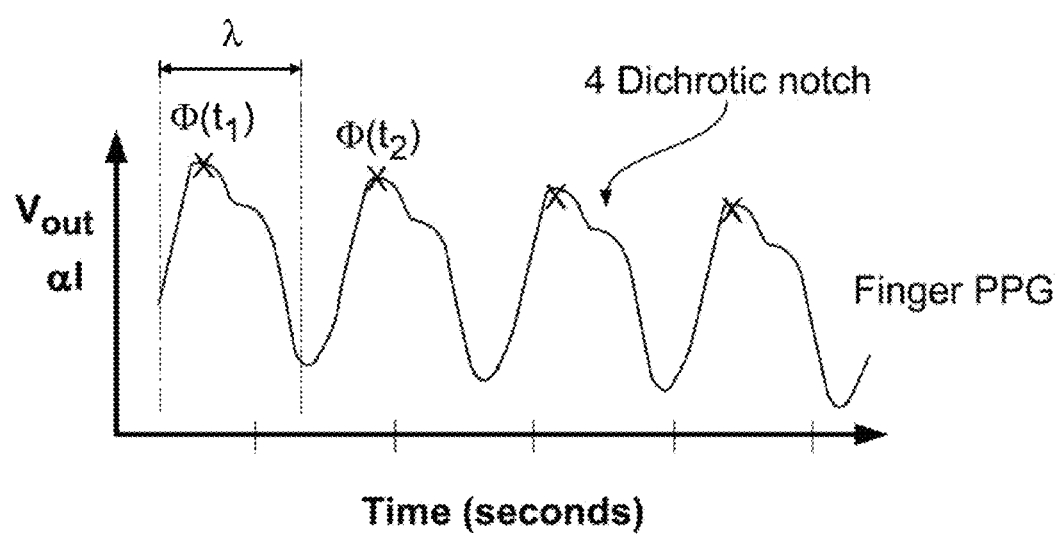
Figure 135A:
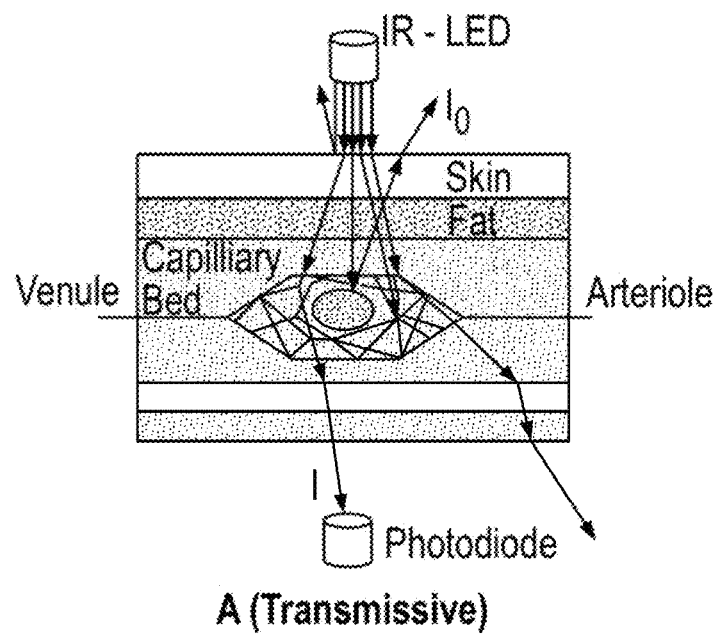
Figure 135B:
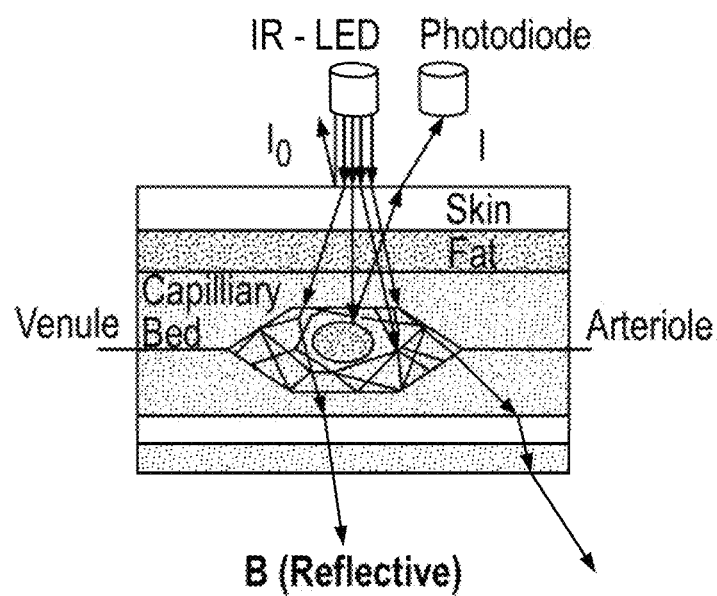
Figure 136A:
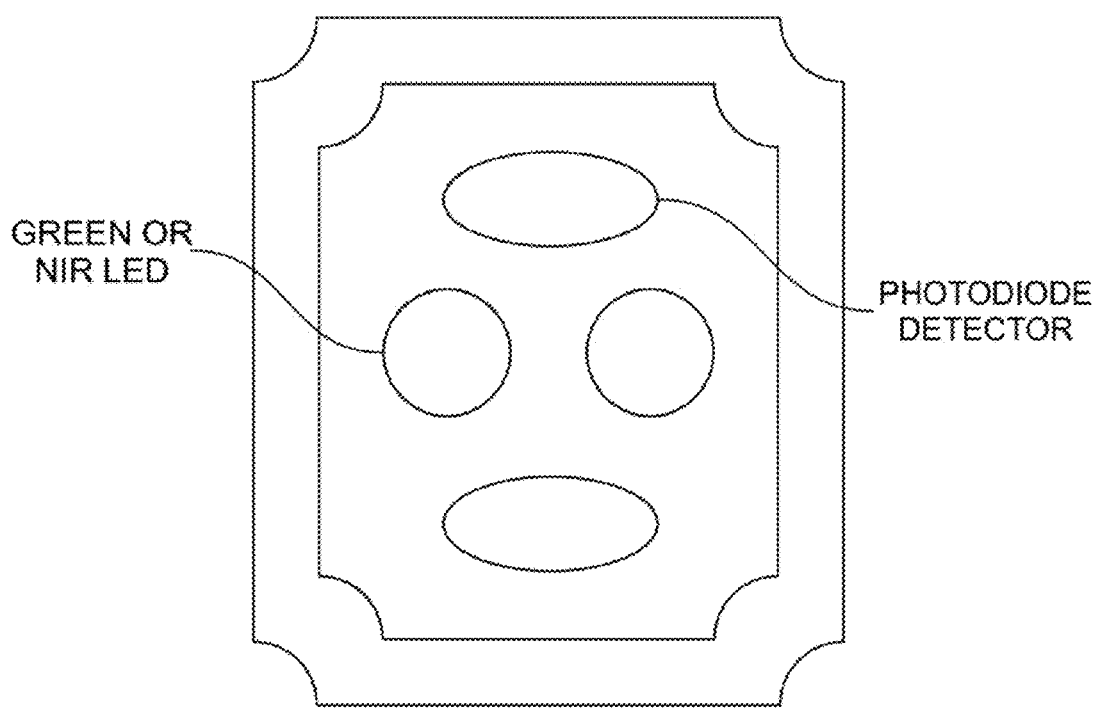
Figure 136B:
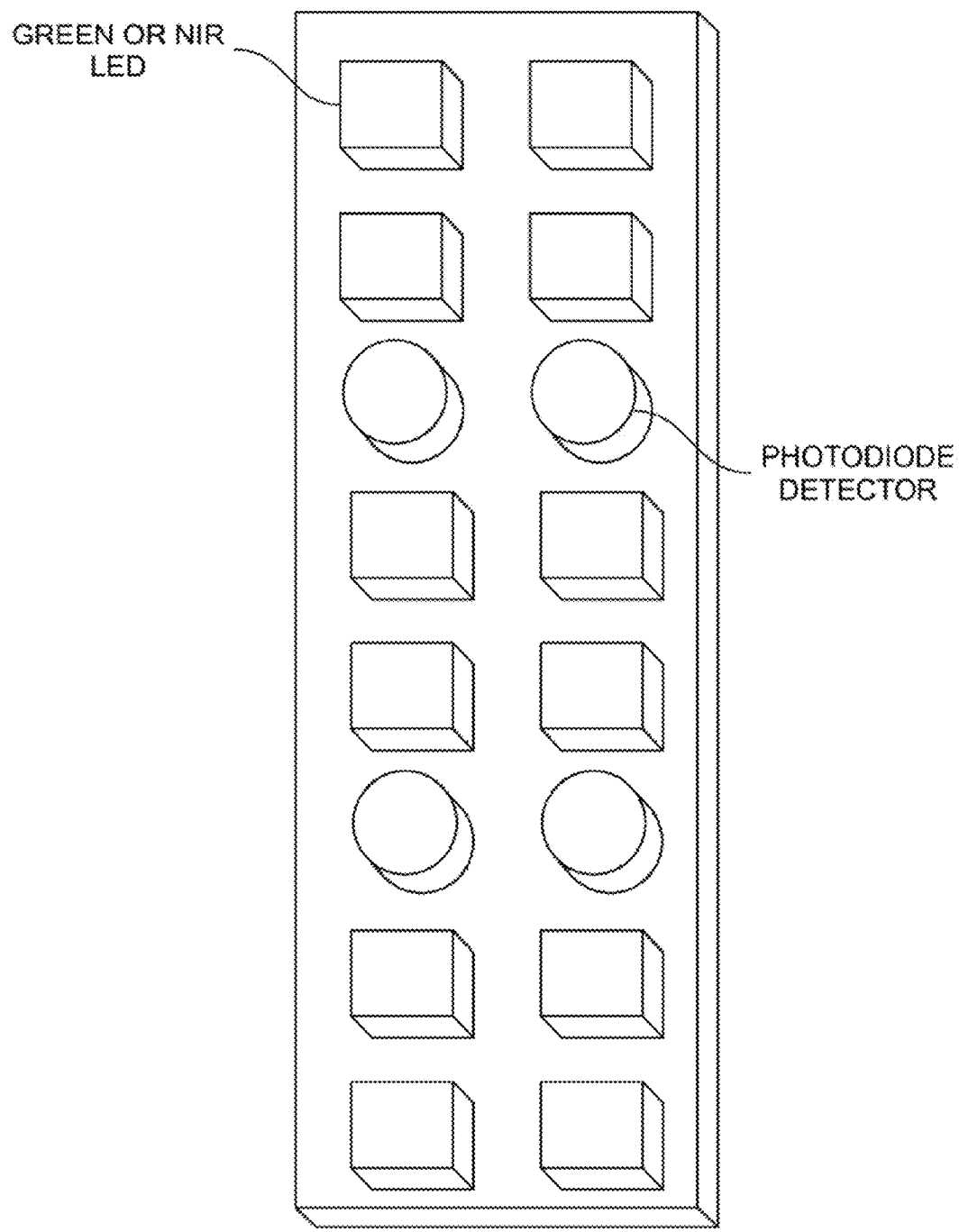
Figure 137:
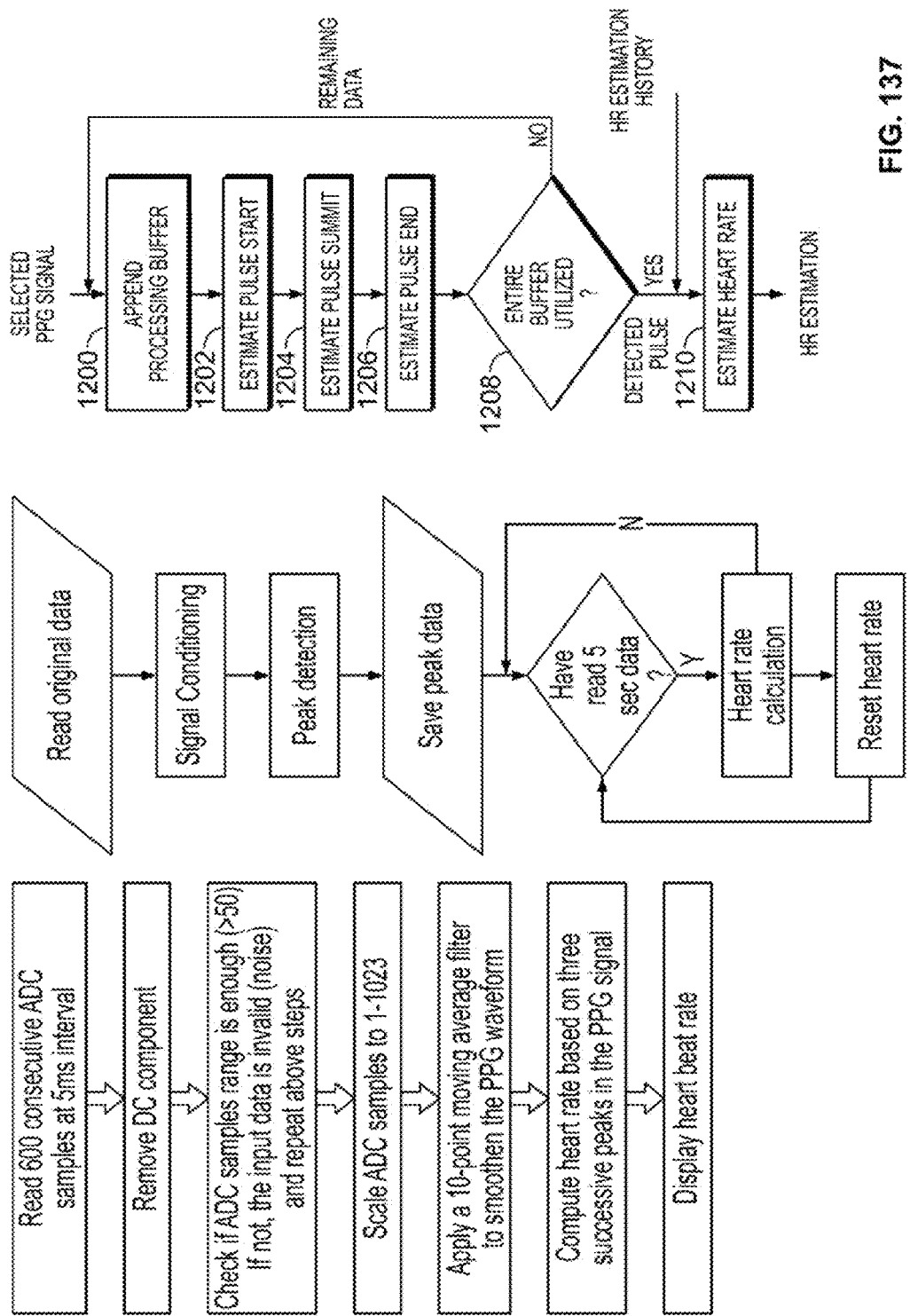
Figure 139A:
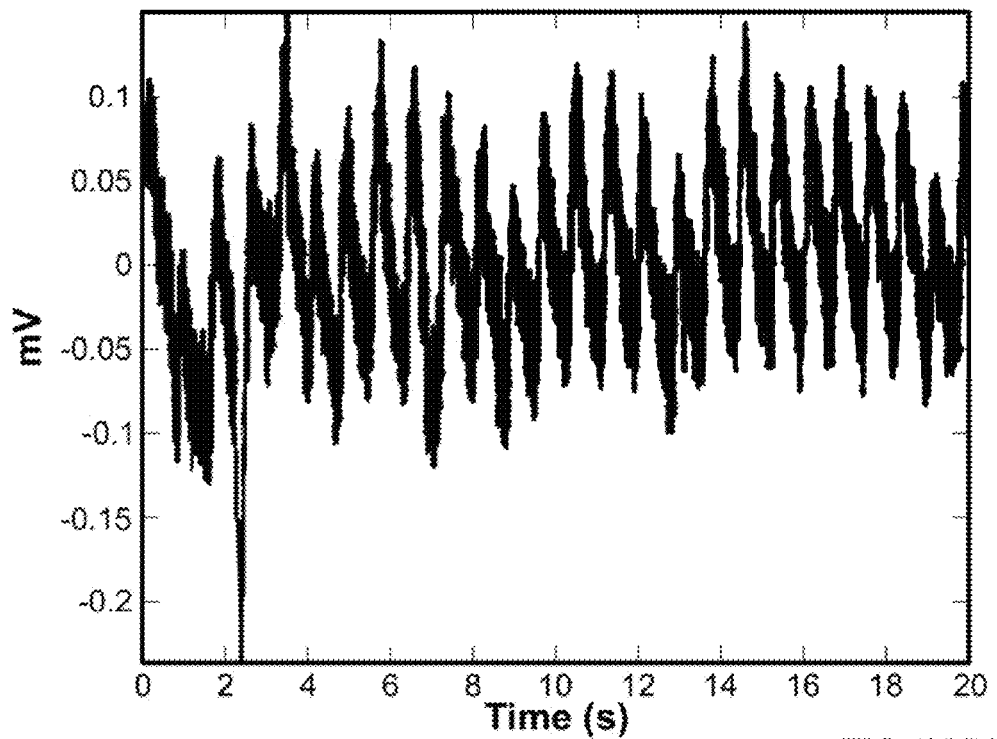
Figure 139B:
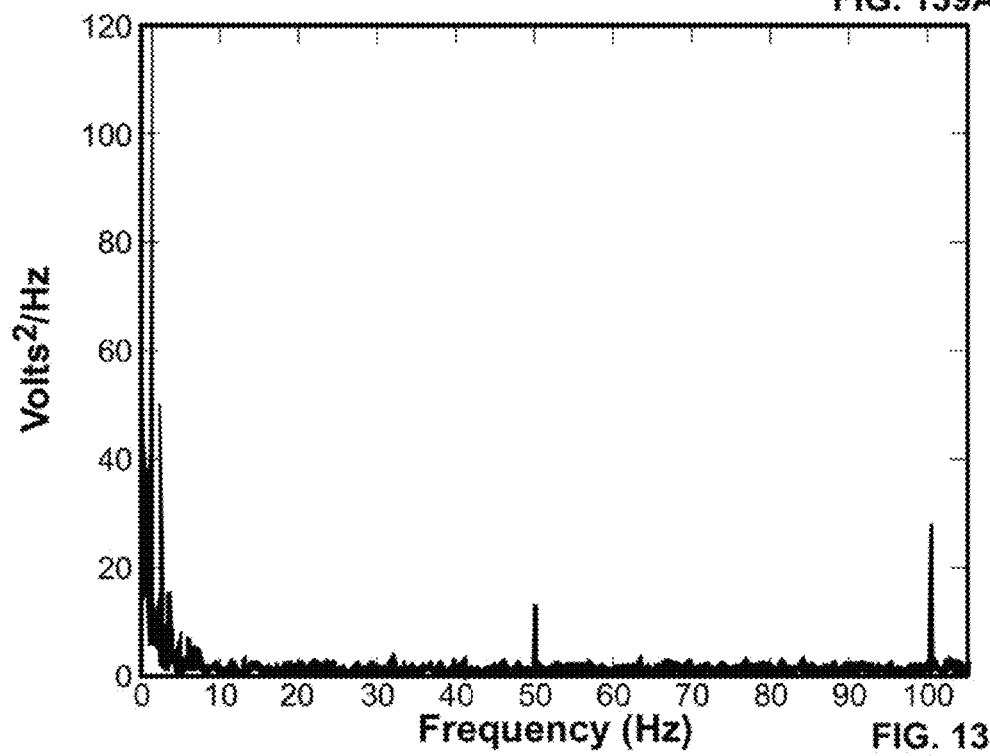
Figure 140:
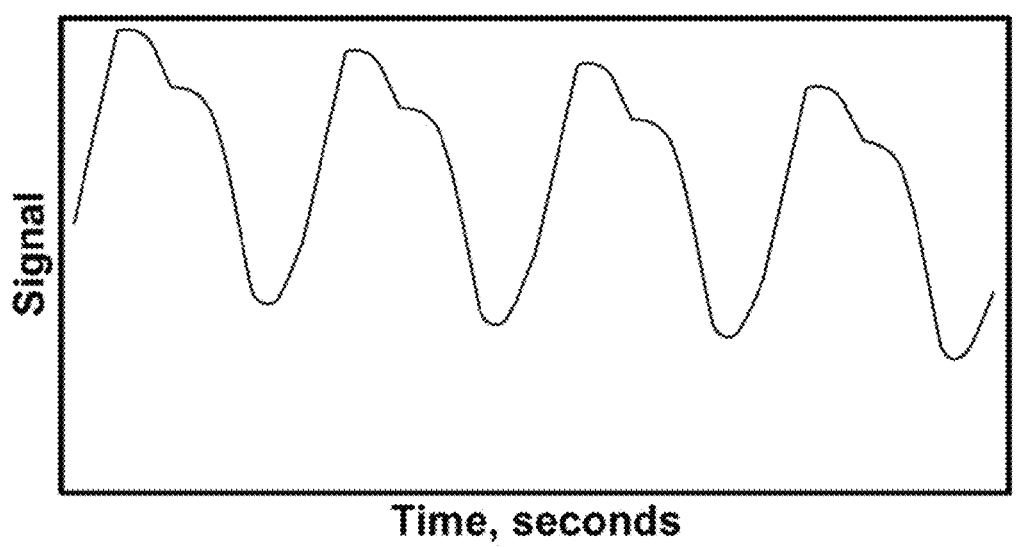
Figure 141:
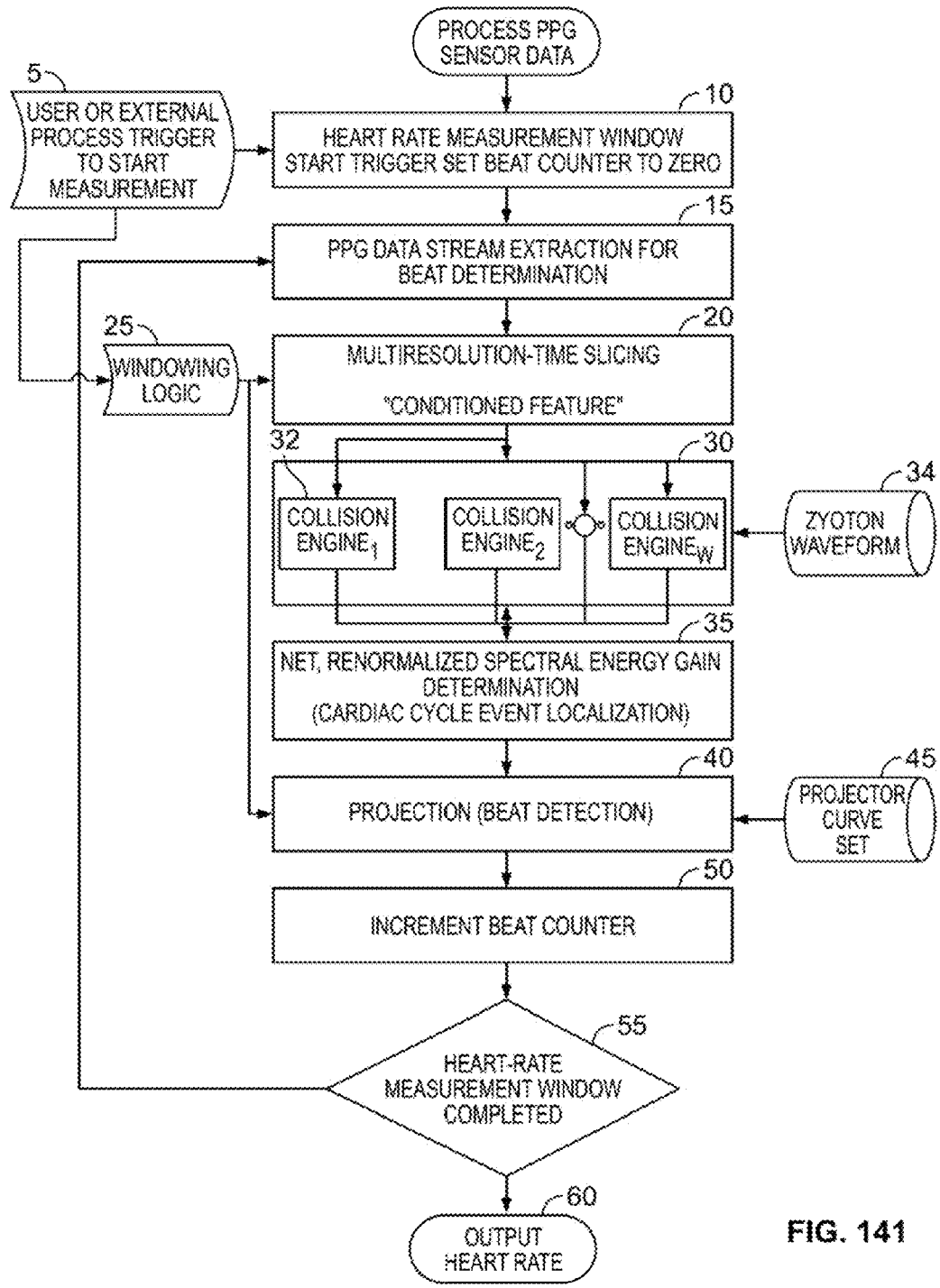
Figure 142:
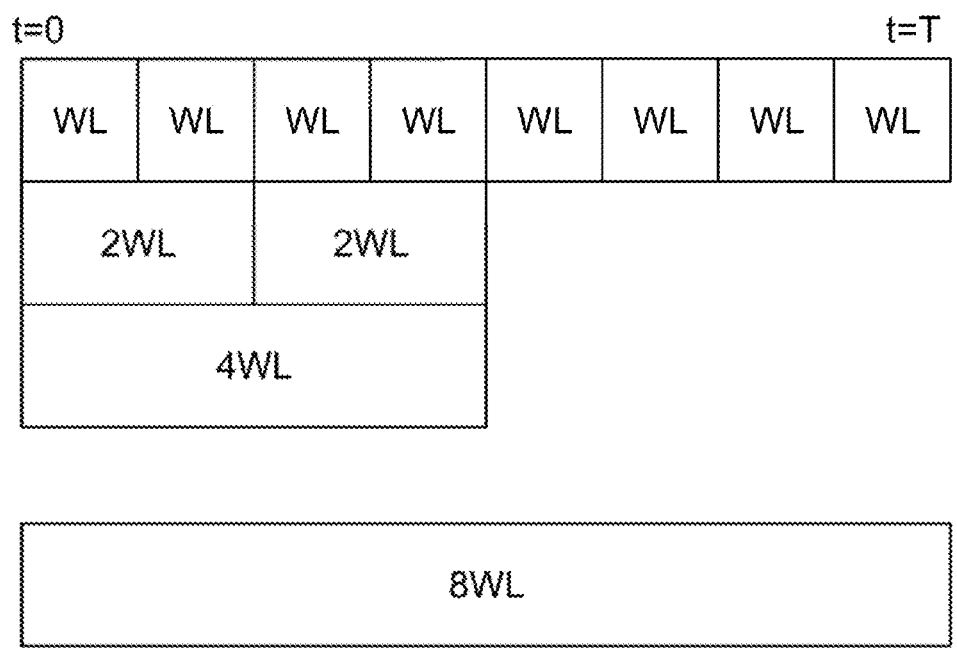
Figure 143A:
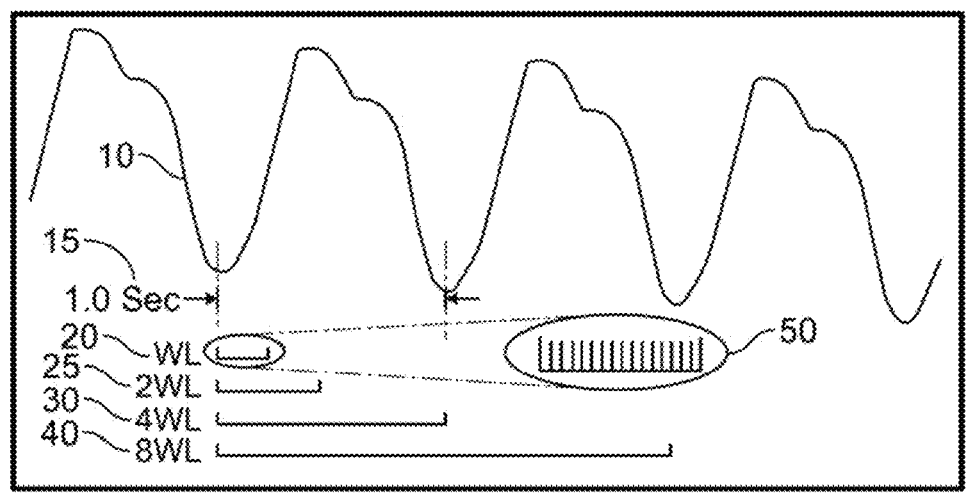
Figure 143B:
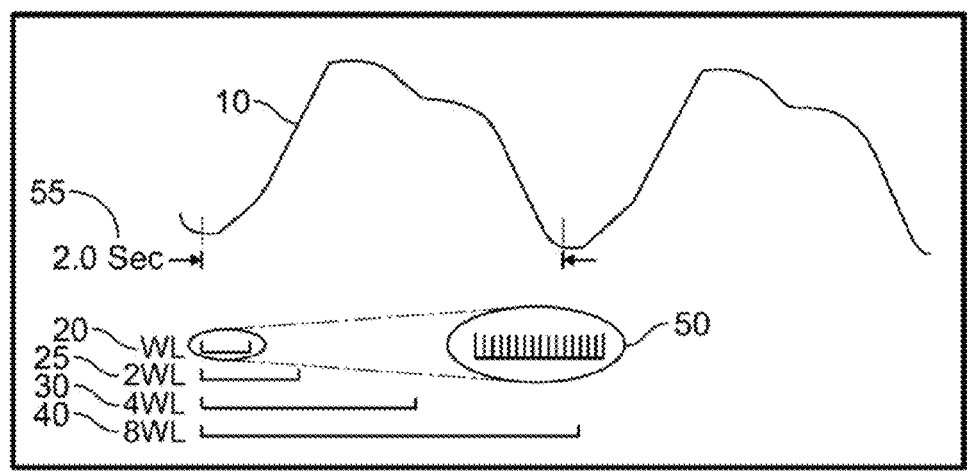
Figure 143C:
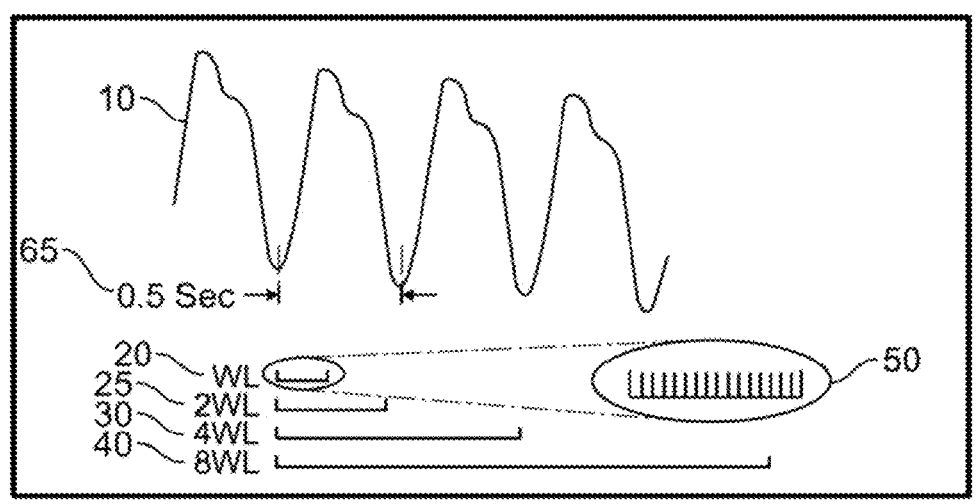
Figure 144:
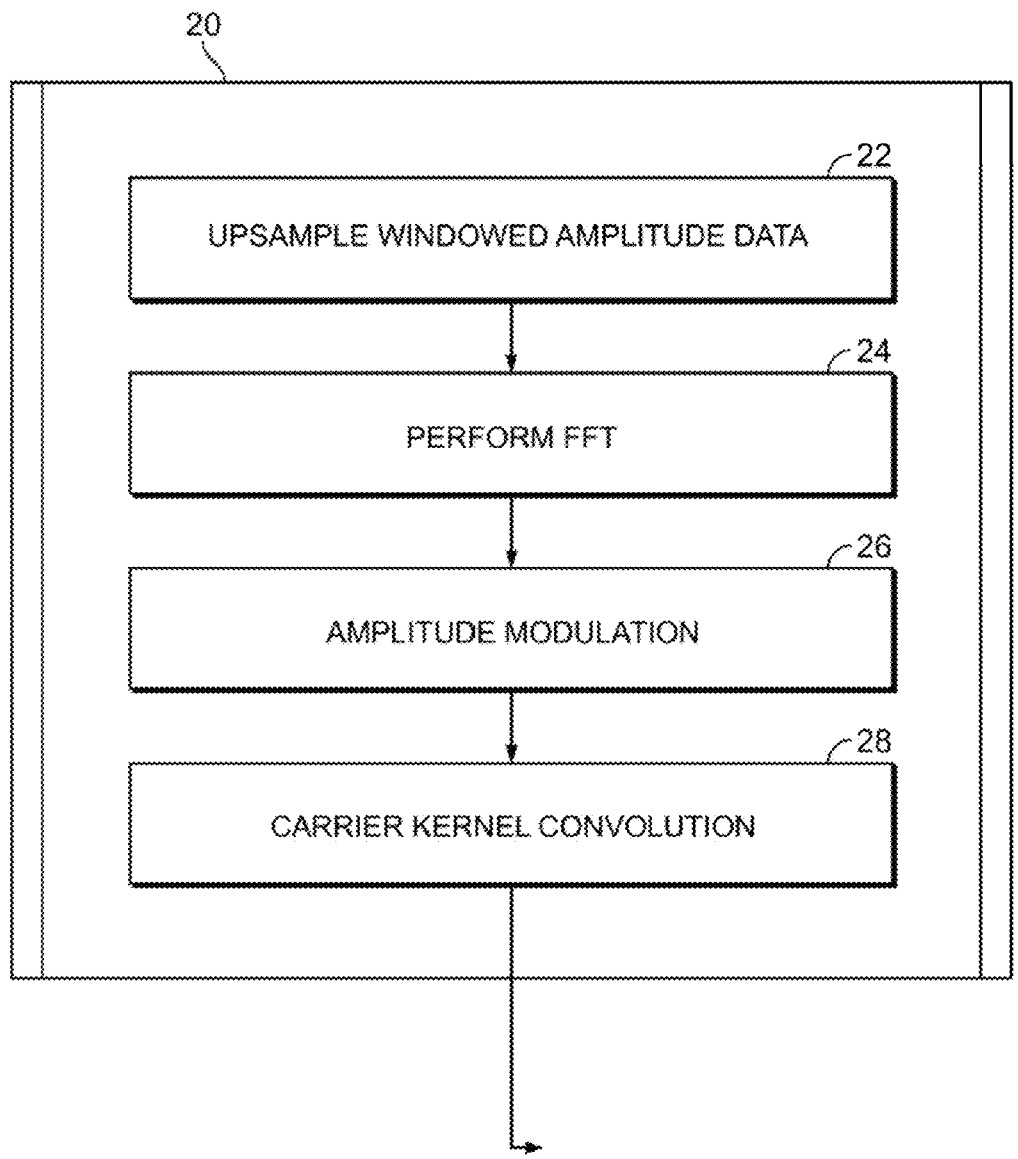
Figure 145:
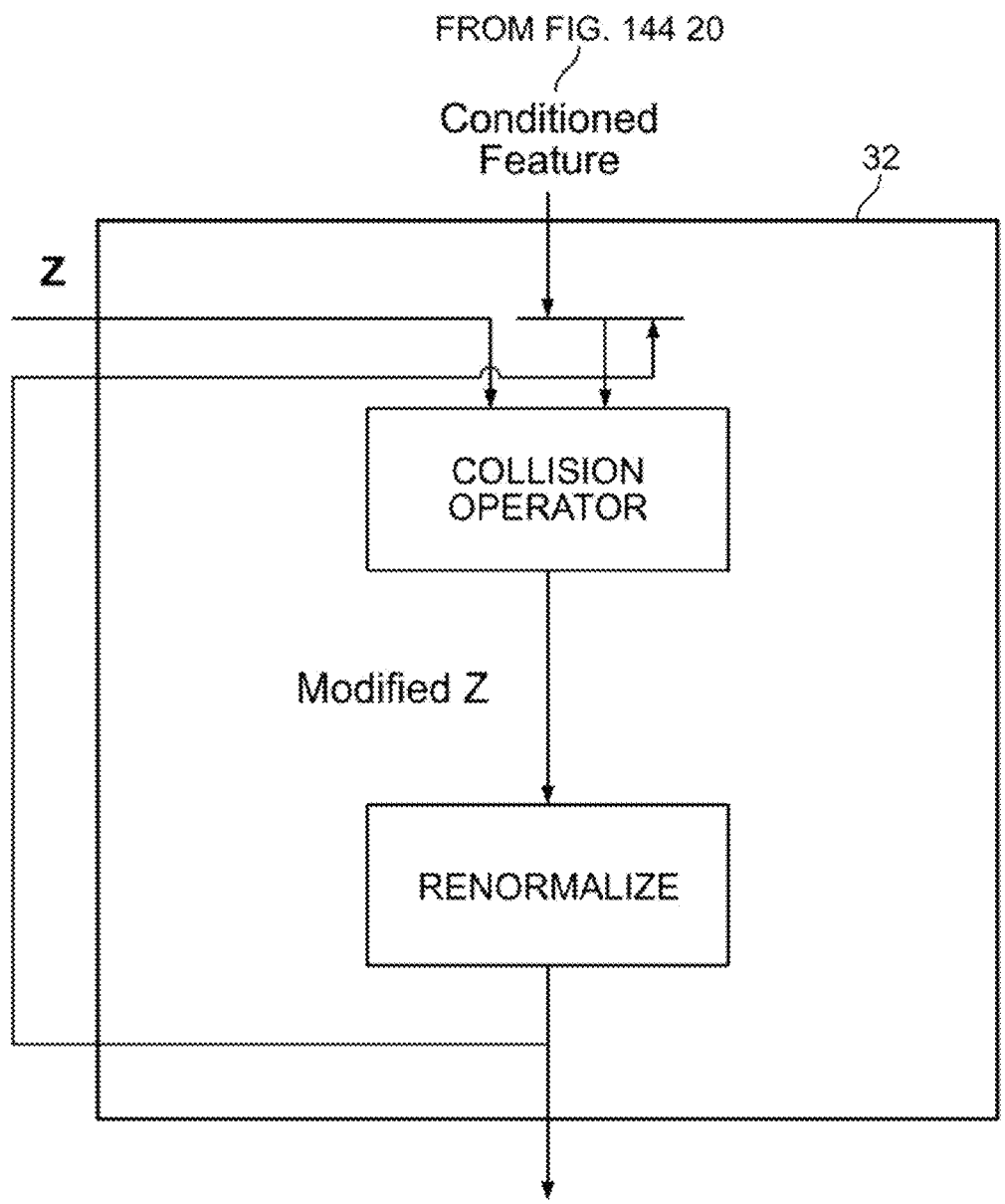

FIG. 118B is an illustration of varying tissue scanned volumes;

FIG. 119A is a diagram of an adjustable illumination system;

FIG. 119B is a diagram of an adjustable illumination system;

FIG. 120 is a schematic diagram illustrating how the numerical aperture of a collection fiber limits the detected photons to a cone-shaped volume;

FIG. 121 is an example optical interface lay-out for launching light into the skin at an angle that varies with the illumination to detection separation;

FIG. 122 is an example optical interface lay-out for preferentially detecting light at an acceptance angle that depends on the illumination to detection separation;

FIG. 123 is an example optical interface lay-out for both launching light and detecting light at various angles;

FIG. 124A depicts a plot of the distribution of detected photons from a perpendicular launch angle;

FIG. 124B depicts a plot of the distribution of detected photons from a 45-degree launch angle;

FIG. 125 depicts optimization results showing the median illumination launch angle versus illumination to detection separation for three different skin types;

FIGS. 126A-126C illustrate the simulated distribution of light absorbance by layer for three different detection angles given a fixed nominal 1 mm illumination to detection distance;

FIGS. 127A-127C illustrate the percent increase in reflectance vs. wavelength for detection angles ranging between 10 and 40 degrees from vertical;

FIGS. 128A-128B depict examples of acquired spectra for glucose measurement in high and low noise environments;

FIGS. 129A-129F show examples of interferograms, corresponding intensity spectra, and corresponding absorbance spectra, generated in response to respective illuminations from an illumination sequence that are directed to the skin using the system shown in FIG. 68;

FIG. 130 shows the wavelengths of a selected region of features;

FIGS. 131A and 131B show the tracking between collision-computing and reference glucose results for a single patient on two visits;

FIGS. 132A and 132B show the tracking between collision-computing and reference glucose results for a second patient on two visits;

FIG. 133 shows waveforms associated with pulse plethysmography ("PPG") measurements;

FIG. 134 shows the fundamental PPG waveform from a finger sensor;

FIGS. 135A and 135B illustrate the primary differences between reflective and transmissive PPG measurements;

FIG. 136A shows the LED sources and photodiodes of a PPG monitor;

FIG. 136B shows one embodiment of a PPG monitor;

FIG. 137 is a prior-art algorithm to determine heart rate based on PPG signals;

FIGS. 138A and 138B illustrate the differences in waveform and frequency of heart rate during stand-still and running PPG measurements;

FIGS. 139A and 139B illustrates a PPG waveform and the PPG figure components as determined using a Fourier transform;

FIG. 140 illustrates the general appearance of a PPG waveform;

FIG. 141 is a flowchart of steps in an algorithm to determine heart rate using collision computing;

FIG. 142 illustrates the window length of features used to determine heart rate using collision computing;

FIG. 143A illustrates the PPG waveform for a normal heart rate of 60 beats per minute, showing the windows used to extract features for collision-computing determination of heart rate;

FIG. 143B illustrates the PPG waveform for a slow heart rate of 30 beats per minute, showing the windows used to extract features for collision-computing determination of heart rate;

FIG. 143C illustrates the PPG waveform for a rapid heart rate of 120 beats per minute, showing the windows used to extract features for collision-computing determination of heart rate;

FIG. 144 shows the initial steps used to determine heart rate using collision computing; and FIG. 145 shows the interaction of waveforms and renormalization of a Zyoton and a conditioned feature used to determine heart rate using collision computing.

DETAILED DESCRIPTION

Introduction

A collision computer and a collision computing process according to various embodiments of the invention can detect and/or quantitate an analyte of interest within a medium, a property of a material, changes in the amount of the analyte and/or properties of the material, and/or an event or anomaly of interest. To this end, some embodiments of a collision computer receive intensity spectra representing the analyte, material, event, and/or anomaly and also the environment thereof, e.g., a medium in which the analyte may be present. In some embodiments, radiation (e.g., near-infra red (NIR) radiation) is directed to the environment/medium, and the radiation reflected from or passing through the environment/medium is detected by a detector, and is provided as one or more intensity spectra. In other instances, a stimulus (e.g., an electromagnetic signal, an acoustic signal, etc.) is directed to an environment and one or more signals generated in response to the stimulus are obtained from one or more detectors. The frequency of the electromagnetic signal may range from 300 EHz (where 1 exahertz or $EHz=10^{18}$ Hz) down to 0.03 Hz or alternatively, with a wavelength ranging from 1 pm (picometer) to 10 Gm (gigameters). The detected signals are transformed to one or more intensity spectra and are presented to various embodiments of a collision computer.

An intensity spectrum presented to a collision computer represents, at least in part, an overall change in the incident radiation/stimulus that is caused by the medium/environment. In general, the change is caused by three factors. The first factor is the analyte and other materials that are present in the medium/environment, including the properties of the analyte or other materials, changes in concentration/properties of the analyte or other materials, an event of interest, and/or an anomaly. The second factor is one or more confounders, i.e., other materials that are present in the medium/environment and can cause a change in the incident radiation or stimulus in a manner similar to the manner in which the analyte causes a change. The third factor is the absorption, dispersion, and/or scattering of the incident radiation or stimulus by the medium/environment. Typically, the intensity spectra also include a significant noise component. The noise may be introduced by sensor errors or variability, analog-to-digital conversion (ADC) of the sensed signal, propagation of the radiation through the medium/environment along different paths, etc.

Both scattering and absorption remove energy from electromagnetic radiation, including light, traversing a turbid medium. Inhomogeneities in a specified environment scatter radiated light, to cause diffuse reflection from the medium by multiple reflections with structures in or particles of the environment. Structures in the medium act as scattering centers, and the overall arrangement of their shape, size, and composition, as well as time-varying fluctuations, including statistical thermal fluctuations, influence the attenuation due to scattering. This type of scattering, where the particles are of approximately the same size as the wavelength of light, is known as Mie scattering. Optionally, confounder molecules may also absorb energy in the same band where the analyte absorbs energy. In various embodiments, a difference between the energy of the incident radiation or stimulus and the energy of the intensity spectra received by a collision computer represents the overall change in the incident radiation or stimulus. The energy of the incident radiation (and the absorbance spectrum) can be computed as the spectral energy of the incident radiation signal (and the absorbance spectrum).

As described below with reference to FIGS. 9-11, the difference between the energies of the radiation incident upon the medium to be analyzed and the radiation received therefrom corresponds to one or more of the three factors, i.e., the energy difference may include the energy absorbed by the analyte or other materials, the energy absorbed by one or more confounders, and/or the energy absorbed or scattered by (also called lost within) the medium/environment. The energy difference may also be affected by one or more sources of noise described above. In various embodiments, a collision computer is constructed and operated to determine the energy difference due to only the first factor, i.e., absorption by the analyte, distinguishing such change in energy from the noise and from the changes in energy caused by absorption by one or more confounders and/or due to loss in the medium/environment. A relationship between the measured energy change and concentration of the analyte, property thereof, parameters of an event or anomaly, etc., can then be used to quantitate the analyte/material, properties thereof, events/anomalies, etc.

As an example of scattering, Rayleigh scattering, defined as dominantly-elastic scattering of light or other electromagnetic radiation by particles much smaller than the wavelength of the radiation, generally does not involve absorption. Rayleigh scattering can result from the electric polarizability of the particles and may not change the state of material. Thus, it is considered a conservative process. The scattered particles may be individual atoms or molecules, and it occurs when light travels through transparent gaseous, solid, or liquid materials.

Relationship Between Zyotons and Energy

As described below, the colliding waveforms used in various embodiments of collision computing are spatio-temporal waveforms having a time dimension and at least one spatial dimension. A spatio-temporal representation of the waveform is also called a time-domain representation. These waveforms can also be represented in a frequency domain and may have one or more frequency components. The frequencies are spatial frequencies. Spectral energy density is one measurable observable of the waveform at various stages of processing—pre-collision, post-collision, and after the renormalization operation that is generally required in embodiments employing several collision iterations. Also, the spectral energy of waveforms can be characterized using one of more subsets of the frequency components.

In various embodiments of collision computing, a stable waveform called a Zyoton, which may change its shape and morphology when collided with another waveform only within limits as specified by certain parameters, is computationally collided with another waveform, called a conditioned feature, derived from the spectral data to be analyzed. The term spectral data generally refers to any data acquired from a spectroscopic measurement or a spectral sensor. A spectral signal can be directly obtained from a spectral sensor, or time-varying data can be transformed into a spectral signal by applying a Fourier transform or other mathematical transform to the data collected over some time window. Such a spectral signal may be referred to as a transformed signal. A conditioned feature is obtained by modulating a pre-selected, carrier waveform referred to as a "carrier kernel" with data (e.g., a feature).

A carrier kernel generally includes one or more (e.g., 2, 4, 6, 10, 15, 1000 or more) fundamental frequencies and/or their respective harmonics, i.e., integer multiples of the fundamental frequencies. The number of harmonics can range from 1 up to 4, 6, 10, 20, 32, 50, or more, and the number of included harmonics of different fundamental frequencies can be different. To illustrate, an exemplary carrier kernel includes three fundamental frequencies $f_0$, $f_1$, $f_2$. Ten harmonics of $f_0$, denoted $h_{0,j}$ for j=0 . . . 9; four harmonics of $f_1$, denoted $h_{1,j}$ for j=0 . . . 3; and 15 harmonics of $f_2$, denoted $h_{2,j}$ for j=0 . . . 14, are also included in this exemplary carrier kernel. Moreover, the harmonics that are included need not start with the first harmonic, i.e., two times the frequency of the corresponding fundamental frequency, or the first overtone, and/or need not be consecutive. For example, only the odd harmonics of one fundamental frequency and only the even harmonics of another fundamental frequency may be included. In general, the harmonics can be selected according to any specified sequence of harmonic indices, such as a geometric sequence, Fibonacci sequence, etc. The one or more fundamental frequencies and their respective harmonics that are included in a carrier kernel are called frequency components of the carrier kernel.

The waveform resulting from the collision, called a modified Zyoton, represents, substantially, the energy loss in the radiation energy incident upon the medium due to the absorption of such energy by the presence of the analyte of interest in the medium, or the presence of one or more confounders in the medium, or both, specifically in the spectral region chosen for the feature. In part due to the shape and morphology preservation properties of the Zyoton, the collision produces a modified Zyoton that can represent a change in energy substantially related only to the absorption energy loss represented by the feature used in the collision, as extracted by the collision operation. Moreover, the collision operator and one or more parameters thereof are selected such that the energy change represented by the feature is amplified when that change is represented in resulting waveforms generated by several iterations of the collision. Therefore, the modified Zyoton can be collided iteratively, following renormalization, with the same or different Zyotons, in order to amplify the energy loss represented by the feature without substantially introducing any noise or distortion.

A modulated carrier kernel, i.e., a conditioned feature, and an original Zyoton are both traveling waveforms that can be represented in the computer memory. The propagation of these waveforms in space and time, and their collisions, are simulated by a programmed processor and/or by one or more hardware modules such as an application specific integrated circuit (ASIC), a field programmable gate array (FPGA), a systolic array, digital signal processor (DSP), etc. The result of the collision, i.e., a modified Zyoton, and the renormalized modified Zyoton derived from the modified Zyoton are also traveling waveforms, each of which can be represented in the computer memory. In various embodiments, the propagation of the renormalized modified Zyoton in space and collision thereof with the original Zyoton or another Zyoton are also simulated using a programmed processor and/or one or more hardware modules.

Typically, the medium being observed contains one or more analytes of interest that need to be characterized qualitatively or quantitatively. It may also have other substances present that are not of interest but spectroscopically absorb, emit, fluoresce, or otherwise interfere with the analyte signal in the data region chosen, in the same bands as the analyte, and may thereby act as confounders to the measurement of analytes of interest. The collision computing paradigm described here can be applied for detecting and characterizing analytes in concentrations from as high as moles/1 or higher to concentrations as low as picomoles/1 or even lower. Individually or collectively, confounders may be present with many orders of magnitude greater concentration compared to analytes of interest. For example, the concentration of glucose, a biochemical blood analyte of interest, can be overshadowed by the concentrations of many other substances present in blood or interstitial fluid.

Zyotons are conditioned feature-complement collision waveforms that are constructed to function as energy amplification mechanisms. Zyotons may be constructed using a variety of waveform families and generator function families suitable for detecting an analyte or compound of interest. Useful waveform families include, but are not limited to: solitons; autosolitons; similaritons; custom solitons generated using a sine-Gordon-based equation; self-compressing similaritons; vortex-solitons; multi-color solitons; parabolic-similaritons; Ricci solitons; wavelets; curvelets; ridgelets; bions; elliptic waves including either or both of Jacobi elliptic functions and Weierstrass elliptic functions; and nonautonomous similinear wave equations.

Useful Zyoton generator function families include, but are not limited to: meromorphic functions; Gamma functions; Riemann Zeta functions; regular instantons; Frobenius manifolds; harmonic oscillators; Hermite polynomials; polynomial sequences; asymptotic Hankel functions; Bessel functions; fractals; Neumann functions (spherical); poweroid coupled with sinusoidal functions; spatial random fields; cyclostationary series; random number generators; spherical harmonics; chaotic attractors; exponential attractors; multipoint Krylov-subspace projectors; Lyapunov functions; inertial manifolds of Navier-Stokes equation; evolution equation for polynomial nonlinear reaction-diffusion equation; evolution equation for Kuramoto-Savashinsky equation; evolution equation of exponential attractors; Fourier series; and Ramanujan theta functions.

Random number generators (RNG) are also useful as generator functions to produce numerical sequences used to synthesize Zyotons. Desirable general properties of RNG used to develop Zyotons include replicability (i.e., generated number sequences would be replicable if the seeds used to generate the random numbers were known and fixed), and the longest practical cycle length or periodicity (i.e., the longest possible time before numbers in the generated sequence start to repeat). Other attributes such as independence (i.e., correlation between numbers generated by the RNG), uniformity, and computational speed are optional for the purpose of developing Zyotons. Classes of RNG that are used to develop Zyotons, in which $r_n$ is the random number generated, include linear congruential generators, (where $r_n=(ar_{n-1}+c) \bmod m$, $n=1,2,\ldots$; where $m>0$ is an integer coefficient used in the modulus operation, and a period up to $2^{31}$), multiplicative congruential generators (where $r_n=(ar_{n-1}) \bmod m$, $m>0$, $n=1,2,\ldots$ and a period up to $2^{31}-2$), and additive congruential generators or Fibonacci RNG generators (where $r_n=(r_{n-1}+r_{n-k}) \bmod m$, $n=1,2,\ldots$; $m>0$; $k\geq 2$ and with a period up to $m^k$).

RNG based on linear, multiplicative, or additive congruential generators may be used as Zyoton generator functions even though they can produce numbers that are not random (also known as pseudorandom), and can be relatively more easily controlled (compared to other methods) to exhibit desired spectral properties in the frequency domain, and thus can be used as a first step to generate numerical sequences used for the synthesis of one or more Zyotons.

Regardless of the generator function used, the generated numbers are collected, fixed (or "frozen"), and then Fourier transformed to frequency distributions with desired properties and amplitude profiles that are useful as Zyotons. RNG are particularly useful for developing collections of related Zyotons (with some common underlying properties in the frequency domain) but where each subsequent collision uses a different Zyoton from such a collection of Zyotons in multiple-iteration collision sequences.

The polynomial sequences described above typically are a sequence of polynomials indexed by the nonnegative integers $0, 1, 2, 3, \ldots$, in which each index is equal to the degree of the corresponding polynomial. Finite and infinite length numerical sequences can be encoded as polynomial sequences and can be Fourier transformed, and are differentiable and integrable and can be represented as continuous geometrical curves and manifolds. Zyotons generated using polynomial sequences can encode arbitrary numerical sequences of interest. Specifically, arbitrarily desired frequency component patterns can be encoded using polynomial sequences. Specific examples of polynomial sequences that can be used as Zyoton generators include Abel polynomials (where n-th term of the polynomial is of the form $p_n(x)=x(x-an)^{n-1}$), and Bell polynomials given by:

$$B_{n,k}(x_1, x_2, \ldots, x_{n-k+1}) = \sum \frac{n!}{j_1! j_2! \ldots j_{n-k+1}!} \left(\frac{x_1}{1!}\right)^{j_1} \left(\frac{x_2}{2!}\right)^{j_2} \cdots \left(\frac{x_{n-k+1}}{(n-k+1)!}\right)^{j_{n-k+1}}, \quad (1)$$

where the sum is taken over all sequences $j_1, j_2, j_3, \ldots, j_{n-k+1}$ of non-negative integers such that:

$$j_1+j_2+\ldots+j_{n-k+1}=k \text{ and } j_1+2j_2+3j_3+\ldots+(n-k+1)j_{n-k+1}=n. \quad (2)$$

As an example, Abel and Bell polynomials can be used to encode combinatorial sets of frequencies (such as the k, m, and j frequency component groups referred to below), and then Fourier transformed to derive Zyoton waveforms which can be used in collisions.

Zyotons can also be created by combining other individual Zyotons, e.g., by multiplying, adding, or phase-shifting (also called subtracting), two or more individual Zyotons. Generation of new Zyotons by dividing or subtracting one Zyoton waveform from another Zyoton waveform can be achieved by using multiplication or addition operation respectively. Zyotons so combined to form a new Zyoton can be from the same or different families of Zyotons. In addition, various waveform functions and numerical sequences generated by a sequence generator can be transformed or reduced to any of the functions listed above. Such other waveforms and/or numerical sequences, which can be transformed or reduced into a waveform family/numerical sequence that is suitable for Zyoton synthesis, may be used to synthesize a Zyoton to be used in the collision process.

Although waveforms derived from all the above families can propagate in a constant medium without substantial change to their morphology, Zyotons derived from the families of optical solitons, autosolitons, similaritons, custom solitons, self-compressing similaritons, vortex-solitons, multi-color solitons, parabolic-similaritons and Ricci solitons generally retain their morphology and exhibit post-collision propagation properties substantially similar to their pre-collision propagation properties.

The above-described pattern-forming systems may be used as generator functions to derive a Zyoton waveform based on three factors: (i) their tendency to produce spatially confined states on the same time-domain spatial (i.e., morphological) and spectral scale as the entire set of anticipated feature waveforms from a spectroscopic sensor, as characterized by the spectral bandwidth, spectral envelope, peak energy, and amplitude distribution; (ii) non-stationarity of confounders, i.e., are they constant or time-varying in concentration during the measurement process resulting in changes in the signal-to-clutter increase required for an accurate measurement; and (iii) cyclostationarity of feature data itself, i.e., degree to which the statistical properties of the feature change over time, as described below, including the morphology of the amplitudes of the feature in the time domain, distribution of spatial frequencies of the feature and distribution of relative amplitudes of frequencies in the frequency domain, and any phase rotation of the waveform in the frequency domain.

A purpose of modulation of a carrier kernel by a feature, which may be preceded by an optional precursor frequency modulation, is to achieve a desired level of cyclostationarity or poly-cyclostationarity in the conditioned feature waveform, and to force the conditioned feature waveform to be represented using a combination of one or more periodic (e.g., sigmoidal) functions. Poly-cyclostationarity can increase the probability of inducing and detecting morphological changes post-collision in specific frequency components. Carrier kernel waveforms with higher frequencies than those of the feature (or the optionally modulated feature) are generally used in the feature modulation step, to condition features by inducing poly-cyclostationary properties.

In summary, Zyotons can be represented as localized traveling-wave packets, which exist as propagating entities through space and/or time. In general, the space and/or time propagation of Zyoton waveforms is scale and shift invariant. As such, transformations may be used to vary space and/or time scales to match the precision and accuracy desired in the data-collection domain, and/or the spectral resolution of sensors producing the feature data. For features with low cyclo-stationarity, complex or more nuanced generator functions may be required, such as Lyapunov functions or meromorphic functions.

In one exemplary embodiment that can be used for non-invasive glucose analyte detection and measurement, Zyotons are derived using a base family of mathematical functions denoted as solitons. This choice of solitons as source family generator for Zyoton derivation, in general, is based on the above three properties for selection of waveforms, but is strongly influenced by the stationary nature of confounders in the data during the course of measurement (generally over a time period of a few milliseconds to a few seconds). Solitons are defined and represented as a permanent localized disturbance in a linear or non-linear wave. In physical systems, such as propagation of light waves in an optical fiber, solitons can result from the offsetting of nonlinear and dispersive effects in the propagation medium. Mathematically, solitons are a solution to weakly nonlinear dispersive partial differential equations describing physical systems, such as optical energy propagation in a telecommunication fiber cable. A detailed treatment and background to soliton dynamics is provided in Ablowitz, Mark J., *Nonlinear Dispersive Waves: Asymptotic Analysis and Solitons* (*Cambridge Texts in Applied Mathematics*) (2011), and in Dauxois, T. and Peyrard, M., *Physics of Solitons*, ISBN-13: 978-0521854214.

Properties that make solitons attractive as a base family for designing collision waveforms or Zyotons include first, localization of the center of mass or confinement of peak energy to a region and resistance to weak external perturbations. Since collision computing involves deconstructed data or spectral features (i.e., fragments of spectra), local energy absorption or losses, and locality and stability of the soliton waveform are generally important. Second, permanency or morphological stability is important—solitons retain their shape. The accurate determination of spectral energy changes in the post-collision waveform, due to energy transfer from the colliding waveforms to the post-collision collided entity (i.e., the modified Zyoton), is important to analyte concentration estimation.

Power spectral density (PSD) of a signal waveform can be defined as the power contributed to the wave by a frequency, per unit frequency in watts/hertz (W/Hz). The PSD is the normalized limit of the energy spectral density (ESD) for a windowed signal $x_N(t)$ and a measure of distribution of signal power. Thus, spectral energy corresponds to the total power within a frequency or wavelength interval. Alternately, spectral energy can also be computed for a set of discrete frequency components by using the power spectral density of the selected frequency components. This definition of power spectral density generalizes the estimation of total spectral energy $S_{xx}(\omega)$ for a discretized and digitized signal waveform (e.g., feature data), represented as a finite time-series $x_n$ with $1 \le n \le N$, such as a signal sampled at discrete times $x_n = x(n\Delta t)$ for a total measurement period $T = N\Delta t$. The spectral energy is given by:

$$S_{xx}(\omega) = \frac{(\Delta t)^2}{T} \left| \sum_{n=1}^{N} x_n e^{-i\omega n} \right|^2 \quad (3)$$

where $\omega = 2\pi f$, and f denotes the frequency of the signal.

Given that mathematically one can compute the spectral energy density and the spectral energy for a signal waveform, waveform propagation and waveform collisions can be represented as energy entities and energy transfer operations, respectively. As Zyoton collisions are inherently nonlinear events, energy representation provides a mathematical framework (or an "energy algebra") for describing and inducing complex behaviors. Collision computing as described herein facilitates detection and/or quantitation of analytes and events using energy algebra. Morphological stability and properties of entire Zyotons, or selected frequency components with high retained fidelity, allows comparison and characterization both before and after collisions for large numbers of features extracted from large numbers of samples, collected under similar conditions, using the same or similar hardware platform and sensors.

Solitons are described in the art as "waves that act like particles." An individual soliton can travel through a propagation medium over a certain distance without distortion of the soliton's morphology and without dissipation of the soliton's energy. If one soliton collides with another, typically the morphology of both solitons is preserved after the collision, and only a phase shift occurs in the respective propagation of one or both solitons as they continue to propagate through the propagation medium. Phase shift in this context generally means that there is an offset in arrival time and phase for either one or both of the colliding solitons relative to the case when no collision occurs, and a phase shift does not introduce any new waveform frequency components that would alter energies of the two solitons. As such, no significant (e.g., more than 0.01%) change generally occurs in the respective energies of the two solitons after a collision between them. In contrast, the morphological envelope of a soliton generally changes during collision with a non-soliton travelling wave. Typically, if a soliton collides with a non-soliton waveform of similar energy, the soliton is destroyed. Thus, in the first interaction (i.e., between two solitons), no measurable energy transfer occurs between the two solitons and, in the second interaction (i.e., between a soliton and a non-soliton waveform), although energy transfer occurs, it cannot be measured because the soliton is destroyed during the collision.

The selection of a soliton family to construct a Zyoton, and its time-domain and frequency-domain parameterization, is based on the consideration of at least one of several specific attributes, which include: the signal-to-noise ratio (SNR) of the measurement system, the anticipated signal-to-clutter ratio (SCR) or signal-to-clutter noise ratio (SCNR), the degree of desired SCR increase, the desired analyte quantitation accuracy and precision, resolution, specificity, dynamic range, sensitivity, and concentration range over which linearity is desired. The SCNR (signal to clutter noise power ratio or signal to coherent noise power ratio) is generally defined as the ratio of signal power to the power of the sum of clutter plus background non-coherent noise power. Clutter can be due to signal from confounders or from coherent noise. Coherent noise is a type of smooth pseudorandom noise which has been usually defined in the art as having three properties: (i) passing in the same input value will always return the same output value; (ii) a small change in the input value will produce a small change in the output value; and (iii) a large change in the input value will produce a random change in the output value. The sources of such coherent noise include: variability due to free space optics (i.e., variability in the radiated and/or collected light traveling through air as it is subjected to variable amounts of water vapor), detector electronic noise, light drift and variability, variable absorption through a fiber optic probe, etc.

As described above, a conditioned feature is particularly constructed to represent the energy absorbed by an analyte or by one or more confounders, and accurate estimation of the absorbed energies can lead to an accurate estimation of the analyte concentration. To facilitate accurate estimation of the absorbed energy represented in a conditioned feature in various embodiments, particularly designed Zyotons are employed. Specifically, a Zyoton is modified after a collision with a conditioned feature but the modification is particularly controlled such that the original Zyoton is transformed into a modified Zyoton that continues to propagate thorough the propagation medium and is not destroyed at least over a certain propagation distance. Therefore, the energy transferred to the original Zyoton during the collision can be measured from the modified Zyoton. As described below, the Zyoton and the conditioned feature are synthesized in a co-dependent manner, such that the energy transferred to the Zyoton over one or more collision iterations is proportional to the energy absorbed by an analyte and/or one or more confounders, as represented by the conditioned feature. The permanency or morphological stability of a Zyoton is important, in general, to properly estimate spectral energy changes therein, which are related to the analyte presence or concentration at the feature level. As described below, the energy changes at the feature level may be aggregated to estimate the net energy change due to the presence and quantity of an analyte.

Collisions between conditioned features and Zyotons lead to minor waveform distortions of the Zyoton that can be used to perform post-collision energy computations, because energy transfer is possible between a conditioned feature and a Zyoton. Therefore, the feature, derived from incoming or acquired data, generally acts as an energy modulator to the Zyoton. Propagation over grids with a sufficient number of points and over sufficient travel distances can filter out post-collision transients and dispersion in high frequency, lower-amplitude peaks. Typically, multiple collision iterations between a conditioned feature and a Zyoton or between a modified Zyoton and a Zyoton are involved in collision-based energy absorption estimation. So each post-collision result is a modified or energy-amplified Zyoton. Specifically, as described above, as a result of a collision between an original Zyoton and a conditioned feature, a modified Zyoton with increased energy is obtained. The amount of energy amplification during a collision is related to the properties of the conditioned feature, e.g., energy absorption at NIR wavelengths due to analyte concentration in the medium irradiated with NIR. The increase in energy is generally related to the energy absorbed by an analyte and/or one or more confounders, as represented by the conditioned feature. The absorbed energy can also be referred to as energy loss or energy lost as a result of the presence of the analyte and/or one or more confounders. As used herein, the absorbed energy or energy loss, however, relates only to analytes and/or confounder(s) and not to energy otherwise dispersed or lost in the environment or medium. It should be understood that a medium to be analyzed in which an analyte and one or more confounders may be present may be different than a propagation medium in which Zyoton(s) and conditioned feature(s) propagate.

In some embodiments, the modified Zyoton is renormalized as described below, and the renormalized Zyoton is collided with the original Zyoton. The result of this subsequent collision is another modified Zyoton, typically with more energy than the original Zyoton and the previously generated modified Zyoton and, again, the increase in the energy is related to the energy absorbed by an analyte and/or one or more confounders. In general, successive collisions between the original Zyoton and the modified, renormalized Zyotons can result in recurring energy increases in the modified Zyotons that relate to the energy absorbed by an analyte and/or one or more confounders, with increasing accuracy and observability. Thus, after a specified number of collision iterations, the energy gain in a modified Zyoton relative to the original Zyoton can be equivalent to or a multiple of the energy loss or the absorbed energy represented by a feature and/or a conditioned feature. Through one or more (e.g., tens, hundreds, thousands, tens of thousands, or more) collision iterations, it is important that underlying properties of the original and successively modified Zyotons are maintained, i.e., the morphological characteristics thereof change in a controlled manner, to enable accurate post-collision energy computations. Normal, non-solition waves generally flatten out, leading to loss of or change in character of dominant frequency components, thereby rendering post-collision energy computations ineffectual.

Assume that the total energy of the original Zyoton is E and that the energy of a conditioned feature is e. Further, assume that e includes the energy $\Delta e$, where $\Delta e$ actually represents a cumulative loss of energy due to absorbance by an analyte and/or one or more confounders in the medium. Prior to the first collision, e is set to be around 0.001 times E and the gain in any individual collision iteration i, denoted $\delta e_i$, is less than $10^{-6}$ E. In the table below, $\delta e_1$ represents the gain in the post-collision spectral energy of the modified Zyoton due to transfer from the conditioned feature after the first collision, prior to the renormalization step. Similarly, $\delta e_i$ represents the gain in the post-collision spectral energy of the modified Zyoton due to transfer from the modified Zyoton after the $i^{th}$ collision, prior to the renormalization step. This gain, $\delta e_i$, is related to the NIR absorption by the analyte, within the wavelength boundary defining the feature. As described below, the collision computing process is designed so that the estimated per collision gain of $\delta e_i$ is proportional to the absorption of energy by the concentration of analyte in the medium. This proportional relationship of E to $\delta e_i$ (between a Zyoton and a renormalized Zyoton after the first collision iteration) is maintained throughout subsequent collisions, as shown below.

TABLE 2

| Iteration/Collision | Energy of Original Zyoton | Energy of Renormalized Zyoton (Energy of Conditioned Feature for Iteration 1) | Post-Collision Energy of Modified Zyoton | Comment |
|---|---|---|---|---|
| 1 | E | e | $E + \delta e_1$ | $\delta e_1 > 0$ |
| 2 | E | $\delta e_1$ | $E + \delta e_2$ | $\delta e_2 \geq \delta e_1$ |
| 3 | E | $\delta e_2$ | $E + \delta e_3$ | $\delta e_3 \geq \delta e_2$ |
| $\mathbb{N}$ | E | $\delta e_{\mathbb{N}-1}$ | $E + \delta e_{\mathbb{N}}$ | $\delta e_{\mathbb{N}} \geq \delta e_{\mathbb{N}-1} \approx \Delta e$ |

The number of iterations/collisions $\mathbb{N}$ is selected such that after $\mathbb{N}$ iterations/collisions, the increase in the energy of the original Zyoton, given by $\delta e \mathbb{N}$ is approximately equal to $\Delta e$, or is a multiple thereof, i.e., the net loss of energy due to absorbance by an analyte and/or one or more confounders. Also, to preserve the propagation integrity of the Zyoton, the frequency components of the carrier kernel are scaled and selected to establish the spectral energy of the conditioned feature waveform to be around $1/100^{th}$, $1/1,000^{th}$, or $1/100,000^{th}$ of that of the Zyoton for the selected wavelength interval, so the feature serves only as a weak perturbation to the Zyoton.

The process of conditioning data features and the generation of Zyotons and their parameterization is driven by the overall analysis objectives—often detection of energy absorption by the analyte—and requires any conditioned features (in some cases just a single feature) and their Zyotons to become co-dependent. The feature conditioning and the Zyoton selection are both dependent on the expected signal-to-clutter ratio (SCR) improvement required, as described above. This co-dependency is captured by the frequency bandwidth and frequency components of both the carrier kernel used in feature conditioning and by the selection of Zyotons. The frequency bandwidth of the carrier kernel is generally set to be between $$\frac{1}{(SCR)^2}$$

and $$\frac{1}{(SCR)^3},$$

so a measurement with a SCR of 0.01 would require a carrier kernel bandwidth of $10^4$ to $10^6$ Hz. A carrier kernel bandwidth of 100 KHz can be used in the analysis of spectroscopic data for a non-invasive glucose monitoring application, for example.

The total set of power-sorted frequency components for the Zyoton is defined as H=k+m+j where k>0, m≥0, and j>0, and the k and j frequency components do not overlap. In general, the k components are related to absorption by the analyte and are called analyte-information representing components, the j components are generally related to the energy lost due to scattering and are called non-analyte information representing components, and the m components serve as a transition zone to the j components, and are called transition components. In general, non-analyte information can be noise, clutter, etc., that this itself can be considered to be information, e.g., about noise, clutter, etc. Therefore, analyte-information-representing generally means representing a property, such as the presence or absence of or a quantity of an analyte and/or one or more confounders, energy absorbed by the analyte and/or one or more confounders, etc.

In various embodiments, the amplitudes of the analyte-representing k frequency components are higher relative to the amplitudes of the m and j components and, as such, in these embodiments, the k components are also called high-energy components. The non-analyte information representing j frequency components may have low amplitudes relative to the amplitudes of the k and m components, and may be called low-energy components. The transition components, i.e., the m frequency components, may have amplitudes greater than the amplitudes of the j components but lower than the amplitudes of the k components, and may be called medium-energy components. In some embodiments, the Zyotons and the corresponding carrier kernels are synthesized such that the analyte-information representing k components of the Zyoton and the co-dependent conditioned feature(s) are low-energy components, and the non-analyte information representing j components of the Zyoton and the co-dependent conditioned feature(s) are high-energy components.

Typically, the high-energy components of a Zyoton and the conditioned feature(s) have spectral energy that is several orders of magnitude greater than the spectral energy of the low-energy components, and the medium-energy components have spectral energy that is a multiple of the spectral energy of the low-energy components but that is not more than an order of magnitude greater than the spectral energy of the low-energy components. In some embodiments, the frequency components of the Zyoton (and also of the conditioned feature) can have amplitudes that can be represented by a continuum, where these are not broken up into specified k, m, and j subsets, each corresponding to a particular energy band. Instead, in these embodiments, certain frequency components can be selected which correspond to energy absorbed by an analyte, while other frequency components can be selected which correspond to absorption by confounders or sources of random noise, such as scattering or absorption variations of a confounder. Those frequency components corresponding to energy absorbed by an analyte may be amplified during the collision computing process, while those corresponding to noise may not be amplified.

The choice of the number k of the frequency components used in the spectral energy computations is driven in part by the dynamic range of spectral energy change desired across the dynamic range of concentration of the analyte of interest, and the desired precision. Example values of k range from 4 through 256 when a carrier kernel with a bandwidth of 100 KHz is used. The value of m ranges, for example, between 0 and a multiple of k, such as (4×k). Example values used in non-invasive glucose measurement are k=6 and m=8.

As described above, Zyotons may be selected from generator functions and/or waveform families that can produce waveforms that retain their properties, e.g., solitons that are stable over the desired frequency bandwidth. As such, and as further described below, the Zyoton and the conditioned feature waveforms, collectively referred to as the collision entities, are co-dependent. The energy scaling relationship between the Zyoton and the conditioned feature imposes the co-dependency condition between the two waveforms; and the scaling step as part of renormalization between the Zyoton and the modified Zyoton (prior to the second and any subsequent collisions) can re-establish the co-dependency condition between those two. Thus, by the algebraic transitive closure property, the Zyoton, the conditioned feature, the modified Zyoton, and the renormalized Zyoton are co-dependent.

As an example, one-dimensional Zyotons existing as a function of time t, $Z_N(xt)$, can be constructed as:

$$Z_N(xt) = 2\partial_x TrB_x(1+B)^{-1} \quad (4)$$

where B is an N×N matrix with elements $$B_{mn} = \frac{1}{p_m + p_n} C_m C_n,$$

with variables $C_m$, $C_n$ defined as $C_m = \exp\{s_m - \frac{1}{2}ln|ia_m|\}$, $C_n = \exp\{s_n - \frac{1}{2}ln|ia_n|\}$, respectively with $m, n \leq N$;

$s_m = p_m x - p_m^3 t + \delta_m$, $$ia_m = \prod_{n(\neq m)} \frac{p_m - p_n}{p_m + p_n} \frac{1}{2p_m},$$

and $\delta_m$ is a real-number constant, $p_m$ is a positive constant such that $p_1 > p_2 > \ldots > p_N$.

Figure 12A:
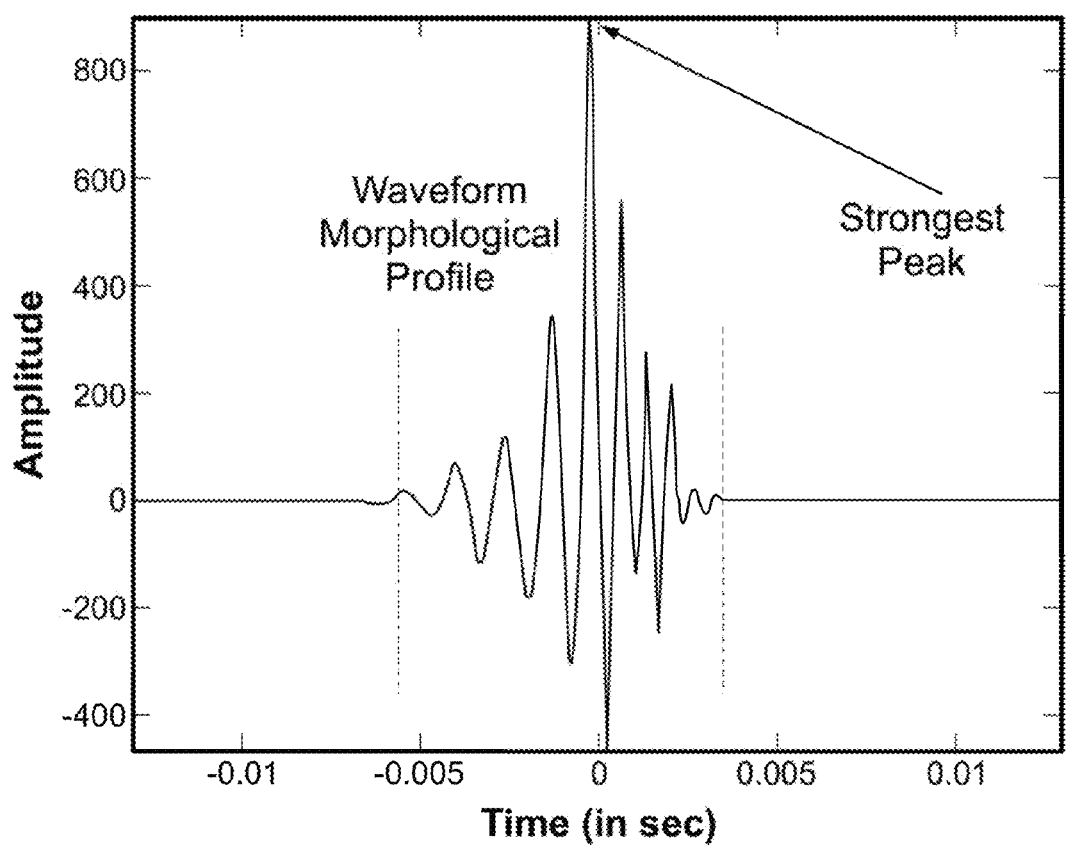
FIGS. 12A and 12B show the morphological profile and amplitude envelope of an example Zyoton waveform used in collision computing.
Figure 12B:
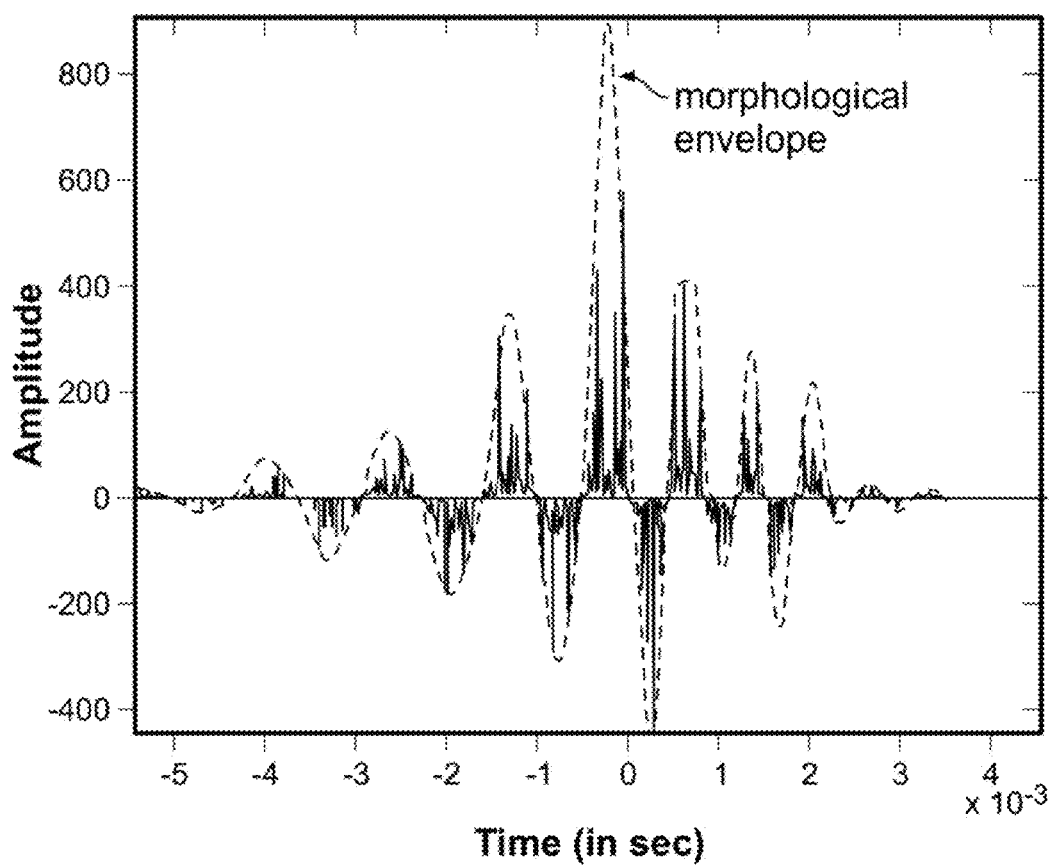
Figure 12C:
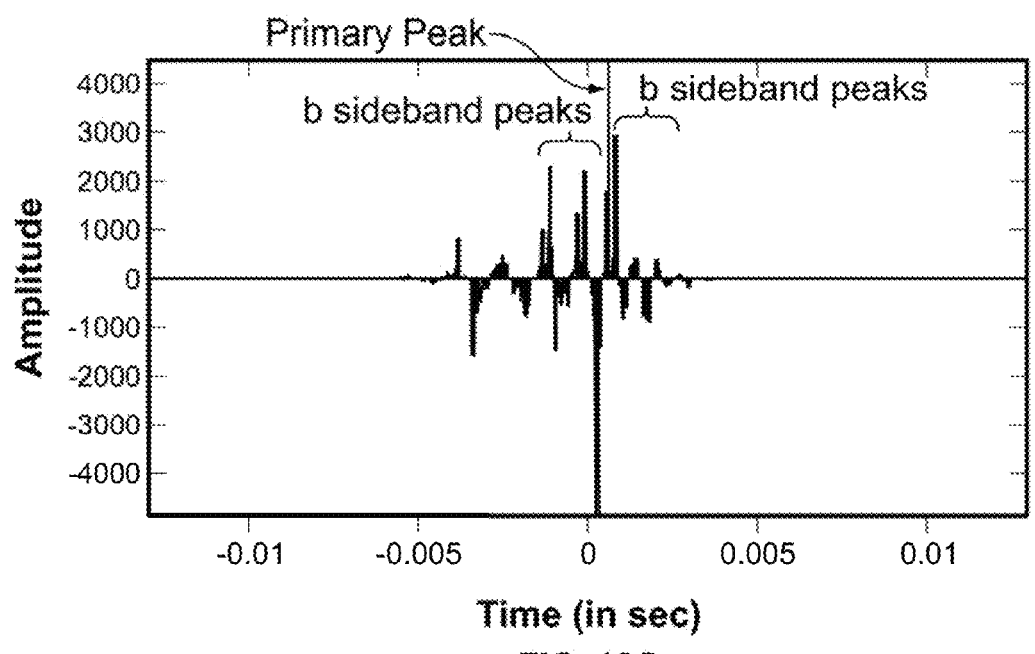
FIG. 12C shows the primary and sideband peaks of a Zyoton waveform.

The selection of $p_m$ and $\delta_m$ in the equations above is not based on the bandwidth of the Zyoton waveform but, instead, is based on the desired amplitude ratio of b sideband peaks on the left and right of the primary amplitude peak as shown in FIGS. 12A-12C. Note that b sideband peaks for the Zyoton waveform are defined as the portion of Zyoton wave amplitudes that are either above or below the frequency component corresponding to the peak amplitude of $Z_N(xt)$. In the above equation for $Z_N(xt)$, Tr is an algebraic operator that denotes the trace of an n-by-n square matrix and is defined to be the sum of the elements on the main diagonal of the matrix (the diagonal from the upper left to the lower right) of A, i.e., $$tr(A) = a_{11} + a_{22} + \ldots + a_{nn} = \sum_{i=1}^{n} a_{ii}$$

where $a_{nn}$ denotes the entry on the n-th row and n-th column of A. This is an example of a Zyoton kernel that can be used for glucose analysis.

Overview of a Measurement System

Figure 13:
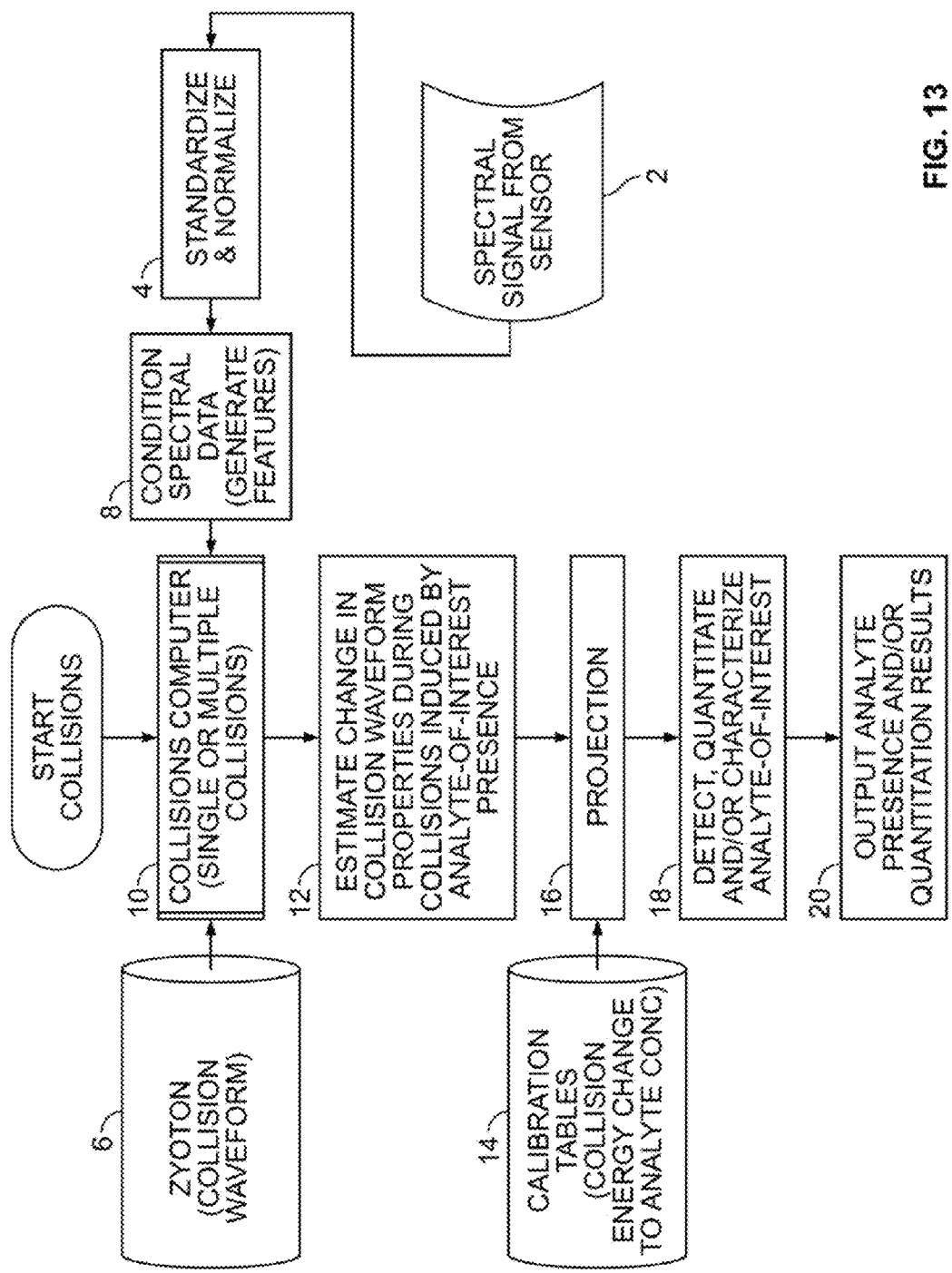
FIG. 13 is a flowchart depicting an exemplary process for detecting and/or quantifying an analyte of interest in a medium, according to an example embodiment.

With reference to FIG. 13, a typical process of detecting the presence of an analyte in a medium and/or quantifying an amount of the analyte in the medium includes acquiring one or more intensity spectra in step 2. Using spectra and the corresponding reference concentration data (also called a reference calibration dataset) that is obtained in step 14, at least in part, from known amounts or concentrations of analyte, the presence of the analyte is detected and/or the quantity thereof is estimated in step 16 via a projection process that uses calibration tables, sets, and/or curves included in the reference calibration dataset. The presence of the analyte and/or the estimated quantity thereof is determined and reported in steps 18, 20.

The method described here utilizes one or more nonlinear, non-invertible computational collisions between two entities—a feature derived and extracted from sample observations, and a purposefully constructed waveform, where the collision yields waveforms that can be processed to determine analyte presence and to estimate analyte concentrations in the uncharacterized samples. This method of detecting the presence and estimating concentration of analytes from sensor data is performed by transforming the incoming sensor data to a wavefront called conditioned feature ($\Psi_{CF}$) (steps 4, 8); selecting another waveform, referred to as the Zyoton ($\Psi_Z$) (step 6); colliding the conditioned feature with the Zyoton to obtain a modified Zyoton ($\Psi_{Z'}$) and/or renormalized Zyoton ($\Psi_{Z''}$) (step 10), which may include additional collision iterations; and assessing the properties of the spectral energy distribution of the modified and/or renormalized Zyoton (also called a coupled waveform complex) (step 12). The step 12 generally incudes determining the total spectral energy transferred to the Zyoton from the analyte-information representing components of the conditioned feature waveform after the collision. The wavelengths used in the synthesis of the Zyoton(s), and that may be present in the co-dependent conditioned feature and the modified and renormalized Zyoton waveforms are not typically the wavelengths associated with the incoming sensor data.

The conditioned-feature waveforms are "domain-based", in that they are derived from features, which have themselves been derived from signals, spectral data, or sensor data in the data-collection domain. The Zyotons, however, are "non-domain-based" or are independent of the data-collection domain in that the waveform kernels they are synthesized from may have no direct relationship to the sensor data acquired in the data collection domain. For example, data collected can be of the form NIR radiation, heat radiation, visible light, etc., while a Zyoton can be generated from various waveform families and/or generator functions that waveforms and functions unrelated to these data domains.

Zyotons represent models of physical waveforms encountered in domains different from the data-collection domain (e.g., solitons in optical communication or cryptography). Non-domain generator functions may be optionally used to construct Zyotons where the generator functions are either closed-form analytical functions (such as Gamma functions, Riemann Zeta functions, Neumann Functions) or are represented as formal power series (e.g., Lambert series, Dirichlet series) in one indeterminate variable, whose coefficients encode information about a sequence of numbers that is indexed by the natural numbers. Zyotons, such as those derived from spherical harmonics, can be optionally derived from generator functions represented as formal power series in more than one indeterminate variable, to encode information about arrays of numbers indexed by several natural numbers. While these waveform families and the generator functions can be mathematical entities (generally functions and sequences), the particular frequencies of the Zyotons are selected, however, according to the properties of the analyte, the properties of one or more confounders, the properties of the medium/environment to be analyzed, and/or the properties of the measurement system.

The spectral energy distribution used in the step 12 for the detection and/or quantitation of the analyte can be described as the distribution of flux density versus frequency or spatial wavelength, or the energy as a function of the spatial wavelength. Depending on the nature of the input data, the characteristics of the sensor used for observing the analyte, the complexity and concentration of confounders, and the expected concentration of the analyte, one or more computational collisions may be implemented by the method described herein. After each collision iteration, the power spectral energy distribution of the collision-modified Zyoton (the resulting waveform: $\Psi_{Z'}$) is computed and compared to the power spectral density of the original Zyoton waveform to determine that the codependency condition (described below) is still met. The waveform collisions may be implemented either in the analog or digital computing domain, and in a time domain or in a frequency domain. Analyte presence and concentration are determined based on the net gain (which can also be represented as an energy loss in some computer implementations) in the spectral energy computed from spectral energy distribution of the modified and/or renormalized Zyoton after a selected number of collision iterations.

The computation of the spectral energy changes requires observability of energy states of the pre- and post-collision waveforms. As introduced in classical control theory, in general, "observability" is a measure of how well internal states of a system can be inferred by knowledge of its external, measurable outputs or observables. In some embodiments described herein, the frequency-domain amplitudes of the pre-collision original Zyoton and, post-collision, the frequency-domain amplitudes of the modified Zyoton and renormalized Zyoton waveforms are treated as system or "collision observables." The collision process is implemented such that collision observables can be computed and compared when features are extracted from different measurements of the sample with different material concentrations, per the precision requirements of the system.

If a Zyoton does not possess the desirable properties described above, the collision observables, harvested from a single collision or from several collision iterations would offer no inferential utility i.e., the ability to determine the presence of and to estimate the concentration of materials in unknown, uncharacterized samples. Instead the computed spectral energy values may appear as random artifacts or noise given the very low signal-to-clutter ratios in the measured samples. The ability to observe consistent patterns in the spectral energy gained (or lost) after each collision iteration between two colliding waveforms is a prerequisite to concluding the integrity and consistency of the collision process. As described below, this is achieved, in part, by maintaining co-dependency between the colliding waveforms. The typical conditions for Zyoton synthesis (e.g., spectral energy $10^3$ or $10^4$ times higher than that of the conditioned feature) may set bounds for the changes in observed spectral energy after each collision.

The processing unit where the collisions are implemented is denoted as the collision computer. Three key elements of collision computing are: (i) the collision process on data, including the design of the collision waveforms, the collision operator, and number of collision iterations required to achieve the desired detection performance; (ii) the preprocessing of the acquired spectroscopic data, including deconstruction into spectral fragments that are a subset of the spectrum and their conditioning for use in the collision process; and (iii) the post-collision estimation of the change in spectral energy of the system as a mechanism to estimate the total energy change due to absorption by the analyte and its use to estimate analyte concentration.

An example of source data includes an intensity spectrum acquired by directing radiation to a medium and by detecting or collecting radiation reflected by the medium, or by directing radiation through a medium and detecting the transmitted radiation. In step 4, the spectral data may be normalized to eliminate amplitude variations, and one or more features (selected wavelength ranges of a spectrum) may be extracted from the optionally normalized spectral data. Different Zyotons may be required to collide with different features. The spectral energy of the Zyoton should be matched to both the spectral energy and the amplitude of the feature as described herein.

One or more Zyotons, with which the conditioned features are computationally collided to enable detection and/or measurement of the analyte, are generated or obtained in step 6. The Zyotons are generated according to one or more of the requirements for precision, accuracy, limit of detection, limit of quantization of desired analysis results, and characteristics of the spectral data acquisition system including: signal-to-noise ratio (SNR), system stability, spectral resolution, spectral bandwidth, illumination process and spatial sequence (if used), expected signal-to-clutter ratio, (SCR) due to the presence of confounders in the medium to be analyzed, and the required signal-to-clutter increase for an accurate measurement. As Zyotons are derived from inherently stable waveforms, the chromatic dispersion of the Zyoton waveform, the peak power and pulse energy (defined as the product of the power of the waveform peak and its width or the area under the peak) in its first k peak-power sorted frequency components (where k is typically <6), collectively control the limit of detection and quantitation that can be achieved in one or more collisions. In various embodiments, a reference to the "k frequency components" generally describes the first k peak-power-sorted frequency components of a waveform such as a Zyoton, a carrier kernel, and a conditioned feature.

In step 8, the features extracted in step 4 are conditioned, so that Zyotons and the conditioned features become codependent. Collectively, we refer below to the constraints on co-dependency imposed by the variables $\kappa_{DV1}$, $\kappa_{DV2}$, $\kappa_{DV3}$, and $\kappa^{SYN}$ as the "Kappa Test." Depending on whether the testing and/or scaling is performed in the time domain or in the frequency domain, a domain-specific value of the applicable Kappa variable is used for various tests of co-dependency in various embodiments.

In a waveform obtained by combining two or more sinusoids, such as in the construction of a Zyoton, construction of conditioned feature, etc., phase velocity is the velocity of a particular phase of the waveform and can be expressed as a ratio of the wave's angular frequency over wavenumber, i.e., $$v_p = \frac{\omega}{k}.$$

For Zyotons constructed using soliton waveforms, the dispersion velocity is same as their phase velocity. In contrast, group velocity is the phase velocity of an envelope representing the combination of the two or more sinusoids, and can be expressed as $$v_g = \frac{d\omega}{dk}$$

The dispersion velocities of a Zyoton and a conditioned feature are generally proportional to the time domain amplitudes of the sideband peaks thereof.

Assume that during the collision process, a conditioned feature waveform $CF_i$, corresponding to a feature $F_i$, is propagating with dispersion velocity $\omega_1$, and a Zyoton $Z_i$ is propagating with dispersion velocity $\omega_2$. Further assume that the collision of the two waveforms produced a modified Zyoton $Z'_i$, propagating with dispersion velocity $\omega_3$. The difference between the pre- and post-collision dispersion velocities of the Zyotons, i.e., the magnitude of $(\omega_2-\omega_3)$ should be less than a preset Kappa parameter $\kappa_{DV3}$, if the conditioned feature waveform $CF_i$ and the original Zyoton $Z_i$ are co-dependent. If a Kappa test is performed in the time domain, the velocity can be obtained as either the L1 norm or the L2 norm of the time-domain amplitudes of a selected number of sideband peaks of the two Zyoton waveforms $Z_i$ and $Z'_i$.

Optionally, a Kappa test can be performed pre-collision, by comparing the velocities of the conditioned feature and the original Zyoton, i.e., $\omega_1$ and $\omega_2$, respectively. As a conditioned feature is generally constructed to have only a fraction of the energy of the original Zyoton, $\omega_1$ is typically only a fraction of $\omega_2$. As such, in comparing $\omega_1$ with $\omega_2$, either one or both of the velocities are scaled, and it is tested whether the magnitude of a difference between the velocities, after scaling one or both, is less than a Kappa parameter $\kappa_{DV2}$.

As described below in various embodiments, the modified Zyoton $Z'_i$ is renormalized to produce a renormalized Zyoton $Z''_i$, having dispersion velocity $\omega_4$ that is comparable to the dispersion velocity $\omega_1$ of the conditioned feature $CF_i$. The energy of the renormalized Zyoton is also expected to be comparable to that of the conditioned feature. Therefore, in some embodiments, Kappa test can be performed by comparing the velocities of the renormalized Zyoton and the original Zyoton, i.e., $\omega_4$ and $\omega_2$, respectively. Here again, as the renormalized Zyoton is expected to have only a fraction of the energy of the original Zyoton, $\omega_4$ is typically only a fraction of $\omega_2$. As such, in comparing $\omega_4$ with $\omega_2$, either one or both of the velocities are scaled, and it is tested whether the magnitude of a difference between the velocities, after scaling one or both, is less than a Kappa parameter $\kappa_{DV1}$. In some embodiments, $\kappa_{DV1}$ can be the same as or approximately equal to $\kappa_{DV2}$. In general, the difference in the velocities to be compared is an absolute difference, i.e., a magnitude of the difference regardless of whether one velocity is greater than or less than the other is compared with an applicable Kappa parameter.

As described above, co-dependency condition can be tested pre-collision, i.e., by testing whether $|\alpha_T^*(\omega_2)-(\omega_1)|$ is less than a Kappa designated $\kappa_{DV2}$, where $\alpha_T$ is the scaling factor applied during testing to the velocity of the original Zyoton. As described above, the velocities can be compared by scaling $\omega_1$ instead of or in addition to scaling $\omega_2$. In order to satisfy this test, a nominal scaling coefficient $\alpha_C$ is applied to achieve a pre-selected ratio ($\alpha_Z$) of spectral energy of Zyoton to the spectral energy of a conditioned feature. The ratio $\alpha_Z$ can be, e.g., 100; 500; 1,000; 2,000; 3,500, etc. In some embodiments, the spectral energies in determining the ratio are computed using only a limited number (e.g., 2, 6, 8, 15, etc.) of frequency components of the Zyoton and the conditioned feature. The nominal scaling coefficient $\alpha_C$ is applied to the original Zyoton or to the conditioned feature, or to both waveforms such that the pre-selected ratio ($\alpha_Z$) of spectral energies of the Zyoton and the conditioned feature are achieved.

The term nominal scaling coefficient is used because different features from the same or different spectra from the same or different media to be analyzed are likely to result in somewhat different scaling coefficients to establish the ratio $\alpha_Z$ of spectral energy of the Zyoton to the spectral energy of the conditioned feature prior to the first collision. Generally, the following condition is imposed on the ratios of the nominal scaling coefficient:

$$\left|\frac{(\alpha C - \alpha \text{Fi\_MAX})}{\alpha C}\right| < 0.1, 0.2,$$

or 0.5, and $$\left|\frac{(\alpha C - \alpha \text{Fi\_MIN})}{\alpha C}\right| < 0.1, 0.2, \text{ or } 0.5,$$

where $\alpha_{Fi\_MIN}$, $\alpha_{Fi\_MAX}$ respectively denote the maximum and minimum scaling coefficients encountered to achieve a desired spectral energy ratio $\alpha_Z$ (e.g., 1000) with an $\alpha_C$ (e.g., 0.001). The parameters $\alpha_{Fi\_MIN}$ and $\alpha_{Fi\_MAX}$ are any members of a set of all spectral energy scaling coefficients $\{\alpha_1, \alpha_2, \ldots, \alpha_\infty\}$ required in a collision computing sequence used to analyze spectral features from a spectroscopically analyzed sample in the frequency domain. It is to be understood that these coefficients $\{\alpha_1, \alpha_2, \ldots, \alpha_\infty\}$ and $\alpha_Z$ may be computed and applied in the time domain or in the frequency domain, and are distinct from the computing-coefficient a described below in the discussion of the collision operator.

Another important co-dependency condition is that the width of the post-collision Zyoton waveform divergence be less than a preset threshold $\tau$. A width of a Zyoton waveform can be described as a time lag between any two phases of a Zyoton waveform, such as time lags t1, t2, and t3 depicted in FIG. 14A. After collision, one or more of these widths can change, as in t1', t2', or t3' shown after a collision in FIG. 14B, but the second co-dependency condition requires that each of these differences, i.e., $\Delta t1 = t1'-t1$, $\Delta t2 = t2'-t2$, and $\Delta t3 = t3'-t3$, be less than $\tau$.

The selection of values for $\kappa$ and $\tau$ are related to the collision grid, bandwidth of the Zyoton, and peak energy of the Zyoton. As the values of $\kappa$ and $\tau$ bound the post-collision spectral energy change that can occur to preserve Zyoton properties, they also bound the original spectral energy of the colliding entity, i.e., the conditioned feature waveform for the first collision by imposing a design constraint on the carrier kernel spectral energy. The number and specifics of frequency components and their amplitudes of the carrier kernel are thus constrained by $\kappa$ and $\tau$. An increase in the $\kappa$ and $\kappa$ values may allow for an increase in the amplitude(s) of the first k frequency components, as well as the number k of analyte-information representing components that are used in the pre-collision and post-collision computations described below. Once $\kappa$ and $\tau$ are established, the properties of the optimized carrier kernel used for conditioning the features can be locked. Exemplary values for $\kappa_{DV2}$ and $\tau$ for noninvasive glucose measurement are $0.6 \times 10^{-6}$ and $1.4 \times 10^{-6}$, respectively, as determined, for example, by an L2 norm. The parameters $\kappa$ and $\tau$ are generally represented as unit-less numbers.

These conditions generally need to be met for every conditioned feature-Zyoton pairing. If these two co-dependency conditions are not achieved, the collisions may not have computational utility or the collision operator may become unstable. In various embodiments, the variables $\kappa_{DV1}$, $\kappa_{DV2}$, $\kappa_{DV3}$, and $\kappa^{SYN}$ are used as tests of collision integrity before the first collision iteration as a limit of the difference in dispersion velocity (or spectral energy) between the Zyoton and the conditioned waveform. Thereafter, before and/or after one or more subsequent collision iterations, these variables can be used as tests of collision integrity between the Zyoton and a modified Zyoton or between a Zyoton and a renormalized Zyoton. Optionally, these variables can also be used to test a limit of the difference in dispersion velocity (or spectral energy) between the Zyoton and the carrier kernel, when they are initially synthesized, in order to verify their codependency. Upon completion of the conditioning process, each conditioned feature can be represented in the computer memory as a parameterized waveform. One or more Zyotons and one or more conditioned features are computationally collided in step 10 (FIG. 13).

Typically, the absorption energy loss due to the analyte is much less than that due to one or more confounders, and the total energy losses due to the analyte and confounders are significantly smaller than the loss due to scattering and/or dispersion of the radiation in the medium. As such, the signal-to-clutter ratio (SCR) of a signal corresponding to the energy loss due to the analyte of interest to the overall energy loss due to confounders and scattering is often very low—e.g., as small as $10^{-4}$ or $10^{-6}$. By tuning the Zyotons, the collision operator, one or more parameters thereof, and the modulation of the feature to a required SCR increase, the energy loss represented by the feature can be amplified, without introducing noise or distortion, in one or more collisions, and can then be measured.

One key objective of the Zyoton tuning process is to configure the Zyoton such that energy loss estimated from a Zyoton collided with a specific conditioned feature, after the one or more prescribed number of collision iterations, is strictly monotonic, that is, trending in the same direction throughout the entire interval, as the concentration of the analyte in the sample over the analyte concentration range of interest, when the feature concentrations and computed energy loss are represented as ordered pairs. It is to be understood that the term monotonic, while used here in the sense of a constantly increasing trend of a data set in which the analyte concentrations are constantly increasing, can also be used to describe the constantly decreasing trend of a data set in which the analyte concentrations are constantly decreasing. The collision process can be thus described as a monotonic transformation of an acquired spectroscopic dataset. A calibration table and/or curve can be used to determine concentration of the analyte in the medium according to the amplified energy loss or change, as represented by the final result of one or more collision iterations yielding a monotonic response.

In various embodiments, several collision iterations are used to expand the dynamic range of the estimated spectral energy changes so that greater precision can be obtained during the post-collision projection process for predicting analyte concentration. Specifically, in various embodiments, the collision process is iterative in which the first collision iteration in a collision sequence is between a Zyoton and a conditioned feature. Subsequent collision iterations may be between the renormalized output of the preceding collision (i.e., a renormalized Zyoton) and the same or a different Zyoton. Whenever more than one collision iteration is used (i.e., the number of iterations $\mathbb{N} > 1$), the colliding entities are usually a renormalized Zyoton and the original Zyoton or a new Zyoton.

Different Zyotons may be used to collide with different conditioned features. Different features extracted from varying regions of the original source data can have vastly varying differences in their measurement scale, sometimes varying over several orders of magnitude. With such variations, in some embodiments, the co-dependency condition cannot be achieved using the same Zyoton for all selected spectral features. Thus, different Zyotons are designed and tested to ensure that each conditioned feature and Zyoton pair satisfies the codependency condition described above.

The analyte in the medium to be analyzed generally induces a change in the measured parameters of the medium (such as absorption or emission of energy) relative to those parameters if no analyte were present in the medium. This change is represented in the acquired spectral data of the medium and, hence, in one or more extracted features. The Zyotons, the conditioning of the features, and the collision operator are designed such that one or more collisions in step 10 (FIG. 13) generally induce a measurable change in one or more properties (e.g., spectral energy reduction due to incident light absorption by the analyte in the measured spectral bandwidth) of the waveform resulting from the collisions. In step 12 (FIG. 13), after a preset number of collisions between a conditioned feature and the corresponding Zyoton have been completed, such change in the resulting waveform is computed to determine the net spectral energy gain or loss for each collided feature. In some embodiments, the process is configured to be represented as an energy gain, but represents a loss in spectral energy due to absorption of energy by the analyte.

Following a collision process involving one or more collision iterations, the changes in the properties of the post-collision waveform (the modified Zyoton) before and after the collisions may be analyzed as a mechanism to infer properties of the feature. Impacted properties may include changes in propagation velocity, peak energy, dispersion velocity, and changes in the spectral envelope. These changes can be quantified through changes in the spectral energy of the modified Zyoton generated after each collision relative to the spectral energy of the original Zyoton. In the first iteration, at least a portion of the energy of the feature that is represented by the conditioned feature is transferred to the modified Zyoton and then to the renormalized Zyoton. In subsequent collision iterations, the energy of the feature is transitively transferred from a renormalized Zyoton generated in a previous iteration to a renormalized Zyoton generated in the current iteration.

In effect, the collision computing process examines how the energy from the incoming, uncharacterized feature interacts with the properties of the stable Zyoton waveform to produce a post-collision waveform with the analyte information content of the original feature. Depending on how the conditioned feature waveform itself has been influenced by the underlying analyte concentration, and by confounders and the media, its interaction with the Zyoton can be different. As such, a Zyoton can be described as a nonlinear amplifier system and a feature as a perturbation. The repeated collision process is thus a protocol for characterizing analyte properties and estimating concentration in the uncharacterized samples.

The absorbed spectral energy, represented as a net gain in the energy of a modified Zyoton relative to the energy of the original Zyoton, is transformed into an analyte concentration using a projection operator. Projection is a generalized process of representing the average estimated post-collision spectral energy absorption in terms of net, renormalized spectral energy changes corresponding to an uncharacterized sample, and associating these net energy changes with those corresponding to known, analyte levels (represented in a "reference system"), as described below in detail. The reference system may or may not have any physical relationship with the samples being analyzed. For example, in non-invasive glucose measurement, as described below, the reference system may be a collection of tissue simulating dispersive liquid or gel samples (also referred to as "phantoms" or "tissue phantoms"), and containing specified glucose concentrations. The projection operator can relate the observed spectral energy absorbed in spectra from uncharacterized human subjects to known concentrations of glucose in an Intralipid fat emulsion or gel-based tissue phantom system. To this end, calibration curves can be used to relate the two disparate systems. As a generalized mechanism, projection can be accomplished by mapping or transforming the computed post-collision spectral energy absorption to an absolute reference system of known concentrations. Projection may optionally involve transforming the estimated spectral energy change (gain or loss) through one or more intermediate systems through the use of calibration curves prior to projecting the spectral energy change onto the reference system.

Collision Computing Process

Figure 15:
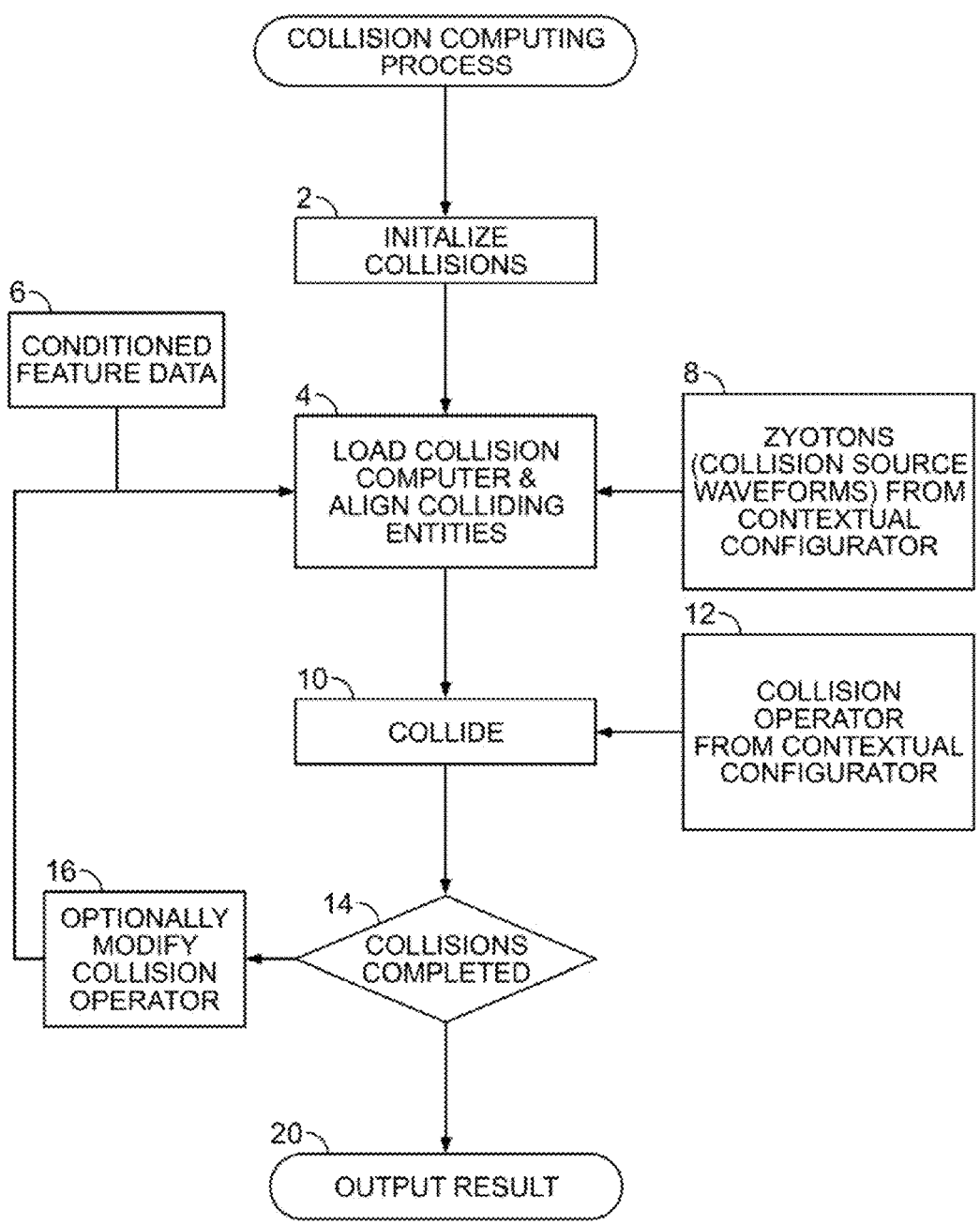
FIG. 15 depicts an exemplary process for determining one or more operating parameters of a collision computer and for generating the inputs thereof, according to one embodiment.

With reference to FIG. 15, in various embodiments, collision computing is performed for selected features, sequentially or in parallel. Features may be conditioned and introduced into the collision computer as one-dimensional vector data objects including one or more numerical vector elements. Prior to introduction into the collision computer at step 4, the complete spectrum (or other data set) may be preprocessed and standardized. The features are transformed at step 6 into a spectral waveform using a form of frequency modulation called the conditioning process.

An optional preprocessing performed on feature data involves numerical scaling of the feature data amplitude vector with respect to another reference data vector. The reference data vector can be derived from an in-line, in-measurement property used to compensate for variability in the measurement. This may be done in systems where there is high measurement-to-measurement variability during the acquisition of feature data (such as when the acquisition involves the detection of NIR light diffusely reflected from tissue). During preprocessing, the raw sensor data can be transformed into a data representation that is appropriate for the follow-on conditioning and collision computing processes. As an example, the acquired raw sensor data could be in the form of discrete counts, current, voltage or some form of flux intensity, with values ranging from a minimum to a maximum as defined by the sensor's dynamic range. The sensor or data acquisition platform may be optionally equipped with a hardware reference channel that can simultaneously collect raw reference data, also in the form of discrete counts, current, voltage or some form of flux intensity under a fixed condition (such as dark current or when there is no sample exposed to the sensor). The preprocessing step can combine sensor data and its reference counterpart to create a data object ("absorbance" or "pseudo-absorbance," as described below) that can be used in subsequent computation. One example is the preprocessing of diffusely reflected spectral intensity amplitudes by combining them with reference amplitudes to transform the intensity data into absorbance or transmittance representations in spectroscopic analysis.

The standardization step can involve computations that are implemented to further transform the preprocessed data to remove the effects of sensor to sensor variability, variability due to data formats and variability due to hardware changes or degradation. Standardization generally helps to ensure syntactic integrity and can enhance semantic equivalence of the data, irrespective of differences in the hardware that was used to collect it. Both preprocessing and modulation are described in detail below.

An optional frequency modulation may be performed as part of the sensor data conditioning process at step 6. This frequency modulation step, referred to as an optional "precursor frequency modulation," has a different purpose compared to preprocessing and standardization. In dealing with sensor measurements to observe materials where interference from clutter is high (SCR<<1), frequency modulation may be used as a mechanism to expand the observability state space, i.e., observable states from which the properties of the material (e.g., an analyte) can be classified, quantified, or inferred. By coupling the sensor data features or preprocessed, standardized sensor data features with carriers of different frequencies in a precursor modulation, the state space over which the data are analyzed can be transformed so as to increase the probability of detection of the amount, event, material or property of material of interest. Unlike the conventional frequency modulation in signal processing where a carrier wave is used to encode the signal or information by varying the instantaneous frequency of the wave, the precursor modulation can increase the observability space of events and materials.

The conditioned feature is then introduced into the collision computer at step 4, along with a complementary entity—the collision waveform or Zyoton, generated at step 8 using the criteria described above. The synthesis of the Zyoton and the carrier kernel used to generate the conditioned feature is also described below. Within the collision computer, the conditioned feature waveform and Zyoton waveforms are represented as waveforms propagating toward each other on a collision grid. During the collision at step 4, the conditioned feature wavefront collides and couples with the Zyoton wavefront, thereby changing the properties of the Zyoton and producing a resulting waveform called a modified Zyoton. The Zyoton and the feature waveforms are fed into the collision computer that performs bracketed interactions between the two propagating waveforms and, in particular, the colliding wavefronts, producing the new post-collision waveform i.e., the modified Zyoton waveform. Unlike conventional modulation techniques, which typically involve multiplication and/or convolution operations, the bracketed interaction operator involves conditional operations and is non-invertible.

The amplitudes of the Zyoton and/or the conditioned feature may be optionally modified prior to the collision thereof, e.g., to ensure the co-dependency conditions described above, and the Zyoton and/or conditioned feature components may be optionally shifted and aligned prior to the collision thereof. Phase modulation may be applied to the modified Zyoton. The collision operation is controlled, as described below, such that a measureable change occurs in a property (e.g., spectral energy) of the modified Zyoton relative to the corresponding property of the original Zyoton, and the change is attributable to the corresponding property of the feature, as represented by the conditioned feature. To this end, various collision operators such as shifting, scaling, phase rotation, number of iterations, etc., can be determined at step 12 based on the properties of the medium to be analyzed, the analyte, the sensor, and the computing system.

In various embodiments, the conditioned feature waveform may be unused after the first collision at step 10. A second collision may occur, at step 4, between the post-collision modified waveform following renormalization thereof (called the renormalized Zyoton), and the original Zyoton or a different Zyoton. The different Zyoton, in general, is selected such that it is co-dependent, as described above, with the renormalized Zyoton. Similarly, additional collisions can be performed between the waveform resulting from the previous collision, after renormalization thereof, and the original Zyoton or a different Zyoton.

In generalized collisions, one of three additional collision modalities can be implemented: (i) successive collisions between the original conditioned feature and the post-collision modified and renormalized Zyoton waveform from the preceding collision; (ii) successive collisions between the original conditioned feature with a new Zyoton waveform; and (iii) successive collisions between the post-collision modified and renormalized waveform from the previous collision and a new Zyoton waveform. Whenever successive collisions are described, a renormalization process described below is generally included as an integral part of the iterative collision process. The renormalization, in general, includes energy scaling and/or removal of one or more frequency components, and redistribution of the energy of the removed component(s). When a modified Zyoton is renormalized and collided with the original Zyoton in a subsequent iteration, the energy scaling that is applied can be different from the energy scaling applied when the modified Zyoton is renormalized and collided with the original conditioned feature.

The measurable changes in post-collision waveform properties relative to the corresponding property of the original Zyoton, e.g., the net gain in spectral energy of the coupled waveform (i.e., the modified Zyoton and/or the renormalized Zyoton), as computed using the difference between the spectral energy of the Zyoton waveform and post-collision modified and renormalized Zyoton waveform following one or more collisions, can be used to estimate the presence and concentration of an analyte in a medium.

An example illustrating the utility of this technique is the non-invasive estimation of glucose (an analyte of interest) in human skin tissue, using optical diffuse reflectance spectroscopy, whereby the concentration of glucose can be determined based on the measurement of selective spectral absorption of energy when skin is illuminated with near-infrared radiation. The analyte concentration can be determined by computing the spectral energy distribution of the post-collision Zyoton waveforms after all collision iterations are completed. The spectral energy gain between the energies of the modified Zyoton obtained after the last iteration and the original Zyoton, as represented by the spectral energy of the last renormalized Zyoton, is related to the feature properties as represented by the conditioned feature waveform properties. The collision process is used to estimate how much of the loss of energy of the incident NIR in the original feature waveform is due to the presence and concentration of the analyte. In a properly selected and designed Zyoton, carrier kernel, and collision operation, an ultra-small net energy loss due to absorption by the analyte can be detected and amplified on a dynamic range that extends to as much as fourteen orders of magnitude, using Zyotons with frequency bandwidths in the MHz region.

One embodiment, used for a non-invasive analyte measurement, employs 20,000 repeated collisions to estimate the net energy gain due to absorption at the feature level and to overcome the high level of interference from confounders. In some embodiments, the collision operator may be modified at step 16, if required, and then the result is re-introduced into the collision computer at step 4, for the next collision at step 10. In some embodiments, the collision operator is not modified between one or more or all of the subsequent collision iterations. The process is repeated until the required number of collisions are completed, as determined at step 14, and the results may be output (reported) and/or may flow at step 20 to the next step for estimating the net energy loss due to absorption.

Post-Collision Renormalization

Figure 16:
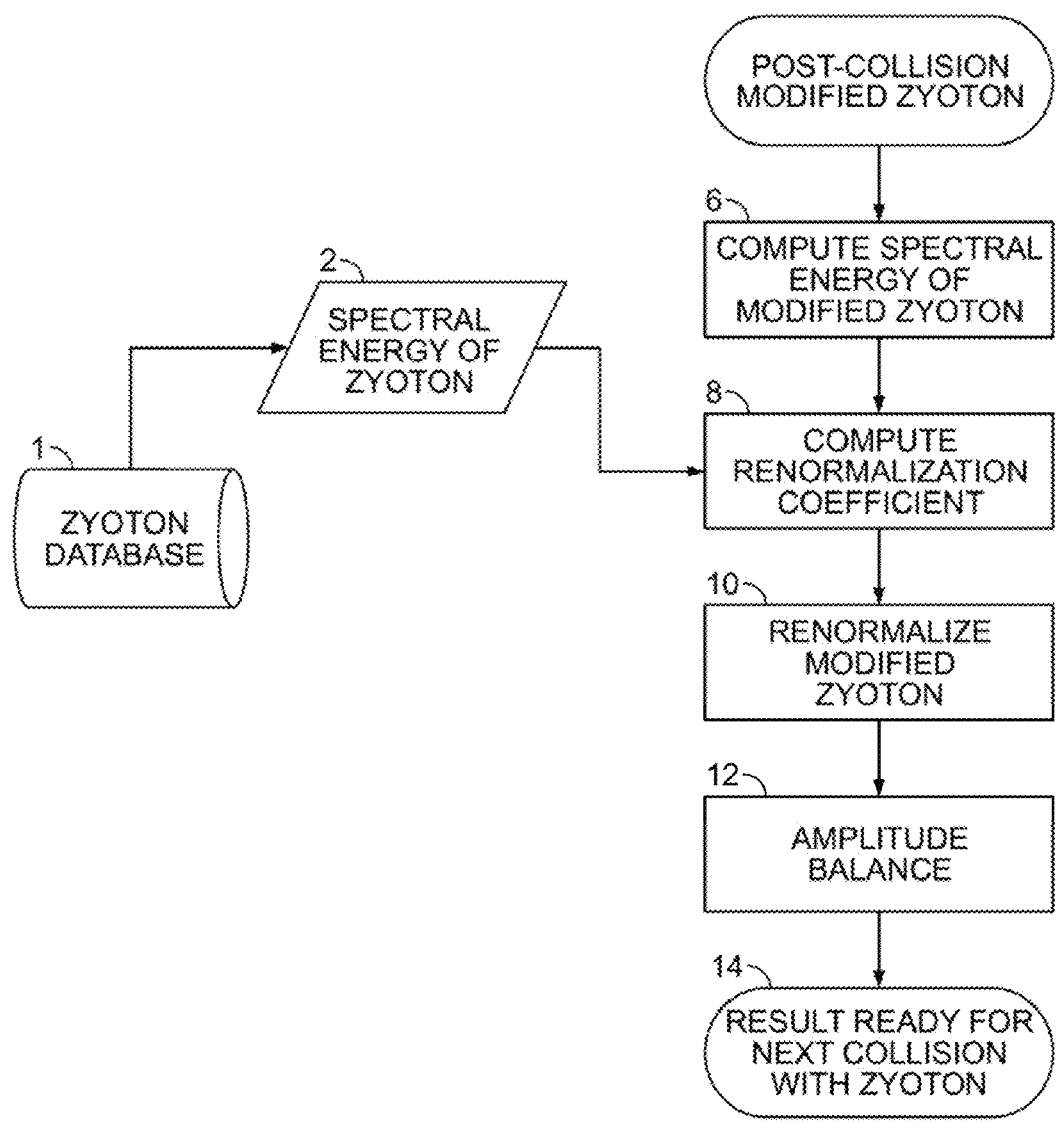
FIG. 16 is a flowchart depicting a process for renormalizing a modified Zyoton prior to a subsequent collision, according to one embodiment.

With reference to FIG. 16, the spectral energy of a post-collision result (e.g., a Zyoton perturbed by a conditioned feature) is computed at step 6 to estimate the change due to the presence and concentration of material exhibited in the spatial, temporal, or spectral window defined by the feature. For systems with several collision iterations, the output after each collision is generally renormalized in steps 8, 10, and 12 before a subsequent collision can occur.

This renormalization is performed for two reasons: (i) removal of the energy of the original Zyoton, and (ii) redistribution of energy lost by a truncation operation. All collisions following the first collision may be between a Zyoton and a renormalized, modified Zyoton resulting from the preceding collision interaction, so the original spectral energy of the Zyoton needs to be removed from the modified Zyoton prior to the next collision by properly scaling the frequency domain amplitudes of the analyte-information representing (e.g., the first k) frequency components.

In statistical field theory and quantum field theory, the pileup of contributions from a large number of measurement scales involved in a measurement problem can lead to intractability of measurements. A renormalization of the measurement scales can address the intractability associated with a large number of measurement dimensions in problem solving, as described in K. G. Wilson, "The renormalization group: critical phenomena and the Kondo problem," *Reviews in Modern Physics,* 47, 4, 773 (1975). The collision computing process does not generally involve analysis of direct measurements of an analyte at different measurement scales and, as such, unlike the renormalization employed in statistical fields theory and quantum fields theory, the renormalization described herein is directed to readjustment of the observable, e.g., the spectral energy, across successive iterations.

In general, collision computing also transforms signal detection and quantitation to a spatio-temporal (space-time) framework, which allows waveform interactions which may not be fully accounted for or modeled, and may include approximations used for numerical stability in computation. The term framework is used here as the space-time scale for implementing collisions and may not be related to the space-time dimension associated with acquiring the data. The framework can be a computational framework, or it may be related to the apparatus for implementing a collision computer such as a digital computer, graphic processing unit processor, or optical computer, or any such examples implemented in firmware.

The result of every collision interaction is baselined observable energy scalar i.e., the spectral energy gain of the modified Zyoton relative to the spectral energy of the original Zyoton as estimated from a fixed subset of frequency components. The spectral energy of the original Zyoton selected from a database 1, and used in the collision, is determined at step 2. That spectral energy is used in step 8 to determine a normalization coefficient, so that the energy of the original Zyoton can be removed from the modified Zyoton at step 10.

As described above, the second objective of the renormalization is truncation of the modified Zyoton, so that the renormalized Zyoton can be effectively collided again with the original Zyoton, or with another Zyoton. New frequency components can be created in the transition and non-analyte information representing bands during a collision iteration. The introduction of these components may cause a change in dispersion velocity and/or divergence, so that the co-dependency condition may not be satisfied for the next collision iteration. As such, one or more of these components may be removed during truncation of the modified Zyoton. In general, subportion(s) of the non-analyte information representing and/or transition portions (these terms are described below) of the modified Zyoton are removed, and the energy thereof is redistributed among the surviving subportions. This energy redistribution can be achieved via amplitude balancing at step 12. If renormalization is implemented in the frequency domain, the amplitude balancing can compensate for the impact of any removal of one or more frequency components of any entity participating in a collision.

The truncation generally results in a loss of spectral energy of the modified Zyoton. The energies of the removed frequency components of the modified Zyoton are computed and re-distributed across the surviving frequency components of the modified Zyoton. This is implemented using an amplitude balancing operation at step 8. Specifically, in the frequency domain, the amplitude re-balancing (or re-distribution) operation entails distribution of the removed spectral energy contribution from the removed frequency components over the remaining m and j frequency components of the modified Zyoton. Thus, the frequency domain amplitudes of the surviving m and j components are adjusted at step 8 during the renormalization process.

Alternatively or in addition, renormalization may further include an additional truncation of the modified Zyoton to select the length thereof. To this end, relatively smaller-amplitude frequency components of the modified Zyoton may be removed to ensure that the frequency-domain length of the renormalized Zyoton waveform matches the frequency-domain length of the original Zyoton and/or a new Zyoton with which the renormalized Zyoton is to be collided. This truncation may also be followed by an additional amplitude balancing operation in step 12, in which the amplitudes of all the remaining m and j frequency components of the truncated modified Zyoton are adjusted to compensate for the energy of the frequency components removed in the additional or alternative truncation process. This renormalized post-collision Zyoton waveform may then be reused in the next collision iteration as described with reference to FIG. 15. Renormalization can be implemented in the time domain by modifying the time-domain velocity and/or dispersion velocity of the modified Zyoton.

In general, the renormalization of the post-collision waveform of the modified Zyoton allows removal therefrom of the energy contained in the original Zyoton after each collision iteration so that energy changes can be successfully accumulated in a multi-collision protocol for quantifying analyte presence and concentration. In some embodiments, two renormalization parameters are derived using spectra generated from a model of waveform propagation over a collision grid. The first renormalization parameter includes a set of numbers associated with the respective amplitudes of every frequency-domain component of the waveform, matched to the length of the truncated (e.g. down-sampled) result after collision. The first renormalization parameter modifies the frequency domain amplitudes of the surviving frequency components, such that the spectral energy of all frequency components of the modified Zyoton, ignoring the first k analyte-information representing components, is the same as the spectral energy of all but the first k frequency components of the conditioned feature used in the collision. This can be tested by comparing the spectral energy of all but the first k components of the renormalized Zyoton with the spectral energy of all but the first k components of the conditioned feature.

The renormalization process also computes a second parameter, i.e., a renormalizing scaling factor, which changes the frequency domain amplitudes of the first k components to provide the next waveform for the next collision. The renormalizing scaling factor is designed such that, the frequency domain amplitudes of the first k frequency components of the renormalized modified Zyoton are within 0.1%, 1%, 5%, 10%, 20%, 30%, or 50%, 100%, etc., of the frequency domain amplitudes of the first k frequency components of the conditioned feature. As a result, the energy of the renormalized modified Zyoton becomes substantially similar to that of the conditioned feature just prior to collision and is within 0.1%, 0.4%, 1%, 2%, 5%, or 10%, etc. of the energy of the conditioned feature. This can also ensure that the Kappa test of co-dependency condition is satisfied for the next collision iteration. In some embodiments, this computation is done up to the fifteenth decimal digit for high precision and to accommodate SCR below 0.0001. In some embodiments that employ only a single iteration of a collision operation, if renormalization is performed, the frequency domain amplitudes of the first k frequency components of the renormalized modified Zyoton are adjusted such that the resulting energy of these k components can be up to two or three orders of magnitude of the energy of the corresponding frequency components of the conditioned feature to expand the dynamic range of energy change. Applications where only one collision iteration is used in conjunction with renormalization include classification of analyte levels into 3, 5, 7, 12 etc., bands or regions.

Figure 17:
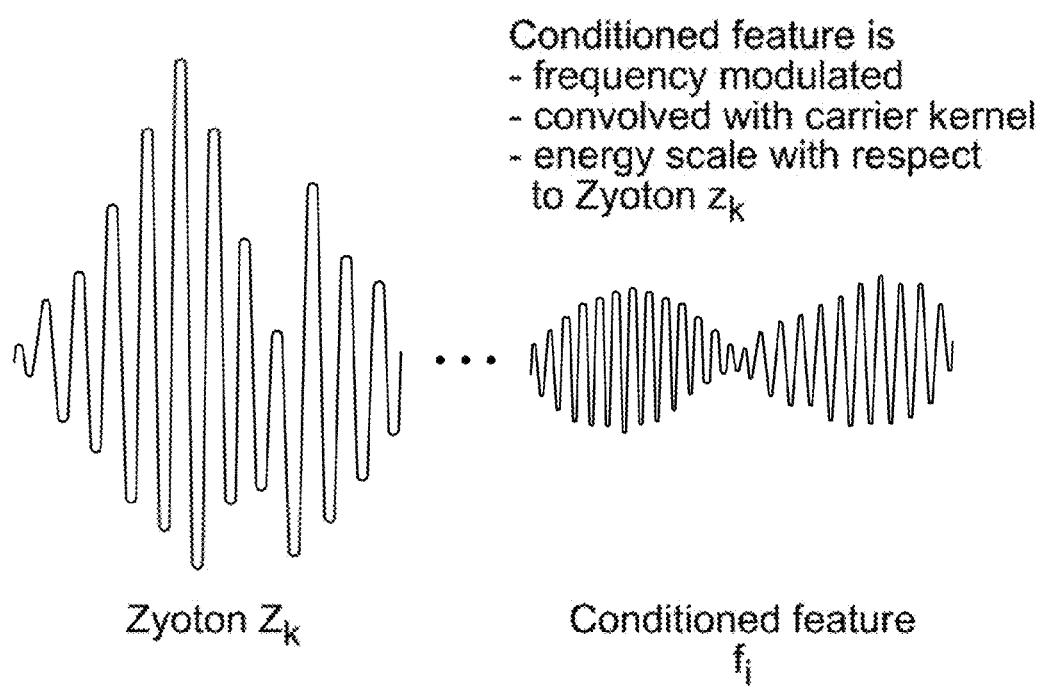
FIG. 17 shows the conditioned feature waveform on the collision grid and Zyoton waveform before a collision.
Figure 18:
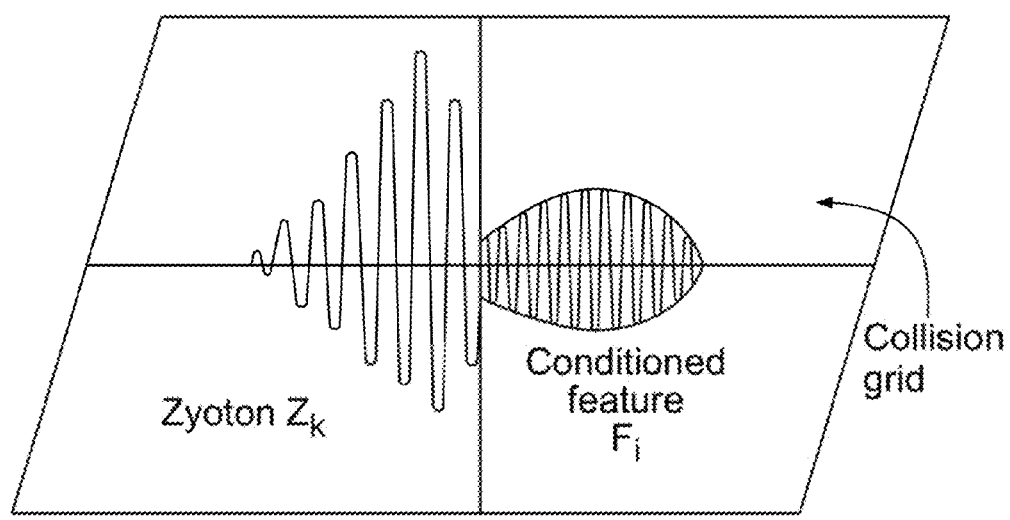
FIG. 18 shows the conditioned feature waveform on the collision grid and zyoton waveform at the beginning of a collision.
Figure 19:
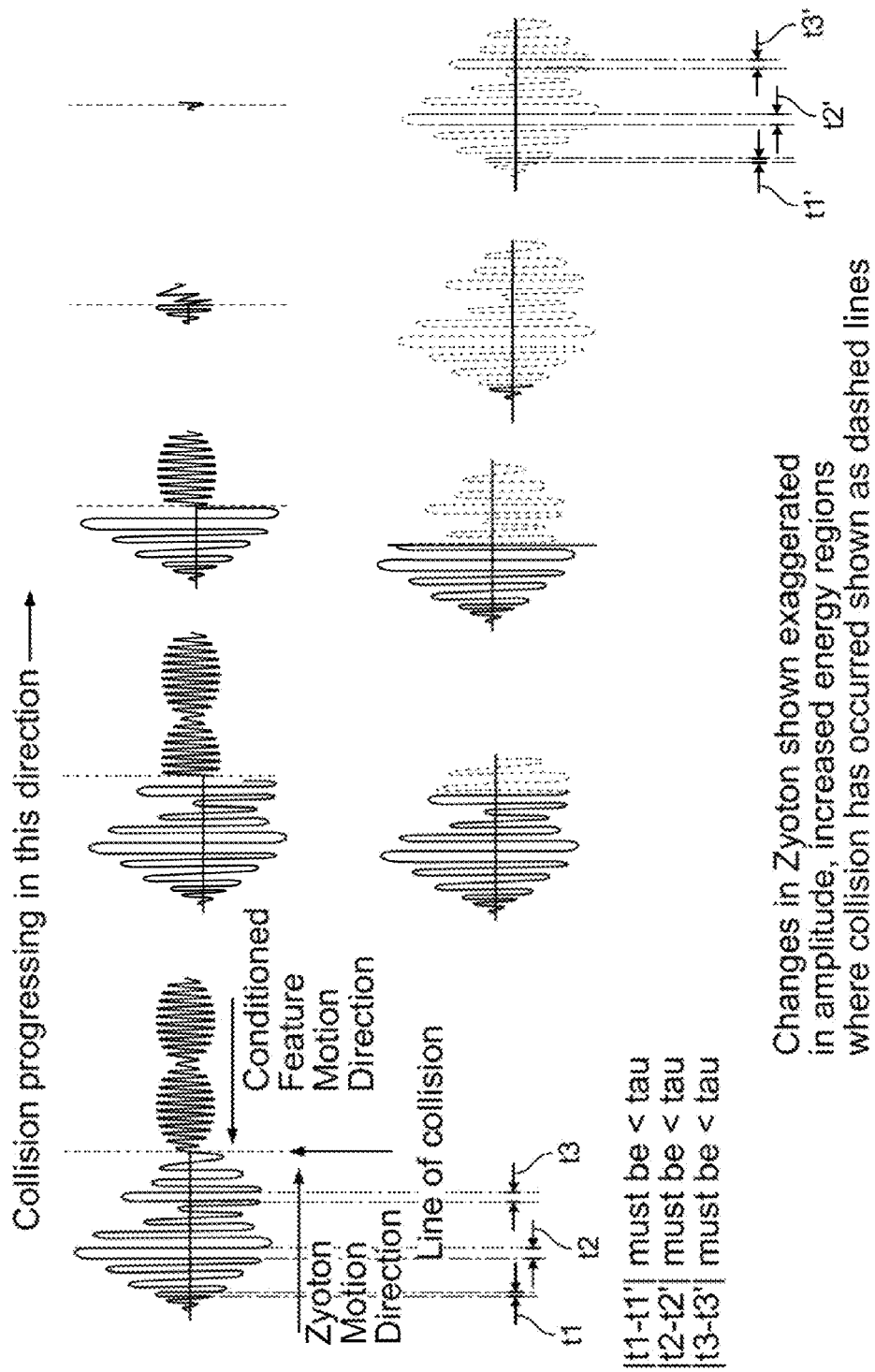
FIG. 19 shows successive views of the collision between a conditioned feature waveform and Zyoton wavefronts during a collision.
Figure 20:
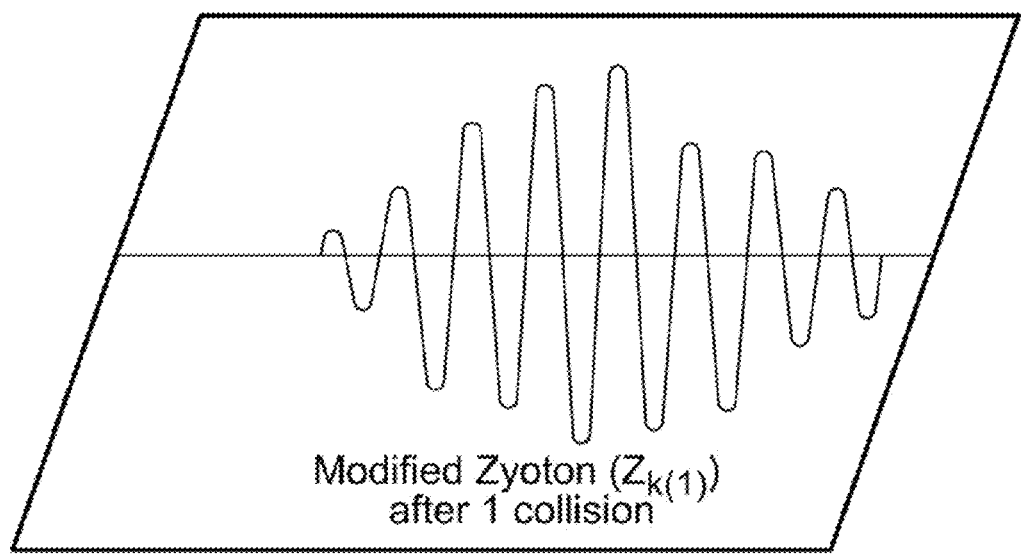
FIG. 20 shows the modified Zyoton after a collision.
Figure 21:
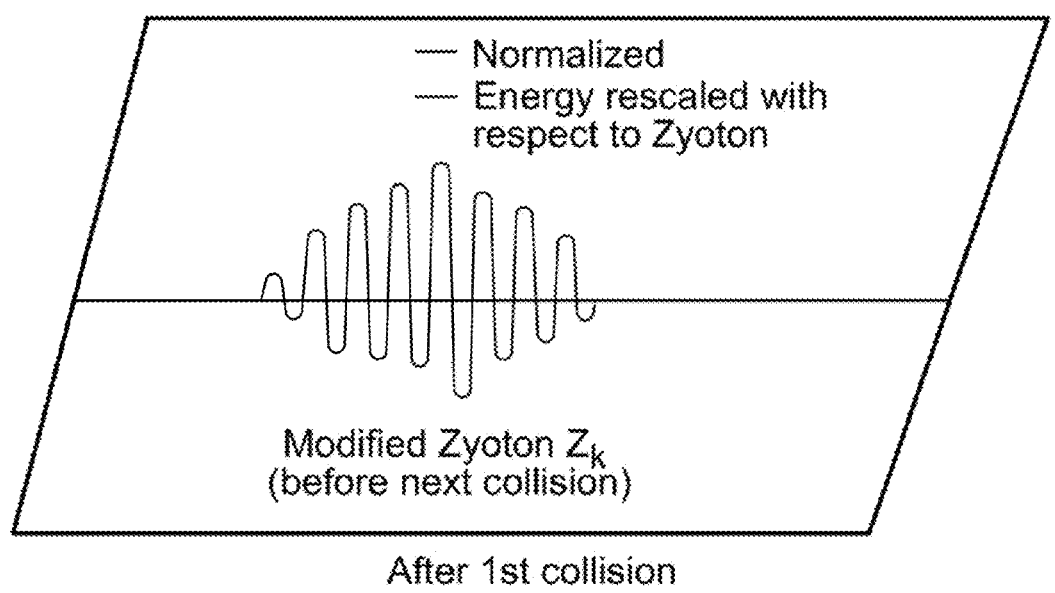
FIG. 21 shows the renormalized modified Zyoton after the collision and preceding the next collision in a multi-collision protocol.
Figure 22:
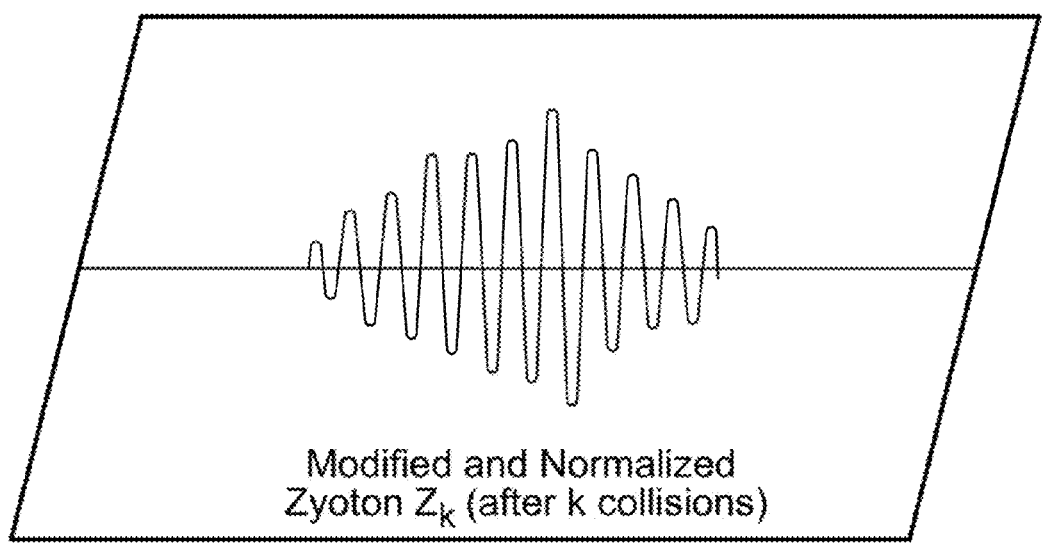
FIG. 22 shows the modified and normalized Zyoton after a finite number of k collisions in a multi-collision protocol.
Figure 23:
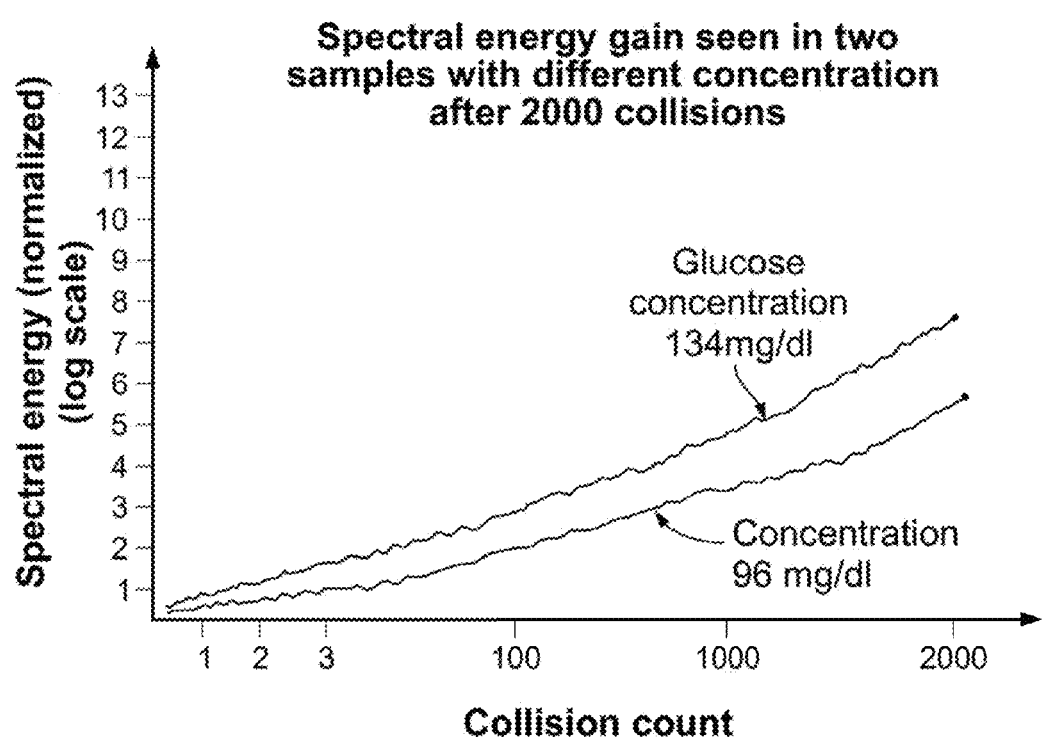
FIG. 23 shows how the normalized energy trajectory evolves for two features drawn from samples with two different material concentrations in a collision computer with the difference in the two waveforms showing the amplification that results from a collision computer.

The renormalization process allows accumulation of energy changes generally only due to absorption of energy by the analyte in each feature. The purpose is to transform all the energy changes to a relative scale and dynamic range which can then be projected onto analyte concentrations using a dataset that provides concentration-specific references. FIG. 17 shows the morphological envelope of an exemplary Zyoton and conditioned feature used in collision computing. FIG. 18 shows the Zyoton and the conditioned feature waveform on a "spatio-temporal" grid and the Zyoton waveform before a collision. FIG. 19 illustrates the progression of a collision between the conditioned feature and the Zyoton wavefronts during a collision. FIG. 20 shows the modified Zyoton after the collision. FIG. 21 shows the modified and renormalized Zyoton after the collision and preceding the next collision in a multi-iteration collision protocol. FIG. 22 shows the modified and renormalized Zyoton after a finite number of ℕ collisions in a multi-iteration collision protocol. FIG. 23 shows a typical energy gain trajectory due to the net spectral energy change resulting from analyte-specific absorption evolving over several collision iterations in a collision computer for two features drawn from samples with two different material concentrations (for example, tissue glucose). The two curves show the amplification resulting from collision computing.

Figure 24:
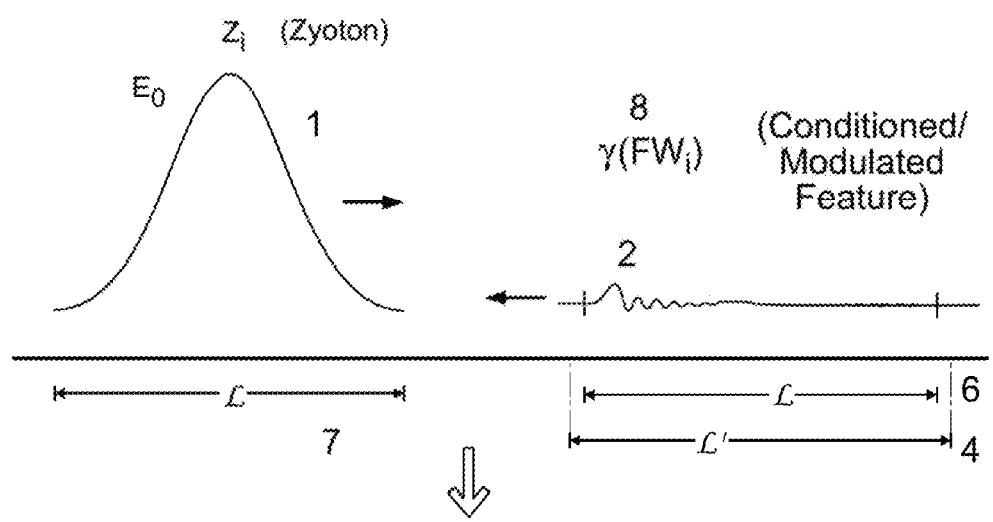
FIG. 24 shows a time-domain representation of a Zyoton and a conditioned feature.
Figure 25:
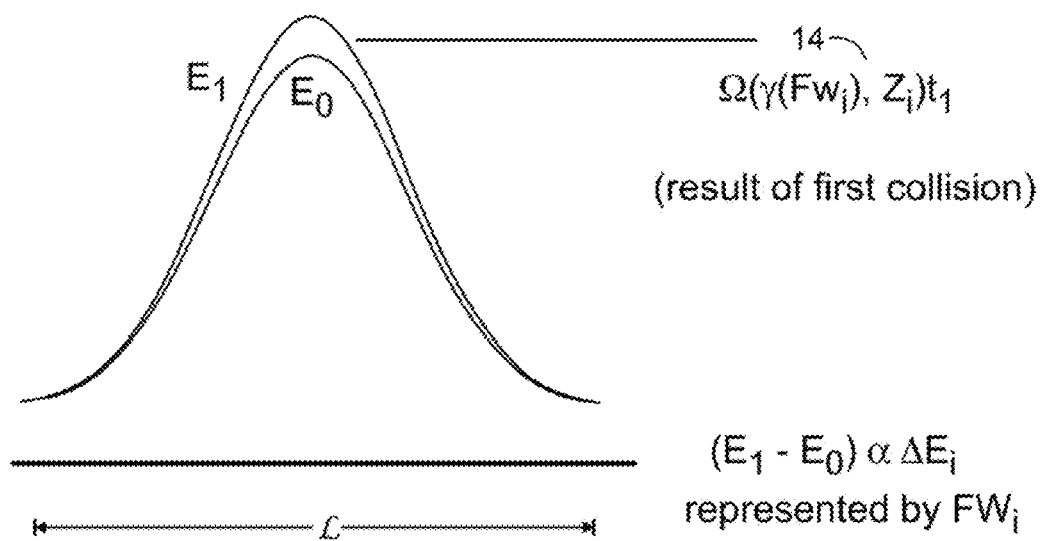
FIG. 25 shows a time-domain representation of a Zyoton after a single collision.

With reference to FIGS. 24-27, the collision and renormalization processes are illustrated schematically in the time domain. FIG. 24 illustrates a collision between a Zyoton $Z_i$ 1 schematically represented by a bell-shaped envelope and a conditioned feature $\gamma(FWi)$ 8. In the time domain, a Zyoton typically includes several peaks such as those shown in FIG. 12A, which, together, can be represented schematically by an envelope such as that shown in FIG. 24. Each Zyoton peak itself can be a schematic envelope, i.e., each peak can be a group of one or more peaks, as shown in FIG. 12B. The conditioned feature may initially have length L' in the time domain, while the zyoton has length L in the time domain. The length of the conditioned feature 6 is adjusted, e.g., by interpolation, down-sampling, and/or truncation, to match the length L of the Zyoton to allow the collision therebetween. The result of the first collision is shown in FIG. 25 as a modified Zyoton envelope 14, $\Omega(\gamma(FW_i),Z_i)t_1$. The energy of the modified Zyoton is $E_1$, the energy of the original Zyoton is $E_0$, and the energy gain $(E_1-E_0)$ or loss, where $(E_1-E_0)$ is less than zero, is proportional to $\Delta E$, i.e., is the energy of the analyte-information representing portion of the conditioned feature FWi. FIG. 25 shows that the modified Zyoton with energy $E_1$ still has length L. In some instances, however, the length of the modified Zyoton can be different from L, e.g., the length can be L".

Figure 26:
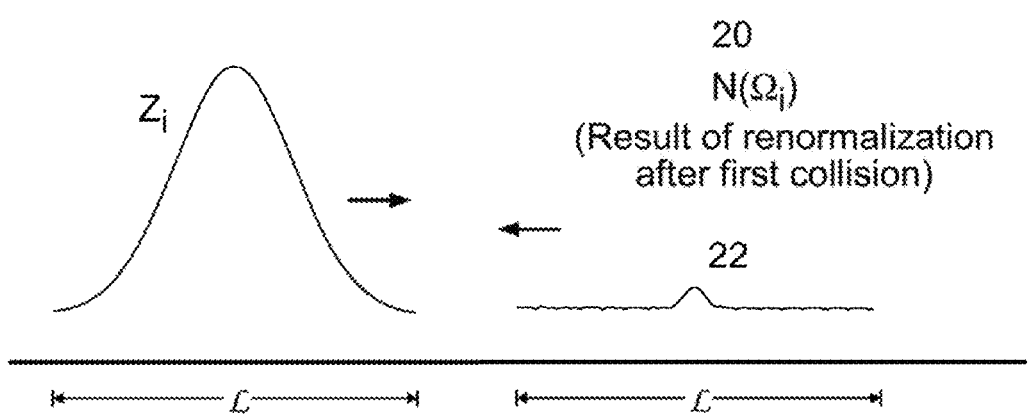
FIG. 26 shows a time-domain representation of a Zyoton and a renormalized modified Zyoton.
Figure 27:
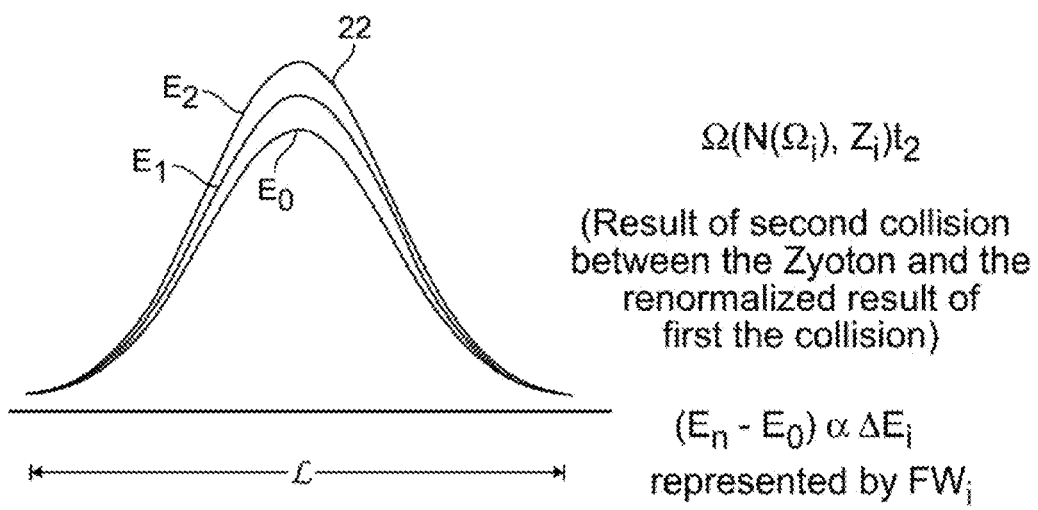
FIG. 27 shows a time-domain representation of the energy of a Zyoton after a second collision.

In FIG. 26, the modified Zyoton $\Omega(\gamma(FW_i),Z_i)t_1$ is renormalized to a renormalized Zyoton $N(\Omega_1)$, 20. The renormalization includes removal of the energy of the original Zyoton and redistribution of the portion of the modified Zyoton removed by truncation. The energy of the analyte-information representing portion of the renormalized Zyoton is $\Delta E_1$. The renormalized Zyoton $N(\Omega_1)$, 20 is collided again with the original Zyoton $Z_i$, to yield the new modified Zyoton shown in FIG. 27 as $\Omega(N(\Omega_i), Zi)t_2$, 22, having energy $E_2$. The energy gain of the new modified Zyoton relative to the original Zyoton, i.e. $(E_2-E_0)$ is proportional to the energy $\Delta E_1$ of the analyte-information representing portion of the renormalized Zyoton $N(\Omega_1)$, which is proportional to the energy $\Delta E$ of the analyte-information representing portion of the conditioned feature.

In each subsequent collision iteration, the energy gain of the modified Zyoton generated in that iteration relative to the energy of the original Zyoton, represented by $(E_n-E_0)$ for the n-th collision iteration, is proportional to the energy of the analyte-information representing portion of the renormalized Zyoton generated in the previous collision iteration, i.e., $\Delta E_i$, which itself is transitively proportional to the energy $\Delta E$ of the analyte-information representing portion of the conditioned feature.

Features, Collision, Renormalization, and Energies

Figure 1:
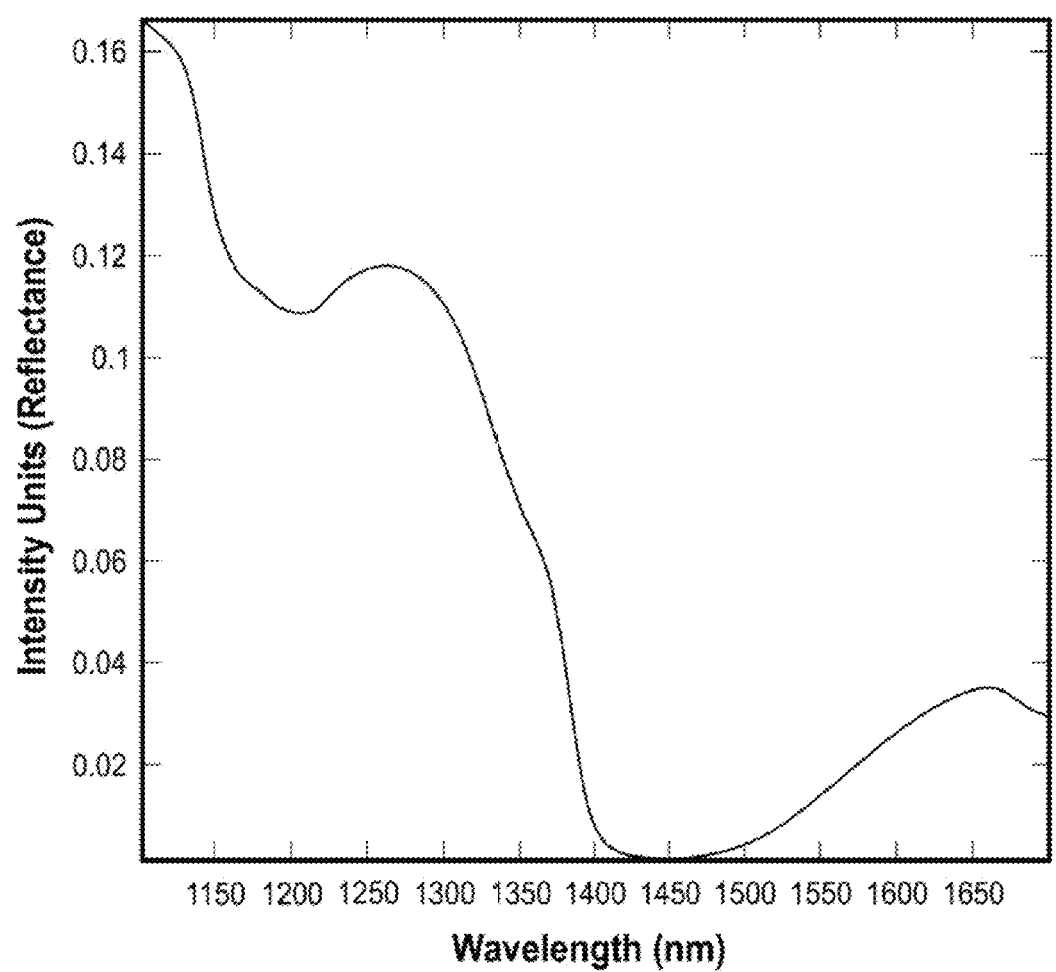
FIG. 1 shows an example of a noninvasive near-infrared intensity (diffuse reflectance) spectrum of a tissue sample.
Figure 2:
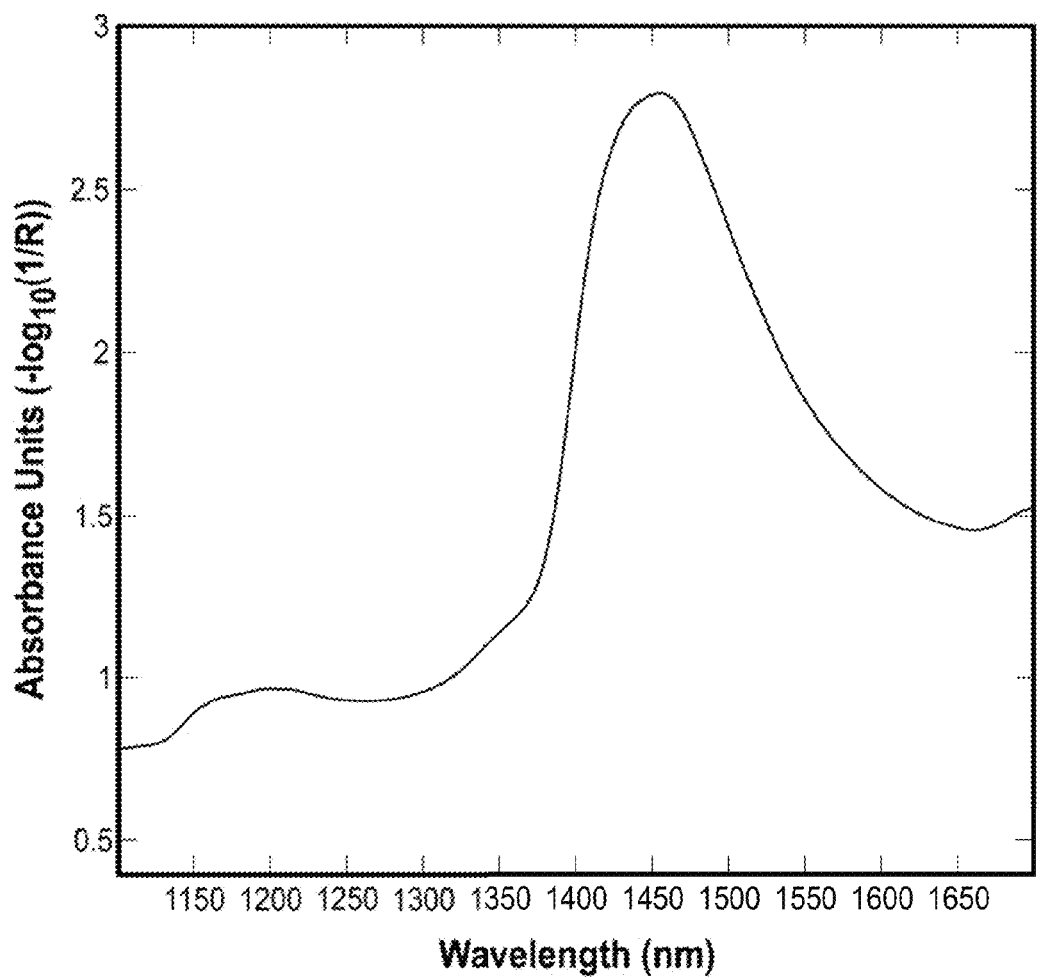
FIG. 2 shows an example tissue absorbance spectrum from a single sample which is used with other similar measurements and their associated reference values to create a multivariate model for analyte measurement.
Figure 3:
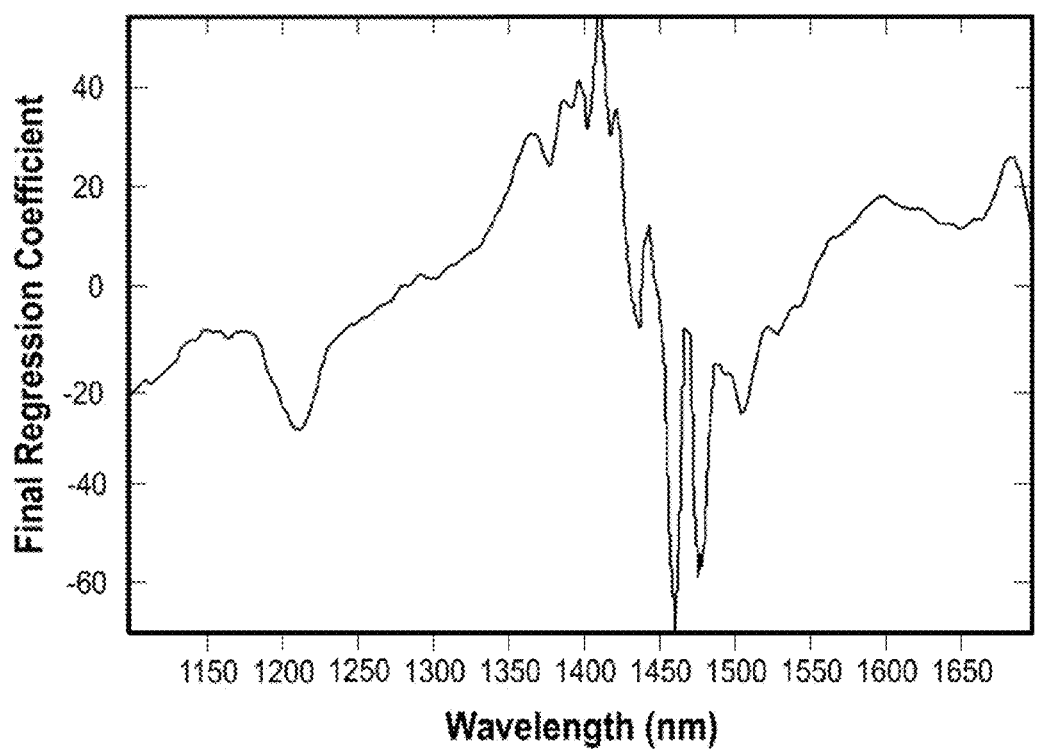
FIG. 3 shows an example set of regression coefficients versus wavelength associated with a model used in multivariate analysis for analyte measurement.
Figure 4:
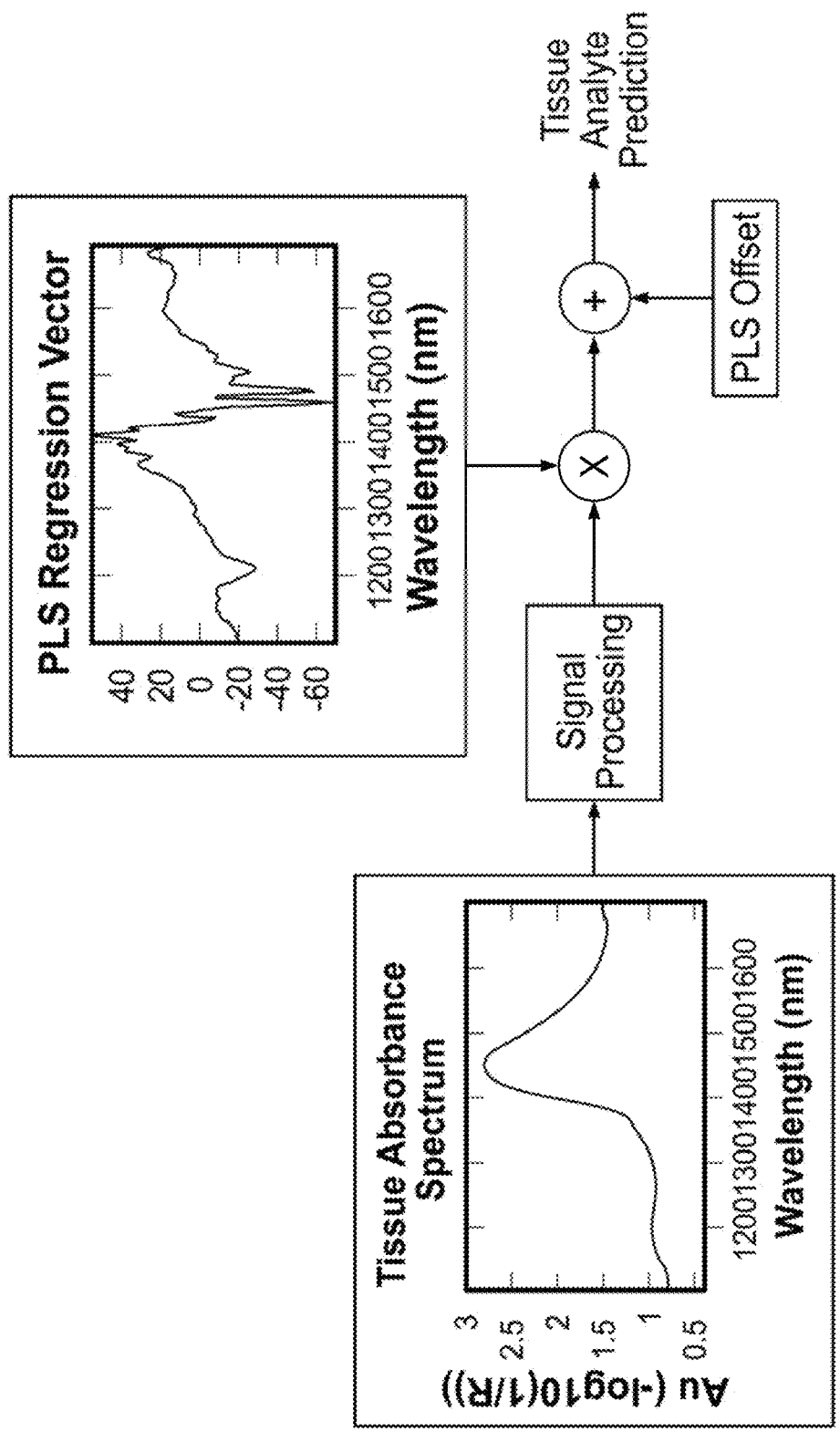
FIG. 4 is a flow-chart depicting the use of a multivariate model to predict a tissue analyte.
Figure 5:
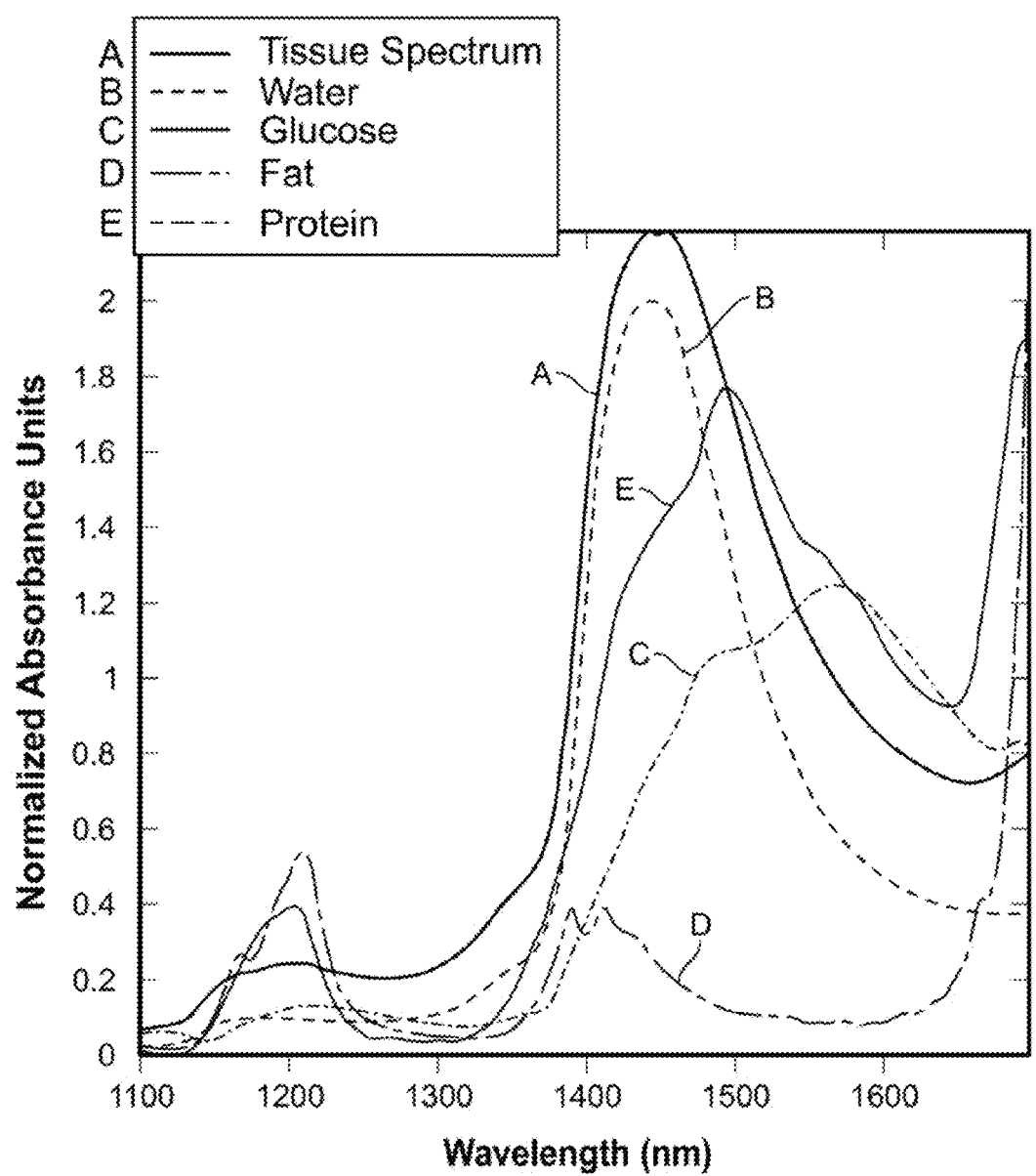
FIG. 5 illustrates normalized absorbance spectra of various tissue constituents with an overlaid tissue absorbance spectrum.
Figure 6:
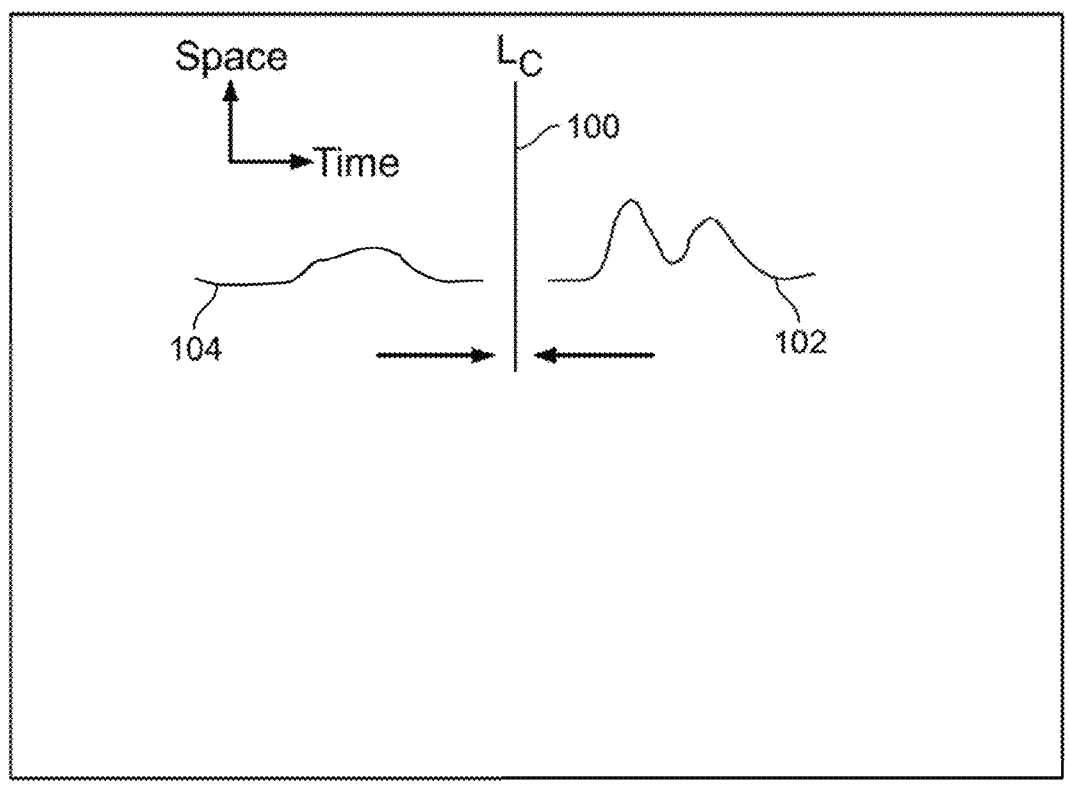
FIG. 6 shows two waveforms on a collision time grid as both approach the collision line.
Figure 7A:
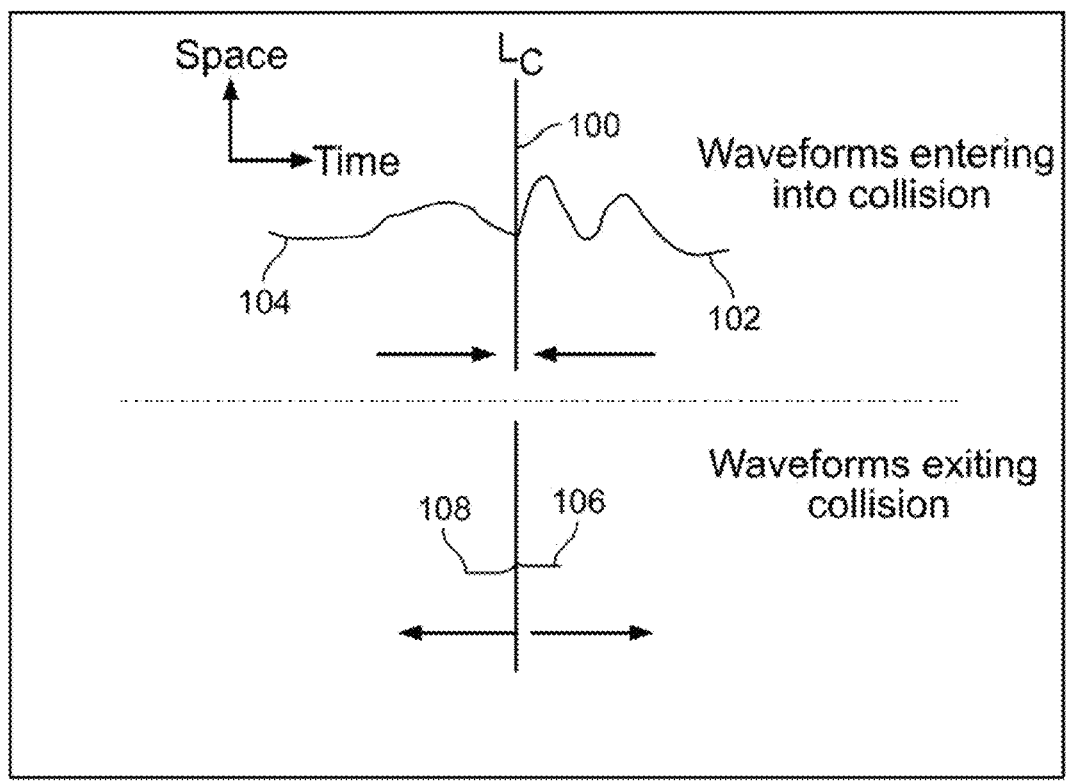
FIGS. 7A-E show two waveforms colliding on a collision time grid at various stages of the collision, with the resulting waveforms as the collision process progresses.
Figure 7B:
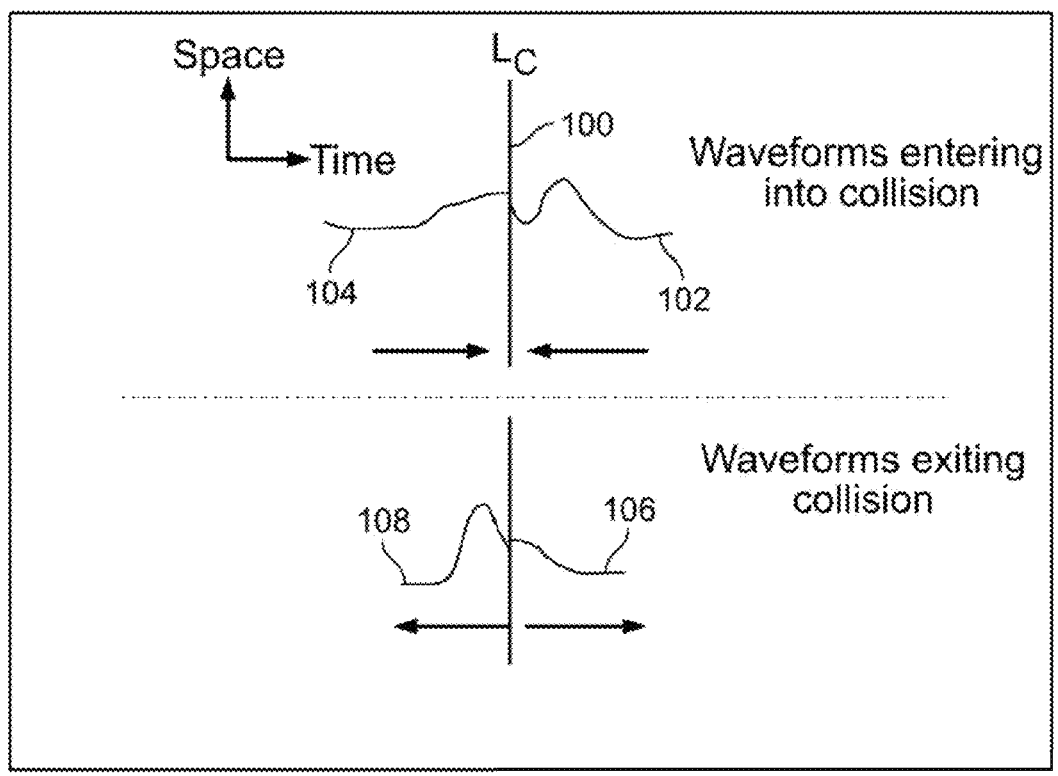
Figure 7C:
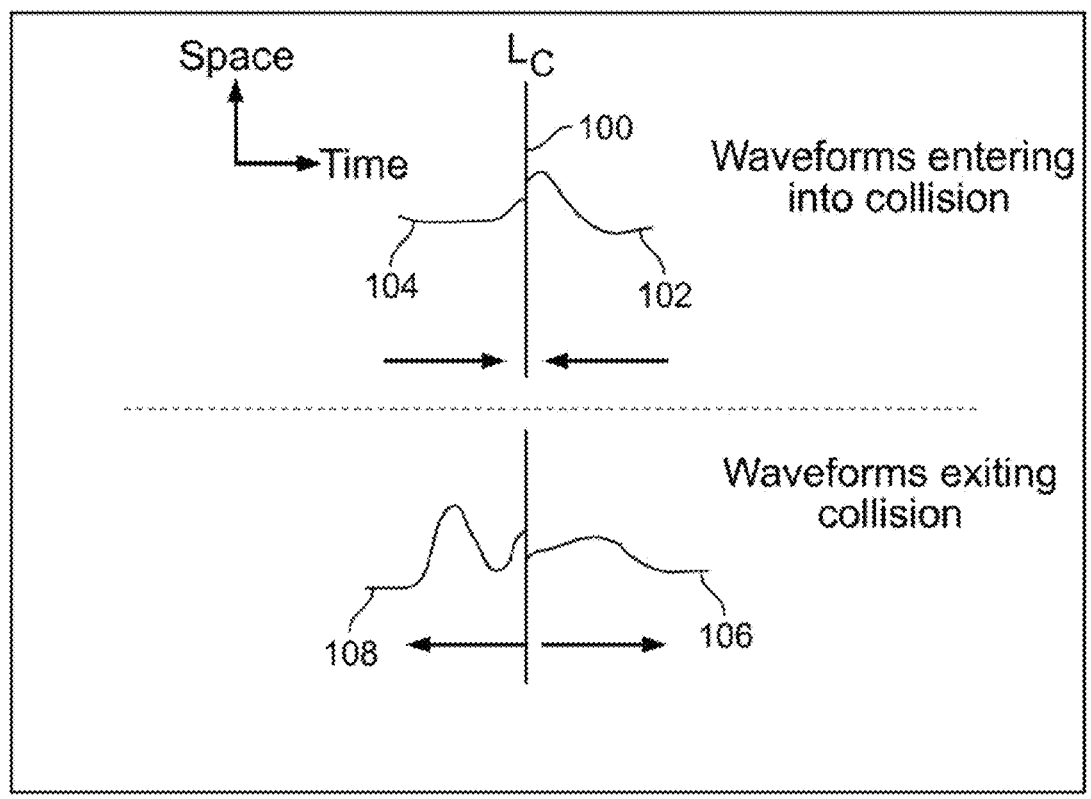
Figure 7D:
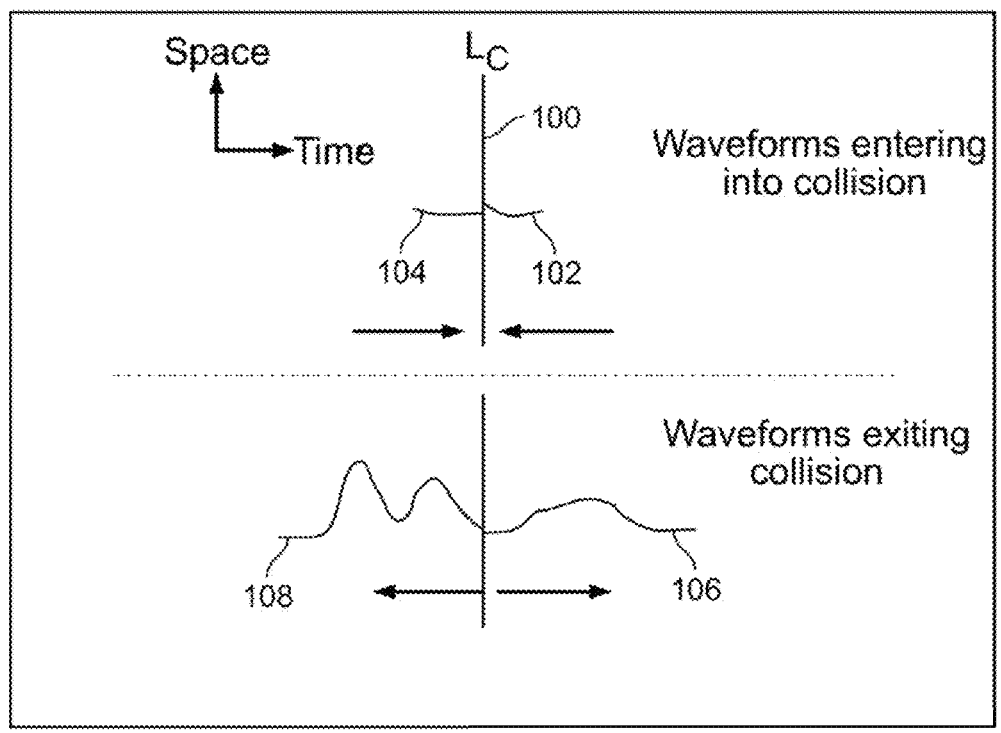
Figure 7E:
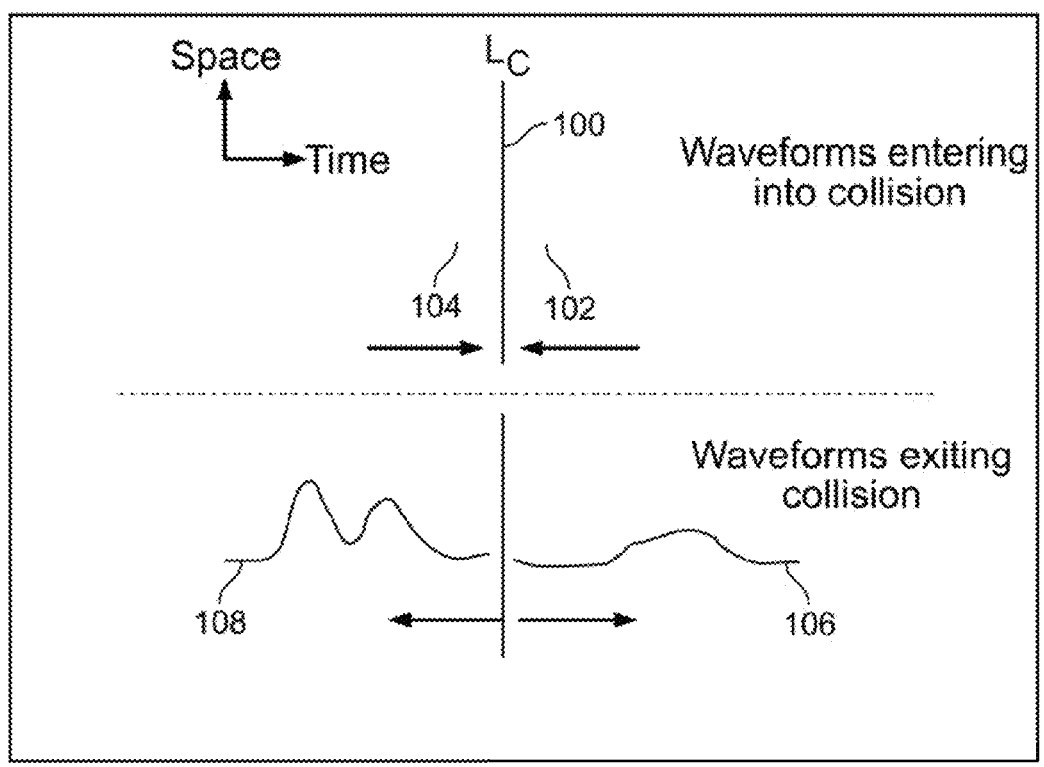
Figure 7F:
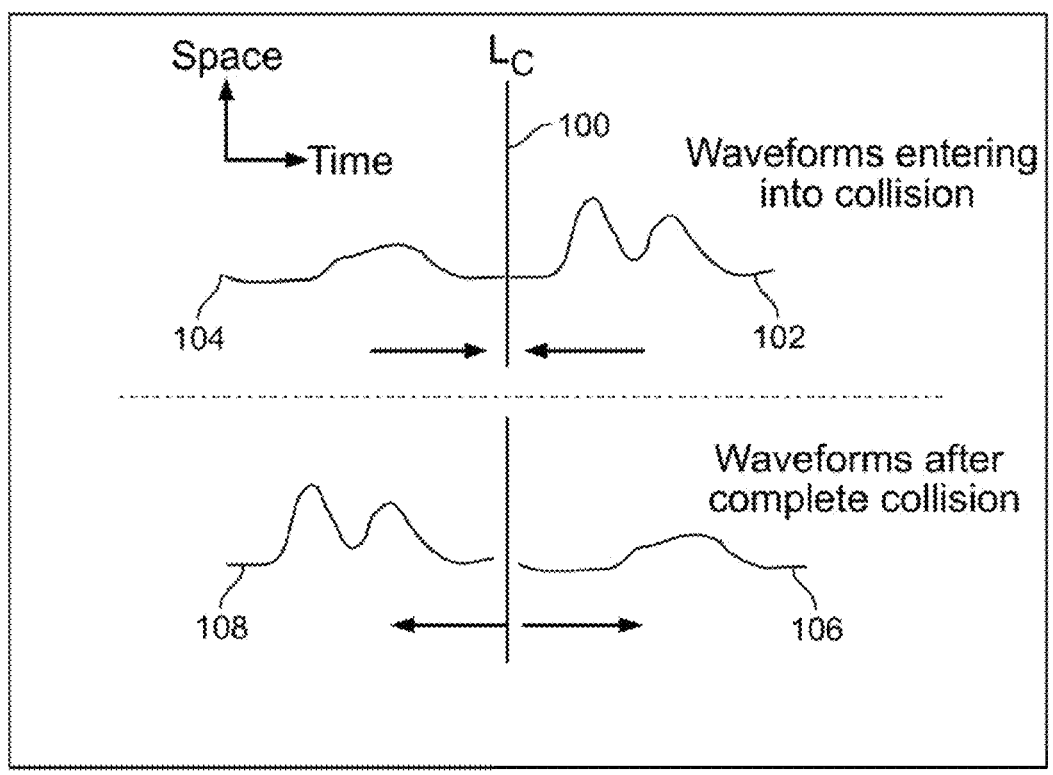
FIG. 7F shows two waveforms such as solitons, which are unchanged after completing the collision process.
Figure 8A:
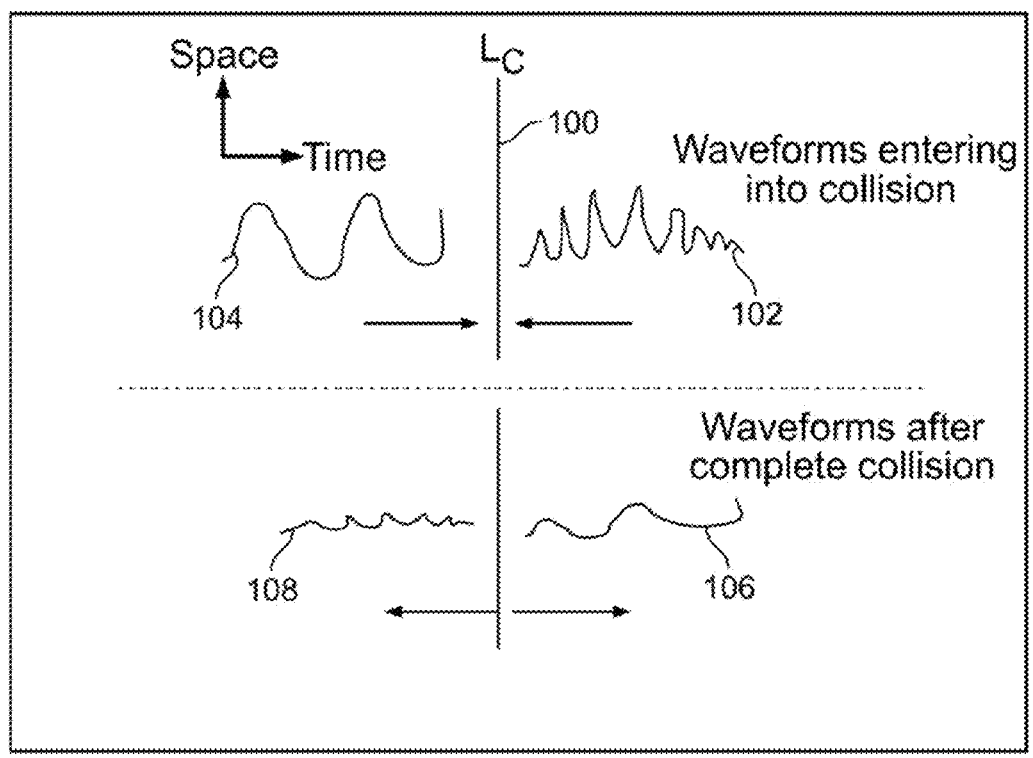
FIGS. 8A-8B show the severe distortion or complete destruction of two non-soliton waveforms after the collision process.
Figure 8B:
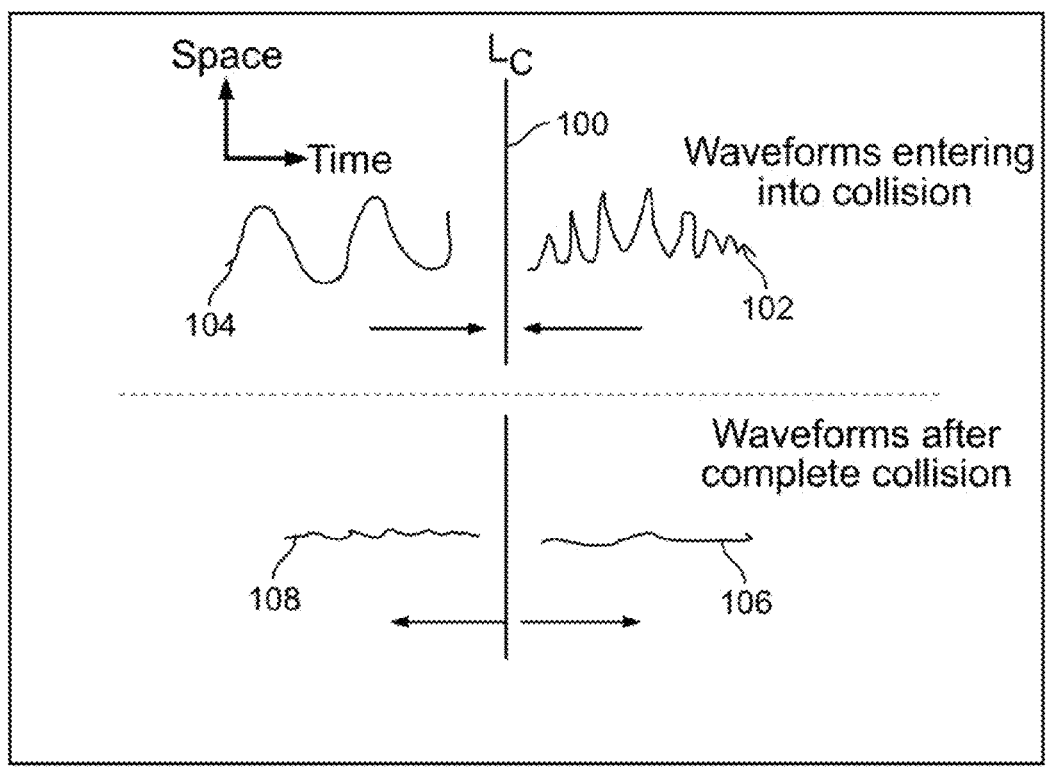
Figure 9:
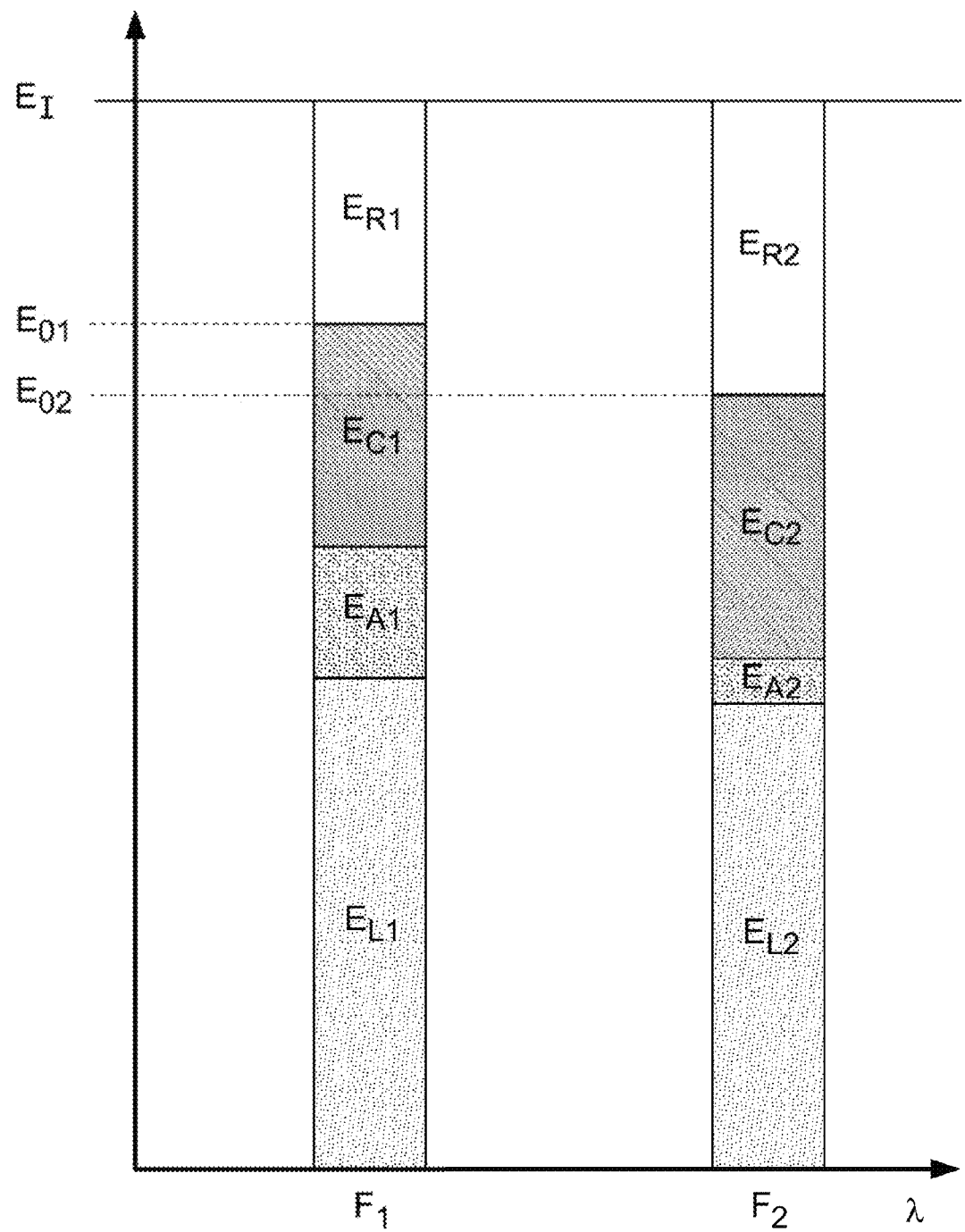
FIG. 9 shows the distribution of energy from two features.

In FIG. 9, $E_I$ represents the spectral energy of the radiation incident upon a medium, in a wavelength band $[\lambda^1_1, \lambda^1_2]$. For simplicity, $E_i$ is assumed to be constant across all wavelength bands and, as such, the spectral energy of the incident radiation (e.g., in the near infra-red region of the electromagnetic spectrum) in another wavelength band $[\lambda^2_1, \lambda^2_2]$ is also $E_I$. In the medium (e.g., a portion of skin), a portion of the incident radiation is absorbed by one or more confounders. That portion can be less than 1%, 2%, 5%, 10%, etc. A portion of the incident radiation, e.g., less than 0.1%, 0.2%, 0.6%, 1%, 1.5%, 3%, 7%, etc., may be absorbed by an analyte of interest, and is denoted by $E_A$. In some instances (e.g., in tissue measurement), an additional portion of the radiation may be scattered within the tissue and lost, and is considered to be the lost portion $E_L$. A portion of the incident radiation is not absorbed by the analyte, any confounders, or otherwise lost (e.g., due to scattering) present in the medium, and is reflected from (or passes through) the medium. The reflected radiation can be detected by a detector.

The analyte of interest may absorb radiation at some wavelengths and may not absorb the radiation, at least at a significant level, at some other wavelengths. For example, in FIG. 9 it is assumed that the analyte absorbs radiation in the wavelength band $[\lambda^1_1, \lambda^1_2]$, designated as Analyte Feature F1, and that the analyte does not substantially absorb radiation in the wavelength band $[\lambda^2_1, \lambda^2_2]$ designated as Non-Analyte Feature F2. For the Analyte Feature F1, the energy absorbed by the analyte is $E_{A1}$, the energy absorbed by one or more confounders is $E_{C1}$, energy lost (i.e., absorbed by elements of the medium other than the confounders and the analyte) is $E_{L1}$, and energy reflected by the medium and detected by the detector (denoted $E_{O1}$) is $E_{R1}$. For the Non-Analyte Feature F2, the energy absorbed by the analyte is $E_{A2}$ (which could be a negligible amount), the energy absorbed by one or more confounders is $E_{C2}$, energy lost is $E_{L2}$, and the energy reflected by the medium and detected by the detector (denoted $E_{O2}$) is $E_{R2}$. Therefore:

$$\Delta E_1 = E_1 - E_{O1} = E_{L1} + E_{C1} E_{A1};$$

$$\Delta E_2 = E_1 - E_{O2} = E_{L2} + E_{C2} + E_{A2} = E_{L2} + E_{C2}, \text{ because } E_{A2} \approx 0;$$

and $$\Delta E_1 - \Delta E_2 = (E_{L1} = E_{L2}) + (E_{C1} E_{C2}) + E_{A1}$$

In the equations above, $E_1$ is known, and $E_O$ values can be obtained by direct measurement from the detector. $E_L$, $E_C$, and $E_A$, are unknowns for each feature.

The spectral energy of feature F1 is represented by $\Delta E_1 = (E_{L1} + E_{C1} + E_{A1})$. The spectral energy of a conditioned feature is also represented by $\Delta E_1 = (E_{L1} + E_{C1} + E_{A1})$. The Zyoton and the collision operator are designed such that after the first collision between the Zyoton and conditioned feature, the energy of the modified Zyoton $(E_Z^1)$ changes relative to the energy of the original Zyoton $(E_Z^0)$, but the change corresponds, in substance, only to $E_{C1}$ or $E_{A1}$, and not as much to $E_{L1}$. In this way, $E_{C1}$ and/or $E_{A1}$ can be extracted, even though $E_{L1}$ is unknown.

In both $\Delta E_1$ and $\Delta E_2$, typically, $E_L \gg E_C > E_A$. As such, if $\Delta E_1$ and $\Delta E_2$ are amplified using a conventional nonlinear amplifier, in the difference between amplified $\Delta E_1$ and amplified $\Delta E_2$, the difference between $E_L$ would dominate. Collision computing can selectively amplify $E_{C1}$ and/or $E_{A1}$ and not $E_L$, so that the difference between $\Delta E_1$ and $\Delta E_2$ can be used to determine the energy absorbed by the analyte, which in turn can be used to determine accurately the analyte concentration.

Figure 10A:
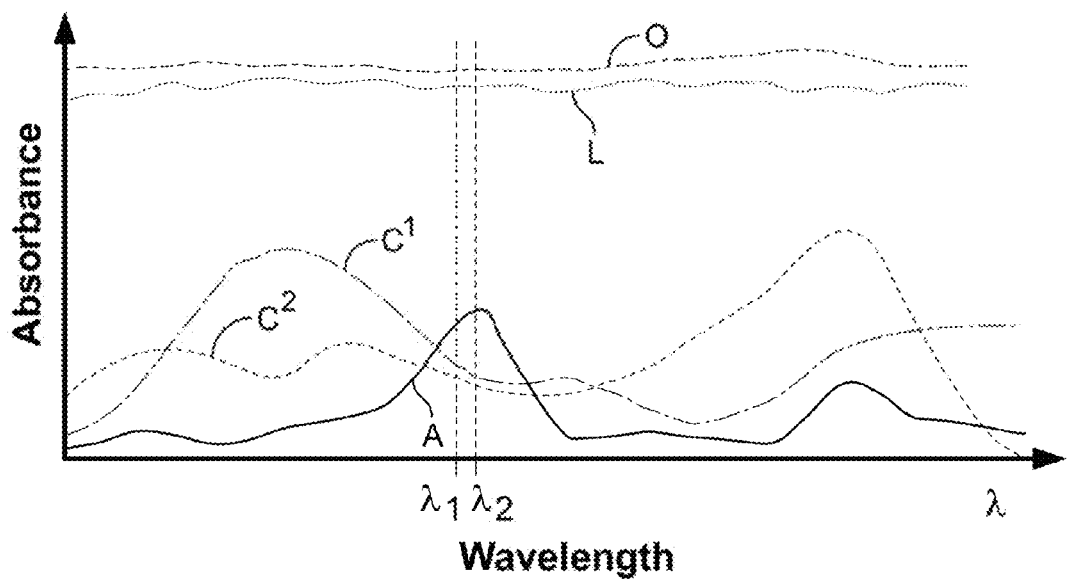
FIG. 10A shows exemplary spectra for an analyte and two confounders.

Referring to FIG. 10A, in one embodiment, radiation of energy $E_I$ is directed to a medium and the radiation reflected by the medium is detected at a detector. An absorbance spectrum "O," representing $E_O$ across a range of wavelengths, is derived from the detected radiation. Waveforms L, $C^1$, $C^2$, and A represent, respectively, the absorbance spectra corresponding to the radiation lost (representing $E_L$), the radiation absorbed by a confounder $C^1$ (representing $E_C^1$), the radiation absorbed by a confounder $C^2$ (representing $E_C^2$), and the radiation absorbed by the analyte A (representing $E_A$). In general, the properties of the medium, which may determine the radiation that is lost, the concentrations of the confounders $C^1$ and $C^2$, and the concentration of the analyte are not known. As such, the absorbance spectra L, $C^1$, $C^2$, and A are also not known. These absorbance spectra, however, are the components of the absorbance spectrum O, which can be derived from the radiation detected at the detector. In FIG. 10A, spectra corresponding to two confounders are shown for illustration. In general, a medium may include no confounders, only one confounder, or more than two (e.g., 3, 5, 8, etc.) confounders.

Figure 10B:
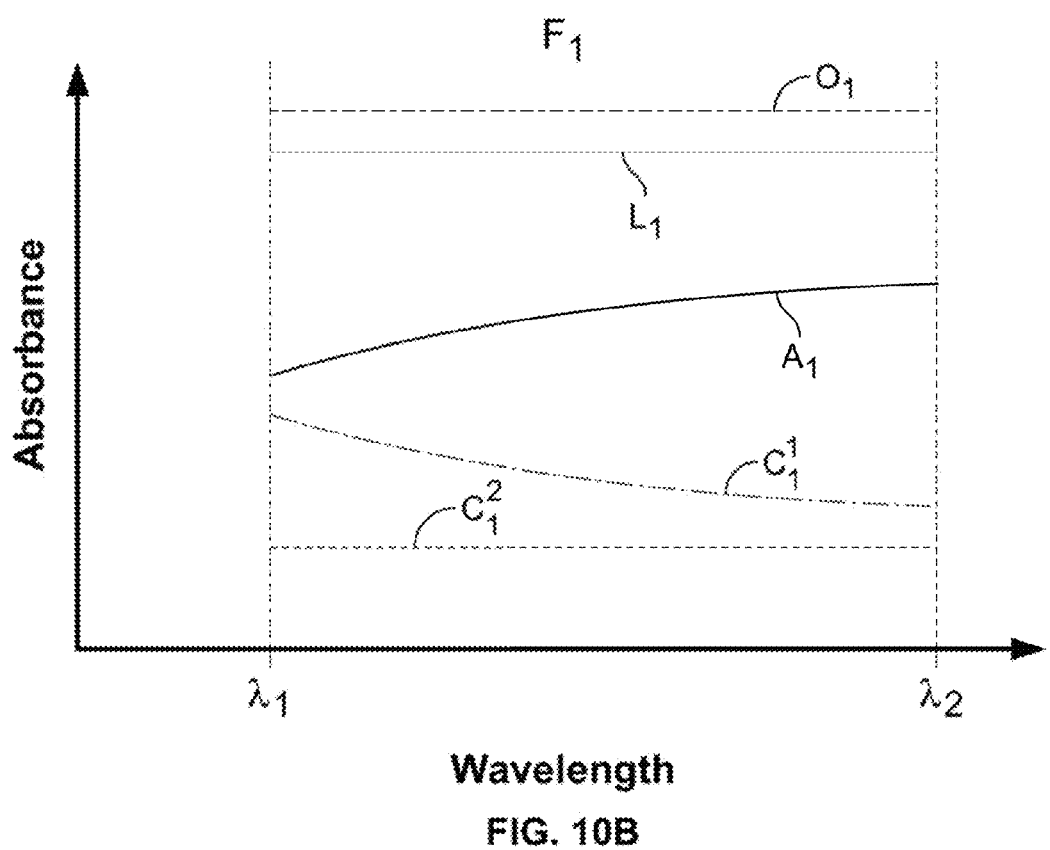
FIG. 10B shows absorption components of a feature.
Figure 10C:
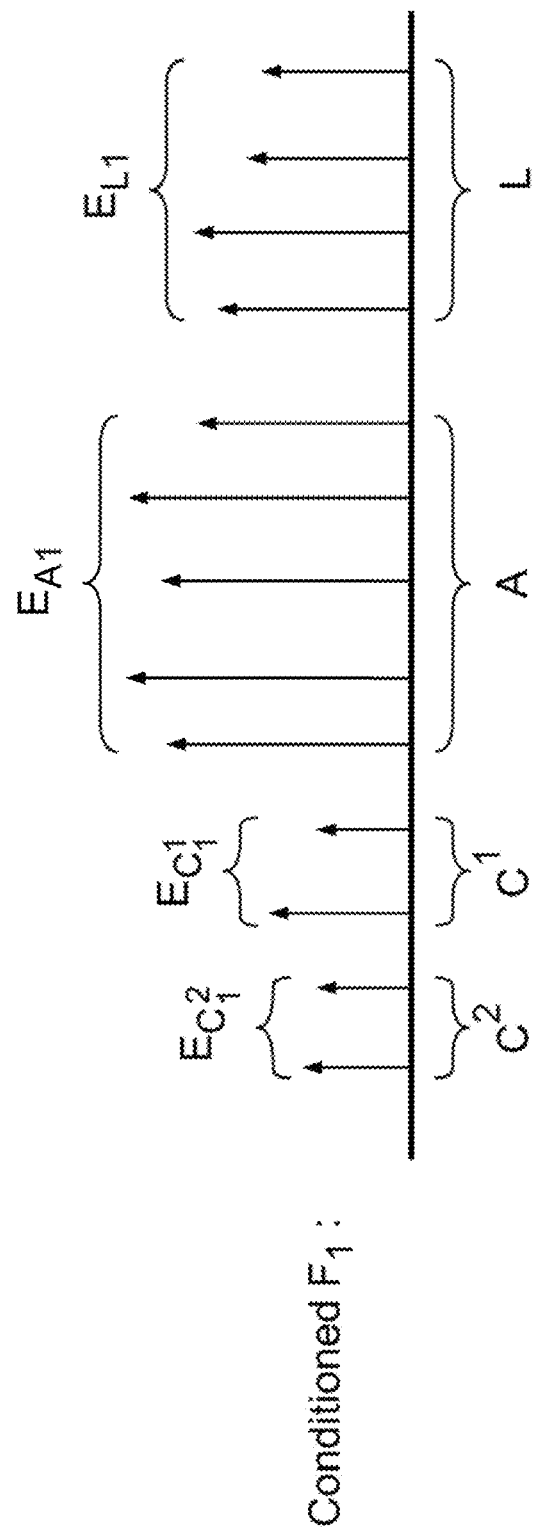
FIG. 10C shows frequency components from a conditioned feature.

The observed spectrum O is divided into several (e.g., 2, 4, 5, 10, 15, 18, 24, 32, 50, etc.) regions called features. With reference to FIG. 10B, a feature $F_1$ includes a region $O_1$ of the observed absorbance spectrum O. Feature 1 also includes regions $L_1$, $C^1_1$, $C^2_1$, and $A_1$ of the absorbance spectra L, $C^1$, $C^2$, and A, respectively. Here again, the spectrum $O_1$ includes the spectra $L_1$, $C^1_1$, $C^2_1$, and $A_1$, but these individual spectra are not known. The spectrum $L_1$ represents $E_{L1}$; spectrum $C^1_1$ represents $E_{C^1 1}$; spectrum $C^2_1$ represents $E_{C^2 1}$; and spectrum $A_1$ represents $E_{A1}$. FIG. 9 also depicts the energy absorbed by one or more confounders as $E_{C1}$. In general, for N confounders, the absorption is additive and can be expressed as $E_{C1} = \Sigma_{i=1}^N E_{C^i 1}$, where $N \geq 0$. This additive absorption is non-invertible and components $E_{C^i 1}$ generally cannot be accurately recovered using a linear transformation, spectral deconvolution, or other passive signal processing technique.

Although the actual spectra $L_1$, $C^1_1$, $C^2_1$, and $A_1$ are not known, from spectroscopic analysis of the analyte alone (in the solid or liquid phase or in solution), also referred to as a "pure component spectrum," certain parameters of features from these spectra, called spectral parameters (such as the amplitude envelope or spatial frequency distribution obtained by computing a Fourier transform of a feature vector), can be determined. Pure component spectra represent the absorbance-wavelength relationship for the analyte of interest and/or for one or more confounders.

A carrier kernel, with at least an order of magnitude higher spatial frequency compared to the frequencies associated with Fourier transformed feature F1, is modulated using the waveform $O_1$ that is called a feature waveform and that represents the feature $F_1$. As an example, a system with an expected concentration range of about three orders of magnitude could require a five-to-six order of magnitude range in post-collision spectral energies, and a carrier kernel with a 1 MHz to 100 MHz bandwidth would generally be suitable. The various spectral parameters are used to select one or more parameters of the carrier kernel and/or one or more parameters of the modulation. The desired target dynamic range of post-collision spectral energies and precision desired for the measurement determine the fundamental frequencies and number of frequency components of the carrier kernel, collectively called modulation parameters. The modulation of the carrier kernel by the feature waveform $O_1$ yields a modulated waveform called a conditioned feature.

In general, a conditioned feature includes several components, each of which is associated with a different spatial frequency. The modulation parameters are selected such that different frequency component combinations of the conditioned feature represent different spectral energies associated with the feature. For example, with reference to FIG. 10C, in the conditioned feature $F_1$, some frequency components represent $E_{C^2_1}$, i.e., the energy absorbed by the confounder $C^2$ at the wavelengths defining the feature $F_1$. Similarly, some frequency components represent $E_{C^1_1}$; some frequency components represent $E_{A1}$; and some frequency components represent $E_{L1}$.

Figure 10E:
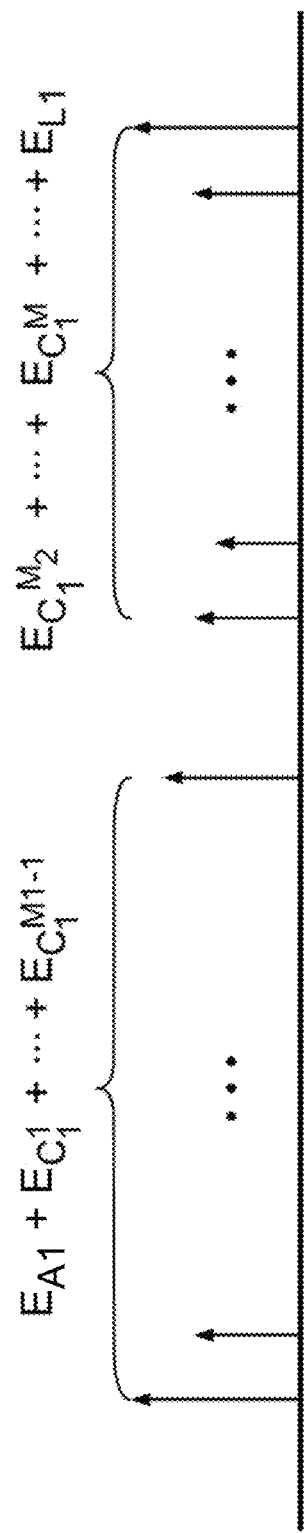
FIG. 10E shows frequency components from an analyte and other confounders.

With reference to FIG. 10D, in some instances, the frequency components representing the energy absorbed by the analyte and the energy components representing the energy absorbed by one or more confounders (e.g., confounders 1 through N1 of a total of N confounders, where N1≤N), overlap. Some other frequency components, such as $E_c^{Ni+1}$, represent the energy absorbed by the confounders (N1+1) through N, and yet other frequency components represent the lost energy. With reference to FIG. 10E, the frequency components (some of which are fundamental frequencies and some of which are harmonics of those fundamental frequencies) representing the lost energy may overlap with the frequency components representing the energy absorbed by one or more confounders, e.g., confounders N2 through N of a total of N confounders, where N2≥1. The term frequency components is used here to describe the sinusoidal spatial frequency components that make up a waveform. Such waveforms result from "adding" together the series of sine wave frequencies that would result from a Fourier transform of the waveform. Thus, whatever its shape, a complex waveform can be split up into its individual spatial frequency components.

The representation of a particular energy (e.g., $E_{C^1_1}$, $E_{A1}$, a combination thereof, or $E_{L1}$), is a function of: (i) the number of frequency components representing that particular energy in the modulated waveform (i.e., the conditioned feature); (ii) the frequencies of those frequency components; and (iii) the amplitudes of those frequency components. In general, for the j-th feature (denoted $F_j$), the relationship between the frequency components and their respective contribution to an energy such as $E_{C^i_j}$, $E_{Aj}$, $E_{Lj}$, where i denotes the i-th confounder, is not known. If it were known, a simple Fourier analysis of the conditioned feature would suffice to reveal the various energies of interest including $E_{Aj}$.

Figure 28A:
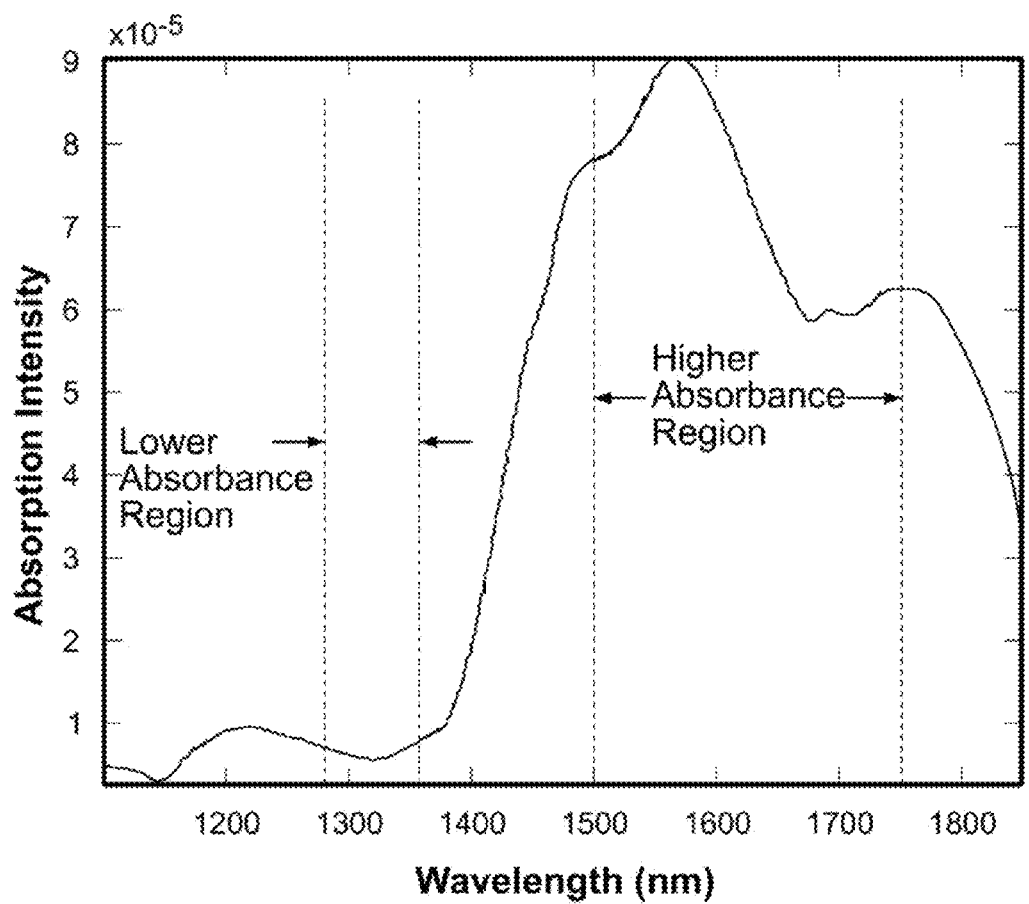
FIGS. 28A and 28B show the pure component absorbance spectra for an analyte of interest and a confounder: glucose and collagen, respectively.
Figure 28B:
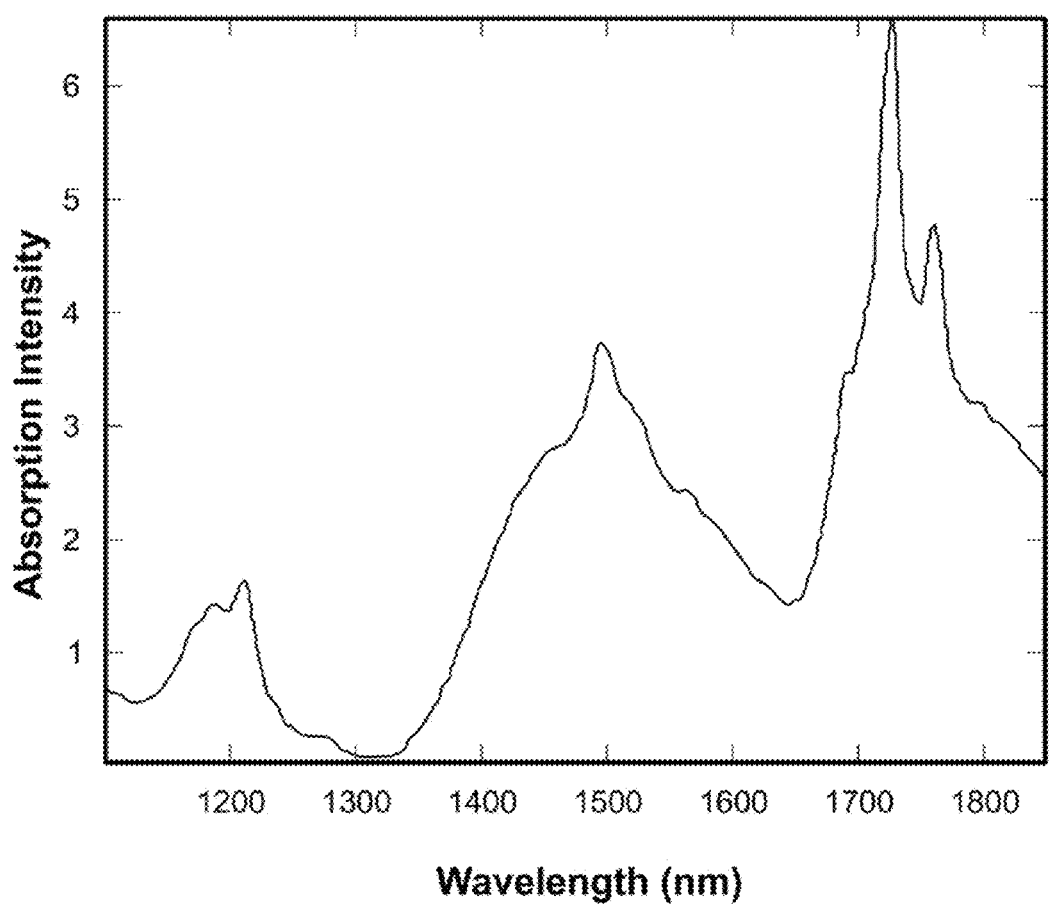
Figure 29A:
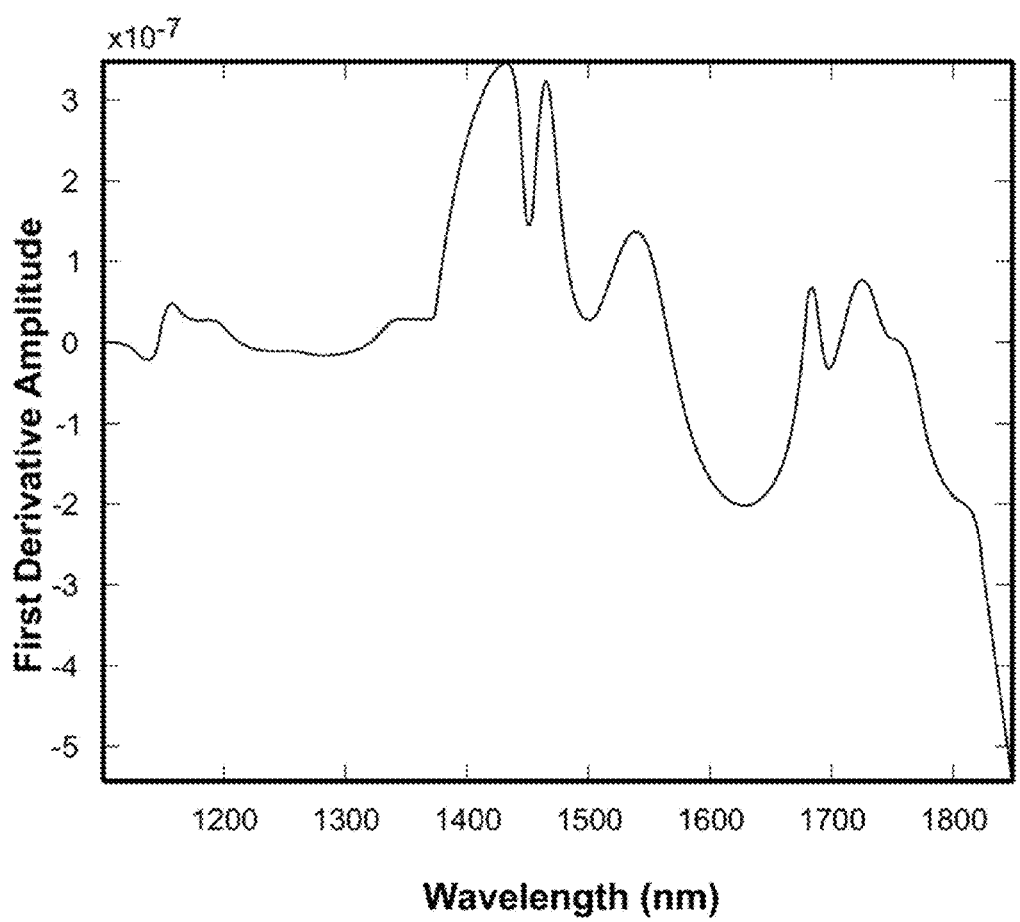
FIGS. 29A and 29B show the first derivative of pure component absorbance spectra for the compounds shown in FIGS. 28A and 28B)
Figure 29B:
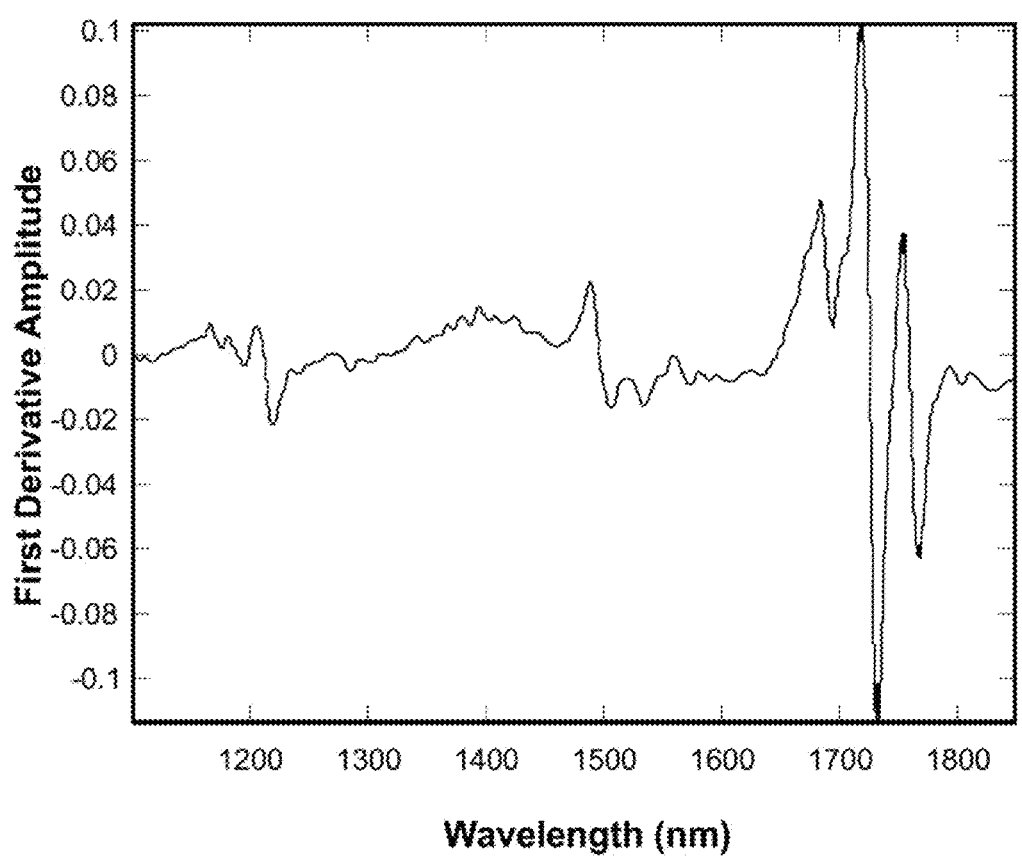
Figure 30A:
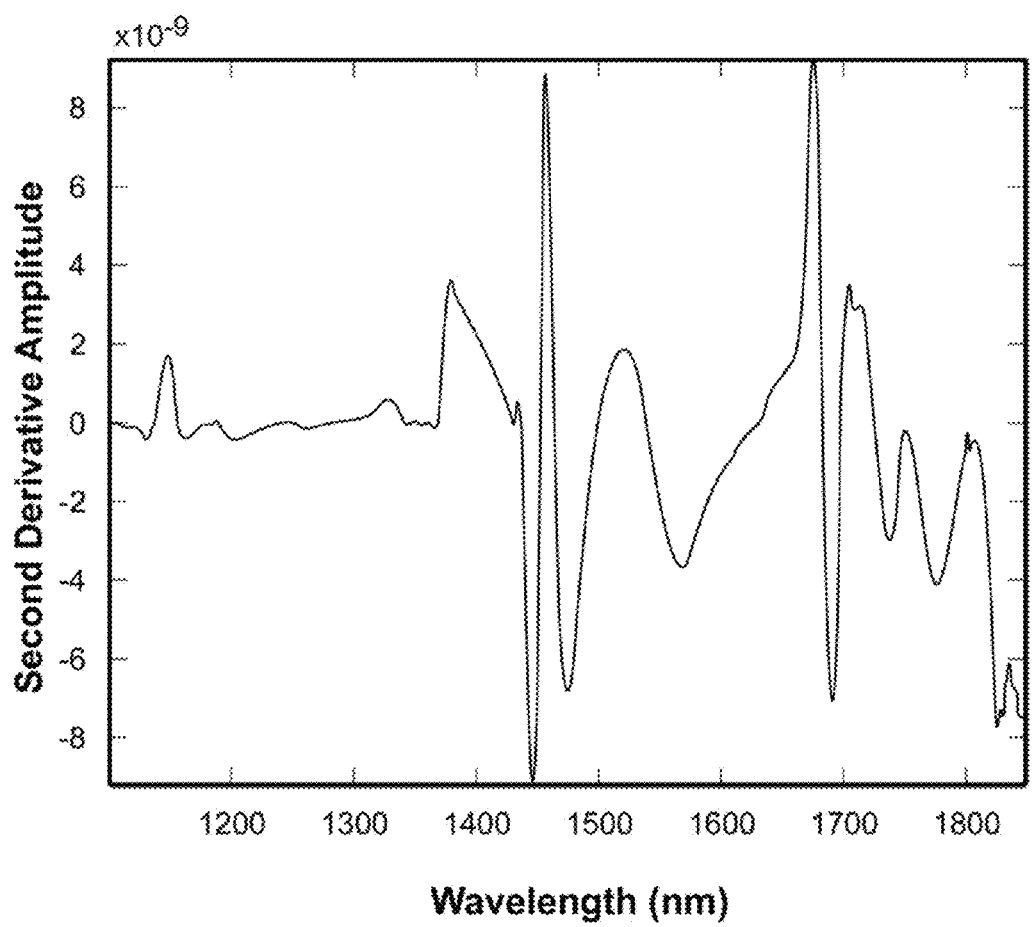
FIGS. 30A and 30B show the second derivative of pure component absorbance spectra for the compounds shown in FIGS. 28A and 28B)
Figure 30B:
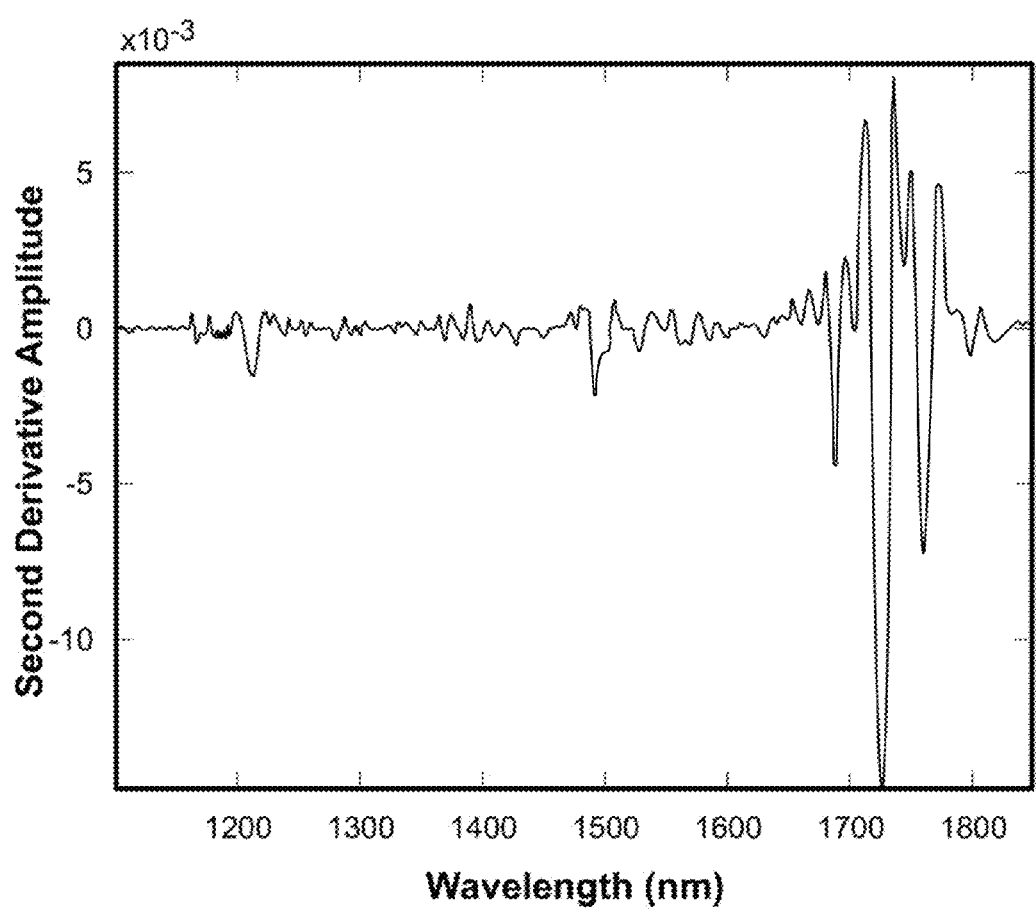

The parameters of a Zyoton with which the conditioned feature is collided and the parameters of the collision operator are also selected using the spectral parameters, i.e., the parameters derived from pure component analysis based on published or experimentally measured pure component spectra. If published spectra are used, knowledge about the noise of the measurement system and the sources of the noise can be used. The frequency bandwidth and amplitude envelope of the b Zyoton sideband peaks shown in FIG. 12C depend on the morphological profile (e.g., the frequency spectrum of the second derivative of the waveform) of the pure component absorption spectrum waveform features. FIGS. 28A and 28B show the pure component absorbance spectra for the analyte and one confounder of interest: glucose and collagen, respectively. FIGS. 29A and 29B show the first derivative of pure component absorbance spectra for the analyte and one confounder of interest: glucose and collagen respectively. FIGS. 30A and 30B show the second derivative of pure component absorbance spectra for the analyte and one confounder of interest: glucose and collagen respectively, computed from the result of FIGS. 29A and 29B.

As can be seen from FIGS. 30A and 30B, the two second derivative graphs for the two compounds have different characteristics. The frequency components and bandwidth of the pure component spectra and/or the first, second, or higher-order derivatives thereof, obtained by taking a Fourier transform of the selected waveform and by determining the range of the frequency components in the Fourier transform, can be used in determining the Zyoton frequencies and carrier kernel frequencies for conditioning the feature data, as described below.

In the example of glucose, the second derivative of a spectrum such as FIG. 30A, after optional interpolation by an amount of about $2^{10}$ to $2^{16}$, is added to random noise with a root mean square (rms) amplitude of the random noise set to be 1000 times the rms amplitude of the second derivative, to yield a combined second derivative waveform. In one embodiment, the random white noise used is a colored grey noise with a C-weighting and correlation time of $10^{-6}$ seconds, but other weightings and/or correlation times could also be used. In the preceding condition, the rms amplitude of the second derivative of the analyte is calculated by taking the square root of the sum of the squares of the instantaneous amplitude values of the second derivative (amplitude as a function of wavelength) over a window size that is twice the length of a feature in the time domain.

The frequency bandwidth of the resulting combined waveform (noise+the second derivative of the interpolated data vector) and the relationship among the frequency component amplitudes over the wavelength region corresponding to the features are used to establish the bandwidth and frequency components of the carrier kernel, as described below. Thus, the Zyoton and carrier kernel frequencies are related to the frequency components of the analyte pure component spectrum or the first, second, or higher-order derivatives thereof, with added noise.

Specifically, as Zyotons are derived from inherently stable waveforms, the chromatic dispersion of the Zyoton waveform, the peak power, and the pulse energy in its first k-peak- power sorted frequency components (where k may be ≤6), may collectively control the limit of detection and quantitation that can be achieved in one or more collisions. Therefore, in some embodiments, Zyoton waveforms are generated that are soliton based and show analyte-specific absorption effects more strongly in changes in the spectral energy of the first k frequency components and scattering effects more strongly in changes in the spectral energy of the j frequency components. As mentioned previously, the total set of frequency components for the Zyoton is defined as H=k+m+j where k>0, m≥0 and j>0, and the k and j frequency components, i.e., the analyte-information representing and non-analyte information representing components do not overlap.

Once the number of frequency components that can yield an estimate for analyte-specific absorption with the desired performance parameters (e.g., accuracy, precision, dynamic range) is established (e.g., 6 in one embodiment for non-invasive glucose measurement), the parameters of the collision grid, e.g., the bracket length in terms of numbers of frequency components of both the conditioned feature or renormalized Zyoton, as described below, grid spacing for propagation of the Zyoton waveform, a window length, etc., are computed. In various embodiments, the window length specifies a total number of points (in the time domain) or a total number of components (in the frequency domain) of the original Zyoton, conditioned feature, and/or renormalized Zyoton that are used in the collision operation. Examples of these parameters for a noninvasive glucose measurement are a window length of 2048 and a grid spacing of $10^{-6}$ seconds. The grid spacing can be additionally based on characteristic of the computing system, e.g., available numerical range and precision, available processing capacity and time, etc.

The window length for the collisions is generally set such that at least those frequency components of a conditioned feature (and a renormalized Zyoton) that are used in the computation of spectral energy change due to analyte-specific collision interactions can be propagated. Changes in the spectral energy of acquired features due to scattering losses may be intentionally filtered out from the post-collision spectral energy computations through the use and choice of the window length that is smaller than the length of all of the data object containing the frequency components of the Zyoton waveform.

Limiting the collision window length can thus reject incorporation of scattering-related spectral energy changes by filtering out the non-analyte information representing spatial frequency components (e.g., L>2048, where L<H=k+m+j) present in the conditioned feature which generally represent the frequencies related to scattering events. The length of a resulting modified Zyoton vector after a collision is typically greater than L (in the frequency domain) and greater than L (in the time domain, as described with reference to FIGS. 24-27), and may contain additional frequency components as a result of the conditional bracketed interactions described below. These additional components may be removed by truncation during renormalization. Each collision interaction in one collision iteration, as described below, may correspond to a point on the collision grid and can describe at least in part the propagation of the two colliding waveforms. In the time domain or in the frequency domain, the length of the collision grid can take on values such as 10, 100, 1000, or up to 1,000,000 grid points or more.

Thus, the original Zyoton and the collision operator are synthesized such that the first k frequency components of the modified Zyoton resulting from the collision between the original Zyoton and the conditioned feature can represent a feature energy component to be quantitated. For example, referring to FIG. 9, in one instance the first k frequency components may represent $E_{A1}$, i.e., the energy absorbed by the analyte at the wavelengths associated with Feature F1. In another instance, the first k frequency components may represent, $E_{C^{1}1}$, i.e., the energy absorbed by the confounder $C^1$ at the wavelengths associated with the Feature F1. The first k frequency components may also represent the total energy absorbed by two or more, or all confounders, e.g., $E_{C1}$. In some instances, the first k frequency components of the conditioned feature may represent essentially the total energy absorbed by the analyte and by one or more confounders, e.g., $(E_{A1}+E_{C1})$. In general, with a properly designed Zyoton and collision operator, the first k frequency components do not represent the lost energy $E_{L1}$.

In a collision computer, in the first iteration, the original Zyoton and the conditioned feature, each of which represents a traveling waveform in the computer memory, and are synthesized as described below, are computationally collided. This collision is "nearly elastic." In a perfectly elastic collision between a Zyoton and another waveform, the dispersion velocity of the Zyoton after the collision would be the same as the dispersion velocity of the Zyoton before the collision. This would typically occur only when a Zyoton collides with another soliton waveform.

In a generally inelastic collision, the post-collision dispersion velocity of a Zyoton colliding with another waveform would be significantly different (e.g., greater than 1%, 2%, 5%, 10%, 20%, etc.) than the dispersion velocity of the original Zyoton, and the Zyoton may be destroyed during the collision. In the nearly elastic collision described herein, the colliding waveforms, i.e., a Zyoton, and a conditioned feature or a renormalized Zyoton colliding with the Zyoton, are constructed such that during the collision the conditioned feature or the renormalized Zyoton perturb the Zyoton only within specified limits. These limits are generally established by the limits on a permissible change in dispersion velocity, as specified by one or more Kappa parameters and/or by a permissible change in waveform divergence, as specified by the divergence parameter τ. In general, the difference between the velocity of the original Zyoton and the velocity of the modified Zyoton resulting from the collision is limited to a specified threshold numerical limit, which can be tested using a suitable Kappa test as described above. In various embodiments, to ensure a near-elastic collision, the collision operator is constructed such that the divergence of the post-collision waveform, i.e., the modified Zyoton, is not greater than a pre-set divergence parameter τ, as described in detail below.

As such, in various embodiments, the difference between the pre- and the post-collision dispersion velocities, i.e., a scaled velocity of the original Zyoton and the velocity of the renormalized Zyoton do not exceed a specified numeric threshold, denoted $\kappa_{DV1}$. A similar constraint can also be applied to the difference between the scaled dispersion velocity of the original Zyoton and the velocity of a conditioned feature, where the threshold is designated $\kappa_{DV2}$. For noninvasive glucose measurement, where the spectral energy of the Zyoton waveform before scaling is about three orders of magnitude higher than the spectral energy of the conditioned feature waveform, an example of the threshold $\kappa_{DV2}$ is $1 \times 10^{-6}$.

Velocities of Zyotons and Conditioned Features

The frequency domain amplitudes of the k, m, and j frequency components of an original Zyoton are denoted $A_k$, $A_m$, and $A_j$, respectively. The frequency domain amplitudes of the corresponding k, m, and j frequency components of a co-dependent conditioned feature are denoted as $a_k$, $a_m$, and $a_j$, respectively. Once $A_k$ are chosen, the corresponding $a_k$ can be determined using a scaling coefficient $\alpha$. The scaling coefficient $\alpha$ may be selected such that the two co-dependency conditions are satisfied. Specifically, the difference between the scaled velocity of the original Zyoton and the velocity of the conditioned feature do not exceed a specified threshold $\kappa_{DV2}$, and the divergence of the post-collision modified Zyoton do not exceed a specified threshold $\tau$. The velocity condition can be tested by scaling the velocity of the conditioned feature instead of or in addition to scaling the velocity of the original Zyoton. A suitable Kappa threshold may be used accordingly.

In various embodiments, if the $\kappa_{DV2}$ test fails, the frequency domain amplitudes of the frequency components of the conditioned feature are adjusted by applying a scaling coefficient to the corresponding frequency domain amplitudes of the frequency components of the original Zyoton. Thus:

$$a_k = \frac{1}{\alpha} A_k;$$

$$a_m = \frac{1}{\alpha} A_m;$$

and $$a_j = \frac{1}{\alpha} A_j,$$

where $A_k$, $A_m$, and $A_j$ are vectors.

The time-domain amplitudes of the Z peaks of the original Zyoton are denoted as $\mathbb{A}_Z$ and the time-domain amplitudes of the CF peaks of the conditioned feature are denoted as $\mathbb{a}_{CF}$. The respective velocities of the original Zyotons and the conditioned feature are functions of $\mathbb{A}_Z$ and $\mathbb{a}_{CF}$, respectively, denoted as $v(\mathbb{a}_{CF})$ and $v(\mathbb{a}_{CF})$, respectively. Once a conditioned feature is generated, the velocity-based co-dependency condition can be tested in the time domain as: $|\alpha_C{}^* v \mathbb{a}_{CF} - v(\mathbb{a}_{CF})| \leq \kappa_{DV2}$, where $\alpha_C{}^* v(\mathbb{A}_Z)$ is the scaled velocity of the original Zyoton. In the time domain, the velocity of a waveform associated with the collision process (e.g., a Zyoton, a conditioned feature, a modified Zyoton, and/or a renormalized Zyoton) can be computed as L1 or L2 norm of the amplitudes of a selected number of sideband envelopes, such as those of a Zyoton that are shown in FIGS. 12A-12C. In the frequency domain, the velocity of a waveform can be represented by L1 or L2 norm of the frequency domain amplitudes of the first k, i.e., the analyte-information representing components of the waveform.

As discussed above, $\alpha_C$ is the nominal scaling coefficient applied to achieve a desired ratio ($\alpha_Z$) of spectral energy of the Zyoton to the spectral energy of a conditioned feature computed using a fixed number (e.g., 6 in one embodiment) of k frequency components, by adjusting the amplitude of the frequency components of the Zyoton so that the spectral energy difference between the scaled Zyoton and the conditioned feature is less than $\kappa_{DV2}$. As noted above, depending on whether the testing and/or scaling is performed in the time domain or in the frequency domain, a domain-specific value of the applicable Kappa variable is used in various embodiments.

The term nominal scaling coefficient is used because different features from the same or different spectra, from the same or different samples, are likely to result in slightly different scaling coefficients to maintain a fixed relationship, $\alpha_Z$, between the spectral energy of Zyoton and spectral energy of the conditioned feature prior to the first collision. The following condition is imposed on the nominal ratio: $|(\alpha_C - \alpha_{Fi\_MAX})/\alpha_C| \leq$ e.g., 0.1, 0.2, 0.5, or 1.0, and $|(\alpha_C - \alpha_{Fi\_MIN})/\alpha_C| \leq$ e.g., 0.1, 0.2, 0.5, or 1.0, where $\alpha_{Fi\_MIN}$, $\alpha_{Fi\_MAX}$ respectively denote the maximum and minimum scaling coefficients required to achieve the desired ratio of the spectral energy of the conditioned feature to the spectral energy of the Zyoton, computed using a preset number of frequency components, for all conditioned features to be collided with the same Zyoton. In some embodiments, $|(\alpha_C - \alpha_{Fi\_MAX})/\alpha_C| \leq 0.1$ and $|(\alpha_C - \alpha_{Fi\_MIN})/\alpha_C| \leq 0.1$.

Examples of Waveform Energies

It is to be understood that in this disclosure, the terms "strongly absorbing" and "weakly absorbing" spectral regions (or similar terms, such as "high absorbing" spectral regions and "low absorbing" spectral regions) as used in connection with the measurement of an analyte, refer only generally to absorption within the pure-component spectrum of a substance which may be either an analyte or a confounder. Thus, for a particular substance, the spectral regions which are strongly absorbing generally have a higher level of absorbance than the spectral regions that are weakly absorbing, but those terms do not imply any sort of strict mathematical relationship between the absorption values of the two regions, nor do they imply any relationship among the absorption values of two different substances. In some cases, a region identified as strongly absorbing in one context could be considered weakly absorbing in a different context and vice versa. For example, in a general broad region of low analyte absorption, some sub-regions may have higher absorption than some other sub-regions. Similarly, high analyte absorption can be significantly low, in absolute terms, relative to a low confounder absorption.

Similarly, the terms "analyte regions" or "analyte features" and "non-analyte regions" or "non-analyte features" as applied to spectral regions or features, refer only generally to variations in absorbance due to the analyte. Generally, the absorbance of an analyte in an analyte feature is greater than in non-analyte features, but in some cases, the absorbance of the analyte in a non-analyte feature or spectral region may be actually higher than the absorbance in an analyte feature or region. This situation can occur because the designations "analyte feature" and "non-analyte feature" may take into consideration the absorbance of one or more confounders, or even a dominant confounder. As noted above in describing "strongly absorbing" and "weakly absorbing" spectral regions, the terms "analyte regions" or "analyte features" (e.g., GL features, for glucose measurement, PPG features for PPG measurement, etc.) and "non-analyte regions" or "non-analyte features" (e.g., NO-GL features, NO-PPG features, etc.), as applied to spectral regions or features, do not imply any sort of strict mathematical relationship between the absorption values of the analyte in those regions or features. Rather, they serve to describe the manner in which the regions or features are used, as further described below.

The table below describes energies at various stages for a feature in a spectral region where the analyte, if present, is known to absorb strongly, using nominal example values to illustrate the process.

TABLE 3

| Description | Example Value | Symbol |
|---|---|---|
| Energy of original Zyoton | 1000 | E |
| Energy absorbed by an analyte, as represented by one feature | 1 | $\Delta e$ |
| The goal is to obtain net energy gain of 1 after $\mathbb{N}$ collisions | | |
| Energy of conditioned feature | 10 | e; represents $\Delta e$, i.e., 1 |
| Energy of modified Zyoton after the first collision | 1000.10 | $\mathbb{C}\{E, e\} \to E_1$; $E_1$ depends on e which is the energy of the conditioned feature. $\mathbb{C}$ represents the collision operation. As the collision is inelastic, $E_1 < E + e$ |
| Energy of the renormalized modified Zyoton after the first collision | 0.15 | $e_1 = \mathbb{R}(E_1) \approx (E_1 - E)$ where $e_1$ is obtained by removing, approximately, the energy (E) of the original Zyoton from the modified Zyoton. $\mathbb{R}$ represents an embodiment of the renormalization operation described herein. As the collision is inelastic $E_1 < E + e$, $e_1 < e$ |
| Energy of modified Zyoton after the second collision | 1000.12 | $\mathbb{C}\{E, e_1\} \to E_2$, where $\mathbb{C}$ is the collision operator |
| Energy of the renormalized modified Zyoton after the second collision | 0.18 | $e_2 = \mathbb{R}(E_2) \approx (E_2 - E)$, where $\mathbb{R}$ is the renormalization operator |
| Energy of modified Zyoton after k collisions | 1000.67 | $\mathbb{C}\{E, e_{k-1}\} \to E_k$ |
| Energy of the renormalized modified Zyoton after k collisions | 0.81 | $e_k = \mathbb{R}(E_k) \approx (E_k - E)$ |
| ... | ... | ... |

The table below describes energies at various stages for a collision involving a feature in a spectral region where the analyte, if present, is known to absorb weakly. This feature could be from a spectral region where confounders show high absorption, using nominal example values to illustrate the process.

TABLE 4

| Description | Example Value | Symbol |
|---|---|---|
| Energy of original Zyoton | 1000 | E |
| Energy absorbed by feature | 0.001 | $\Delta e$ |
| The goal is to obtain no net energy gain or a gain of $\leq 0.001$ after $\mathbb{N}$ collisions | | |
| Energy of conditioned feature | 10 | e; represents $\Delta e$, i.e., 1 |
| Energy of modified Zyoton after the first collision | 1000.0004 | $\mathbb{C}\{E, e\} \to E_1$; $E_1$ depends on e which is the energy of the conditioned feature. As the collision is inelastic, $E_1 < E + e$ |
| Energy of the renormalized modified Zyoton after the first collision | 0.00006 | $e_1 = \mathbb{R}(E_1) \approx (E_1 - E)$ where $e_1$ is obtained by removing, approximately, the energy (E) of the original Zyoton from the modified Zyoton. As the collision is inelastic $E_1 < E + e$, $e_1 < e$ |
| Energy of modified Zyoton after the second collision | 1000.0007 | $\mathbb{C}\{E, e_1\} \to E_2$ |
| Energy of the renormalized modified Zyoton after the second collision | 0.0009 | $e_2 = \mathbb{R}(E_2) \approx (E_2 - E)$ |
| Energy of modified Zyoton after k collisions | 1000.0009 | $\mathbb{C}\{E, e_{k-1}\} \to E_k$ |
| Energy of the renormalized modified Zyoton after k collisions | 0.002 | $e_k = \mathbb{R}(E_k) \approx (E_k - E)$ |
| ... | ... | ... |
| Energy of modified Zyoton after $\mathbb{N}$ collisions | 1000.004 or 1000.000081 (could be greater or less than 0.00001) | $\mathbb{C}\{E, e_{\mathbb{N}-1}\} \to E_{\mathbb{N}}$ |
| Energy of the renormalized modified Zyoton after N collisions | 0.004 or 0.000032 (could be greater or less than 0.00001) | $e_{\mathbb{N}} = \mathbb{R}(E_{\mathbb{N}}) \approx (E_{\mathbb{N}} - E)$ $e_{\mathbb{N}} \approx \Delta e$ |

In the same example, the "net renormalized spectral energy gain," after $\mathbb{N}$ collisions, for a feature pair (with one feature covering the analyte absorption spectral region and a second feature covering a spectral region where the analyte is known not to absorb strongly, but with strongly absorbing confounders), can be computed as $\Delta e=1.060-0.004=1.056$. Using calibration tables, this result value, i.e., 1.056, can be used to obtain the concentration of the analyte present in the sample as used in this example.

Amplitude Notation

In the table and discussion below, upper case letters represent Zyoton amplitudes; lower case letters represent conditioned feature amplitudes. Plain symbols without any prime represent the original Zyoton; symbols with a single prime represent a modified Zyoton; and symbols with double prime represent a renormalized modified Zyoton. Symbols representing the k-th iteration, representing a collision between the original Zyoton and the renormalized Zyoton generated after the (n−1)-th collision, include superscript "(n) ." For the sake of convenience, the superscript (1), indicating the modified and renormalized Zyotons generated after the first collision, is omitted. Ordinary, non-stylized letters represent frequency domain amplitudes; stylized letters represent time domain amplitudes. Thus:

TABLE 5

| Symbol | Meaning |
| --- | --- |
| $A_k$, $A_m$, and $A_j$ | Frequency domain amplitudes of the k, m, and j frequency components of the original Zyoton, respectively. In general, k, m, and j are greater than one and, as such, $A_k$, $A_m$, and $A_j$ are row or column vectors of k, m, and j elements, respectively. |
| $a_k$, $a_m$, and $a_j$ | Frequency domain amplitudes of the k, m, and j frequency components of the conditioned feature, respectively |
| $A'_k$, $A'_{m'}$, and $A'_{j'}$ | Frequency domain amplitudes of the k, m, and j' frequency components of the modified Zyoton after the first collision/iteration, respectively. Compared to the original Zyoton, the modified Zyoton may have different m and j frequency components, denoted m' and j' frequency components |
| $A''_k$, $A''_m$, and $A''_j$ More specifically, $A''_k = A''^{(1)}_k$; $A''_m = A''^{(1)}_m$; and $A''_j = A''^{(1)}_j$ | Frequency domain amplitudes of the k, m, and j frequency components of the renormalized Zyoton after the first iteration or collision, respectively. Due to renormalization, the renormalized and original Zyotons have the same k, m, and j frequency components in terms of frequencies, though their respective frequency domain amplitudes are different. Typically, $A''_k$ is less than $A_k$ by a factor of 1,000. |
| $A''^{(2)}_k$; $A''^{(2)}_m$; and $A''^{(2)}_j$ | Frequency domain amplitudes of the k, m, and j frequency components of the renormalized Zyoton after the second iteration or collision, respectively. |
| $\bar{\mathbb{A}} = [\mathbb{A}_1, \ldots, \mathbb{A}_{l_Z}]$ | Time domain amplitudes of $l_Z$ peaks of the original Zyoton containing 1 peaks. Dispersion velocity of the original Zyoton is proportional to the time domain amplitude of one or more b sideband peaks (as exemplified in FIG. 12C) excluding the strongest peak of the Zyoton waveform, denoted $\mathbb{A}^{*Z}$. For example $b_Z = l_Z - 1$. |

TABLE 5-continued

| Symbol | Meaning |
| --- | --- |
| $\bar{\mathbb{a}} = [\mathbb{a}_1, \ldots, \mathbb{a}_{l_{CF}}]$ | Time domain amplitudes of $l_{CF}$ peaks of the conditioned feature. Dispersion velocity of the conditioned feature is proportional to the time domain amplitude of one or more b sideband peaks (as exemplified in FIG. 12C excluding the strongest peak of the conditioned feature waveform, denoted $\mathbb{a}^{*CF}$. For example, $b_{CF} = l_z - 1$. In the general case, it is assumed that prior to a collision, even though the number of space-time points in the Zyoton and the conditioned feature are the same, the number of peaks in the Zyoton ($l_z$) can be different than the number of peaks in the conditioned feature ($l_{CF}$). |

Co-Dependency of Waveforms

In various embodiments, the nearly elastic collision described herein satisfies two conditions: (i) that the collision must not be perfectly elastic, and (ii) that the collision must not be generally inelastic. According to the first condition, the collision is not perfectly elastic so that the original Zyoton and the post-collision, modified Zyoton are not identical. Specifically, with reference to FIG. 11, the collective energy of the first k frequency components of the modified Zyoton, denoted by scalar $SE\_A'_k$ is greater than the collective energy of the first k frequency components of the original Zyoton, denoted by scalar $SE\_A_k$. The spectral energy $SE\_A_k$ can be computed as the L1 or L2 norm of the amplitude vector $A_k$, and the spectral energy $SE\_A_k$ can be computed as the L1 or L2 norm of the amplitude vector $A'_k$. Similarly, the spectral energy of the conditioned feature, denoted $SE\_a_k$, can be computed as the L1 or L2 norm of the amplitude vector $a_k$.

In general, the dispersion velocity of a waveform (also called the velocity) is proportional to the spectral energy thereof. Therefore, the velocity of a Zyoton is proportional to the L1 or L2 norm of the frequency-domain amplitudes of all k, m, and j components of the Zyoton, represented by the combined amplitude vector $[A_k, A_m, A_j]$. In many embodiments, the spectral energy of the k components (the analyte-information representing components) is significantly greater than the spectral energy of the m transition components and the j non-analyte information representing components. As such, in some embodiments, the velocity of a waveform associated with a collision is proportional to the spectral energy of the analyte-information representing k components of that waveform.

Thus, in some embodiments the velocity of the original Zyoton, denoted v(Z), is represented by $SE\_A_k$. The velocity of the conditioned feature, denoted v(CF), is represented by $SE\_a_k$. Therefore, in various embodiments, the second requirement of near elasticity, i.e., the collision must not be inelastic, can be met by synthesizing the Zyoton and the carrier kernel and, optionally, by scaling the Zyoton, such that the scaled velocity of the Zyoton is not different from the velocity of the conditioned feature by $\kappa_{DV2}$. This test can be expressed as: $|\alpha_T * SE\_A_k - SE\_a_k| \leq \kappa_{DV2}$. Instead of scaling the velocity of the Zyoton, or in addition to such scaling, the velocity of the conditioned feature can be scaled during this test.

In the time domain, the dispersion velocity of a waveform is proportional to the L1 or L2 norm of the sideband peaks excluding the highest peak by amplitude. The velocity can be approximated by a selected number of prominent sideband peaks instead of considering all peaks. Therefore, in some embodiments the velocity of the original Zyoton, v(Z), is represented by the L1 or L2 norm of the sideband amplitudes [$A_2, \ldots, A_{l_Z}$], where the amplitude $A_1$ of the highest peak of the Zyoton waveform is excluded. There is no requirement for one-to-one or direct correspondence between the first k frequency components of a Zyoton and the $l_Z$ peaks of the time-domain Zyoton waveform. Similarly, the velocity of the conditioned feature, v(CF), can be represented by the L1 or L2 norm of the sideband amplitudes [$a_2, \ldots, a_{l_{CF}}$], where the amplitude $a_1$ of the highest peak of the conditioned feature waveform is excluded. As such, in some embodiments, the velocity test to ensure the second requirement of inelasticity can be expressed as: $|\alpha_T^*\| [A_2, \ldots, A_{l_Z}]\|-\|[a_2, \ldots, a_{l_{CF}}]\| | \leq \kappa_{DV2}$. The double bars represent the L1 or L2 norm of the amplitudes. The scaling factor $\alpha_T$ and the Kappa parameter $\kappa_{DV2}$ can take on different values based on whether the test is performed in the frequency domain or in the time domain.

After the first collision iteration, a modified Zyoton is generated. The co-dependency of the original Zyoton and the modified Zyoton can be tested in the frequency domain, to ensure that the collision was near elastic, by testing the condition: $|SE\_A_k - SE\_A'_k| \leq \kappa_{DV3}$. In the time domain, velocity test can be performed as: $| \|[A_2, \ldots, A_{l_Z}]\| - \|[A'_2, \ldots, A'_{l_{Z'}}]\| | \leq \kappa_{DV3}$. The Kappa parameter $\kappa_{DV3}$ can take on different values based on whether the test is performed in the frequency domain or in the time domain. In addition, the divergence test can be performed in the time domain by determining the widths of selected b peak envelopes of the original Zyoton, denoted [$\delta_1, \delta_2, \ldots, \delta_b$] and the widths of the corresponding peak envelopes of the modified Zyoton, denoted [$\delta'_1, \delta'_2, \ldots, \delta'_b$]. FIG. 19 depicts $\delta_1$, $\delta_2$, and $\delta_3$ as t1, t2, and t3, and $\delta_1'$, $\delta_2'$, and $\delta_3'$ as t1', t2', and t3'. For each peak-envelope pair, a difference can be computed. In some embodiments, the divergence condition is satisfied if $|\delta_p - \delta'_p| \leq \tau$, for each p=1, . . . , b. In some embodiments, an L1 or L2 norm of the differences ($\delta_p - \delta'_p$) may then be computed. If the L1 or L2 norm is less than the specified threshold $\tau$, the divergence condition is determined to be satisfied.

After the modified Zyoton is renormalized, the co-dependency of the original Zyoton and the renormalized Zyoton can be tested in the frequency domain, to ensure that the next collision iteration would be near elastic, by testing the condition $|\alpha_T^* SE\_A_k - SE\_A''_k| \leq \kappa_{DV3}$. Instead of scaling the velocity of the Zyoton, or in addition to such scaling, the velocity of the renormalized Zyoton can be scaled during this test. In some embodiments, the scaling coefficient $\alpha_T$ used to scale the velocity of the original Zyoton, represented in the frequency domain by the spectral energy of the analyte-information representing k components of the original Zyoton, may be different than that used when the co-dependency between the original Zyoton and the conditioned feature was tested, to account for the difference between the energies of the conditioned feature and the renormalized Zyoton. In some embodiments, the difference between the values of $\kappa_{DV2}$ and $\kappa_{DV3}$ can account for this energy difference. In some embodiments, the values of $\kappa_{DV2}$ and $\kappa_{DV3}$ can be the same. In the time domain, the velocity test between the original Zyoton and the renormalized Zyoton can be performed as: $|\alpha_T^* \|[A_2, \ldots, A_{l_Z}]\| - \|[A''_2, \ldots, A''_{l_{Z''}}]\| | \leq \kappa_{DV3}$. Here again, the scaling factor $\alpha_T$ and the Kappa parameter $\kappa_{DV3}$ can take on different values based on whether the test is performed in the frequency domain or in the time domain.

After the first collision between the original Zyoton and the conditioned feature, in some embodiments, the subsequent collisions occur between a renormalized Zyoton from a preceding iteration (typically the previous iteration), and the original Zyoton or a new Zyoton. For the i-th collision iteration, the velocity of the original Zyoton, if used in that iteration, is v(Z). The velocity of the other colliding waveform is the renormalized Zyoton from the previous collision iteration, and the velocity thereof is denoted $v(Z''_{(i-1)})$. The velocity of the modified Zyoton generated in the i-th iteration is denoted v(Z'i) and the velocity of the renormalized Zyoton generated in the i-th iteration is denoted v(Z"i). As described above, these velocities can be computed in the frequency domain or in the time domain.

Optionally, prior to the i-th collision iteration, the velocity test $|\alpha_T^* v(Z) - v(Z''_{(i-1)})| \leq \kappa_{DV1}$ is performed. Optionally, after the i-th collision iteration, but before the corresponding renormalization, the velocity test $|v(Z) - v(Z'_{(i)})| \leq \kappa_{DV3}$ is performed. Optionally, the divergence test using the envelope peaks of the original Zyoton Z and the modified Zyoton $Z'_i$ is performed. Optionally, after the renormalization corresponding to the i-th collision iteration, the velocity test $|\alpha_T^* v(Z) - v(Z''_i)| \leq \kappa_{DV1}$ is performed. One or more tests may be performed in each collision iteration and in different collision iterations, different tests may be performed. The collective objective of these tests, however, is that each collision iteration is near elastic as described above, and that the colliding waveforms are co-dependent.

Figure 11:
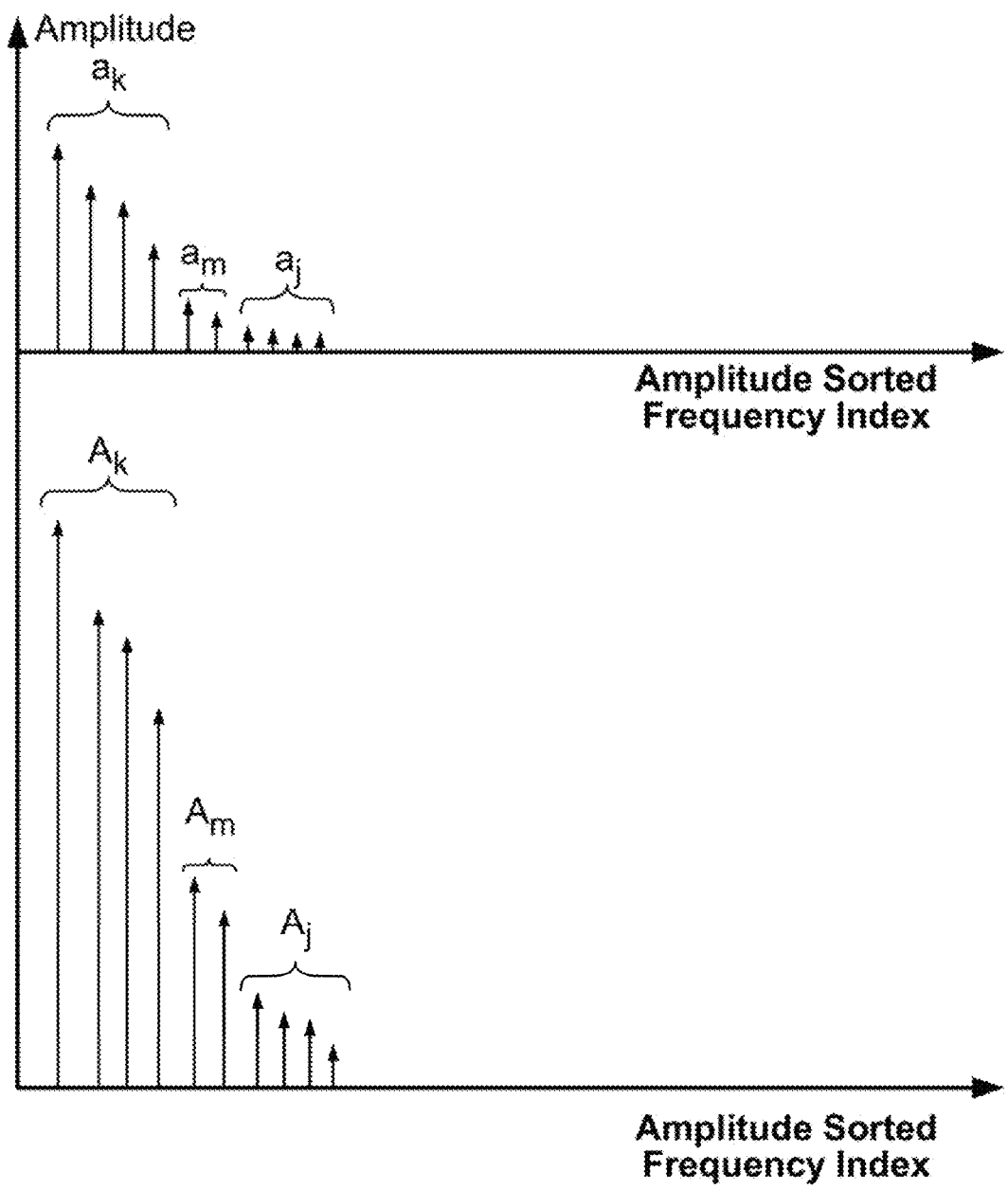
FIG. 11 shows frequency components for an modified Zyoton and a renormalized Zyoton.

To illustrate a collision of the two traveling waveforms in the frequency domain, the k, m, and j frequency components of both the Zyoton and the conditioned feature are depicted (as shown in FIG. 11) as ordered from left to right. A Zyoton or a conditioned feature can be represented as frequency components increasing from left to right or could be represented as frequency components increasing from right to left. The ordering of the frequency components is based on the power spectral densities (PSDs) of the respective frequency components. In some embodiments, the PSD of the k components>the PSD of the m components>the PSD of the j components. In some embodiments, the PSD of the k components<the PSD of the m components<the PSD of the j components.

The conditioned feature and the original Zyoton are synthesized such that the increase in the collective energy of the first k frequency components of the original Zyoton due to a collision is proportional to the collective energy represented by the first k frequency components of the conditioned feature. As described above, the first k frequency components of the conditioned feature may capture $E_{A1}$, $E_{C1}$, ($E_{A1}+E_{C1}$), a fraction of $E_{C1}$, e.g., $E_{C[n]}=\Sigma_{i=1}^{n} E_{Ci1}$, where there are a total of N confounders and n<N, or ($E_{A1}+E_{C[n]}$). As such, after the first collision, $(\|A'_k\|-\|A_k\|)$ can be proportional to any one of $E_{A1}$, $E_{C1}$, ($E_{A1}+E_{C1}$), $E_{C[n]}$, and ($E_{A1}+E_{C[n]}$). These feature energy quantities, generally referred to as $E_{M1}$, represent the concentration of a material (e.g., the analyte, a combination of the analyte and at least some confounders, a single confounder, or a combination of at least some confounders) in the medium. Therefore, a change in the spectral energy of a post-collision result (e.g., a Zyoton perturbed by a conditioned feature)

relative to the spectral energy of the original Zyoton can be used to estimate the concentration of material exhibited in the spatial, temporal or spectral window defined by the feature.

According to the second condition, the collision is not generally inelastic, i.e., at a minimum, the collision operation does not introduce into the modified Zyoton any new frequency components within the first k frequency components that were not present in the original Zyoton. Introduction of such frequency components can represent energies that are not related to the energies absorbed by the analyte and any confounders. Therefore, if any such frequency components are introduced, the difference ($\|A'_k\|-\|A_k\|$) may not accurately represent the concentration of material exhibited in the spatial, temporal, or spectral window defined by the feature. A Zyoton design rule requires that the conditioned feature and the Zyoton not introduce new frequency components in the set of the first k Zyoton frequency components. In some embodiments, this is ensured by scaling the Zyoton waveform energy to be approximately three or more orders of magnitude higher than the spectral energy of the conditioned feature with which it is collided.

In an embodiment for glucose measurement, where: (i) the absorbance level due to the analyte may be less than 0.01% of the total absorbance, and (ii) there can be up to a three orders of magnitude dynamic range of the analyte (i.e., glucose) concentration range, in the first collision, the threshold value $\kappa_{DV2}$ used to ensure that the Zyoton energy is at least three orders of magnitude greater than the energy of the conditioned feature can be $1\times10^{-6}$. Recall, the Kappa threshold is also used in the velocity test described above, to ensure the co-dependency of the Zyoton and the conditioned feature to be collided therewith. In general, the threshold $\kappa$ can be decreased as the collision iteration count is increased. Thus, as the number of collision iterations increases, the amount of dispersion permitted in each iteration can become smaller.

While the difference ($\|A'_k\|-\|A_k\|$) after the first collision can represent $E_{M1}$ (i.e., any one of $E_{A1}$, $E_{C1}$, ($E_{A1}+E_{C1}$), $E_{C[n]}$, and ($E_{A1}+E_{C[n]}$)), the accuracy of such representation can be improved, especially when the signal-to-clutter ratio (SCR) is low, using several collision iterations. In various embodiments, the elasticity of a single collision, as measured by $\kappa_{DV1}$, which corresponds to a collision between the original Zyoton and a renormalized Zyoton, is generally inversely proportional to the SCR. Low SCR generally implies that the value of $\kappa_{DV1}$ for insuring compliance with co-dependency condition is small, e.g., a value of $1\times10^{31\ 6}$ used for a SCR of $10^{-3}$ or a value of $1\times10^{-8}$ for a SCR of $10^{-4}$ and, as such, the change in the velocity of the modified Zyoton, and the corresponding renormalized Zyoton, relative to the velocity of the original Zyoton is small. For an order of magnitude reduction in SCR, the threshold $\kappa_{DV1}$ may be generally reduced by two orders of magnitude. As the permitted change in the dispersion velocity after one collision is small, the observed change in energy after one collision, i.e., ($\|A'_l\|-\|A_k\|$), is also small. Therefore a single collision iteration may not be sufficient to produce a discernible change in the spectral energy due to analyte absorption estimated using the first k frequency components. The energy change after a single collision may be only visible if k were large or if the window length approaches the total number of frequency components of the conditioned feature. The latter case, however, can represent change in energy due to not only analyte and/or confounder absorption, but also due to energy loss or absorption of energy in the medium. Therefore, several collision iterations may be required to induce a change in the spectral energy computed using the first k frequency components to discern and characterize changes due to absorption by the analyte and/or one or more confounders.

In one embodiment, the subsequent collisions involve the modified Zyoton and the original Zyoton. Therefore, before the next collision, the modified Zyoton is renormalized to remove therefrom the spectral energy of the original Zyoton so that the gain in the energy of the original Zyoton caused in the next iteration is proportional substantially only to $E_{M1}$, as represented by the modified Zyoton produced in the subsequent iteration. As used herein, substantially means the contribution from noise and/or clutter is no more than 0.01%, 0.2%, 0.5%, 1%, 10%, etc. As explained above, in applications with extremely low SCR (e.g., SCR<$10^{-4}$) the ($\|A'_l\|-\|A_k\|$) may be nearly zero post renormalization. This can lead to numerical instabilities in the computation, such as divide-by-zero instabilities. To prevent such instabilities, book-keeping is employed, e.g., by ensuring that after each collision, or at least after a selected number of successive iterations (e.g., 2, 3, 5, 10, 25, 50, etc.), the total change between the energies of the first k frequency components of the modified Zyoton and the energy of the first k frequency components of the original Zyoton monotonically increases. This change may be tracked as a change in the ratio of energies of the k frequency components of the modified Zyoton and original Zyoton from a starting value of unity (i.e., 1) or 100%.

In addition, post-collision renormalization can compensate for the impact of any pre-collision up-scaling of any entity participating in a collision (e.g., the Zyoton, the conditioned feature, and/or the renormalized Zyoton from the previous iteration) or the down-scaling of any of these entities by the factor $\overline{\alpha}$, as described below. For example, the down-scaling of the modified Zyoton waveform, to obtain a renormalized Zyoton, removes some of the inherent waveform energy.

As described above, this renormalization computation typically targets two objectives in the same computational step. Specifically, in the first objective of renormalization, it is necessary to remove the spectral energy of the original Zyoton. In addition, it is often necessary to compensate for the energy of frequency components that were removed in any post-collision down-sampling step, also called truncation. Without this compensation, numerical artifacts and energy inaccuracies may be introduced into follow-on collision iterations. The first aspect of the renormalization is generally directed to the removal of the energy of the k components of original Zyoton from the modified Zyoton, often producing a renormalized Zyoton in which the amplitudes of the first k frequency components are similar to the respective amplitudes of the first k frequency components of the conditioned feature.

The second aspect is generally directed to preserving the energy contributions of any frequency components in the modified Zyoton that were removed post-collision for computational efficiency, and/or to ensure that the subsequent collision iterations would be near-elastic, as described above. In particular, any new frequency components that are transition (i.e., m) components and/or non-analyte-information representing (i.e., j) components, can cause a subsequent iteration to be inelastic. As such, one or more of these new frequency components are removed, but the energy thereof is redistributed among the surviving m and/or j components. Alternatively or in addition, one or more transition components and/or one or more non-analyte-information representing components that were present in the original Zyoton and/or the conditioned feature may be removed, and the energy thereof may be redistributed among the surviving m and/or j components.

Therefore, referring again to FIG. 11, the amplitudes of all of the k, m, and j components of the modified Zyoton, denoted [A']=A'[1, . . . , k+m+j], are scaled using a renormalized scaling vector $\bar{\alpha}$, computed based on the amplitudes of the k components of the original Zyoton and the corresponding k components of the modified Zyoton. In some embodiments, the scaling vector $\bar{\alpha}$ is based on a ratio $S_1$ of the spectral energy of the k components of the original Zyoton and the spectral energy of the corresponding k components of the modified Zyoton, expressed as:

$$S_1 = \frac{\|A_k\|}{\|A'_k\|}.$$

In some embodiments, this can cause the respective amplitudes of various or all components of the renormalized modified Zyoton, denoted [A'']=A''[1, . . . , k+m'+j'] to be within 10%, 20%, or 50%, etc., respectively, of the amplitudes of the corresponding frequency components of the conditioned feature, denoted [α]=α[1, . . . , k+m+j]. Thus:

$$[A''] = S_1[A'] \Rightarrow A[1, \ldots, k+m'+j'] \approx a[1, \ldots, k+m+j] \quad (9)$$

In some embodiments, the a preset amount of energy, e.g., E* is removed. To this end, a pre-set scaling vector $S_1=[S_1{}^1, S_1{}^2, \ldots, S_1{}^k, \ldots, S_1{}^{k+m+j}]$ may be used to scale the amplitudes of the components of the modified Zyoton [A']. The energy level E* can be selected according to the energy of the original Zyoton or independently thereof.

The cardinality of the transition components of the modified Zyoton, denoted m', and the cardinality of the non-analyte-information representing components of the modified Zyoton, denoted j', indicate that the modified Zyoton may have some new transition and/or non-analyte-information representing components. Any of these transition and/or non-analyte-information representing components, including new and/or previously existing ones, may be removed during truncation. The amplitudes of some or all of the surviving transition and/or non-analyte-information representing components of the modified Zyoton may then be adjusted further using another scaling factor $S_2$, such that the spectral energy of the surviving m and j components of the renormalized Zyoton is approximately equal to the spectral energy of all of the transition and/or non-analyte-information representing components of the modified Zyoton after scaling thereof but its truncation. Thus:

$$[A''_{m,j}]=S_2[A'_{m,j}]_{TR} \quad (10)$$

where $[A'_{m,j}]_{TR}$ represents a modified Zyoton as truncated. The scaling factor $S_2$ may be based on the ratio $$\frac{S_1 \times \|A'_{m',j'}\|}{\|A_{m,j}\|}.$$

A subsequent collision between the original Zyoton and the renormalized modified Zyoton yields a second modified Zyoton. The spectral energy of the first k frequency components of the second modified Zyoton is denoted $\|A'^{(2)}{}_k\|$, and the difference $(\|A'^{(2)}{}_k\|-\|A_k\|)$ can represent $E_{M1}{}^{(2)}$, which is a refined estimate of $E_{M1}$, i.e., a refined estimate of any one of $E_{A1}$, $E_{C1}$, $(E_{A1}+E_{C1})$, $E_{C[n]}$, and $(E_{A1}+E_{C[n]})$. After a selected number of iterations, $\mathbb{N}$, which can vary from one embodiment to another, as described below, $E_{M1}^{(\mathbb{N})}$ can provide an accurate estimate of the energy absorbed at the wavelengths associated with the feature F1 by the concentration of a material in the medium to be analyzed. As described above, in the general case, the material can be only the analyte, a single confounder, a combination of one or more confounders, or a combination of the analyte and one or more confounders.

The above described process can be repeated for another feature F2 to obtain $E_{M2}^{(\mathbb{N})}$. In some embodiments, the two features F1 and F2 are selected such that there is a difference between the absorption of at least one constituent of the material (i.e., the analyte and/or at least one confounder) in the respective wavelengths bands of the two features. Therefore, the difference between $E_{M2}^{(\mathbb{N})}$ and $E_{M1}^{(\mathbb{N})}$ or a function of these two variables can be used in determining the concentration of the constituent that absorbs differently in the two wavelength bands. In one embodiment for noninvasive glucose measurement, in which the analyte does not absorb substantially in the wavelength bands of the Feature F2 and if the total absorption of the confounders remains substantially unchanged between the wavelength bands of Features F1 and F2, and where $E_{M1}^{(\mathbb{N})}$ represents $(E_{A1}+E_{C1})$ and $E_{M2}^{(\mathbb{N})}$ represents $E_{C2}$, the difference $(E_{M1}^{(\mathbb{N})} - E_{M2}^{(\mathbb{N})})$ can represent $E_{A1}$, which can be used in determining the concentration of the analyte. These specific conditions generally may not be true, however. Therefore, particular functions or relations, as described below, based on the estimates of energies corresponding to one or more features and/or one or more feature pairs can be used to determine more accurately the concentration of the analyte.

Synthesis of Zyotons and Carrier Kernels

Figure 31A:
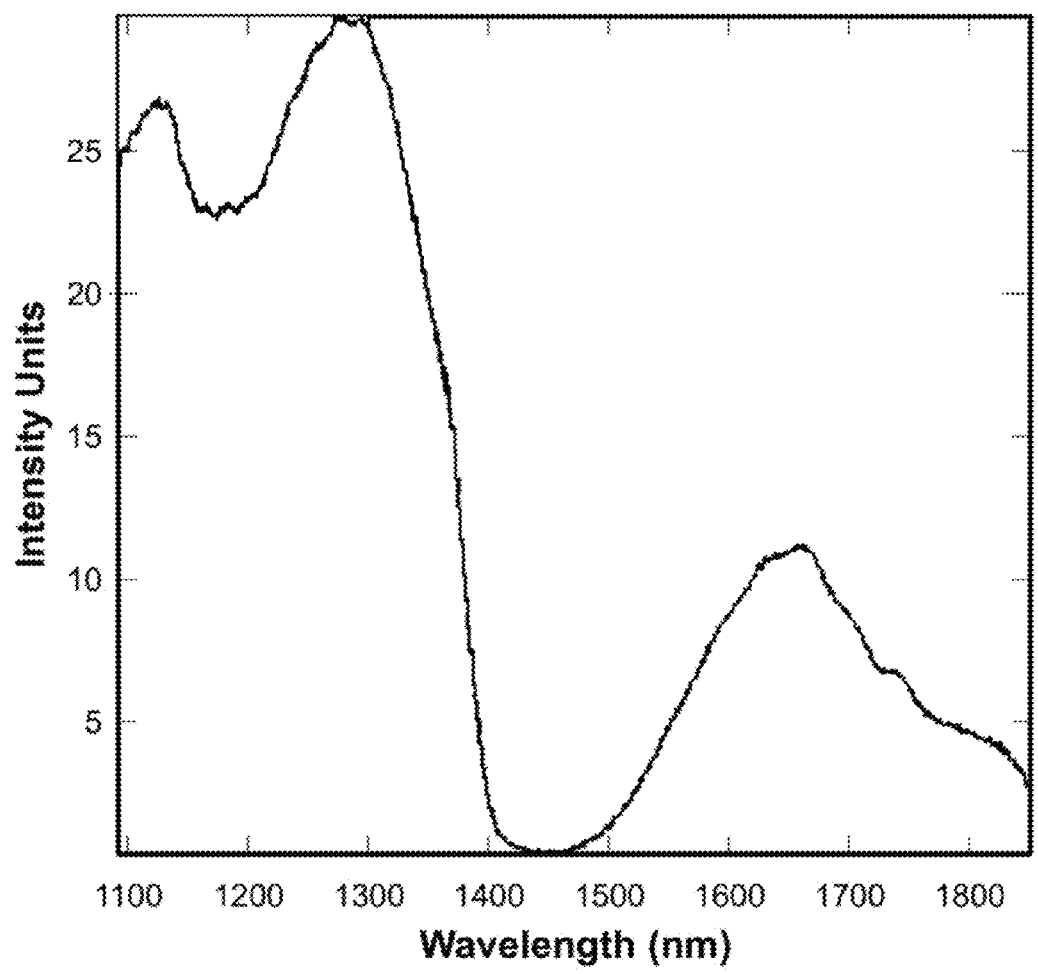
FIG. 31A shows the near-infrared diffuse reflectance intensity as a function of wavelength for human skin.
Figure 31B:
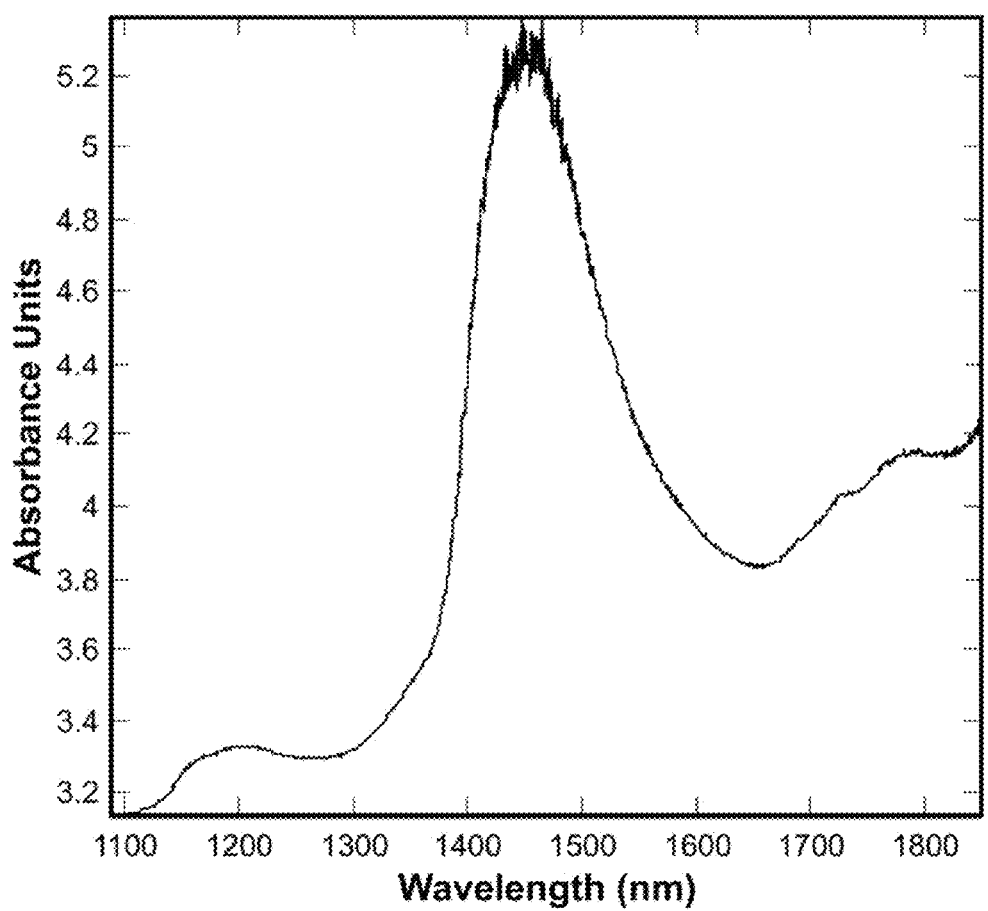
FIG. 31B shows the associated absorbance spectrum of human skin.

With reference to FIG. 10B, a feature is generally related to the intensity of radiation reflected from or transmitted through a medium, or to the absorption of incident radiation within the medium to be analyzed, corresponding to a specified range of wavelengths [λ1, λ2], also called feature boundaries. Typically, a feature (e.g., Feature F1) does not have a smooth profile as shown in FIG. 10B. Examples of intensity and absorbance spectra are shown in FIGS. 31A and 31B. The features obtained from any of these spectra, typically have a saw-toothed, somewhat jagged profile, such as that shown in FIG. 32. Such a profile generally results from sampling errors, device and detector noise, ADC discretization artifacts, and/or path length effects of summing absorbance from many individual NIR photons. Noise in an intensity spectrum produced from radiation collected at a detector typically results from several sources. The quantization error of the analog-to-digital converter (ADC) is one source. Another source of noise is the variation in total travel distances of individual photons as they propagate through a medium to be analyzed (e.g., the skin tissue), and this variation in combination with scattering losses within the medium can introduce measurement noise in a received or detected intensity spectrum.

Figure 34:
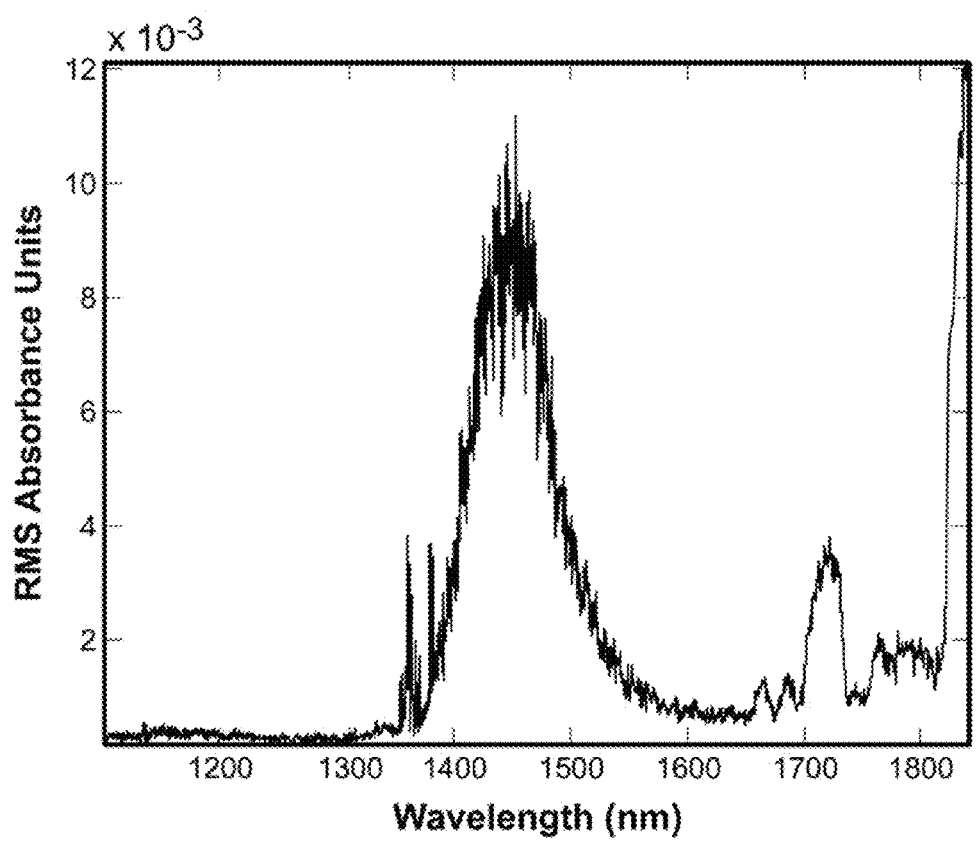
FIG. 34 gives an example of a wavelength by wavelength RMS noise estimate based upon a set of spectra.
Figure 35:
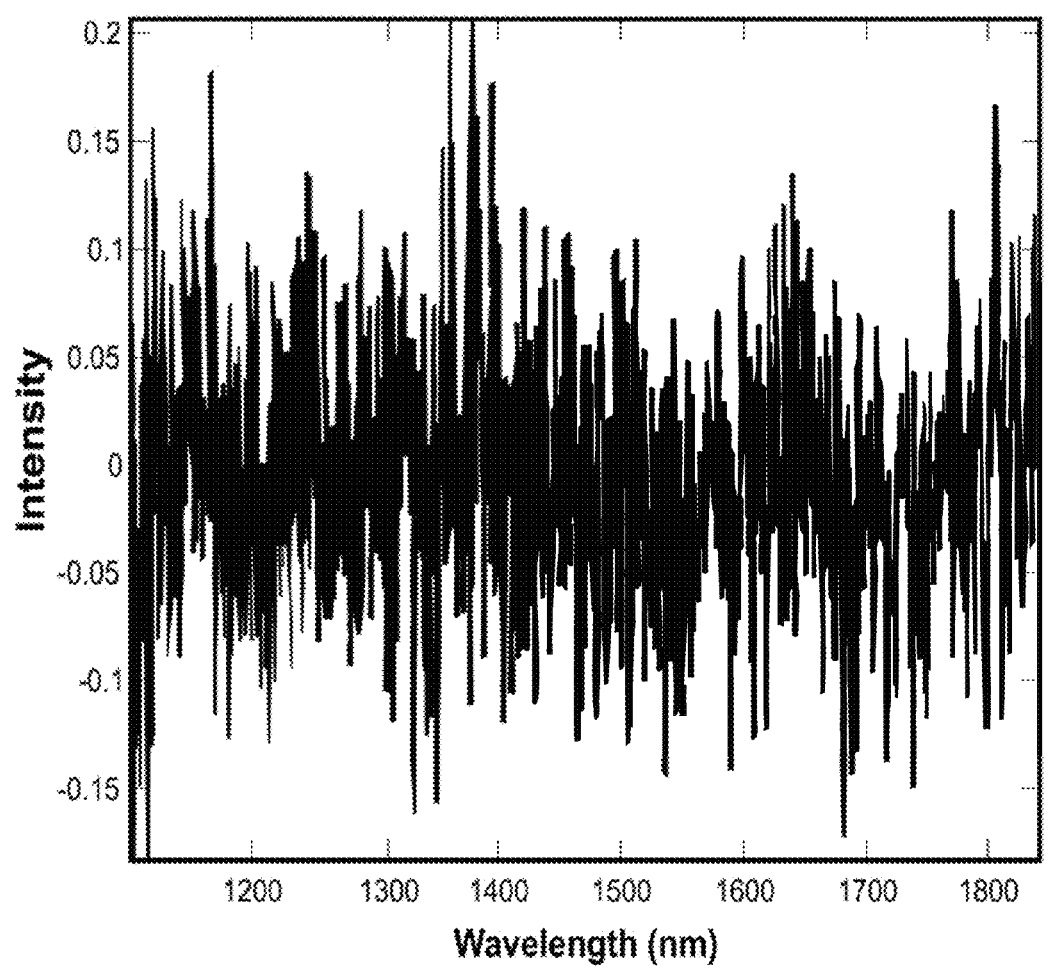
FIG. 35 provides an example of a noise intensity spectrum in NIR wavelengths.

Moreover, the noise in an intensity or absorbance spectrum may not be uniform across the spectrum, and may vary according to the wavelength. As such, the noise in a feature within the wavelength range [λ1, λ2] can be non-uniform and may vary non-monotonically with the wavelength. The variations in noise across a spectrum can be determined by the difference between any single spectrum and a mean spectrum obtained from multiple spectra generated using the same incident radiation and medium. FIG. 31A provides an example of a diffuse reflectance intensity and FIG. 31B shows the associated absorbance from a NIR spectrum from human skin. An example of noise in a captured spectrum is shown in FIGS. 33 through 35.

Figure 33:
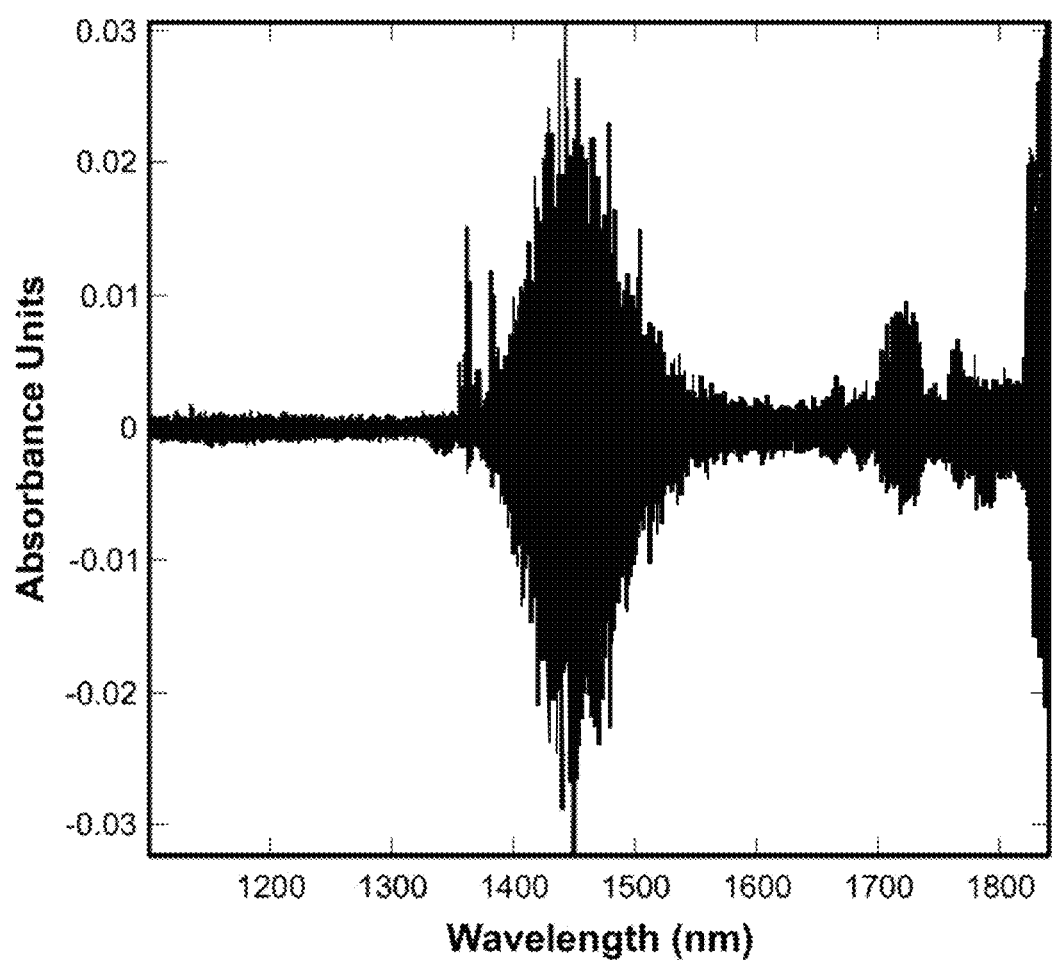
FIG. 33 provides an example of a set of mean-centered absorbance spectra to show instrument related spectral variability as a function of NIR wavelength.

FIG. 33 provides an example of a set of mean-centered absorbance spectra to show instrument related spectral variability as a function of NIR wavelength. FIG. 34 shows an example of wavelength-by-wavelength RMS noise, based upon a set of spectra. FIG. 35 depicts a difference between a single spectrum and the mean spectrum and provides an illustration of the variation in noise across wavelengths. FIG. 36 shows the scaled intensity and absorbance spectra associated with a single feature on the same plot. As shown in the legend for FIG. 36, different absorbance and intensities profiles have been normalized by multiplying with different factors. The ultra-weak absorbance of pure-component spectrum of glucose, in the feature region delineated by 1540 nm to 1554 nm, has been multiplied by a factor of 40,000 to plot at the same scale as the absorbance from confounders: fat (multiplied by factor of 8) and water (multiplied by factor of 2). These scaled absorbances for glucose and the confounders fat and water are overlaid on the same plot. The legend provides all the factors used for normalizing the spectra (in intensity or absorbance units) to plot them on the same graph.

The fluctuations in the feature absorbance profiles shown in FIG. 36 typically result from sampling errors, device and detector noise, analog-to-digital conversion (ADC) discretization artifacts, and path length effects of summing absorbance from the travel-path of many individual NIR photons launched in each illumination of the sample. A feature such as that shown in FIG. 36, thus may have both periodicity and frequency content.

The process of generating a conditioned feature begins with the synthesis of a Zyoton waveform and a carrier kernel waveform. The Zyoton is generated using a number of frequency components. The first k (e.g., six) frequency components are selected, e.g., for measuring the energy absorbed by an analyte (such as energy absorbed by glucose in tissue), according to pure component spectrum of the analyte and the characteristics of instrument noise, such as the RMS value in the amplitude domain, power spectral density in frequency domain, and/or periodicity.

In various embodiments, the selected frequency components are related to frequencies of radiation that are absorbed strongly by the analyte and those absorbed weakly or negligibly by the analyte. The analyte-specific frequency components may be selected following a Fourier transform of the selected spectral feature either before or after an optional interpolation, a sort of the frequency components by peak power, and a selection of the first k (e.g., 6) frequency components. A Fourier transform of a feature includes sinusoidal waveforms at different frequencies/frequency components that, when summed, represent the feature waveform.

The feature data extracted from the spectrum has low spatial frequency content, often due to a limited data vector length. The spatial frequency content may therefore be insufficient to characterize changes in the feature properties due to analyte concentration and interference from confounders. Coupling the feature with a complex carrier kernel with a higher spatial frequency content can provide additional degrees of freedom to characterize the underlying analyte. Pre-cursor modulation 10 in FIG. 37 of the feature can also increase the degrees of freedom by increasing the bandwidth of the feature waveform prior to modulating the carrier kernel. Different features, associated with different wavelength regions, with different underlying analyte concentrations generally modulate the carrier kernel differently.

A carrier kernel typically includes k high amplitude frequency components, where k≥1, and j low amplitude frequency components, where j>1, and may include m medium-amplitude components. While the specific values of the amplitudes of these frequency components can be selected according to the amplitudes of the frequency components of the Zyoton to be used in the collision process and/or other parameters of the collision process, the amplitudes of the k high amplitude (also called high energy) frequency components of the carrier kernel are typically two or three orders of magnitude greater than the amplitudes of the j frequency components of the carrier kernel. The high energy k frequency components are employed primarily for extraction of the energy absorbed by the analyte from a feature.

The carrier kernel may optionally include m frequency components (called medium energy components or transition zone components) having amplitudes that are generally two to three times the amplitudes of the low energy j components. The Zyoton used during the collision process also has high energy k components, low energy j components and, optionally, medium energy m components. Likewise, a conditioned feature generated by modulating the carrier kernel by a feature also has the high energy k components, low energy j components and, optionally, medium energy m components. During various frequency-domain implementations of the collision process, the respective Zyoton and conditioned feature components are amplitude sorted. Therefore, the discussion below usually refers to the high-energy components of a waveform (e.g., a Zyoton, a carrier kernel, a conditioned feature, a modified Zyoton, a renormalized Zyoton, etc.), as the first k frequency components or the first k components.

In various embodiments, the first k frequency components of a Zyoton are determined by examination of the second derivative of the pure component spectrum (e.g., glucose) in order to identify areas of the greatest rate of change of energy absorption within the features derived from the spectrum. For example, FIG. 28A depicts an absorbance spectrum of glucose, and FIG. 30A shows the second derivative of that absorbance spectrum. The ratio of the magnitude of the second derivative in the regions that correspond to high and low analyte absorption regions (as shown in FIG. 28A) may be used to establish the relation (e.g., relative ratio of magnitudes of first k frequency components of the Zyoton and/or the carrier kernel) between the first k frequency components, as described below with reference to FIG. 38.

The second derivative may also be used, as discussed below, as an indicator of how confounder interference will distort high and low absorbing regions in the frequency domain for the specific wavelength region from which features are selected. In the absence of noise, the second derivative can be used to provide a numerical classifier for identifying the areas of greatest change in either of the high and low absorbance wavelength regions of the pure component spectrum of the analyte. Use of the second-order derivative is generally described in Ferraty, F. and Vieu, P, "The Functional Nonparameteric Model and Application to Spectrometric data", Computational Statistics, 17(4), 2002, which shows that by taking the second- and higher-order derivatives, one can focus on curvature rather actual values taken by functions to build more robust classifiers and improve prediction performance in the presence of noise and other uncertainties.

The number k, i.e., the cardinality of the set of high-energy components, can be determined by estimating the number of frequency components required to separate (as defined below) spectral regions of the second derivative corresponding to higher and lower absorbing regions of the pure component spectrum in the presence of at least three orders of magnitude of added RMS pseudo-random noise (PRN). Commonly known techniques for generating pseudo-random noise may be employed and addition is typically represented as wavelength-by-wavelength addition of the PRN value to the pure component absorbance amplitude value. In various embodiments discriminant classification is further used to develop a quadratic discriminant classifier using combinations of different numbers of frequency components, i.e., using 2, 3, 4, . . . k components.

A quadratic classifier can be used to separate two or more classes of objects or events by a quadric surface (where quadric is any D-dimensional hypersurface in (D+1)-dimensional space defined as the locus of zeros of a quadratic polynomial). In coordinates $x_1, x_2, \ldots, x_{D+1}$, the general quadric is defined by the algebraic equation:

$$\sum_{i,j=1}^{D+1} x_i Q_{ij} x_j + \sum_{i=1}^{D+1} P_i x_i + R = 0 \quad (11)$$

where $x=(x_1, x_2, \ldots, x_{D+1})$ is a row vector, $x^T$ is the transpose of x (a column vector), Q is a (D+1)×(D+1) matrix and P is a (D+1)-dimensional row vector and R a scalar constant. The values Q, P and R are often taken to be over real numbers or complex numbers. The set of "vectors of observations" used in the discriminant analysis includes features drawn from the selected regions of the second derivative waveform combined with noise (PRN), each of which is associated with a higher or lower absorption region of the analyte pure component spectrum.

To generate the vectors of observation to be used in discriminant analysis: (i) the values of the second derivative of the pure component absorbance spectrum, to which PRN has been added, in the high and low absorbance regions as defined above, are extracted and copied into two new vectors HighAbs and LowAbs respectively; (ii) in some embodiments, the HighAbs and LowAbs vectors from the pure component absorbance spectrum for the analyte are then both up-sampled to the twice the up-sampled length used for up-sampling a spectral feature vector (e.g., 2*2048=4096) as used in collision computing. The resulting vectors are denoted as up-sampled-HighAbs and up-sampled-LowAbs vectors respectively; (iii) up-sampled HighAbs and up-sampled LowAbs vectors are then Fourier transformed into spatial frequencies. The results are denoted as F{Upsampled HighAbs)} and F{Upsampled LowAbs} vectors.

Additional steps include: (iv) magnitude sort F{Upsampled HighAbs} and F{Upsampled LowAbs} on the basis of the amplitude of frequency components to yield F'{Upsampled HighAbs} and F'{Upsampled LowAbs} vectors; (v) construct observation test vectors, to be used in discriminant analysis test, by selecting subsets of F'{Upsampled HighAbs} and F'{Upsampled LowAbs} vectors with variable number of frequency components such as v=2,3,4, . . . k components, where each value v is a candidate k value; and (vi) optionally repeat this sequence of step (i)-step (v) 2, 5, 10, 50, 100, or 500 times, where different amounts of random noise are added to the pure component spectrum to generate different test sets of observation vectors of different numbers of frequency components.

The value of "k" may then be set to the number of components that can separate the high and low absorbance noisy second derivative regions of the analyte pure component spectra, in the case of a single test, or the maximum number of components that are required to separate these high and low absorbing regions in repeated tests. In various embodiments, the quadratic discriminant technique is used to build a classifier that can associate combinations of frequency components with the absorption regions associated with an analyte of interest. In general, high and low absorbing spectral regions are said to be separated when the result of the discriminant classifier, normalized to a value of 1, is less than 0.1, 0.2, or 0.5.

Figure 39:
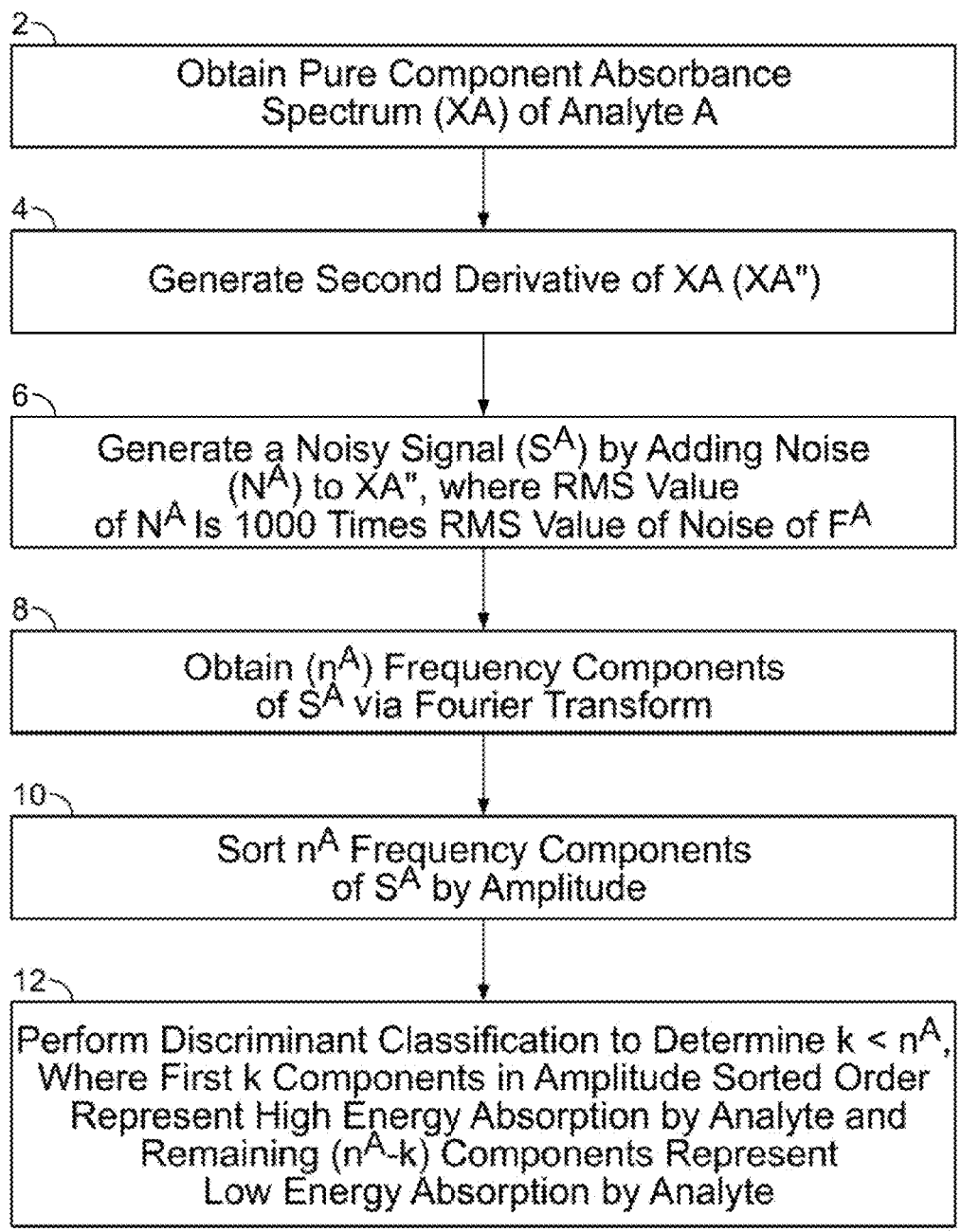
FIG. 39 is a flowchart showing the steps in the determination of the number k of the frequency components of a Zyoton and a carrier kernel, according to one embodiment.

In one embodiment, the number of high energy components (k) of the original Zyoton (and of the carrier kernel, as well), where the k high energy components represent absorption by the analyte, is determined using: (a) the Fourier transform of a noisy signal obtained by adding a certain amount of noise to the second derivative of the analyte pure component spectrum, and (b) discrimination classification. With reference to FIG. 39, the pure component spectrum of the analyte of interest, denoted XA, is obtained in step 2. This spectrum is typically generated using the source of radiation and the detector (e.g., an optical probe, examples of which are described below) to be used in the non-invasive measurement system. The spectrum XA may be optionally interpolated in step 2. In step 4, a second derivative of the spectrum XA, denoted XA" is obtained.

Pseudorandom noise $N^A$ is added to the second derivative XA", in step 6, to obtain a noisy signal $S^A$. The noise $N^A$ can be gray noise with a correlation time of $10^{-6}$ seconds, and may have a root-mean-squared (rms) value that is a multiple of (e.g., 100, 1000, 1500, 5000, 10,000 times, etc.), the rms value of the noise introduced by the sensor, i.e., the noise of the spectrum signal XA. Alternatively, the rms value of NA can be a multiple of the RMS value of the first or higher-order derivative of XA. In step 8, Fourier transform of the noisy second derivative signal $S^A$ is computed to identify the various frequency components therein. These components are sorted by amplitude in step 10, though in some embodiments, this step is optional.

Discriminant classification is performed in step 12 to determine the value of k, i.e., the cardinality of the set of high-energy components of the Zyoton and the carrier kernel. Specifically, k is set to be equal to the number of frequency components of the noisy signal that are needed to separate the high and low absorbance regions as defined above. Thus, the determination of k for the Zyoton (and for the carrier kernel, as well) is based, at least in part, on the SNR of the measurement system. In some embodiments, the value of k may be incremented by a suitable integer constant, e.g., 1, 2, 4, etc. The actual frequencies of the k Zyoton and the carrier kernel frequencies are generally determined by the selected Zyoton family/generator and need not be related to the frequencies of the components of the noisy second derivative signal. In summary, k is concluded when the discriminant classification technique using k-components can separate regions of the second derivative of the pure component spectrum corresponding to higher and lower absorbance regions of the pure component spectrum in the presence of noise.

Figure 40:
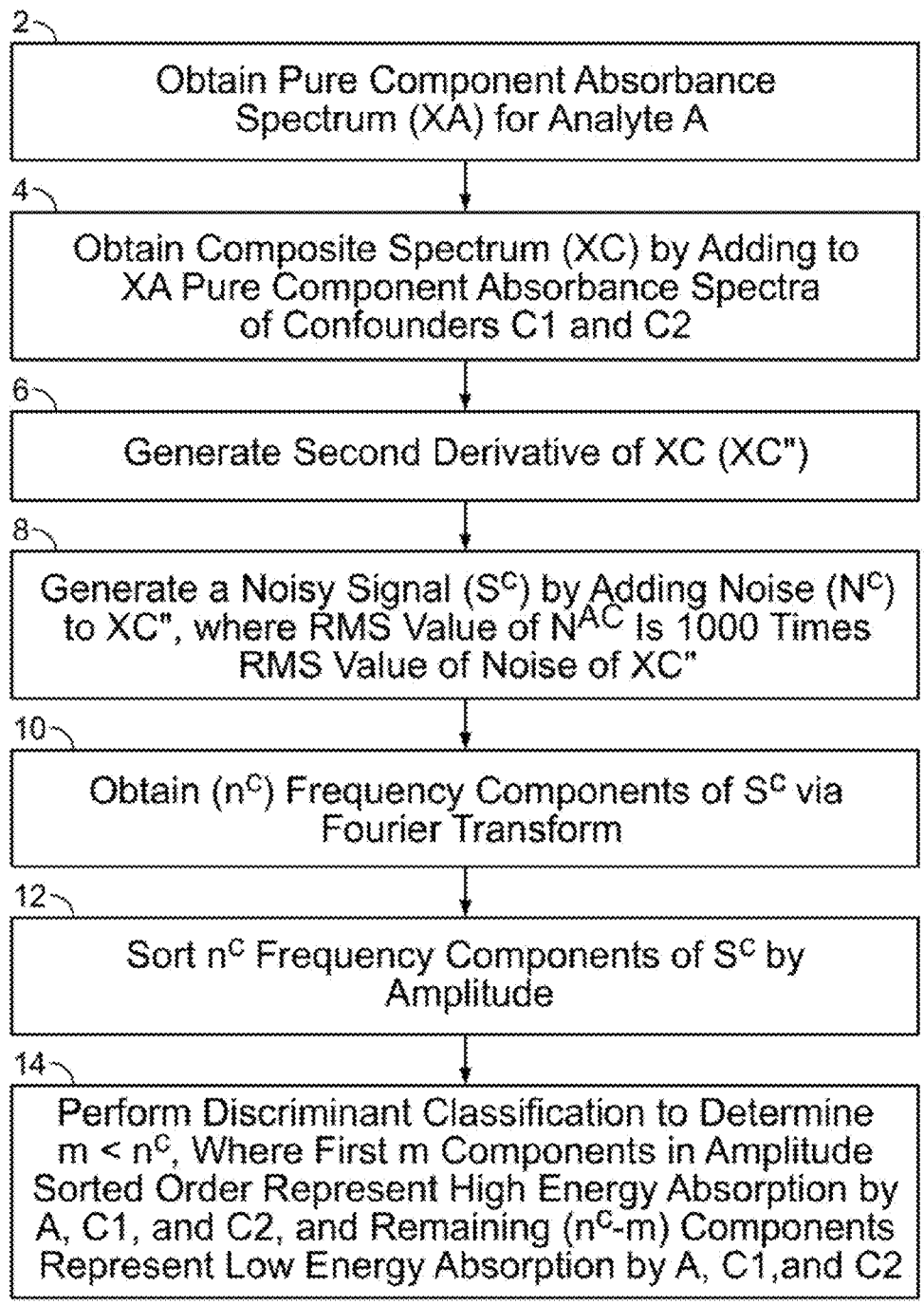
FIG. 40 is a flowchart showing the steps in the determination of the number m of the frequency components of a Zyoton and a carrier kernel, according to one embodiment.

The next m (e.g., 4, 6, etc.,) frequency components are designed as a transition zone to the lower amplitude j frequency components. The discriminant classification technique may be used to determine m, i.e., the number of frequency components in the transition zone of the Zyoton (and the carrier kernel, as well). With reference to FIG. 40, pure component spectra from one or more confounding materials, e.g., urea and collagen if glucose is the analyte of interest, are added in step 4 to the pure component spectrum of the analyte (XA) obtained in step 2, to produce a composite spectrum, denoted XC, in step 4. The second derivative of the composite spectrum XC, denoted XC", is obtained in step 6.

In step 8, XC" is further combined with random white noise $N^C$ (e.g., colored grey noise with correlation time of $10^{-6}$ seconds) having an rms value equal to a multiple (e.g., 100, 1000, 2500, 10,000 times, etc.), the rms value of the signal-to-noise ratio of the second derivative of the composite spectrum, i.e., XC", where all the absorbances of the confounders are normalized to the maximum absorbance of the analyte. In some embodiments, the rms value of $N^C$ is a multiple of the rms value of XC, a first derivative thereof, or third and higher-order derivatives of XC. In some embodiments, the rms value of $N^C$ is a multiple of the rms value of sensor noise, i.e., the rms value of the pure component spectrum of the analyte XA, or a first or higher-order derivative of XA. The number m of the frequency components required to separate, according to the discriminant classification described above, the spectral regions of the second derivative of the composite spectrum, with added noise, where the separated spectral regions correspond to higher and lower absorbance regions of the pure component spectrum of the analyte can be determined in steps 10-14. The discriminant classification in step 14 may include several trials of different candidate values of m. This provides the number of frequency components k+m. The discriminant analysis used to determine the number m of the medium energy components is similar to the discriminant analysis described above that is performed in the determination of the number k of the high-energy components. In finding m, however, the candidate values for the length of the observation vectors for discriminant analysis are set to be of length k+1, k+2, k+3, . . . , k+m frequency components.

Figure 41:
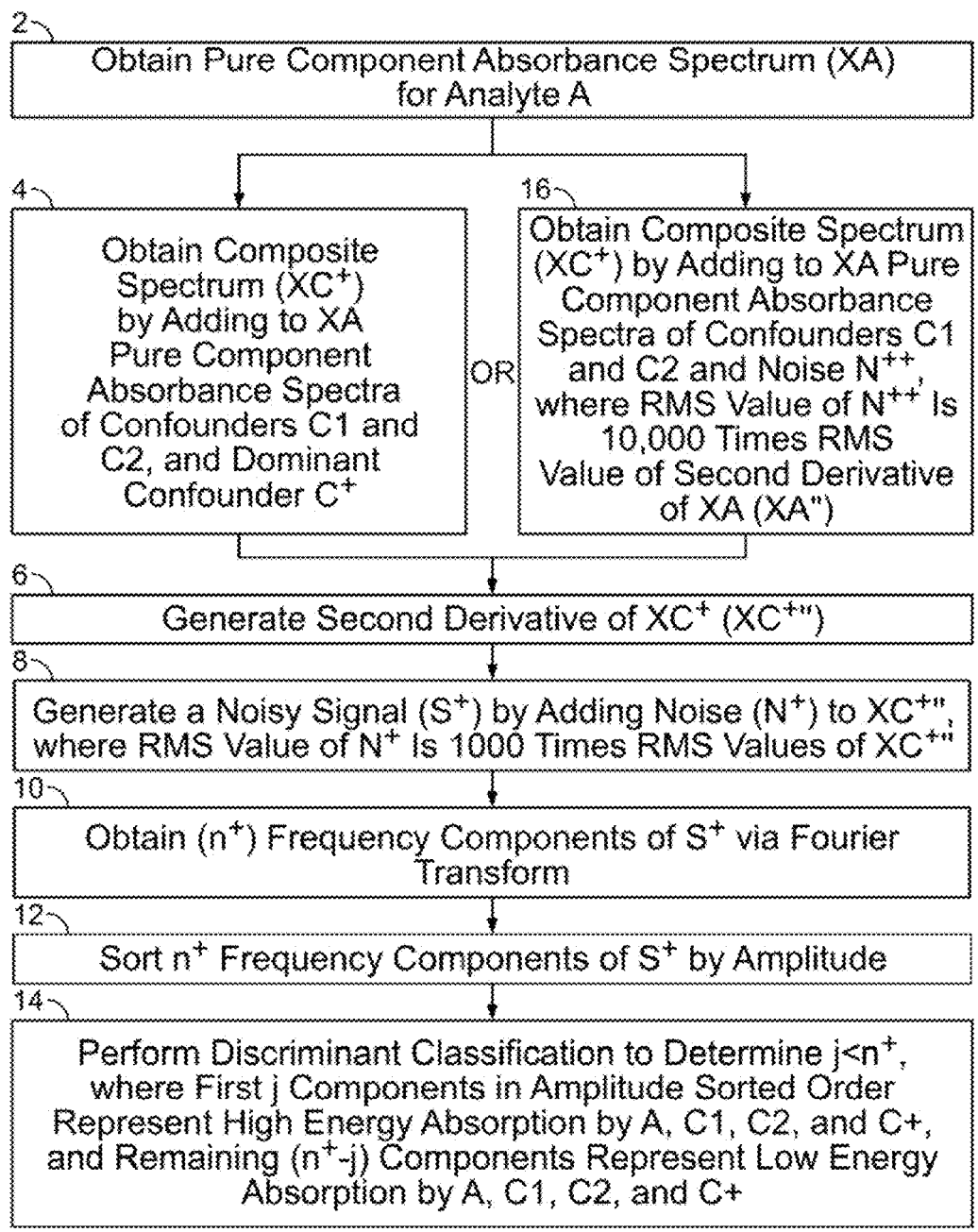
FIG. 41 is a flowchart showing the steps in the determination of the number j of the frequency components of a Zyoton and a carrier kernel, according to one embodiment.

For the determination of j, a dominant confounder may be used in the analysis. For example, if glucose is the analyte of interest, the spectrum of water (generally known to have much higher absorbance than glucose in tissue) can be used to create additional distortion. With reference to FIG. 41, the pure component spectrum of the analyte (i.e., XA), one or more confounders, and the water spectrum (all normalized to the absorbance of water, because the water spectrum dominates the spectrum of glucose) are combined to obtain a composite spectrum or signal, denoted $XC^+$ in steps 2 and 4. In step 10, the second derivative of this composite spectrum, denoted $XC^{+''}$ is mixed with random noise $N^+$ having, e.g., the A-weighting and correlation time of $0^{-6}$ seconds. The noise $N^+$ is constructed such that the rms value of $N^+$ is a multiple of (e.g., 400, 800, 1000, 2000, 7500, 12,000, times, etc.), the rms value of the SNR of the second derivative of the composite spectrum $XC^{+''}$.

In some embodiments, the rms value of $N^+$ is a multiple of the rms value of $XC^+$, a first derivative thereof, or third and higher-order derivatives of $XC^+$. In some embodiments, the rms value of $N^+$ is a multiple of the rms value of XC used to determine m, or the rms value of the pure component spectrum of the analyte XA, or a first or higher-order derivative of XC or XA. Fourier analysis followed by discriminant classification are applied in steps 10-14, as in the determination of the values of k and m, to determine the number j of the low-energy components required to separate the spectral regions of the second derivative with added noise corresponding to regions of higher and lower absorbance of the analyte pure component spectrum, as described above. Including the water spectrum generally increases the range of the frequency components beyond those corresponding to the random noise from scattering. Because of the magnitude of the absorbance of the dominant confounder (water), very small local variations in in its concentration typically manifest as noise in the absorbance that are added to the noise contribution from light scattered by the medium.

In some embodiments, instead of adding a dominant confounder, random white noise denoted $N^{++}$ (e.g., grey colored random noise with, e.g., A-weighting and correlation time of $10^{-6}$ seconds) with a magnitude that is a multiple (e.g., 20, 50, 100, 125, times etc.) the noise $N^+$ that was added in step 8 is added in step 16 and, optionally, pure component spectra of one or more confounders are also added to the pure component spectrum of the analyte XA. Thus, the rms value of the noise $N^{++}$ can be 100,000 times the rms value of the SNR of the second derivative of the analyte pure component spectrum without confounders, i.e., the signal XA". In some embodiments, the rms value of $N^{++}$ is a multiple of the rms value of XA, a first derivative thereof, or third and higher-order derivatives of XA. In some embodiments, the rms value of $N^{++}$ is a multiple of the rms value of $XC^+$, or XC used to determine m, or a first or higher-order derivative of $XC^+$ or XC. Instead of adding a dominant confounder spectrum, such as water spectrum, such noise may be added to increase the frequency range to include the scatter-related frequency components.

The discriminant analysis used to determine the number j of the low energy components is similar to the discriminant analysis described above that is performed in the determination of the number k of the high-energy components and the number m of the medium energy components. In finding j, however, the candidate values for the length of the observation vectors used for the discriminant analysis are set to be of length k+m+1, k+m+2, . . . , k+m+j frequency components.

Figure 38:
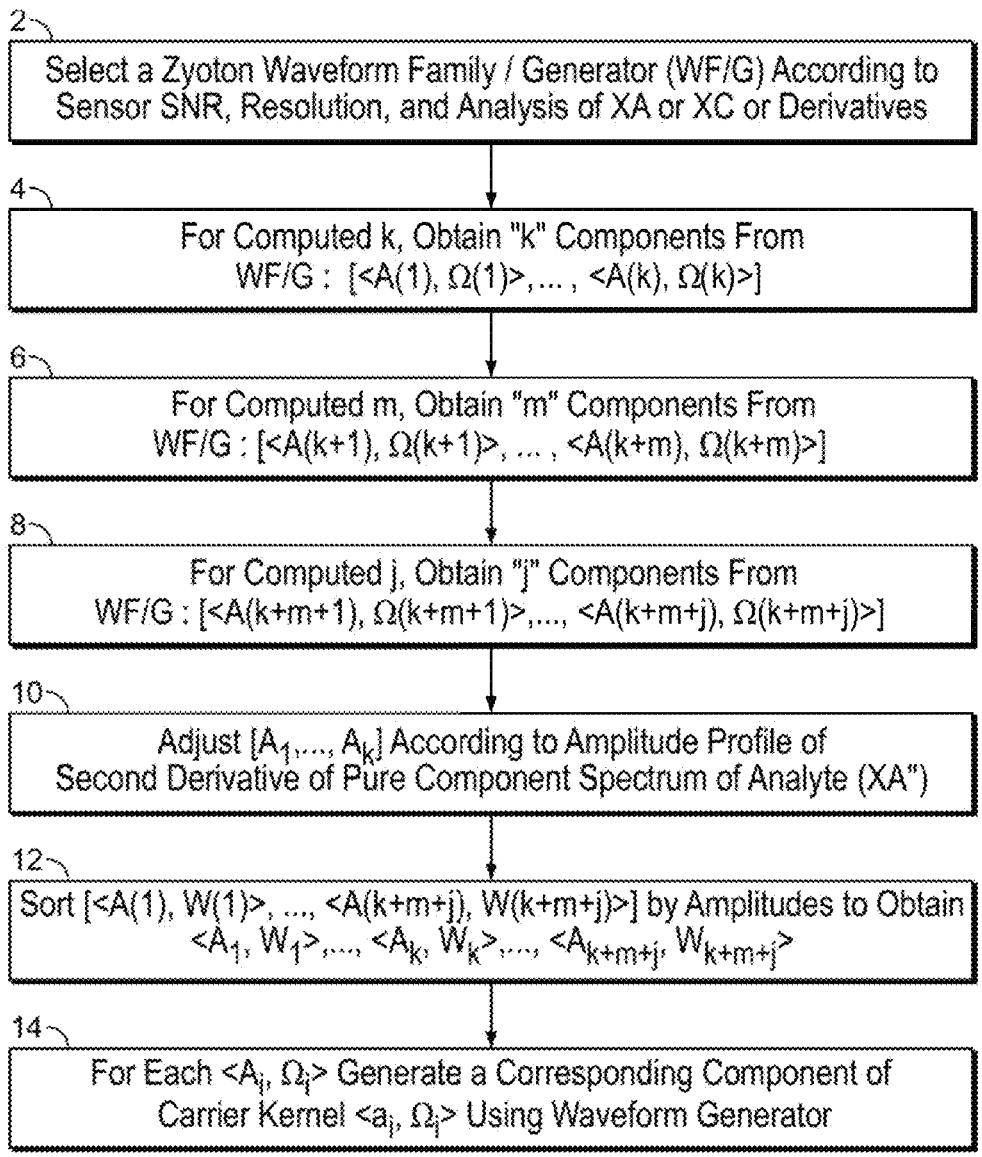
FIG. 38 is a flowchart showing the steps in the generation of a Zyoton and a carrier kernel waveform.

After the values of the number of Zyoton and carrier kernel components in the high, medium, and low energy regions, i.e., k, m, and j, respectively, are determined, the actual components of the waveforms are selected. With reference to FIG. 38, the bandwidth and/or a morphological profile of the noisy signal $S^+$ (generated in step 8 of FIG. 41) is computed in step 2 (of FIG. 38). A Zyoton waveform family and/or a generator is selected in step 2 according to the morphological properties of: (a) the pure component spectrum of the analyte, optionally combined with the pure component spectrum/spectra of one or more confounders, or (b) the first or higher-order derivative of the pure component or combined spectrum, optionally with added noise. The following examples illustrate the selection of a waveform family and/or generator.

If the spectral bandwidth of the signal used in step 2 is high, e.g., greater than 1 kHz, 100 kHz, 1 MHz, 100 MHz, etc., high spectral bandwidth Zyotons can be synthesized using waveform families such as solitons; vortex-solitons; wavelets; or multi-color soliton and/or, optionally, using waveform generator functions such as harmonic oscillators or chaotic attractors.

If the spectral envelope of the signal used in step 2 is symmetrical, Zyotons with symmetrical spectral envelop can be synthesized using waveform families such as solitons; wavelets; ridgelets; or multi-color solitons and/or, optionally, using generator functions such as cyclostationary series or Lyapunov functions. On the other hand, if the spectral envelope of the signal used in step 2 is monotonic, Zyotons with a monotonic spectral envelop can be synthesized using waveform families such as solitons; autosolitons; similaritons; wavelets; curvelets; ridgelets; bions; or elliptic waves and/or optionally, using generator functions such as Frobenius manifolds; harmonic oscillators; Hermite polynomials; polynomial sequences; asymptotic Hankel functions; or Neumann spherical functions. If the spectral envelope of the signal used in step 2 is random, Zyotons with a random spectral envelop can be synthesized using waveform families such as solitons; multi-color solitons; Ricci solitons; or nonautonomous similinear wave equations and/or, optionally, using generator functions such as random number generators.

If the peak spectral energy of the signal used in step 2 is greater than a selected threshold, Zyotons with high peak energy can be synthesized using waveform families such as solitons; autosolitons; self-compressing similaritons; vortex-solitons; multi-color solitons; and/or, optionally, using waveform generators such as Gamma functions; Riemann Zeta functions; polynomial sequences ; spatial random fields; spherical harmonics; chaotic attractors; exponential attractors; or evolution equation of exponential attractors.

If the spectrum of the signal used in step 2 has linearly distributed amplitudes, Zyotons with a linear amplitude distribution can be synthesized using waveform families such as solitons; autosolitons; similaritons; wavelets; curvelets; ridgelets; and/or, optionally, using waveform generators such as Gamma functions; Riemann Zeta functions; polynomial sequences; or spherical harmonics. If the spectrum of the signal used in step 2 has non-linearly distributed amplitudes, however, e.g., exponentially distributed amplitudes, Zyotons with an exponential amplitude distribution can be synthesized using waveform families such solitons; vortex-solitons; multi-color solitons; and/or, optionally, using waveform generators such as Fractals; poweroid coupled with sinusoidal functions; chaotic attractors; exponential attractors; evolution equation for polynomial nonlinear reaction-diffusion equation; evolution equation for Kuramoto-Savashinsky equation; or evolution equation of exponential attractors.

In step 4, "k" high energy components are obtained from the selected Zyoton family/generator. This process is repeated in steps 6, 8, respectively, to obtain the m transition components and the j low energy components. Each component (e.g., the i-th component) can be represented in terms of its frequency Ω(i) and frequency-domain amplitude A(i).

In some embodiments, a base Zyoton obtained from a Zyoton family/generator may be represented in the time domain, as described above, as:

$$Z_N(xt)=2\partial_x Tr\, B_x(1+B)^{-1} \quad (12)$$

By applying the Fourier transform to this time-domain representation, the frequency components thereof can be determined. These frequency components of the base Zyoton, each represented as an amplitude-frequency pair $<A^*_i, \Omega^*_i>$, sorted by the amplitude, can be expressed in terms of k, m, and j as shown in Table 6:

TABLE 6

| | | | | | | | | | | |
|---|---|---|---|---|---|---|---|---|---|---|
| Amplitudes | $A_1^*$ | $A_2^*$ | . . . | $A^*_{\mathbb{k}}$ | $A^*_{\mathbb{k}+1}$ | . . . | $A^*_{\mathbb{k}+\mathbb{m}}$ | $A^*_{\mathbb{k}+\mathbb{m}+1}$ | . . . | $A^*_{\mathbb{k}+\mathbb{m}+\mathbb{j}}$ |
| Frequencies | $\Omega_1^*$ | $\Omega_2^*$ | . . . | $\Omega^*_{\mathbb{k}}$ | $\Omega^*_{\mathbb{k}+1}$ | . . . | $\Omega^*_{\mathbb{k}+\mathbb{m}}$ | $\Omega^*_{\mathbb{k}+\mathbb{m}+1}$ | . . . | $\Omega^*_{\mathbb{k}+\mathbb{m}+\mathbb{j}}$ |

The amplitude-sorted components of the base Zyoton can be grouped into high, medium, and low-energy components (i.e., k, m, and j components) according to the amplitudes thereof. The boundaries between the high-energy and the medium-energy components and between the medium-energy and low-energy components are not absolute, and can change, depending on the embodiment. Thus, the designations of one or more frequency components to a particular group can change.

Using the value of k, computed, e.g., as described with reference to FIG. 39, the first k components of the base Zyoton, i.e., the components $\{<A^*_1, \Omega^*_1>, \ldots <A^*_k, \Omega^*_k>\}$ may be selected to be included as the high-energy k components in the Zyoton to be synthesized. Using the value of m, computed, e.g., as described with reference to FIG. 40, the first m components of the base Zyoton from the medium-energy group thereof, i.e., the components $\{<A^*_{\mathbb{k}+1}, \Omega^*_{\mathbb{k}+1}>, \ldots <A^*_{\mathbb{k}+m}, \Omega^*_{\mathbb{k}+m}>\}$ may be selected to be included as the medium-energy m components in the Zyoton to be synthesized. Similarly, using the value of j, computed, e.g., as described with reference to FIG. 41, the first j components of the base Zyoton from the low-energy group thereof, i.e., the components $\{<A^*_{\mathbb{k}+\mathbb{m}+1}, \Omega^*_{\mathbb{k}+\mathbb{m}+1}>, \ldots <A^*_{\mathbb{k}+\mathbb{m}+j}, \Omega^*_{\mathbb{k}+\mathbb{m}+j}>\}$ may be selected to be included as the medium-energy m components in the Zyoton to be synthesized. In general, $\mathbb{k}>k$; $\mathbb{m}>m$; and $\mathbb{j}>j$.

In some embodiments, the amplitudes A(i) of the Zyoton thus formed, require no further adjustment. In other embodiments, however, the amplitudes of these components, initially set to be $A^*_i$ according to the selected components of the base Zyoton, are adjusted in step 10. These adjustments may be performed according to the ratio of the average, median, minimum, or maximum magnitude of the second derivative in the regions that correspond to high and low analyte absorption wavelength regions. To this end, the pure component spectrum XA of the analyte of interest is partitioned into a number of wavelength regions, where each wavelength region corresponds to a particular range of wavelengths $[\lambda_1, \lambda_2]$ of the spectrum XA. The wavelength regions are thus similar to features but, in general, features correspond to wavelength regions of the spectral signals obtained from a medium to be analyzed. The wavelength regions described herein are generally derived from pure component spectra.

Some of these wavelength regions, where the absorption of energy by the analyte of interest is high are designated as analyte wavelength regions. Some wavelength regions, where the absorption of energy by the analyte is low, are designated as non-analyte wavelength regions. The terms high absorption of energy and low absorption of energy should be understood in the context of analysis, as described above. One or more of the several analyte wavelength regions are selected to interact (via conditioning thereof) with the Zyoton and the carrier kernel to be synthesized. The number of the selected analyte wavelength regions is n. Each of these n selected analyte wavelength regions is denoted Fi, and is paired with a corresponding non-analyte wavelength region denoted NFi, forming n wavelength region pairs FP.

For each wavelength-region pair FPi, two regions of the second derivative of XA, i.e., XA", are identified, where the first region of the second derivative corresponds to the wavelength boundaries of Fi, i.e., $[\lambda_{1i}, \lambda_{2i}]$, and the second region of the second derivative corresponds to the wavelength boundaries of NFi. A ratio Ri of the average, median, minimum, or maximum magnitude of the first region of the second derivate to the average, median, minimum, or maximum magnitude of the second region of the second derivative is then computed. These steps are performed for each of the n wavelength-region pairs, to obtain n ratios. The maximum and minimum of these ratios, denoted $R^{max}$ and $R^{min}$ are then computed.

The amplitudes of the k Zyoton components, i.e., the high-energy or analyte-information representing components, are then selected such that the pair-wise ratios thereof are distributed in the range $[R^{max}, R^{min}]$. In particular, if the amplitudes of the k Zyoton components are [A1, A2, . . . , Ak], A1 is designated a specified value, e.g., (1,000; 1,600; 4,000; 10,000; 50,000; 125,000, etc.). In some embodiments, the value of the amplitude $A^*_1$ of the base Zyoton may be retained. A2 is then selected such that $A1/A2=R^{max}$. An intermediate ratio value R2 less than $R^{max}$ but greater than $R^{min}$ is then selected, and A3 is selected such as A2/A3=R2. Another intermediate ratio value R3 less than R2 but greater than $R^{min}$ is then selected, and A4 is selected such as A3/A4=R3. The amplitudes of the k Zyoton components are thus selected such that, finally, the ratio A(k−1)/Ak=$R^{min}$. In some embodiments, the ratios are distributed in the ascending order, in the range $[R^{min}, R^{max}]$. In various embodiments, the distribution of ratios, i.e., the selection of the intermediate ratios R2, R3, etc., can linear, quadratic, or exponential, for example.

In various embodiments, the amplitudes of the j frequency components, i.e., the non-analyte-information representing components, may be selected randomly as a fraction (e.g., in a range from about 1/100 to 1/1000$^{th}$) of the amplitude of any of the k Zyoton components. In some embodiments, the amplitudes of the j components can be a percentage such as 2%, 5%, 10%, 50% of the amplitudes of the k components. The amplitudes of the m transition component can be a multiple (e.g., 2, 3, 5, 10, etc.) of the amplitude of any of the j Zyoton components. The (k+m+j) frequency components may then be sorted by amplitude in step 12. In the time domain, a Zyoton thus constructed is a traveling waveform that can be perturbed if collided with another waveform such as an unmodulated carrier kernel or a conditioned feature. The perturbation generally results in a change in the morphological profile of the Zyoton, e.g., a change in dispersion velocity, divergence, etc. Without a collision with another waveform, however, the Zyoton can propagate substantially unperturbed, i.e., without a substantial change in dispersion velocity, divergence, etc., at least over a preselected distance, such as the length of a collision grid (e.g., 2000 points; 10,000 points; 20,000 points; 100;000 points; or more) in the time domain. Substantial in this context can be a more than 0.001%, 0.005%, 0.02%, 0.1%, 1%, 5%, 10%, 20%, etc. change in a parameter of interest such as dispersion velocity over the distance of propagation.

The frequency components of the carrier kernel may be selected to correspond to those of the Zyotons in step 14. In general, the amplitudes of the k, m, and j components of the carrier kernel are selected such that the spectral energy of the carrier kernel is only a fraction (e.g., 1/100, 1/1,000, etc.) of the spectral energy of the Zyoton. In some embodiments, the amplitudes of the frequency components of a Zyoton are determined as described above, and then the amplitudes of the corresponding frequency components of the carrier kernel are set using a constant scaling factor such as 0.25, 0.2, 0.1, 0.08, 0.03, 0.01, etc.

In some embodiments, the scaling factor is selected such that the Zyoton and the unmodulated carrier kernel are co-dependent. This can be achieved by applying a Kappa test to these two waveforms. In particular, if a magnitude of a difference between a scaled velocity of the Zyoton and the velocity of the carrier kernel is not greater than the value of a Kappa parameter $\kappa_{SYN}$, used during synthesis, the Zyoton and the carrier kernel are likely co-dependent. The co-dependence typically cannot be ascertained during waveform synthesis because a conditioned feature obtained by modulating the synthesized carrier kernel with one or more features, and used in a collision operation, typically has a different energy and velocity than that of the carrier kernel.

In various embodiments the parameter $\kappa^{SYN}$ is similar to the parameter $\kappa_{DV2}$ discussed above. In performing the above-described Kappa test, the velocity of the unmodulated carrier kernel may be scaled during the comparison, instead of or in addition to scaling the velocity of the Zyoton. The Kappa test using the parameter $\kappa^{SYN}$ can be performed in the time domain or in the frequency domain. If this Kappa test fails, the frequency-domain amplitudes of the frequency components of the Zyoton, the carrier kernel, or both, may be scaled using a scaling coefficient $\alpha_{SYN}$, which is similar to the normalized scaling coefficient $\alpha_C$ discussed above, such that the Kappa test would succeed using the adjusted Zyoton and/or the carrier kernel.

An example of some of the frequencies and amplitudes in a carrier kernel for the k, m, and j components is shown in Table 7 below.

TABLE 7

| Region | Frequency (KHz) | Frequency Component Amplitude (dBm/Hz) |
|---|---|---|
| K | 218.7 | 625.4878 |
|   | 277.4 | 260.5532 |
|   | 317.2 | 233.3075 |
|   | 123.4 | 233.3075 |
|   | 87.16 | 194.6868 |
|   | 412.9 | 194.6868 |
| M | 497.3 | 38.5267 |
|   | 511.1 | 38.5267 |
|   | 732.42 | 35.9625 |
|   | 614.9 | 35.9625 |
|   | 507.2 | 33.6208 |
|   | 843.1 | 33.6208 |
|   | 328.6 | 25.5264 |
| J | 1832.4 | 6.3816 |
|   | 7322.1 | 5.0936 |
|   | 5376.2 | 5.0936 |
|   | 11236.5 | 4.0355 |
|   | 9032.5 | 4.0355 |
|   | 18043.1 | 3.8207 |
|   | 7344.5 | 3.8207 |
|   | 11264.4 | 2.5359 |
|   | 14090.2 | 2.5359 |
|   | 9433.7 | 1.2619 |
|   | . . . | . . . |

In the table above, the first six frequency components are the k components, the next seven components are the m components, and the rest are a subset of the j frequency components. To design a carrier kernel, a desired amplitude profile for the k, m, and j components is set. The example relationship among the amplitudes described here, assigned to their respective frequency components, was established for an embodiment of glucose measurement, such that all the frequency components interact and mix with the selected Zyoton. A function generator and/or a waveform synthesizer can generate the carrier kernel from the frequency components selected as described above. The carrier kernel is then modulated using the feature waveform to obtain a corresponding conditioned feature. In some embodiments, a time-domain representation of the carrier kernel is discretized into a selected number (e.g., 2048) of points.

Figure 32:
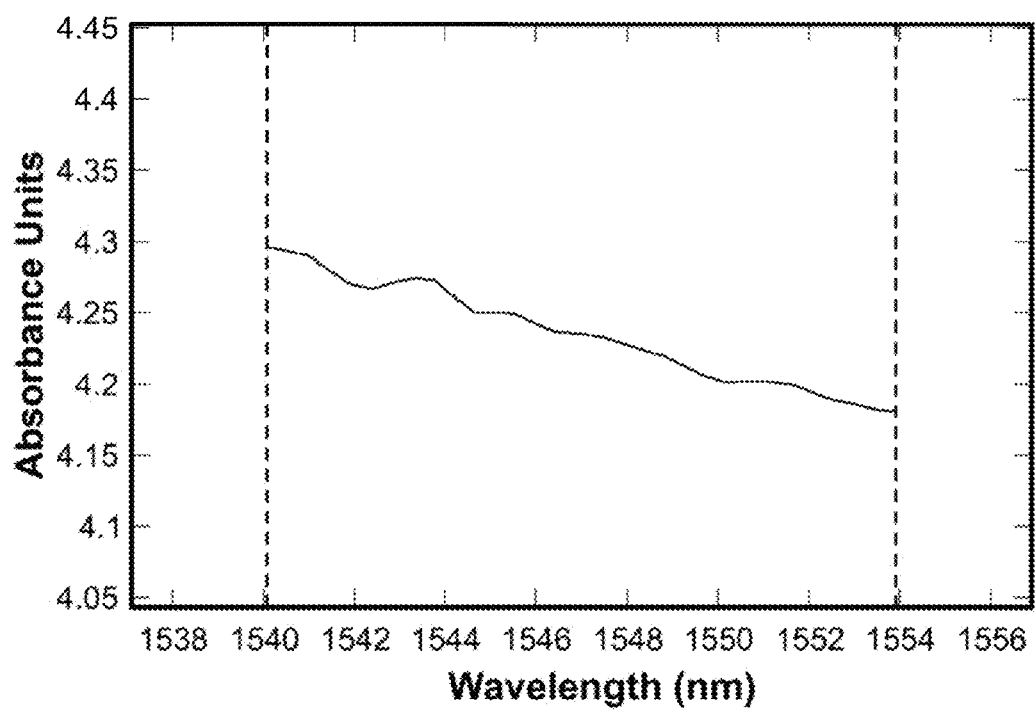
FIG. 32 provides an example of the absorbance spectrum of a single feature from a single illumination of tissue.
Figure 42:
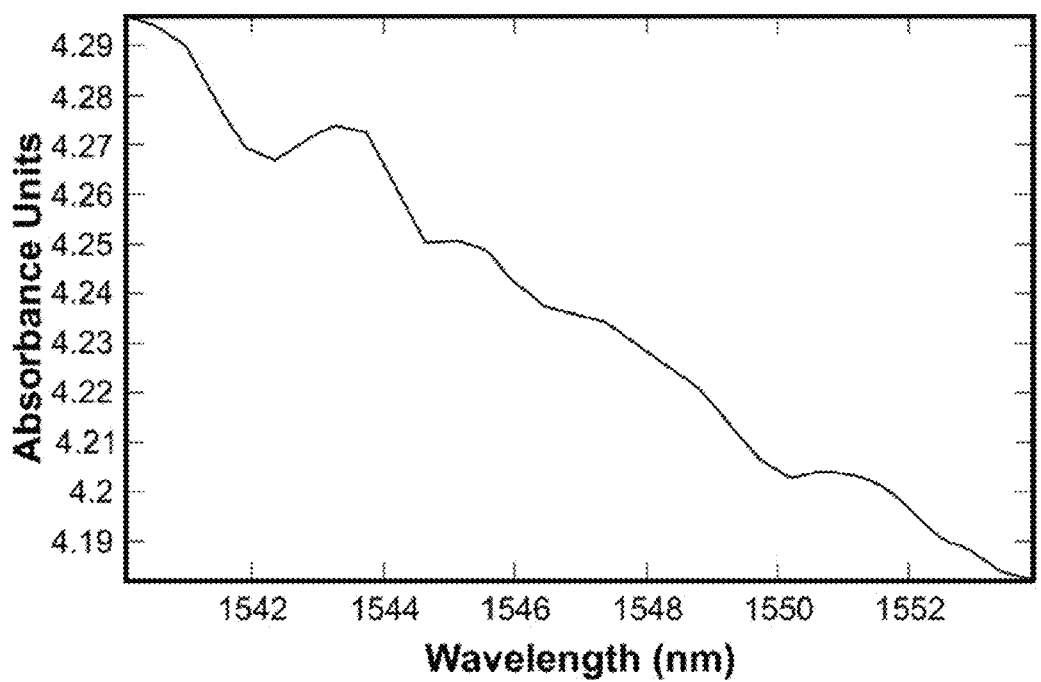
FIG. 42 displays the absorbance spectrum of the single feature shown in FIG. 32, interpolated to 2,048 points.

A feature as extracted from an absorbance spectrum may be initially represented as a 32 point waveform. FIG. 32 shows an absorbance profile of a single feature, extracted from a reflectance intensity spectrum in the region between 6493 $cm^{-1}$ (1540 nm) and 6433 $cm^{-1}$ (1554 nm). The initial feature length here, as extracted from an absorbance spectrum, is 32 data points (60 $cm^{-1}$) for a resolution of the spectrum of 2 $cm^{-1}$ (including the two endpoints of the spectral range). In various embodiments, that feature waveform is up-sampled to the length of the carrier kernel (e.g., 2048) using e.g., spline interpolation to match the length of the two waveforms. FIG. 42 shows the feature absorbance of FIG. 32, up-sampled by interpolation to 2048 data points from the initial 32-data point spectral feature. This up-sampling may be done to match the length of the carrier kernel and Zyoton waveforms, and is followed by the optional precursor frequency modulation described above. Features can be obtained from reflectance/intensity signals and then such features can be transformed into absorbance-representing features. Alternatively, as described above, the reflectance/intensity signal can be transformed into an absorbance signal and the features can be obtained therefrom.

Figure 43:
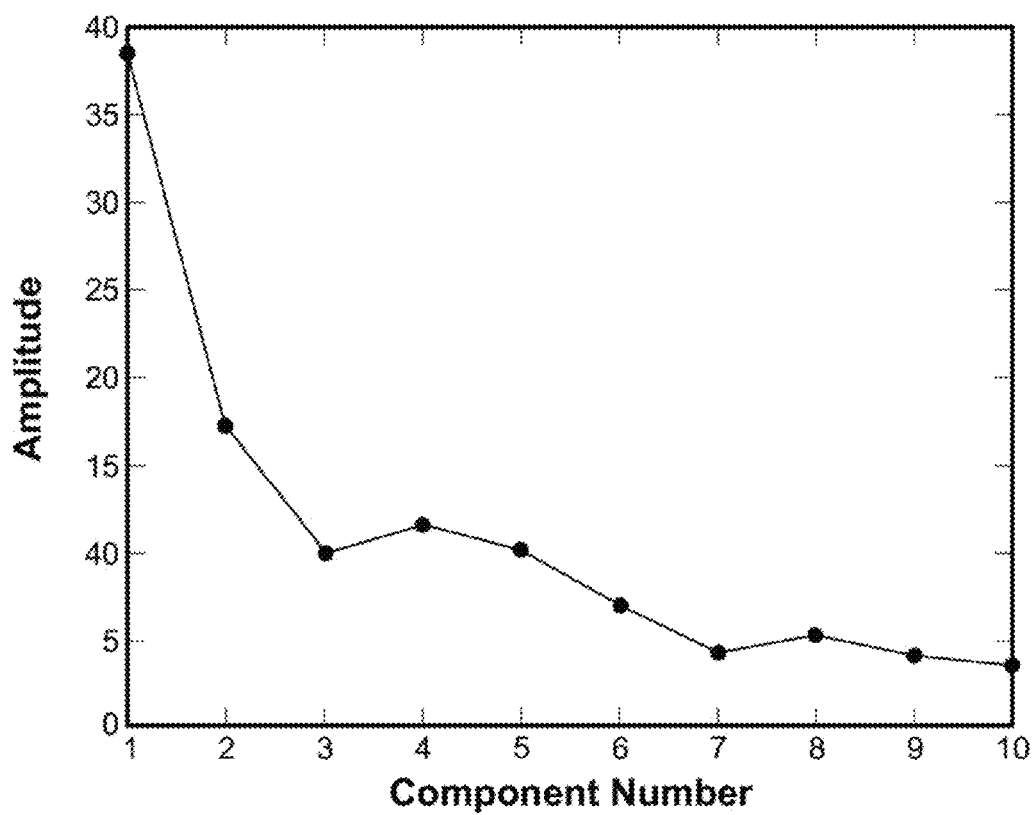
FIG. 43 provides an example of the first 10 frequency components associated with the interpolated feature shown in FIG. 42.

A Fourier transform is then applied to the up-sampled and optionally modulated feature (also called a feature vector) to obtain a Fourier transformed feature. FIG. 43 shows an example of the first 10 frequency components associated with the up-sampled feature shown in FIG. 42. A Fourier transform of the carrier kernel is also generated to obtain a Fourier transformed carrier kernel, which includes the k, m, and j frequency components, as described above. In some embodiments, the Fourier transformed feature and carrier kernel are convolved to obtain a Fourier transformed conditioned feature waveform. In some embodiments, the carrier kernel is frequency and/or phase modulated by the original or up-sampled feature, to obtain the conditioned feature. This modulation can be performed in the time (wavelength) domain or in the frequency domain. If the modulation is performed in the frequency domain, a time-domain representation of the conditioned feature waveform can be generated using the inverse Fourier transform of the frequency-domain representation of the conditioned feature, e.g., the result of a convolution of the Fourier transformed carrier kernel and the Fourier transformed up-sampled feature.

In various embodiments, the co-dependency between a Zyoton and a conditioned feature to be collided therewith is achieved by ensuring that: (i) an absolute difference between their respective dispersion velocities is less than a specified threshold $\kappa_{DV2}$, and (ii) divergence of the envelopes of a selected number of sidebands of the modified Zyoton created as a result of a collision is less than another specified threshold τ. As described above, the first condition can be tested prior to a collision between the original Zyoton and the conditioned feature, using the constraint variable $\kappa_{DV2}$. Additionally, or in the alternative, the first condition may be tested post collision, between the original Zyoton and a modified Zyoton using the constrain variable $\kappa_{DV3}$, or between the original Zyoton and a renormalized Zyoton, using the variable $\kappa_{DV1}$. It should be noted that while $\kappa_{DV1}$, $\kappa_{DV2}$, $\kappa_{DV3}$, and τ may optionally take on different values, they all serve to enforce the co-dependency conditions.

The first type of constraints, $\kappa_{DV1}$, $\kappa_{DV2}$, and $\kappa_{DV3}$, are related to the dispersion velocity, which can be represented in the time domain as the amplitudes of the selected sideband peaks of the time-domain representation of the waveforms considered, as discussed above. In the frequency domain, the dispersion velocity can be represented by the amplitudes of the first k frequency components or, as described above, by $(\|A'_k\|-\|A_k\|)$. The second type of constraint, τ, is related to the divergence of the sideband envelopes which may be caused by the introduction of new m and/or j frequency components in the post-collision modified Zyoton—which can result in a subtle change in the morphology (e.g., the overall shape) of the modified Zyoton.

In general, the dispersion velocity can be described as the velocity with which the narrow-band peak envelope of a Zyoton (e.g., the strongest peak of the underlying soliton kernel as shown in FIG. 12A) propagates in a medium over time, ignoring higher order chromatic dispersion and non-linear effects such as those arising from the propagation of lower amplitude pulses (or higher frequency components) in the Zyoton. Chromatic dispersion of the Zyoton generally results from the introduction of new m and/or j frequency components and the nonlinear effects from changes in the amplitudes of the m and/or j frequency components.

Energies associated with peaks at these new frequencies can distort the shape of the waveform. The computation of dispersion velocity of solitons, which can be used to analyze Zyotons, is discussed in Haus and Ippen, "Group velocity of solitons," Optical Letters 26 (21), 1654 (2001), the entirety of which is incorporated herein by reference.

Changes in the post-collision dispersion velocity, i.e., the dispersion velocity (or the velocity) of a modified Zyoton can be constrained by the asymmetric energy relationship between the conditioned feature waveform and the Zyoton waveform, or between the renormalized Zyoton waveform from the previous iteration and the Zyoton, as described above, where the energy of the Zyoton may be three or more orders of magnitude more than that of the conditioned feature and/or the renormalized Zyoton. In various embodiments, the conditioned feature waveform and the renormalized Zyoton can be scaled (as described below in the collision equation) to a small fraction of the total spectral energy of the selected Zyoton, in order to achieve the desired energy balance.

Figure 14A:
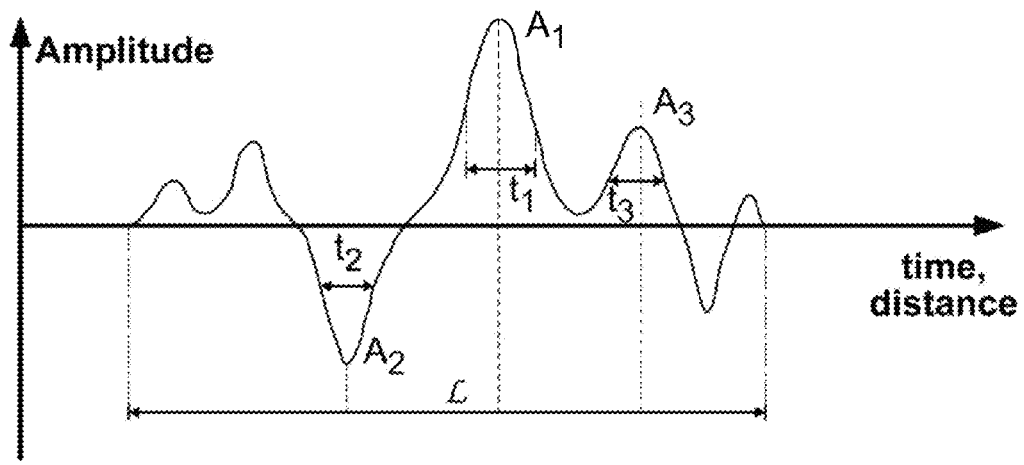
FIGS. 14A-14B shows the dispersion of a Zyoton before and after a collision.
Figure 14B:
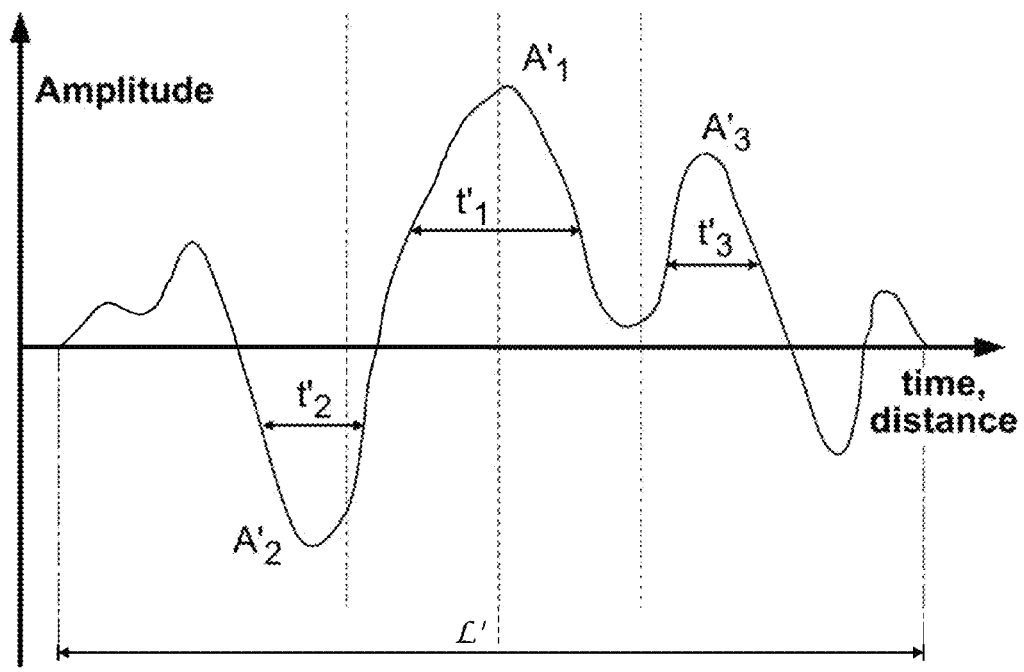

As described above, the introduction of additional m and/or j frequency components can change the shape of the modified Zyoton relative to the shape of the original Zyoton. This shape divergence can be described as a change in the width of the post-collision Zyoton waveform envelope. FIGS. 14A-14B are time-domain representations of a Zyoton and a modified Zyoton resulting from a collision of the Zyoton and a conditioned feature. FIG. 14A shows that the time-domain length of the original Zyoton is $\mathcal{L}$ and FIG. 14B shows the time-domain length of the modified Zyoton is $\mathcal{L}_1$. The post-collision, pre-renormalization time-domain length of the modified Zyoton can be stated as $\mathcal{L}_1 = \mathcal{L} + \Delta l_1$, where $\Delta l_1$ is the width of divergence after the first collision. In order for the collision to be nearly elastic, $\Delta l_1$ is required to be less than a specified threshold τ. An example of a numerical value of τ is $\mathcal{L}/100$.

The renormalization can change the width of the modified Zyoton such that the width of the renormalized Zyoton is reset to $\mathcal{L}$. Such renormalization can be achieved via truncation and/or re-sampling in the time domain. If the modified Zyoton is represented in the frequency domain, re-sampling can be implemented by performing an inverse Fourier transform of the frequency components of the modified Zyoton, followed by truncation and/or down-sampling, to adjust the width of the modified Zyoton. Then a Fourier transform followed by an amplitude sort of the frequency components can establish the amplitudes that may be used to obtain the renormalized Zyoton. The co-dependency condition requires that the amplitude vectors described above and/or the corresponding frequency components be selected during the synthesis of the Zyoton and the carrier kernel such that conditions described above in terms of the thresholds $\kappa_{DV1}$, $\kappa_{DV2}$, $\kappa_{DV3}$ and $\tau$ are satisfied.

Formation of Conditioned Features

Figure 44A:
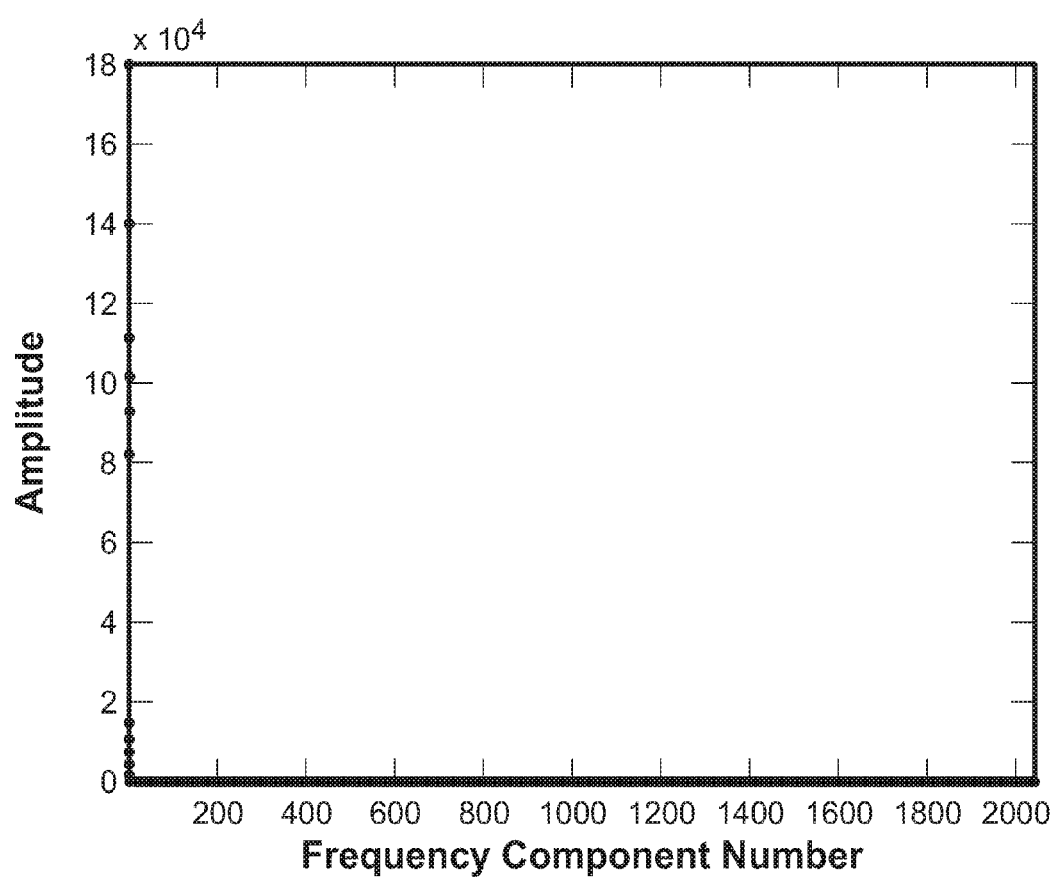
FIGS. 44A and 44B respectively show the distribution and detailed profile of frequency components used in the construction of a carrier kernel.
Figure 44B:
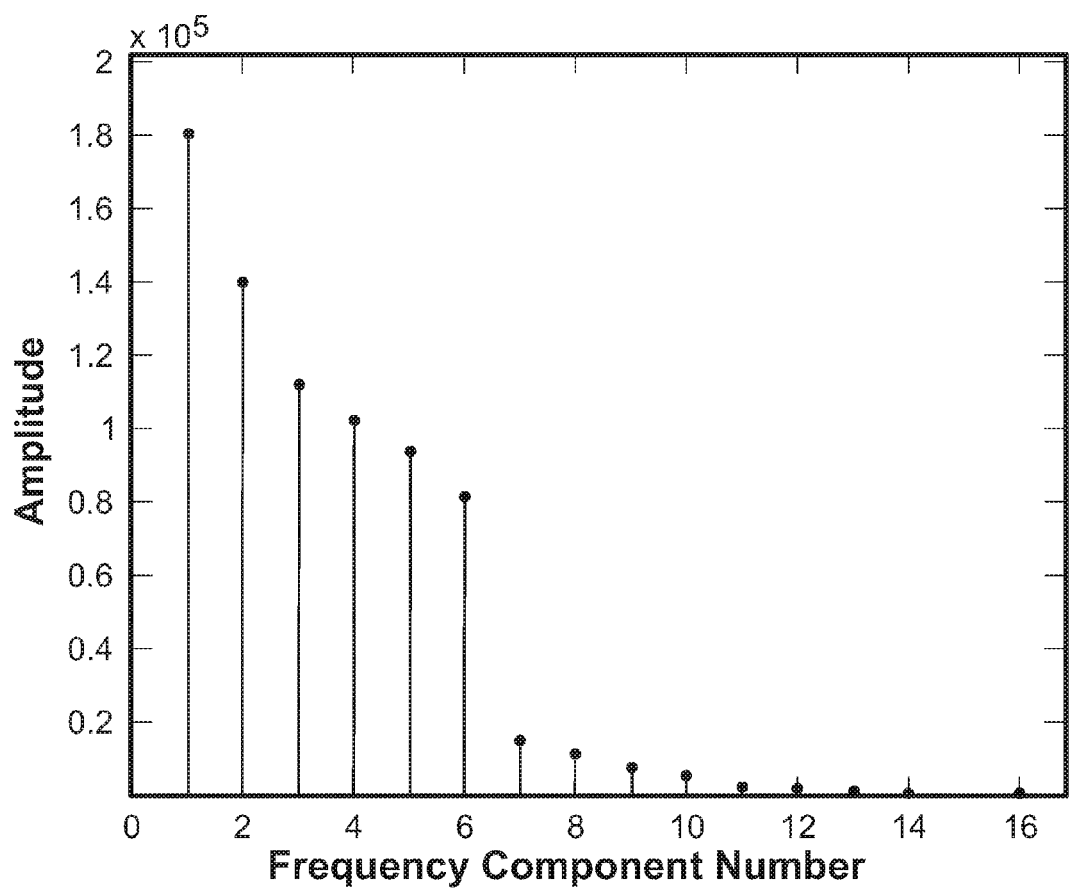
Figure 45A:
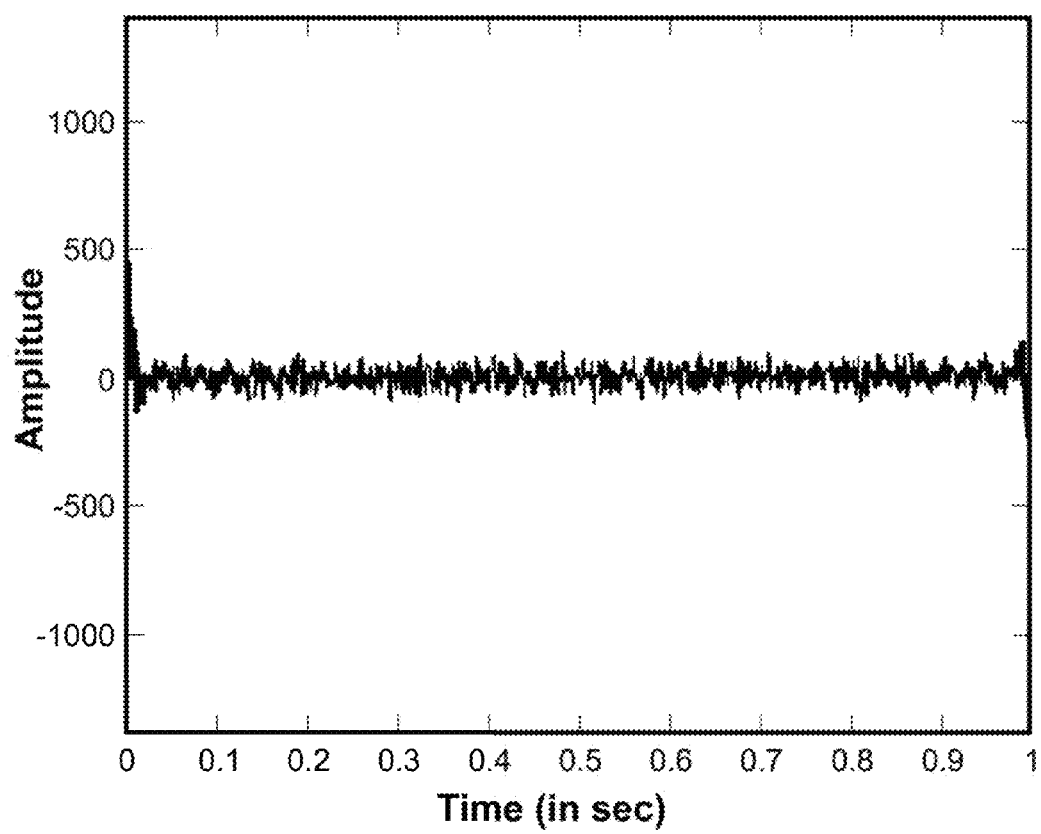
FIGS. 45A-45D illustrate the distribution of carrier kernel frequencies and their frequency components in the time and frequency domains.
Figure 45B:
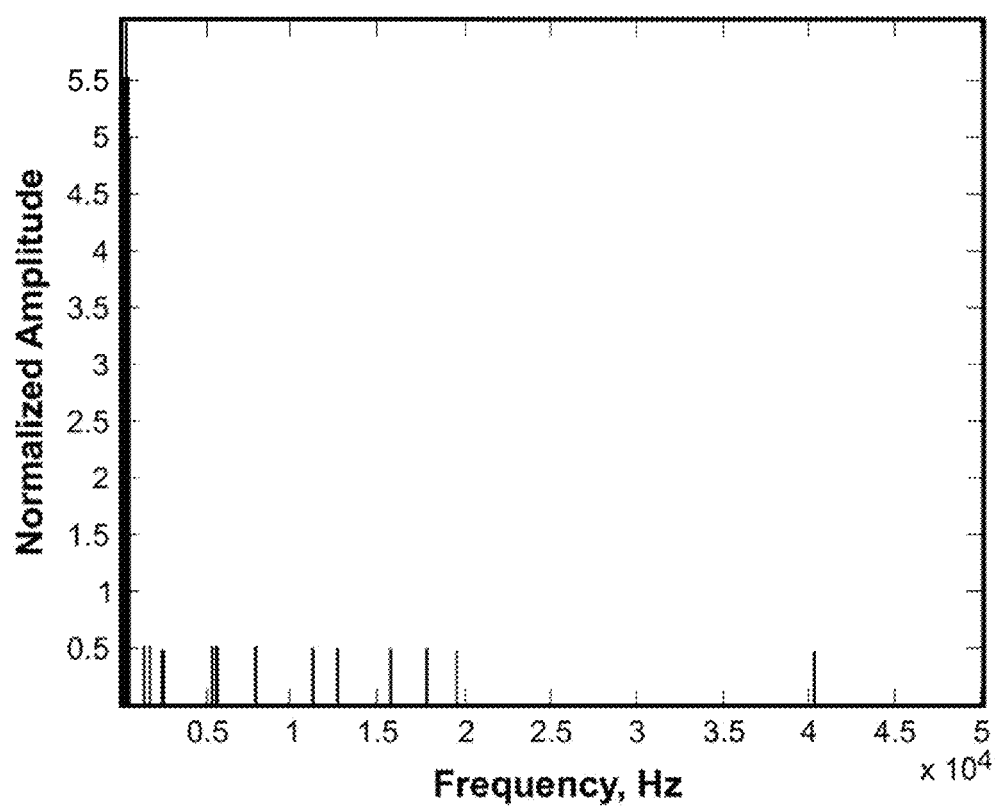
Figure 45C:
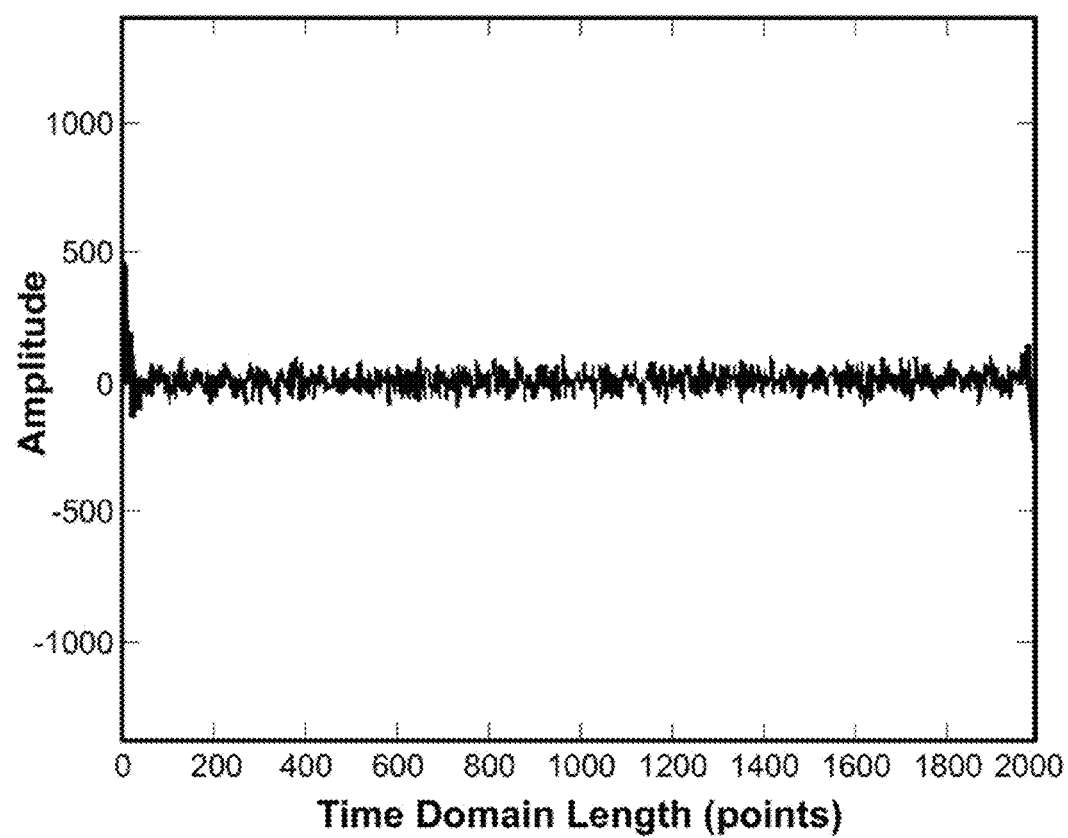
Figure 45D:
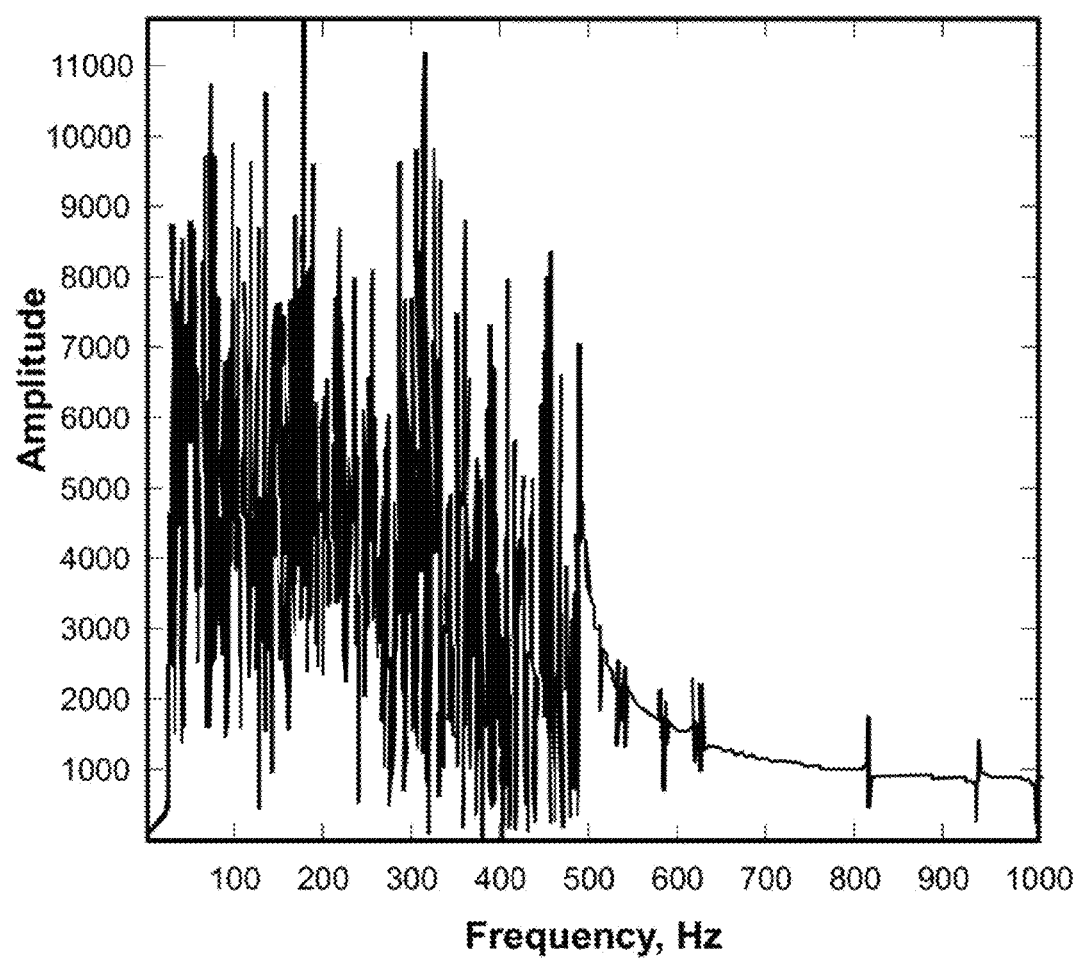

The process for ensuring co-dependency is related to the process of synthesizing a carrier kernel, as described above, and to the process of generating one or more conditioned features. FIGS. 44A and 44B respectively show the distribution and a detailed profile of base frequencies used in the synthesis of one carrier kernel. FIG. 44A shows the plot of amplitudes of base sinusoidal frequencies as a function of a frequency index, that can be used to generate the carrier kernel. FIG. 44B illustrates the distribution of the first 16 frequency components as an example. A frequency index is created by sorting the frequency components on the basis of the amplitudes of their Fourier components.

In one embodiment, pure-component spectra of the analyte of interest over the wavelengths of interest are deconstructed into spectral fragments (also referred to as wavelength regions or spectral regions of). The boundaries of these spectral fragments generally correspond to those of spectral features to be used to generate conditioned features using the carrier kernel. The pure-component-spectra-based spectral fragments can be used to determine the values of one or more Kappa parameters described above. To this end, interpolation and/or pre-cursor modulation are optionally applied to the spectral fragment. A carrier kernel is modulated using the spectral fragment to obtain a conditioned fragment. The conditioned fragment is collided with a Zyoton, and a change in dispersion velocity of the modified Zyoton relative to the dispersion velocity of the original Zyoton is computed.

Noise such as randomly generated gray noise with a correlation time of $10^{-6}$ seconds may then be added to the spectral fragment. The amount of noise can be a fraction of (e.g., 2%, 25%, 50%, etc.), equal to, or a multiple of (e.g., 2, 5, 10, 100, 1000, 10000times, or more) the expected and/or measured noise of the non-invasive measurement system. The above-described steps may then be repeated using the noisy spectral fragments to obtain corresponding changes in the dispersion velocity of the modified Zyoton. The steps of adding noise, generating a conditioned fragment, colliding it with a Zyoton, and computing a change in the dispersion velocity may be repeated for different amounts of noise. The parameter $\kappa_{DV1}$ may then be set according to these observed changes. For example, $\kappa_{DV1}$ can be a minimum, average, median, or maximum of different observed changes in the dispersion velocity. Other Kappa parameters discussed above can be set relative to $\kappa_{DV1}$.

FIGS. 45A through 45D illustrate the distribution of amplitudes of carrier kernel frequencies and their frequency components in the time and frequency domains. The profile of the full carrier kernel and a zoom-in to the high-amplitude frequency components are shown. FIG. 45A shows the time domain representation of a carrier kernel waveform generated using the frequencies shown in FIG. 44A. FIG. 45B provides a distribution of carrier kernel waveform frequency components, specifically a distribution of the amplitudes of these components, as a function of spatial frequency. FIG. 45C shows a time-domain representation of the waveform shown in FIG. 45A, down-sampled to 2048 data points. The down-sampling is optional and a down-sampled waveform may include less than 2048 (e.g., 2000, 1024, 1000, 600, 512, 200, etc.) or more than 2048 (e.g., 3000, 5000, 10,000, 40,960, etc.) points. FIG. 45D shows the distribution of the spatial frequencies of the down-sampled carrier kernel waveform and amplitudes of the frequency components as a function of spatial frequencies.

In ordinary frequency modulation (FM), a signal modulates the frequency of a carrier wave where the modulated output does not have any nonlinear dependence on the original signal. In various embodiments described herein, the carrier kernel is frequency modulated by a feature. The carrier kernel is created with several selected frequencies, and the result of modulation by the feature creates a non-linear relationship to the feature. A non-linear relationship is achieved because the carrier wave is a summation of several frequencies instead of a single one. Other types of modulation, e.g., amplitude modulation, phase modulation, etc., and/or combinations of two or more modulation techniques can be used to modulate a carrier kernel using a feature.

In general, a carrier kernel includes a set of distinct carrier frequencies $\overline{F}_c=[f_{c1}, f_{c2}, \ldots, f_{cN_K}]$, where $N_K$ is the number of component carrier frequencies in the kernel. Optionally, there are several harmonics of each frequency $f_{c1}$ embeded in the carrier kernel. As stated above, the feature data extracted from a spectrum has low spatial frequency content, generally due to a limited data vector length of the feature. This spatial frequency content is often insufficient to characterize changes in the feature properties due to low analyte concentration and interference from confounders. Coupling the feature with a complex carrier kernel with a high spatial frequency content, after an optional precursor modulation, can provide additional degrees of freedom to characterize the underlying analyte. Different features, associated with different wavelength regions, with different underlying analyte concentrations and corresponding absorption of energy, modulate the carrier kernel differently. When the carrier kernel, modulated by the feature (and thus transformed to a conditioned feature) with an expanded range of spatial frequencies, is collided with the Zyoton (which also has an expanded range of corresponding spatial frequencies), the analyte absorption properties can be extracted and amplified. In some embodiments, the same carrier kernel is used for all features, regardless of the wavelength regions from which those features are derived. Different carrier kernels and/or different Zyotons can be optionally used for different features.

A set of carrier frequency component amplitudes $\overline{C}=[C_1, C_2, \ldots, C_{N_K}]$ is associated with $\overline{F}_c$. As described above in the discussion of Zyoton and carrier kernel synthesis, the choice of the frequencies $f_{ci}$ for i=1, . . . , $N_K$, and $N_K$ relate to the relationship between absorbing and non-absorbing feature wavelength regions in the Fourier transform of the analyte's pure component spectrum, and/or noise characteristics of the feature, and by the anticipated confounder interference, as expressed by the SCR. Specifically, the selection of at least some of the carrier kernel frequency components was described above, relating them to the number of components of a frequency-component based discriminant classifier required to overcome the introduced distortion of the second derivative of the pure component spectrum for an analyte of interest in the presence of confounders and added random noise. All the frequency components and their amplitudes can be provided to a signal generator or synthesizer to generate the carrier kernel waveform.

Figure 46A:
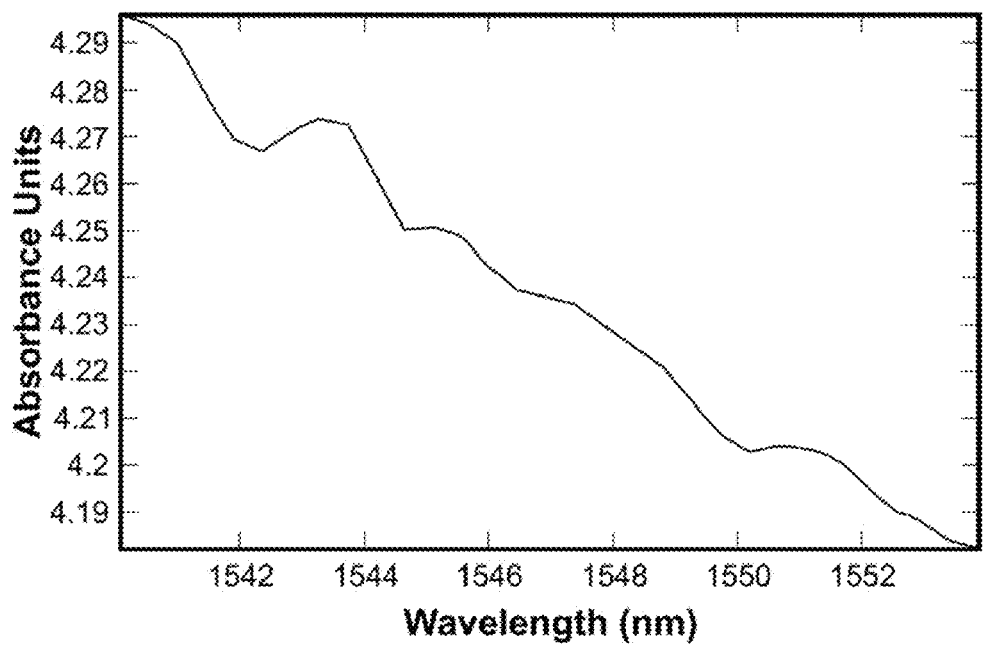
FIG. 46A shows a feature.
Figure 46B:
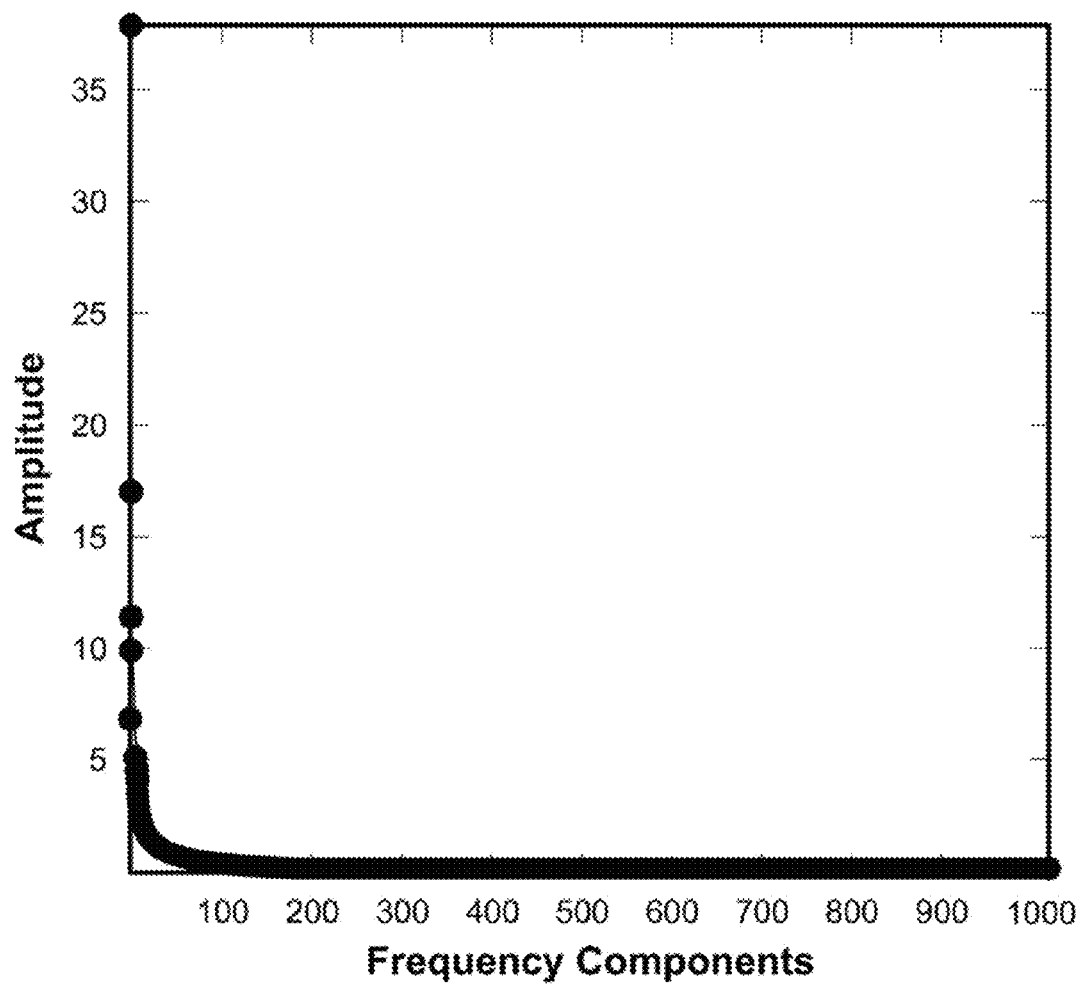
FIG. 46B shows frequency components of the feature.
Figure 46C:
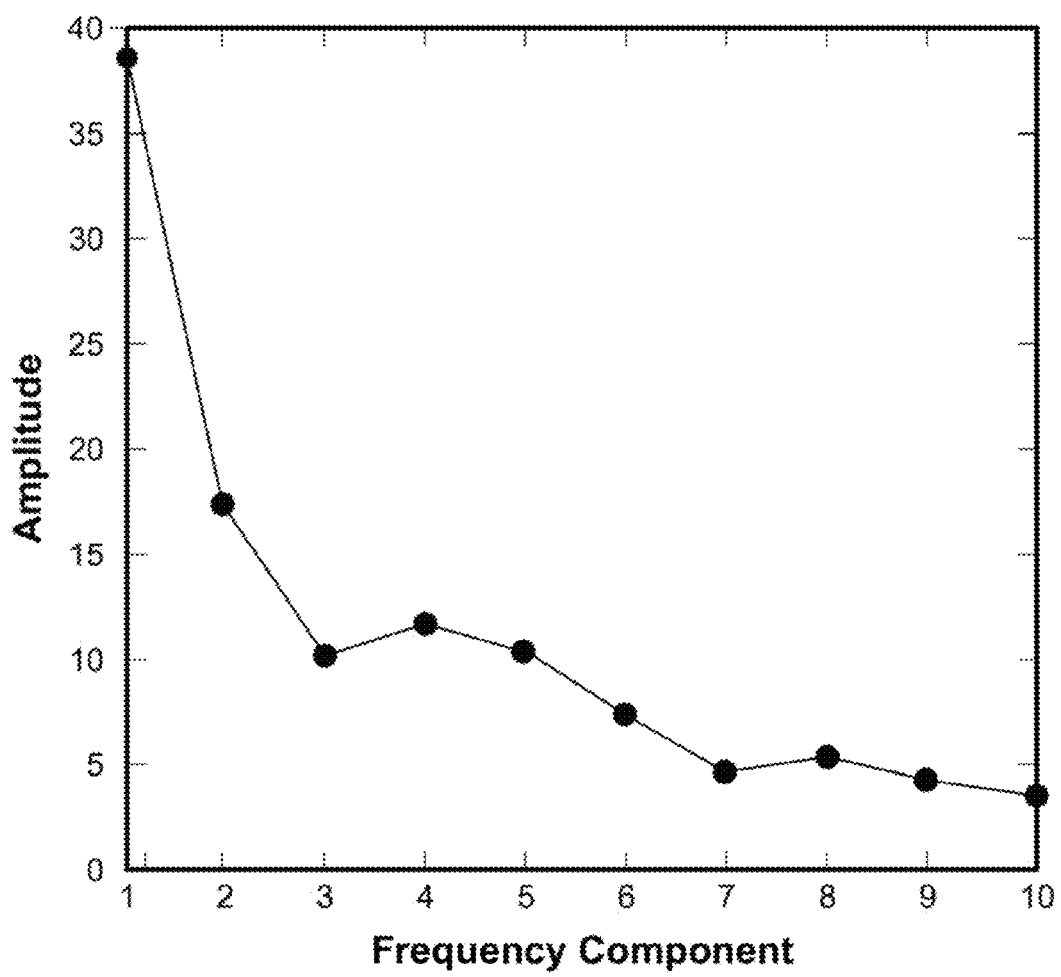
FIG. 46C shows the first ten frequency components of the feature.

Spectral features need to be appropriately prepared before modulating a carrier kernel by those features. FIGS. 46A through 46C show a feature prepared in the absorbance domain and the distribution of spatial frequencies and their amplitudes in sorted order. In particular, FIG. 46A shows the absorbance spectrum of a feature, which can obtained by transforming an intensity spectrum obtained from a sensor, as described below. FIG. 46B shows all frequency components of the feature in the amplitude-sorted order, and FIG. 46C shows the first ten frequency components of the feature in the amplitude-sorted order.

When a carrier kernel is modulated by a feature waveform, a Fourier transform of the resulting conditioned feature typically includes more than $N_K$ frequency components. In general, the modulated carrier kernel, i.e., the conditioned feature includes $(k+m_{CF}+j_{CF})$ frequency components. The first k frequency components represent the energy absorbed by the analyte and/or one or more confounders. The amplitudes of these frequency components are denoted $a_k$, $a_{m_{CF}}$, and $a_{j_{CF}}$, as depicted in FIG. 11. The Zyoton with which the conditioned feature is collided generally includes $(k+m_z+j_z)$ frequency components, and the amplitudes of the frequency components of the Zyoton are denoted $A_k$, $A_{m_z}$, and $A_{j_z}$, as also depicted in FIG. 11. The respective frequency components of the Zyoton and the conditioned feature, however, need not have exactly the same frequencies.

Figure 47A:
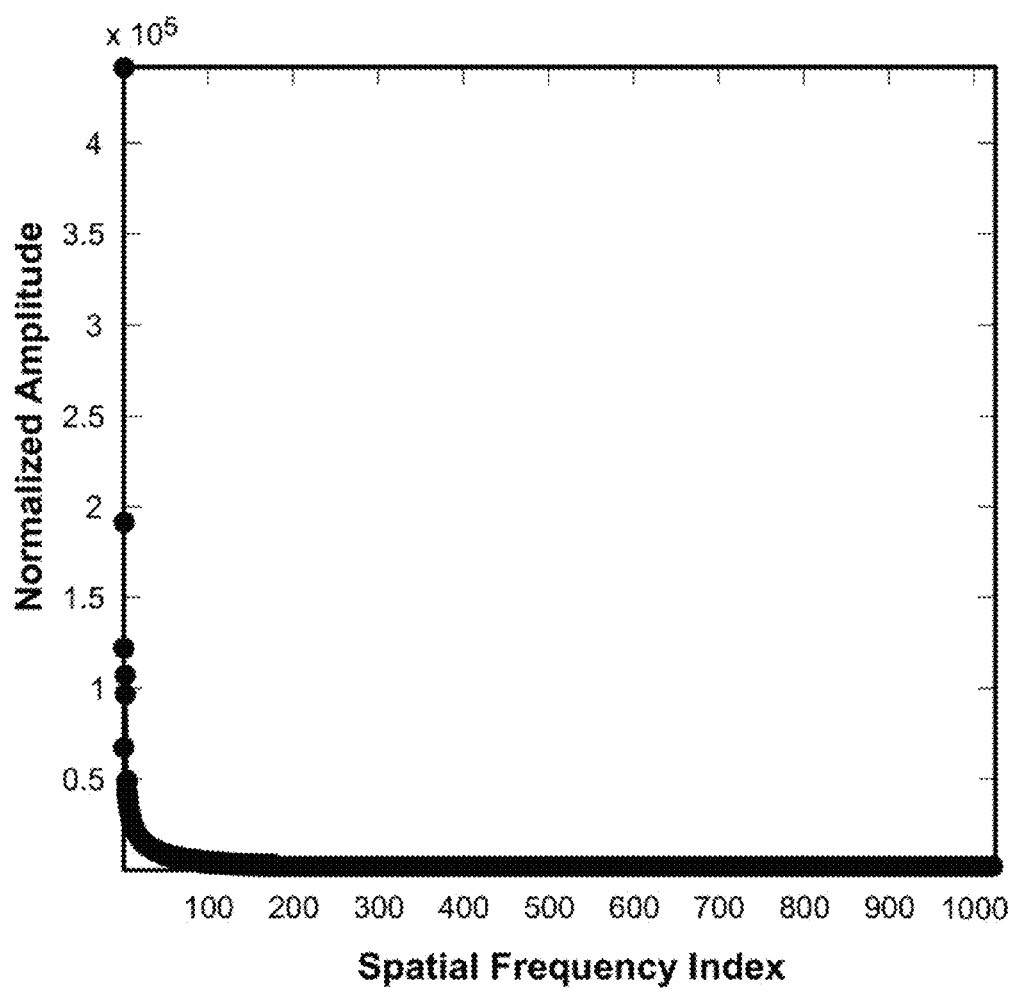
FIG. 47A-47D illustrate the distribution of frequency components of a conditioned feature after applying carrier modulation.
Figure 47B:
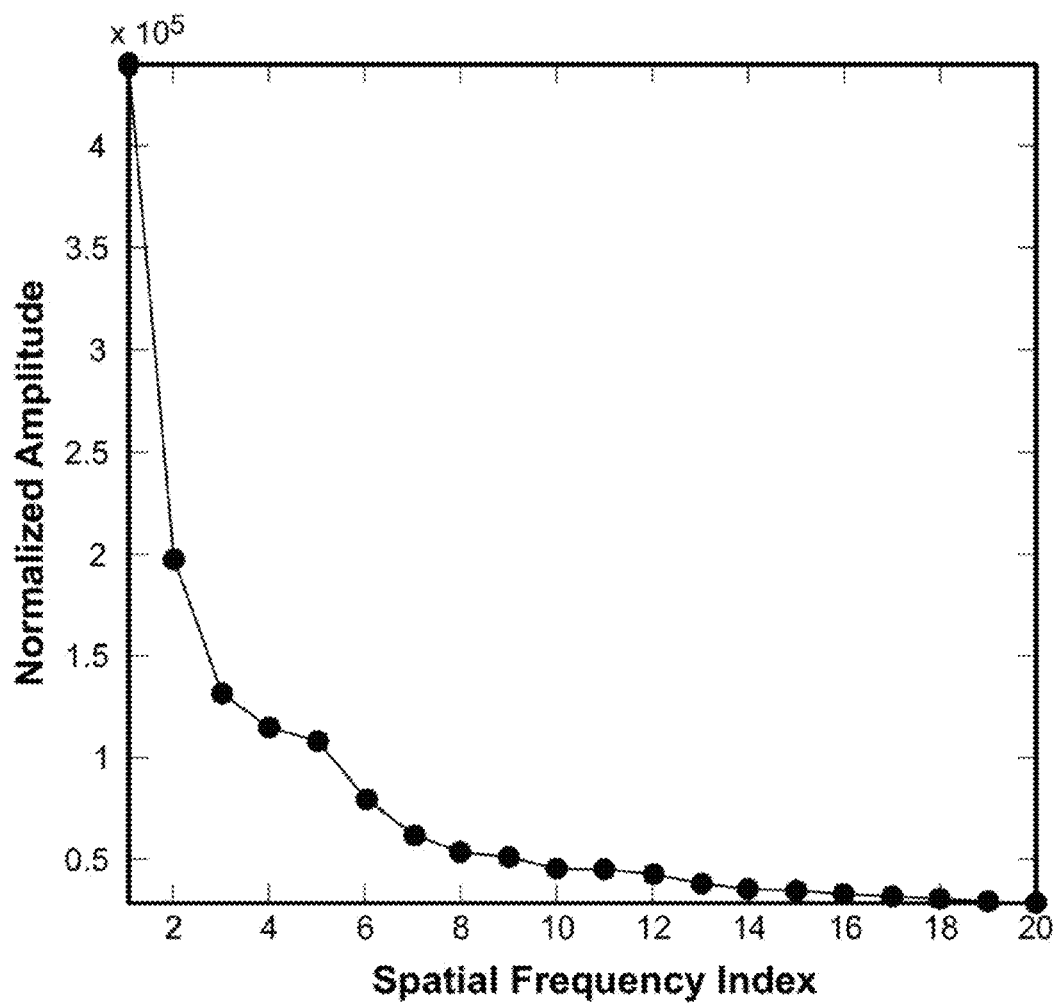
Figure 47C:
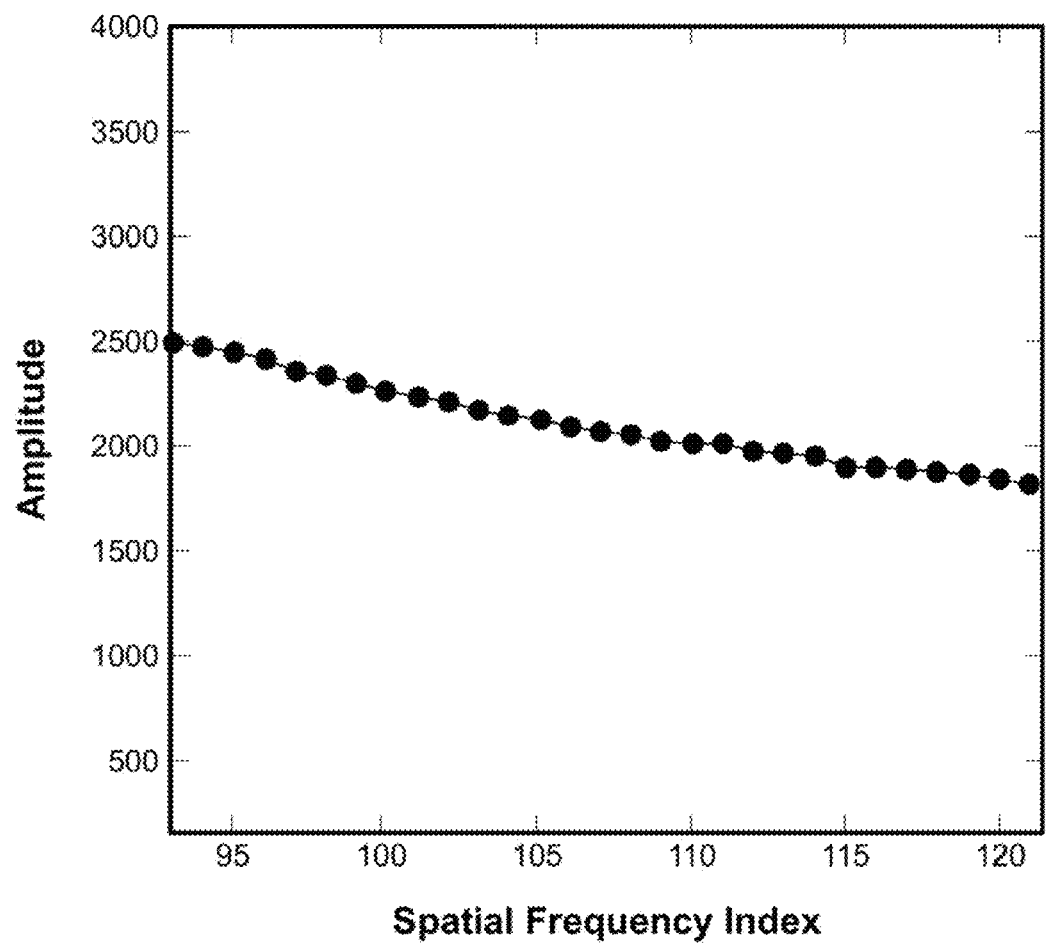
Figure 47D:
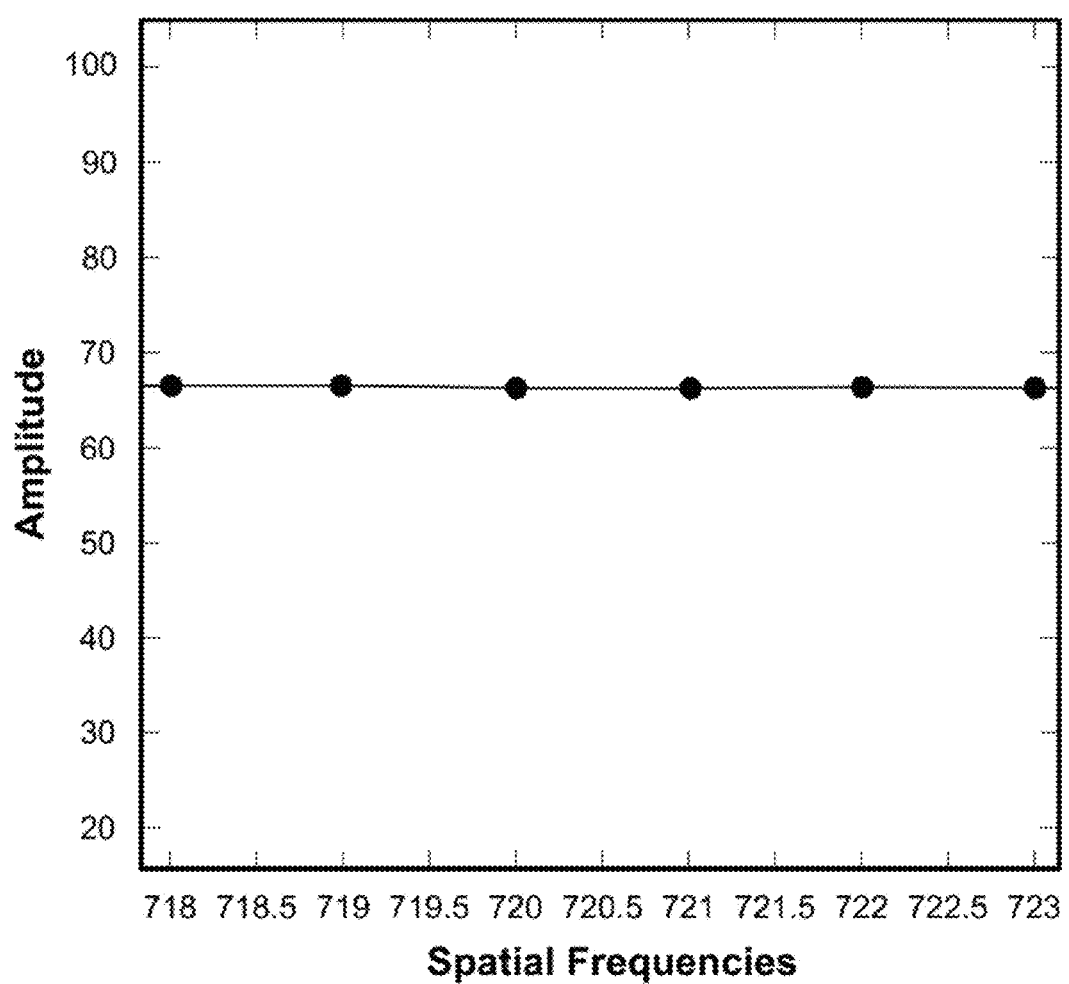
Figure 48A:
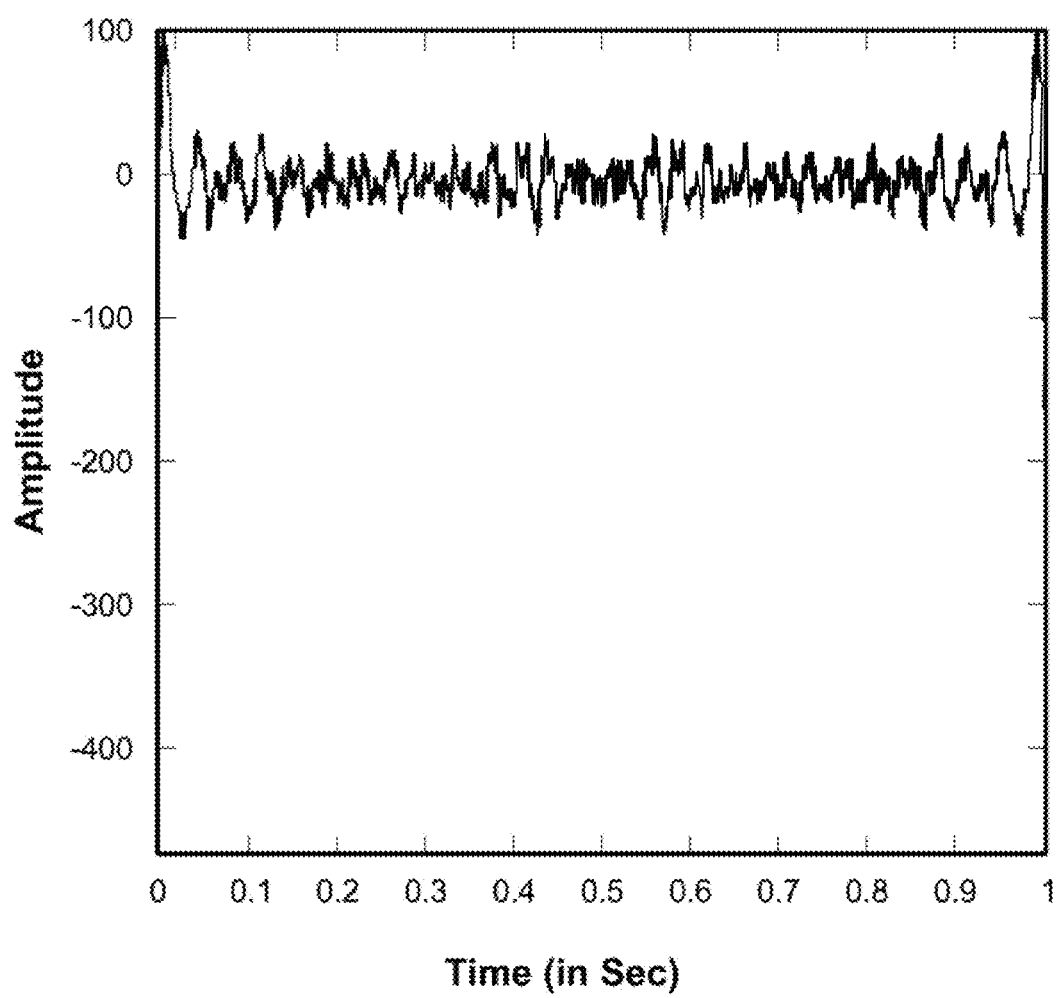
FIGS. 48A and 48B provide an example of a conditioned feature waveform in the time domain after modulation with a carrier kernel, and a zoom-in to the first portion of the waveform.
Figure 48B:
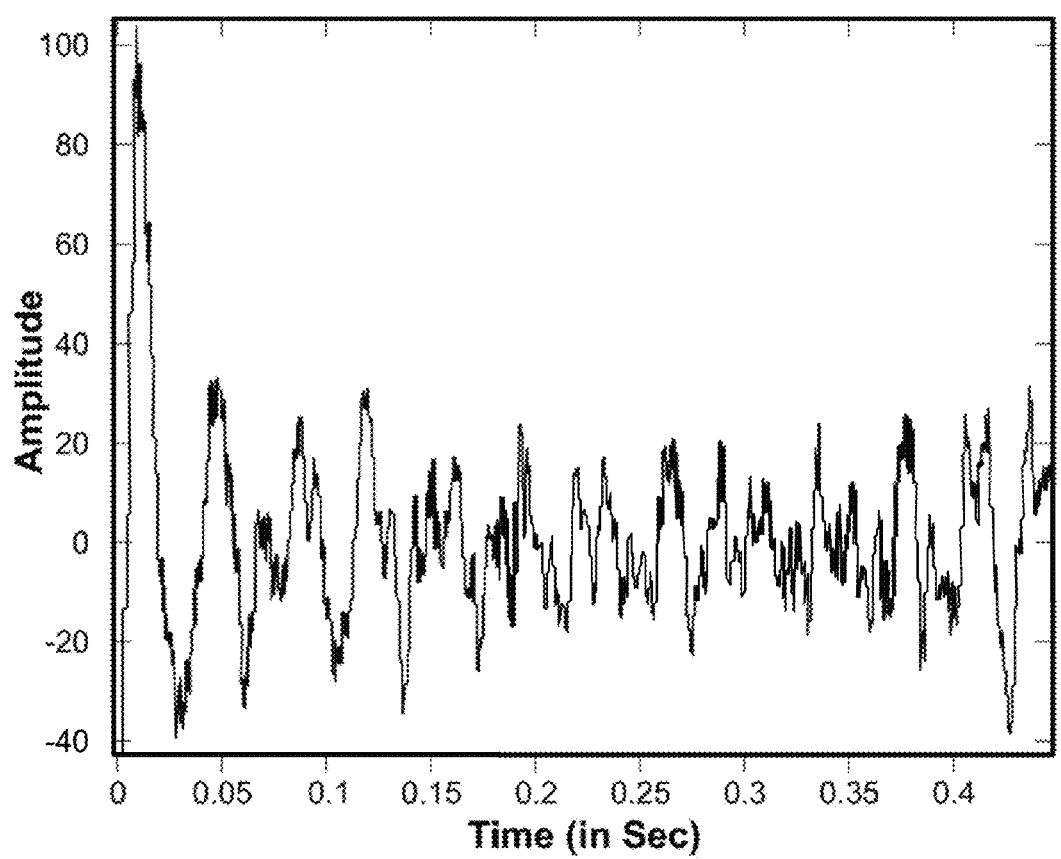

FIGS. 47A through 47D illustrate the distribution of frequencies and the normalized amplitudes of the frequency components of a conditioned feature after modulation of the waveform by a feature. All of the frequency components of the conditioned feature waveform, sorted by amplitude, are shown in FIG. 47A. The analyte-information-representing k components of the conditioned feature are shown in FIG. 47B. FIG. 47C zooms in to the transition zone or mid-amplitude range m components of the conditioned feature, and FIG. 47D zooms in to non-analyte-information representing j components of the conditioned feature. FIGS. 48A and 48B show a time-domain representation of the conditioned feature having a frequency domain profile shown in FIGS. 47A through 47D. A zoom-in to the overall time-domain profile of the conditioned feature waveform from FIG. 48A is shown in FIG. 48B.

Figure 50A:
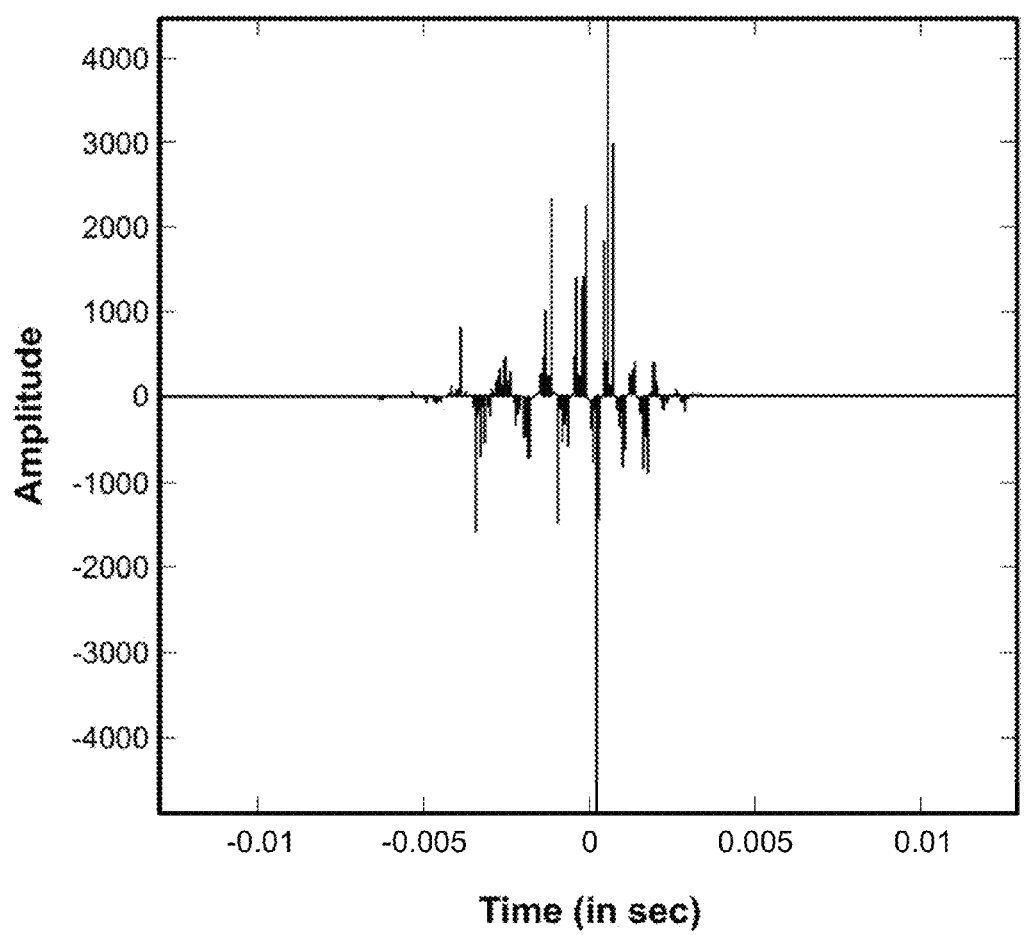
FIGS. 50A-50C provide examples of different Zyoton waveforms used in collision computing, the Zyotons in the figures correspond to the Zyotons referred to in FIG. 49.
Figure 50B:
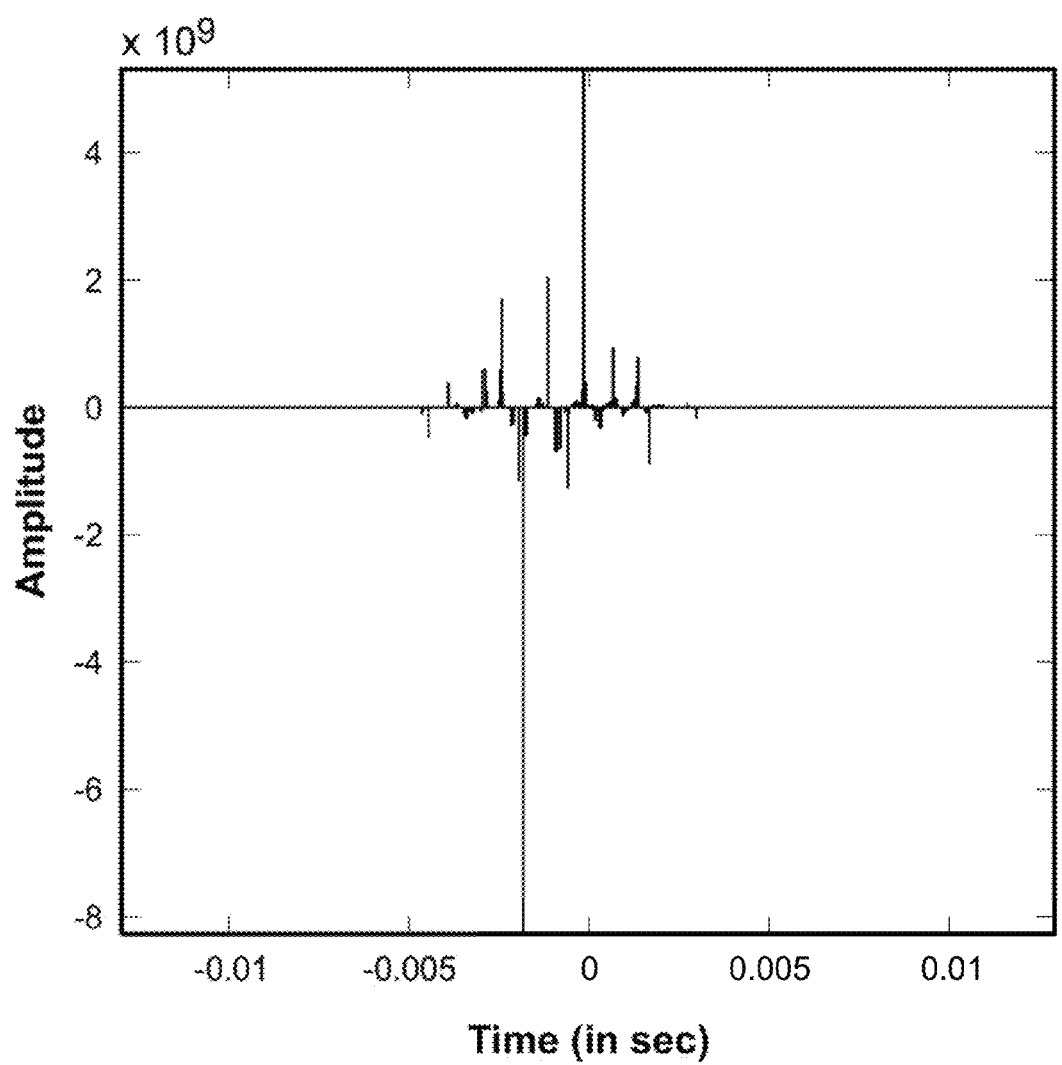
Figure 50C:
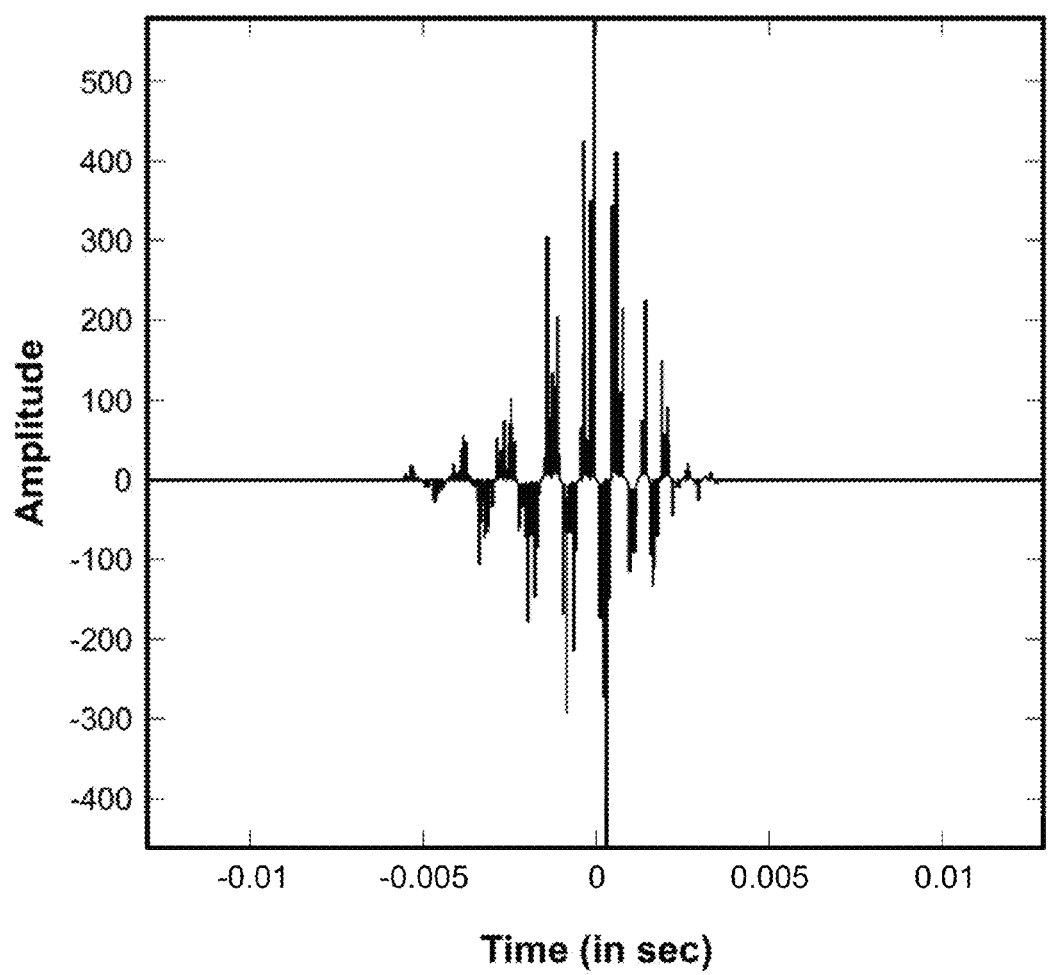

FIGS. 12A through 12C show the morphological profile and amplitude envelopes of an example one-dimensional Zyoton, derived from solitons, and corresponding to the Zyoton_D1 (shown in FIG. 49). FIG. 12A shows a time-domain representation of the Zyoton and FIG. 12B shows a zoomed-in representation of the Zyoton. FIG. 12C shows the primary peak in the time domain, and selected b sideband peaks on both sides of the primary peak. FIGS. 50A through 50C show time-domain representations of other Zyoton waveforms that may be used in collision computing. Specifically, these Zyotons waveforms correspond, respectively, to Zyoton D3, Zyoton D1, and Zyoton MM1 (shown in FIG. 49).

Figure 51A:
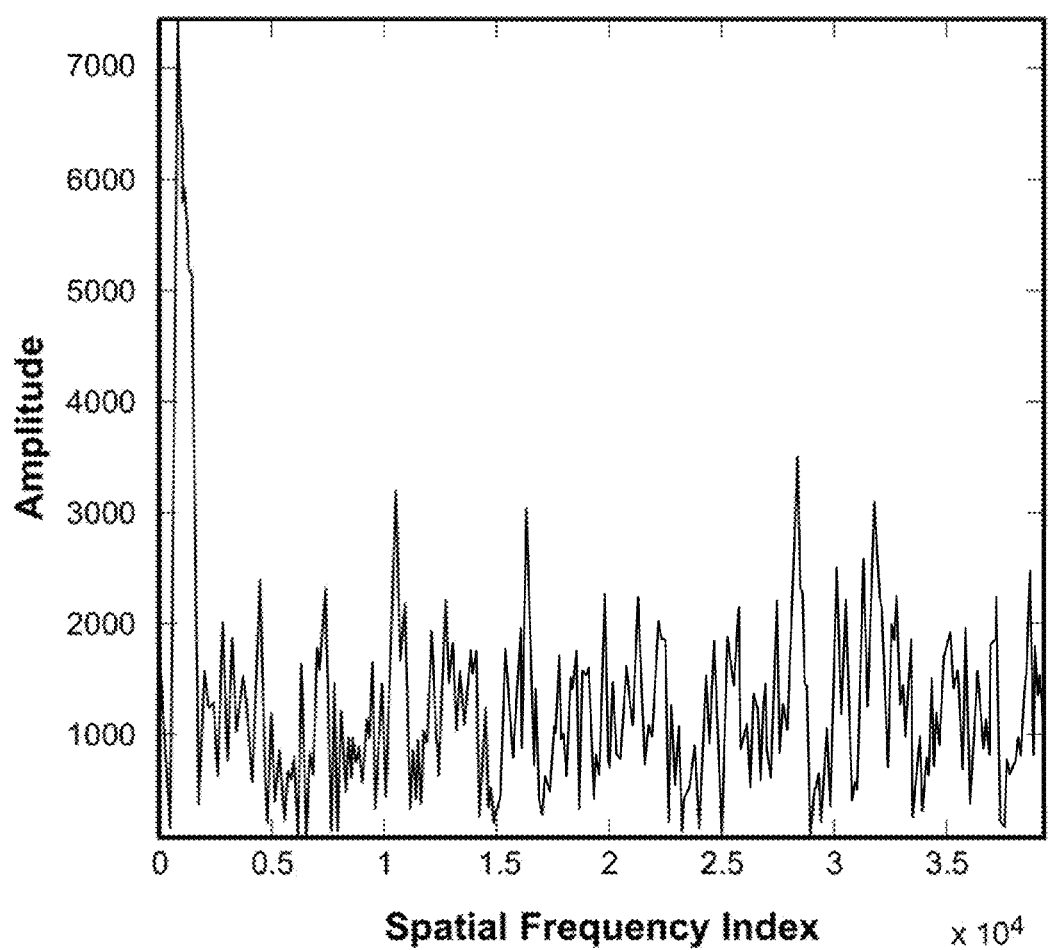
FIGS. 51A-51D show the frequency domain representation of different Zyoton waveforms (corresponding to the specific Zyotons shown in FIGS. 50A-50C)
Figure 51B:
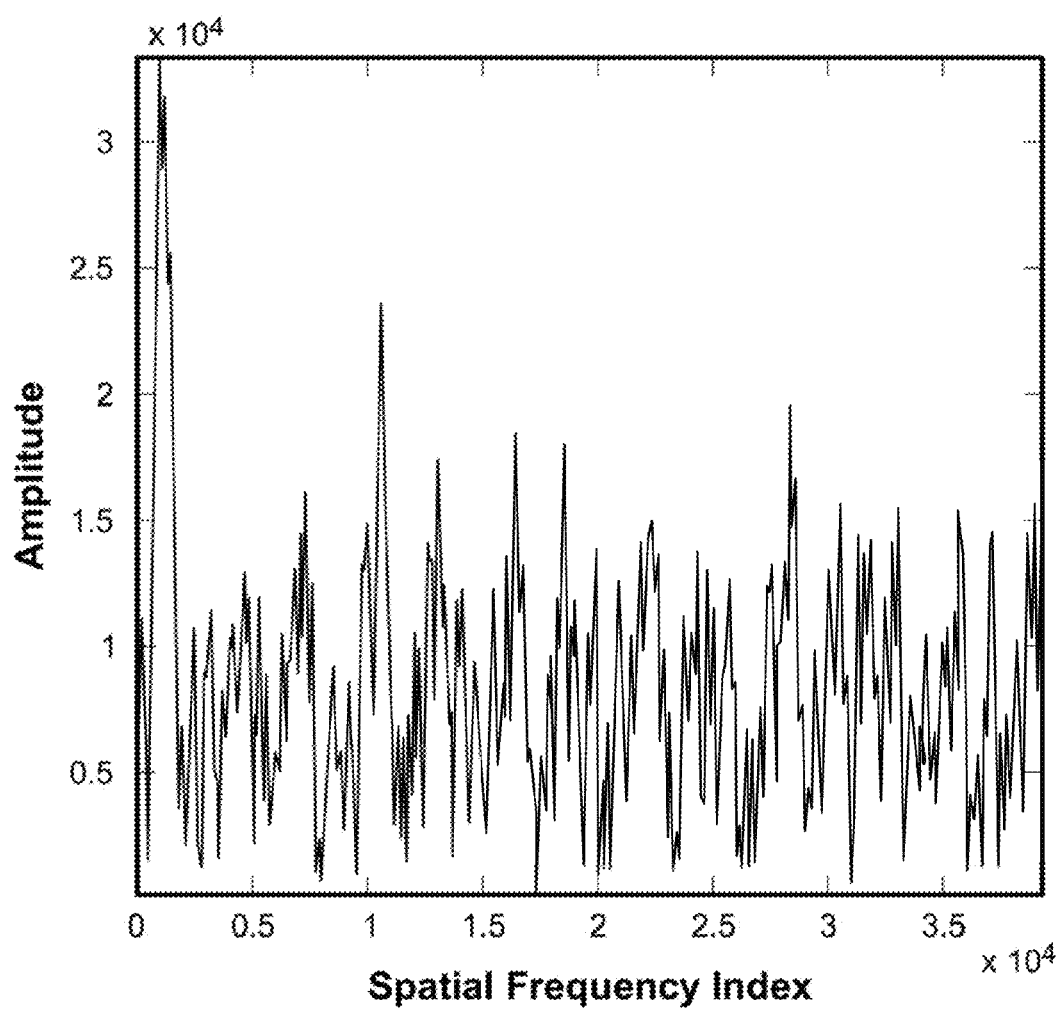
Figure 51C:
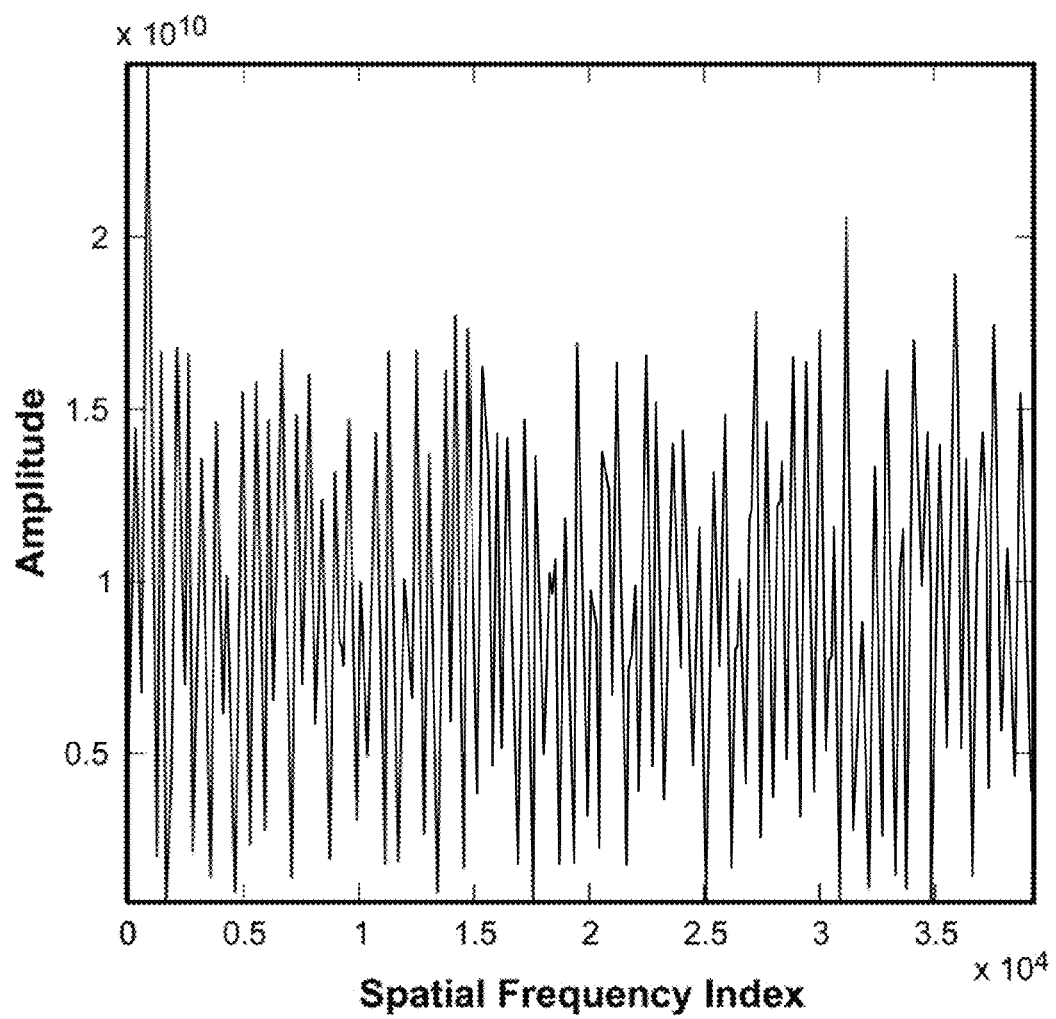
Figure 51D:
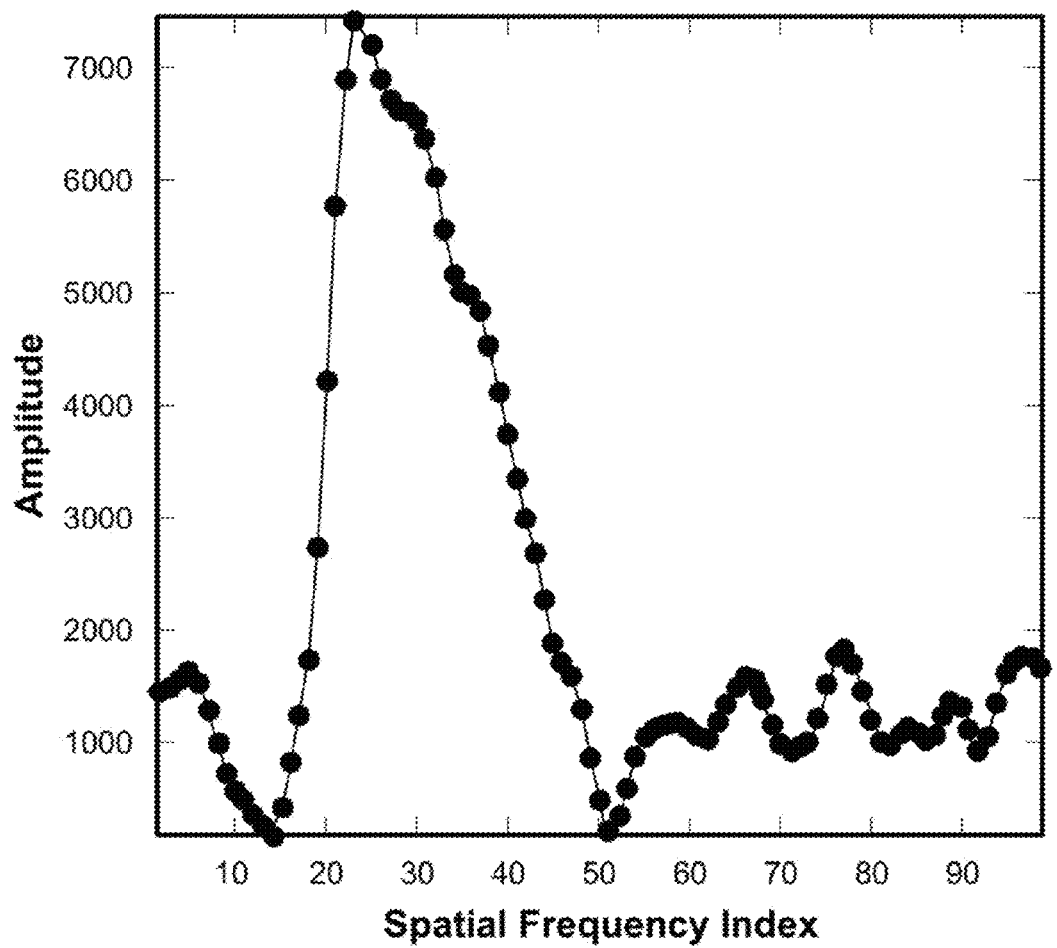
Figure 52A:
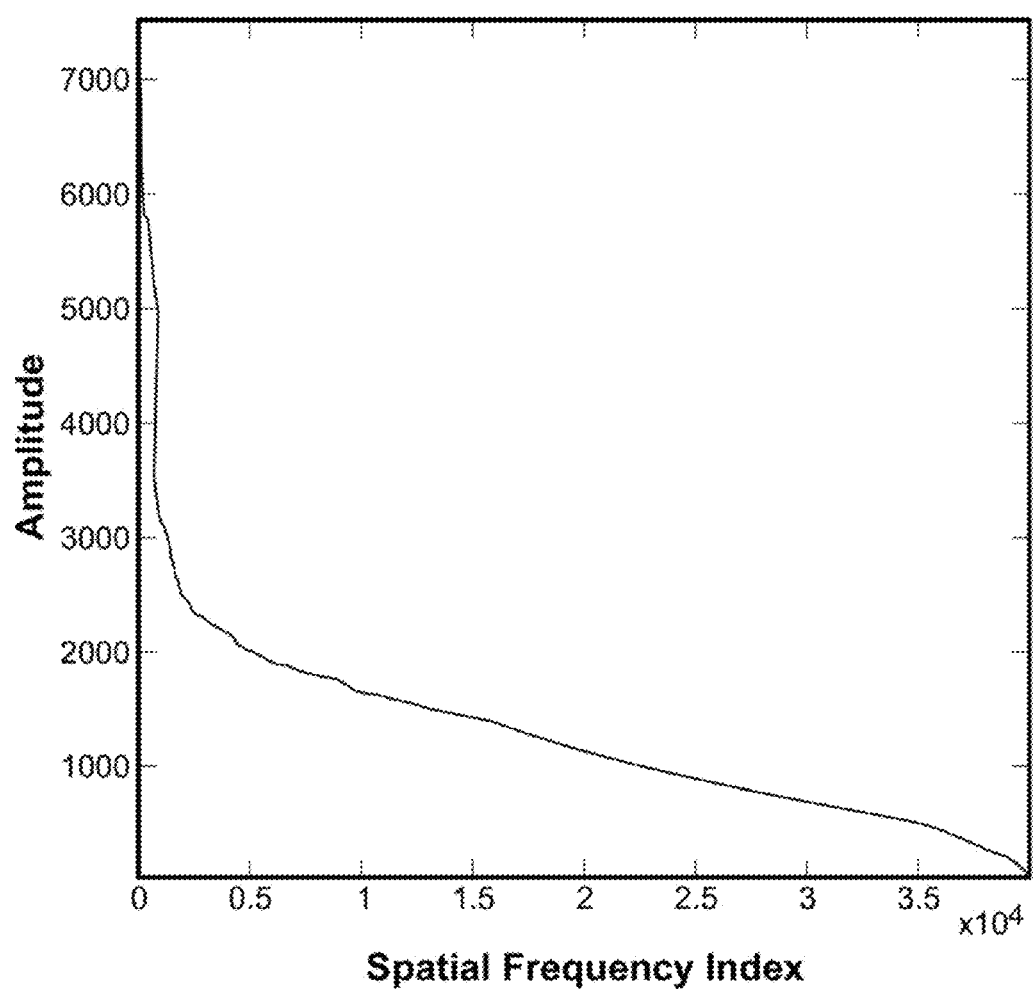
FIGS. 52A-52C show the amplitude profile of sorted frequency components for the Zyoton waveforms shown in FIGS. 50A-50C.
Figure 52B:
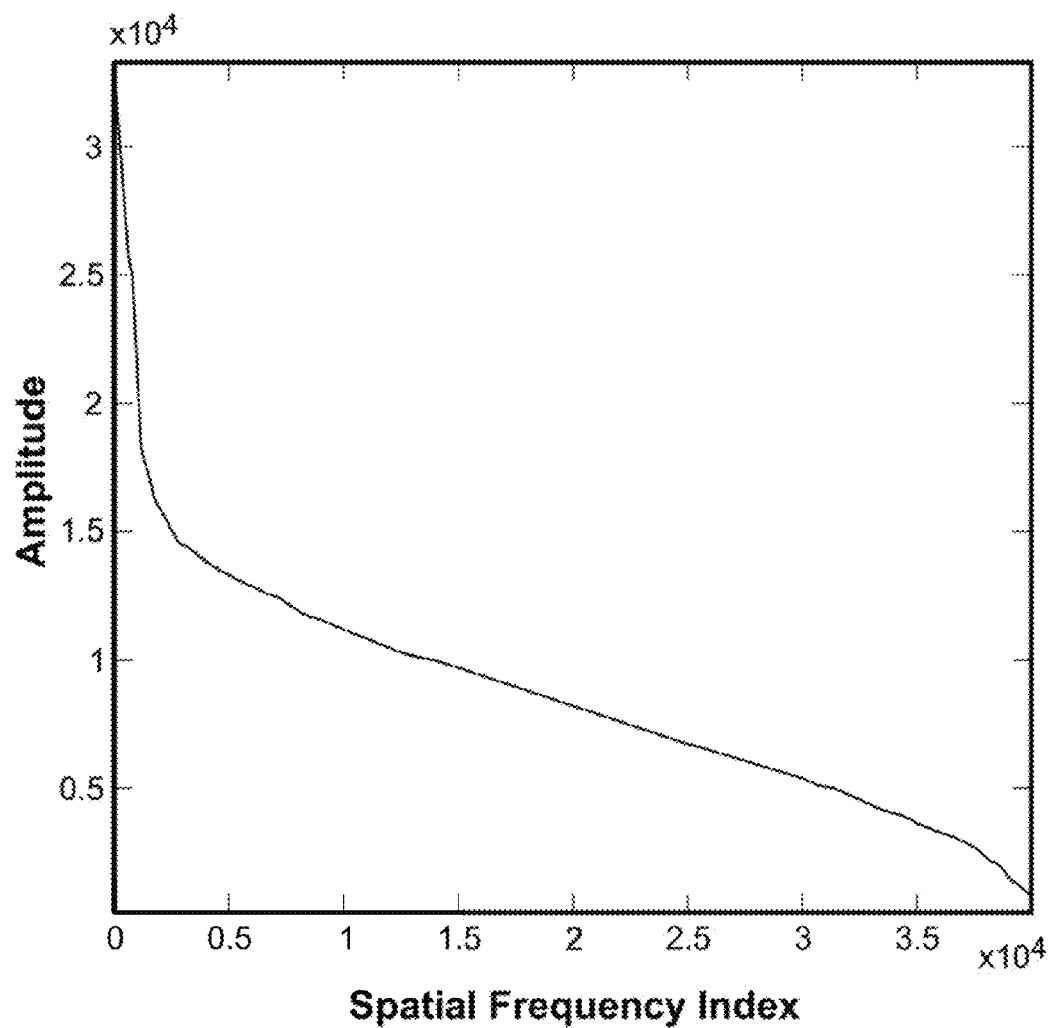
Figure 52C:
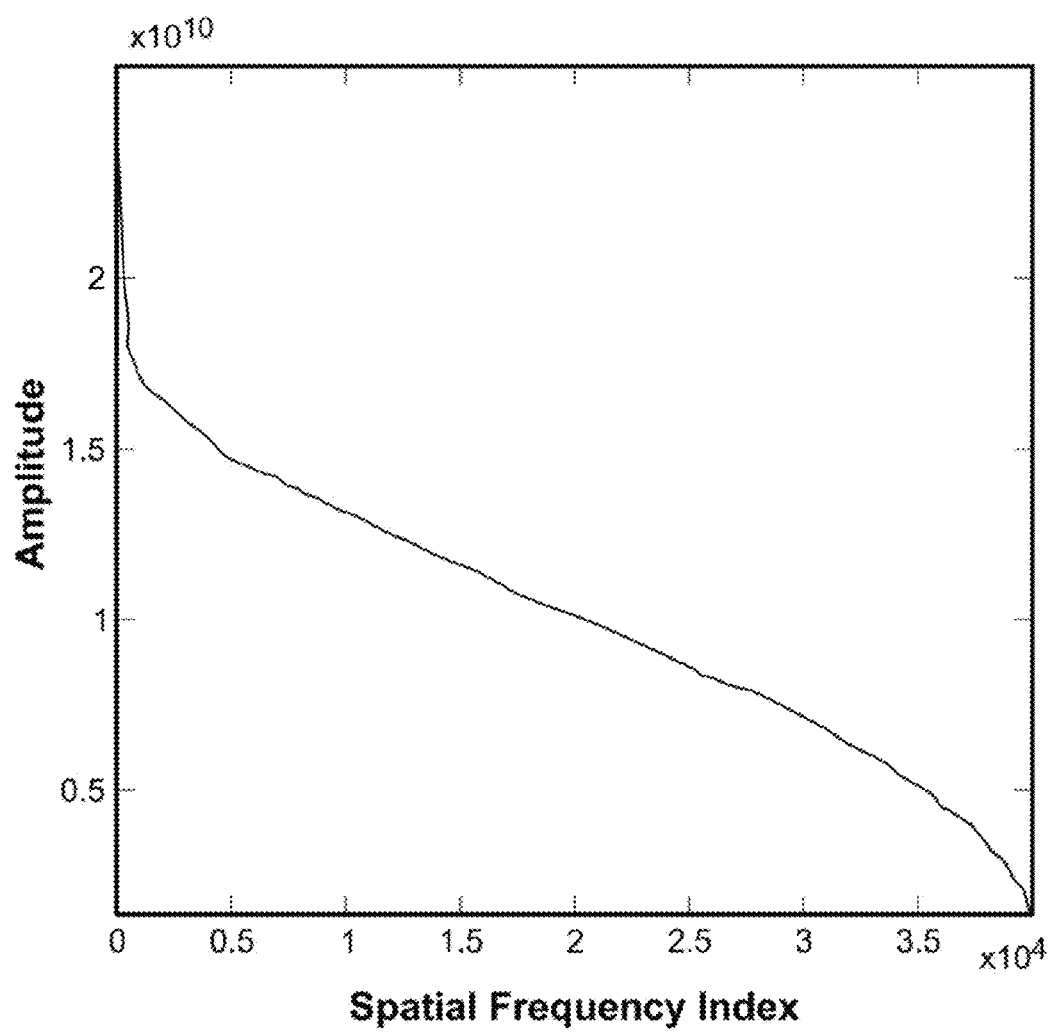

FIGS. 51A through 51C show the frequency domain representation of the different Zyoton waveforms, i.e., Zyoton_D1, Zyoton_D3, and Zyoton_MM1. These frequency-domain representations correspond, respectively, to the time-domain representations shown in FIGS. 50A through 50C. FIG. 51D shows a zoom-in to the frequency components of Zyoton_MM1. FIGS. 52A through 52C show the profile of amplitude-sorted frequency components for the Zyoton waveforms Zyoton_D1, Zyoton_D3, and Zyoton_MM1, respectively.

In various embodiments, the parameters $\delta$ and $\Phi$ (as described below in the collision equation), are applied to the Zyoton and/or conditioned feature waveform vectors. In various embodiments, for computational efficiency, Zyotons are expressed as one-dimensional traveling waves in the x, y or z dimension over time. The Zyotons may be synthesized, however, using complex-valued waveform families (e.g., solitons) and/or generator functions that are plane-wave, i.e., two-dimensional constructs (having x and y dimensions over time), or even three-dimensional constructs (having x, y, and z dimensions over time). As the corresponding Zyotons may be represented as one-dimensional traveling waveforms, a compensating mechanism may be employed for this dimensional simplification between Zyotons and the travel models of the waveforms from which they are derived. As an example, a general form of a two-dimensional soliton plane wave is $S(x, t) = Ae^{i\rho}e^{i(kx-\omega t)}$, where A is a positive constant called the amplitude, $\rho \in [0, 2\pi)$ (which symbolizes that $\rho$ can vary from 0 to $2\pi$) is called the initial phase, k and $\omega$ are two real-valued parameters called the wave number and the angular frequency, and $$\frac{k}{2\pi}$$

is the number of waves per unit length, while $$\frac{\omega}{2\pi}$$

is the number of waves per unit time. For one-dimensional Zyotons, the dispersion velocity along the propagation axis is expressed as $$\frac{\omega(k)}{k}.$$

In various embodiments, the collision operation is notionally one-dimensional, but the complete collision operations may need to be planar or three dimensional. Therefore, a phase rotation operation can capture the phase distribution effects. In some embodiments, a total phase rotation space of $2\pi$ is set for the entire collision process. The total $2\pi$ phase rotation is then divided by the number of collision iterations, to compute the rotation on a per collision iteration basis. This can compensate for the random variability in the collision process that may result from restricting the collision operation to a single dimension.

Figure 53A:
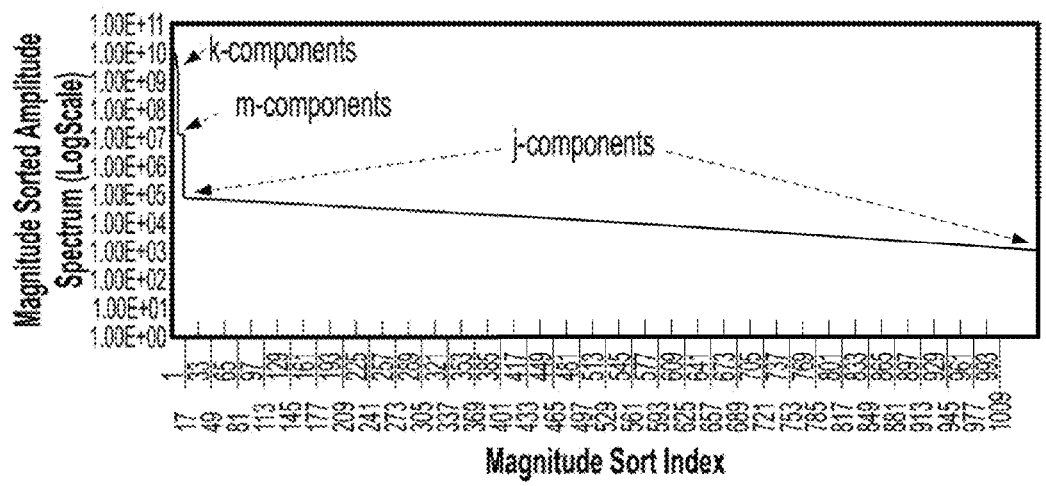
FIGS. 53A and 53B shows the power spectral density profile of an unscaled Zyoton.
Figure 53B:
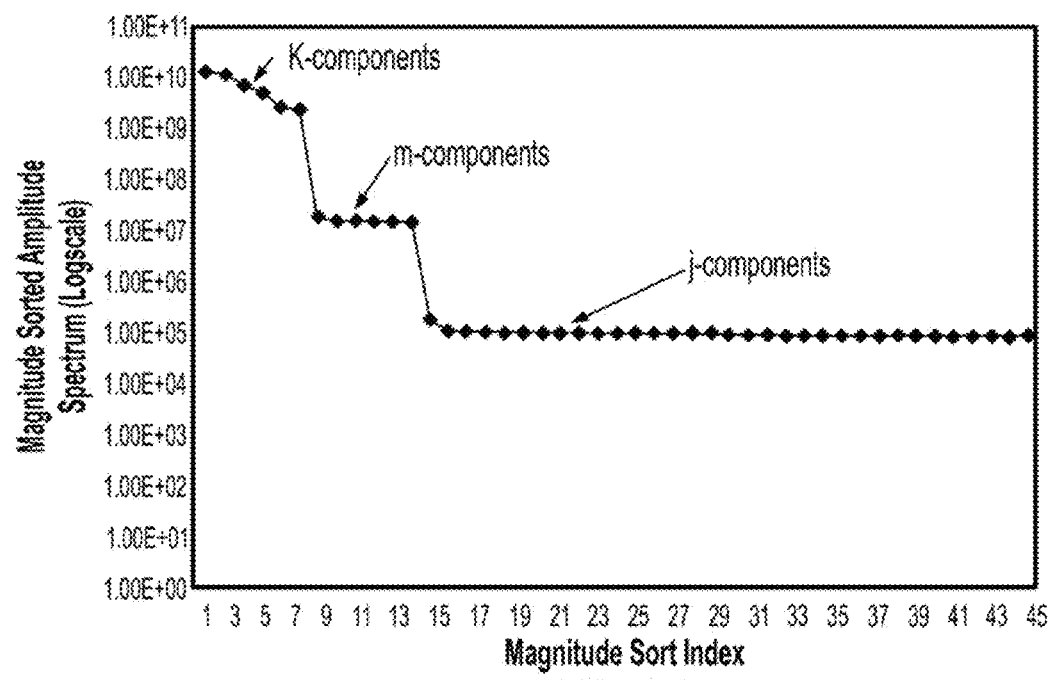
Figure 53C:
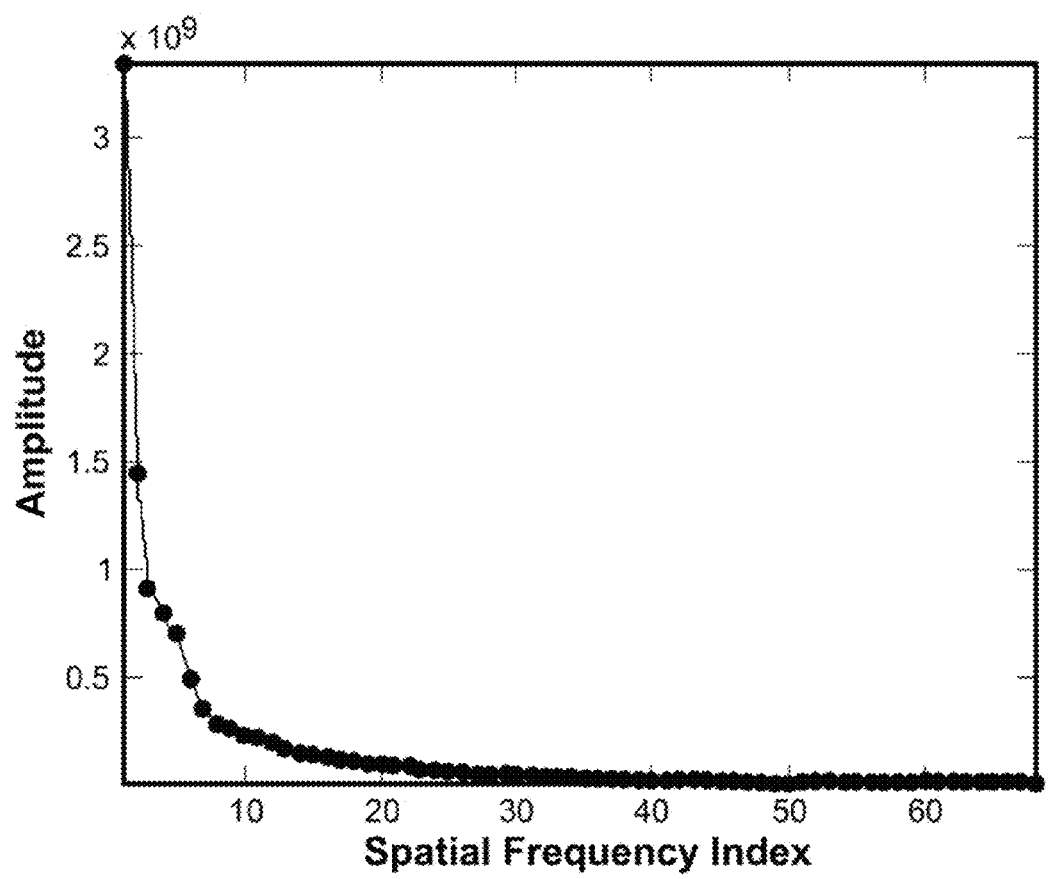
FIG. 53C shows an amplitude-sorted frequency component profile of a conditioned feature to be collided with a Zyoton.
Figure 54A:
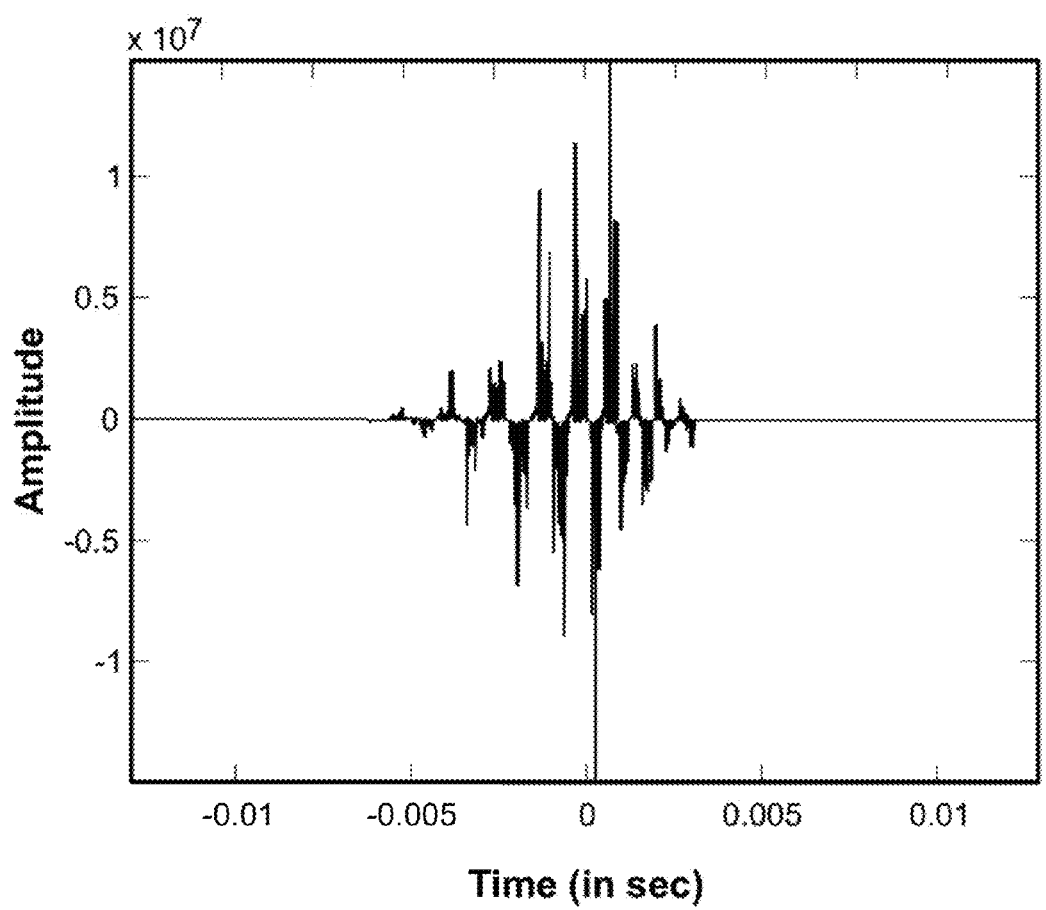
FIGS. 54A-54C respectively show the amplitude, frequency distribution and power spectral density profile of a scaled Zyoton waveform prior to a collision; with FIG. 54C showing the power spectral density on a decibel scale.
Figure 54B:
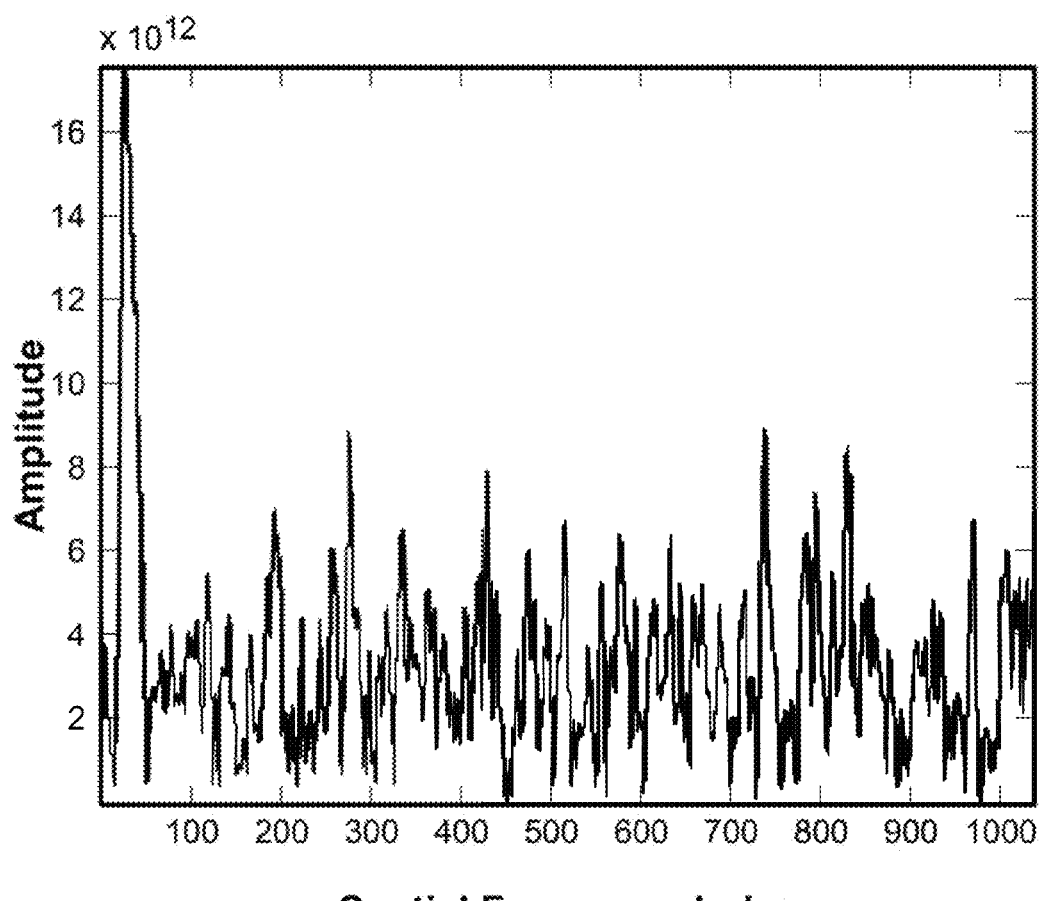
Figure 54C:
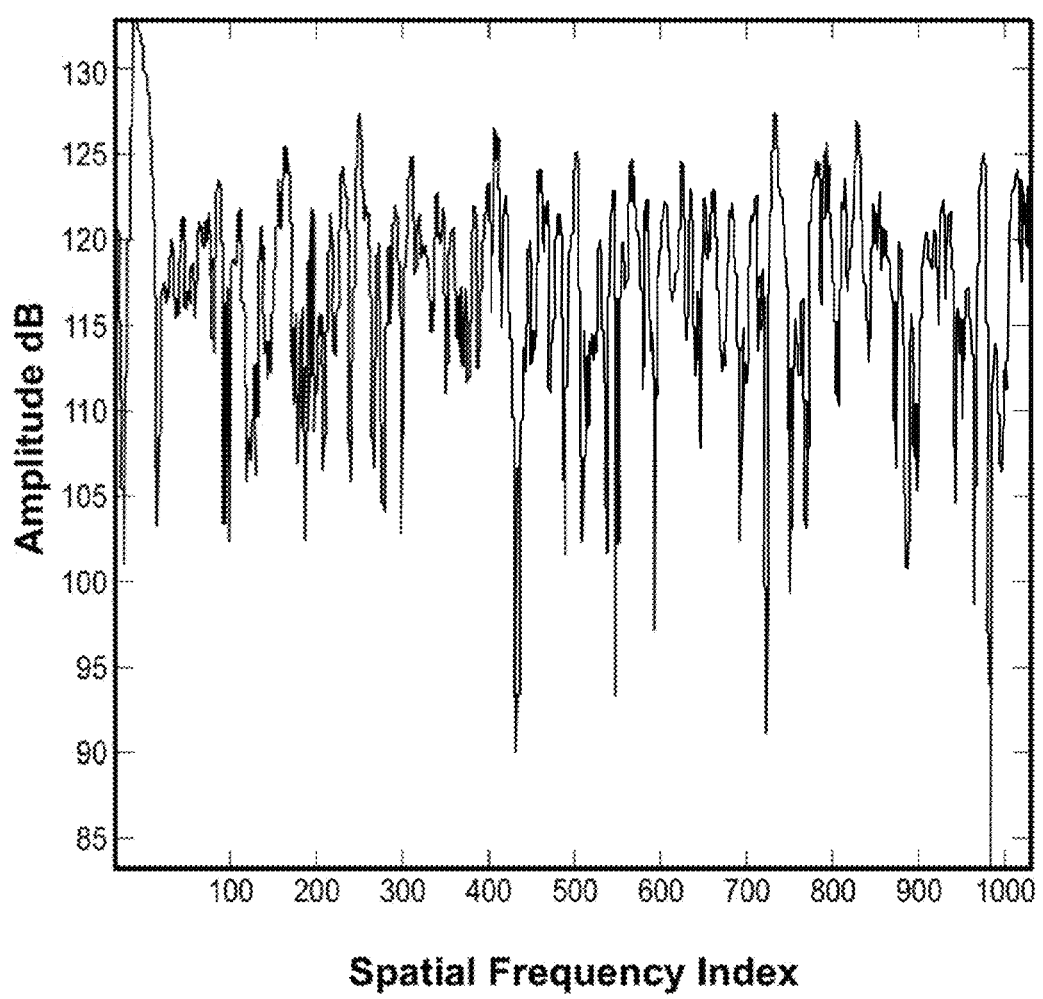
Figure 55A:
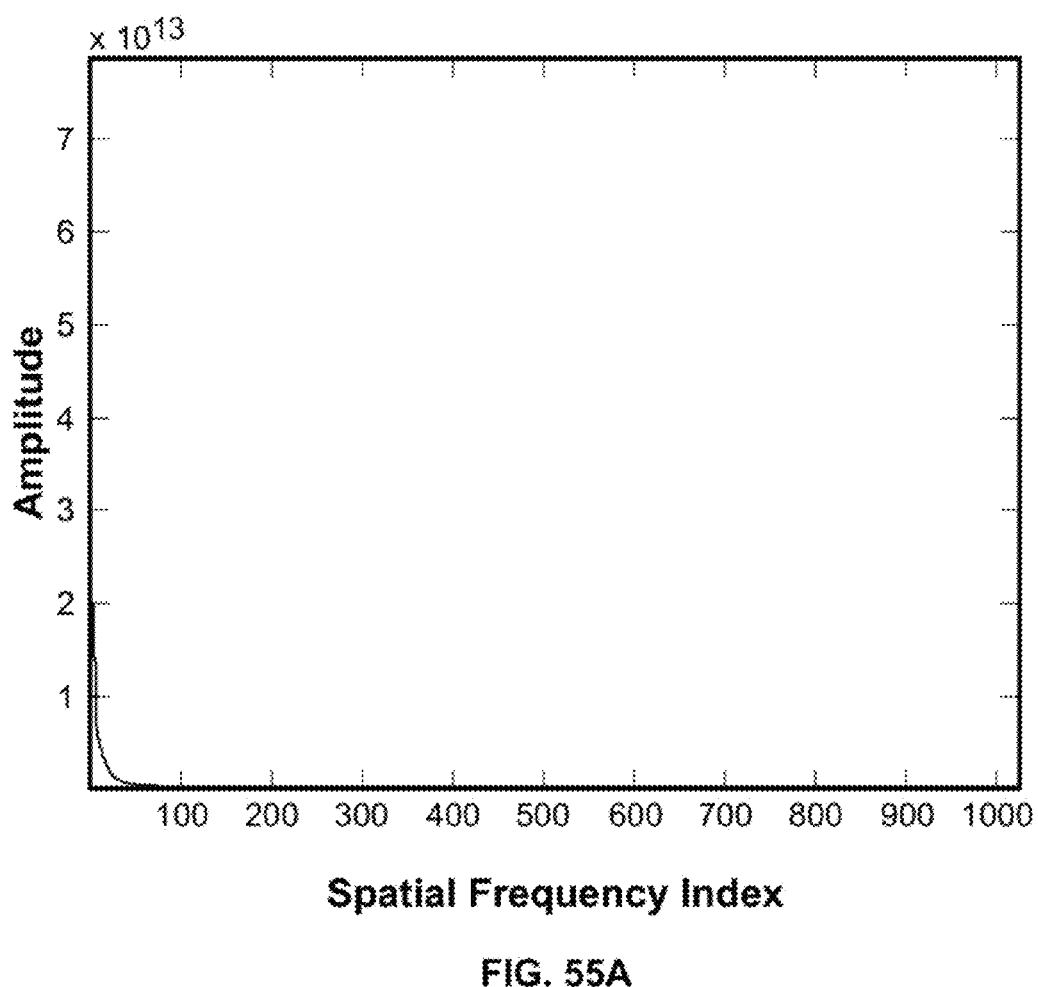
FIGS. 55A and 55B show the full and zoom-in views of the frequency profile of a modified Zyoton waveform obtaining by colliding a scaled Zyoton with a conditioned feature.
Figure 55B:
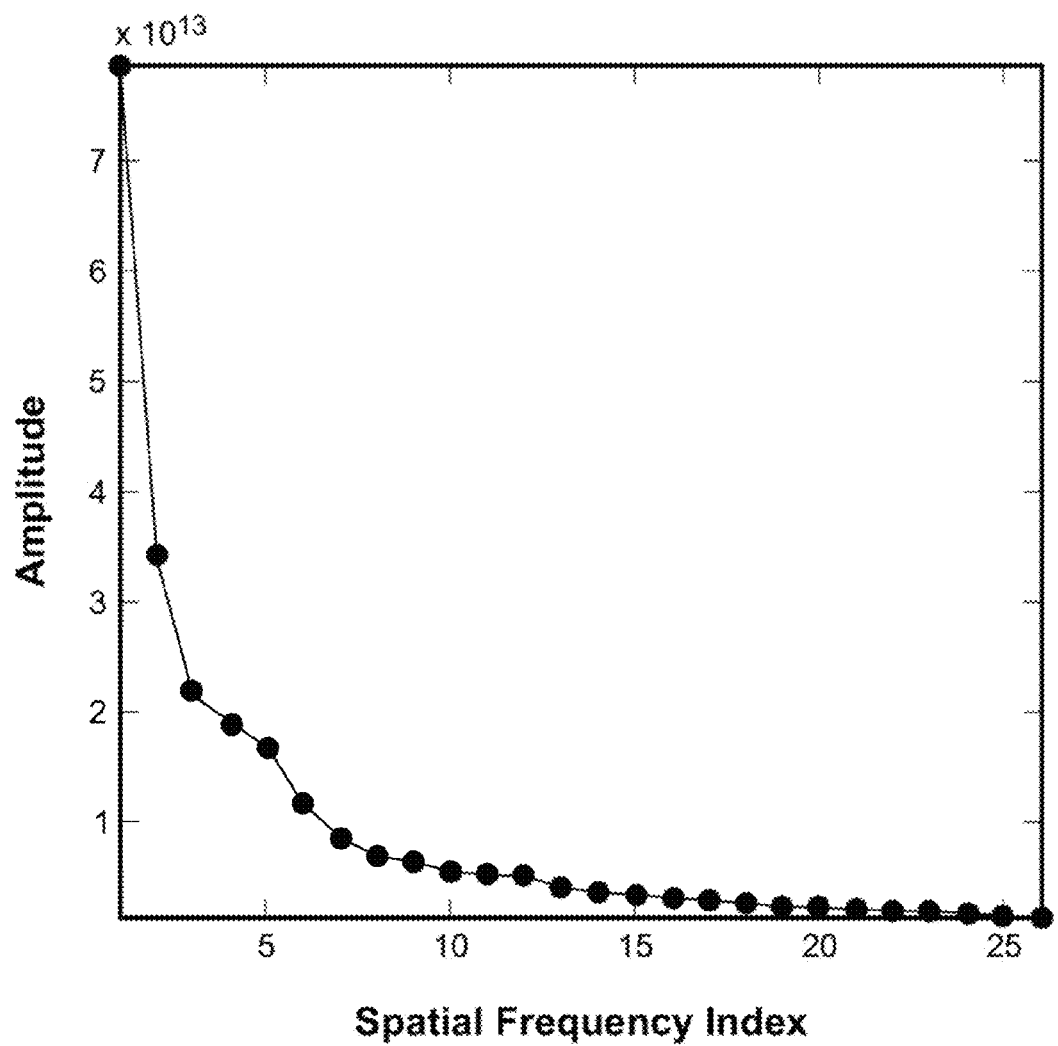

The power spectral density profile of the unscaled Zyoton (Zyoton_D1) is shown in FIGS. 53A-53B. An amplitude-sorted frequency component profile of a conditioned feature to be collided with Zyoton_D1 as shown in FIG. 53C. FIGS. 54A through 54C respectively show amplitude time-domain profile, frequency distribution, and power spectral density profile of Zyoton_D1 waveform, prior to a collision. The scaling coefficient $\alpha_z$ was used match the spectral energy ratio of the Zyoton waveform to the spectral energy of the conditioned feature as described above. FIGS. 55A and 55B show the amplitude-sorted frequency component profile of a modified Zyoton waveform obtaining by colliding the scaled Zyoton_D1 with the conditioned feature described with reference to FIG. 53C. A zoom-in to the amplitude-sorted frequency component profile of the modified Zyoton is shown in FIG. 55B.

Construction of the Collision Operator

Figure 56:
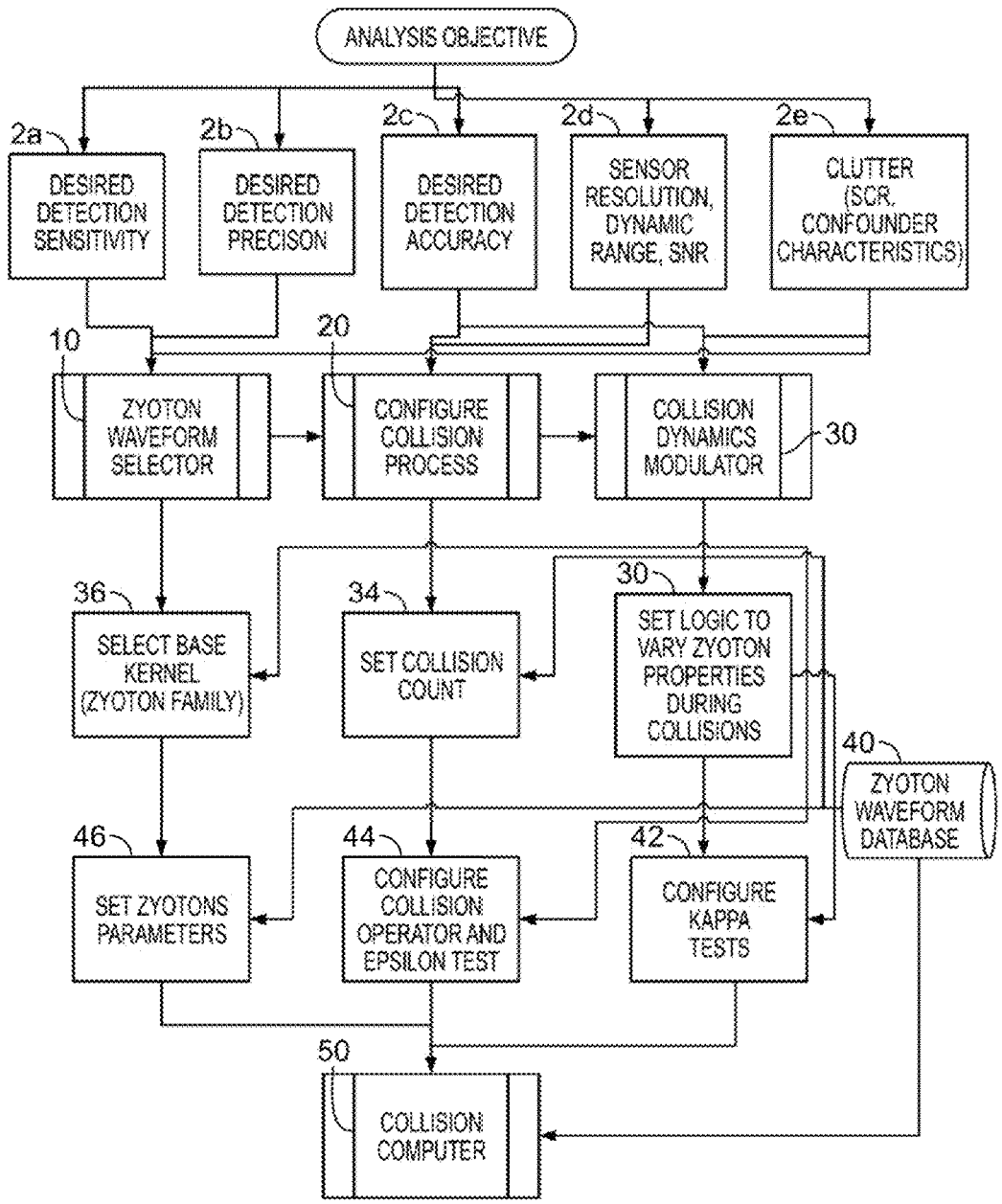
FIG. 56 depicts an exemplary process for determining one or more operating parameters of a collision computer and for generating the inputs thereof, according to one embodiment.

With reference to FIG. 56, in various embodiments, one or more of certain specific analysis objectives, 2a, 2b, 2c, 2d, and 2e are used for the selection of waveform families and/or waveform generators to be used in Zyoton and/or carrier kernel synthesis, and/or in the synthesis of Zyoton and/or carrier kernel waveforms. One or more of these objectives may also be used in selecting parameters for conditioning the extracted features, and the parameters defining the process of collision computing. The analysis objectives include: analyte detection sensitivity, i.e., how small a change in analyte quantity is required to be detected, the output concentration precision, and the accuracy of measurement with respect to a reference standard for the analyte.

One or more sensor parameters, such as resolution, sampling interval, dynamic range, sensor bandwidth, and the expected clutter absorption (i.e., expected signal-to-clutter ratio (SCR) increase that is required), may also be used for Zyoton and carrier kernel synthesis and/or in the selection of collision parameters and configuration of the collision computer. The specific Zyoton waveform selection depends on the expected required signal-to-clutter increase and the overlap between the signal and clutter observables. Both magnitude and shape similarity between the analyte and the confounders overall may drive the selection of the waveform families and/or generator functions used in Zyoton synthesis, as described above.

One or more of the sensor resolution, drift, precision, and noise characteristics may be used to set the number of frequency components of the synthesized Zyoton waveform to be used in the spectral energy computations as well as the number of frequency components of the carrier kernel waveform used for feature conditioning. The relative scale of peak energy of the Zyoton waveform and its co-dependent conditioned feature waveform are used in the determination of the scaling coefficients and scaling vectors for the conditioning process and for the collision process. The number of collision iterations required is generally proportional to the expected required SCR increase. In some embodiments, the number of collision iterations may be increased by a partial or full order of magnitude for each order of magnitude increase in the expected required SCR.

The number of collisions (also referred to as collision count parameter) may be set depending on the sensor signal-to-noise characteristics. In some embodiments, the number of collisions is initially set to 100 when the signal to noise ratio (SNR) of the sensor is 1000:1. As an example, the SNR of a spectroscopic standard can be determined by the ratio of power of a selected band (e.g. a 1 nm band) at a wavelength of interest (e.g., 1650 nm) to the ratio of background power in the same band using an NIR Diffuse Reflectance Standard with known reflectance value. The collision count parameter may be altered during calibration of the collision computer to accommodate sampling variability. The number of collisions is generally increased by an order of magnitude if the SNR of the sensor or SCR decreases by an order of magnitude. For example, in an embodiment for non-invasive glucose measurement in tissue, with SCR of $10^{-4}$, a collision count of 20,000 was used with a sensor SNR of $10^3$. In a similar manner, the number of collisions can be decreased if the SNR and/or SCR were to increase. The minimum number of collision iterations required is one. In various embodiments, the expected required SCR increase is determined by analyzing expected overlap and energy absorption due to dominant confounders which have spectroscopic absorption peaks in the same region as the analyte in the spectral bandwidth where the spectrum is acquired.

As described above, the specific properties of the collision process that are selected to estimate accurately the presence, absence, concentration, and/or rate of change of concentration over a fixed time interval (e.g., in seconds or minutes) of an analyte include the selection (or synthesis) of the collision waveform or Zyoton 10, which depends, at least in part, on the expected required SCR increase. This includes the selection of a base family of usable waveforms and the setting of one or more Zyoton parameters during synthesis thereof. Selecting the collision parameters, 20, includes selecting the number of collision iterations to be performed to assess the net absorption of energy due to the analyte of interest, and setting the collision operator, i.e., the delay shift, scaling, and phase adjustment parameters. The interaction between the frequency components of a conditioned waveform and a co-dependent Zyoton waveform generally provides a robust estimate of energy changes due to selective energy absorption by the analyte. In some embodiments, the net energy change is an energy gain in successive collision iterations. The collision computer can be configured and the colliding waveforms can be constructed such that the energy change in successive collision iterations is an energy loss.

In general, the collision between a Zyoton and a conditioned feature or between a Zyoton and a renormalized Zyoton resulting from the previous collision iteration creates a finite-range frequency component perturbation. As scattering due to the medium is inherently random, but statistically bounded in time and space, in some embodiments, Zyoton waveforms are selected that are soliton-based and which show absorption effects more strongly in the analyte-information representing k frequency components, which in some embodiments are high-amplitude components. The scattering effects are generally represented more strongly in non-analyte information representing j frequency components, which in some embodiments are low-amplitude components. The total set of frequency components of the Zyoton is described as $H=k+m+j$ where $k>0$, $m>0$, and $j\geq0$, and k and j frequency components generally do not overlap.

Such a Zyoton waveform can be constructed, as described above, using the pure component spectra of analytes (such as glucose) and pure component spectra of one or more confounders, including dominant confounders, and by modeling the scattering effects, if any, of the medium to be analyzed. The wavelength dependent absorption and scattering properties of the medium may be modeled in order to synthesize the Zyotons and carrier kernels to be used in the collisions. This knowledge from bio-optical models and chemistry generally yields suitable waveform families and generator functions for synthesizing Zyoton waveforms, and can also guide the number of frequency components that are used in the estimation of analyte-specific absorption energy.

Once the number of frequency components that can yield a robust estimate for analyte-specific absorption is established for the analyte-information representing (i.e., k), transition (i.e., m), and non-analyte information representing (i.e., j) regions of the Zyoton and carrier kernel waveforms, (e.g., k=6, 7, 10, etc., in some embodiments for non-invasive glucose measurement), the parameters of the collision grid can be computed. In addition, for computational efficiency and to limit the computer memory requirements, windowed and/or bracketed interactions may be used to implement the waveform collisions.

In various embodiments, the window length is set such that interaction of frequency components that are used in the computation of spectral energy changes due to the analyte-specific spectral absorption can be propagated from one collision to the next. In some embodiments, the window length is set such that the frequency component changes resulting from scattering effects are substantially eliminated during the truncation operation built into the collision process. In some embodiments, variations in the scattering properties of the medium may contain analyte information and, as such, at least some frequency components corresponding to the scattering properties of the medium may be retained. The renormalization performs a truncation according to the window length. Optionally, the collision parameters can be altered, 30, during the collisions. Specifically, one or more properties of Zyotons may be modified and the constraints or boundary conditions for the collision operation, e.g., the Kappa parameters described above, may be modified, to ensure that each collision is a valid interaction.

The overall process of constructing a collision computer can be summarized as follows: (a) Frequency components of the second derivative of a signal generated from pure component spectra, or frequency components of the pure component spectra themselves or of the first or other higher order derivatives of the pure component spectra, with added random noise may be used to determine the numbers (k, m, and j) of frequency components of the carrier kernel; (b) The same analysis can be used to determine the numbers (k, m, and j) of frequency components of the Zyoton, as well; (c) The spectral properties (e.g., bandwidth, morphology, etc.) of the signals and/or frequency components in step (a) above can be used to select a suitable Zyoton family; (d) The frequency of the peak component of the Zyoton can be any frequency within the family that supports the bandwidth of the signals and/or frequency components; (e) Frequencies of other Zyoton components can be selected according to the numbers k, m, and j.

Moreover, (f) Frequencies of the frequency components of the carrier kernel in some embodiments must match respective frequencies (e.g., within a value σ, where σ is defined as:

$$\frac{BW}{2(k+m+j)})$$

of the corresponding Zyoton components, where BW is the bandwidth of the carrier kernel (in Hz) and k, m and j refer to the number of frequency components of the carrier kernel as described above; (g) The amplitudes of the frequency components of the Zyoton and the carrier kernel determine the relative spectral energies of the Zyoton and the carrier kernel. (h) The amplitudes of the respective time-domain waveforms corresponding to the frequency components determine the respective velocities of the Zyoton and the carrier kernel.

During the collision iterations, truncation of a modified Zyoton, i.e., the removal of one or more frequency components of the modified Zyoton during the post-collision renormalization may cause the renormalized Zyoton (which is typically the "feature proxy" for the next collision), to be clipped. The amplitudes of the surviving components of the renormalized Zyoton frequency components are generally rescaled to reintroduce the effect of this clipping. In various embodiments, renormalization performs the rescaling (also called amplitude balancing).

Some Zyotons, however, have severe nonlinearities and such rescaling is difficult to apply to a modified Zyoton. Therefore, in some embodiments, the rescaling is applied to the original Zyoton waveform instead, to offset the clipping of the modified Zyoton that was performed to obtain the renormalized Zyoton, which is then collided with the original Zyoton as rescaled, in the next collision iteration. This may allow for a consistent, repeatable correction to be applied in each collision iteration, so as to ensure the co-dependency of the colliding waveforms. Truncation of the modified Zyoton (and downscaling thereof to remove the energy of the original Zyoton), to obtain a renormalized Zyoton, and a modification of the original Zyoton instead of amplitude rebalancing of the renormalized Zyoton, can improve the computational efficacy of the collision process and/or may reduce latency in producing the result for real-time analysis of sensor data.

In some embodiments, e.g., for glucose detection, the Zyoton properties are not changed between collisions, i.e., the same Zyotons are used. The collision operator is also not altered. In some configurations of the collision computer, however, the collision operator may be modified after each successive collision for certain applications. The selection of the parameters as described above generally specifies the collision computer 50.

As a Zyoton represents a traveling wave, its instantaneous amplitude coefficients (i.e., the absolute value of the magnitude of amplitude peaks as a function of different frequencies in the envelope of the waveform at a particular time where the envelope function of wave has a smooth curve outlining its extremes, as shown in FIGS. 12A-12C serve as initial conditions for analyzing propagation behavior through a propagation medium over time. In various embodiments, the Zyotons are synthesized such that numerical differences in propagation properties before and after collision are small and propagation of the Zyoton remains substantially unchanged in terms of the dispersion velocity and divergence thereof.

To ensure that Zyoton properties are preserved, i.e., the Zyoton is perturbed but only within certain limits, the post-collision velocity of the modified Zyoton is compared to that of the original Zyoton. Unless the difference is within a given threshold $\kappa_{DV3}$, the original Zyoton and the modified Zyoton are not acceptable for additional collisions, and the collisions are not "nearly elastic," as described above. In some embodiments, the modified Zyoton is renormalized and the velocities of the original and renormalized Zyotons can be compared to ensure that the difference therebetween does not exceed the threshold $\kappa_{DV1}$. In addition, it is also tested whether divergence of the modified Zyoton is not greater than the threshold τ. If the kappa and tau tests are both met, the collision is determined to be nearly elastic, and the perturbation of the Zyoton is determined to be within limits specified by the kappa and tau parameters. In some embodiments, the collision operator is constructed such that the divergence test need not be performed explicitly. In various embodiments, the velocity and divergence tests may be performed in the time domain and/or in the frequency domain and, accordingly, the various kappa and tau parameters may take on suitable values.

If the velocity difference and/or the divergence are outside the respective thresholds, the Zyoton may be sub-optimal as a collision entity. A new Zyoton may then be selected or synthesized, or the feature data may have a gross artifact and may be examined. One or more new features may be obtained from additional samples.

Figure 37:
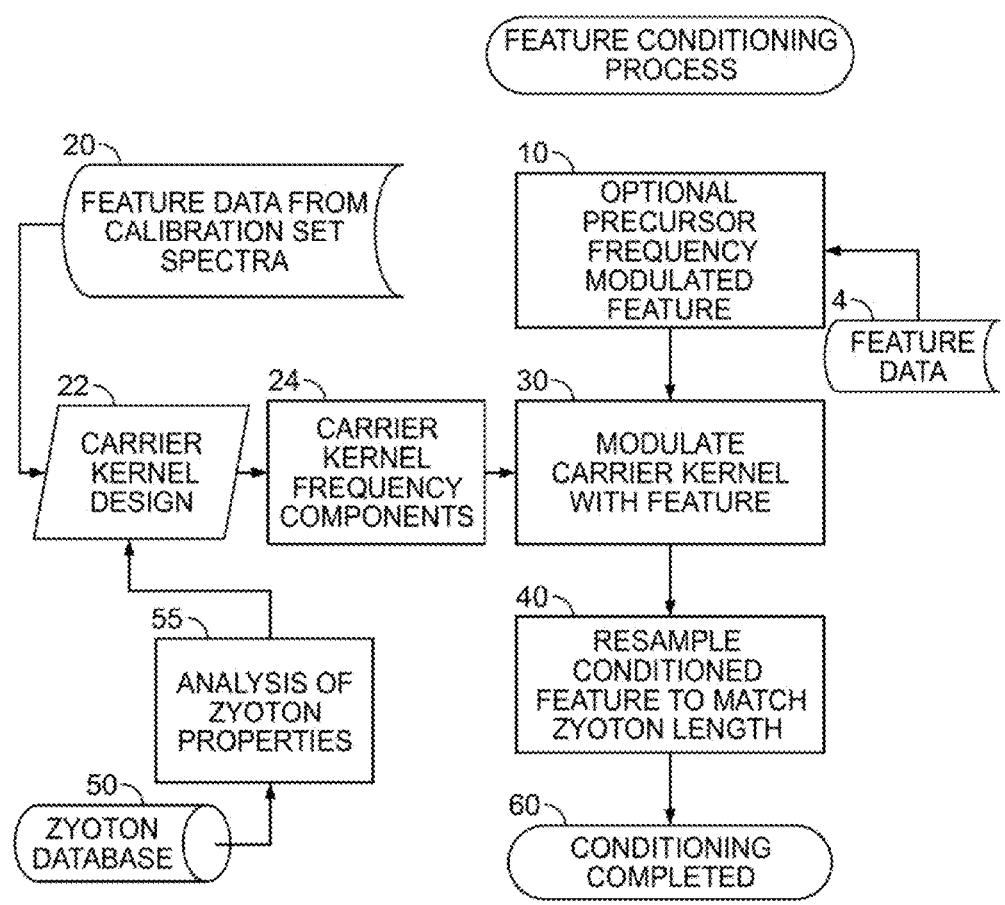
FIG. 37 depicts a process for conditioning a feature prior to collision thereof with a collision waveform, according to one embodiment.

In some embodiments, in addition to selecting/synthesizing Zyotons and carrier kernels and configuring the collision computer, the extracted features are conditioned for collisions using the process shown in FIG. 37. In particular, in some embodiments, a selected feature 4 is modulated in step 10 using a signal such as 16.5 Hz, 30 Hz, 75 Hz, 125 Hz, 500 Hz, 1 kHz, 40 kHz, 100 kHz, 260 kHz, 1 MHz, or a signal having even higher frequency. This modulation in step 10, called precursor modulation, is optional. The precursor modulation can be amplitude, frequency, or phase modulation or a combination of any two or all three of these. Alternatively, or in addition, in some embodiments, the feature is interpolated at step 10, to match its time-domain length with that of the carrier kernel. The interpolation of the feature is also optional. The feature (which may be precursor modulated and/or interpolated) is used to frequency modulate a carrier kernel at step 30, to turn that feature into a conditioned feature. To this end, frequency modulation is performed.

As described above, in some embodiments, the spectral properties of one or more spectral fragments obtained from one or more pure component spectra are used in the synthesis of the Zyoton and/or carrier kernel. In general, a spectral fragment is the portion of a spectrum between two wavelengths within the total wavelength range of the spectrum. The wavelength boundaries of these spectral fragments may correspond to the wavelength boundaries of one or more features to be conditioned using the carrier kernel. In some embodiments, the spectral properties (e.g., bandwidth, frequency distribution, etc.) of the spectral fragments are obtained at step 20 by applying a Fourier transform to a spectral fragment of the pure component spectra of the analyte of interest and/or one or more confounders typically present in the medium to be analyzed. Examples of analytes and confounders include glucose, urea, fat, collagen, water, if the medium to be analyzed is tissue or blood; gases such as radon, helium, etc., if the medium or environment to be analyzed is the atmosphere of the earth, another planet, etc.; or a chemical, if the medium to be analyzed is water in a reservoir, ocean, etc.

In step 22, one or more carrier kernels are synthesized using the spectral properties obtained in step 20 and/or additional properties such as the expected required SCR increase, and/or the SNR of the system to be used for data acquisition and measurement. In some embodiments, these various properties are used to synthesize a carrier kernel directly, while in some embodiments, these properties are used to design a Zyoton. A Zyoton may be obtained from a database 50, and the properties thereof (e.g., the frequency distribution, amplitude profile, and numbers of k, m, and j components) may be determined at step 55. As described above, a carrier kernel may then be synthesized according to the properties of the Zyoton such that the carrier kernel and the Zyoton are co-dependent.

Based on the selection of a Zyoton to be used in collision, a co-dependent carrier kernel is selected, e.g., in terms of the frequency components and amplitude profile thereof, in step 24. The selected carrier kernel is modulated in step 30 using the feature, which may be precursor modulated and/or interpolated, to obtain a conditioned feature. The conditioned feature may be resampled at step 40 to match its length with that of the Zyoton. The resampling may result in removal of one or more frequency components that were not included in the carrier kernel and/or the Zyoton, but were introduced by the modulation in step 30. The modulation in the step 30 may be performed in the time domain or in the frequency domain.

The conditioned feature may then be adjusted to ensure co-dependency thereof with the Zyoton. If the adjustment is performed in the time domain, the time-domain amplitudes of the envelope peaks of the conditioned feature are adjusted such that the absolute difference between the velocity of the conditioned feature and the scaled velocity of the Zyoton is not greater than a kappa parameter $\kappa_{DV2}$. If the adjustment is performed in the frequency domain, the frequency domain amplitudes of the k, m, and j components of the conditioned feature are adjusted such that the absolute difference between the spectral energy of the analyte-information representing k components of the conditioned feature and scaled spectral energy of the k components of the Zyoton is not greater than a frequency-domain value of kappa parameter $\kappa_{DV2}$. Alternatively or in addition, the velocity/spectral energy of the conditioned feature may be scaled and, accordingly, a suitable kappa parameter can be used to adjust the conditioned feature. The numeric scaling coefficient that establishes the spectral energy of the Zyoton with respect to the spectral energy of the conditioned feature, is denoted $\alpha_Z$.

In one embodiment for non-invasive glucose measurement, the various parameters described above were selected such that: (i) the spectral energy of the conditioned feature was adjusted to match $1/100,000^{th}$ the spectral energy of the Zyoton with which the conditioned feature was to be collided. (ii) the conditioned feature waveform was propagated on a 10,000 point grid, and (iii) in this embodiment, precursor modulation using a modulation signal at a frequency of 16.5 Hz was used in step 10.

The optional precursor modulation in step 10 is different from modulation of the carrier kernel in step 30. In systems having low instrument resolution, low SNR, and/or low SCR, (i) the number of k frequency components selected is typically greater than six, in order to create a collision computing system that may achieve the desired accuracy, and (ii) the frequency of the signal used for the optional precursor modulation in step 10 is also generally greater than 16.5 Hz, generally to bring the frequency components of the feature to a range comparable to those of the Zyoton and the carrier kernel. For example, the modulating frequency used for a system where the SNR is reduced by an order of magnitude and resolution reduced by a factor of two is 100 KHz.

In various embodiments, the collision grid is not related to the wavelength or wavenumber scale associated with the acquired data from which the features are generated. Instead, it is typically related to the maximum of the cardinality of the total set of Zyoton frequency components used in collision computing. The extracted feature can be treated as a one-dimensional data object including a vector of numbers. Once conditioned, the feature can represent an object on a spatial grid. The collision process is generally implemented on a spatio-temporal collision grid having a time dimension and at least on spatial dimension, such as x, y, or z dimension, that captures waveform propagation over time and a distance. The spatio-temporal collision grid can thus represent traveling waveforms, i.e., the Zyoton, the conditioned feature, and the modified and renormalized Zyotons. The number of spatial dimensions of the collision grid is equal to the number of spatial dimensions of the waveforms used in the collisions. Thus, if the waveforms are planar, the collision grid has two spatial dimensions. If the waveforms have three spatial dimensions, the collision grid also has three spatial dimensions and the time dimension. The conditioned feature, the Zyoton, the modified Zyoton, and the renormalized Zyoton, are all travelling waveforms on the spatio-temporal collision grid. A single collision iteration may analyzed over e.g., a 1,000; 2,000; 5,000; 10,000; 20,000; 100,000 point collision grid.

The carrier kernel and the Zyoton properties are related and the two are co-dependent, because, among other reasons as described above, they both depend on the expected required SCR increase and/or the SNR of the measurement system. Thus, both waveforms are dependent on the expected SCR increase required to discern energy loss due to absorption at the feature level. For some media/environments to be analyzed, the expected required SCR increase can range from four to six orders of magnitude using Zyoton frequency bandwidths of hundreds of kHz to tens of MHz. In some embodiments, the carrier kernel may optionally be frequency matched to the Zyoton or may have a higher frequency bandwidth.

As described above, a conditioning process is applied to all of the features of the acquired spectra, which generally involves frequency modulation of a carrier kernel. Unlike a constant-frequency carrier signal typically used in typical amplitude modulation (AM) or frequency modulation (FM), as in modulation of radio-frequency (RF) signals, the carrier kernel modulated by the feature is a complex waveform itself, having several frequency components having different amplitudes. A carrier kernel has three specific properties: (i) it is frequency matched, at least to some degree, to the Zyoton; (ii) the Zyoton is designed so that its properties are unchanged within limits specified by dispersion velocity and divergence parameters when collided with the conditioned feature, in terms of morphology and peak frequency components. As the preservation of Zyoton properties is a key design constraint, the carrier kernel modulated by each feature is selected such that Zyoton propagation after collision is not significantly altered, as specified by the dispersion velocity and divergence parameters; and (iii) the carrier kernel is constructed to mitigate interference from random noise, sampling variability, and other measurement transients in the feature and to improves the dynamic range of measurements.

Modulation of a carrier kernel generally provides smoothing of random noise in the feature and can increase dynamic range of measurement at the same time. An example of a waveform family used to generate a carrier kernels, denoted $G(t)$, is:

$$G(t) = \frac{1}{2\pi i} \int_{-i\infty}^{i\infty} [E(s)]^{-1} e^{st} ds \quad (-\infty < t < \infty), \quad (12)$$

where $$E(s) = \prod_{1}^{\infty} \left(1 - \frac{s}{a_k}\right) e^{s/b_k},$$

and $a_k = b_k + i c_k$ ($k = 1, 2, \ldots$) being a sequence of complex numbers such that $$\Sigma_{k=1}^{\infty} (1/b_k)^2 < \infty,$$

and $$\Sigma_{k=1}^{\infty} (c_k/b_k)^2 < \infty.$$

The constant k in the above equation (which is different from the number of analyte-information representing components k in a carrier kernel and/or a Zyoton), is set to 2000 in some embodiments so that the conditioning process can eliminate sampling-related transients that may occur.

A conditioned feature denoted as a Feature Waveform (FWi) in the collision equation below, i.e., a carrier kernel modulated using a feature, must optionally match the time-domain length of its paired Zyoton (Zi). But the two, the Zyoton waveform and the conditioned feature waveform, have typically different lengths in the time domain. To match the morphology, including the waveform lengths, a conditioned feature may be down-sampled as described above in step 40 (FIG. 37), e.g., from 10,000 points to 2,000 points. Additionally, or in the alternative, the Zyoton can be down-sampled to match the lengths of the two waveforms. In some embodiments, the conditioned feature and/or the Zyoton are up-sampled so that the lengths of their time-domain representations match. Optional truncation of FWi is implemented to prune the collision spatio-temporal grid, e.g., for computational efficacy. The choice of collision grid parameters is related to the selected properties of the Zyoton. For example, the length of the collision grid must be greater than the length of a time-domain representation of the Zyoton.

As described above, the co-dependency condition requires the change in post-collision dispersion velocity to be less than a threshold $\kappa_{DV1}$. The collision grid can establish a reference scale for the variable $\kappa_{DV1}$. In general, the parameter $\kappa_{DV1}$ is inversely proportional to both the time and space dimensions of the collision grid. This has the general effect of numerically establishing $\kappa_{DV1}$ as a target value for each system.

Amplitude adjustment of the conditioned feature is typically performed as described above, generally to adjust the amplitudes of the frequency components of the conditioned features FWi to a fraction of the peak amplitudes of all Zyotons that may be used in the collision. Amplitude adjustment completes the feature conditioning process, and is implemented for all features e.g., those extracted from all acquired spectra in a multiple illumination sequence (MIS), as described below.

The collision operation generally entails six steps. The first step is initialization of the collision time scale. The next step is computation of the collision-computing parameters. The generalization of the collision operator is given by equation (13):

$$\Omega(\overline{FW}_i, \overline{Z}_i)_{t_k} = \begin{cases} \varepsilon(\eta(\varpi(\overline{Z}_i, \overline{\alpha}, \overline{\delta}, \phi) \otimes \rho(\overline{FW}_i, \overline{\beta}, \overline{\delta}))) & k=1 \\ \varepsilon(\eta(\varpi(\overline{Z}_i, \overline{\alpha}, \overline{\delta}, \phi) \otimes \rho(\Omega(\widehat{FW_i, Z_i})_{t_{k-1}}, \overline{\beta}, \overline{\delta}))) & k>1 \end{cases} \quad (13)$$

where $\Omega(\overline{FW}_i, \overline{Z}_i)_{t_1}$ is the result of a collision interaction between the feature wavefront FWi and Zyoton $\overline{Z}_i$ after the first collision. Also, $\Omega(\overline{FW}_i, \overline{Z}_i)_{t_k}$ is the result of collision interaction between the renormalized feature wavefront resulting from the (k−1)th collision and Zyoton $\overline{Z}i$.

The term k denotes collision iteration count in the above equation, and covers the case that includes only a single collision, as well as multiple (or $\mathbb{N} = k > 1$) collisions, where $\mathbb{N}$ is the total number of collision iterations, and is a collision-computing parameter.

Variable $t_k$ ranging from 1 to k denotes the index on the grid for collision, with $t_k$, representing the kth point on the grid. k typically ranges from 1 to 100,000 depending on the signal-to-clutter increase desired.

$\Omega(\widehat{FW_i, Z_i})_{t_{k-1}}$ are the renormalized results of (k−1)th collision that is used in the kth collision. The collision iterations can be performed in the time domain or in the frequency domain.

In the time domain, the collision-computing parameter $\bar{\alpha}$ denotes the scaling vector. The scaling depends on the desired dynamic range in the post-collision energy change desired. In one embodiment, the scaling vectors are chosen to amplify the change in detected energy over a dynamic range that extends over eight orders of magnitude. Such a dynamic range can be required, e.g., if the original feature were extracted from a spectrum acquired from a human subject with tissue glucose concentrations varying between 20 mg/dl and 600 mg/dl. In the mathematics of Zyoton wavefront propagation dynamics, the scaling vector relates to the speed at which the zyoton wavefront propagates in media, some of which may be anisotropic or time-varying. In physical terms, the scaling vector $\bar{\alpha}$, can control the speed of the Zyoton wavefront propagation, and thus controls the amplification applied to the spectral energy of the conditioned feature during the collision operation. Values of elements of $\bar{\alpha}$ typically range between $10^5$ and $10^{-5}$, depending on the amplitude of the Zyoton waveform peaks in the time domain.

The collision-computing parameters of delay and phase rotation can mitigate noise. Some portion of the noise may be correlated with the overall measurement system, e.g., the radiation emission and detection subsystem. Some portion of the noise, e.g., noise resulting from properties of the medium to be analyzed, may be uncorrelated to the overall measurement system. $\bar{\delta}$ denotes the delay shift vector used to align the elements of the Zyoton and the conditioned feature wavefronts. The delay $\bar{\delta}$ and phase rotations $\Phi$ may be optionally applied to the time-domain representation of the Zyoton or conditioned feature. Zyoton morphology is related to the delay shift parameter, in that specific zyotons may have substantial numbers of closely-related frequency components that require an appropriate selections of $\bar{\delta}$. This delay is related, in the glucose example, to the actual spectral wavelength resolution of the instrument used to acquire the spectrum from which the feature is extracted, with lower resolutions requiring larger delay values. This same $\bar{\delta}$ may be used if all features have the same cardinality in terms of the number of spectral elements, e.g., 32 points in the noninvasive glucose embodiment. If the cardinality or feature length is different, then a different $\bar{\delta}$ is used for each feature. This delay can also capture the expansion of the frequency bandwidth in the original feature by the optional precursor modulation by the conditioning operation. Physically, $\bar{\delta}$ compensates for the delay in transferring energy from principal frequency components of the original feature and those of the Zyoton. The numerical elements of the delta vector are related functions of the length of the Zyoton waveform in the time domain, and to the amount of sensor noise. If a delay is not desired, all values of $\bar{\delta}$ are set to null. Proper $\bar{\delta}$ selections allow precise time-scale alignment of the feature waveform and Zyoton in the computer memory prior to collision.

Collision-computing parameter $\Phi$ represents the phase rotation applied to the Zyoton in the time domain, with values below $\pi$ radians and typically ranging between 0.1 radian and 0.0001 radian. If no phase rotation is to be applied, then $\Phi$ is set to $2\pi$ radians. In addition to compensating for the dimensional deficiency of the zyoton described above, phase rotation is used to eliminate the impact of spectrum-to-spectrum variations of random noise in the data, changes in scattering which could be due to changes in the medium, and changes in the absorption of confounders whose absorption overlaps with that of the analyte in the spectral region as of the feature.

Optionally, $\bar{\beta}$ and $\check{\beta}$ are used to insure that the kappa test is met in the time domain. Collision-computing parameter $\bar{\beta}$ denotes the optional scaling vectors for the conditioned feature wavefront, and can be used if the Zyoton is not scaled in performing the Kappa test. If scaling is not desired, all values of $\bar{\beta}$ are set to unity. The $\bar{\beta}$ scaling generally impacts the amplitude of the time-domain peaks of the conditioned feature waveform, and can adjust the velocity of the conditioned feature waveform. Implicitly, this results in the scaling of the frequency domain amplitudes of the conditioned feature, leading to an adjustment of the energy of the conditioned feature waveform.

Collision-computing parameter $\check{\beta}$ denotes the optional scaling vectors for the renormalization of the modified Zyoton following the collision. If scaling is not desired, all the values of $\check{\beta}$ are set to unity. This $\check{\beta}$ scaling of amplitudes of the modified Zyoton is used to adjust its velocity in the time domain, and results in the scaling of frequency domain amplitudes of the renormalized modified Zyoton, and thereby and adjusts the energy of the Zyoton. In various embodiments, this scaling is done so that kappa tests, e.g. $\kappa_{DV1}$ and/or $\kappa_{DV3}$ tests, are met in the next collision iteration. The scaling vectors $\bar{\beta}$ and $\check{\beta}$ are not necessarily related; the former is used in testing the velocity condition of the two co-dependency conditions, and the latter is used to adjust the velocity during renormalization.

The parameter $\bar{\omega}$ represents the fully conditioned Zyoton vector prior to a collision, wherein the conditioning operation includes of scaling using $\bar{\alpha}$, and delay-shift $\bar{\delta}$ and phase rotation $\Phi$ operations. The parameters $\bar{\alpha}$, $\bar{\delta}$ and $\Phi$ are interrelated and chosen such that the spectral energy change during a collision between, for example, a feature with strong analyte signal and one with weak analyte signal content derived from the same spectrum could be separated by six to eight orders of magnitude. Calibration set data, using known concentrations of the analyte of interest in a calibration medium, can be used to derive these parameters. Improper or inconsistent selection will yield limited utility in detection of analytes in the presence of confounders and biological or instrument noise. If no scaling, delay shift or phase rotation is applied, then $\bar{\omega}$ is set to unity. Typically $\bar{\omega}$ is set to unity for in-vitro analysis embodiments where the medium is much simpler than in the tissue glucose embodiment.

The parameter $\rho$ represents the fully conditioned feature-derived wavefront $\overline{FW}i$ vector prior to a collision, wherein the conditioning operation includes optional scaling using $\bar{\beta}$, and delay-shift $\bar{\delta}$ operations. The coefficients $\bar{\beta}$ and shift $\bar{\delta}$ are selected in the similar manner as for the Zyoton Wavefront. The collision operator, Zyoton design and selection, feature conditioning and collision operator parameters are codependent. The parameters $\bar{\beta}$ and $\bar{\delta}$ are interrelated and chosen such that the spectral energy change during a collision between for example, a feature with a strong analyte signal and one with a weak analyte signal content derived from the same spectrum can be separated by six to eight orders of magnitude during a collision. Calibration set data, using known concentrations of the analyte of interest in calibration media are used to derive these parameters. If no scaling or delay shift is applied, then $\rho$ is set to unity.

As discussed herein, scaling takes two forms in the collision process. Prior to the first collision, the spectral energy of a Zyoton waveform is initially designed set to a multiple of the spectral energy of an expected conditioned feature. After a collision, the modified Zyoton is renormalized, which entails down-scaling in the frequency domain. The design of the carrier kernel and zyotons is an iterative process, and the initial waveforms chosen are refined as indicated by performance of the collision-computing process. The scaling vectors need to be computed prior to and after each collision, and are feature dependent.

The collision-computing parameter η denotes the bracket operator to which the delay-shift $\bar{\delta}$ is applied during collision. It represents the localization parameter for the collision. Different bracket lengths, e.g., of 100, 1000, or 2000 may be used. For example, a bracket length of 2000 frequency components is used for non-invasive measurement of the concentration of some analytes. If no bracket operator is applied then, η is set to unity and the collision reduces to a phase rotation with a shift delay operation.

The collision-computing parameter s denotes the compression operator applied to the collision process. This is used to squeeze the result (i.e., down-sample) the results of the wavefront to a fixed length post-collision. If no compression is applied, then s is set to unity. The generalized collision operator $\Omega(FW_i, Z_i)$ achieves a localized excitation of the Zyoton wavefront, propagating in a system with constant velocity and colliding with a feature-derived wavefront such that the feature-wavefront presents a modulating influence on the stable Zyoton. The energy transfer, i.e., loss during the collision, is related to the energy of the feature wavefront.

The collision grid is established prior to the collision. Optional scaling of the Zyoton by $\bar{\alpha}$ is also performed prior to the first collision. Any optional scaling of the conditioned feature waveform by $\bar{\beta}$ is also conducted prior to collision. Alignment of the frequency components, achieved via delay and phase shift operations, is performed during collisions. The alignment could optionally be performed before or after the collisions in the frequency domain as well. The collision-computing parameters, including phase shift, delay, bracket, compression are used during the collision process.

Bracketing in the time domain can be achieved by truncating the time-domain representations of a Zyoton waveform, a conditioned feature, and/or a renormalized Zyoton according to the time-domain length of the bracket. However, bracketing in the frequency domain is preferred. Alternatively or in addition, bracketing in the time domain can restrict the zyoton dimensionality and/or or phase. The selected points of a time-domain waveform generally result in a corresponding bracket in the frequency domain. As such, in various embodiments, bracketing is implemented in the frequency domain by selecting a subset of fixed number of frequency components k, m, and j of the conditioned feature. The frequency domain bracket length specifies the total number of frequency components of a waveform that are selected. In various embodiments, the k components are not removed during the truncation that is performed during the implementation of a bracket. A key difference between truncation as part of renormalization and frequency domain bracketing is that in renormalization the energy of the removed components is redistributed, while in bracketing such redistribution is not done because frequency components (typically the j components) from the Zyoton and the conditioned feature or renormalized Zyoton are removed.

During the overall collision process, the truncation operation is optionally performed at three steps: In step (i) during the feature conditioning process when convolving the feature with the carrier kernel for the purpose of making a conditioned feature and the Zyoton the same length in the time domain, and optionally for computational efficacy as truncation reduces the size of the collision grid; in step (ii) during the collision operation, through the bracketing operation in the frequency domain to constrain the set of resulting frequency components to capture energy changes in the spectral feature due to absorption by the analyte and to delete frequency components that are only related to random scattering losses; and in step (iii) during the renormalization step, in the frequency domain, to remove frequency components that not are not related to energy absorption by the analyte.

In some embodiments, the collision process may be implemented in the frequency domain, where the symbol ⊗ represents a bracketed interaction operator which effects the collision process described below. The bracketed interaction typically involves from one to several thousand frequency components of the Zyoton and the conditioned-feature waveforms. For computational efficacy, efficient use of storage, and to immunize the system against random noise, typically only selected frequency components are used in the post-collision energy change computations. The bracketed interactions are set such that all frequency components in the conditioned feature waveform and original Zyoton that contribute to the computation of energy gain are used.

More importantly, the truncation window (or the number of frequency components retained after collision) is typically chosen to be long enough to accommodate all the frequency components of original waveforms that are likely to contribute to the computation of the energy gain due to the analyte over the complete set of collisions in each collision iteration and over all collision iterations. For example, in one embodiment where the energy computation uses 6 to 20 k-frequency components, but involves 20,000 collisions, the number of retained frequency components was chosen to be 1,000, after several trials, to amplify energy absorbed by the analyte while eliminating the absorption of energy by confounders and the effects of scattering and random noise.

The table below describes different stages of the overall collision process for different types of collisions. (All operations are assumed to occur in the frequency domain):

TABLE 8

| | Number of Frequency Components in the Original Zyoton (Z) | Number of Frequency Components in The Conditioned Feature (CF) | Number of Frequency Components in the Modified Zyoton (Z') | Number of Frequency Components in the Renormalized Zyoton (Z'') |
|---|---|---|---|---|
| At Synthesis, Prior to Any Collisions | (k + m + j) = 10,000 | (k + m' + j') = 11,000 | (Z') does not exist | (Z'') does not exist |
| After the Bracketing Performed Prior to the First | (k + m + j) = 2,000 Energy of the 8,000 frequency components that | (k + m + j) = 2,000 Energy of the 9,000 frequency components that | (Z') does not exist | (Z'') does not exist |

TABLE 8-continued

| | Number of Frequency Components in the Original Zyoton (Z) | Number of Frequency Components in The Conditioned Feature (CF) | Number of Frequency Components in the Modified Zyoton (Z') | Number of Frequency Components in the Renormalized Zyoton (Z") |
|---|---|---|---|---|
| Collision | are removed is not redistributed across the remaining 2,000 components | are removed is not redistributed across the remaining 2,000 components | | |
| After the First Collision | With respect to the completed collision iteration, Z does not exist. For the next collision iteration, previously bracketed Z can be extracted from memory (k + m + j) = 2,000 | CF does not exist | (k + m" + 30j") = 2,200 | (Z") does not exist prior to renormalization |
| After the First Renormalization, Which Is Same As Prior to the Next Collision Iteration | Same as above. (k + m + j) = 2,000 | CF does not exist | (Z') does not exist after renormalization | (k + m + j) = 2,000 Energy of the 200 frequency components that are removed is redistributed across the surviving (m + j) components |

Collision computing provides a mechanism whereby a source waveform is collided, (through the pseudo-convolution process described above in a computer processor) with a Zyoton, a waveform constructed to function as an energy amplification mechanism. The medium properties may be constant or time-varying (due to diffusion, flow, etc.). Also, the medium may be isotropic or anisotropic, and of uniform composition or spatially varying composition.

Process of Collision Computing

As described earlier, a Zyoton is a traveling waveform, i.e., a Zyoton has a temporal dimension and at least one spatial dimension. A representative Zyoton Z includes k high energy components having amplitudes and frequencies as: $(A_1, \Omega_{Z1}), (A_2, \Omega_{Z2}), \ldots, (A_k, \Omega_{Zk})$, where k>0; optionally, m medium energy components having amplitudes and frequencies as: $(A_{k+1}, \Omega_{Zk+1}), (A_{k+2}, \Omega_{Zk+2}), \ldots, (A_{k+m}, \Omega_{Zk+m})$, if m>0; and j low energy components having amplitudes and frequencies $(A_{k+m+1}, \Omega_{Zk+m+1}), (A_{k+m+2}, \Omega_{Zk+m+2}), \ldots, (A_{k+m+j}, \Omega_{Zk+m+j})$, where j>0. A representative conditioned feature CF that is to be collided with the representative Zyoton Z, where CF is also a traveling waveform, generally has at least k+m'+j' frequency components: $(a_1, \Omega_{CF1}), (a_2, \Omega_{CF2}), \ldots, (a_k, \Omega_{CFk}), (a_{k+1}, \Omega_{CFk+1}), (a_{k+2}, \Omega_{CFk+2}), \ldots, (a_{k+m'}, \Omega_{CFk+m'}), (a_{k+m'+1}, \Omega_{CFk+m'+1}), (a_{k+m'+2}, \Omega_{CFk+m'+2}), \ldots, (a_{k+m'+j'}, \Omega_{CFk+m'+j'})$, where m'+j'≥m+j.

FIG. 17 illustrates the collision between a representative zyoton Z and a representative conditioned feature CF on a synthetic "collision space-time" domain grid. FIG. 18 symbolically depicts the synthetic-domain collision, where the wavefronts of Z and CF collide at a synthetic line of collision on the synthetic space-time grid at time $t_0$. In the real time domain, the velocity of a Zyoton is several times (e.g., a few hundred, a few thousand, a few hundred thousand times, etc.) greater than the velocity of the conditioned feature. Therefore, in the real time-domain collision, the conditioned feature is virtually stationary relative to the Zyoton, and during collision, the Zyoton sweeps across the conditioned feature.

In various embodiments, the Zyoton-conditioned feature collision is computationally implemented in the frequency domain. To this end, a magnitude spectrum of the frequency components of a Zyoton can be obtained by applying a Fourier transform to a time-domain Zyoton waveform, and, similarly, a magnitude spectrum of the frequency components of a conditioned feature can obtained by applying a Fourier transform to a time-domain conditioned feature waveform. Zyotons synthesized from generator functions, polynomial sequences, or one or more waveform families enumerated above, are first generated as numerical sequences, where the elements of the numerical sequence are considered to be analogous to a time domain representation of the Zyoton.

Figure 57:
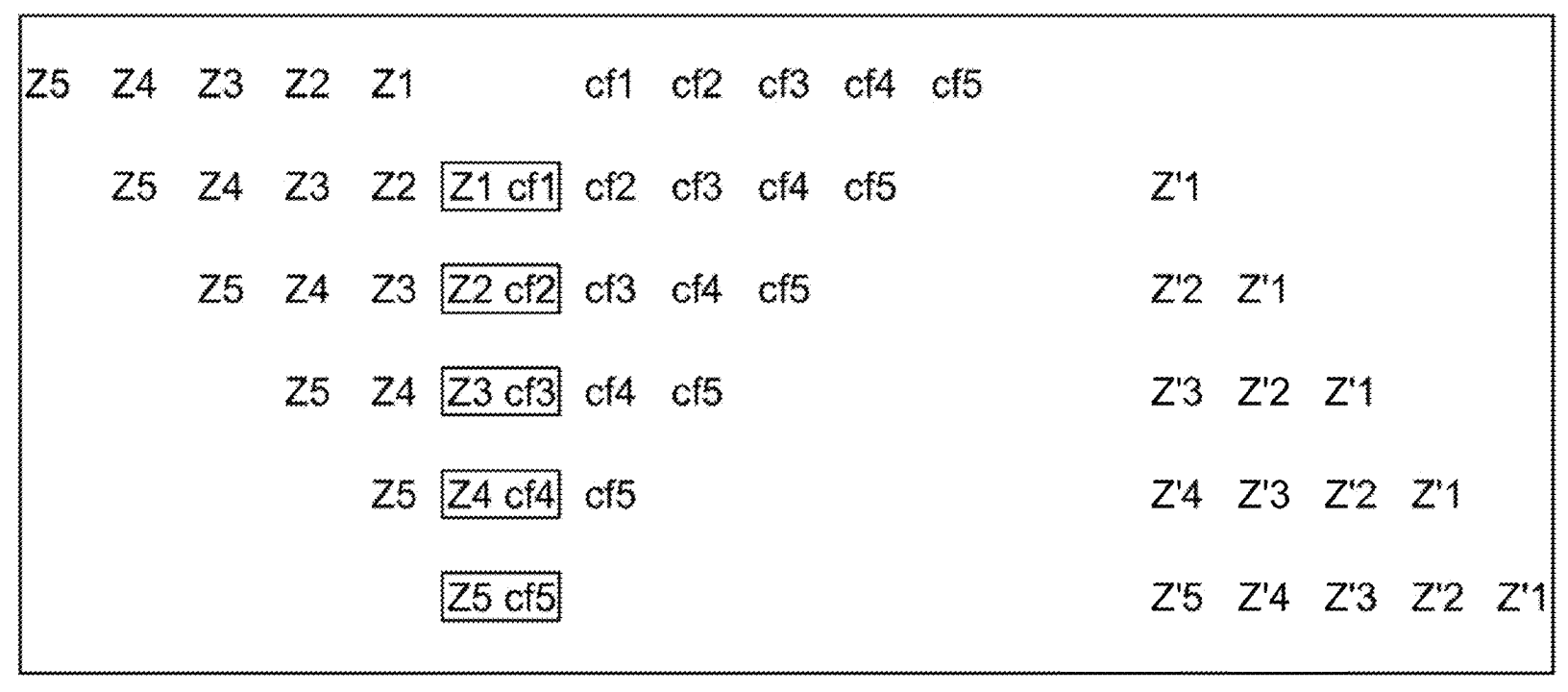

In various embodiments, the frequency-domain collision of Z and CF is implemented using the respective sorted magnitude spectra thereof, i.e., magnitude spectra sorted by amplitudes. In a frequency-domain collision, the frequency components of the Zyoton interact ("collide") with selected components of the conditioned feature in a carefully controlled process called bracketed collision interaction. A pictorial representation of the collision process is shown in FIG. 57 in a synthetic grid, i.e., regardless of the domain of implementation, where the components of the zyoton Z are shown as moving from left to right, and the components of the conditioned feature, CF move from right to left toward a line of collision or interaction at the center.

Each successive row, moving from top to bottom, represents one "time unit" of this synthetic grid, i.e., the in the top row, the two components Z1 and CF1 have not yet interacted; on the second row Z1 and CF one have interacted, indicated by "Z1CF1" in the center. The "Z1CF1" designation and similar designations "ZiCFi" in the subsequent rows in FIG. 57 does not imply a conventional convolution or a simple multiplication of the two elements. Rather this designation symbolically represents the collision interaction between elements Zi and CFi. In actuality, the collision interaction with each Zi involves more than one conditioned feature components, as controlled by the collision bracket length, as described below, but in the symbolic representation only CFi is shown for clarity. At the right of the second row is shown a new frequency component, Z'1, of the modified Zyoton. Here again, in actuality as described below, a number of new modified Zyoton components may be produced in each collision interaction, but only one is shown in this symbolic representation for clarity.

Each pair of components interacts successively as described below, producing new frequency components of the modified zyoton, Z'2, Z'3, etc., from the interaction. These new components include the energy transferred from the conditioned feature to the modified Zyoton during the collision process. FIGS. 46B-47C depict a sorted (in descending order) magnitude spectrum of a Zyoton. The Y axis shows the amplitudes and the X axis shows frequencies according to an index and not actual frequencies because in a sorted magnitude spectrum, the frequencies are typically not in a sorted order.

In the representations of Zyotons and conditioned-feature described above, without the loss of generality:

$$A_1 > A_2 > \ldots > A_k > A_{k+1} > A_{k+2} > \ldots > A_{k+m} >$$
$$A_{k+m+1} > A_{k+m+2} > \ldots > A_{k+m+j};$$

and $$a_1 > a_2 > \ldots > a_k > a_{k+1} > a_{k+2} > \ldots > a_{k+m} >$$
$$a_{k+m'+1} > a_{k+m'+2} > \ldots > a_{k+m'+j'}.$$

In general, for a component index v, amplitude $A_v > A_{v+1}$ and amplitude $a_v > a_{v+1}$, but $\Omega_{Zv}$ can be greater than or less than $\Omega_{Zv+1}$ and, similarly, $\Omega_{CFv}$ can be greater than or less than $\Omega_{CFv+1}$.

The Zyoton and the conditioned feature to be collided therewith are constructed, however, such that for each of the k components: $|\Omega_{Zv^k} - \Omega_{CFv^k}| \leq \epsilon_k \Omega_{Zv^k}$, $v^k = 1, \ldots, k$. In various embodiments, $\epsilon_k$ can range from 0.0001 up to 0.0005. Thus, if $\epsilon_k = 0.005$, for each k component, having a component index $v^k$, the frequency of the conditioned feature, denoted $\Omega_{CFv^k}$, is within (i.e., neither greater than nor less than) 0.05% of the frequency of the Zyoton, denoted $\Omega_{Zv^k}$. Furthermore, for each of the m components: $|\Omega_{Zv^m} - \Omega_{CFv^m}| < \epsilon_m \Omega_{Zv^m}$, $v^m = (k+1), \ldots, (k+m)$, and for each of the j components: $|\Omega_{Zv^j} - \Omega_{CFv^j}| < \epsilon_j \Omega_{Zv^j}$, $v^j = (k+m+1), \ldots, (k+m+j)$. Collectively, we define the constraint imposed by $\epsilon_k$, $\epsilon_m$ and $\epsilon_j$ as Epsilon Tests. In various embodiments, $\epsilon_m$ can range from 0.001 up to 0.025, and $\epsilon_j$ can range from 0.001 up to 0.1. Thus, if $\epsilon_m = 0.025$, for each m component, having a component index $v^m$, the frequency of the conditioned feature, denoted $\Omega_{CFv^m}$, is within 2.5% of the frequency of the Zyoton, denoted $\Omega_{Zv^m}$. Similarly, if $\epsilon_j = 0.1$, for each j component, having a component index $v^m$, the frequency of the conditioned feature, denoted $\Omega_{CFv^j}$, is within 10% of the frequency of the Zyoton, denoted $\Omega_{Zv^j}$.

In some situations, a conditioned feature CF may have extra m and/or j components. In one example, the Z has six k components (Z1-Z6), three m components (Z7-Z9), and five j components (Z10-Z14). The CF to be collided with Z has six k components (indexed CF1-CF6), but four m components (CF7-CF10), and six j components (indexed CF11-CF16). In such cases the frequency relationship $|\Omega_{Zv^m} - \Omega_{CFv^m}| < \epsilon_m \Omega_{Zv^m}$ and $|\Omega_{Zv^j} - \Omega_{CFv^j}| < \epsilon_j \Omega_{Zv^j}$ is imposed as before for the corresponding Z and CF components identified by the indices $v^m$ and $v^j$. For some CF components, however, there is no corresponding Z component. In the foregoing example, CF10, an m component, does not correspond to Z10, which is a j component of the Zyoton. The Epsilon Tests are nevertheless satisfied in various embodiments for these unmatched components by ensuring that the frequency of an unmatched CF component of the "m" group is within $\epsilon_m$ of at least one m component of Z. Similarly, it is ensured in various embodiments that the frequency of an unmatched CF component in the "j" group is within $\epsilon_j$ of at least one j component of Z. For example, CF10 must be within $\epsilon_m$ of any one of Z7 through Z9, and each of CF15 and CF16 must be within $\epsilon_j$ of any one of Z10 through Z14. If this condition is not met, the kappa test(s), described elsewhere, may fail and a redesign of either the zyoton, the carrier kernel, or both, may be required.

The conditioned feature is obtained via a frequency modulation of the carrier kernel by the feature. The feature may have been optionally frequency modulated, using a pre-cursor modulation signal such as a sinusoidal signal having a frequency of 16.5 Hz, 60 Hz, 100 Hz, 1.2 kHZ, 100 kHz, 175 kHz, etc. Even if frequencies of all k (and m and/or j) components of the carrier kernel are initially selected to be identical to the corresponding Zyoton component frequencies, this modulation can create slight differences between the frequencies of the k (and m and/or j) components of the conditioned feature and those of the unmodulated carrier kernel. The amplitude/magnitude sorted Zyoton and conditioned feature, where the frequencies of the respective Zyoton and conditioned feature components are related according to $\epsilon_k$, $\epsilon_m$, or $\epsilon_j$, are denoted F(Z) and F(CF), respectively.

The frequency-domain collisions are implemented on a frequency domain collision grid, with collision coefficients including a collision grid length $K \leq (k+m+j)$ and a bracket length $CB < (k+m+j)$. If the collision begins at the interaction step $g_0$ on the collision grid, at step $g_{(i)}$ the frequency component $F_{Z(i)}$ of the Zyoton F (Z) interacts with a corresponding frequency component $F_{CF(i)}$ of the conditioned feature F (CF). Note that these interaction steps do not necessarily correspond to the real time associated with the traveling waveforms in the time domain. In a computer implementation, the time period between successive grid points, i.e., computation steps can be set to the reciprocal of the length of the Zyoton frequency vector used in the collision times the square of the length of the collision bracket, i.e., time period=

$$\frac{1}{(k+m+j) * CB^2}.$$

"Time" here is the duration of computation/interaction steps involved in a collisions that includes all interactions between Zyoton and conditioned feature frequency components during a single iteration of the overall collision process. A single collision iteration can produce a maximum of (K−δ)*CB frequency components of the modified Zyoton, where δ represents a shift-delay. If no shift-delays are needed, δ is equal to zero. The frequency-domain collision grid can therefore be represented as a numerical vector of time points or indices $\{g_0, g_1 \ldots g_{(K-\delta)*CB}\}$. This number of interaction steps in a single collision iteration is different from the number of steps required in an element-by-element multiplication, and in a conventional convolution, as well, for the reasons described below.

The collision interactions can be carried out in configurations ranging from completely parallel implementation, where each Zyoton frequency component interacts simultaneously with each conditioned feature frequency component from the corresponding bracketed set of CF frequency components, to a completely sequential implementation, where each operation in each interaction occurs one at a time, in sequence. In various embodiments, the number of grid points of the collision grid in the frequency domain can vary depending on the computational configuration employed, but more grid points are generally required as the configuration becomes more sequential.

The collision-computing coefficient, $\delta \geq 0$, is an index shift parameter (i.e., it shifts frequency components of the Zyoton) or a delay coefficient in frequency domain collisions. If $\delta$ takes values greater than 0, it can result in shifts of the Zyoton frequency components that interact with the frequency components of the conditioned feature.

With reference to FIGS. 38-41, in one example, N=k+m+j=10 and CB=4, and $\delta$=0, and, as such, collisions can be performed for the Zyoton components Z1 through Z7. The collision grid length K=N−CB+1 is 7, for a partially sequential, partially parallel implementation. The minimum number of interaction steps, however, is (K)*CB where each frequency component interaction is performed in a sequential manner over all K Zyoton components and associated K brackets of CF components; or K where each CF component of the collision bracket interacts with the corresponding Zyoton component in parallel. In this example, the shift coefficient $\delta$ is zero. For computational efficacy, a collision grid can be set to be evenly spaced with a time interval of 1 picosecond, 1 nanosecond, 1 microsecond, 1 millisecond, or 1 second, up to 1 minute. In some embodiments, the time interval is set to be less than $$\frac{1}{(k+m+j)*CB^2}.$$

seconds.

The result of a collision interaction between the Zyoton Z and the conditioned feature CF according to various embodiments, when converted back to the time domain, is a non-invertible combination of the Zyoton and the conditioned feature. In the frequency domain, this interaction can be described as bracketed conditional amplitude multiplications between each Z and a set of CF components, and conditional summations of the amplitudes of two or more components resulting from the bracketed multiplication. As described below, the conditions for the conditional amplitude multiplication and for the conditional amplitude summations are whether the frequencies of interacting components match.

For the conditional multiplication, the amplitudes of a pair of Z and CF components are multiplied if and only if the frequencies of those two components satisfy an applicable Epsilon test. The applicable Epsilon value (i.e., $\epsilon_k$, $\epsilon_m$, or $\epsilon_j$) is determined according to the energy group (i.e., k, m, or j) to which the Z component of the interaction belongs. Similarly, for a conditional summation the amplitudes of two or more resulting components of the overall collision interaction are summed if and only if the frequencies thereof satisfy the Epsilon test applied to the Zyoton component with the largest magnitude. The conditional multiplications and summations generally makes the collision interaction non-invertible. While conventional modulations techniques are generally invertible, the overall collision process described herein, which may additionally include scaling, shifting, and/or phase rotation of frequency components, is not a conventional modulation, and is generally not invertible.

Post-collision, the modified Zyoton generally includes new frequency components that were not present in the original Zyoton and the conditioned feature. Interactions between the Zyoton and the conditioned feature described below may introduce new frequency components, but because of the amplitude mismatch between the frequency components of the Zyoton and those of the conditioned feature, the amplitudes of those new frequency components are typically smaller than the amplitudes of the k components of the Zyoton. The renormalization process is designed to remove some of these components via truncation.

The frequency-domain collision of the Zyoton and the conditioned feature may then be expressed in the form of a pair-wise (i.e., component by component) conditional multiplication of the (optionally shifted, scaled, and/or phase-rotated) components of the zyoton by all the components of the conditioned feature within a bracket. This can be expressed as:

$$F'(Z') = \sqcup_1^k \left( \sqcup_{t-\delta}^{t-\delta+CB} \left( \varpi^f \left( \phi^F \left( Z_{g_{(t-\delta f)}} \right) \right) \otimes CF_{g_{(t)}} \right) \right), \qquad (14)$$

$$t = 0, 1, \ldots, (k+l+m) - CB$$

where F' (Z') is the unsorted magnitude spectrum of modified Zyoton frequency components produced by the collision, and may include additional frequency components. The operator $\sqcup_1^{CB}(\ldots)$ represents the set of conditional co-products that includes the product terms resulting from the interactions between a single Zyoton component $Z_g$ with all the conditioned feature components $CF_g$, $CF_{g+1}$, . . . , $CF_{(g+CB-1)}$ over the bracket length CB, and the operator $\sqcup_1^K(\ldots)$ represents the conditional co-product over the interactions of all the components of the Zyoton $Z_{g1}$, $Z_{g2}$, . . . , $Z_K$, with all the conditioned feature components within the respective brackets $[g_1, g_{1+CB-1}]$, $[g_2, g_{2+CB-1}]$, . . . , $[g_K, g_{K+CB-1}]$ that occur during all the steps of a single collision. The term co-product generally refers to one or more multiplications and sums of the products. Unlike the conventional co-product, multiply-add, and/or multiply-accumulate operations, however, these co-products are conditional, as described herein.

A bracketed conditional multiplication operator, $\otimes$, of $Z_{gp}$ and $[CF_{gp}, CF_{gp+1}, \ldots, CF_{(gp+CB-1)}]$ can yield $[Z'_{gp}, Z'_{gp+1}, \ldots, Z'_{(gp+CB-1)}]$ as follows:

Case (a) Zgp is a k component: By the construction of Z and CF, as described above, the frequencies of the pair $\Omega_{Zgp}$ and $\Omega_{CFgp}$ must satisfy the $\epsilon_k$ test. Therefore, the frequency of the result of an interaction between $Z_{gp}$ and $CF_{gp}$, which would produce the modified Zyoton component $Z'_{gp}$, is designated the frequency $\Omega_{Zgp}$; thus, $\Omega_{Z'gp} = \Omega_{Zgp}$. The amplitude of $Z'_{gp}$ is computed as $A'_{gp} = A_{gp} \times a_{gp}$.

For the remainder of the collision bracket, i.e., for each CF component $CF_{gp+l}$, where l=1 . . . CB−1, unless the frequencies $\Omega_{Zgp}$ and $\Omega_{CFgp+l}$ satisfy the $\epsilon_k$ test, no interaction between $Z_{gp}$ and $CF_{gp+l}$ occurs. If the $\epsilon_k$ test would succeed for a particular value of 1, by construction, $\Omega_{Zgp+l}$ would be within $\epsilon_k$ times $\Omega_{Zgp}$. In this situation, the shift-delay operator, as described below, may be applied and, interaction of the collision bracket may not occur with either $Z_{gp}$ and $Z_{gp+1}$. Thus, in general, for the k components, $Z_{gp}$ interacts only with $CF_{gp}$ in the collision bracket and not with $CF_{gp+l}$, l=1 ... CB−1. Thus, no new k components are generated, in general.

Case (b) Zgp is an m component: By the construction of Z and CF, as described above, the frequencies of the pair $\Omega_{Zgp}$ and $\Omega_{CFgp}$ must satisfy the $\epsilon_m$ test. Therefore, $Z_{gp}$ and $CF_{gp}$ would interact, producing a modified Zyoton component $Z'_{gp}$. The amplitude of $Z'_{gp}$ is computed as $A'_{gp} = A_{gp} \times a_{gp}$. If the frequencies $\Omega_{Zgp}$ and $\Omega_{CFgp}$ satisfy the stricter $\epsilon_k$ test, the frequency of $Z'_{gp}$ is designated the frequency $\Omega_{Zgp}$; thus, $\Omega_{Z'gp} = \Omega_{Zgp}$. Otherwise, the frequency designated to of $Z'_{gp}$ is the sum of $\Omega_{Zgp}$ and $\Omega_{CFgp}$.

For the remainder of the collision bracket, i.e., for each CF component $CF_{gp+l}$, where l=1 ... CB−1, unless the frequencies $\Omega_{Zgp}$ and $\Omega_{CFgp+l}$ satisfy the $\epsilon_m$ test, no interaction between $Z_{gp}$ and $CF_{gp+l}$ occurs. If the frequencies satisfy the $\epsilon_m$ test, a new modified Zyoton component $Z'_{gp+l}$ is generated, and the amplitude thereof is computed as $A'_{gp} = A_{gp} \times a_{gp}$. If $\Omega_{Zgp}$ and $\Omega_{CFgp+l}$ satisfy the $\epsilon_k$ test, the frequency of $Z'_{gp+l}$, i.e., $\Omega_{Z'gp+l}$, is set to $\Omega_{Zgp}$; otherwise $\Omega_{Z'gp+l} = \Omega_{Zgp} + \Omega_{CFgp+l}$. If all CF components in the collision bracket satisfy the $\epsilon_m$ test, CB−1 new modified Zyoton components would be created. If no CF component in the collision bracket satisfies the $\epsilon_k$ test, however, all of the newly created modified Zyoton components would be designated frequencies according to $\Omega_{Z'gp+l} = \Omega_{Zgp} + \Omega_{CFgp+l}$. Unless all of these frequencies strictly match (i.e., they satisfy the $\epsilon_k$ test) with frequencies of the original Zyoton and/or conditional feature, the modified Zyoton would have one or more new frequencies. Often, one or more but not all of the CF components of the bracket may interact with $\Omega_{Zgp}$ and one or more new frequencies may be generated.

Case (c) Zgp is a j component: By the construction of Z and CF, as described above, the frequencies of the pair $\Omega_{Zgp}$ and $\Omega_{CFgp}$ must satisfy the $\epsilon_j$ test. Therefore, $Z_{gp}$ and $CF_{gp}$ would interact, producing a modified Zyoton component $Z'_{gp}$. The amplitude of $Z'_{gp}$ is computed as $A'_{gp} = A_{gp} \times a_{gp}$. If the frequencies $\Omega_{Zgp}$ and $\Omega_{CFgp}$ satisfy the stricter $\epsilon_k$ test, the frequency of $Z'_{gp}$ is designated the frequency $\Omega_{Zgp}$; thus, $\Omega_{Z'gp} = \Omega_{Zgp}$. Otherwise, the frequency designated to of $Z'_{gp}$ is the sum of $\Omega_{Zgp}$ and $\Omega_{CFgp}$.

For the remainder of the collision bracket, i.e., for each CF component $CF_{gp+l}$, where l=1 ... CB−1, unless the frequencies $\Omega_{Zgp}$ and $\Omega_{CFgp+l}$ satisfy the $\epsilon_j$ test, no interaction between $Z_{gp}$ and $CF_{gp+l}$ occurs. If the frequencies satisfy the $\epsilon_j$ test, a new modified Zyoton component $Z'_{gp+l}$ is generated, and the amplitude thereof is computed as $A'_{gp} = A_{gp} \times a_{gp}$. If $\Omega_{Zgp}$ and $\Omega_{CFgp+l}$ satisfy the stricter $\epsilon_k$ test, the frequency of $Z'_{gp+l}$, i.e., $\Omega_{Z'gp+l}$, is set to $\Omega_{Zgp}$; otherwise $\Omega_{Z'gp+l} = \Omega_{Zgp} + \Omega_{CFgp+1}$. If all CF components in the collision bracket satisfy the $\epsilon_j$ test, CB−1 new modified Zyoton components would be created. If no CF component in the collision bracket satisfies the $\epsilon_k$ test, however, all of the newly created modified Zyoton components would be designated frequencies according to $\Omega_{Z'gp+l} = \Omega_{Zgp} + \Omega_{CFgp+l}$. Unless all of these frequencies strictly match (i.e., they satisfy the $\epsilon_k$ test) with frequencies of the original Zyoton and/or conditional feature, the modified Zyoton would have one or more new frequencies. Often, one or more but not all of the CF components of the bracket may interact with $\Omega_{Zgp}$ and one or more new frequencies may be generated.

After the bracketed interactions for all Zyoton components are generated, the components of the modified Zyoton are amplitude sorted, and designated as k, m, j components according to the amplitudes thereof. Thereafter, all of these components are compared in a pairwise manner. For a component designated as a k component, if the frequency of that component matches with the frequency of any other component, i.e., the frequencies satisfy the $\epsilon_k$ test, those two components are merged. To this end, the amplitudes of these two components are summed the sum is set as the amplitude of one of the components in the matching pair, and the other component is removed. In some embodiments, the component that is retained is designated the greater of the frequencies of the components of the pair. In some embodiments, the lesser frequency may be designated to the retained component, while in some embodiments, the frequency of the retained component is not changed.

In the pairwise comparisons, for a component designated as an m component, the frequency comparison and conditional merging, i.e., conditional sum of the amplitudes, is performed as described above, except the $\epsilon_m$ test is applied instead of the $\epsilon_k$ test. In the pairwise comparisons, for a component designated as an j component, the frequency comparison and conditional merging, i.e., conditional sum of the amplitudes, is performed as described above for a k component, except the $\epsilon_j$ test is applied instead of the $\epsilon_k$ test. The retained components may be amplitude sorted, yielding a modified Zyoton.

To illustrate the collision interactions, with reference to FIGS. 58A-58D, for the Zyoton component Z1, the collision bracket includes the CF components: {CF1, CF2, CF3, CF4}. With reference to FIG. 58B, the only collision interaction that occurs for the component Z1, however, is Z1CF1, because CF1 is the only CF component in the bracket that satisfies the $\epsilon_k$ test. For the Zyoton component Z2, the collision bracket includes the CF components {CF2, CF3, CF4, CF5}. Only the Z2CF2 interaction occurs, because CF2 is the only component in Z2's bracket that satisfies the $\epsilon_k$ test with respect to Z2. Similarly, for the Zyoton component Z3, only the Z3CF3 interaction occurs. In each of these interactions, the amplitude of the resulting modified Zyoton components, denoted Z1', Z2', Z3', respectively, are the respective products of the amplitudes of the corresponding Z and CF components. For example, the amplitude of Z1' is the product of the amplitudes of Z1 and CF1. The frequency of Z1' is set to be the frequency of Z1 because, by definition, the frequencies of Z1 and CF1 satisfy the $\epsilon_k$ test.

In FIG. 58B, this is illustrated by the computation of Z'1, Z'1_1, Z'1_2, and Z'1_3. As the bracket length is 4, the collision bracket corresponding to Z1 includes four CF components, namely {CF1, CF2, CF3, and CF4}. By construction, the frequencies of Z1 and CF1 satisfy the $\epsilon_k$ test and, as such, Z'1 is designated the frequency of Z1, 260 kHz. In some embodiments, the frequency of the Zyoton component is chosen as the frequency of the modified Zyoton component, if a k component of the Zyoton is involved in the collision interaction. Otherwise, if an m or j component of the Zyoton is involved, the frequency of either the Zyoton component or the conditioned feature component may be chosen as the frequency of the resulting modified Zyoton component. The amplitude of Z'1 is the product of the amplitudes of Z1 and CF1. Z1 conditionally collides with the other CF components in the bracket, but the frequencies of these CF components do not satisfy the $\epsilon_k$ test when compared to the frequency of Z1 and, as such, the results of these unperformed interactions are shown as shown as "--" entries. The interaction of Z1 and CF2 fails to meet the $\epsilon_k$ test and, hence, the corresponding entry Z'1_1 is designated "--"; similarly, Z'1_2 and Z'1_3 are also designated "--". The frequency of Z'1 is the frequency of Z1, and no k components having new frequencies are created.

With reference to FIG. 58C, for the m component Z5, the collision bracket includes the CF components {CF5, CF6, CF7, CF8}. The components Z5 and CF5 interact because their frequencies satisfy the $\epsilon_m$ test. There is no interaction between Z5 and the components CF6 and CF7, because the pairs (Z5, CF6) and (Z5, CF7) do not satisfy the $\epsilon_m$ test. The components Z5 and CF8 interact, however, because they satisfy the $\epsilon_k$ test. Thus, the collision of Z5 with the CF components within Z5's collision bracket produces two modified Zyoton components, namely, Z5' and Z5'_3. The amplitudes of these two modified Zyoton components are determined by the product of the amplitudes of Z5 and CF5 and the product of the amplitudes of Z5 and CF8, respectively.

The components Z5 and CF8 satisfy the stricter $\epsilon_k$ test and, as such, the frequency of Z5' is set to be the frequency of Z5. While the components Z5 and CF8 satisfy the $\epsilon_m$ test, they do not satisfy the $\epsilon_k$ test and, as such, the frequency of Z5'_3 is set to be the sum of the frequencies of Z5 and CF8. As such, a modified Zyoton component having a frequency different from the frequencies of any of the Zyoton and conditioned feature components is created. The amplitudes of these new components are most likely to be within the m region of the modified Zyoton, but depending on the amplitudes of Z5, CF5, and CF8, one or both of these amplitudes may be in the j region of the modified Zyoton. In general, because the m-component amplitudes are much lower than the k-component amplitudes, the new component magnitudes typically do not reach the magnitude region of the k components.

With reference to FIG. 58D, for the j component Z7, the collision bracket includes the CF components {CF7, CF8, CF9, CF10}. Here again, by construction, the frequencies of Z7 and CF7 satisfy the $\epsilon_j$ test and, as such, an interaction between these two components is permitted. That interaction produces the modified Zyoton component Z'7. The components CF8 and CF9 do not satisfy the $\epsilon_k$ test with respect to Z7 and, as such, these two CF components do not interact with Z7. The component CF10 satisfies the $\epsilon_k$ test, however, and interacts with Z7, producing the modified Zyoton component Z'7_3.

As described above, the amplitude of Z'7 is the product of the amplitudes of Z7 and CF7, and the amplitude of Z'7_3 is the product of the amplitudes of Z7 and CF10. Neither CF7 nor CF10 satisfies the stricter $\epsilon_k$ test and, as such, the frequency of Z'7 is set to be the sum of the frequencies of Z7 and CF7 (i.e., 510 kHz), and the frequency of Z'7_3 is set to be the sum of the frequencies of Z7 and CF8 (i.e., 480 kHz). While 480 kHz is a new frequency, the frequency of Z'5 is 500 kHz. Z'5 is likely an m component of the modified Zyoton, and the components Z'5 and Z'7 satisfy the $\epsilon_m$ test. Therefore, these two components can be merged. As Z'5 is the larger component by amplitude, the amplitude of Z'5 is reset as the sum of the initially computed amplitude of Z'5 (i.e., 1482) and the amplitude of Z'7 (i.e., 12.54). Thus, the new amplitude of Z'5 is set to be 1494.94. The merged component Z'7 is removed from the modified Zyoton. In this example, the frequency of the retained component Z'5 is not modified, and remains to be 500 kHz. In some embodiments, the larger of the frequencies of the two components may be designated to the retained components. In other embodiments, the smaller frequency may be designated, and in some embodiments the frequency of the removed component may be designated to the retained component.

In general, for each of K Zyoton components, up to CB modified Zyoton components may be generated initially, as described above, for a total of (K*CB) initial modified Zyoton components, where CB is the bracket length. Frequencies of these components are checked pairwise to determine pairs having matching frequencies, where the match can be determined according to the applicable Epsilon test. To determine the applicable Epsilon test, for a pair of components of the modified Zyoton that are under evaluation for a possible frequency match, the energy region (i.e., the k, m, or j region) to which the component having the greater amplitude likely belongs is determined. If the component likely belongs of the k region, the $\epsilon_k$ test is applied. If the component likely belongs to the m region, $\epsilon_m$ test is applied. Otherwise, the $\epsilon_j$ test is applied. The matching pairs are merged, similarly as Z'5 and Z'7 are merged, by summing the respective amplitudes thereof. Two or more initially generated modified Zyoton components may be conditionally merged together. In various embodiments, the final components of the modified Zyoton, obtained after conditional merging, are sorted by amplitudes. The conditional merging typically removes one or more modified Zyoton components. The renormalization process describe above may additionally remove one or more components of the modified Zyoton and may redistribute the energy of such additionally removed components.

As described above, these collision interactions, even during a single iteration of the overall collision process, typically results in new modified Zyoton frequency components having frequencies that are not present in the original Zyoton and/or the conditioned feature in the j and m regions.

In general, in the bracketed interaction, the Zyoton components are ordered by amplitudes thereof and, as such, gp through gp+K−1 correspond to the component indices of Z. One or more new frequencies may be associated with the modified Zyoton components identified by the indices $Z'_{gp\_1}$ through $Z'_{gp\_(CB-1)}$, for all gp in the range from 1 through K. All of these modified Zyoton components may be sequentially indexed from 1 through K+U, where U is the number of new components of the modified Zyoton in the m and j regions. All of the K+U components of the modified Zyoton are not necessarily amplitude-sorted after the collision interactions. As such, the collision of Z and CF produces modified Zyoton components that are not necessarily magnitude sorted. In some embodiments, prior to renormalization, these components are sorted according to the amplitudes thereof. The frequencies of the k components of the Zyoton Z are preserved during the generation of the modified Zyoton, as described above, and these k components are not removed by truncation during renormalization.

In Expression (14) for the collision operation, optionally, one or more of the collision computing parameters: shift delay $\delta^f$; scaling vector $\overline{\alpha}^f$; and phase shift $\Phi^f$; are applied to the Zyoton frequency components in the frequency domain. The superscript "f" indicates that the collision computing parameters are frequency-domain coefficients; and each $\Omega$ represents a frequency component undergoing interaction at a time point on the collision grid. Sorting the components of F' (Z') on a descending amplitude order yields the resulting magnitude spectrum of the modified Zyoton F' (Z').

As shown in the expression for F'(Z'), the collision computing parameter shift delay $\delta^f$ is optionally introduced as an integer shift delay in the index of the Zyoton components that interact with the components of conditioned feature or modified zyoton. Values of $\delta^f$ can range from 0 thru k–1 where k is the number of k-frequency components. As an example, shift delay $\delta^f$ may be used in Zyotons derived from waveforms such as parabolic-similaritons; wavelets; curvelets; ridgelets; or elliptic waves, any of which can yield multiple components which are very close in frequency to each other, or yield groups of components that are close in frequency to each other.

With reference to FIG. 59A, the three k components of the Zyoton are close in frequencies. The closeness for the delay shift operation need not be determined by the $\epsilon_k$ test and, instead, another suitable threshold such as frequency difference of no more than 0.2%, 0.5%, 1%, 2% etc., of the larger or smaller frequency can be used to determine the closeness. If such close frequency components are observed, the collision process may start by setting the shifting value equal to the number of close components minus one. Thus, in the example shown in FIG. 59A, $\delta=2$. In one embodiment, the collision begins not with the component Z1, but with the component Z3. The bracket of the CF components to be collided with the component Z3, however, is not shifted. Instead, the collision bracket for Z3 includes the CF components {CF1, CF2, CF3, CF4}. Once the value of the shift-delay $\delta$ is set, it is uniformly applied for all collision interactions. Thus, the collision bracket for the Zyoton component Z8 includes the CF components {CF6, CF7, CF8, CF9}.

In some embodiments, the first of the close Zyoton components may be used and the remaining components or not used in the collision process. Instead, the collision continues with the next Zyoton component in the ordered set that is not determined to be close in frequency. In some embodiments, the center component is selected and the remaining close components are not used in the collision process. Here again, the collision continues with the next Zyoton component in the ordered set that is not determined to be close in frequency. For each of these collisions, the corresponding bracket of the CF components is shifted by the delay-shift value $\delta$. For example, FIG. 59B shows that the collision of Z2, the center component, is performed using the bracket {CF1, CF2, CF3, CF4} and the next collision operation involves the Zyoton component Z4, which is not close to Z1, Z2, and Z3, and the collision bracket for Z4 is {CF2, CF3, CF4, CF5}. The center component can be determined according to the frequencies of the close components or according to the amplitudes of the close components.

The phase shift $\Phi^f$ shown in the expression for F'(Z') can be introduced, either as a constant phase shift (which reduces to a scalar) in the frequency domain; or as a rotation vector where the amplitude of each frequency component of the Zyoton $Z_{(g_{t-\delta^f})}$ participating in the collision is multiplied by a variable phase shift coefficient $$\phi^f_{g_{(t-\delta^f)}} = \phi^f_{g_{(t-\delta^f-1)}} + (t-\delta^f)\frac{2\pi}{360*(k+m+j)}$$

where $$\phi^f_1 = \frac{2\pi}{360*(k+m+j)}.$$

For subsequent (second and later) collisions, the frequency components of the conditioned feature would be replaced by the frequency components of the renormalized modified zyoton, and the other collision computing coefficients would optionally remain unchanged. The expression can be written as:

$$F'(Z'') = \prod_1^K \left( \prod_{t-\delta}^{t-\delta+CB} \left( \overline{\alpha}^F \left( \phi^F \left( \Omega_{Z_{(g_{(t-\delta^F)})}} \right) \right) \right) \otimes \Omega_{Z'(g_{(t)})} \right), \quad (15)$$

$$t = 0, 1, \ldots, (k+l+m)-1$$

where Z" is the new resulting modified zyoton, Z' is the renormalized modified zyoton resulting from a previous collision, and other terms are as defined above.

Post collision, the sorted magnitude spectrum of modified zyoton F' (Z') would have more than k+m+j terms and would include any new frequencies created. For example, depending on the modality of the interaction, the co-product term of multiplying a frequency component of Zyoton $\Omega_Z$ with a corresponding frequency component of the conditioned feature $\Omega_{CF}$ could result in new frequency components with frequencies similar to those of the colliding entities, but with substantially reduced amplitudes compared to those of the original zyoton. When all the resulting frequency components are amplitude sort-ordered, the k frequencies remain as the highest amplitude components, with the newly-created frequencies appearing in lower energy bands.

The collision thus does not create new frequency components in the energy range of the first k components of the modified Zyoton, and may only increase the collective spectral energy of those k components. Similarly, the forced frequency alignment described above, after applying a combination of delay, phase shift and scaling operations, ensures that no new frequency components, sort-ordered in the range of original k components, are generated, because the new frequency components generated by the modulation have amplitudes ordered substantially below the original k components. The new frequency components generated by the collision process are removed by truncation of the amplitude-scaled frequency components as part of renormalization.

The different tests that are performed in the time domain and frequency domain during various optional stages of collision between the Zyoton (Z) and conditioned features (CF), for all three of: the case of one specific embodiment for non-invasive glucose; for embodiments for analytes where the SCR, SNR, concentration, or intensity of signal may be different from those in noninvasive glucose; and for other embodiments only; are summarized in the table below.

TABLE 9

| Operation/Test | Glucose Embodiment | Embodiments analytes with differing conditions | Other embodiments |
|---|---|---|---|
| Just prior to collision, the original Zyoton (Z) and the | Yes, but they can also be represented | Yes, but they can also be represented | Yes, but they can also be represented |

TABLE 9-continued

| Operation/Test | Glucose Embodiment | Embodiments analytes with differing conditions | Other embodiments |
|---|---|---|---|
| conditioned feature (CF) are represented in the frequency domain | in the time domain | in the time domain | in the time domain |
| Collisions are preferentially performed in the frequency domain, but can be described in the time domain. | Yes | Yes | Yes |
| Collisions are performed in the time domain | No, because removal of certain frequency components, e.g., by using filters, can lead to loss of numerical accuracy, and loss of accuracy of information content, which can cause the collision computing to be inaccurate. Performing collision computing in the time domain can also be inefficient, because it is difficult to ensure co-dependency conditions with low SNR and low SCR. | Yes, but removal of certain frequency components using filters can lead to loss of numerical accuracy, and loss of accuracy of information content, which can cause the collision computing to be inaccurate. | Yes. Can be used in systems with high SNR, high SCR, systems with few frequency components (i.e., $k + j + m < 100$), and/or Zyoton frequencies below 1KHz. |
| Z and CF can be represented as time-domain waveforms. | Yes, but the two waveforms must have the same number of points. | Yes, but the two waveforms must have the same number of points. | Yes, but the two can have different number of time points. Collision-computing parameters - delay - shift and collision grid may be changed accordingly. |
| Just prior to a frequency-domain collision the spectral energy of Z is designed to be much greater (e.g., 1,000 times) than the spectral energy of CF | Yes, and the spectral energies are represented by the frequency-domain amplitudes, i.e., the amplitudes of the frequency components of the Z and CF. | Not necessarily, this condition may not be required for all analytes. | Not necessarily. |
| Just prior to the first frequency-domain collision, a velocity test is performed and in which the velocity of Z is scaled down and compared with the velocity of CF, or the velocity of CF is scaled up and is compared with the velocity of Z | Yes, but in this embodiment the CF is preferentially not scaled. | Yes | Yes |
| The above test (kappa test) can be performed in the frequency domain | Yes, by comparing the amplitudes of the frequency components. | Yes | Yes |
| If the time domain kappa test prior to the first collision fails, the velocity of either Z, CF, or both, can be adjusted by scaling the frequency domain amplitudes, so that the test passes. | No, failing the kappa test generally requires a redesigned Z or carrier kernel. | No, failing the kappa test typically requires a redesigned Z or carrier kernel. | No, failing the kappa test typically requires a redesigned Z or carrier kernel. |
| During a frequency-domain collision, the spectral energy of Z remains much greater (e.g., 1,000 times, etc.) than the | Yes, if it began with that spectral-energy ratio. | Yes, if it began with that spectral-energy ratio. | Yes, if it began with that spectral-energy ratio. |

TABLE 9-continued

| Operation/Test | Glucose Embodiment | Embodiments analytes with differing conditions | Other embodiments |
|---|---|---|---|
| spectral energy of CF, and of the renormalized modified zyoton that replaces the CF. Prior to the first frequency-domain collision, an Epsilon Test is satisfied for all the k, m and j components individually and collectively. | Yes | Yes | Yes |
| After the first collision a kappa velocity test in the time domain (or a kappa spectral energy test in the frequency domain) can be applied to the scaled Z and the renormalized, modified Zyoton Z" | Yes | Yes, | Yes |
| If the test fails, the collision is discarded and the process starts with a new original Zyoton Z or a new carrier kernel. | Yes | Yes | Yes |
| Post renormalization, and during all subsequent frequency-domain collisions, an Epsilon Test must remain satisfied for all k components, individually and collectively. | Yes. The frequencies of the k components are typically not changed by a collision. New m and j frequency components can be created. | Yes. The frequencies of the k components are typically not changed by a collision. New m and j frequency components can be created. | Yes. The frequencies of the k components are typically not changed by a collision. New m and j frequency components can be created. |
| No new frequency components in the amplitude range of the k components are created by a collision. | Yes | Yes | Yes |

Iterative Collision Process

Figure 60A:
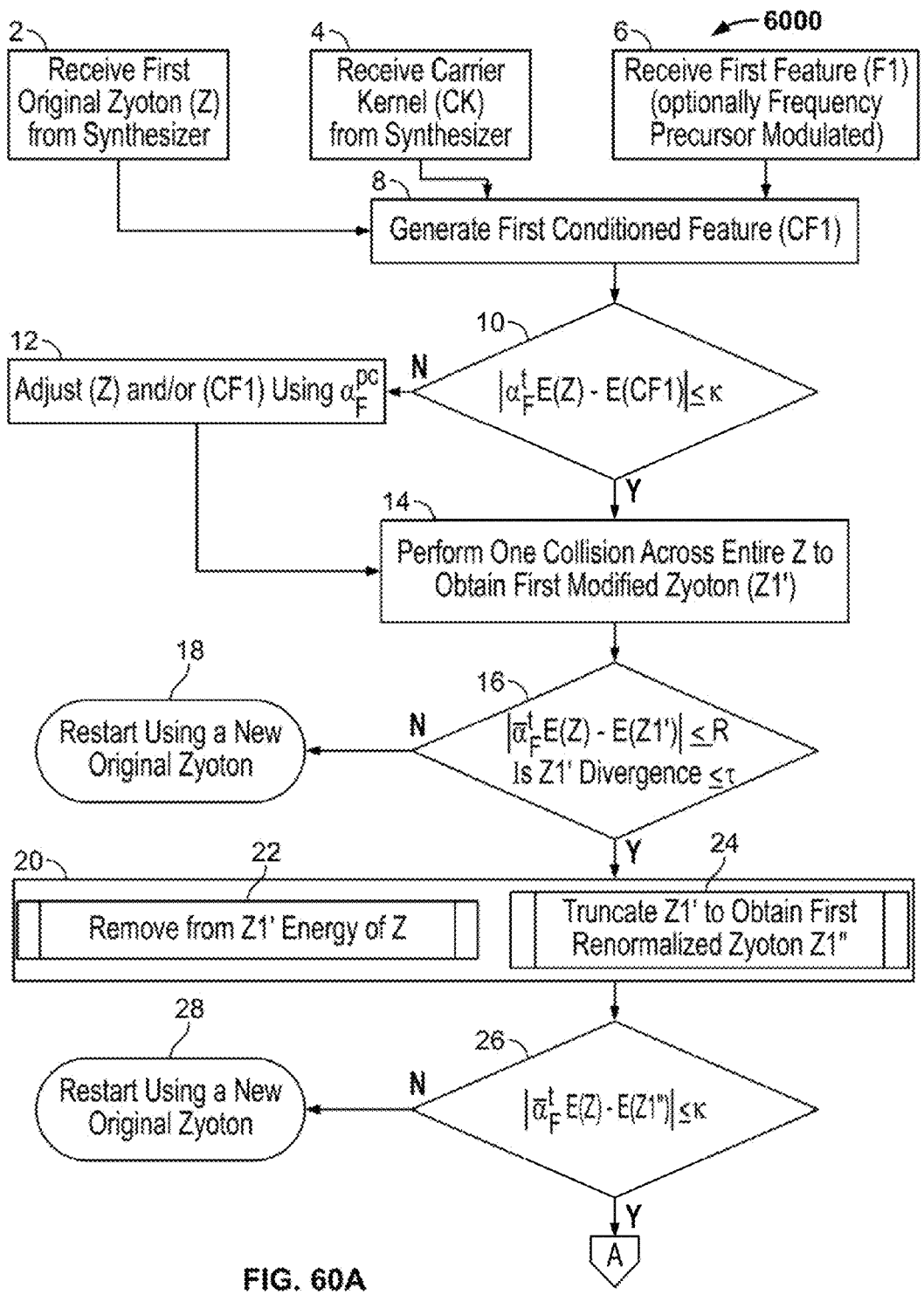
FIG. 60A is a flowchart illustrating a collision between an original Zyoton and a conditioned feature, to form a renormalized Zyoton, according to one embodiment.
Figure 60B:
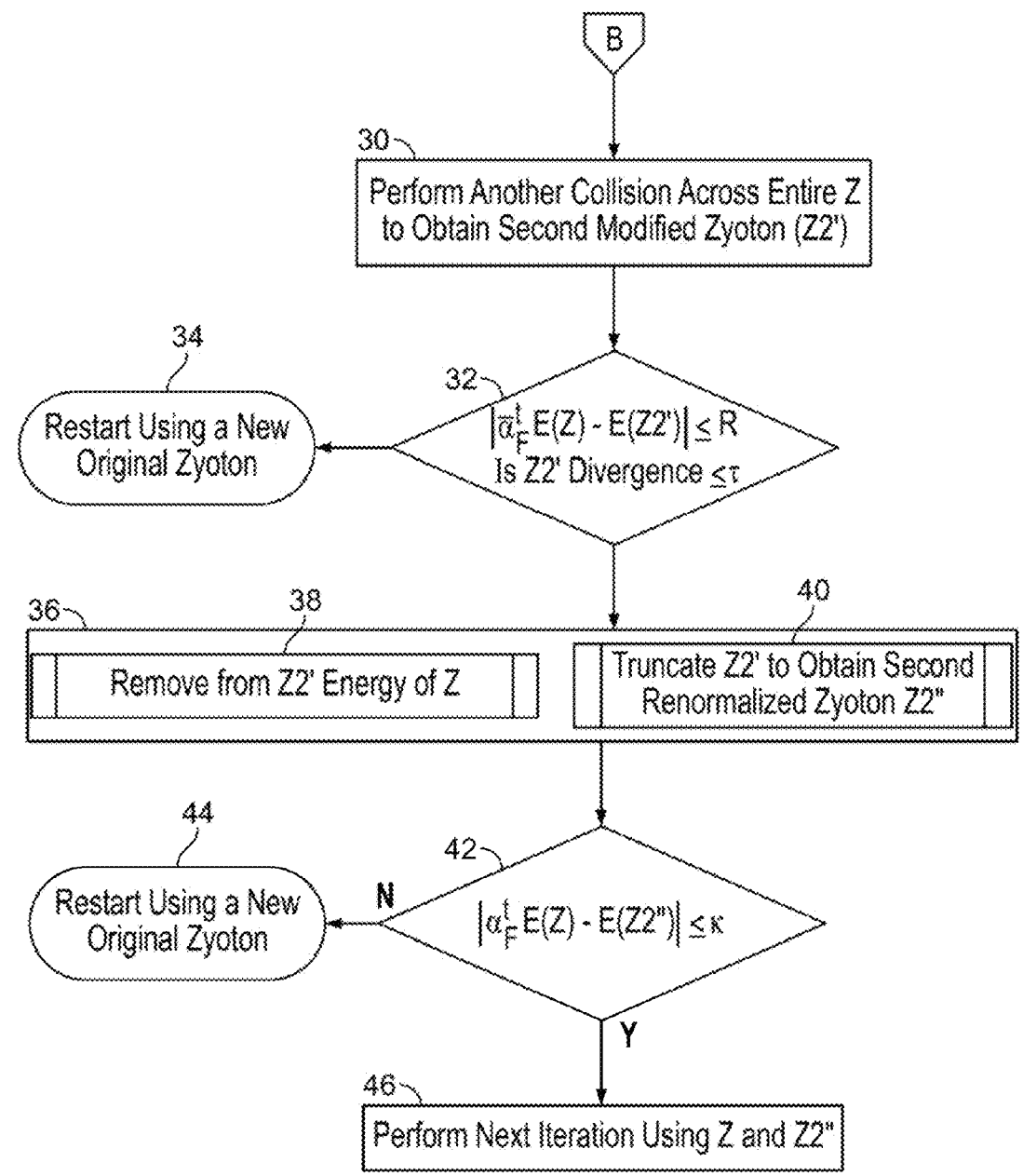
FIG. 60B is a flowchart illustrating iterative collisions between a renormalized Zyoton and an original Zyoton, according to one embodiment.

With reference to FIGS. 60A-60B, an original Zyoton (Z) is obtained from a synthesizer or a Zyoton database in step 2. In step 4, a co-dependent carrier kernel (CK) is obtained from a synthesizer or a carrier kernel database. A single database may store one or more Zyotons and one or more carrier kernels. A feature (F1), generated as described above, is obtained in step 6 from a feature generator (described below). The feature may be optionally modulated by a pre-cursor modulating signal (e.g., a 16.5 Hz signal, a 50 Hz signal, a 1 kHz signal, a 100 kHz signal, a 225 kHz signal, etc.). In step 8, the carrier kernel (CK) is modulated using the feature F1, to obtain a conditioned feature (CF1).

In step 10 a Kappa test is performed to ensure that the original Zyoton (Z) and the conditioned feature (CF1) satisfy the co-dependency test. To perform this test in the frequency domain, the scaled spectral energy $\alpha_t^F E(Z)$ of the original Zyoton may be compared with the spectral energy of the conditioned feature $E(CF1)$, where $\alpha_t^F$ is the scaling coefficient. The superscript F identifies that this scaling coefficient is applied in the frequency domain, and the subscript t indicates that this scaling coefficient is applied while performing a test. The properties of the actual waveforms Z and CF1 do not change by applying this scaling coefficient. If the difference between the two spectral energies is less than or equal to a specified threshold κ, (as described above), the co-dependency condition is satisfied. This test can also be performed in the time domain, where Z and CF1 are represented as time-domain waveforms, and the velocities of the two time-domain waveforms are computed. If the scaled velocity of the original Zyoton and the velocity of the conditioned feature are within a specified threshold, the co-dependency condition is satisfied.

If the Kappa test fails, the frequency domain amplitudes of the original Zyoton are actually scaled in step 12 according to a scaling factor $\alpha_{pc}^F$, where the superscript F identifies again that this scaling factor is applied in the frequency domain. The subscript pc indicates that this scaling factor is applied prior to the collision operation. The scaling factor $\alpha_{pc}^F$ can change the frequency-domain amplitudes of one or more components of the original Zyoton Z. Alternatively, a scaling factor can be applied to the conditioned feature. In some embodiments, both the conditioned feature and the original Zyoton may be changed. Regardless of the waveform to which the scaling coefficient is applied, one or both waveforms Z and CF are scaled such that the Kappa test, i.e., the velocity test between the original Zyoton Z and the conditioned feature CF1 is satisfied. In some embodiments, e.g., those in which the collisions are performed in the time domain, a scaling factor is applied to one or both waveforms in the time domain.

In some embodiments, a sensor provides a soliton based spectrum and the features derived from such spectra are soliton based. In these embodiments, precursor modulation is performed to modulate the soliton-based features, e.g., using a modulating signal having a frequency of a few hertz, a few hundreds of hertz, a few kHz, a few MHz, or more. In some embodiments, these modulated features can be collided directly with a Zyoton, without generating a conditioned feature. Therefore, a Kappa test may be applied directly to the Zyoton and the modulated feature, to test co-dependency therebetween.

The Kappa parameter used in this testing, denoted $\kappa_F$ is similar to the parameter $\kappa_{DV2}$ used in testing the co-dependency between a Zyoton and a conditioned feature. In performing this Kappa test, the velocity of the Zyoton and/or the velocity of the precursor-modulated feature may be scaled. The Kappa test using the parameter $\kappa_F$ can be performed in the time domain or in the frequency domain. If this Kappa test fails, the frequency-domain amplitudes of the frequency components of the Zyoton, the precursor-modulated feature, or both, may be scaled using a scaling coefficient $\alpha_C$, such that the Kappa test would succeed using the adjusted Zyoton and/or the precursor-modulated feature.

After the co-dependency condition is satisfied, the first collision interaction between the original Zyoton and the conditioned feature is performed in step 14, which yields the first modified Zyoton Z1'. As described above, the collision operator also includes an optional scaling operator. The collision interactions, as described above, can generate a modified Zyoton having frequency-domain amplitudes greater than the amplitudes of the Zyoton. Also, some of the frequency component amplitudes of the Zyoton are significantly greater than some amplitudes of the conditioned feature due to scaling of the Zyoton relative to the conditioned feature prior to the collision. For example, in some embodiments spectral energy of Zyoton is set to be $10^3$ times relative to the spectral energy of the conditioned feature which generally results in large scaling of frequency domain amplitudes of the modified Zyoton in the k-region. The scaling operator applied during the collision interactions scales the amplitudes to control the overall dynamic range of the amplitudes, so that a computer can perform the processing efficiently and with the required precision. Thus, the scaling operator is customized to the computing apparatus and may adjust the waveform properties primarily to facilitate computations using the selected computing apparatus. The scaling factor $\alpha_F^{pc}$ on the other hand actually adjusts the properties of the waveforms to be collided so that they become co-dependent.

After the first collision, whether the original Zyoton Z and the first modified Zyoton Z1' are co-dependent is determined in step 16. In a frequency-domain implementation, the spectral energy of the original Zyoton E(Z) is scaled using a scaling factor $\bar{\alpha}_F^t$, and the scaled spectral energy is compared with the spectral energy E(Z')of the first modified Zyoton. If the two energies are within the Kappa threshold the first co-dependency condition, i.e., the velocity test is satisfied. Similar to step 10, this test can be performed in the time domain. The co-dependency also requires that the divergence of the post-collision waveform, i.e., the first modified Zyoton Z1', be within a specified threshold $\tau$. This condition is also tested in the step 16. In some embodiments, the collision interactions and the Epsilon tests in particular, can ensure that the divergence condition is satisfied and, as such, the divergence test is not performed explicitly in the step 16. If either test fails, it is determined that the selected Zyoton is not suitable for collisions with the particular conditioned feature CF1. Therefore, a new original Zyoton may be selected in step 18, and the collision process can restart from step 10, with the new original Zyoton.

If both the velocity and divergence tests succeed, the first modified Zyoton Z1' is renormalized in step 20. As described above, renormalization includes removing the energy of the original Zyoton from a modified Zyoton, which may be performed in step 22. Renormalization may also include truncating the modified Zyoton, and redistributing the aggregate energy of the components removed during truncation, among the surviving m and j frequency components of the renormalized Zyoton, such as the first renormalized Zyoton Z1". Truncation and redistribution (also called amplitude balancing or rebalancing) may be performed in step 24. Either step 22 or 24 can be performed before the other renormalization step.

The renormalization process is controlled such that the energy of the renormalized Zyoton is on the scale of the energy of the conditioned feature. The renormalized Zyoton is then collided again with the original Zyoton in a subsequent collision iteration. Therefore, to ensure the co-dependency between the first renormalized Zyoton Z1" and the original Zyoton Z, a Kappa test is applied to these two waveforms, in step 26. In the frequency domain, the scaled spectral energy of the original Zyoton, $\alpha_F' E(Z)$ is compared with the spectral energy of Z1", denoted E(Z1"). If the absolute difference is less than the parameter $\kappa$, the next iteration of the collision may be performed. This test can also be performed in the time domain.

If the Kappa test fails, it is determined that the energy represented by the conditioned feature CF1 cannot be extracted using the first original Zyoton Z; a new original Zyoton is selected in step 28. The collision iteration may start again at step 10 using the new original Zyoton and the conditioned feature CF1. If the Kappa test in step 26 succeeds, a collision interaction is performed in step 30 between the original Zyoton Z and the first renormalized Zyoton Z1", which yields a second modified Zyoton Z2'. Whether the original Zyoton Z and the second modified Zyoton Z2' are co-dependent is determined in step 32, similarly as in the step 16. If one or both co-dependency tests fail, a new original Zyoton may be selected in step 34, and the collision process may restart from the step 10. Otherwise, i.e., if both co-dependency tests in step 32 succeed, the second modified Zyoton Z2' may be renormalized in step 36. The step 36 is similar to the step 20, and includes the energy removal step 38 and the truncation and redistribution step 40. The renormalization yields a second renormalized Zyoton Z2".

In step 42, which is similar to the step 26, the co-dependency between the original Zyoton Z and the second renormalized Zyoton Z" is tested. If either or both tests fail, a new original Zyoton may be selected in step 44 and the overall collision process may restart in step 10. Otherwise, the next collision iteration (i.e., steps 30-42) may be performed using the original Zyoton (Z) and the second renormalized Zyoton Z". This iterative collision process may continue for the specified number of iterations $\mathbb{N}$, as described above.

Thereafter, in various embodiments, the renormalized spectral energy gain of the renormalized Zyoton produced after the $\mathbb{N}$ iterations is computed. This energy gain generally corresponds to the spectral energy loss represented by the conditioned feature CF1, which corresponds to the energy absorbed by the analyte of interest and/or one or more confounders in the wavelength range associated with the feature F1. The entire process 6000 may then be repeated with another feature $\overline{FT}$ that is matched with the feature F1, to compute the renormalized spectral energy gain associated with $\overline{FT}$. The two energy gain values may be used, as described above, to compute net renormalized spectral energy gain (NRSEG) for the feature pair (F1, $\overline{FT}$). This overall process 6000 is typically repeated for different feature pairs. The original Zyoton used to collide with the two features of a particular feature pair is generally the same. Different original Zyotons may be used, however, for different feature pairs.

System for Collision Computing

With reference to FIG. 61, a non-invasive measurement system or a collision-computing system 6100 includes a sensor 6102. The sensor includes a radiation source 6104 and a detector 6106. The radiation source 6104 can be selected according to the medium to be analyzed 6108 and/or an analyte to be detected and/or quantitated. For example, in-vivo or in-vitro measurements of compounds such as glucose, cholesterol, etc., or for measurement of properties such as heart-beat rate, the radiation source 6104 can be an NIR radiation source. In other situations, e.g., for detection/measurement of an atmospheric gas, the radiation source 6104 can be, e.g., an X-ray source, a gamma-ray source, an ultra-violet radiation source, a source of visible light, an acoustic/SONAR source, or an electromagnetic radiation source such as a RADAR. The detector 6106 is configured to receive the radiation reflected from and/or transmitted through the medium to be analyzed 6108. The sensor 6102 also includes an analog-to-digital converter (ADC) 6110, to convert the received radiation into a digital signal, also called the sensor signal.

The sensor signal is received by a feature generator 6112, which includes a spectrum generator 6114. If the spectrometer is a Fourier transform (FTIR) spectrometer, the spectrum generator may convert the frequency components of the sensor signal, e.g., via an inverse Fourier transform to a spectral signal or spectrum (e.g., intensity spectrum) corresponding to the sensor signal. In some embodiments, the spectrum generator 6114 may transform the initially generated spectrum into a different form. For example, an intensity spectrum may be transformed into a corresponding absorbance spectrum. Typically, the intensity and absorbance spectra represent absorption of the energy transmitted by the radiation source 6102 to the medium to be analyzed 6108 by an analyte and/or one or more confounders in the medium, and losses due to scattering.

The feature generator 6112 also includes a feature extractor 6116, which divides the spectrum generated by the spectrum generator 6114 into one or more regions determined according to wavelength or wavenumber ranges. The individual portions of the spectrum corresponding to these region(s) are called features. The absorption of energy by the analyte and one or more confounders may vary according to the wavelength of the incident radiation and, as such, some features may represent strong absorption of the incident energy by the analyte relative to that by one or more confounders. Such features are generally called analyte features. Some features may represent weak absorption of the incident energy by the analyte relative to that by one or more confounders, and such features are generally called non-analyte features.

The feature extractor 6116 may generate one or more analyte features and one or more non-analyte features. In some embodiments, an optional pairing module 6118 pairs one or more analyte features with a respective non-analyte feature.

The features are prepared for collision by the feature conditioner 6120, which may include a precursor modulator 6122 that modulates a feature using a modulating signal (e.g., a waveform having a frequency of 16.5 Hz, 1 kHz, 100 kHz, etc.) from a waveform database 6124. The modulator 6126 receives a carrier kernel from the waveform database 6124 and modulates the carrier kernel using a feature or a pre-modulated feature, to obtain a conditioned feature. As described above, each feature represents the energy absorbed by the analyte and/or one or more confounders, typically in the presence of noise and along with scattering losses, in the wavelength region associated with the feature. Therefore, the conditioned features derived from one or more features and one or more carrier kernels also generally represent the energy absorbed by the analyte and/or one or more confounders, along with noise and scattering losses, in corresponding wavelength regions.

The collision computer 6130 receives one or more conditioned features and one or more Zyotons from a Zyoton database 6132. In order to perform a collision between a selected Zyoton and a conditioned feature, for each frequency component of the selected Zyoton, the bracketed-collision module 6134 performs the collision operations (e.g., the conditional multiplications of amplitudes, conditional sums of frequencies, and conditional sums of resulting amplitudes, as described above), using frequency components of the conditioned feature in the corresponding bracket thereof. After the collisions with a specified number of Zyoton components are completed, a modified Zyoton is obtained which may be renormalized by the renormalization module 6136. Before, during, and after the collision process one or more co-dependency tests (i.e., the velocity (Kappa) tests and divergence (tau) tests) and Epsilon tests for collision computations can be performed by the collision condition testing module 6138. The Epsilon tests may be performed by the bracketed collision module 6134, as well. As described above, in various embodiments, the operations of the bracketed collision module 6134 and the renormalization module 6136 may be repeated for a specified number of collision iterations. In general, a renormalized Zyoton may be iteratively collided with the original Zyoton or with a different Zyoton. Alternatively, a renormalized Zyoton may be collided with the conditioned feature.

After the specified number of collision iterations are completed, the projector 6140 may receive one or more renormalized Zyotons. The NRSEG module 6142 may compute net, renormalized spectral energy gain (NRSEG) using the received renormalized Zyoton(s), which may correspond to pairs of features. The NRSEG module 6142 may also compute normalized NRSEG values, as described above. The AG module 6144 may compute absorption gradients and normalized absorption gradients (NAGs) from the NRSEG values computed by the NRSEG module 6142. The projection conditions testing module 6146 may test various conditions such as monotonicity of the computed NRSEG values across illumination states, etc. Based on these tests, the NRSEG module 6142 and the AG module 6144 may reject one or more feature pairs, as described below.

The quantitation module 6148 can receive a mapped projector curve set from a mapped projector curve set database 6150 and may use an NAG value to select a suitable projector curve from the curve set. The quantitation module 6148 may also use a normalized NRSEG value and the selected projector curve to determine a quantity (e.g., concentration) of the analyte of interest. Based on the measured quantity, the quantitation module 6148 can determine whether the analyte is present or absent in the medium to be analyzed 618. For example, the analyte may be determined to be present if the analyte quantity or concentration is greater than a specified threshold. Further details of the process of projection are described below.

The presence and the quantity can be presented to a user on a display device 6160. The display can be in a binary form, such as "Detected" or "Not Detected;" "Yes/No;" or other suitable symbols. Additionally or in the alternative, the display can indicate the measured quantity e.g., as an absolute value, a percentage, or a percentile rank. The display can also indicate a concentration band such as a designated "High," "Medium," or "Low" band, a color code such as "Red," "Yellow," "Green," corresponding to a concentration band etc. The number of concentration bands can be two, three, five, seven, ten, etc.

Figure 62:
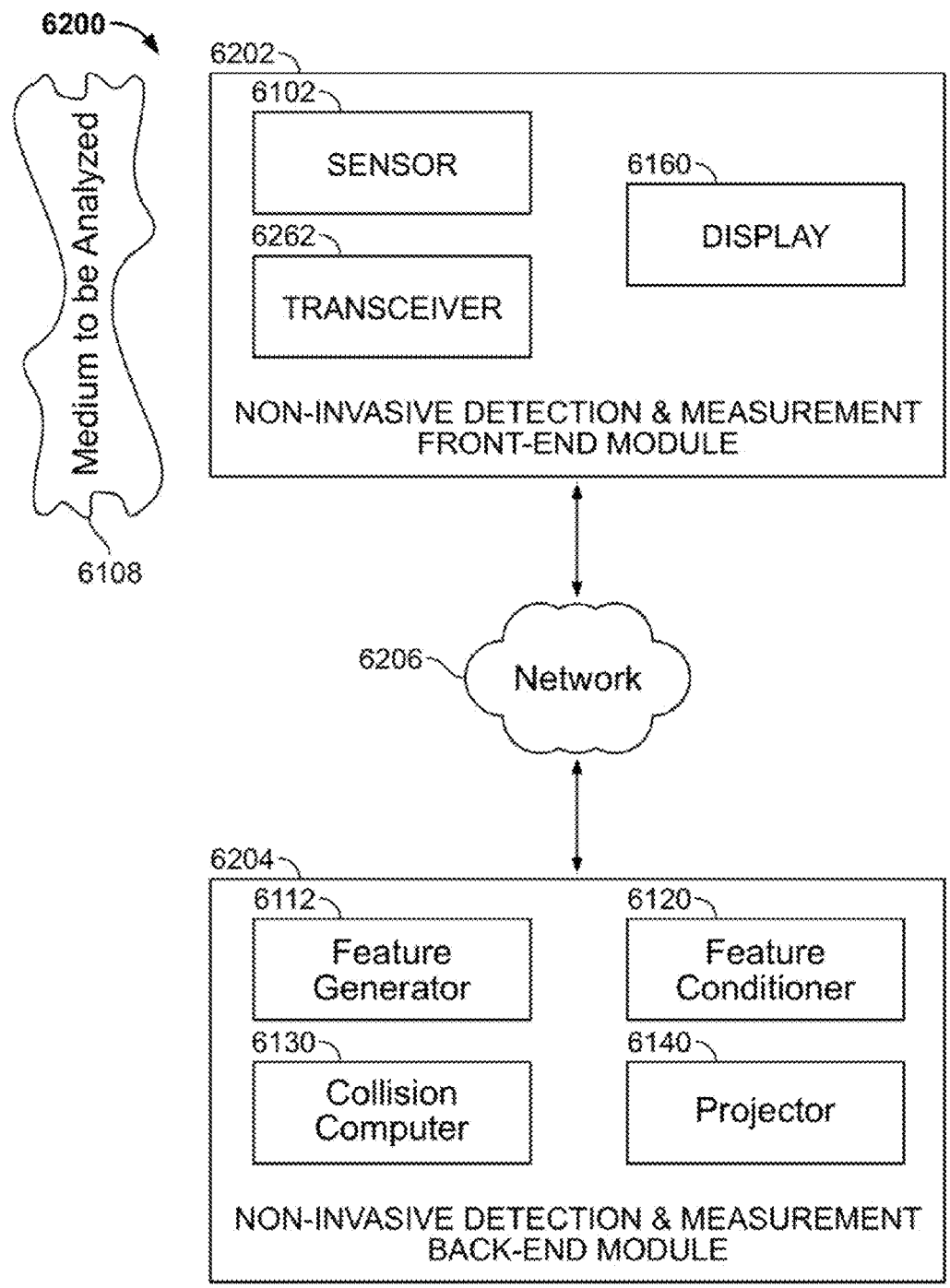
FIGS. 62 and 63 schematically show distributed non-invasive measurement systems using collision computing, according to different embodiments.

In different embodiments, the various components of the non-invasive measurement system (the collision-computing system) 6100 may be included in one or more physical units. In one embodiment, all system components are included in a single unit, such as a hand-held unit. With reference to FIG. 62, the overall non-invasive measurement system 6200 includes a front-end module 6202 and a back-end module 6204. The front-end and back-end modules are in electronic communication with each other via a network 6206, such as a private, physical and/or wireless network, the Internet, and/or a combination thereof.

The front-end module 6202 includes the sensor 6102, the display 6160, and a transceiver 6262. The back-end module 6204 includes the feature generator 6112, the feature conditioner 6120, the collision computer 6130, and the projector 6140. The back-end module 6204 also includes a communications module (not shown). In this embodiment, the front-end module 6202 collects data from the medium to be analyzed 6108, transmits it to the back-end module 6204 for processing of the collected data, and displays the received results. In the embodiment illustrated with reference to 6202, the overall system may be operated as a hosted service, where the front-end module collects data and displays results, while the back-end module performs the operations necessary to obtain the results.

Figure 63:
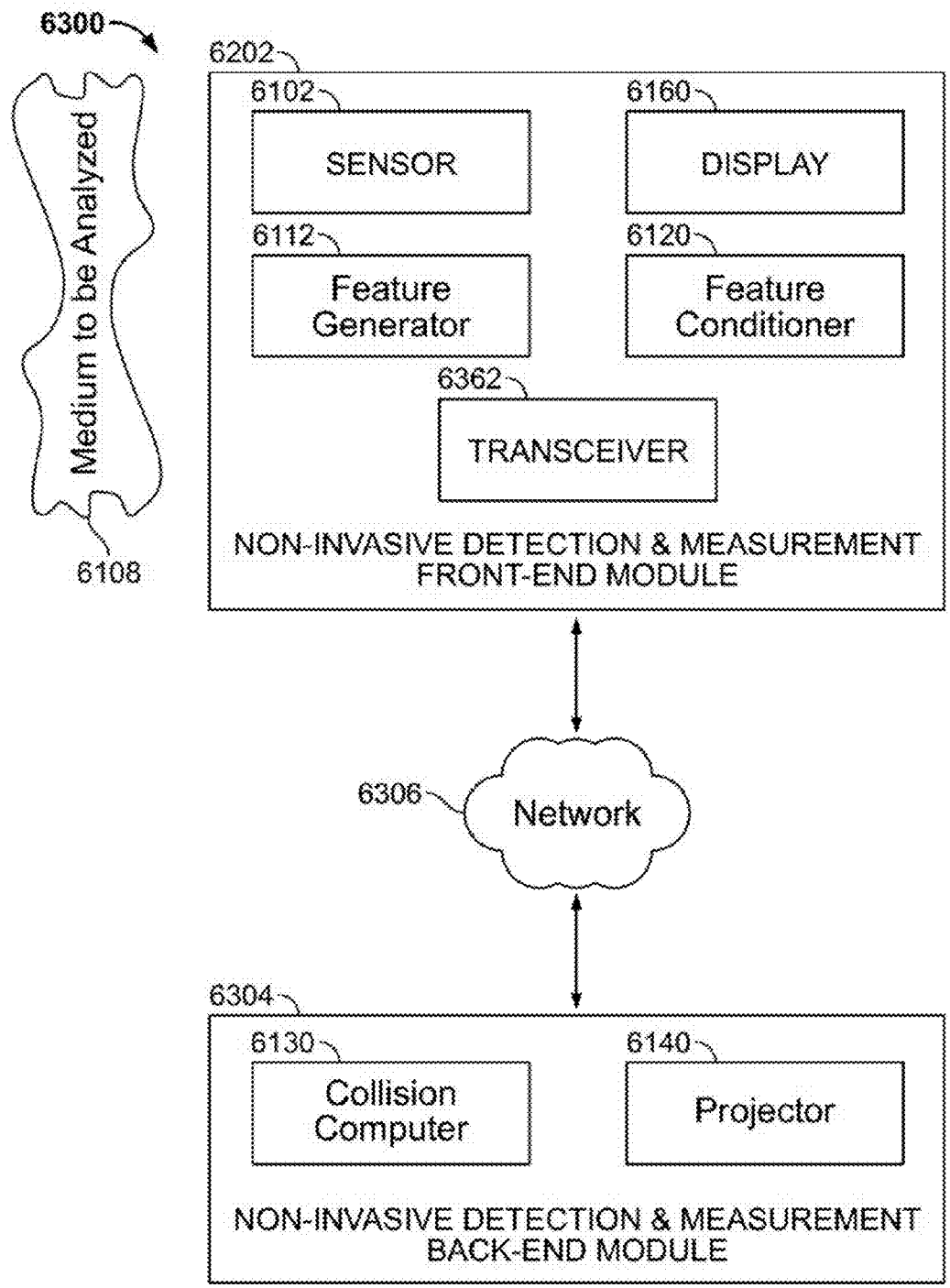

With reference to FIG. 63, in another embodiment, a front-end module 6202 includes the sensor 6102, the display 6160, the feature generator 6112, the feature conditioner 6120, and the transceiver 6362. The back-end module 6304 includes the collision computer 6130 and the projector 6140, and also a communications module. In this embodiment, the front-end module 6302 collects data from the medium to be analyzed 6108, generates conditioned features and transmits the conditioned feature data to the back-end module 6304 via the network 6306 for processing of the conditioned features, and displays the received results.

It should be understood that in various embodiments the non-invasive measurement system (the collision-computing system) 6300 may include more than one front-end units and/or more than one back-end units, and that other combinations of the various system components across the front-end unit(s) and back-end unit(s) are possible. Any of these system components (except for the radiation source 6104 and the detector 6106) can be implemented using custom hardware, e.g., application-specific integrated circuit(s) (ASIC(s)), field-programmable gate array(s) (FPGA(s)), etc.

Any of the components and sub-components of the non-invasive measurement system (the collision-computing system) 6100 (except for the radiation source 6104 and the detector 6106) may also be implemented using software, such as embedded software and/or software that can be downloaded, optionally compiled and/or interpreted, and executed on one or more processors. One or more system components and sub-components can be implemented in part using a hardware module and partially in software.

Figure 64:
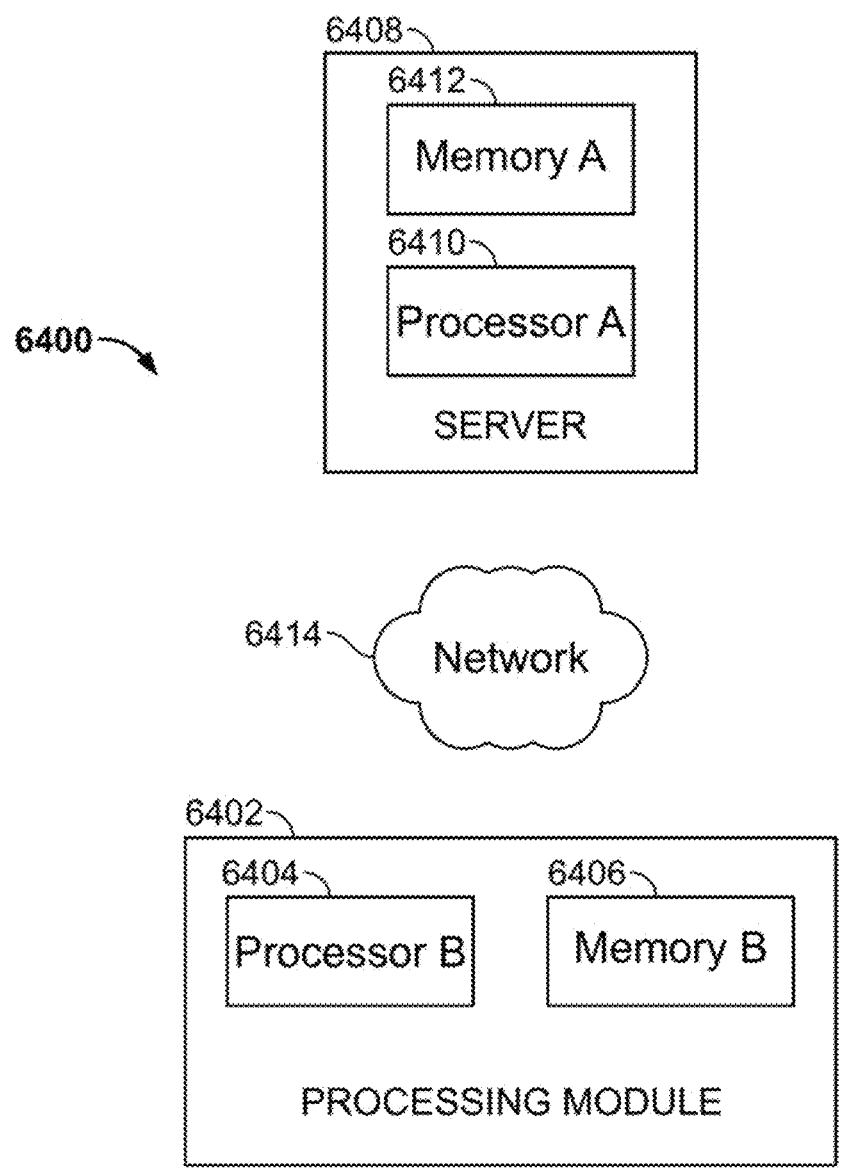
FIG. 64 schematically shows a processing system for performing collision computing and/or for providing software for collision computing, according to various embodiments.

With reference to FIG. 64, a component (e.g., the feature conditioner 6120) or a sub-component (e.g., the bracketed collision module 6134, the AG module 6144, etc.) can be executed by a processing module 6402 having a processor 6404 and a memory module 6406. The instructions to implement the particular component or subcomponent may be stored in the memory module 6406. Such instructions can be pre-loaded in the memory module 6406, or the processing module 6402 may receive such instructions from the server 6408. The server includes a processor 6410 and a memory module 6412. The processor 6410 may retrieve the instructions from the memory module 6412 and may transmit those instructions to the processing module 6402 via a network 6414.

In some embodiments, all operations of the component or the subcomponent may be performed by the processor 6404. In some embodiments, the processor 6404 may transmit data to be processed to the server 6408 and the processor 6410 may perform one or more of the operations associated with the component or the subcomponent to be implemented.

Zyoton and Carrier Kernel Synthesis System

Figure 65:
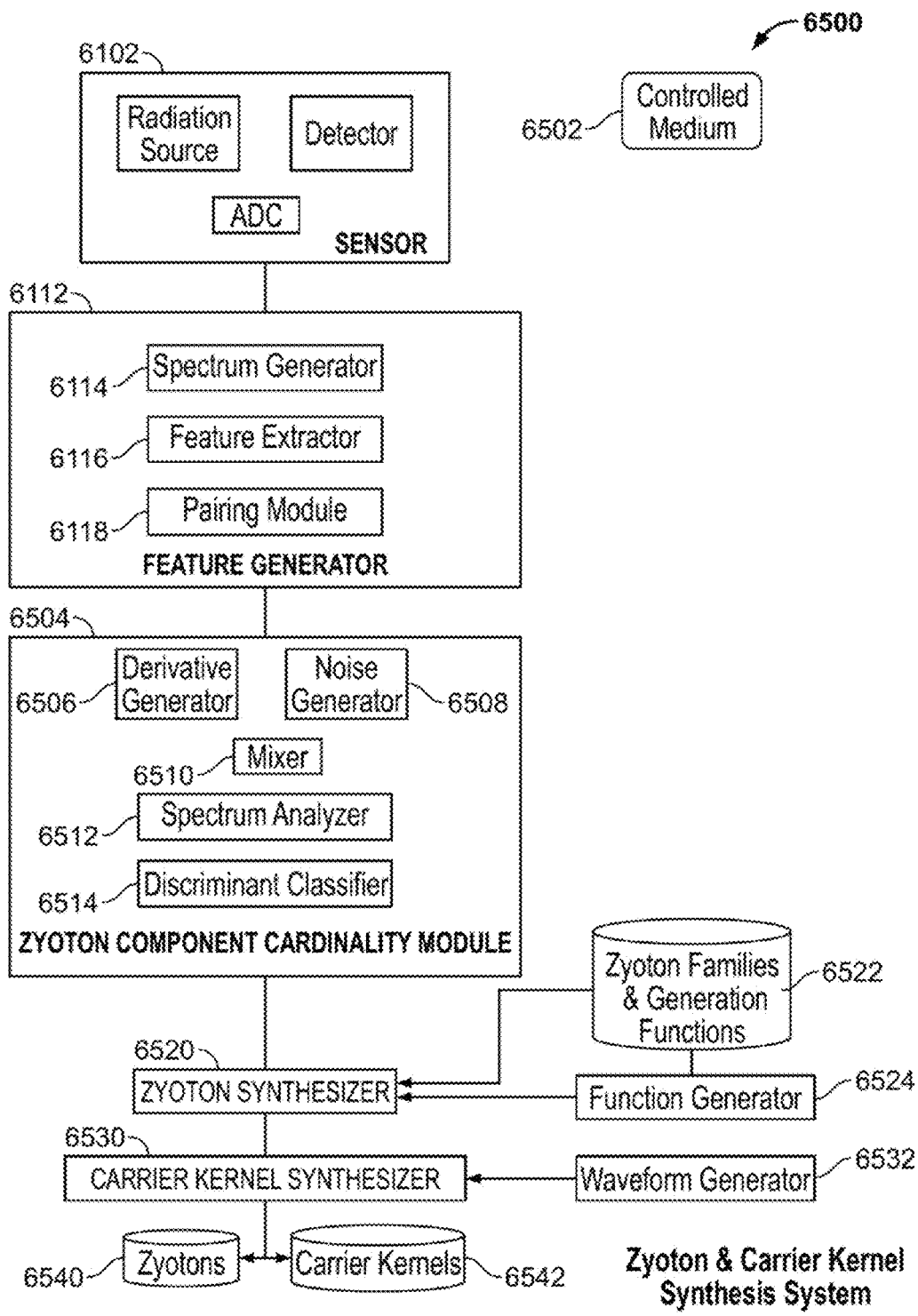
FIG. 65 schematically shows a system for Zyoton and/or carrier kernel synthesis, according to one embodiment.

The process of synthesizing the Zyotons and carrier kernels to be used for collision computing are described above with reference to FIGS. 38-41. Some of the components of the non-invasive measurement system (the collision-computing system) 6100 (FIG. 61) are used to synthesize Zyotons and carrier kernels. With reference to FIG. 65, in the waveform synthesis system 6500, the sensor module 6102 is used to obtain radiation corresponding to an analyte of interest from a controlled medium 6502. In some embodiments, the controlled medium 6502 may include a diluting substance such as distilled water and a pre-measured quantity of the analyte. The spectrum generator 6114 of the feature generator module 6112 generates a pure component intensity or absorbance spectrum for the analyte. The feature generator 6112 may generate one or more feature pairs, for optionally determining the amplitudes of the high amplitude k components of a Zyoton. In some embodiments, the k components have higher power than the m and j components.

The Zyoton component cardinality module 6504 determines the respective cardinalities k, m, and j of the high, medium, and low energy components of a Zyoton. To this end, the Zyoton component cardinality module 6504 includes a derivative generator 6506 that can generate first, second, and/or higher-order derivatives of a spectrum received from the feature generator 6112. The noise generator 6508 generates noise according to the properties of the received spectrum and/or a derivative thereof, and the mixer 6510 combines the spectrum and the noise to produce a noisy signal. The spectrum analyzer 6512 determines the frequency components of the noisy signal via Fourier analysis. The discriminant classifier 6514 initially determines the number k of the high-energy components required in a Zyoton.

In a subsequent iteration, the controlled medium is modified to include pre-measured quantities of one or more confounders, and the process described with reference to FIG. 40 is carried out using the sensor 6102, the feature generator 6112 and the Zyoton component cardinality module 6504, to determine the number m of the medium-energy components required in the Zyoton. In this iteration, the spectrum generator 6114 provides a spectrum corresponding to pre-measured quantities of the analyte and one or more confounders.

The controlled medium may then be modified to include a pre-measured quantity of a dominant confounder, and the process described with reference to FIG. 41 is carried out using the sensor 6102, the feature generator 6112 and the Zyoton component cardinality module 6504, to determine the number j of the low-energy components required in the Zyoton. In this iteration, the spectrum generator 6114 provide a spectrum corresponding to pre-measured quantities of the analyte and one or more confounders of which one is a dominant confounder. Alternatively, in some embodiments, instead of using a dominant confounder, the noise generator 6508 generates noise as described with reference to step 16 of the process described using FIG. 41, and the number j of the low-energy components required in the Zyoton is determined.

After the cardinalities k, m, and j of the high, medium, and low energy components of the Zyoton are determined, various properties of the one or more spectra generated by the spectrum generator 6114 and/or properties of one or more noisy signals generated by the mixer 6510 are analyzed by the spectrum analyzer 6512. Using these properties, such as bandwidth, amplitude distribution, etc., the Zyoton synthesizer 6520 selects a suitable Zyoton family or a Zyoton generation function from a database 6522. If a Zyoton generation function is selected, a function generator is used to generate the base Zyoton. Otherwise, the selected Zyoton family provides the base Zyoton. The base Zyoton provides the high, medium, and low-energy components, in terms of frequencies and amplitudes thereof, that can be included in the Zyoton to be synthesized.

The Zyoton synthesizer 6520 selects k high-energy components of the base Zyoton, m medium-energy components of the base Zyoton, and j low-energy components of the base Zyoton, to construct a new Zyoton. In some embodiments, the Zyoton synthesizer 6520 selects a number of features of the pure component analyte spectrum and the corresponding portions of a derivative of the pure component spectrum to compute the ratios of the amplitudes of the high-energy k components, as described above. The Zyoton synthesizer 6520 may then set or adjust the amplitudes of the one or more k components of the Zyoton, and may also set or adjust the amplitudes of the one or more m components and/or one or more j components of the Zyoton.

The carrier kernel synthesizer 6530 receives the values of the frequencies of the k, m, and j Zyoton components and uses a waveform generator 6532 to generate frequency components at the received frequencies. The carrier kernel synthesizer 6530 then sets or adjusts the amplitudes of these frequency components such that the spectral energy of the carrier kernel is approximately equal to a selected fraction (e.g., 1/100; 1/500; 1/800; 1/1,000; 1/2,400; etc.) of the spectral energy of the Zyoton. In some embodiments, the carrier kernel synthesizer 6530 may set or adjust the amplitudes of the frequency components of the carrier kernel as a pre-selected fraction (e.g., 0.06, 0.1, 0.15, 0.2, 0.23, 0.5, etc.) of the amplitudes of the corresponding components of the Zyoton. The Zyoton synthesizer 6520 may store the synthesized Zyoton in the Zyotons database 6540, and the carrier kernel synthesizer 6530 may store the synthesized carrier kernel in the carrier kernels database 6542.

These waveforms can be used by a non-invasive measurement system (a collision-computing system), such as the system 6100 described above with reference to FIG. 61. Because some of the components of the non-invasive measurement system (the collision-computing system) 6100 (FIG. 61) are used for synthesizing Zyotons and carrier kernels, the synthesized waveforms can account for one or more properties of that system such as sensor noise, resolution, sensitivity, etc.

One or more components or sub-components of the waveform synthesis system 6500 can be implemented using hardware, software, or a combination thereof, as described above in describing the system 6100. The software components can be implemented using a computer system such as that described with reference to FIG. 64.

Mapped Projector Curve Set Generation System

Figure 66:
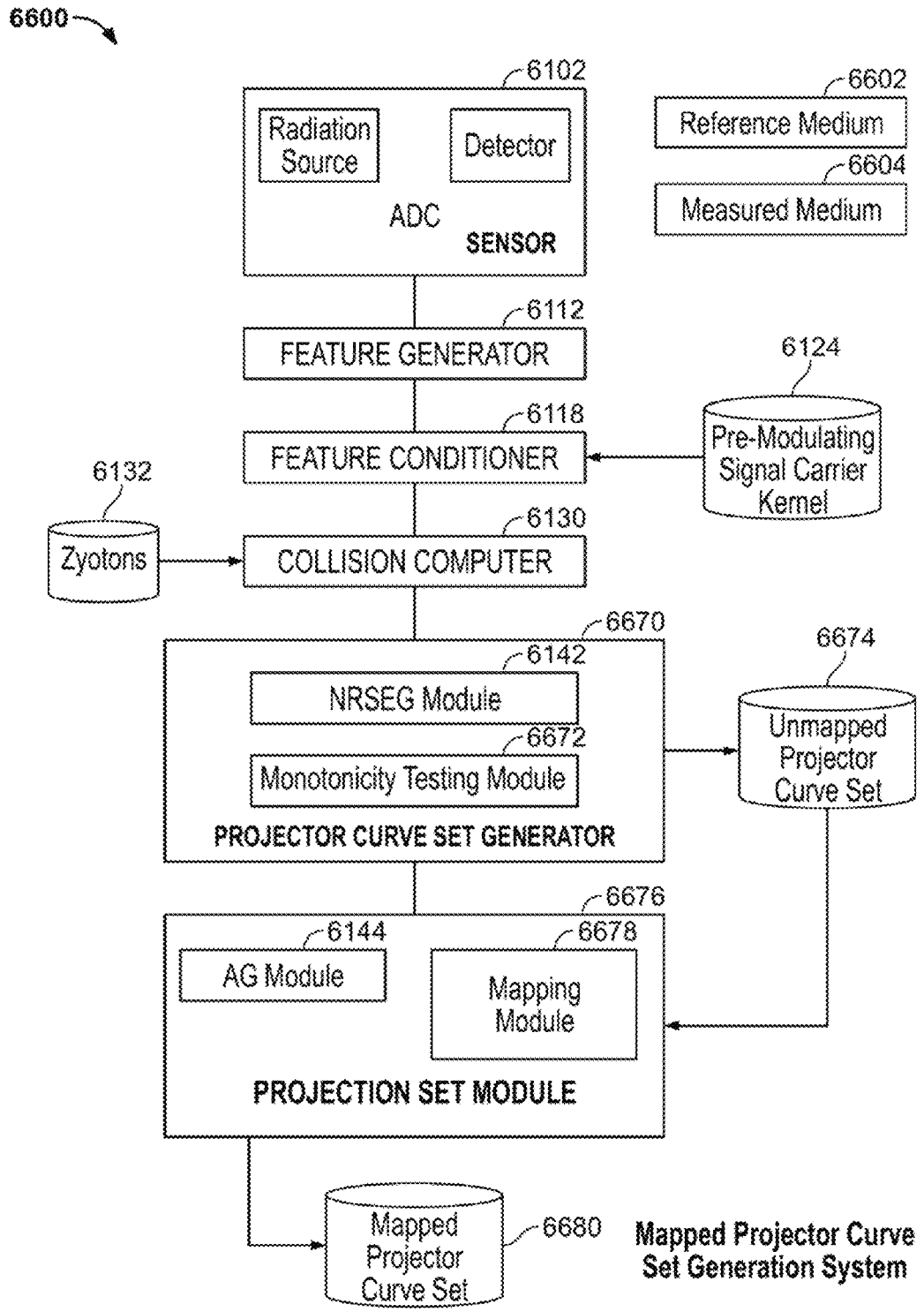
FIG. 66 schematically shows a system for generating a projector curve set that can be used for projection of collision-computing results, according to one embodiment.

Some of the components of the non-invasive measurement system (the collision-computing system) 6100 (FIG. 61) can be used in a system for generating the initial unmapped projector curve set using a reference medium (e.g., tissue phantom) and the projection sets using a measured medium (e.g., human subjects), and to map the projection sets onto the individual projector curves. With reference to FIG. 66, the mapped projector curve-set-generation system 6600 includes the sensor 6102, the feature generator 6112, the feature conditioner 6118, and the collision computer 6130. To facilitate operation of these components, the system 6600 also includes the waveform database 6124 and the Zyoton database 6132.

The sensor 6102 is used to obtain radiation from a reference medium 6602 (e.g., tissue phantom), having a known quantity of analyte (e.g., glucose). The projector curve set generator 6670 includes the NRSEG module 6142, which computes the NRSEG values corresponding to the reference concentrations of the analyte. After ensuring monotonicity across illumination states and/or for different reference concentration values, using the monotonicity testing module 6672, a relationship between the NRSEG values and reference concentrations is determined by the projector curve set generator 6670. This relationship can be depicted as a composite curve. The projector curve set generator 6670 can perform the change in slope analysis described above and generate individual projector curves, as further described above. These unmapped individual curves may be flipped as described above and stored in the unmapped projector curve set database 6674.

The sensor 6102 is also used to obtain radiation from a measured medium 6604 having a known quantity of analyte (e.g., glucose). The measured media can be one or more human subjects, where the analyte is measured, and the quantity thereof is thus known, using a reference system such as an invasive measurement system, in addition to measuring it with the non-invasive measurement system 6100 (FIG. 61). The projection set module 6676 includes the AG module 6144 of 6100. The AG module is used to compute absorption gains (AGs) or normalized absorption gains (NAGs) after optionally testing monotonicity of various NRSEG values across illumination states for one or more feature pairs using the monotonicity testing module 6672.

The projection set module 6676 generates one or more projection sets corresponding to one or more ranges of analyte concentrations measured using the reference system. The projection set module 6676 also computes the ranges of AGs/NAGs corresponding to each projection set (e.g., minimum and maximum AG/NAG values for each projection set). The projection set module 6676 receives the unmapped flipped projector curve set, and the mapping module 6678 associates the computed AG/NAG ranges with the corresponding individual projector curves, to produce a mapped projector curve set. The projection set module 6676 may store the mapped projector curve set in the mapped projector curve set database 6680.

The mapped projector curve set can be used by a non-invasive measurement system (a collision-computing system), such as the system 6100 described above with reference to FIG. 61 to quantitate and/or detect the analyte of interest via non-invasive measurements. One or more components or sub-components of the waveform synthesis system 6600 can be implemented using hardware, software, or a combination thereof, as described above in describing the system 6100. The software components can be implemented using a computer system such as that described with reference to FIG. 64.

Measurement of Glucose in Tissue Using Near-infrared Spectroscopy

Numerous attempts, as described above, have been made over several decades to measure glucose in tissue using measurements with optical spectroscopic instrumentation, even including fiber optical sensing probe variants with multiple sources and/or multiple detectors. Some approaches used absorbance values in specific wavelength windows to attempt the separation of a glucose signal from confounders, with corresponding data processing, while other approaches used entire spectral regions and a variety of multivariate data processing techniques.

The collision computing approach described herein, however, rather than attempting to separate the glucose signal from confounders using just absorbance data and geometric variations in tissue, generally accumulates, post-acquisition, spectral energy changes from spectral regions, extracted via one or more collision iterations, and uses them to extract the signal due to glucose as distinct from that due to the confounders. As described above, this is achieved, in part, by colliding once or several times carefully modified spectral regions (conditioned features) with selected waveforms having a certain propagation structure and that are unrelated to the data-acquisition domain (Zyotons) to isolate and amplify the spectral energy from different compounds, allowing an enhancement of signal to clutter (glucose to other absorbing molecules). A mapping or projection of this analyte signal can yield clinically accurate glucose measurements using the noninvasive system. Although the following example describes the noninvasive measurement of glucose in tissue, as described below, data from other sources such as those depicted in FIG. 67 can all be transformed so that they can be processed using a collision computer.

Near-Infrared (NIR) spectroscopy is one commonly used modality for characterization of organic and organometallic analytes, including those found in human tissue. When a sample is illuminated using near-infrared light, this technique utilizes the measurement of intensity of absorption by molecules. As the wavelength of NIR absorption bands is somewhat separated for different types of chemical bonds, NIR spectroscopy can be used to estimate analytes in complex matrices with some degree of selectivity. The absorption of NIR light as it passes through a medium to be analyzed such as human tissue, generally varies linearly with the distance the light travels, denoted l; with the concentration of the absorbing substance, denoted C; and with $\epsilon$, a characteristic constant for each substance at a given wavelength (known as the molar extinction or molar absorption coefficient).

The attenuation of NIR light due to a given material can be expressed by the Beer-Lambert law, whereby the Absorbance $A=\log(I_0/I)=\epsilon \times C \times l$ where $I_0$ represents the intensity of incident light and I denotes the intensity of the light transmitted through the medium. For example, if 90% of the incident light is absorbed, and 10% is transmitted, the absorbance is 1.0. A similar expression can be used for converting light reflected by the medium, designated $I_r$ to obtain a similar absorbance value, $A=\log(I_0/I_r)$. This quantity is formally designated "pseudo-absorbance," but the use of the term "absorbance" to describe this quantity is in common use in near-infrared spectroscopy.

The propagation of NIR light in human tissue is generally attenuated by the combination of absorption, scattering, and reflection of NIR photons. Absorption and scatter in tissue are generally dependent on the wavelength, while reflection may depend on the angle between an incident NIR light beam and a tissue surface, and differences in refractive indices of the materials on either side of the interface. Absorption may occur variably at different wavelengths, depending on the molecular properties of all substances in the light path.

When NIR light is scattered in tissue, the collisions between photons and atoms, molecules, or physical structures in the tissue are elastic, implicating that no energy is lost due to the scattering event; the photon merely changes direction. It should be understood that the elastic collisions in this context are the collisions between photons and atoms/molecules in the tissue, and not between two co-dependent waveforms. The direction in which a scattered photon travels is generally dependent upon the wavelength of the light and the size of the scattering particle. If the photon crosses a boundary where the two layers have different refractive indices, the direction of travel of the photon may be further altered.

A Beer-Lambert expression for a sample can be written by using the absorption coefficients of all substances $\epsilon_1$, $\epsilon_2, \ldots, \epsilon_N$ in the tissue in the travel path of NIR light, multiplied by the concentration of each substance, as: $A=(\epsilon_1 \times C_1 + \epsilon_2 \times C_2 + \epsilon_3 \times C_3 + \ldots + \epsilon_N \times C_N) \times l$. However, as multiple photons are launched in a typical spectroscopic imaging system, the optical path length l is not the same for all photons due to scattering. Also, the numbers of different molecules in the tissue these photons may encounter cannot be accurately estimated, owing to spatial variations in the composition of tissue. In fact, as a practical matter, there is no unique path length through a scattering medium such as tissue, but a distribution of path lengths. The net effect is that scattering both increases and broadens the range of path lengths and thus the total attenuation (photon loss), leading to a risk of errors in analyte-specific absorption estimation.

Thus, deconvolution of total attenuation of light to analyte-specific absorption generally cannot be accurately achieved, even with multiple measurements. This particularly applies to non-invasive spectroscopic methods for tissue spectroscopy using different arrangements that may include transmission-mode (using contralateral source-detector configuration), and either a specular reflectance mode or a diffuse-reflectance mode (using ipsilateral source-detector configurations). Inversion, i.e.,, the extraction of quantitative component information of tissue spectroscopic data from the total absorption observed to the concentrations of components, is typically an ill-posed, ill-conditioned problem and generally cannot be solved by linear deconvolution methods, including a technique called matched filtering.

These problems are usually inherent to various types of spectrometers, including dispersive and interferometric NIR spectrometers. Other challenges stem from interference from confounders: other substances which may be present in the same or significantly greater concentrations compared to an analyte, may have the same or substantially higher molar absorptivities, and may absorb in or around the same spectral region as the analyte. The variable pathlength issue described above can also lead to unknown scattering losses. Because the water content of tissues is typically very high, and water is a very strong absorber in the NIR, the absorption of water can have a particularly large optical effect, and small local variations in water concentrations, across even small distances in tissue, can lead to large absorbance errors relative to the total absorbance due to an analyte such as glucose.

When NIR light is directed at tissue, some light is reflected from the surface in a process called specular reflection, and the amount of this reflection is typically determined by the angle between the illumination and the surface, and any differences in refractive indices at the interface where the light is introduced to the tissue. Light which penetrates into a scattering medium such as tissue may be re-emitted by a process known as diffuse reflection, and the distribution of re-emitted light may depend on the angle of illumination and the nature of the scattering medium. If the re-emitted light distribution intensity corresponds to the cosine of the angle between the illumination and the surface, the material is described as exhibiting Lambertian diffuse reflection.

Various embodiments described herein facilitate the measurement of clinical analytes generally known to be present in the blood, interstitial fluid, tissue, and cellular compartments, with a dynamic range of concentrations from below picomoles/liter to tens of moles/liter. The techniques described herein can be applied to samples in solid, liquid, or gas phases. Alternatively, or in addition, embodiments of the methods and systems described herein can be used to analyze the blackbody thermal emission spectrum of tissue (in the mid-IR region) to quantify the presence of glucose, where the spectrum is influenced by the tissue composition and the glucose concentration. As in the case of absorption spectroscopy, the well-defined fingerprint spectrum of glucose in the mid-IR region may be confounded and modulated by thermal emissions from other interfering substances and the background tissue thermal emission. Collision computing described herein can nevertheless isolate the analyte (e.g., glucose) signal, i.e., the emission due to glucose as separated from both the emission due to the interfering substances and background emission.

Clinical analytes may be analyzed in-vitro, using data derived from observing standard body fluids such as blood, urine, cerebral spinal fluid (CSF), sweat, saliva, tears, dialysate, synovial fluid, amniotic fluid, or cyst fluid. In-vitro analysis can be implemented on measurements made on exudates, internal secretions or transudates. Such analysis has significant clinical utility in areas such as screening, monitoring, diagnosing, therapy, remediation, transplantation and personalized outcome-focused coaching.

Various embodiments described herein can be used to characterize clinical analytes in- vitro and/or in-vivo by analyzing data obtained through spectroscopic measurement of, e.g., skin tissue. In-vivo measurements can be obtained using sensors that make physical contact with the skin, such as optical, electro-optical, electromagnetic, electrical, magnetic, radiological, or ultrasonic sensors; or in a "standoff" mode where the sensor does not make physical contact with the skin or tissue. Distances in standoff imaging may range from few nanometers to a few meters.

Clinical measurements with high medical or therapeutic utility that can be made using collision computing as implemented in various embodiments include, but are not limited to: detecting the presence or absence of an analyte; assessing the concentration of an analyte in an unknown sample; tracking and monitoring concentration changes of the analyte over time; comparing relative concentrations of the analyte across different areas of tissue, subjects and test populations; monitoring the instantaneous or time-averaged rate of change of analyte concentration; and measuring the spontaneous depletion, spontaneous regeneration, forced depletion or forced replenishment of the analyte. During the process of measurement, a contacting sensor may alter the properties of the medium (e.g., contact or pressure induced changes upon skin contact). Also, the medium may be subject to external electromagnetic, magnetic, thermal, chemical, mechanical, vibration, external forces or stress which are typically observed as coherent or non-coherent spectral noise or transients in the data. Various embodiments described herein can account for these variations.

The generalized collision-computing process for spectroscopic non-invasive determination of analyte concentration in a medium (e.g., the glucose content of tissue) changes the old paradigm of classical spectral feature analysis, which uses a variety of methods that are generally considered to be equivalent to computation of the Fisher-information matrix, which may then be used to calculate covariance matrices associated with a likelihood estimate. A Fisher information matrix may be used as a technique for selecting features from spectral data that carry information about the analyte.

In one sense, various known techniques can be described as "training by priors," such as using training data from human subjects, and then applying a "goodness of fit" or Fisher information metric that attempts to minimize the variance expected value or other likelihood statistic of the observed information, to select one or more features to estimate the analyte concentration. Fisher information is generally known in the field of information theory as a method to measure the amount of information that an observable (such as a spectral feature) carries about an unknown parameter of interest on which the characteristics of the feature depends. It is commonly defined and expressed as the "variance of the score," or the expected value of the observed information. For a class of problems where the signal-to-noise or signal-to-clutter ratio is below a threshold, the Fisher information metric, applied directly to observations, often yields sub-optimal observable selection (e.g., the selection and length of spectral features), and tends to be a poor predictor of the parameter of interest (e.g., glucose concentration in tissue).

To offset the limitation of classical Fisher information measures for spectral feature selection based on experimental "data from priors" (i.e., spectral measurements from human subjects with different glucose concentrations) a process of feature modulation, as described above, is used in various embodiments. The conventional "data from priors" process uses, in general, a trial selection of spectral features and algebraic transformations in an attempt to yield monotonic, consistent separability of samples, as ordered by their analyte concentration reference measurements in the Fisher information space. Instead, various embodiments employing collision-computing can establish both the separability and monotonicity of the modulated spectral features in the Fisher information space. Initial feature sets may be selected based on knowledge of the absorption spectra of the analyte and known or expected confounders, and may be selected to include spectral regions of both higher analyte absorption and lower analyte absorption, as described above.

The procedure then can be summarized as follows: Select a carrier kernel such that when coupled with a feature, it can deliver an increase of up to three orders of magnitude in the amplitude of the analyte-information representing k frequency components (high amplitude components in various embodiments) of a Fourier transformed feature after one or more collisions, as described above. The selection of the carrier kernel is based at least in part, on the frequency components of a spectral signal corresponding to the analyte and/or first or higher-order derivatives thereof, typically with added noise. The expected analyte (e.g., glucose) concentration range is implicitly used in the selection of the carrier kernel, as the value of the variable k is set in various embodiments by estimating the number of frequency components required to separate higher and lower absorbance regions of the spectral signal corresponding to the analyte, i.e., a transformed pure component spectrum of the analyte, in the presence of up to three orders of magnitude added RMS random colored noise, as described above. Information about feature morphology, i.e., the frequency component profile of a feature, may also be used in synthesizing the carrier kernel, as described above.

In one embodiment for glucose measurement, a carrier kernel waveform included 128 frequency components in a frequency-domain representation thereof. Features from a set of ten optical spectra (acquired from tissue phantoms with known glucose concentrations separated by about 40 mg/dl), were used to modulate the selected carrier kernel waveform. Sets with concentration separation as low as to 10 mg/dl can optionally be used. A spectrum acquisition system with a spectral resolution of 2 $cm^{-1}$ led to a candidate feature length of 8 $cm^{-1}$.

The Fisher information matrix was calculated using non-invasively acquired spectral data from human subjects participating in a clinical study, with reference glucose values ranging from 50 mg/dl to 450 mg/dl as measured by a reference method. The observed Fisher information matrix (I) is the negative of the inverse of the expected value of the Hessian matrix H, or $I(\Theta)=-H(\Theta|Z_n)^{-1}$ where $\Theta$ is the observed parameter (e.g., reference glucose measurement) and Z is the set of n spectral feature observations in the dataset. Computation of the Hessian Matrix can be performed using utilities in software packages such as Matlab™ and Mathematica™. The gradient of a Fisher vector (FV), computed from the Fisher information matrix, for tissue phantoms separated by 40 mg/dl reference glucose concentration, can be used to separate the samples of tissue phantoms.

If the separation of the gradients of the FV is less than a threshold (e.g., sec ($\pi/9$) radians, having a numerical value of 0.111111), it was determined that Fisher information matrix failed to separate the tissue phantom samples. In that event, the feature length can be increased, e.g., doubled and/or the number of frequency components in the carrier kernel waveform can be increased, e.g., doubled. The increasing of the feature length and the increasing of the carrier kernel waveform frequency component may be performed in an alternating sequence.

If monotonicity of glucose concentration values determined via collision computing with reference glucose concentrations is not achieved with a carrier kernel waveform of a selected size (e.g., the size in terms of the number of frequency components can be 512, 1000, 2048, 4000, etc.), and a selected feature length (e.g., 60 $cm^{-1}$), then the feature start location may be shifted e.g., by the smallest selected feature length such as 8 $cm^{-1}$ up to a maximum of 48 $cm^{-1}$ in either direction from the initial feature start position. In some embodiments, a set of 22 features with length of 60 $cm^{-1}$ and a carrier kernel waveform with 2048 frequency components yielded acceptable separation results for a set of tissue phantoms with reference glucose concentrations separated by 40 mg/dl.

Features may be selectively paired, for example, to emphasize differences between the spectral properties of the analyte and the confounders, or to reflect differences in the level of absorption by the analyte at different wavelength regions. Zyotons are generally chosen with morphology such that their peak frequency component energy (i.e., the spectral energy of the analyte-information representing k components) is large enough so that when collided with a conditioned feature derived from any of the selected data features, the Zyoton would be perturbed but within limits specified by the dispersion velocity and divergence parameters, as described above.

In some embodiments, a single carrier kernel is selected to be used for conditioning all features. The frequency-domain amplitudes of the frequency components of the carrier kernel are scaled to establish the spectral energy of the conditioned feature waveform to be around $1/1,000^{th}$ to $1/100,000^{th}$ (i.e., $\alpha_Z$=0.001 to 0.00001, as described above) of the spectral energy of the Zyoton. After the selected carrier kernel is modulated by the features, a test may be performed to determine if collisions performed using the Zyoton and the conditioned features can separate the spectral energy levels between two or more tissue phantom samples with known differing levels of analyte concentration. If the separation cannot be achieved, a new carrier kernel waveform may be selected or synthesized. In some embodiments, for different features, different carrier kernel waveforms are selected and are paired with different Zyotons, according to the general selection process described herein.

During a selected number of collisions, first between a Zyoton and the conditioned feature, and then between the renormalized Zyoton (obtained by renormalizing the resulting waveform from the collision called the modified Zyoton) and the original or another Zyoton, the spectral energy of the modified Zyoton and/or the renormalized Zyoton is tested to determine if the energy of selected frequency components of the waveform after each collision iteration (or at least a specified number of collision iterations such as 2, 3, 5, 6, 10, 25 etc.) is changing (i.e., increasing or decreasing) in a monotonic fashion. If this monotonicity is not achieved, a new Zyoton (and/or a new carrier kernel) may be selected and the monotonicity test (and the separation test if a new carrier kernel waveform is selected) may be repeated. When the monotonicity condition is met, and a selected number of collisions between the Zyoton and the conditioned feature are completed, the spectral energy of the final waveform, i.e., the final renormalized Zyoton is used in various embodiments to determine the presence or absence of the analyte or to calculate the analyte concentration, or a change in the concentration.

In spectral signals obtained from NIR radiation received from a tissue sample, the energy loss due to the analyte is typically much less than that due to one or more confounders, and the total energy losses due to the analyte and confounders are often significantly less than the loss due to scattering and/or dispersion of the radiation in the tissue. As such, the signal-to-clutter ratio (SCR) of a signal corresponding to the energy loss due to the analyte of interest to the overall energy loss due to confounders and scattering can be very low, e.g., often as small as $1\times10^{-6}$. By tuning one or more of the Zyotons, the collision operator, one or more parameters thereof, and the carrier kernel waveform modulated by the feature, to an expected required SCR increase, the energy loss represented by the feature can be amplified without introducing noise and/or distortion in one or more collision iterations, and can thus be measured.

One objective of the Zyoton tuning process is to configure the Zyoton such that energy loss estimated from a Zyoton collided with a specific conditioned feature, after one or more selected number of collision iterations as described above, is monotonically increasing, that is, unidirectional with the concentration of analyte in the sample, as measured by a reference system, over the analyte concentration range of interest, when the analyte concentrations and measured energy loss are represented as ordered pairs. The collision process can be thus described as a monotonic transformation of an acquired spectroscopic dataset. A calibration table, curve, or set of curves can be used to determine accurately the concentration of the analyte in the medium to be analyzed according to the amplified energy loss or gain, as represented by the final result of one or more valid collisions, where the validity of the collision iterations can be verified by monotonicity, as described above.

The collision process is not only used to assess absorption energy changes in the NIR band due to analyte presence but also to deconvolve those energy changes from attenuation due to scattering losses resulting from the medium and absorption from confounder molecules. A single collision iteration may be adequate to deconvolve these changes with high confidence in some situations. Many situations typically require several (e.g., 10; 100; 500; 1000; 2000; 10,000; 100,000; or more) collision iterations. By varying the phase of one or more of the frequency components of one of the colliding entities, e.g., a Zyoton, in each successive collision, artifacts due to random noise, instrument drift and instabilities, sampling errors, and ambient conditions can be filtered out. The phase operator may be applied in the time domain or frequency domain. In the frequency domain phase changes are introduced as scaling of frequency components in the collision step. Also, several collisions can be used to expand the dynamic range of estimated spectral energy changes so that greater precision can be obtained during the post-collision projection process for estimating the analyte concentration. In a sequence of several (e.g., $\mathbb{N}$ ) collisions of well-designed entities, the renormalized energy gain increases (or energy loss decreases) monotonically over a subsequence of successive collision iterations of a specified cardinality n, where $2 \leq n \leq \mathbb{N}$. At the end of the $\mathbb{N}$ collisions, a cumulative net, positive gain or loss is achieved in various embodiments.

Utility can be optionally derived from the use of a single collision iteration. For example, while accurate glucose concentrations are typically not easily determined with a single collision iteration, the glucose range can be classified in a "glycemic wellness" application for an individual as "low," where the glucose level is approximately below 80 mg/dl, "normal," where the glucose level is approximately between 80 mg/dl and 180 mg/dl, or "high," where the tissue glucose is approximately over 180 mg/dl. The net, renormalized spectral energy gain obtained after a single collision iteration can be used to classify the tissue glucose in such a glycemic wellness regime.

Different Zyotons may be used to collide with different conditioned features. As described above, different features extracted from spectral regions where analyte absorption occurs relatively strongly and regions where absorption occurs more minimally can have large differences on the absorbance scale. These differences for analytes of interest can vary over several orders of magnitude. With such variances in absorption properties, the co-dependency condition cannot be easily achieved using the same Zyoton for all features. Thus, in some embodiments, different Zyotons are designed and tested to ensure that each conditioned feature and Zyoton pair satisfies the co-dependency condition described above. As also described above, the classification of features into "strongly absorbing" and "minimally absorbing" regions is only approximate. In some cases, the features represented as being from "minimally absorbing regions" may be from regions that correspond to substantial analyte absorption but which also correspond to substantial absorption from confounders.

By absorbing radiation, the analyte in the medium generally causes a change in the amount of radiation reflected by the medium or transmitted therethrough relative to the radiation that would be reflected or transmitted therethrough if no analyte were present in the medium. This change is generally represented in the acquired spectral data of the medium and, hence, in one or more extracted features, but is usually hidden in frequency components of extremely low amplitude. The Zyotons, the conditioning of the features, and the collision operator are constructed such that one or more collisions generally induce a measurable change in one or more properties (e.g., the spectral energy loss due to absorption of the incident light/radiation by the analyte in the selected NIR spectral bandwidth) of portions of the waveform resulting from the collisions. After a preset number of collisions between a conditioned feature and the corresponding Zyoton have been completed, as described above, such change in the resulting waveform is measured to determine the net spectral energy gain/loss due to each conditioned and collided feature.

In various embodiments, during a collision process involving one or more collisions, the changes in the properties of the Zyoton waveform before and after collision are analyzed as a mechanism to infer properties of the feature. As described above, impacted properties include changes in propagation velocity, peak energy, dispersion velocity and changes in the spectral envelope as represented, at least in part, by divergence and/or a change in the time-domain length of the waveform or the number of frequency components therein. These changes are quantified through measurement of changes in the spectral energy of the resulting waveform after each collision, the difference being that in the first collision the conditioned feature waveform and Zyoton waveforms collide, and in subsequent collision the Zyoton collides with the renormalized result of the prior collision, which includes the effect of the feature.

In effect, the process examines how the conditioned feature alters the properties of the Zyoton waveform, i.e., the collision yields changes in the energy of the Zyoton waveform. Depending on how the conditioned feature waveform itself has been influenced by the underlying analyte absorption, and by absorption and scattering due to confounders and the medium to be analyzed, the impact on the Zyoton can be different. A Zyoton can thus be described as a nonlinear amplifier system and a feature as a perturbation. In general, the iterative collision process is thus a protocol for characterizing analyte properties and estimating analyte concentration in uncharacterized samples.

One specific embodiment of a non-invasive measurement system employing collision computing generally described above is now discussed for non-invasive glucose detection and measurement in human tissue using diffuse reflectance NIR spectroscopy, where the radiation sources and detectors are both in contact with the skin. The distances of different sources from one or more detectors are different and, as such, this approach can be called "tomographic spectroscopy."

For non-invasive measurement of an analyte using spectral absorption in tissue in the NIR region, the presence and/or concentration of the analyte can be determined by using the collision process described herein to estimate the net photon energy losses due to absorption by the analyte molecules. The energy losses due to the confounders can be significantly larger (e.g., two, three, five times, etc., or even one to four orders of magnitude larger) than the energy absorbed by the analyte of interest. The scattering losses can also be high, often more than two, four, ten, etc., orders of magnitude greater than the energy absorbed by the analyte. For example, for non-invasive measurement of blood glucose concentration, empirical measurements and bio-optical simulation models for skin and sub-cutaneous tissue show that over 99.9% of photon energy losses are due to scattering and due to absorption from molecules other than glucose. The mechanism of scattering and scattering losses were described above. The scattering losses generally depend on the attenuation coefficient for the medium, and the wavelength of incident light.

This embodiment employing collision computing exploits three fundamental differences in scattering and absorption losses during light propagation through tissues: First, human skin has a layered structure, and there are well-understood compositional differences in the near-surface skin tissue layers. For example, the epidermis or outer layer has large amounts of protein but is generally lacking in glucose, the intermediate dermis layer has larger amounts of glucose, the lower subcutaneous layer has a preponderance of fats, and the different layers have varying protein structures present. Thus, both scattering and absorption properties are different for the different layers. By designing an imaging strategy and combining features obtained from the measured spectra that target different tissue layers, absorption and scattering effects were separated on a per-layer basis.

Second, each chemical compound has a wavelength-specific characteristic "fingerprint" or spectral signature. However, in the near-infrared region, these spectral signatures are often not distinctive because the absorption bands are broad and overlap frequently. Scattering and absorption energy losses from other compounds can create intensity changes in the same regions as the analyte, thereby further obscuring the analyte absorption signal. Collision computing generally allows for recapturing a weak signal where such a spectral fingerprint is available but cannot be clearly distinguished from other substances using conventional techniques. A pathological case is where other substances have the identical spectroscopic fingerprint as glucose and are present in substantial concentrations. The two may then become indistinguishable. However, there are no known substances with identical absorption profiles present in concentrations high enough to cause significant errors in the measurement of glucose in the tissue layers interrogated using the spectroscopic tomographic process described above, thereby rendering this technique generally applicable to the practical, non-pathological situations.

Third, the wavelength dependency of scattering in human tissue is largely different from the absorption profile. Scattering losses follow a different mechanism, having values that generally increase with decreasing wavelength. This property is generally in effect at the feature level and generally applies to all features. In various embodiments, the Zyoton waveforms are synthesized with the ability to separate wavelength-dependent attenuation from the patterned attenuation of absorption, which can allow for elimination of this major source of clutter.

Post-processing of collision results from all features and all tissue compartments focuses on exploitation of the first and second properties described above. Also, the scattering properties of the various tissue compartments are generally dependent on both time and physiology, and cannot be accurately estimated in many situations. However, the distribution for scattering attenuation typically follows a normal distribution, and this normal distribution manifests in the spectra as random noise. The parameters of the distribution can be different in each layer and among different subjects. The generalized collision protocol, specifically with the variations in phase and delay for the collision operator described above, can overcome these sample-to-sample differences in scattering that may manifest as random noise artifacts.

In various embodiments, in order to measure the analyte concentration accurately, a three step process is used, where each step may employ collision computing: (i) estimation of the net energy absorbed in each extracted feature due to analyte presence; (ii) net energy absorbed in all the features from a single spectrum acquired during a multiple illumination sequence (MIS) (as described below), and; (iii) the net energy absorbed, as estimated from multiple spectra acquired corresponding to each illumination state in an MIS (all the spectra acquired may be employed).

As described here and below, in some embodiments, an illumination state is implemented by turning on several sets of illumination sources (each set corresponding to a particular illumination state), geometrically arranged in concentric rings around a detector. Let the simultaneous turn-on condition of one or more illuminators in a set (e.g., individual illuminators in a ring; groups of illuminators in one or more rings; all illuminators in a ring; or all illuminators in multiple rings), correspond to an "illumination state," denoted $R_t$. Furthermore, an illumination sequence is designated as $I^1$, $I^2$, and $I^3$, where each $I^n$, i.e., an illumination state, can be any combination of simultaneous turn-on of one or more rings (sets of illumination sources, in general).

In one example, features F1 and F2 were captured and selected from reflectance spectra acquired corresponding to each illumination state $I^n$ during an illumination sequence, having three illumination states. In this example, step (i) described above involves the determination of Δe corresponding to F1 or F2 based on each $I^n$, i.e., based on $\Delta e_1^1$, $\Delta e_1^2$, and $\Delta e_1^3$ or based on $\Delta e_2^1$, $\Delta e_2^2$, and $\Delta e_2^3$. In some embodiments, the determination of Δe requires analysis of a feature pair. In such embodiments, the determination of Δe may be based on any one feature pair but not on all feature pairs in step (i).

Step (ii) described above involves the determination of Δe ($\Delta e_1^1 + \Delta e_2^2$), i.e., energy corresponding to illumination state $I^1$ and both features F1 and F2; ($\Delta e_1^2 + \Delta e_2^2$); and ($\Delta e_1^3 + \Delta_2^3$). If additional features are available, they may also be used in the determination of Δe. Step (iii) involves the determination of Δe using $\Delta E^1$, $\Delta E^2$, and $\Delta E^3$, where $\Delta E^n$ is the energy change absorbed using two or more spectra corresponding to two or more repeats of at least one of the illumination states (i.e., $I^n$, where n=3, in this example) for each feature (i.e., F1 and F2 in this example). In different embodiments, $\Delta E^n$ can represent an aggregate or an average of the energies computed for the repeats of a particular illumination state $I^n$. For simplicity, the numerical value of the net, renormalized, spectral energy gain that is described in detail below, for a "feature pair" is referred to as "NRSEG." In some embodiments, the NRSEG can be a value less than zero, where collision iteration(s) are constructed to produce modified Zyoton(s) that have less spectral energy than the original Zyoton.

Illumination sequences are often useful because the resulting NRSEGs can be used to directly generate additional metabolic, clinical, and anatomical attributes. For example, NRSEG obtained from an illumination sequence for non-invasive glucose detection also enables identification of non-glucose containing tissue such as the stratum corneum layer and rejection of unsuitable samples. With this approach, spectroscopic measurements from the palm of the hand may be rejected if the skin tissue contained an unusually thick stratum corneum layer.

The post-collision Δe term corresponds to the net energy absorbed by the analyte in the features. Also, a distinction between steps (ii) and (iii) is as follows: Step (ii) involves a single spectrum for each illumination state. For example, if the sequence is (R1), (R1+R3), (R3), and (ALL Rings) (where R1 stands for Ring 1, R2 stands for Ring 2, etc.), for each illumination state in this sequence, only one spectrum is collected while performing Step (ii) and in computing the energies in that step. However, while performing Step (iii) and in computing the associated energies, optionally multiple spectra are acquired for each illumination state. For example, ten spectra for each of (R1), (R1+R3), (R3), and (ALL Rings). Either the spectral intensities or the spectral absorbances can be added and averaged for the entire spectra, or each spectrum can be deconstructed into features, and then Δe computed for each feature, after which all Δes can be averaged.

The process of analyte estimation may additionally include a spectrum standardization step for compensating variability due to the optical sampling process, ambient factors (e.g., temperature, humidity) that may impact analyte absorption, and variability in optical coupling between the optical sensor/detector and the medium. In non-invasive analyte measurement using spectra obtained by NIR illumination of skin, normalization may also be provided for variability in tissue hydration (a strong spectral confounder), variability due to demographic differences such as age, sex, skin pigmentation, skin thickness, skin topography, and fat content, and sampling inconsistencies due to variability in sensor contact with the skin.

Figure 69:
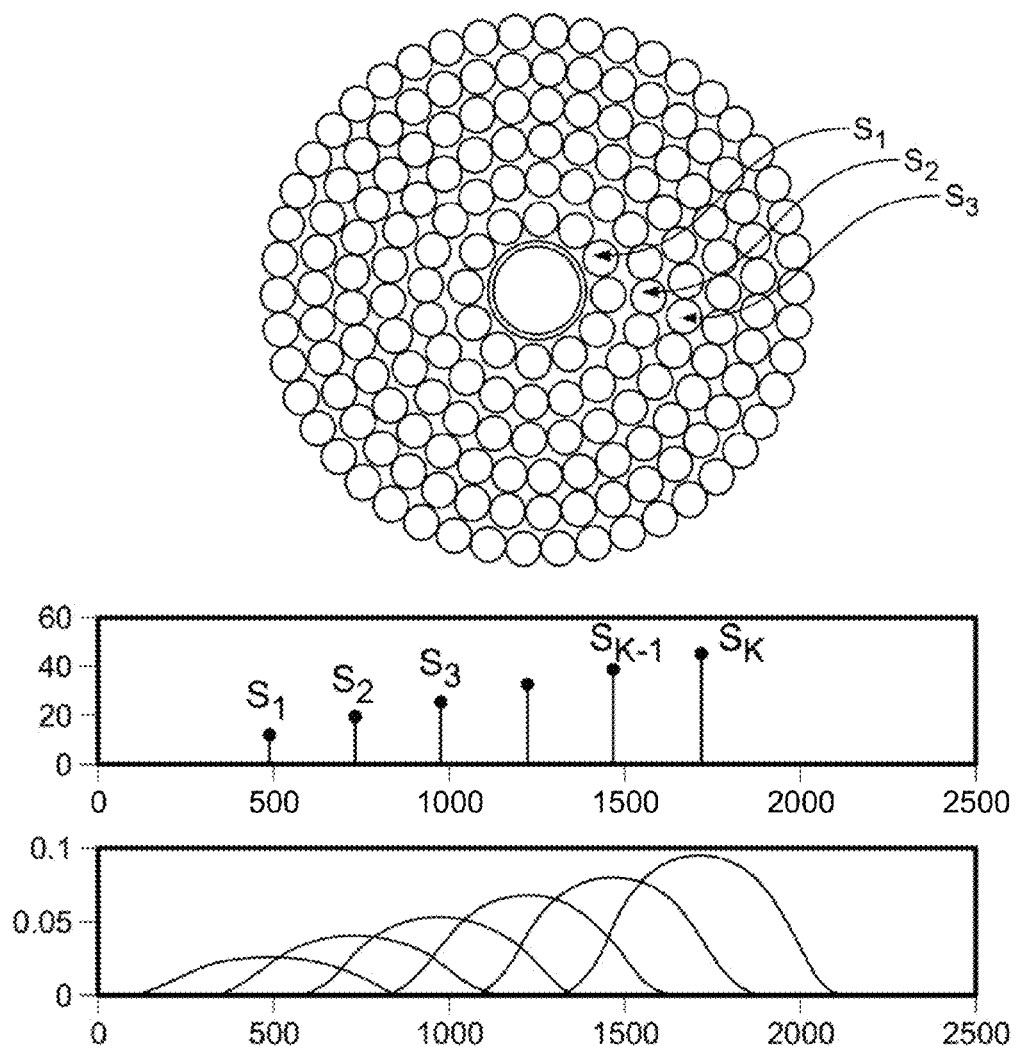
FIG. 69 schematically depicts an exemplary illumination/detection probe that can be used in the system shown in FIG. 68.
Figure 70:
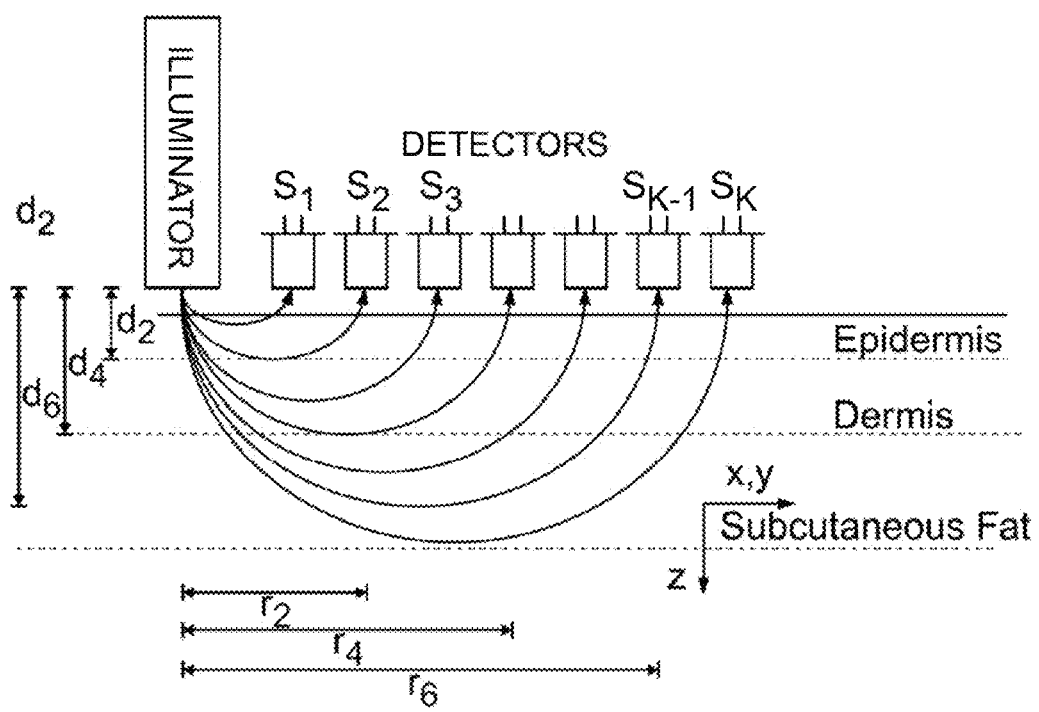
FIG. 70 schematically depicts an illumination/detection system for non-invasive glucose measurement, according to another embodiment.

Using a spectroscopic measurement system such as that shown in FIGS. 68 through 70, with several illumination states, normalization may be performed through a differential comparison of spatially resolved spectral measurements from different rings. In one example, the difference between two different ring absorbance measurements is utilized and optionally ratioed, wavelength by wavelength, to a third ring or to "ALL Rings." Another normalization procedure may utilize multiplicative scatter correction which may be windowed over selective wavelength ranges, across all the illuminations in an MIS, to provide a set of template spectra representative of a calibration data set, as described below.

Creation of a Calibration Curve Set with Tissue Phantoms

Synthetic media called tissue phantoms are engineered, calibrated, time-stable, tissue-like materials for calibrating, comparing and assessing NIR spectroscopic imaging system performance. The bulk phantom material may include, for example, gelatin, Intralipid (a synthetic emulsion of triglycerides in water that mimics the scattering properties of tissue), polystyrene beads of defined size and optical properties, and application-specific compounds. Well engineered tissue phantoms have variability, absorption, and scattering bulk properties comparable to those observed when imaging human tissue with the same instrument. In order to use these phantoms as part of a calibration set, it is important that the scattering and absorption properties of the tissue phantom match reasonably well those of the actual medium in which the analyte concentration is to be measured, such as human tissue. Concentrations of known confounders in these phantoms typically range from zero to twice their highest anticipated concentration in actual tissue, with the exception of water, which in tissue is often close to its maximum concentration. Each different concentration level of the analyte of interest and confounders defines an independent, unique sample.

Thus, predefined absorbance and scatter properties can be constructed in a volume of liquid or solid material, and complex tissue phantoms can be constructed to capture variations of analyte concentration, tissue layering and optical properties. A calibrated set of tissue phantoms, each with a representative reference glucose concentration measurement to assess monotonicity of estimated spectral energy gains due to glucose absorption with concentration, may be used in Zyoton design, as described above, and in calibration and optimization for non-invasive glucose measurement at the desired precision and accuracy.

In an embodiment for the noninvasive measurement of glucose in tissue, analyte detection and quantitation estimation is made on the basis of computing the net relative perturbation in the renormalized spectral energy gain of the Zyoton waveform resulting from collisions with each feature extracted from a spectral region corresponding to relatively strong glucose absorption ("GL features"), compared to the perturbation in the renormalized spectral energy gain of the same Zyoton waveform resulting from collisions with a different spectral feature extracted from a region corresponding to less strong glucose absorption ("NO-GL features"). In other embodiments, for other analytes of interest, a similar process is employed with respect to feature(s) extracted from spectral region(s) corresponding to relatively strong analyte absorption, called analyte feature(s), and feature(s) extracted from spectral region(s) corresponding to relatively less strong glucose absorption, called non-analyte feature(s).

This process may be repeated for each illumination state. As the analyte absorption and scattering in human skin tissue are both known to be pathlength and wavelength dependent, and different GL and NO-GL features represent different average levels of analyte absorbance, their renormalized spectral energy gain aggregated over the N collisions is further standardized in this embodiment to obtain the net, renormalized spectral energy gain (NRSEG).

This standardization can be achieved by colliding the Zyoton with the carrier kernel γ, frequency modulated by the same frequency (e.g., 16.5 Hz or 100 KHz in specific embodiments) used to modulate the GL and NO-GL features, but without the use of any feature data. As described above, only the amplitudes from the k frequency components are used in the spectral energy computations in some embodiments. Thus, the NRSEG due to analyte (e.g., glucose) presence is given by:

$$\Delta \vec{e}_{(GL_{F_p}, NO-GL_{F_q}, Z_r, R_t)} = \frac{\Delta \vec{e}_{(GL_{F_p}, Z_r, R_t)} / \Delta \vec{e}_{(NO-GL_{F_q}, Z_r, R_t)}}{\overline{\Delta \vec{e}}_{(GL_{F_p}, Z_r, R_t)} / \Delta \vec{e}_{(Y, Z_r, R_t)}} \quad (16)$$

where the term $$\Delta \vec{e}_{(GL_{F_p}, NO-GL_{F_q}, Z_r, R_t)}$$

represents the relative renormalized spectral energy gain of the Zyoton waveform ($Z_r$) resulting from collisions (with a collision iteration count of $\mathbb{N}$) with a conditioned feature extracted from the analyte-absorbing region of the acquired spectrum (e.g., $GL_{F_p}$) vis-à-vis the renormalized spectral energy gain of the same Zyoton waveform, $(Z_r)$, resulting from collisions with a different feature extracted from a region known to be minimally absorbing (i.e., NO-$GL_{F_q}$), for each illumination state.

As described above, an illumination state generally represents simultaneous turn-on condition for all the separate illumination sources in an entire illumination set (ring or rings), $R_t$, where t=1, 2, 3, 4, 5, 6, or "ALL Rings" (where "ALL Rings" corresponds to illuminating all rings at the same time, e.g., 6 in a 6-ring illumination system), for illuminators similar to those shown in FIGS. 68 through 70. To reemphasize, "illumination state" is generally expressed in terms of which rings are illuminated. An illumination sequence (also called multiple illumination sequence (MIS)), is a sequence [$R_t$], of multiple illumination states, $R_t$, where an illumination state can be an illumination of a single ring or the illumination of two or more rings. For example, [$R_t$] can be:

(R1), (R2), (R3), (R5), (ALL);

or ($I^1 \triangleq R1$), ($I^2 \triangleq R2+R3$), ($I^3 \triangleq R4+R5$), ($I^4 \triangleq R5$), ($I^5 \triangleq ALL$).

The number of unique illumination states is denoted M. One or more illumination states may be replicated, as described below. In either of the two examples above, M=5, including the illumination state ALL rings. In general, M can be less than or greater than 5. In a different embodiment, where only three rings of illumination are used, the Illumination States in the MIS could be described as R1, R2, R3, and "All Rings," and M would equal 4.

An example of paired features $GL_{F_p}$, NO-$GL_{F_q}$ is GL-1, NOGL-1, as defined in FIG. 49; and, the corresponding zyoton $Z_r$ given by Z-kernel-E1, Z-kernel-D1, Z-kernel-S1, and Z-kernel-MM1, corresponding to the illumination states of rings R1, R2, R3, and ALL Rings.

In Equation (16) the term $$\Delta \vec{e}_{(GL_{F_p}, Z_r, R_t)}$$

represents the renormalized spectral energy gain of the zyoton waveform $(Z_r)$ resulting from collisions (with a collision count $\mathbb{N}$) with a conditioned feature extracted from the analyte-absorbing region of the acquired spectrum, e.g., $(GL_{F_p})$. The symbol "$\Delta \vec{e}$" indicates a vector over $R_t$=1, 2, 3, ALL. The term $$\Delta \vec{e}_{(GL_{F_p}, Z_r, R_t)}$$

is computed using the results of applying the collision-operator (defined above) as $\Omega(\overline{GL_{F_p}}, \overline{Z_r})_{t_l}$ over $\mathbb{N}$ collisions. The term $$\Delta \vec{e}_{(NO-GL_{F_q}, Z_r, R_t)}$$

is the cumulative renormalized spectral energy gain of the same zyoton waveform, $(Z_r)$, resulting from collisions with a different conditioned feature extracted from a region known to be minimally absorbing (i.e., NO-$GL_{F_q}$), and $$\Delta \vec{e}_{(NO-GL_{F_q}, Z_r, R_t)}$$

is computed using the results of applying the collision-operator (defined above) $\Omega(\overline{NO-GL_{F_q}}, \overline{Z_r})_{t_n}$ over n=1, ..., $\mathbb{N}$ collisions.

The term $$\Delta \widetilde{\vec{e}}_{(NO-GL_{F_p}, Z_r, R_t)}$$

in Equation (16) represents the renormalized spectral energy gain of the zyoton waveform $(Z_r)$ resulting from the first collision with a conditioned feature extracted from the minimally analyte-absorbing region of the acquired spectrum, e.g., (NO-$GL_{F_p}$). Thus, in the unique case in which only one collision is used, the equation above simplifies to:

$$\Delta \vec{e}_{(GL_{F_p}, NO-GL_{F_q}, Z_r, R_t)} = \frac{\Delta \vec{e}_{(GL_{F_p}, Z_r, R_t)}}{\Delta \vec{e}_{(NO-GL_{F_q}, Z_r, R_t)}^2 / \Delta \vec{e}_{(Y, Z_r)}} \quad (17)$$

The term $\Delta \vec{e}_{(Y, Z_r, R_t)}$ is the renormalized spectral energy gain of the same zyoton waveform, $(Z_r)$, due to collisions with the carrier kernel Y, that has been frequency modulated, in the same manner as the GL and NO-GL features. No feature data are used in this computation of $\Delta \vec{e}_{(Y, Z_r, R_t)}$. Therefore, this term is independent of $R_t$ and, in fact, is generally constant across all values of $R_t$. This term is computed using the results of applying the collision-operator (defined above) $\Omega(\overline{Y}, \overline{Z_r})_{t_l}$ over l=1, ..., $\mathbb{N}$ collisions.

In various embodiments, this term, $$\Delta \vec{e}_{(GL_{F_p}, NO-GL_{F_q}, Z_r, R_t)},$$

i.e. the NRSEG due to analyte absorption, is computed for all (p, q) pairings of GL-p and NO-GL-q features exemplified in FIG. 49, for a particular illumination state $R_t$, where t=1, 2, 3 or ALL Rings (as in this example). The computation for all feature pairings is then repeated in some embodiments for all illumination states.

Optionally, if the signal-to-clutter (SCR) ratio is relatively high, e.g., above 0.1, features need not be selectively paired with other features (e.g., from wavelength regions of differing absorption) to compute the post-collision net renormalized spectral energy gain. Therefore, in some embodiments, the post-collision results of the analyte and non-analyte features (e.g., the GL and NO-GL features as shown in FIG. 49) are not paired. Examples of applications where relatively high SCR may be encountered include in-vitro analysis of blood or body fluid analytes where the samples to be analyzed have been pre-amplified using biochemical assays, or blood analysis using fluorescence assays using detection techniques such as high affinity fluorescence tags. In-vivo examples include analysis of data from invasive, implanted fluorescence tags. Thus, the NRSEG $\Delta \vec{e}_{(F_p, R_t)}$ due to analyte presence in a feature $F_p$ for an illumination state $R_t$ can be computed using:

$$\Delta \vec{e}_{(F_p, R_t)} = \frac{\Delta \vec{e}_{(F_p, Z_r, R_t)}}{\Delta \vec{e}_{(Y, Z_r, R_t)}} \qquad (18)$$

where the terms $\Delta \vec{e}_{(F_p, Z_r, R_t)}$ and $\Delta \vec{e}_{(Y, Z_r, R_t)}$ are described above.

In spectroscopic systems constructed using multiple sources and single detection element or single illumination element and multiple detection elements, averaging may be required to process repeat spectra or replicated sequences of illumination states, denoted as "replicates." For example, an optical imaging system configured as in FIG. 69, includes a central detection fiber and concentric rings of NIR illuminators, $R_1$ through $R_K$. Table 14 below provides the dimensions and measurements of an embodiment corresponding to this configuration.

Let the state where an entire ring of illuminators of Ring 1, surrounding the detection element is turned on, be denoted as R1. In a similar vein, {R1, R2, R3, ALL} represents a sequence where Ring 1, Ring 2, Ring 3 and ALL Rings are turned on sequentially. A sequence {R1, R2, R3, ALL, R1, R2, R3, ALL} represents a "replicate" where the entire sequence {R1, R2, R3, ALL} is repeated. Another example of a replicate sequence is {R2, R3, R4, R1, ALL, R2, R3, R4, R1, ALL, R2, R3, R4, R1, ALL}, where a different sequence of illuminators is turned on and repeated three times. Additionally, {R1, R1, R2, R2, R3, R3, ALL} represents a sequence where Rings R1, R2, and R3 are "repeats" but ALL is a singleton with no replicate. In the sequence {R1, R2, R3, ALL, R1, R2, R3, ALL}, M=4, and the number of replicates, denoted U, is equal to 2. In the sequence {R2, R3, R4, R1, ALL, R2, R3, R4, R1, ALL, R2, R3, R4, R1, ALL}, M=5 and U=3.

Let the set of NRSEGs from all pairings of GL-p and NO-GL-q features be denoted by $\{\Delta \vec{e}_{(p,q,R_t)}\}$ where p=1, ..., P, and q=1, ..., Q. To process repeats, NRSEG is computed for all pairings of GL and NO-GL features for each illumination state, $R_t$, that is repeated. Say an illumination sequence presents up to U repeats for certain illumination states, where u≥1 and u=1, ..., U. NRSEG for the feature pair (p,q) is then $\{\Delta \vec{e}_{(p,q,R_t,REP_u)}\}$ for the repeat REPu associated with state t or the t-th illumination state including two or more rings (e.g., R2 and R4) for all p=1, ..., P, and q=1, ..., Q.

The set of U repeated NRSEG values from all pairings of GL-p and NO-GL-q features are then averaged in some embodiments to yield sets $\{\Delta \vec{e}_{(\bar{p},\bar{q},R_t)}\}$ corresponding to all feature-pairs (p,q). As an example, the cardinality of the set $\{\Delta \vec{e}_{(\bar{p},\bar{q},R_t)}\}$ corresponds to the number of distinct feature pairings as shown in FIG. 49, is 88, i.e., 22 times for each illumination state $R_t$ where M=4, and where the number of feature pairs, denoted Π, is 22. Each value in the set is averaged over the corresponding U repeats, and the averaging of repeats for each illumination state is performed prior to normalization of NRSEG for use in the Projection operation described below.

This $\{\Delta \vec{e}_{(\bar{p},\bar{q},R_t)}\}$ set corresponds to the NRSEG for all features, averaged for all repeats, for all illumination states for the sample over the entire spectral bandwidth covered by the GL features. Monotonicity of the NRSEG values of each feature pair across different illumination sets is tested, and feature pairs having non-monotonic NRSEG values are rejected in some embodiments. The remaining feature pairs having monotonic NRSEG values across illumination states are generally called "acceptable" feature pairs.

Next, a weighting transform is applied in some embodiments to the NRSEG values $y_C^i$ for i=1,2, ... Π, to normalize all the feature pairs to provide an appropriate weighted contribution to the NRSEG, denoted "normalized NRSEG" for each concentration. Each normalized or weighted NRSEG appears as a data point by itself. From these, outliers may be omitted and a mean of the weighted NRSEG values may be used in further computations. Here, Π denotes the cardinality of the total set of feature pairs, the superscript i indicates the i-th feature pair, and subscript C represents a particular analyte concentration in the set of tissue phantom concentrations, e.g., {0 mg/dl, 20 mg/dl, 40 mg/dl, ..., 900 mg/dl}. Thus, C can be 40 mg/dl, 80 mg/dl, 180 mg/dl, etc.

The normalized NRSEG values $\bar{y}_C^i$ may then be computed for all Π feature pairs, or, alternatively, all of the acceptable feature pairs, as defined below, for each sample of the tissue phantoms using the product term given by:

$$\bar{y}_C^i = y_C^i * W(i_{(p,q)}) \qquad (19)$$

where $W(i_{(p,q)})$ is a numerical weighting coefficient, associated with an $i^{th}$ feature pair $i_{(p,q)}$ where p and q represent the GL and NO-GL feature comprising the pair. The weighting coefficient for the feature pair (p,q), i.e., $W(i_{(p,q)})$ is calculated using the pure component absorbance spectrum of the glucose analyte (as shown in FIG. 28A) and the knowledge of spectral boundaries of the GL feature p and NO-GL feature q (as exemplified in FIG. 83). The product of $y_C^i$ and $W(i_{(p,q)})$ is defined as a "normalized feature pair."

In the term $$AvgAbsorbance_{(f)} = 1/W \Sigma_{l=1}^{W} Absorbance(W(f, l)) \qquad (20)$$

the variable W corresponds to the window width (number of distinct absorbance values) of each feature, λ(f, l) is the lth wavenumber of feature, f, and Absorbance(W) is the absorbance of the pure component spectrum at wavenumber W, and the integration is performed separately for both the p and q features. Then, $$W(i_{(p,q)}) = \frac{\max_{u,v}(AvgAbsorbance_u / AvgAbsorbance_v)}{(AvgAbsorbance_p / AvgAbsorbance_q)} \qquad (21)$$

such that a dimensionless quantity, $\max_{u,v}$(Avg Absorbance$_u$/AvgAbsorbance$_v$) is the maximum of the ratio of average absorbance of any GL feature u to its associated NO-GL feature v (over the total feature-pair set as shown, e.g., in FIG. 49), computed using the glucose pure component spectrum shown in FIG. 28A. The terms, AvgAbsorbance$_p$ and AvgAbsorbance$_q$, which refer to the average absorbance of features p and q computed using the above definition of AvgAbsorbance, can be used to compute the dimensionless number (AvgAbsorbance$_p$/AvgAbsorbance$_q$).

In summary, in various embodiments, the weighting coefficient $W(i_{(p,q)})$ may be used to scale all acceptable feature pairs from any one illumination state to normalized feature pairs that have the correct net contribution to the NRSEG corresponding to each glucose concentration. Weighting coefficients can also be defined using minimum, maximum, or median value of the absorbance over the region of interest of the pure component spectrum corresponding to the feature.

In one embodiment where the number of total available feature pairs=22, the number of illumination states is 4, and the number of computed NRSEG (un-weighted) is 88. These 88 values are used to determine monotonicity and slope in order to determine which feature pairs are acceptable. The acceptable feature pairs are then weighted as discussed above and outliers are removed that are more than two standard deviations away from the mean. As an example, if the number of acceptable feature pairs is 17, one illumination state, e.g., R2, may be selected, and the respective weights may be applied to the 17 NRSEG values corresponding to R2, for the acceptable 17 feature pairs, to obtain 17 normalized NRSEG values. From these 17 normalized NRSEG values, outliers (e.g., >2 times the standard deviation away from the mean), may be removed. If the number of outliers removed is 3, the mean of the remaining 14 normalized NRSEG values may be used to determine two segments (or only one segment, if the corresponding analyte concentration is the lowest or highest), of the composite projector curve. It should be understood that the numerical values described above are illustrative only, and that in different implementations, the numbers such as the total number of feature pairs, the number of acceptable feature pairs, the statistical threshold for outlier rejection, etc., can be different.

Figure 71:
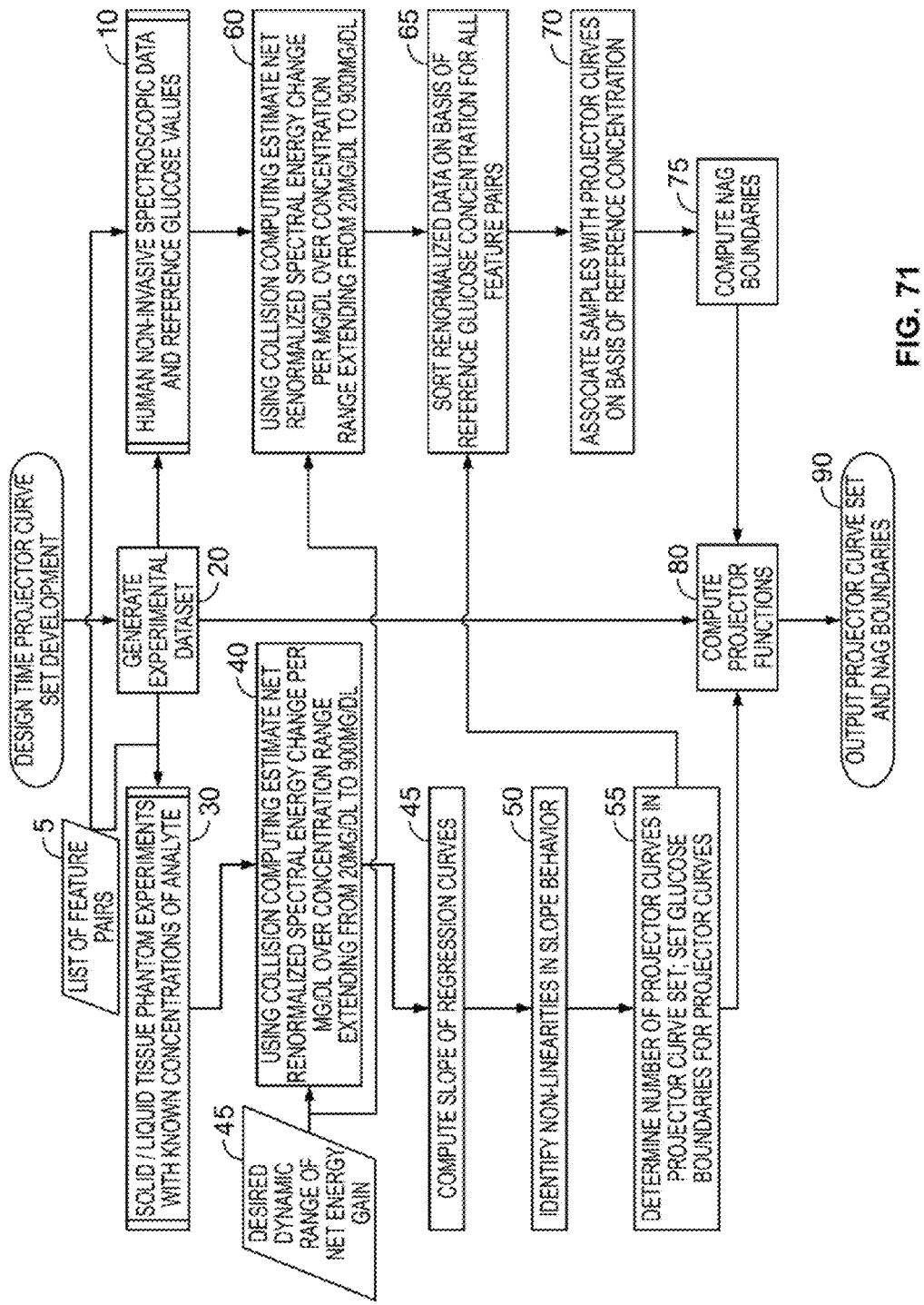
FIG. 71 shows the steps by which experimental datasets are acquired using a set of prepared tissue phantoms with known glucose concentrations and a paired set of noninvasively acquired human tissue spectra.

FIG. 71 shows one embodiment of the overall process of derivation of a mapped projector curve set with NAG boundaries. Feature pairs corresponding to different, known concentrations of the analyte (e.g., glucose) in a synthetic medium (e.g., tissue phantom) are obtained at step 30. The concentration values can be adjusted according to an expected dynamic range of the analyte in the media to be analyzed. An embodiment of a collision computer, as described above, is used to obtain NRSEG values for each feature pair at step 40. An NRSEG-analyte concentration curve is then generated at step 40 using the computed NRSEG values. At step 45, slopes of the curve are computed, and at step 50 non-linearities in the slope, i.e., changes in the slope (also called discontinuities), as described below, are determined. These changes in the slope can be used to partition a single composite slope into a number of intervals, each interval corresponding to individual slopes and projector curves. At step 55 the number of curves in a projector curve set is determined.

Figure 72:
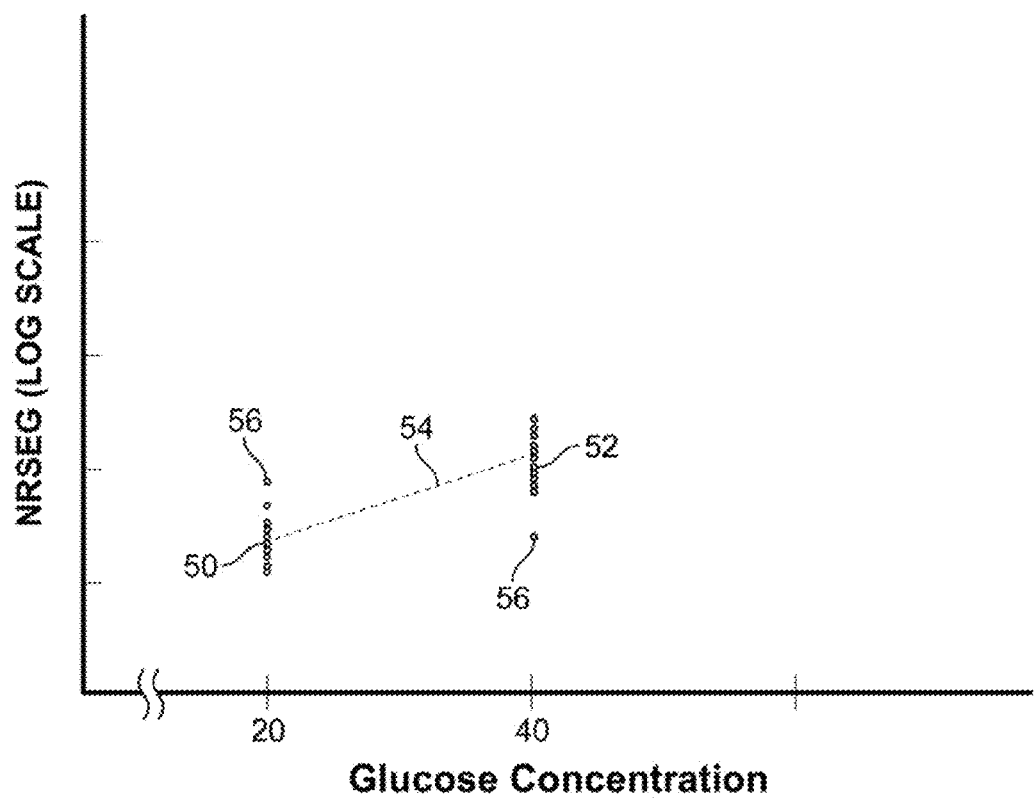
FIG. 72 shows how the NAG values for feature pairs are used to compute the regression slope used as a Projector Curve sub-interval.

In some embodiments, the NRSEG-analyte concentration curve is generated as a linear regression using a logarithm (base 10, base e, etc.) of the NRSEG values and the known or measured analyte (glucose) concentrations in the set of tissue phantoms. The measurements can be obtained using a reference measurement system such as an system that measures analyte (glucose) concentration in a sample. Thus, logs of the NRSEG values are regressed against the known/ measured glucose concentration of tissue samples. In determining the number of individual projector curves in step 55, in one embodiment piecewise computation of the slopes of the regression lines over samples separated by 10 mg/dl (or 5 mg/dl, 20 mg/dl, 25 mg/dl, 40 mg/dl, etc.) sub-intervals over the entire range of glucose concentrations of the tissue phantoms is performed. This entails generation of linear regression coefficients between the logs of the NRSEG values and the known/measured glucose concentration of the tissue phantoms, as shown in FIG. 72. Steps in the generation and parameterization of all individual projector curves included in a projector curve set are described with reference to FIG. 73.

As an example of piecewise computations of the regression slopes, the slope of a linear regression line between the logs of the NRSEGs for tissue phantoms with 20 mg/dl and 40 mg/dl glucose concentrations was computed from all samples with those concentrations and averaged over all the non-excluded replicates (described below), on a normalized feature by feature basis, as described below. The range of concentration from 20 mg/dl to 40 mg/dl is one such piecewise sub-interval.

FIG. 72 illustrates this process. The log of the normalized NRSEG values for several feature pairs (where the NRSEG value of a particular feature pair prior to normalization is based on an average of the corresponding NRSEG values over all replicates), measured for a tissue phantom with a glucose concentration of 20 mg/dl are shown plotted as points 50, and the corresponding points for a tissue phantom with a glucose concentration of 40 mg/dl are shown as points 52. In general, there can be up to Π (e.g., 22) times M (e.g., 4) normalized NRSEG values, where all Π feature pairs are acceptable and each set of Π values corresponds to one of the M illumination states.

In the generation of a projector curve set, in some embodiments, only one set of up to Π normalized NRSEG values is used. For example, in one embodiment, the illumination state R2, i.e., Ring_2, of the illumination/detection probe is selected, and the corresponding NRSEG values from the acceptable features pairs are normalized, as described above, in the generation of the projector curve set. Any feature pairs whose normalized NRSEG values are different according to a threshold (e.g., a deviation from the mean by more than one, two, three, etc., standard deviations, a deviation from the mean by more than a threshold specified as an absolute limit or a percentage, etc.) (points 56) may be omitted from the regression calculation as outliers. A regression line 54 is drawn through the mean of all remaining points at each concentration and becomes the piecewise sub-interval for the projection curve between 20 mg/dl and 40 mg/dl.

Figure 73:
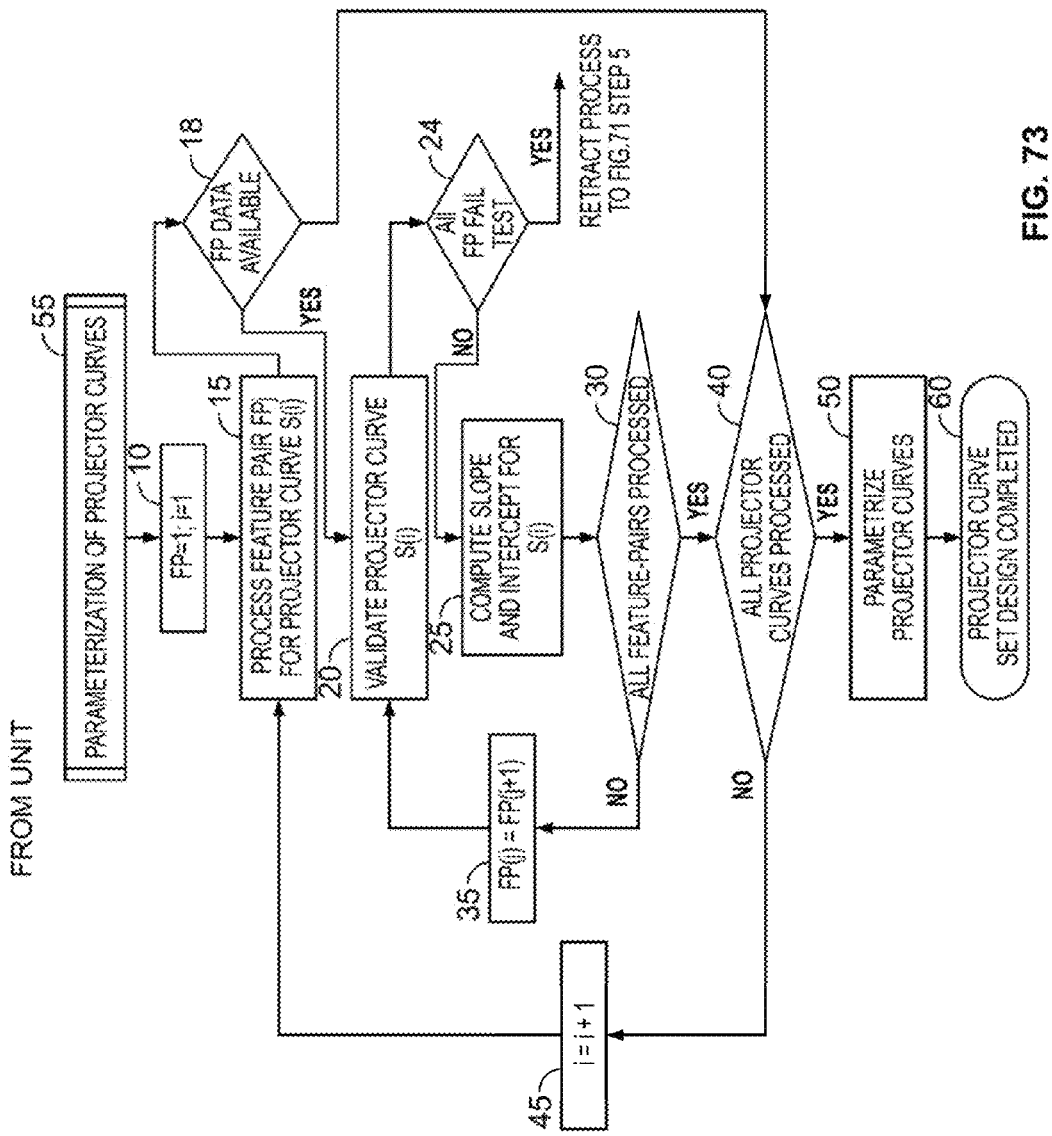
FIG. 73 shows the steps in the generation and parameterization of projector curves.

With reference to FIG. 73, in general, this process is repeated (steps 10 through 35) for the normalized NRSEG computed using all tissue-phantom samples ("sample pairs") at various concentration sub-intervals, e.g., 10 mg/dl and 20 mg/dl, 40 mg/dl, 50 mg/dl, 50 mg/dl and 60 mg/dl, and so on, up to the pair of samples between 800 mg/dl and 900 mg/dl in the tissue phantom calibration dataset 30 in FIG. 71, wherein the sample pair sets may be arranged in order of increasing glucose concentrations. The piecewise sub-intervals used over the total concentration range may have different sub-interval ranges such as 10 mg/dl, 15 mg/dl, 20 mg/dl, 40 mg/dl, etc. As several feature pairs may be processed at each concentration, in some embodiments the normalized NRSEG for each feature pair in a piecewise sub-interval is used as shown in FIG. 73. NRSEG values without normalization thereof may also be used in some embodiments. The projector curve set is typically based on all of the feature pairs (FP) or all the acceptable feature pairs and all individual projector curves.

In general, each tissue-phantom sample, except those tissue-phantom samples at the lowest and highest concentrations, may be used to generate two regression sub-intervals: (i) in the piecewise sub-interval preceding that concentration; and, (ii) the piecewise sub-interval succeeding that concentration. For example, if the sub-interval length is set to 10 mg/dl, the NRSEG for all features at the concentration of 70 mg/dl would be used in the regression slope computation when considering the piecewise sub-interval 60 mg/dl to 70 mg/dl, as well as the sub-interval 70 mg/dl to 80 mg/dl. A linear regression slope for each piecewise sub-interval, based on all feature pairs for those samples, is computed.

In various embodiments, a straight-line section of the composite projector curve in each sub-interval (e.g., the sub-interval [20 mg/dl, 40 mg/dl]) is determined by plotting a linear regression line between the log of all the non-omitted normalized (i.e., weighted) NRSEG values $\bar{y}_{20}^i$ (for i=1, 2, 3 . . . , Π), for the tissue phantom with a glucose concentration of 20 mg/dl, and all the non-omitted, normalized (i.e., weighted) NRSEG values $\bar{y}_{40}^i$ (for i=1, 2, 3 . . . , Π) for a tissue phantom with a glucose concentration of 40 mg/dl. This process is illustrated with reference to FIG. 72, and was described above. In particular, for each concentration C (e.g., 20 mg/dl, 40 mg/dl, etc.), all Π (e.g., 22, in one embodiment) the log of the normalized NRSEG values are plotted, the outliers according to a threshold as described above are omitted, and the respective means of the remaining log values of the normalized NRSEG values is used to determine the corresponding regression lines.

Figure 74:
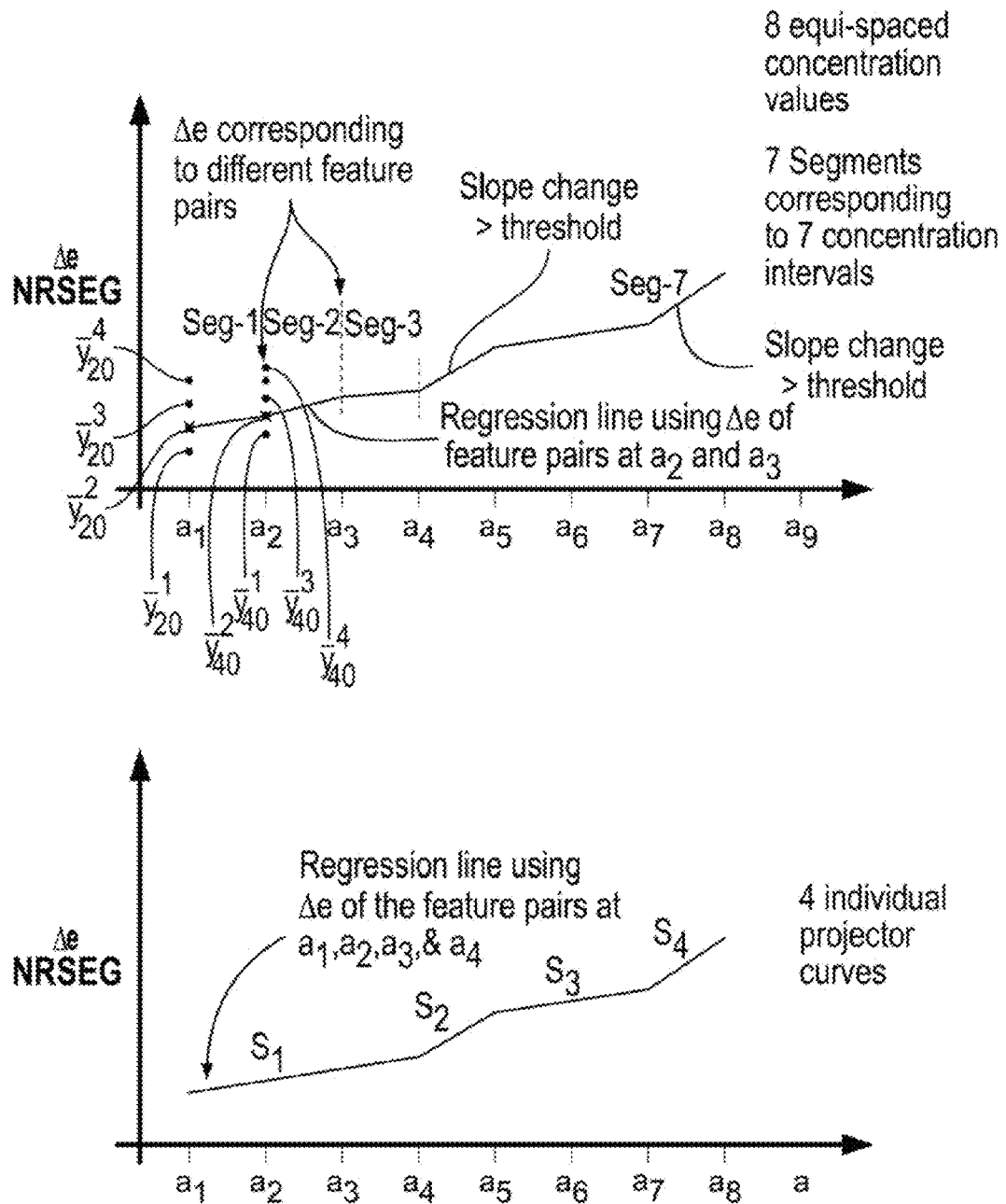
FIG. 74 schematically depicts the synthesis of a projector curve set according to one embodiment.

With reference to FIG. 74, assume that at a glucose concentration of 20 mg/dl, four feature pairs, $FP_{20}^1$, $FP_{20}^2$, $FP_{20}^3$, and $FP_{20}^4$ yield normalized NRSEG values $\bar{y}_{20}^1$, $\bar{y}_{20}^2$, $\bar{y}_{20}^3$, and $\bar{y}_{20}^4$. Also assume that at glucose concentration of 40 mg/dl, four feature pairs, $FP_{40}^1$, $FP_{40}^2$, $FP_{40}^3$, and $FP_{40}^4$ provided normalized NRSEG values $\bar{y}_{40}^1$, $\bar{y}_{40}^2$, $\bar{y}_{40}^3$, and $\bar{y}_{40}^4$. Monotonicity requires that for at least one feature pair, the NRSEG value prior to normalization, $\bar{y}_{40}^j$ (for j=1, 2, 3, 4) be greater than the corresponding feature pair $\bar{y}_{20}^j$ (for j=1, 2, 3, 4). It is necessary to ensure that the slope of each such line is positive, that is that the normalized NRSEG $\bar{y}_C^i$ is monotonically increasing with glucose concentration. If monotonicity is not confirmed, alternate feature pairs must be selected.

Table 10 below illustrates projector curve set generation in some embodiments where an NIR data collection subsystem has M illumination states $R_t$=1, 2, . . . , M. There are a total of Π feature pairs $FP^i$, where i ranges from 1 through Π. For analyte concentration $C_k$ corresponding to a particular tissue phantom, for each feature pair $FP^i$, for each repeat of each illumination state Rt, an NRSEG value is computed using collision computing. For the analyte concentration $C_k$, for each feature pair $FP^i$, for each illumination state Rt, the NRSEG values computed for all repeats of $R_t$ are averaged to obtain an averaged NRSEG value $y_{C_k}^{i^t}$.

Monotonicity of $y_{C_k}^{i^t}$ is tested across all illumination states $R_t$, i.e., $R_1$ through $R_M$ and, in some embodiments, only those features pairs that exhibit monotonicity are accepted for further processing. For all the accepted feature pairs, the averaged NRSEG values corresponding to any one illumination state (e.g., $R_2$, $R_3$, ($R_2$+$R_4$), etc.) are selected, and are represented as $y_{C_k}^i$. Each of these averaged NRSEG values corresponds to a particular accepted feature pair, and is weighted using a weight W(i(p, q)) associated with the corresponding feature pair, to obtain a normalized NRSEG value $\bar{y}_{C_k}^i = y_{C_k}^i \times W(i(p, q))$. The computation of the weight is described above. The computation of $\bar{y}_{C_k}^i$ is repeated for different analyte concentrations Ck using different phantom tissue samples.

TABLE 10

| Feature Pairs $FP^i$\ Illumination States $R_t$ | $R_1$ | $R_2$ | . . . | $R_M$ |
|---|---|---|---|---|
| i = 1 | | | | |
| i = 2 | | $\bar{y}^2{}_{c_k}$ | | |
| . | | | $\bar{y}^{i^t}{}_{c_k}$ | |
| . | | | | |
| . | | | | |
| i = Π | | | | |

Referring again to FIG. 73, the slopes of these piecewise linear regression lines (at step 40) correspond to sub-intervals of increasing glucose concentrations. The concentration sub-intervals chosen are non-overlapping and do not have any gaps. If the concentration-sample pair set does not include samples separated by 10 mg/dl, then the next largest sub-interval available is used for computing the piecewise regression slopes. For example, the sub-interval 100 mg/dl to 120 mg/dl was used in one example, as no sample was prepared with 110 mg/dl concentration. This generally ensures that there are no gaps between the regression curves corresponding to different concentration boundaries.

Figure 75:
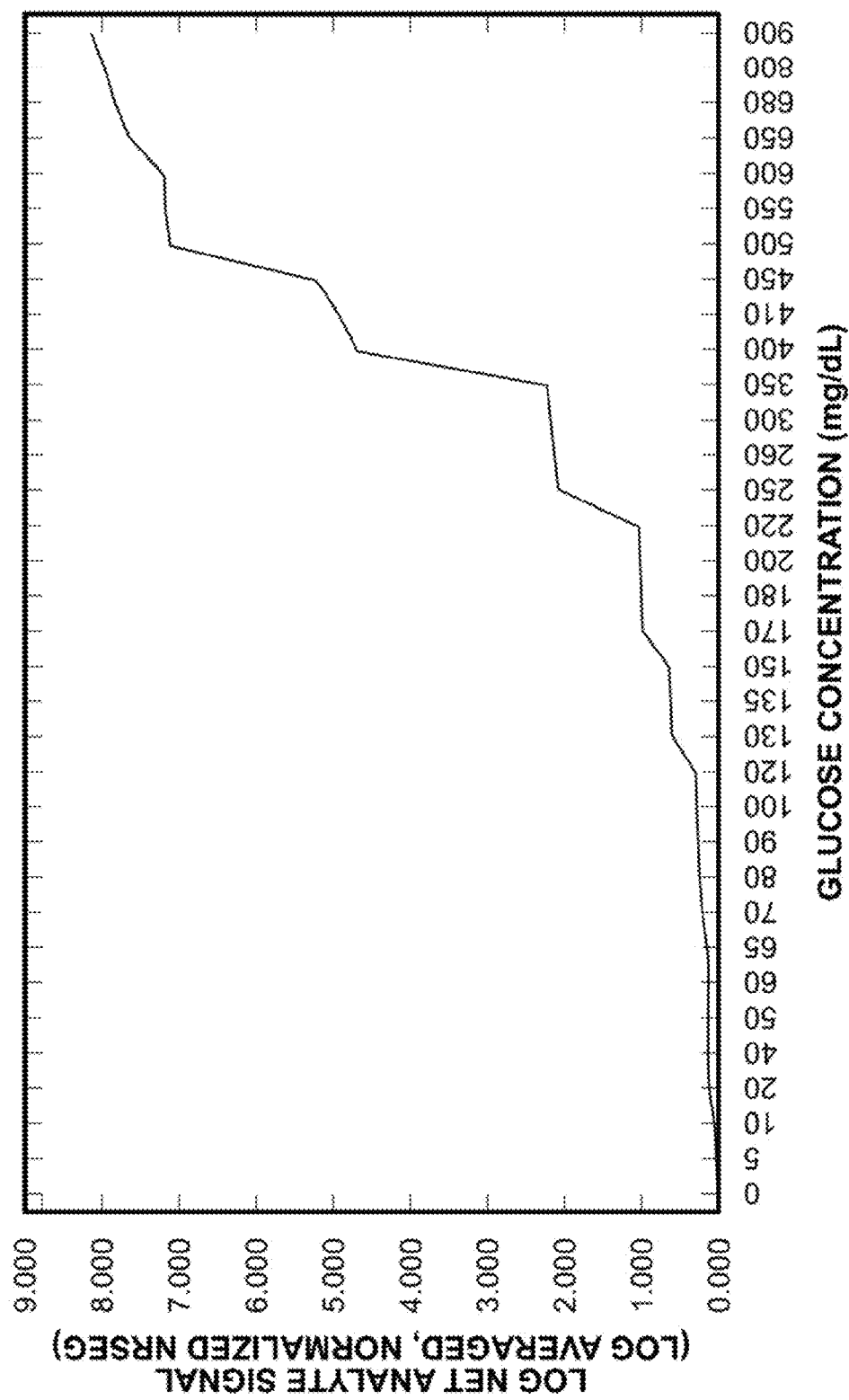
FIG. 75 shows the relationship between the net, renormalized spectral energy gains (NRSEGs) and glucose concentration in a set of tissue phantoms.

All the individual regression lines corresponding to different glucose sub-intervals over the entire range of concentration spanning 20 mg/dl to 900 mg/dl, as shown in FIG. 75, are then concatenated to form a continuous, strictly increasing, single graph whose Y axis represents the log of the mean of normalized NRSEG values after outlier elimination, due to NIR absorption by the analyte, and where the X axis represents the concentration of the analyte corresponding to sub-interval boundaries. This continuously increasing function is computed and shown in FIG. 76.

Figure 76:
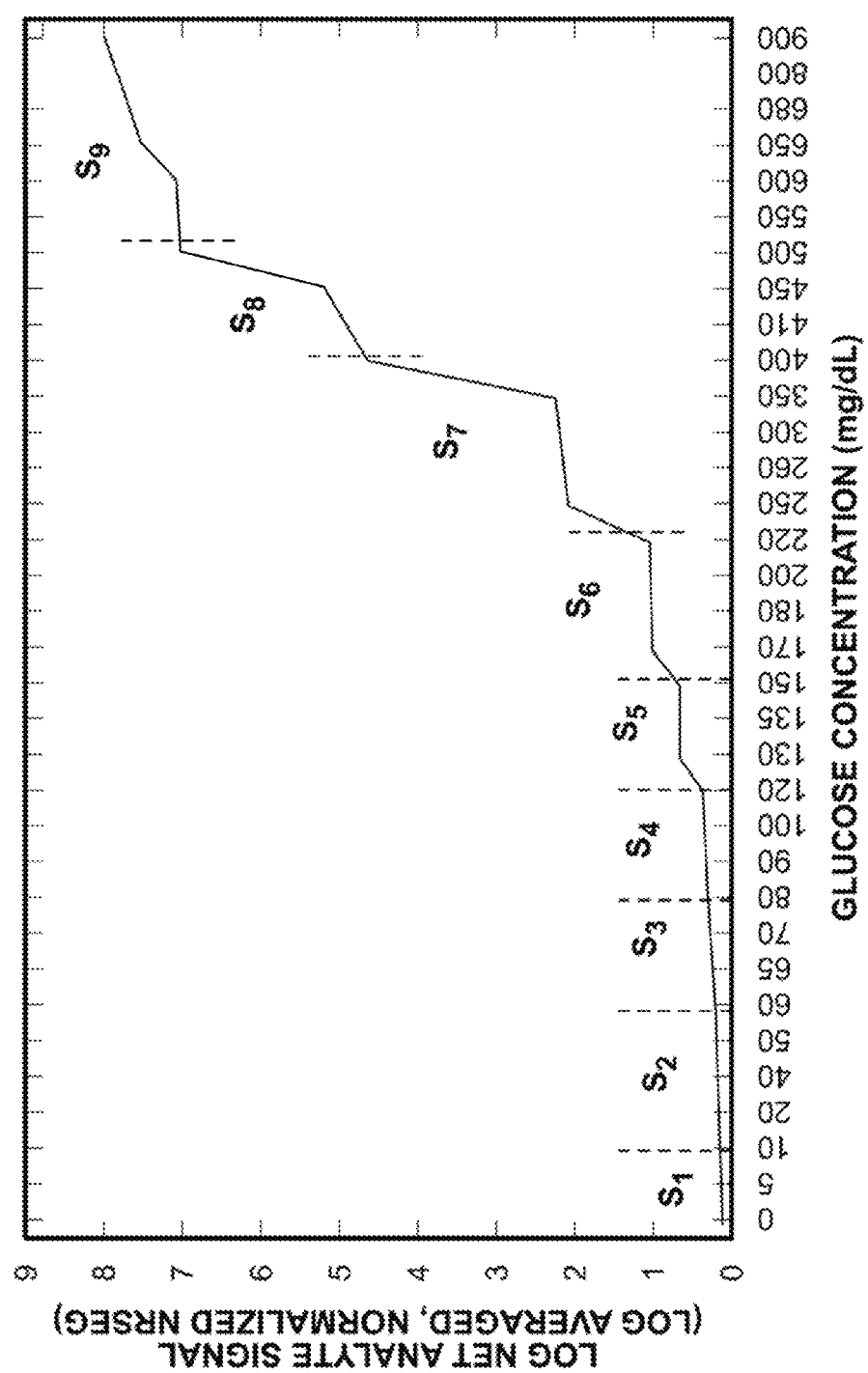
FIG. 76 shows discontinuities in the curve of the NRSEGs as a function of glucose concentration.

In various embodiments, a change in the value the slope of the continuous function constructed by concatenating the these linear regression lines over discrete piecewise sub-intervals, (an empirically determined slope-change value that balances the need for smoothing of individual variations of slope against the number of intervals) is treated as a point of discontinuity in the NRSEG response to the concentration of the analyte. The change in the value of the slope can be specified as an absolute change or as percentage (e.g., 10%, 20%, 50%, 60%, 100%, 150%, 200%, etc.) of the instantaneous slope. The points of slope change, where the change in slope is greater than 50%, of the continuous concatenated curve are shown in FIG. 76. The points of slope change describe intervals of the composite curve, and the segments of the composite curve between a pair of consecutive points of change is called an individual projector curve. An individual projector curve may correspond to one or more sub-intervals.

In various embodiments, the continuous function, for all sub-intervals of tissue phantom reference concentrations extending over the entire concentration range, as shown in FIG. 76, is deconstructed into individual functions or curves where the first function extends from the lowest concentration to the concentration identified as the first slope discontinuity. The second function extends from the concentration associated with the first slope discontinuity to the second slope discontinuity, and so on, until the entire range is covered, as illustrated in step 40 of FIG. 73. The composite curve of NRSEG vs. concentration, incorporating the contribution of all feature pairs, is partitioned into several individual projector curves, where each individual curve is identified by a change in the slope (as described above) from the previous curve. It is to be understood that any suitable threshold value for a change in slope can be used to identify the boundaries of individual projector curves. For example, changes in linear regression line slopes of greater than 5%, 10%, 20%, 60%, etc., or an absolute difference in slope of greater than a specified threshold can be used to identify the boundaries of individual projector curves.

In general, if there are $N_a$ distinct reference concentration values, there could be up to $(N_a-1)$ concentration sub-intervals and, accordingly, there would be up to $(N_a-1)$ regression line segments of the composite projector curve. The composite projector curve that is a concatenation of the $(N_a-1)$ segments can be partitioned into a set of $N_g$ individual projector curves, where $N_g \leq (N_a-1)$. A partition boundary or a boundary of an individual projector curve, $\Gamma_P$, can be identified where the slope of an individual projector curve or regression line segment changes by more than a specified threshold relative to the slope of an adjacent individual projector curve or regression line segment. An individual projector curve, $\Gamma_P$, may include only a single regression line sub-interval corresponding to a single concentration sub-interval (e.g., from 20 mg/dl up to 30 mg/dl, where the interval length is 10 mg/dl), or may include more than one regression line sub-intervals. For example, a certain individual projector curve may combine the regression line segments corresponding to the concentration intervals [60-70], [70-80], and [80-90] mg/dl into a single interval [60-90]. In some embodiments, the slope of an individual projector curve is determined by plotting a new regression line that includes the log of the normalized NRSEG values for all feature pairs obtained as sub-intervals that include 60, 70, 80, and 90 mg/dl.

In general, the projector curve is an invertible, one-to-one function (i.e., the curve cannot be intersected at more than one point by a vertical or horizontal line). Intersection by a vertical line at two different points would mean that there are two different net energy gain values for the same concentration. Intersection by a horizontal line at two different points would mean that for two different concentrations the net energy gain is the same. For a one-to-one mapping, neither condition can be true.

Figure 77:
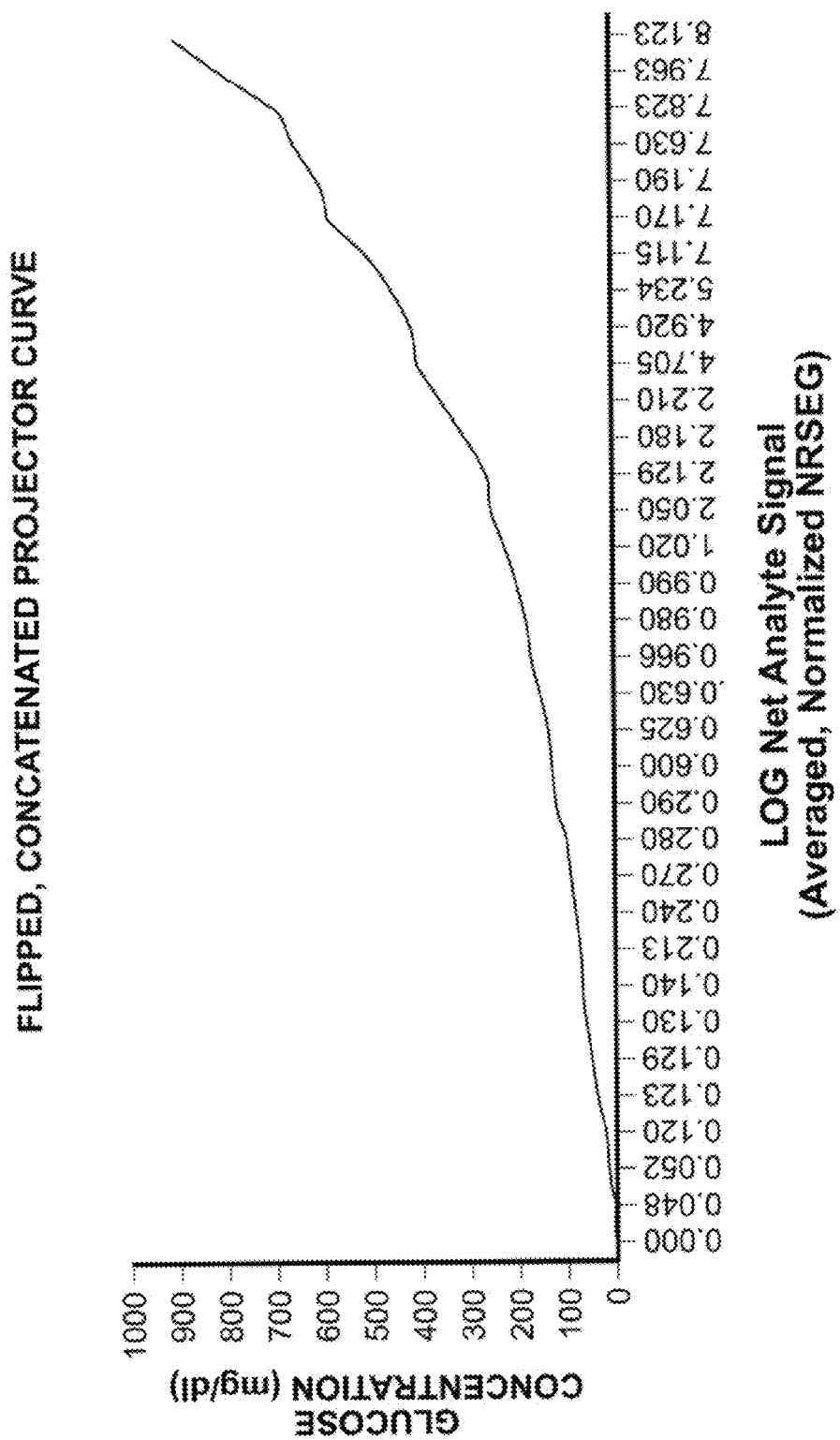
FIG. 77 shows the flipped, concatenated projector curve.

FIG. 77 shows a "flipped" concatenated (also called composite) projector curve, where known analyte (glucose) concentration was the independent variable (and is now plotted on the Y axis on the linear scale) and the log of the normalized net, renormalized spectral energy gain was the dependent variable (and is now plotted on the X axis on a linear scale), as described below. With reference to FIG. 73, as the next step in the parameterization of the individual projector curves (step 50), the axes of the composite projector curve are reversed, such that the response variable or Y axis represents the analyte (glucose) concentration and the logarithmic values of the normalized NRSEG is the explanatory variable represented on the X axis, to yield a "flipped projector curve," as shown in FIG. 77. The log of the value of the averaged, normalized NRSEG values is also referred to as the log of the net analyte signal (NAS) on the X axis of FIG. 77.

The overall processes of generating a flipped projector curve set that is described above is summarized below in a pseudo-code form.

Select any one illumination state (IS) (also called illumination pattern)
For each concentration value $C_k$ {
  For each feature pair i {
    Compute NRSEG, averaged over all repeats of the selected illumination state, i.e., $y^i$
    Compute normalized NRSEG, $\bar{y}^i$, by applying a weight $W(i,(p, q))$ corresponding to the feature pair
  }
  From all $\bar{y}^i$ across all feature pairs, remove outliers
    Compute mean of normalized NRSEGs of the remaining, i.e., acceptable feature pairs denoted $Y_{C_k}$.
}
For each analyte concentration $C_k$ in $C_1$ through $C_{K-1}$ {
  Draw a regression line segment joining $Y_{C_k}$ and $Y_{C_{k+1}}$.
    Alternatively, generate a regression line segment using $y_{C_k}^i$ over all acceptable feature pairs, and $y_{C_{k+1}}^i$ over all acceptable feature pairs.
}
Concatenate all regression line segments to obtain an composite projector curve
Deconstruct the composite projector curve to obtain individual projector curves (i.e., the projector curve set
Flip the composite projector curve Measurement of Human Tissue for a Calibration Set One or more calibration sets are generated to transform the net, renormalized spectral energy changes accumulated in the modified Zyoton waveform to the analyte concentration. For example, in the case of non-invasive glucose measurement, calibration data are generated in two steps, as described below.

In the first step, described above, a series of in-vitro experiments is performed whereby different, known concentrations of the analyte of interest are added to tissue phantoms which are then spectrally imaged using the same sensor hardware and illumination sequence that are used for analyzing glucose in human subjects. The spectra from these tissue phantom samples are processed by the collision computing process to ensure that the resulting, computed spectral energy changes (e.g., gains) are monotonically increasing or decreasing with an increase or decrease in the concentration of the analyte. When monotonicity is achieved (by refinements of the components of the collision computing process, if necessary) a composite projector curve is generated between concentration (as the independent variable) and spectral energy gain (as the dependent variable), as described above.

In the second step, a series of paired measurements are made on one or more human subjects, where tissue spectra are acquired along with paired reference glucose values, which may be obtained using a conventional invasive technique requiring a blood sample. Two terms are used to describe the accuracy of results in such an experiment: ARD and MARD. ARD, expressed as a percentage, is the "absolute relative difference" of a single result from a reference value: ARD=|(reference value-experimental result)/reference value|×100. MARD, also expressed as a percentage, is the mean of more than one absolute relative difference values for either an individual or for multiple subjects: MARD=Average of all (|(reference value-experimental result)/reference value|)×100. In general, the reference values can be obtained using a single human subject or more than one (e.g., 2, 5, 9, 11, 15, etc.) human subjects.

In one embodiment that demonstrated glucose estimation accuracy with a MARD under 15%, such paired measurements are taken within one minute of each other, as glucose was found to be increasing or decreasing at rates as high as 8 mg/dl per minute, as in the case of people with type 1 diabetes who use insulin. Spectral energy gains due to glucose absorption in subjects' tissue using NIR diffuse reflectance measurements are then estimated using this collision-computing technique, at the same time the reference glucose measurement was also taken. The conditioning and collision computing processing for tissue spectra from human subjects is essentially the same as that used for processing spectral data from tissue phantoms. If monotonicity between reference glucose concentration and NRSEG is not achieved, then processing of the data is further refined by modification of Zyotons, collision parameters, number of collisions, selection of frequency components in the spectral energy computation, or changes to the collision operator between collisions.

As described above, changes to the collision operator are achieved by modifying a combination of one or more parameter that include the collision grid bracket length ($\eta$), or the bracketed interaction operator ($\widehat{\times}$), or revising the shift delay window ($\delta$), or the phase operator ($\Phi$), or optionally the compression operator ($\epsilon$), to adjust the length of the collision window. As described above, changes to the collision operator can be used to increase the tolerance of the measurement to both coherent and non-coherent noise in the acquired sensor data due to unpredictable changes to the medium, unpredictable drift in the sensor (e.g., detector or illumination elements), and also to address changes in the confounder concentrations that impact SCR, and to address time-varying scatter losses. Changes in the collision operator can be made to avoid the need for additional data or reacquisition of a calibration dataset due to failure to achieve monotonicity between analyte reference concentration and the net, renormalized spectral energy changes obtained through collision computing. One or more of the preceding collision operator parameters may be revised to achieve a monotonic relationship of spectral energy gain by the modified Zyoton over the glucose analyte concentration range. Once monotonicity has been achieved in the calibration dataset derived from human subjects, the spectral energy levels are projected against, or recast in terms of energy absorption levels observed, as described above, in the tissue phantoms with known glucose concentration, to derive a calibration set. The process is described in detail below.

In estimating tissue glucose concentration in human subjects, the averaged (over repeats of respective illumination states) NRSEG for all features, extracted from all replicate spectra for all illumination states is first computed as described below. Optionally, other estimators such as L2 norm, median, and maximum likelihood (MLE) ratio can be used instead of averaging. This averaged NRSEG is then transformed into an estimated "glucose value" through the projection process shown in FIG. 78. The projection process is a generalized method and is applicable to determination of concentration of any analyte of interest such as urea, collagen, or lactate. For analytes that absorb in different NIR bands, different detectors or sources may be used.

Projection Process

Projection can be generally described as the process of representing the equivalence of the averaged NRSEG due to an analyte of interest (e.g., glucose) in one measurement system (e.g., tomographic diffuse reflectance spectroscopy) in one medium (e.g., human skin tissue) to the estimated, averaged NRSEG observed from another medium (e.g., synthesized tissue phantoms created with different known levels of the analyte), and imaged using the same sensor or instrument measurement system, in conjunction with the same processing (e.g., the same Zyotons, the same Zyoton collision operator, the same feature boundaries and the same feature conditioning process, all of which are described above).

Figure 78:
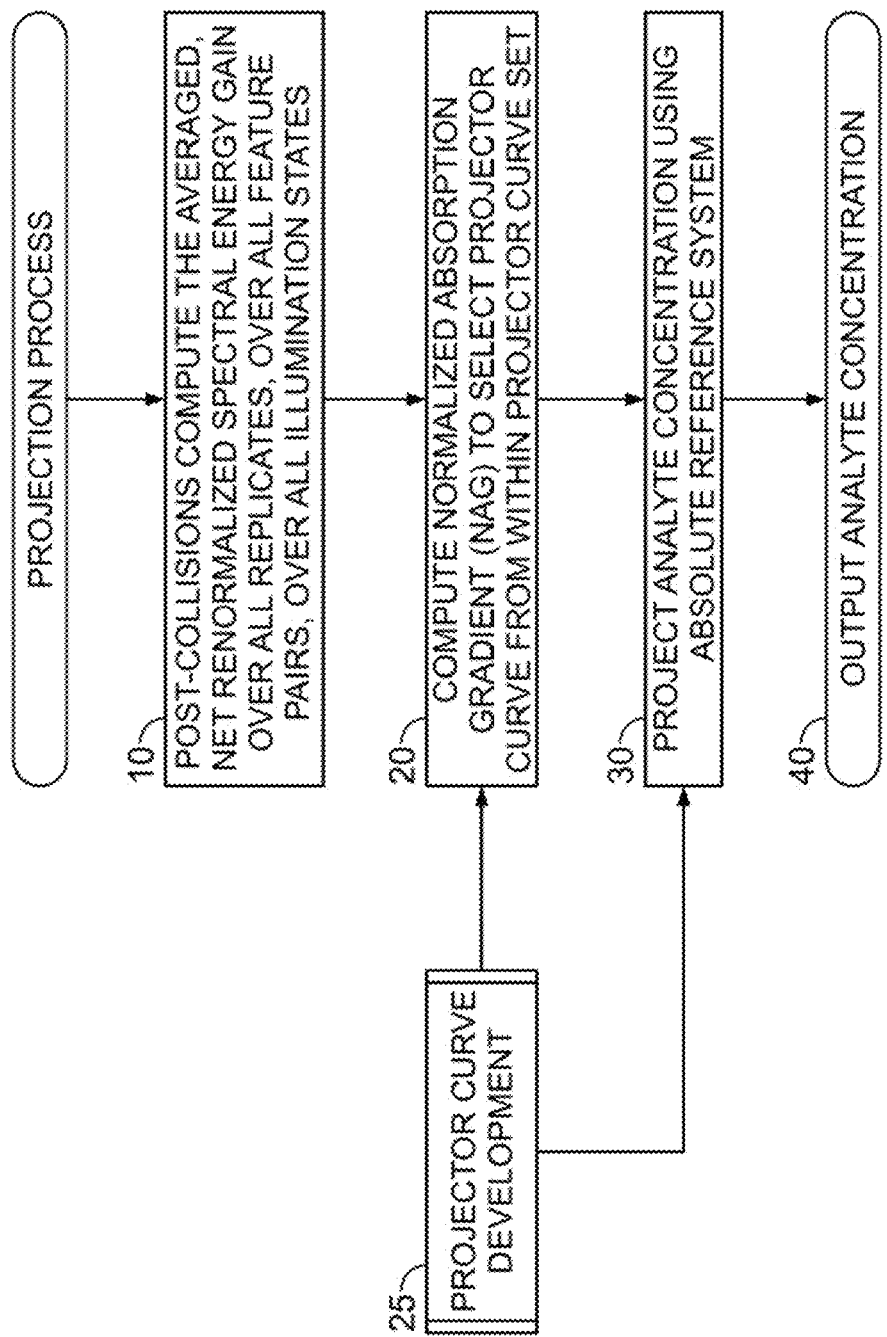
FIG. 78 shows the flow for the generalized projection process implemented to transform spectral energy changes generated in the collision computing process into analyte concentrations.

As shown in FIG. 78, using tissue spectra, the NRSEGs are computed for all feature pairs for all illumination states and are averaged over all repeats of the respective illumination states on a feature pair by feature pair basis. For each of the feature pairs for each sample found to be acceptable as defined below, a Normalized Absorption Gradient (NAG) numerical value is computed (step 20) to select the appropriate mapped individual projector curve, from a set of several mapped individual projectors curves included in a mapped projector curve set. In some embodiments, there may be only one individual mapped projector curve in the mapped projector curve set. Once the applicable mapped projector curve is selected, it is used to transform the NRSEG into an analyte concentration in step 30. The analyte concentration 40 can be output to the user, or further used in computation of clinical, diagnostic, screening, therapy effectiveness or regimen monitoring or wellness analytics; alarms provided to users, their care-team, friends and family; population analytics; and longitudinal analysis. Details on processes for computing NAG, developing and using the mapped projector curve set (step 25) are described below.

In some embodiments, laboratory synthesized tissue phantoms in the form of liquid suspensions or gels serve as calibration systems for projection. Projection, in general, is a two-step process: (i) The first step includes the design and optimization of "mapped projector curves," based on experimental data and samples, collected using both tissue-phantom and human subjects, associated with known analyte (e.g., glucose) concentrations, as described with reference to FIG. 71, and (ii) the second step includes the use of a mapped projector curve set, to transform the Normalized Absorption Gradient derived from the averaged NRSEG in acceptable feature pairs, as estimated from uncharacterized spectra (e.g., uncharacterized human tissue spectra) using the collision computing process, to determine the analyte levels.

The projector curves for analyte quantitation may be developed in a different medium than the uncharacterized media in which the analyte is to be detected and/or measured. The projector curves generally transform an information measure (the explanatory variable or averaged NRSEG generated through the collision computing process) to a response variable e.g.,, analyte concentration such as tissue glucose concentration expressed in mg/dl or mM/l). In estimating analyte concentration in complex media, with high levels of interference from confounders with varying levels of absorption and scattering effects, more than one projector curve (denoted together as a "projector curve set") may be used to cover the anticipated range of the response variable associated with the concentration of analyte of interest. For example, some embodiments for non-invasive glucose measurement use a nine-member projector curve set.

As described above, the accuracy and precision of analyte concentration estimation in unknown samples can be increased by designing the Zyoton such that the desired dynamic range of net, renormalized spectral energy changes can be measured, and that the Zyotons, along with properties of other waveforms involved in the collision process, and the parameters of the collision operator, produce collisions that yield changes in the net, renormalized spectral energy of the modified Zyoton that are monotonic to analyte concentration levels, e.g., as described in step 60 in FIG. 71, while analyzing human subjects in generating calibration sets.

In the example of noninvasive glucose measurement, the NRSEG range is set to have a dynamic range of 8 to 10 orders of magnitude by controlling the collision count and parameters of the collision operator, while the actual range of glucose concentration seen in human tissue and blood generally extends over less than three orders of magnitude. Thus, Zyotons are designed to amplify small, linear changes in spectroscopic absorption due to changes in the analyte concentration in the medium to large, logarithmic scale changes in the net, renormalized spectral energy gains. As a properly configured collision operator yields spectral energy gains that are monotonic to analyte concentration, lower values of analyte concentration show smaller changes in post-collision renormalized spectral energy and larger analyte concentrations yield larger post-collision renormalized spectral energies. Such nonlinear amplification generally results from varying inelasticity of the collisions between Zyotons and conditioned spectral features extracted from spectra of samples with varying analyte concentrations.

The relationship between the net, renormalized spectral energy changes and varying analyte concentrations is typically not linear over the range of glucose concentrations seen in human tissue, thereby requiring the using of several projector curves. Instead, this relationship, as shown below, is typically semi-linear, or linear in log-transformed space. A relationship between a dependent and an independent variable can be defined to be semi-linear if it includes the sum of a linear term and a low order nonlinear term. Semi-linear relationships may become linear when one or both of the variables are converted to logarithms or plotted on a graph with a logarithmic axis.

The mapped projector curve sets (also called projector curve sets) may be developed for quantitation of any biochemical or chemical analyte of interest (and are not limited to the example glucose analyte) that are also present in the tissue at the same time, and are of medical or therapeutic value (e.g., non-invasively estimated collagen, urea, lactate, insulin, hemoglobin and other biochemical compounds). In samples with several analytes of interest that absorb and scatter in the same wavelength region accessible to the sensor, and where the different analytes of interest act as confounders against each other, different configurations of the collision operator and different projector curve sets are generally required, with one set for each analyte. These may be called multiplexed projector curve sets.

Typically, the projector curve sets are designed ahead of their use for projection analysis, in a batch or an off-sequence mode as described with reference to FIG. 71. The operational use of the projector curve set may be batch-mode, off-sequence (for non-real-time applications) or in-line for real-time analysis. Off-line and in-line here refer to analysis and processing of acquired-data at times that are different from or concurrent with data acquisition times.

In some embodiments, referring to FIG. 71, the design-time calibration step and development of the projector curve set uses two experimental datasets in step 20: (a) a calibrated set of tissue phantoms that are created with known values of the analyte (e.g., glucose), and (b) a set of duplicate, paired reference measurements of blood glucose in human subjects, obtained at step 10. For the first set, tissue phantoms with a range of glucose reference values used in one embodiment (as an input to the projector curve set design process) included the following concentrations denoted as set C: 0 mg/dl, 20 mg/dl, 40 mg/dl, 50 mg/dl, 60 mg/dl, 70 mg/dl, 80 mg/dl, 90 mg/dl, 100 mg/dl, 120 mg/dl, 150 mg/dl, 200 mg/dl, 250 mg/dl, 300 mg/dl, 350 mg/dl, 400 mg/dl, 450 mg/dl, 500 mg/dl, 600 mg/dl, 800 mg/dl and 900 mg/dl.

Optionally, other concentrations than those listed above may be used. As the glucose concentration or the scattering properties of the synthetic tissue phantoms may change over time, a reference measurement of glucose concentration in the tissue phantom may be taken within a one minute time window of imaging the tissue phantom.

The step 10 of FIG. 71 in one embodiment entails (a) acquisition of five repeated spectroscopic measurements (called "replicates") taken at each concentration level (enumerated above), which includes the step of making and breaking contact with the tissue phantom surface (in a gel or solid phase phantom) or immersion and removal (if a stirred liquid Intralipid-based phantom was used); and, (b), duplicate, paired reference measurements of blood glucose analyzed from an area on the dorsal side of the human subject's arm within two inches of where the spectroscopic human tissue data is acquired (or measurement of blood glucose from the finger), for a group of individuals with different levels of blood glucose.

In generating some calibration datasets, the individuals included subjects with diabetes, those at risk of diabetes (such as with prediabetes), and, healthy subjects. Again, a maximum time lag of one minute was generally maintained between the spectroscopic tissue measurement and an invasive glucose measurement with a reference method. To extend the range of glucose values in the calibration set, a modified Oral Glucose Tolerance Test (OGTT) protocol and/or meal/exercise challenge can be used in addition to daily-lifestyle measurements of the subjects.

All the preceding procedures were used to develop complete datasets for calibration purposes.

The calibration datasets having the two tissue-phantom and human constituent datasets described above, acquired ahead of operational-use time, were analyzed using collision computing, in step 40 in FIG. 71 (for tissue phantoms) and in step 60 (for human subjects), to develop a mapped calibration curve set between NRSEGs, as computed from the spectral datasets, and the true value of glucose measured in the sample using a reference measurement system. In some embodiments, a projector curve set with boundaries of individual projector curves determined in step 55, as described above, that is derived from a tissue-phantom calibration dataset, is denoted as $\Gamma_P$.

Similarly, the calibration sets obtained using the averaged NRSEGs, as computed from a spectral dataset acquired from human skin tissue, and the value of glucose measured in the subjects' tissue using a reference system such as a high-quality blood-glucose meter, is denoted $\Gamma_H$. In various embodiments, in step 70, portions of the calibration sets are associated with individual projector curves according to the analyte sub-interval boundaries. For each portion of the calibration sets associated with an individual projector curve, the NAG boundaries are computed at step 75, as described below. A projection or a mapping is computed at step 80, whereby each value over the entire range of $\Gamma_H$ can be represented in terms of $\Gamma_P$. This projector curve set is called a mapped projector curve sent and is denoted as $\hat{\Gamma}_P$ as in. The construction of $\Gamma_P$, $\Gamma_H$ and $\hat{\Gamma}_P$ is described below. The cardinality of set $\Gamma_P$ may range from 1 through a maximum number $\Xi$ (e.g., 5, 9, 12, 20, etc.) for an analyte with a dynamic range extending over a number of orders of magnitude. Also, the members of set $\Gamma_P = \{(\Gamma_{P,1}), (\Gamma_{P,2}), \ldots, (\Gamma_{P,\Xi}), \}$, where $\Xi$ is the number of individual projector curves in a projector curve set.

Figure 79:
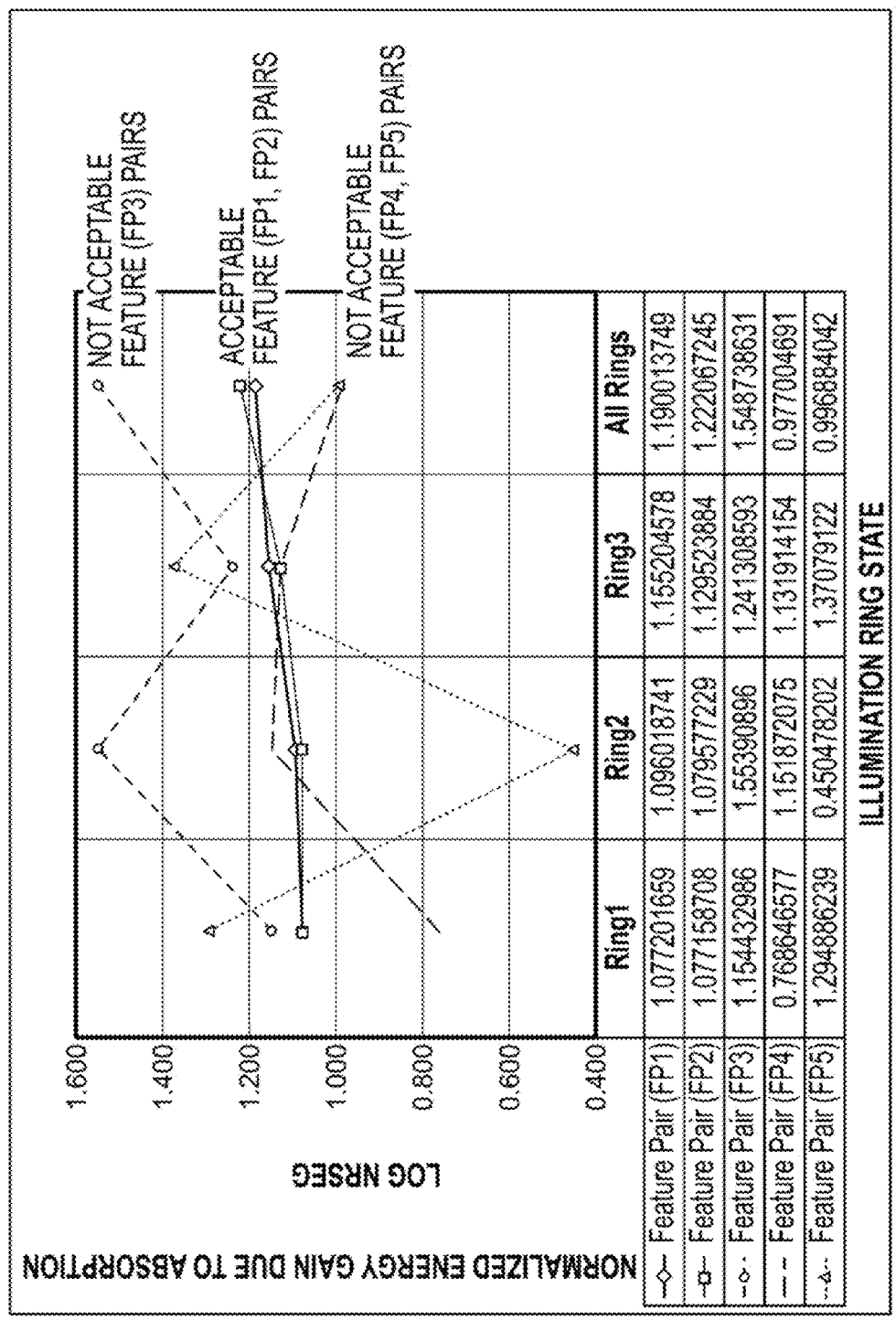
FIG. 79 shows examples of acceptable and not-acceptable feature pairs on the basis of their absorption gradient.

In some embodiments, in the steps 40, 45, 60, and 65 of FIG. 71, any feature pairs that yield negative slopes or show a change of sign in the slope over the illumination states as shown in FIG. 79, are eliminated from feature pair set from further consideration. If any of the projector curves has all the feature pairs eliminated due to lack of positive slope, then all the feature pairs are considered suboptimal, and they are all rejected. Such a projector curve may then be labeled as Null, and the boundaries of the adjacent projector curves may be adjusted to subsume the entire concentration range of that nullified projector curve. In some embodiments, an individual projector curve set to Null due to all the starting feature pairs failing the positive slope test is considered differently from an individual projector curves re-initialized to Null because there were no sample points acquired in the concentration sub-interval associated with that individual projector curve.

Figure 80A:
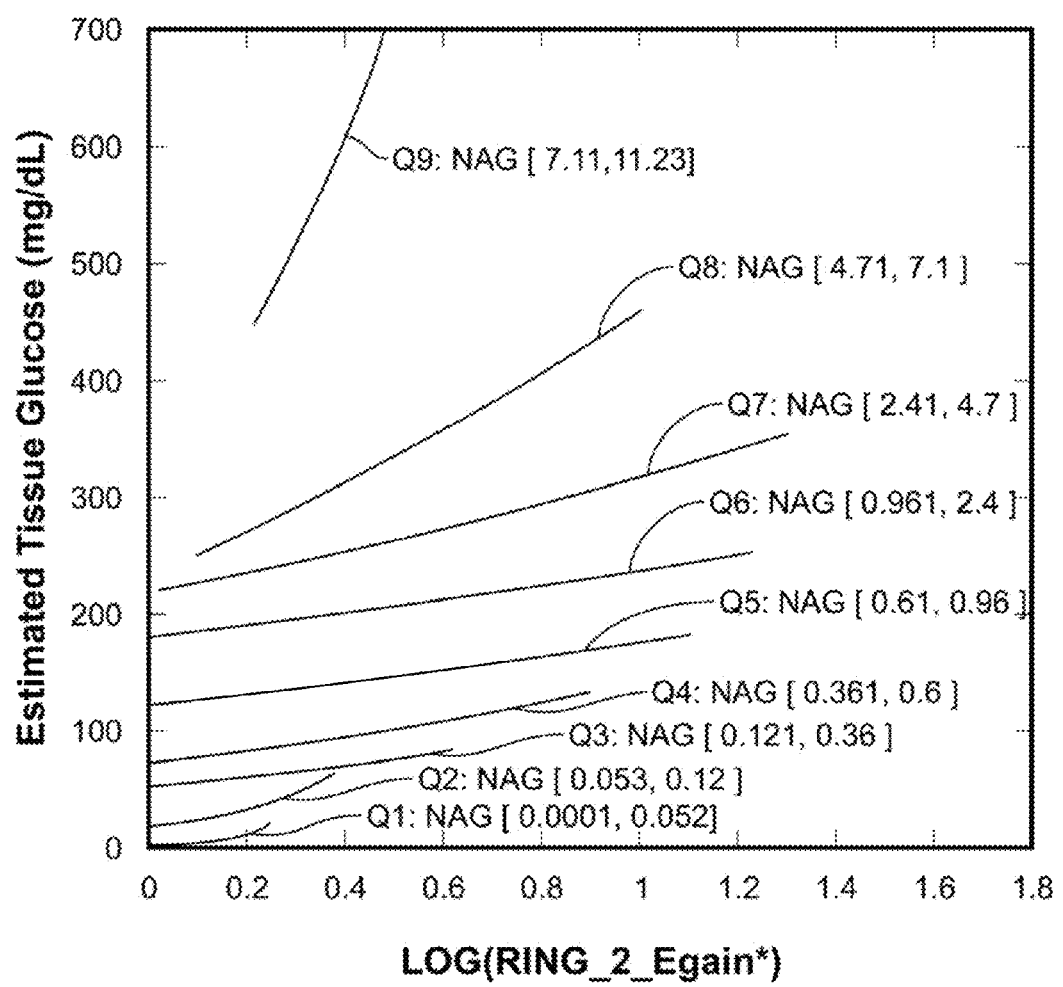
FIG. 80A shows a Projection Curve Set for an example embodiment for non-invasively measuring glucose in human skin tissues.
Figure 80B:
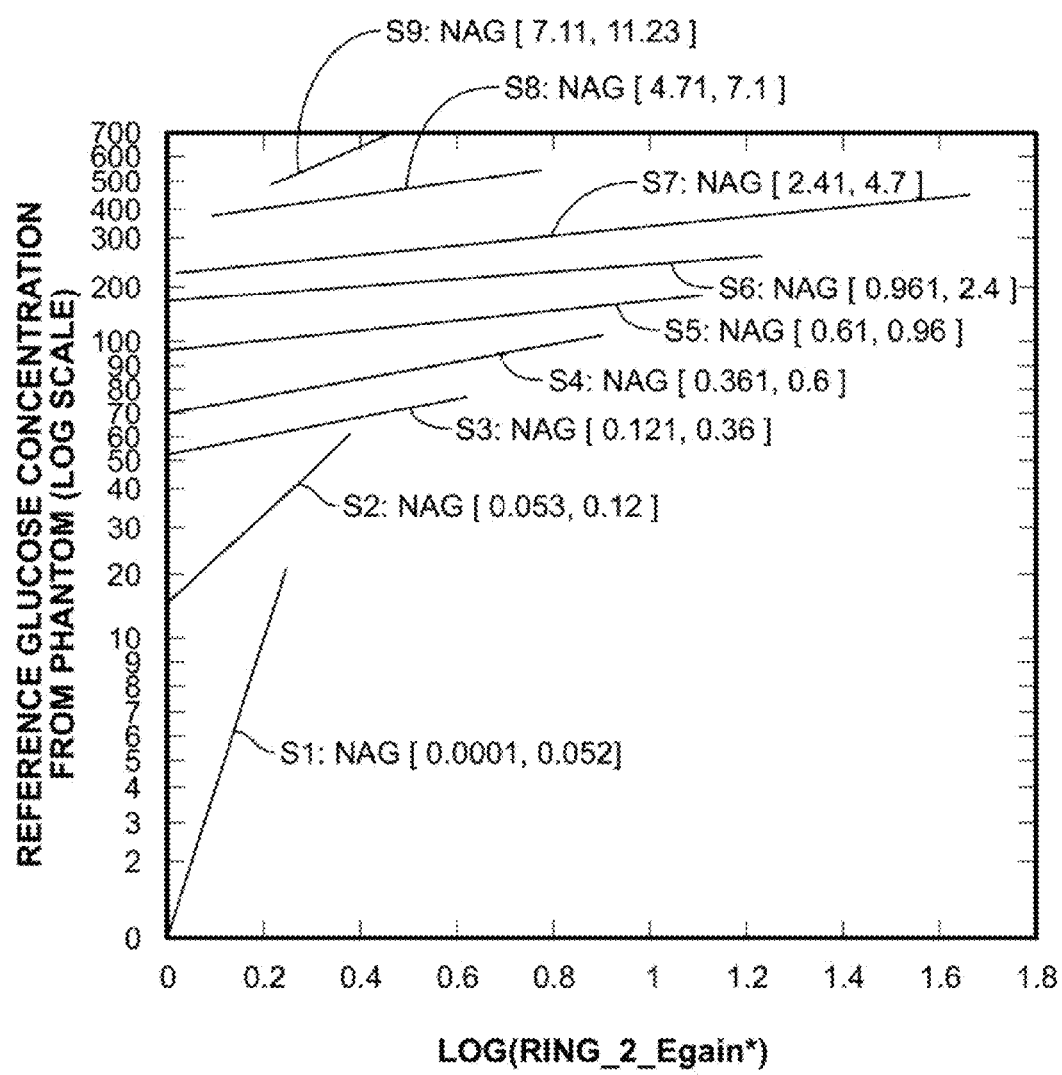
FIG. 80B shows a linearized representation of a Projector Curve Set for an example embodiment for non-invasively measuring glucose.
Figure 81:
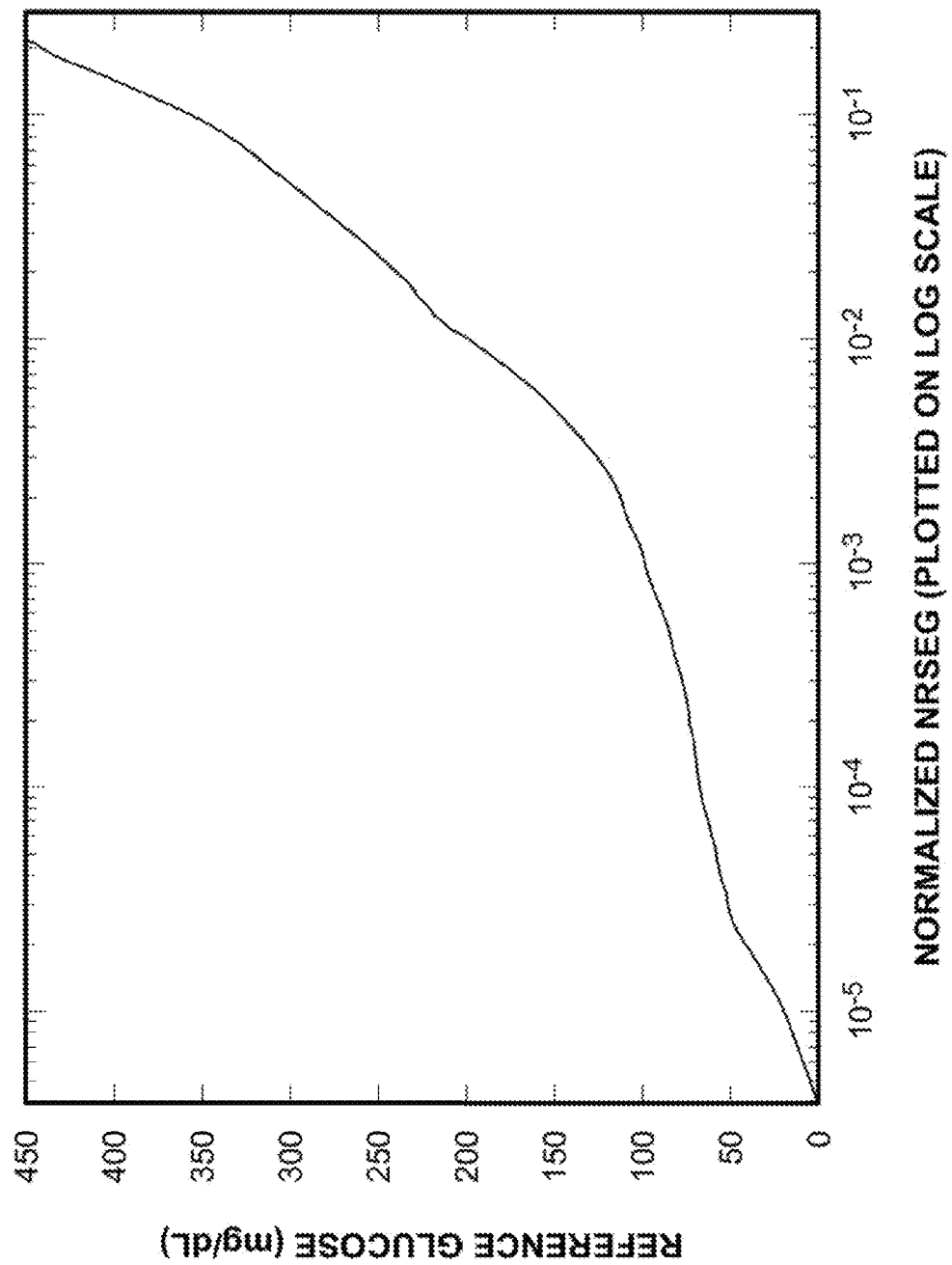
FIG. 81 shows a composite Projection Curve for noninvasively measuring glucose in human tissue using the normalized net analyte signal obtained using collision computing.

FIGS. 80A and 80B show an example of the set of nine flipped individual projector curves (Q1 through Q9 with associated NAG values) used in some embodiments for non-invasive glucose measurement. The curves in FIG. 80A are nonlinear with the glucose range covered by each projector curve as shown on the composite projector curve in FIG. 77. In these flipped curves, the glucose concentration is shown on the Y axis and the X axis shows normalized NRSEG value obtained from the Ring 2 illumination state on a log scale. This example shows that the curves in the flipped projector curve set can be overlapping. Such an overlap can result from different points of slope discontinuity when all the feature pairs taken together do not meet the monotonicity condition described above. FIG. 81 shows a single flipped projector curve covering a range of tissue glucose concentrations as a function of normalized net analyte signal (also called normalized NRSEG) estimated using collision computing.

Mapping of Human Tissue and Glucose Measurements to Projection Curves

Referring again to FIG. 71, the calibration sets obtained using the average NRSEG, as computed from a spectral dataset acquired from human skin tissue, and the value of glucose measured in the subject's tissue using a reference system, are denoted, as described above by $\Gamma_H$. One difference between how the collision-computing results are obtained from spectra generated using a synthetic medium (e.g., tissue phantom) and how the collision-computing results are calculated for the calibration datasets. Unlike in a tissue phantom, the glucose concentration is only available at the time of measurement and cannot be controlled. Therefore, in various embodiments, the interval boundaries of the portions of calibration datasets are selected such that those boundaries can be matched with the interval boundaries of the projector curve determined from tissue phantom samples, as determined in step 55. As such, a particular interval of the calibration set, such as 100 mg/dl to 120 mg/dl, may contain within it several net, renormalized spectral energy gains of several concentrations between 100 mg/dl and 120 mg/dl, such as 101, 104, 107, 110, 112, 114, 117, and 119 and (all in mg/dl), in one example.

The NRSEG values in steps 40 and 60 (FIG. 71) are determined by combining the net, renormalized spectral energy absorption from the entire dataset over several acceptable feature pairs. The spectral energy absorption profiles are typically complex and non-uniform over the concentration range, and cannot often be represented or parameterized in terms of a single linear regression curve. They are instead represented using several projector curves, denoted by the term projector curve set $\Gamma_P$, as described above. In some embodiments for the non-invasive estimation of glucose in human skin tissue, where calibration glucose levels may vary from 20 mg/dl to 900 mg/dl a, , a projector curve set with nine individual projector curves, as shown in FIG. 80B, is used to fully represent the relationship between: (a) the averaged NRSEG, individually computed over different illumination states over all acceptable feature pairs, and then combined to compute the Normalized Absorption Gradient ("NAG"); and (b) the glucose concentration.

Each analyte and non-analyte feature pair (e.g., GL and NO-GL feature pair) for each tissue spectrum is first examined to determine if it is "acceptable." FIG. 79 shows curves called absorption gradients "AG" computed for five feature pairs FP1 . . . FP5 from a human spectroscopic sample. As an illustrative example, the four data points on the dashed line corresponding to FP3 represent the prior to normalization, i.e., un-weighted NRSEG averaged over two repeats acquired using illumination states Ring 1, Ring 2, Ring 3 and All Rings. The specific values of spectral energy gain are given in the table below the graph in FIG. 79. The absorption gradient computed for each feature pair, based on an illumination sequence using four illumination states as in this example, must be monotonically increasing over those four illumination states to be determined to be an "acceptable" feature pair.

It is noted that the dashed line in the graph corresponding to feature pair FP3 does not have a monotonically increasing linear behavior over the four illumination states as expected for this embodiment for this feature pair. It shows an increasing value of spectral energy gain with Ring 2 compared to Ring 1, which then decreases for Ring 3, but again increases for the ALL Rings illumination. This behavior is not consistent with the model of glucose presence in human tissue, where interrogation of a thicker section of tissue would be expected to show more absorbance due to glucose, and contravenes the response expected using tomographic imaging described above for non-invasive glucose, which is an increasing amount of glucose included within the photon path moving from Ring 1 to Ring 2 through Ring 3, with the greatest amount of glucose in "all rings," as those illuminations sequentially target the epidermis (Ring 1), the dermis (Ring 2), the subcutaneous through the dermis (Ring 3), and all three skin layers (All Rings).

Based on the above expected response, the feature pair FP3 in FIG. 79, is sub-optimal and the slope of the line is not usable to use in computing a NAG for projection to select the appropriate projector curve, and the feature pair is not acceptable. In a similar vein, FP4 and FP5 in FIG. 79 are not acceptable feature pairs as their renormalized spectral energy gain response also is different from what is expected in tomographic imaging. On the other hand, the two solid lines corresponding to the renormalized spectral energy gains over different illumination states using feature pairs FP1 and FP2 both have a positive slope, are monotonically increasing, and match the expected behavior of NIR absorption of glucose in the different layers of skin. FP1 and FP2 are thus both acceptable features, and the slopes of their respective regression lines are usable for the Projection process. Feature pairs meeting the monotonicity test are referred to as "acceptable feature pairs."

It is to be understood that, in the context of calculating absorption gradients and the Normalized Absorption Gradient, "monotonicity" for feature pairs is assessed by regressing the NRSEG values for the illumination states in an illumination sequence against the distance between the source and detector, with the additional consideration here that monotonicity is maintained when the illumination sequence includes, for example, two sequential illuminations using at least one ring with the same separation distance, without a reversal in direction of the measured energy. For example, duplicates of rings as in the illumination sequence R1, R2, R2, R3, or when a following illumination state has at least one ring with the same maximum separation distance as the previous illumination state, as in R1, R2, R3, ALL Rings, a feature pair exhibiting increasing or constant energy values across all the illumination states would be considered "monotonic" and thus "acceptable." In these cases, when the duplicate measurements of energy for the two R2 states in the first example, or the sequential measurements of energy for the "R3, ALL Rings" pair of illumination states in the second example do not change direction, a feature pair with these example illumination sequences and energy values would display a "monotonic" gradient, and the feature pair would be considered "acceptable."

It is also to be understood that, if the illumination states were considered in an opposite sequence, acceptable feature pairs could also display monotonically decreasing values, and still match the expected absorption behavior, thus becoming considered "acceptable feature pairs." This example also clarifies the rationale for the selection and validation of feature pairs during design time, i.e., when the projector curves, calibration sets, and mapped projectors curves are generated.

The slope of the regression line, as determined above over the log of the NRSEG values for the four illumination states shown in FIG. 79, is denoted the "absorption gradient" or "AG." The determination of NAG, e.g., at step 40 (FIG. 82), for any sample entails two steps: Step 1 is the computation of an absorption gradient, as above, for each acceptable analyte and non-analyte feature pair (e.g., a GL and NO-GL feature pair) using the NRSEG averaged over one or more ring repeats for a sample (if necessary), and Step 2 is a normalization of the absorption gradient over all the feature pairs determined to be acceptable feature pairs (as described below).

Figure 82:
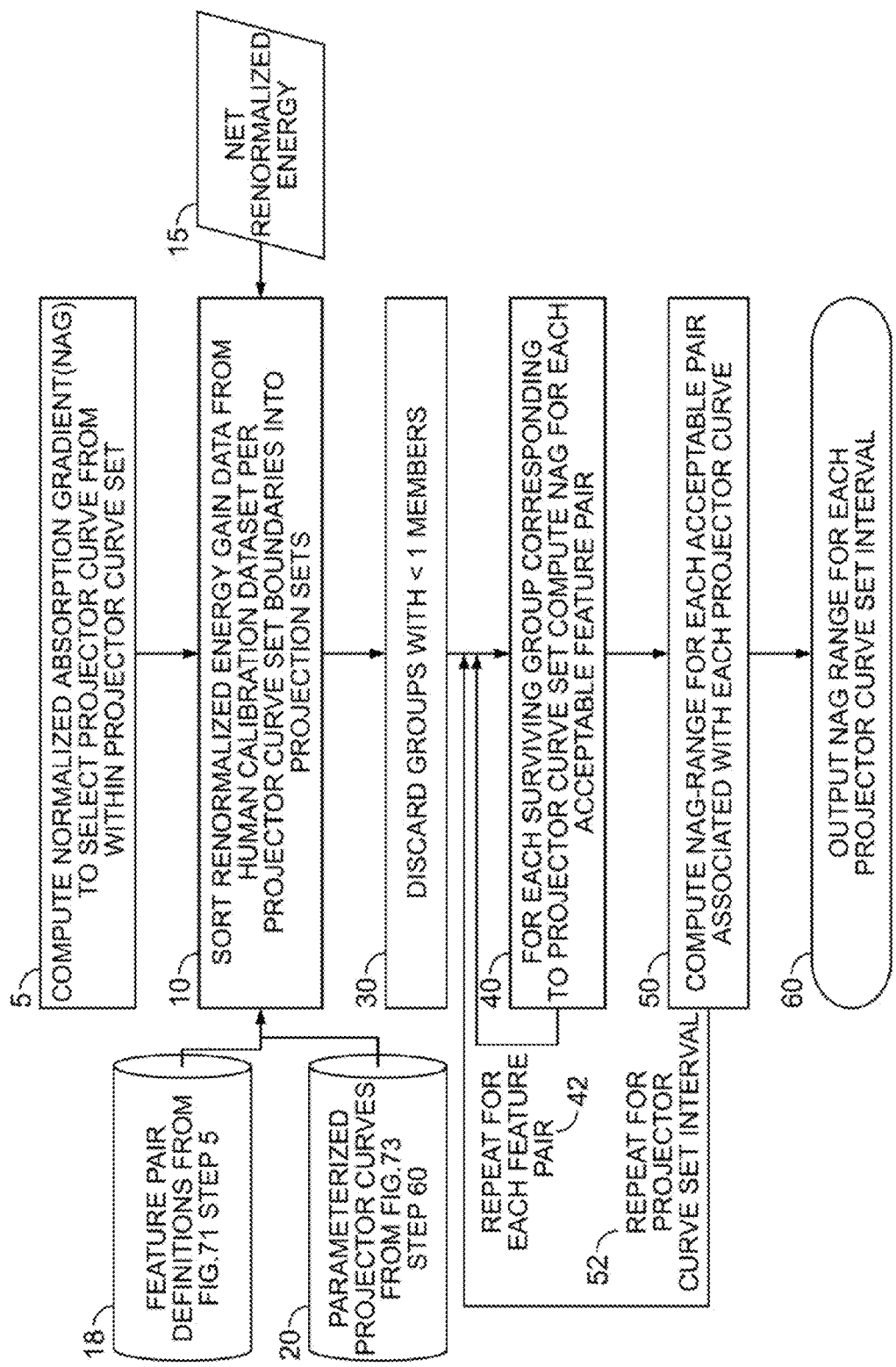
FIG. 82 shows the steps in creating a Normalized Absorption Gradient (NAG) using the net, renormalized spectral energy gains (NRSEGs) from feature-pair data derived from human tissue spectra as inputs.

Referring to FIG. 82, the two steps in computation of the NAG are as follows: In the first step, the absorption gradient computation, where the absorption gradient (AG) can be described as the slope of the regression line computed using the log of the numerical values of the NRSEG for all illumination states $t=1, \ldots, M$ over each acceptable analyte and non-analyte feature pair (e.g., GL and NO-GL feature pair) $\{p, q\}$ where $p=1, \ldots, P$, and $q=1, \ldots, Q$, regressed against the total power of light delivered to the tissue in each illumination state, as measured with a light power meter with a detection range typically centered at 1550 nm.

TABLE 11

Typical Value of Total Light Power
for Various Illumination States

| Illumination State | Total Power @ 1550 nm |
|---|---|
| Ring 1 | 1.00 |
| Ring 2 | 1.50 |
| Ring 3 | 2.08 |
| ALL Rings | 4.58 |

The optional second step of the NAG computation involves normalization of the absorption gradients (AGs), as computed above, across all the acceptable feature pairs associated with a sample including all spectra acquired during an illumination sequence and their replicates. Let $AG(t_{p,q})$ denote the computed AG of the $t^{th}$ acceptable feature pair in Step 40 of FIG. 82, in the first step of NAG computation. In the second step the separate AG values are normalized and averaged over all $AG(t_{p,q})$ for all $N_t$ acceptable feature pairs, by taking the average of the product term given by:

$$\overline{NAG}=1/Nt(\Sigma_1{}^t AG(t_{p,q})*W(p,q)) \quad (22)$$

where the result $\overline{NAG}$ is the Averaged Normalized Absorption Gradient for the sample; with $AG(t_{p,q})$, is as defined above, i.e., the absorption gradient of the $t^{th}$ acceptable feature pair (p,q) associated with a sample, combining results from several illuminations of an illumination sequence; and W(p,q) is a numerical weighting coefficient associated with an acceptable feature pair (p,q) where p and q represent the analyte (e.g., GL) and non analyte (e.g., NO-GL) features, respectively. The weighting coefficient for the feature pair (p,q), i.e., W(p,q) is calculated as defined above, using pure component absorbance spectra of glucose (as shown in FIG. 28A) and the knowledge of spectral boundaries of the analyte feature p and non-analyte feature q. An example of GL and NO-GL features is shown in FIG. 83.

In various embodiments, $AvgAbsorbance_{(f)}=1/W\Sigma_{l=1}^{W}(Absorbance_{(l)})$ where the average absorbance $AvgAbsorbance_{(f)}$, for a feature f, with a feature length of W, in wave numbers, is the average of l pure component absorbance values (scaled to any absorbance unit), at each discrete wavenumber position contained in the feature, such that W is the product of l and resolution of the sensors (in wavenumbers). Thus:

$$W(p, q) = \frac{\max_{u,v}(AvgAbsorbance_u / AvgAbsorbance_v)}{(AvgAbsorbance_p / AvgAbsorbance_q)} \quad (23)$$

such that a dimensionless quantity, $\max_{u,v}(AvgAbsorbance_u/AvgAbsorbance_v)$ is the maximum of the ratio of average absorbance of any analyte (e.g., GL) feature u to its associated non analyte (e.g., NO-GL) feature v over the total feature set, such as that shown in FIG. 83, computed using the pure component spectrum. An example of the pure component spectrum for glucose is shown in FIG. 28A. The values, $AvgAbsorbance_p$ and $AvgAbsorbance_q$, which generally refer to the average absorbance of features p and q computed using the above definition of AvgAbsorbance, are used to compute the dimensionless number ($AvgAbsorbance_p/AvgAbsorbance_q$).

In summary, the weighting coefficient W is used to scale all feature pairs to have the same net contribution for the purpose of projecting the NRSEG to analyte quantity or concentration, averaged over all replicate illumination sequences in a tomographic acquisition. Once the Normalized Absorption Gradient values have been computed for all acceptable feature pairs and averaged to obtain $\overline{NAG}$, this value is used is various embodiments in selection of the applicable projector curve and in the determination of the analyte concentration at step 10 (FIG. 78).

Referring again to FIG. 71, steps 65 through 80 show how the projector curve set mapping, represented as $\hat{\Gamma}_P:\Gamma_H \to \Gamma_P$, is established using data from both human and tissue phantom datasets. The human calibration dataset (including NRSEGs derived from several pairs of tissue spectra and their associated blood glucose reference values), is partitioned into subsets (referred to as "projection sets"), such that paired data are separated on the basis of their reference values into the same glucose intervals as used for the tissue-phantom dataset, i.e., the intervals defining the individual projector curve set $\Gamma_P$ boundaries.

The processing of NRSEGs for different illumination states obtained using collision computing, associated with the feature pairs in the projection sets constructed using a human dataset is typically different from those in the tissue-phantom dataset. The NAG values are computed, as described above, in generating the projection sets, which are groups according to the concentration values measured using a reference system, and associated with concentration value boundaries of individual projector curves. A different net energy gain is expected due to an expected increase in pathlength in the phantoms. Specifically, (i) as the tissue phantoms used are one-layered system, no NAG is computed for the NRSEG obtained using tissue phantoms for the feature pairs when different rings are illuminated. However, a check is made for:

$$\Delta e_{(GL_{F_p}, NO-GL_{F_q}, Z_r, R_1)} < \Delta e_{(GL_{F_p}, NO-GL_{F_q}, Z_r, R_2)} <  \quad (24)$$
$$\Delta e_{(GL_{F_p}, NO-GL_{F_q}, Z_r, R_3)} < \Delta e_{(GL_{F_p}, NO-GL_{F_q}, Z_r, R_{ALL})}$$

for all feature pairs (p,q). This check is due to an increase in pathlength through the glucose-containing phantom successively in rings 1, 2, 3 and ALL.

Also, the slope of the linear regression line obtained using the log values for $$\Delta e_{(GL_{F_p}, NO-GL_{F_q}, Z_r, R_1)}, \Delta e_{(GL_{F_p}, NO-GL_{F_q}, Z_r, R_2)},$$
$$\Delta e_{(GL_{F_p}, NO-GL_{F_q}, Z_r, R_3)}, \text{ and } \Delta e_{(GL_{F_p}, NO-GL_{F_q}, Z_r, R_{ALL})},$$

regressed against the illumination states R1, R1, R3, ALL Rings, must generally be positive (or negative, if the illumination sequence is such that the successive illumination states correspond to decreasing depth of photon paths under the skin). NRSEG monotonicity as specific by relationship in Equation (24) may be required in various embodiments having several illumination rings and states, e.g. $R_1$, $R_2$, $R_3$, ..., $R_i$, $R_{i+1}$, ..., $R_T$, ALL where T>1 and the ring indices 1, 2, ..., i, i+1, ..., T, ALL are sorted by total power delivered to the skin by individual ring. If this slope condition is not met, the feature pair is not an acceptable feature pair, and it may be eliminated from normalization calculations and/or another feature pair may be selected.

In one embodiment, the paired data of tissue spectra and their corresponding glucose concentration reference values in the human calibration dataset, are arranged according to the same interval boundaries as computed in steps 50 and 55 in the process described with reference to FIG. 71, and grouped into nine or fewer projection sets, depending on the range of reference glucose values. Typically, no slope discontinuity check computations are performed as in the case of data from tissue phantoms.

Based on the grouping results, some individual projector curves may not be associated with any data points (i.e., they are empty and may be labeled as "Null"). This implies that no human calibration data were obtained for such intervals. The Null labeled projectors curves may be discarded from further consideration similarly as projections sets labeled as Null may be discarded (in step 30 FIG. 82), as described above. The boundaries of the adjacent individual projector curves may then be adjusted to subsume the discarded individual projector curve.

The process for generating the mapping $\hat{\Gamma}_P:\Gamma_H \to \Gamma_P$ in some embodiments is shown in FIG. 82. This process typically uses the NAG values, and generally maps the NRSEG, which can also be denoted as the normalized net analyte signal (NAS), from human non-invasive calibration measurements to estimate glucose levels for uncharacterized subjects. Once the projector curve set ($\Gamma_P$) has been parameterized (step 50 of the process shown in FIG. 73), the mapping $\hat{\Gamma}_P$ development can be completed using the process flow starting at 5 as shown in FIG. 82.

In some embodiments, calibration sets including the NRSEG data, i.e., gain $$\Delta \vec{e}_{(GL_{F_p}, NO-GL_{F_q}, Z_r, R_t)}$$

for all t=1, ..., M for each analyte (e.g., GL) and non-analyte (e.g., NO-GL) feature pair {p, q} where p=1, ..., P, and q=1, ..., Q, are obtained at step 15 (FIG. 82). The human calibration dataset is partitioned into subsets (called projection sets) corresponding to the projector curves, where analyte-concentration boundaries of the subset (i.e., each projection set) are the same as the analyte-concentration boundaries of the projector curves. Also, one or more projection sets can be Null, as described above, i.e.., human data may not be available for any concentration within the boundaries of that particular projector curve (e.g., 0-20 mg/dl, 640-700 mg/dl). In concentration regions such as these, where human data are not available, a correction factor, based on the values obtained for NAG using the nearest available concentration regions for which human data are available, may be used to extrapolate the tissue-phantom spectral data to provide NAG values for these regions. A check for monotonicity in the NRSEG as a function of reference glucose concentration may be made for human samples over the total range of analyte (e.g., glucose) concentrations collected, in order to validate the selection of feature pairs and selection of the collision computing parameters. For example, the NRSEG for a concentration of 125 mg/dl must be greater than that for 101 mg/dl in the human calibration dataset.

The absorption gradient obtained by regressing NRSEG (on a log scale or any other numerical scale that can linearize the regression relationship) against signal power delivered to the medium, the source-detector distance, or the reciprocal of either, where the NRSEG values are obtained using collision-computing or via estimation of absorption due to analyte using another computation technique, is used to select a suitable projector curve, as described below. The NAG can account for variations in the uncharacterized media to be analyzed, such as variation in skin properties of one person to another and, as such, allows for the selection of a projector curve that corresponds to the properties of the medium to be analyzed without having to calibrate that particular medium. The use of the NAG thus facilitates universal calibration, i.e., calibration that does not depend on the particular medium to be analyzed.

Radiation/detection systems having several detection elements and a single source, or several illumination elements and a single detector, or several radiation sources and several detection elements can be used in computing the NAG. The use of AG or NAG in transforming acquired data to an analyte concentration is a robust mechanism to obtain analyte concentrations in a medium with high levels of interference from confounders. For systems implementing spectroscopic tomography, use of AG and NAG provides a robust mechanism for also determining if the underlying measurement hardware is functioning properly. A null AG value, over time, as seen in several samples can indicate a system malfunction. In various embodiments, AG or NAG can be used in both in-vitro and in-vivo analysis of uncharacterized samples that are spectroscopically imaged using one or more radiation sources and one or more detectors.

Referring back to FIG. 82, for each projection set that is not labeled as Null, a check is made at step 30 to ensure that there is at least one acceptable feature pair (pairing of analyte (e.g., GL) and non-analyte (e.g., NO-GL) features as described above. The NAG is a weighted average of AGs across acceptable feature pairs. Any Null projection set within $\Gamma_H$, and any projection set without at least one acceptable feature pair yielding a positive AG value, are discarded from any further processing at step 30. The NAG computed using the normalized, averaged AG values from all acceptable feature pairs associated with all paired sample members of $\Gamma_H$, are used to compute a range at step 50 as $\Gamma_H\{\phi_i\}<\phi_{iL}, \phi_{iU}>$ where $\Gamma_H\{\phi_i\}$ represents the $i^{th}$ member of the set $\Gamma_H$, and $\phi_{iL}$ and $\phi_{iU}$ represent the lowest and highest value of the NAG for the interval, over all acceptable feature pairs associated with all samples in the interval. As indicated by the flow loops 42 and 52, this computation is repeated for all the samples with all acceptable feature pairs for all the groups in $\Gamma_H$. This process is further illustrated with reference to FIGS. 84A and 84B below. The NAG values thus relate the NRSEG values or the logs thereof for a projection set in $\Gamma_H$ to its associated member in set $\Gamma_P$ through a mapping process.

Figure 84A:
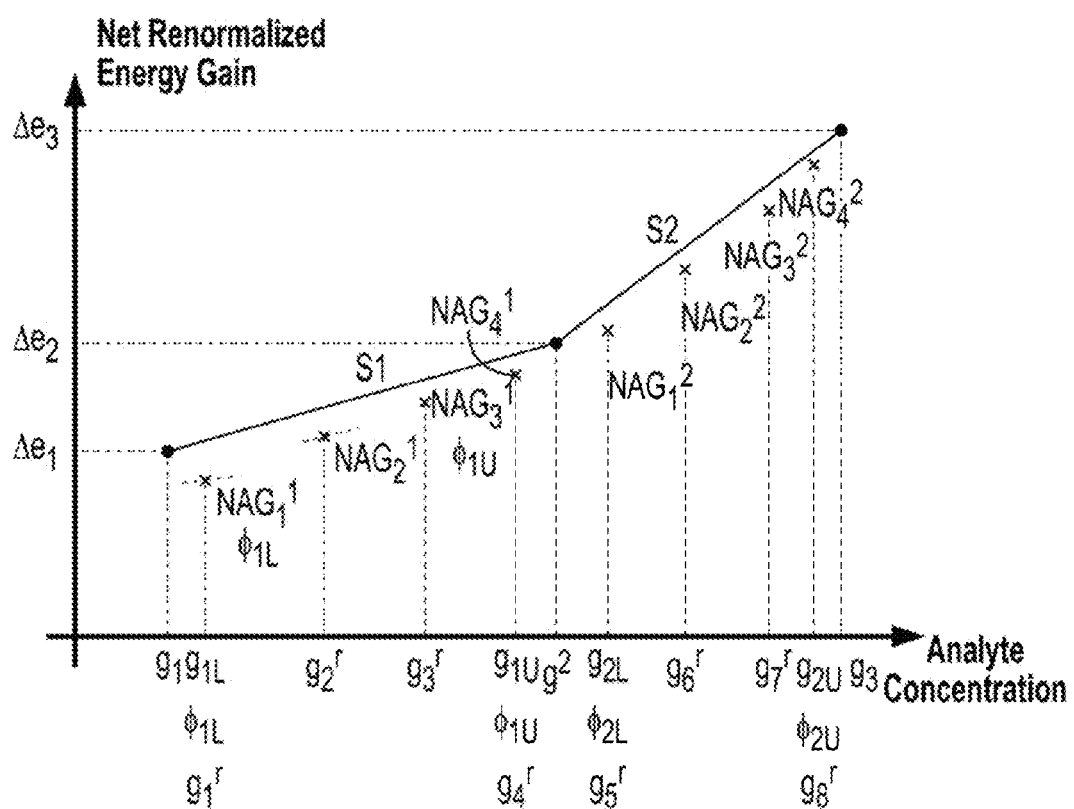
FIG. 84A schematically depicts a mapping between two individual projector curves and two projection sets, according to one embodiment.

With reference to FIG. 84A, a portion of the composite projector curve is partitioned into two individual projector curves $S_1$ and $S_2$. The analyte concentration boundaries of $S_1$ and $S_2$ are [g1, g2] and [g2, g3], respectively. The values g1, g2, and g3 can be obtained from a selection of the tissue phantom samples. In one example, where the analyte is glucose, these boundaries can be [80, 110], [110, 130], all in mg/dl. It is to be understood that a composite projector curve may be partitioned into more than two, e.g., 5, 6, 9, 10, 12, 15, etc., individual projector curves.

The NAG values are computed from calculation of NRSEG corresponding to analyte concentrations in human tissue spectra. During calibration, the analyte concentrations are measured using an invasive reference method. In one example, let the analyte concentration values for which NAG value were computed be: $g_1^r, g_2^r, g_3^r, g_4^r, g_5^r, g_6^r, g_7^r$, and $g_8^r$, the superscript "r" indicating that these concentration values were obtained using a reference method. After these concentrations and the corresponding NAG values are determined, it is further determined that $g_1^r, g_2^r, g_3^r$, and $g_4^r$ are included in the range [g1, g2] and $g_5^r, g_6^r, g_7^r$, and $g_8^r$ are included in the range [g2, g3]. Therefore, the concentration values $g_1^r, g_2^r, g_3^r$, and $g_4^r$ and the corresponding NAG values are associated with $S_1$, and the concentration values $g_5^r, g_6^r, g_7^r$, and $g_8^r$ and the corresponding NAG values are associated with $S_2$. It should be understood that fewer or more than four, and/or different numbers of value pairs can be associated with different individual projector curves $S_i$. In one example where the analyte is glucose, $g_1^r, g_2^r, g_3^r$, and $g_4^r$ are 83, 87, 94, and 106, respectively, and $g_5^r, g_6^r, g_7^r$, and $g_8^r$ are 112, 116, 121, and 128, respectively.

In some embodiments, the computed NAG is within the lower and upper bound NAG values if the computed NAG is equal to or greater than the lower bound NAG value and is equal to or less than the upper bound NAG value. In some embodiments, the computed NAG is within the lower and upper bound NAG values if: (i) the computed NAG is greater than the lower bound NAG value and is equal to or less than the upper bound NAG value; or (ii) the computed NAG is equal to or greater than the lower bound NAG value and is less than the upper bound NAG value; or (iii) the computed NAG is greater than the lower bound NAG value and is less than the upper bound NAG value.

With reference to Table 12 below, consider an interval [110, 130] of one example of a composite projector curve S. An individual projector curve $S_4 \equiv S_{[110-130]}$ is associated with this interval. Assume that a complete set of feature pairs includes five feature pairs, namely, FP1, FP2, FP3, FP4, and FP5. It is to be understood that in general, there can be fewer than five or more than five (e.g., 10, 20, 30, 50, etc.) feature pairs that can be considered for the analysis described herein. Assume further that for the selected interval [110, 130], three reference concentration values, namely, 112, 121, 126, were obtained using a reference invasive method. Here again, it is to be understood that these values are illustrative only in that different reference values and different numbers of reference values, e.g., 1, 2, 4, 6, 10, etc., may be obtained within a selected interval. For each reference concentration value, for each available feature pair, the monotonicity is tested as described above.

In addition, unlike the embodiment described above, where monotonicity is tracked only over adjacent ring illumination states, it would be possible to utilize varying illumination states for certain samples with particular features or tissue layer thicknesses, and an embodiment could be constructed with a probe having 6 illumination (or detector) rings. For example, the same glucose concentration, data from person A may show monotonicity across rings 2-3-4 while data for person B may show monotonicity across rings 3-4-5-6. Thus using either the same features or different features, the projection system could test monotonicity while rejecting data from rings 1, 5, and 6 for person A, and from rings 1 and 2 for person B.

TABLE 12

| Concentration | 112 | 121 | 126 |
|---|---|---|---|
| FP1 | × | × | $AG_{126}^1$ |
| FP2 | $AG_{112}^2$ | $AG_{121}^2$ | × |
| FP3 | $AG_{112}^3$ | × | $AG_{126}^3$ |
| FP4 | × | × | × |
| FP5 | $AG_{112}^5$ | × | × |
| $\overline{NAG}$ | $\overline{NAG}_{112} = \frac{1}{3}(W_2 AG_{112}^2 + W_3 AG_{112}^3 + W_5 AG_{112}^5)$ | $\overline{NAG}_{112} = (W_2 AG_{121}^2)$ | $\overline{NAG}_{126} = \frac{1}{2}(W_1 AG_{126}^1 + W_3 AG_{126}^3)$ |

As illustrated in Table 12 above, for the reference glucose concentration value 112, three of the five feature pairs are accepted; for the reference glucose concentration value 121, only one feature pair is accepted; and for the reference glucose concentration value 126 two feature pairs are accepted. For the accepted feature pairs, respective absorption gradients $AG_{C_k^r}^i$ are computed, where the subscript $C_k^r$ represents the corresponding reference analyte concentration, and the superscript i indicates the corresponding acceptable feature pair. For each reference analyte concentration $C_k^r$, the absorption gradient(s) of the acceptable feature pairs are weighted using the weights computed as described above, and these weighted absorption gradients are averaged to obtain a normalized absorption gradient $\overline{NAG}_{C_k^r}$. In the table above, the weight $W_i$ represents the weight W(i(p,q) described above.

The individual projector curve $S_4$ is associated with the minimum and maximum of all $\overline{NAG}_{C_k^r}$ values, where all reference analyte concentration values $C_k^r$ are associated with the individual projector curve $S_4$, as: $\Phi_{4L}$=min($\overline{NAG}_{112},\overline{NAG}_{121},\overline{NAG}_{126}$); and $\Phi_{4U}$=max($\overline{NAG}_{112}, \overline{NAG}_{121},\overline{NAG}_{126}$). This subprocess is repeated for each individual projector curve. The overall processes of generating a projection set that is described above is summarized below in a pseudo-code form.

Similarly, the rings used in a specific embodiment to calculate NAG and NRSEG will depend upon the selected wavelength range. For example, in a 6-ring system, in the region above 1500 nm, only the first four rings may be used for the computation of NAG, with the combined energy gain from rings 2 and 3 being used for glucose prediction. Below 1350 nm, all six rings may be used to compute NAG and the mapping from NRSEG to glucose is based upon rings 2-4, 3-5 or 2-5 depending upon the embodiment.

This process is described in the pseudo-code below:
For each individual in a group of individuals {
  Perform an analyte (e.g., glucose) measurement (e.g., determination of analyte concentration) using a reference method
  Perform a corresponding collision computing (CC) measurement, where the CC measurement is associated one or more analyte-non-analyte feature pairs, and to perform the CC measurement, for each feature pair {
    Obtain up to M NRSEG values, where M is the number of unique illumination states (IS) such as ($I_1, I_2, \ldots, I_M$), e.g. (R2, R3, R4, ALL), in an illumination sequence
    // Each NRSEG value is associated with a respective, particular
    // illumination pattern (e.g., R4), and can be an average of NRSEG
    // values across the repeats of that particular illumination pattern
    Test monotonicity of the MNRSEG values across the MIS (ordered by the amount of power delivered to the sample)
    Accept only those feature pairs that satisfy the monotonicity condition
  }
  For each accepted feature pair
    Compute absorption gradient (AG) using the corresponding MNRSEG values
  }
  Compute NAG as a weighted average of AGs of all accepted feature pairs, normalized by the weighting coefficients established on basis of the relative absorbances of the individual features for pure component spectra for the analyte
  }
  Repeat for the selected individual, the above iteration at a different time to obtain a different reference analyte measurement and a corresponding different CC measurement, and a different NAG associated therewith
}
// At the end of this sub-process, several reference analyte measurements and
// corresponding NAG values would be obtained Sort the pairs <ref_analyte_measurement, NAG> by analyte measurement values
For each individual projector curve $S_i$ {
  Associate one or more pairs to $S_i$ according to the analyte measurement boundaries of $S_i$.
  The association can be represented as:
    $S_i(g_L, g_U)$<==>Projection_Set_i [<$g'_L$, NAG>, ..., <$g'_U$, NAG>],
    where $g_L \le g'_L$ and $g_U \ge g'_U$.
  Associate min (Projection_Set_i (NAG)) and max (Projection_Set_i (NAG)) with $S_i$.
}

Use of Projection Curves to Determine Glucose in Noninvasive Samples

For each flipped, individual Projector Curve respectively, the variables slope$_i$ and y-intercept$_i$ denote the slope and y-intercept of the linearized $i^{th}$ individual projector curve with analyte (e.g. glucose) concentration on the Y axis and the log values of NRSEG on the X axis, as shown in FIG. 80B. Thus, in general, a mapping $\hat{\Gamma}_P:\Gamma_H \to \Gamma_P$ can be represented as $$\hat{\Gamma}_P:\{\{\Gamma_H\{\phi_1\}<\phi_{1L}, \phi_{1U}> \to S_1\{<g_{1L},g_{1U}>, \text{slope}_1, y\text{-intercept}_1\}\},$$

$$\{\{\Gamma_H\{\phi_2\}<\phi_{2L}, \phi_{2U}> \to S_2\{<g_{2L},g_{2U}>, \text{slope}_2, y\text{-intercept}_2\}\},$$

$$\ldots,$$

$$\{\{\Gamma_H\{\phi_9\}<\phi_{9L}, \phi_{9U}<\} \to S_9\{<g_{9L},g_{9U}>, \text{slope}_9, y\text{-intercept}_9\}\}\}$$

where the variables in the set notation are as described above, with the variable i being set to 1, 2, ..., 9, in one embodiment. This $\hat{\Gamma}_P$ is a set of mappings to project NRSEG values from human subject tissue to analyte concentration values in tissue phantoms, and is used for selecting the appropriate mapped individual projector curve, from a set of mapped individual projector curve as shown in FIGS. 80A and 80B, prior to calculating the analyte concentration for a subject.

In some embodiments for noninvasive glucose measurement, the NAG values for the nine mapped individual projector curves range from a curve with NAG values of approximately 0.001 to about 11.23, as shown in FIG. 80A, from a first curve with a NAG range of 0.001 to 0.052 covering the glucose range 0 mg/dl to about 20 mg/dl, to the ninth curve with a NAG range of 7.11 to 11.23 covering glucose concentrations from about 450 mg/dl to 700 mg/dl.

In various embodiments, the mapped individual projector curves $\hat{\Gamma}_p$ are denoted as $\{\phi_1, \ldots, \phi_9\}$. Each curve, $\phi_i \in \hat{\Gamma}_p$, spans a range associated with analyte concentration ranging between a lower limit $GL_{iL}$ and an upper limit $GL_{iU}$. Furthermore, each of the mapped individual projector curves, represented by $\phi_i$ is associated with a NAG range given by $\{<\phi_{iL}, \phi_{iU}>$ where i=1, ..., 9} and has the attribute of a range of NAG values with a <lower,upper> value pair, as described above, and as listed, e.g., in Tables 12 and 13. Thus, for a curve Si, let the coordinates of the start pair be $(g_{iL}, e_{iL})$ and the end pair be $(g_{iU}, e_{iU})$, where g represents the analyte concentration obtained via a reference method, and e represents the logarithm of the corresponding normalized, averaged NRSEG due to absorption by the analyte in a tissue phantom, as determined by collision computing.

TABLE 13

| Curve Si | Glucose Range (low) | Glucose Range (upper) | Slope of Si (on log scale) | Intercept of Si (on log scale) | NAG ($\Phi_{iL}$) | NAG ($\Phi_{iU}$) |
|---|---|---|---|---|---|---|
| 1 | 1 | 20 | 12.015 | −5.12E−05 | 0.0001 | 0.052 |
| 2 | 15 | 60 | 3.6115 | 2.708 | 0.053 | 0.12 |
| 3 | 50 | 80 | 0.7522 | 3.912 | 0.121 | 0.36 |
| 4 | 70 | 130 | 0.68763 | 4.2484 | 0.361 | 0.60 |
| 5 | 120 | 180 | 0.36595 | 4.7865 | 0.610 | 0.96 |
| 6 | 180 | 250 | 0.26772 | 5.1909 | 0.961 | 2.40 |
| 7 | 220 | 400 | 0.36208 | 5.3889 | 2.41 | 4.70 |
| 8 | 350 | 500 | 0.51773 | 5.8101 | 4.71 | 7.10 |
| 9 | 450 | 700 | 1.6182 | 5.7618 | 7.11 | 11.23 |

As shown, in FIG. 80A, each of the example NAG curves generally displays a nonlinear relationship between NRSEG and glucose concentration. These mapped individual projector curves are semi-linear, and their log-transformed relationship (i.e., the log of the NRSEG values against the corresponding glucose reference values), is generally linear over the interval $<g_{iL}, g_{iU}>$ with slope$_i$ and y-intercept$_i$. The linearized curves corresponding to the curves shown in FIG. 80A are shown in FIG. 80B. In some embodiments, the linearized Projector curves in FIG. 80B, with reference glucose concentration plotted on the log scale on Y axis and the log of Ring_2_Egain* (or normalized NRSEG from Ring 2) plotted on the X axis are used in the overall projection process to estimate glucose concentration values.

In various embodiments, in addition to the ($g_{iL}$, $e_{iL}$) and ($g_{iU}$, $e_{iU}$) pairs, there is a min and max NAG value associated with each $\phi_i$. This means that NAG values mapping to each curve $S_i$ will vary in a range [$\Phi_i^{min}$, $\Phi_i^{max}$]. The slope of the mapped individual projector $S_i$ maps the log of NRSEG to analyte concentration. The intervals [$\Phi_i^{min}$, $\Phi_i^{max}$] are set by computing AG over all $N_t$ acceptable feature pairs for each calibration subject tissue sample, and are associated with analyte concentration data points that fall within the boundaries of $S_i$. Thus, in various embodiments [$\Phi_i^{min}$, $\Phi_i^{max}$] are the minimum and maximum NAG values for the projection set associated with an individual projector curve. For example, if $S_K$ ranges from 70 mg/dL to 100 mg/dL, the data points 72, 75, 83, 90, and 96 mg/dL would correspond to $S_K$. Then $\Phi_i^{min}$ would correspond to the NAG value associated with the data point with a glucose concentration of 72 mg/dL and $\Phi_i^{max}$ would correspond to the NAG value associated with the data point with a glucose concentration of 96 mg/dl, and the Curve $S_K$ is extrapolated to cover glucose concentrations as low as 70 mg/dl or as high as 100 mg/dl, i.e., to the boundaries of the adjacent curves, e.g., the boundaries of the curves $S_{K-1}$ and $S_{K+1}$.

In general, this range results from subject-to-subject tissue morphology and physiology differences, sampling variability, and sensor drift in multiple samples. This means that the estimated NAG value used to map the log of the NRSEG on to any curve Si can vary in a range [$\Phi_i^{min}$, $\Phi_i^{max}$], also denoted [$\phi_{iL}$, $\phi_{iU}$] to allow for sampling, experimental and other variabilities described above.

Referring again to FIG. 84A, without the loss of generality, $g_1^r, <g_2^r <g_3^r <g_4^r <g_5^r <g_6^r <g_7^r <g_8^r$. Therefore, concentration boundaries [$g_{1L}=g_1$, $g_{1U}=g_2$] and [$g_{2L}=g_2$, $g_{2U}=g_3$] are associated with the individual projector curves $S_1$ and $S_2$, respectively. The map $\hat{\Gamma}_P$, $\Gamma_H\{\phi_1\}$ can be specified as $<\Phi_{1L}, \Phi_{1U}>$, and the map $\hat{\Gamma}_P$, $\Gamma_H\{\phi_2\}$ can be specified as $<\Phi_{2L}, \Phi_{2U}>$. The NAGs corresponding to the reference analyte concentrations [$g_1^r$, $g_2^r$, $g_3^r$, $g_4^r$] are associated with the individual projector curve $S_1$, and are denoted [$\overline{NAG}_1^1$, $\overline{NAG}_2^1$, $\overline{NAG}_3^1$, $\overline{NAG}_4^1$]. Similarly, the NAGs corresponding to the reference analyte concentrations [$g_5^r, g_6^r, g_7^r, g_8^r$] are associated with the individual projector curve $S_2$, and are denoted [$\overline{NAG}_1^2$, $\overline{NAG}_2^2$, $\overline{NAG}_{hu\ 2}$, $\overline{NAG}_4^2$]. In this notation, ($\overline{NAG}_k^i$, in general), $\overline{NAG}$ represents the normalized absorption gradient computed as described above, the superscript "i" indicates the particular individual projector curve with which the NAG is associated, and the subscript "k" indicates an analyte concentration, determined using the reference system, belonging to a member of the projection set corresponding to the i-th individual projector curve. As such, in the two example of maps described above, $\Phi_{1L}$=min($\overline{NAG}_1^1$, $\overline{NAG}_2^1$, $\overline{NAG}_3^1$, $\overline{NAG}_4^1$) and $\Phi_{1U}$=max ($\overline{NAG}_1^1$, $\overline{NAG}_2^1$, $\overline{NAG}_3^1$, $\overline{NAG}_1^4$). Similarly, $\Phi_{2L}$=min ($\overline{NAG}_1^2$, $\overline{NAG}_2^2$, $\overline{NAG}_3^2$, $\overline{NAG}_4^2$) and $\Phi_{2U}$=max($\overline{NAG}_1^2$, $\overline{NAG}_2^2$, $\overline{NAG}_3^2$, $\overline{NAG}_4^2$).

It is to be understood that in some embodiments, only a single individual projection curve is generated from synthetic calibration samples, calibration subjects, and corresponding glucose value ranges. In these embodiments, the analyte concentration can be determined using the average of the normalized NRSEG values corresponding to all acceptable feature pairs corresponding to one particular illumination state. This average NRSEG value can be mapped directly to the analyte concentration using the available projector curve, and the NAG need not be used to select a projector curve as only one curve is available. Optionally, the NAG value may nevertheless be computed in such embodiments to test monotonicity across different illumination states.

Example of A Calculated Glucose Result

In some embodiments for non-invasive glucose measurement, the above calculated average NRSEG for each illumination state of an illumination sequence describes a point. When three single-ring illumination states are used, three NRSEG values are generated for all feature pairs, one associated with each illumination state. In another embodiment, where there are six illuminations states are available, up to six NRSEG values may be used in AG and NAG computations.

The four NRSEG points shown in FIG. 79 corresponding to four illumination states are first used to determine whether the feature pairs are acceptable. If the slope of the curve for a feature pair is negative in some embodiments or generally shows a reversal of direction, the feature pair is unacceptable. If the slope of the line is positive or monotonic, the feature pair is deemed "acceptable," and the absorption gradient for each feature pair is determined by regressing the NRSEG for the feature pair against the power of light injected into the tissue for each illumination state of R1, R2, R3 and ALL Rings, and the slope of the regression line is computed as the absorption gradient (AG) for that feature pair. In an embodiment where the "All Rings" illumination state is not used, the absorption gradient is determined by regressing the log value of the NRSEG for each acceptable feature pair against the source-to-detector distance for each ring, which is generally proportional to the amount (the power) of light introduced in each illumination state.

The AGs from all acceptable features (p,q) in an spectroscopic sample are then normalized and averaged as described above to compute $\overline{NAG^*}$. The superscript "*" indicates that this NAG value is obtained not from data relating to subjects used to generate the projection sets and projector curves, but from data relating to a person whose glucose concentration is to be determined. The normalized, averaged, computed slope (or $\overline{NAG^*}$) may also be denoted by $\hat{\phi}$. In some embodiments, a hash table mapping may be used find the associated projection curve $S_i$, using the Projector Set Mapping $\hat{\Gamma}_P$:{{$\Gamma_H\{\phi_1\}<\phi_{1L}, \phi_{1U}>\rightarrow S_1\{g_{1L}, g_{1U}>, $ slope$_1$, y-intercept}},{{$\Gamma_H\{\phi_{Q2}\}<\phi_{2L}, \phi_{2U}>\rightarrow S_2\{<g_{2L},g_{2U}<, $ slope$_2$, y-intercept$_2$}}, . . . , {{$\Gamma_H\{\phi_9\}<\phi_{9L}, \phi_{9U}>\}\rightarrow S_9\{<g_{9L},g_{9U}>, $ slope$_9$, y-intercept$_9$}}such that $\hat{\phi}$ within the limits of [$\Phi_i^{min}, \Phi_i^{max}$] associated with $S_i$. The computed value of NAG, $\hat{\phi}$, is used to select the appropriate curve from the set of $S_1$ to $S_9$ curves. The determination of $S_i$ provides a pair of boundaries ($g_{iL}$ and $g_{iU}$) between which the level of glucose in the sample lies, and the slope and intercept of the curve $S_i$.

Once the $S_i$ has been determined, its upper and lower interval values may be used to estimate tissue glucose concentration from spectral measurements in conjunction with the average of all normalized Ring 2 NRSEG values, $\overline{y}_C^2 = y_C^2 * W (i_{(p,q)})$, where $y_C^2$ is the Ring 2 NRSEG value associated with feature-pair C in the set of all acceptable feature pairs (p,q), as given by equation (19) and $W(i_{(p,q)})$ denotes the weighting coefficient for that feature pair (as defined above). In one embodiment, the mapped individual projector curves shown in FIG. 80B are used to generate glucose values from the Ring 2 NRSEG obtained using collision computing. The Ring 2 value of Egain*, described below, was selected in some embodiments for projection of glucose concentration because Ring 2 most accurately reflects illumination of the dermis, which has the highest concentration of glucose. According to the structure of the radiation/detection system used, examples of which are discussed below, different illumination states or sets of illumination sources may be used in different embodiments.

To compute the glucose concentration level, the following relationship is used:

$$GL = y_i + \{(slope_i \times Ring\_2\_Egain^*)\} \quad (25)$$

where Ring_2_Egain* is the log of the NRSEG from Ring 2, averaged over all the replicates in the illumination sequence, and normalized and averaged over all acceptable feature pairs in the sample. The process of using the slope and intercept of the projection curve to calculate the glucose concentration (analyte concentration, in general) is termed "interpolation," and this use of that term is distinct from other contexts herein, where interpolation refers to adding additional points to a waveform to extend the length of the waveform in the time domain. In Equation (26)

$$Ring\_2\_Egain^* = \frac{1}{N_t}\left(\sum_1^t \overline{Ring\_2\_\Delta e(t_{p,q})} * W(p,q) \middle| \forall p, q \text{ in } N_t\right) \quad (26)$$

where $$\overline{Ring\_2\_\Delta e(t_{p,q})} = \log\left(\frac{1}{M}\sum_1^M \{Ring2_{\Delta e(t_{p,q})}\}\right)$$

and Ring_2_$\Delta e(t_{p,q})$ is the log of net, renormalized spectral gain over all acceptable feature pairs (p,q), M denotes the number of replicates, and $W(p,q)|\forall p,q$ represents the weighting coefficients that were obtained and also used during the AG normalization process, as described above. The glucose value, GL is then output as the estimated concentration of glucose.

Figure 84B:
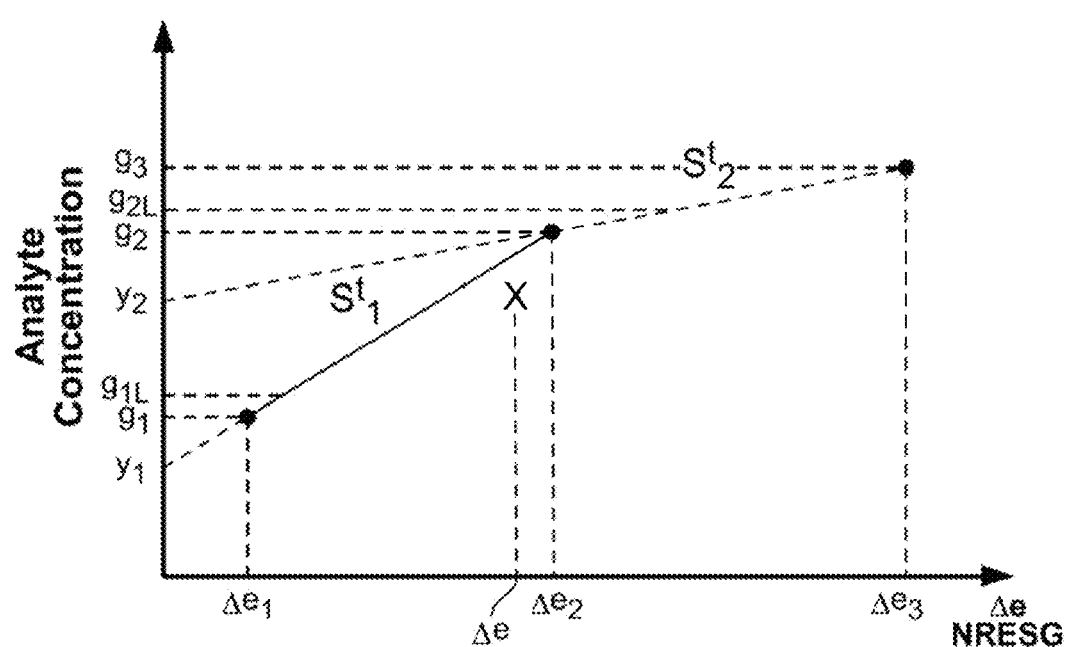
FIG. 84B illustrates projection and measurement of an analyte concentration using the mapping depicted in FIG. 84A.

FIG. 84B depicts flipped individual projector curves $S_1^T$ and $S_2^T$ corresponding to the individual projector curves $S_1$ and $S_2$, respectively that are depicted in FIG. 84A. The point "X" denotes a value $\Delta e$, Ring_2_Egain*, obtained from a non-invasive measurement and using an embodiment of collision computing, as described above. A value of NAG, denoted NAG*, is also computed for this non-invasive measurement, as described above. If NAG* falls within [$\phi_{1L}, \phi_{1U}$] associated with $S_1$, the flipped individual projector curve $S_1^T$, i.e., the slope of $S_1^T$, and the corresponding y-intercept y1 are used to determine the concentration of the analyte corresponding to the NRSEG value $\Delta e$, i.e., Ring_2_Egain*. If, however, NAG* falls within [$\phi_{2L}, \phi_{2U}$] associated with $S_2$, the flipped individual projector curve $S_2^T$, i.e., the slope of $S_2^T$, and the corresponding y-intercept y2 are used to determine the concentration of the analyte corresponding to the NRSEG value $\Delta e$, i.e., Ring_2_Egain*.

Thus, for the same value of Ring_2_Egain* different analyte concentrations can be obtained based on the corresponding different NAG values. In various embodiments, the NAG values account for variations due to skin properties such as thickness, pigments contained in the skin, etc. The NAG-based determination of analyte concentration thus allows the collision computer to be calibrated universally, i.e., without needing individualized calibration of the non-invasive measurement system for each individual. One of the reasons the tomography-based approach described herein yields accurate analyte values for virtually all uncharacterized subjects is that the amount of analyte represented by the illumination state corresponding to Ring2 can be distinguished from that represented in other illumination states. The variation across different illumination states, represented by the NAG* may be used to select the correct individual projection curve to estimate the concentration of the analyte.

In general, there is a one-to-one mapping between the lower and upper boundaries of $\Gamma_P$ and $\Gamma_H$. It was described above with reference to FIG. 82 that one or more members of $\Gamma_H$ can be Null or do not have any acceptable feature pairs. A projection set not having any acceptable feature pairs may also be designated as a Null set. In that situation, the NAG computations used for the mapping process as described above are not available. Let such a Null member of set of $\Gamma_H$, a member corresponding to the $r^{th}$ projector set, be denoted by $\Gamma_{H_r}$. For such members, the range for $\Gamma_{H_{r-1}}$ may be extended to estimate analyte concentration over the interval covering the lower boundary of the non-Null individual projector curve $\Gamma_{H_{r-1}}$ to the upper boundary of the one or more contiguous Null members with the highest upper boundary corresponding to $\Gamma_{H_{r+u-1}}$, where u=1, 2 . . . , 9 or the number of contiguous Null members of $\Gamma_H$.

One likely exception case includes the scenario where there are Null members of $\Gamma_{H_r}$ for the lower/lowest concentrations, such as 20 mg/dl-40 mg/dl, 40 mg/dl-50 mg/dl, etc., and for the higher/highest concentration ranges (e.g., 800 mg/dl-900 mg/dl). In such cases, the estimation range on the lower end and/or on the higher end is extrapolated. The higher end extension is handled in the manner described above. For the lower end extrapolation, let a Null member of the set $\Gamma_H$ be the $w^{th}$ projection set be denoted by $\Gamma_{H_w}$. For such a member, the range for $\Gamma_{H_{w+1}}$ is extended to estimate analyte concentration over the interval covering the lower boundary of the non-Null individual projector curve $\Gamma_{H_{r-1}}$ to the upper boundary of the one or more contiguous Null members, with the highest upper boundary corresponding to $\Gamma_{H_{r+u-1}}$, where u=1, 2, or the number of contiguous null members of $\Gamma_{H_r}$.

The overall projection process can thus be summarized referring back to FIG. 73 as follows: (a) The glucose concentrations are varied from 0 mg/dl up to 900 mg/dl in 10 mg/dl (or other) increments, and for each concentration; (b) The NRSEGs are computed (step 15) via collision computing for all the feature pairs extracted from tissue phantom samples with different concentrations for the GL and NO-GL features defining the pair. This is performed for all spectra acquired over the complete set of illuminations and for all replicates. The NRSEG values are partitioned (step 18) into piecewise sub-intervals over the entire range of concentrations;

Thereafter, (c) using weighting coefficients for each feature pair, computed as described above from pure component spectra of glucose, normalized NRSEG values are obtained.; (d) Using all the normalized NRSEG values associated with all the feature pairs for all tissue- phantom samples associated with a particular sub-interval, the slope of the regression line between the normalized NRSEG as the dependent variable and glucose concentration as the independent variable is computed in steps 20, 25, 30, 35, and 40. A single slope is obtained for each sub-interval;

Then, (e) The slopes are used to plot a concatenated or composite curve "ST" of normalized NRSEG vs glucose concentration at steps 40, 45, and 15 through 40; (f) Based on more than 50% changes in the slope of the concatenated ST curve across the range of glucose concentration, the "points of discontinuity" in the composite (concatenated) curve are determined; (g) Using the points of discontinuity the concatenated curve ST is partitioned into a number of individual projector curves (e.g., ST1-ST9);

Thereafter, (h) once the individual projector curves have been determined, they are parameterized at step 60. This entails determination of the lower and upper glucose concentration boundaries for each individual projector curve, flipping of each individual projector curve, and determining the slope and Y intercept of each flipped individual projector curve. The boundaries (in terms of glucose concentration) of the flipped individual projector curves are used in the glucose estimation process; The axes of the curve ST are flipped to obtain the concatenated flipped projector curves ("S") S1-S9, as shown in FIG. 77.

Figure 85:
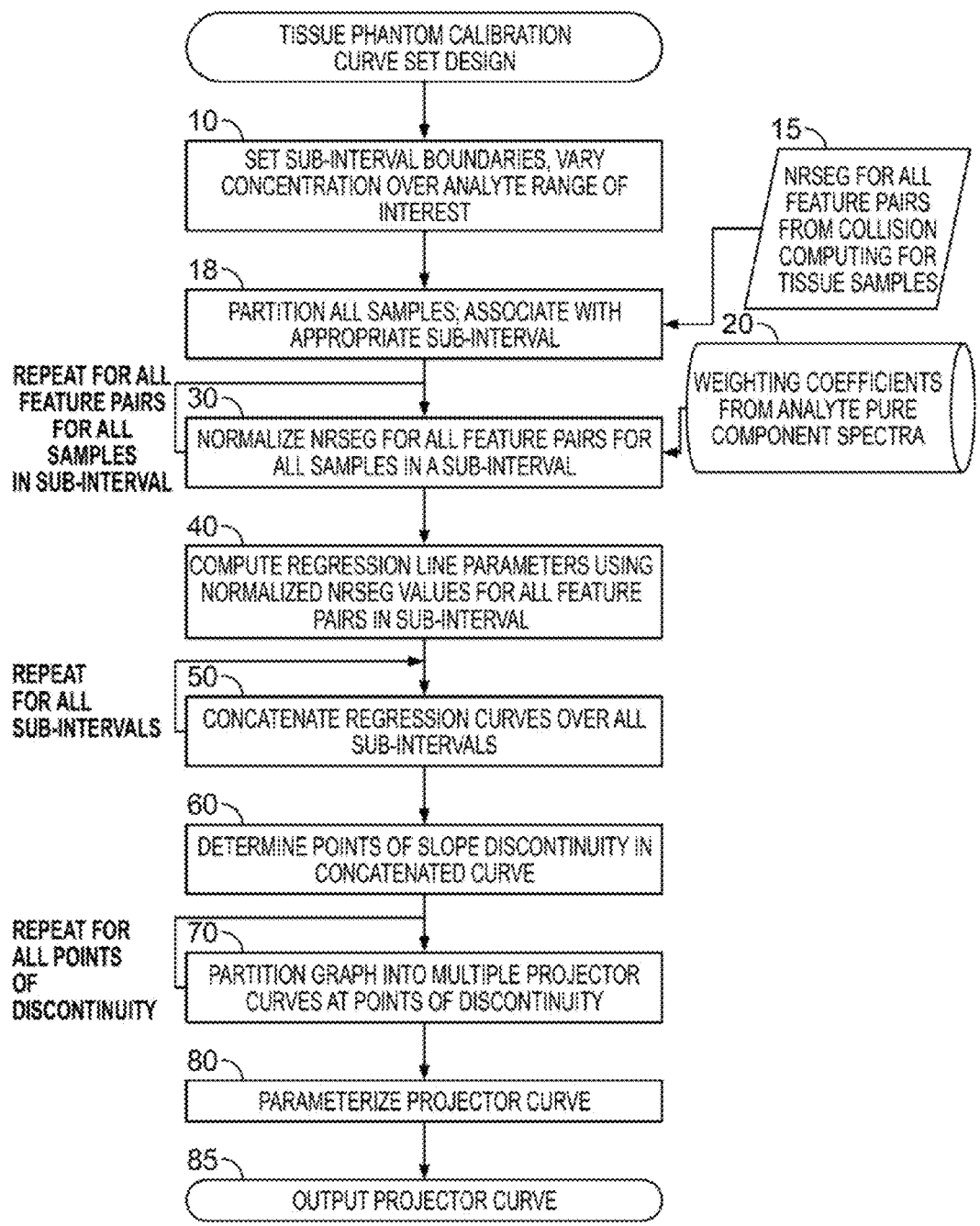
FIG. 85 shows steps in the tissue phantom calibration curve set design.

With reference to FIG. 85 (a) boundaries of sub-intervals of analyte concentration, (e.g., 10 mg/dl, 20 mg/dl, 25 mg/dl, 40 mg/dl, etc., for glucose), over the expected range of variation in analyte concentration are set in step 10; (b) Tissue phantom samples are selected for each sub-interval in step 18, and NRSEG values for feature pairs are obtained in step 15; (c) All NRSEG values are normalized according to the weights corresponding to the feature pairs, computed or obtained in step 20, and the normalization is performed for all feature pairs. Non-monotonic NRSEG values according to monotonically changing concentration values may be excluded.

Thereafter, (d) for each sub-interval, a regression line is generated in step 40, where the normalized NRSEG values are plotted against known analyte concentration values. Optionally, for each feature pair, NRSEG values that are outliers, as described above, may be excluded. The slope of the regression line is also computed in step 40; (e) The regression lines (curves in general) are concatenated in step 50, over all sub-intervals, to obtain a concatenated or a composite projector curve.

Then, (f) the points discontinuity in the concatenated or composite curve, as described above, are determined at step 60; (g) The composite curve is partitioned into analyte (e.g., glucose) concentration intervals, according to each point of discontinuity. This may yield one, if there are no discontinuities, or more (e.g., 3, 5, 9, 12, 15, 20, etc.) individual projector curves; (h) The individual curves may be flipped and can be parameterized in terms of analyte concentration boundaries, slopes, and Y intercepts.

Figure 86:
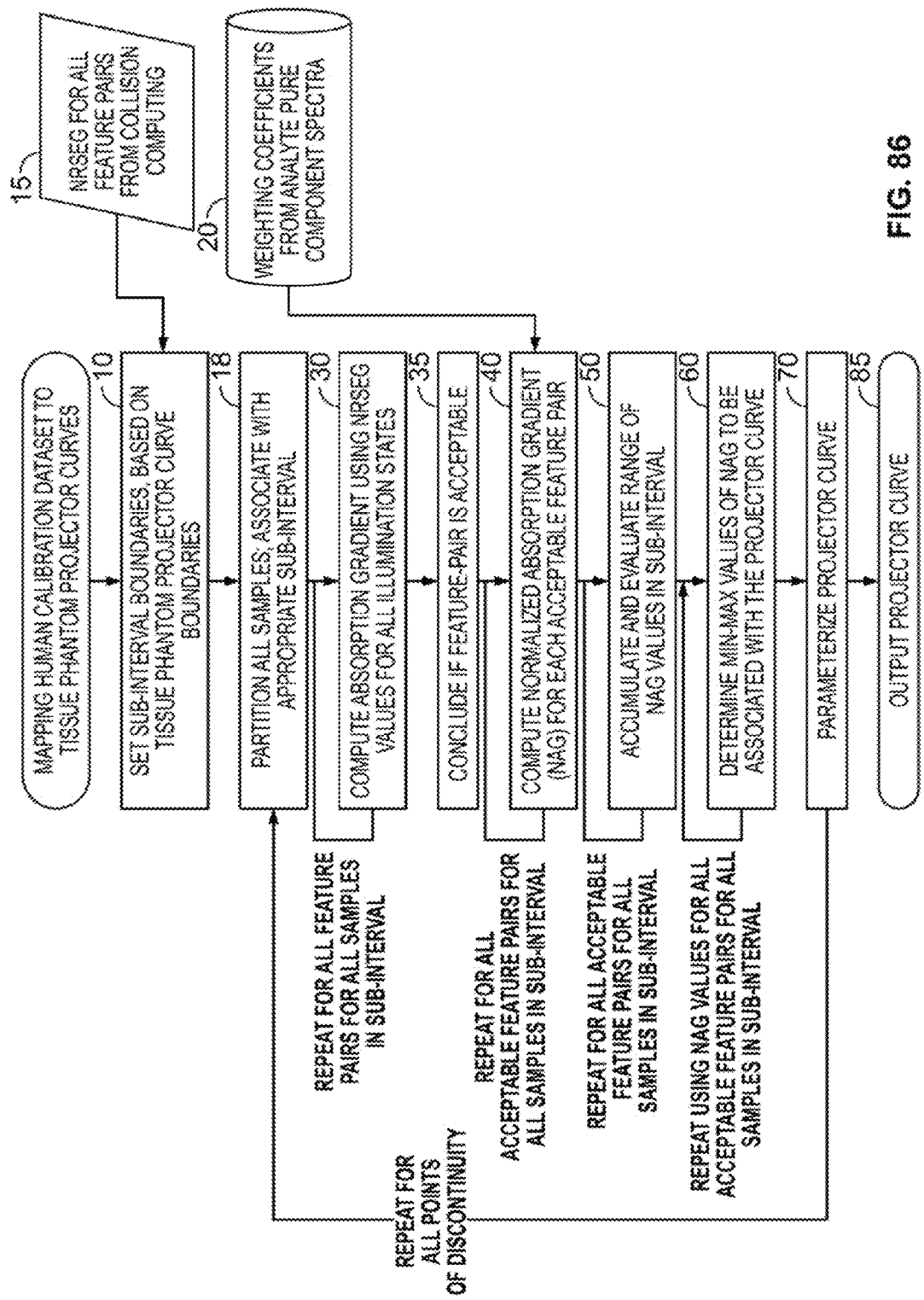
FIG. 86 shows the steps in the use of a human calibration dataset to complete the projector curve set design.

FIG. 86 summarizes the use of a human calibration dataset to complete the mapped projector curve set design. In this process: (a) The boundaries set for individual projector curves using tissue phantom data and the process described above with reference to FIG. 85 are used to establish the piecewise sub-intervals for partitioning the human calibration data in step 10. These sub-intervals may or may not be related to the fixed sub-intervals of 10 mg/dl or 20 mg/dl that were used in the processing of tissue phantom data.

At step 15, the NRSEGs are computed via collision computing for all the feature pairs extracted from human tissue spectra for both GL and NO-GL features defining the pair. This is performed for all spectra acquired over the complete set of illuminations and for all replicates. The NRSEG are then partitioned into sets based on the boundaries established in step 10, on the basis of invasively collected reference blood glucose values. Some sub-intervals may not have any sample NRSEG values associated with them. As one example, the concentrations of 112, 113, 115, and 117 mg/dl may belong to a projector curve bounded by 110-120 mg/dl. The interval of a projector curve may be a multiple of 10 mg/dl.

Then, (b) an absorption gradient is computed for each feature pair for each sample for each interval in step 30 using the process described above. Feature pairs with a positive absorption gradient (i.e., monotonic values of normalized NRSEGs) are considered acceptable feature pairs; (c) The AGs of the acceptable feature pairs are further normalized at step 40, using the weighting coefficients obtained at step 20 from pure analyte component spectra. The same weighting coefficients that are used to compute normalized NRSEG for feature pairs in the tissue phantom calibration data can be used to compute NAG values for each acceptable tissue spectra feature pair;

Thereafter, (d) the NAG values for acceptable feature pairs for all spectroscopic samples associated with an interval are used to set the minimum and maximum range of NAG to be used in mapping human data with a particular individual projector curve; (e) The NAG bounds computed in step 60, over all intervals or projector curve boundaries define the relation between human tissue NRSEG and reference glucose concentrations used in the calibration tissue phantoms. A monotonicity check is performed at step 70 to ensure that acceptable feature pairs are valid. In summary, the NAG value is used to select the appropriate Projector Curve, and the normalized NRSEG value from Ring 2 is used to estimate the glucose level.

Universal Calibration

Since noninvasive measurement technologies do not employ a chemical reaction between glucose and a color-producing or electrical current-forming reagent as in conventional invasive blood glucose testing, these technologies generally require some sort of "calibration," i.e., establishment of a response factor that converts a measurement made by the measurement system into a glucose concentration result associated with a reference invasive method. Many conventional noninvasive techniques use an "individual" (or "personalized" calibration process) in which a response factor is calculated for each individual person making measurements with the technique. This conventional personalized calibration may require one or more blood glucose measurements using an invasive blood-based reference measurement—the "calibration factor" is typically calculated and retained by the instrument for that patient. Many of these conventional methods, owing to physiological variations in the patient over time, usually also require periodic recalibration to prevent errors.

Some known universal calibration techniques generally employ the multivariate techniques described above, but have typically not provided accurate, consistent, results. In general, these known techniques do not provide robust universal calibration. For example, a Mean Absolute Relative Difference (MARD) of 38%, which is generally considered to be clinically unacceptable, was reported by Lipson, et al. in "Requirements for Calibration in Non-Invasive Glucose Monitoring by Raman Spectroscopy," J. Diabetes Science and Technology, pp. 233-241, 3(2), 2009.

These known attempts at universal calibration appear to have relied on the stabilization of the sensor or measurement device hardware; physics or physiology-based measurement techniques for normalization; assisted blood perfusion in the tissues; sufficiency of the size of training, validation and cross-validation datasets; and empirical adjustments of the training error-minimization threshold, with limited success. One of the largest sources of variation among individuals with regard to tissue glucose measurement is skin thickness. As glucose is less than 0.1% of human tissue by weight, variations of skin properties generally produce changes in a spectroscopic signal much greater than the changes due to glucose concentration variations. Variances in a spectroscopic signal may be further exacerbated by thermal, mechanical, optical and contact variations. A glucose signal measured in skin typically comes from multiple tissue layers and from a mix of blood and interstitial fluid, with different skin layers having different concentrations of glucose and confounders.

Various known methods, due to their inability to reject variations in absorbance in the background signal from tissue, were often unable to see different quantities of glucose in two different skin samples as measurable changes of absorbance in the NIR spectrum. As a result, the apparent glucose concentration varied depending on the tissue site, with both variations of the location and over time. In general, it is recognized that linear approaches, such as multivariate techniques, have not provided an acceptable universal calibration.

Various embodiments described herein allow for a much more convenient and less error-prone approach by providing factory calibration or "universal calibration:" a measurement and calculation procedure that is sufficiently robust to allow analyte (e.g., glucose) measurements to be accurately made for virtually any person, without the need for any reference calibration measurements. To successfully compensate for variations in the composition and thickness of skin layers, the various embodiments herein can sense and adjust the calculation for each of these components in each layer. The collision-computing approach for non-invasive tissue glucose measurement described herein can achieve universal calibration as described below.

Figure 87A:
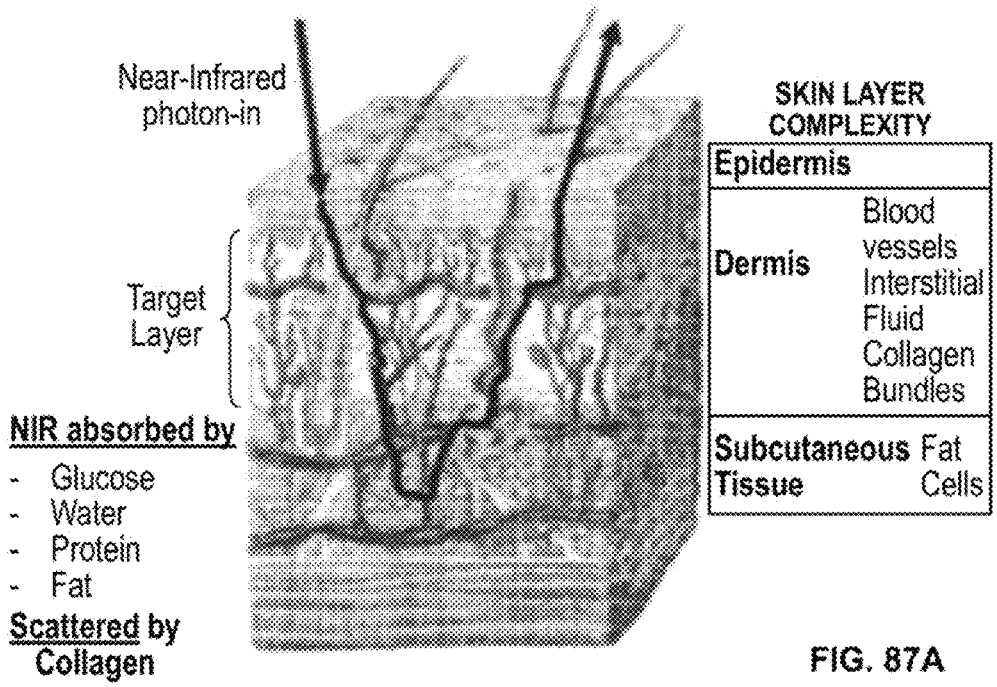
FIG. 87A shows the arrangement of the layers in human skin.
Figure 87B:
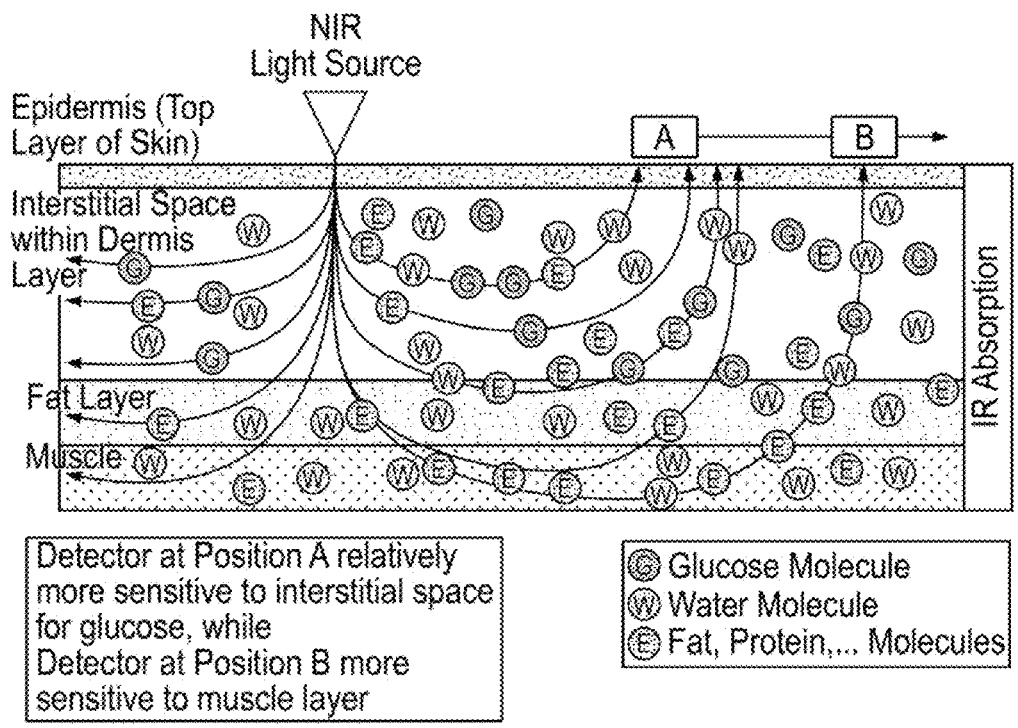
FIG. 87B shows the interrogation of different layers of skin with different source-detector distances.
Figure 88:
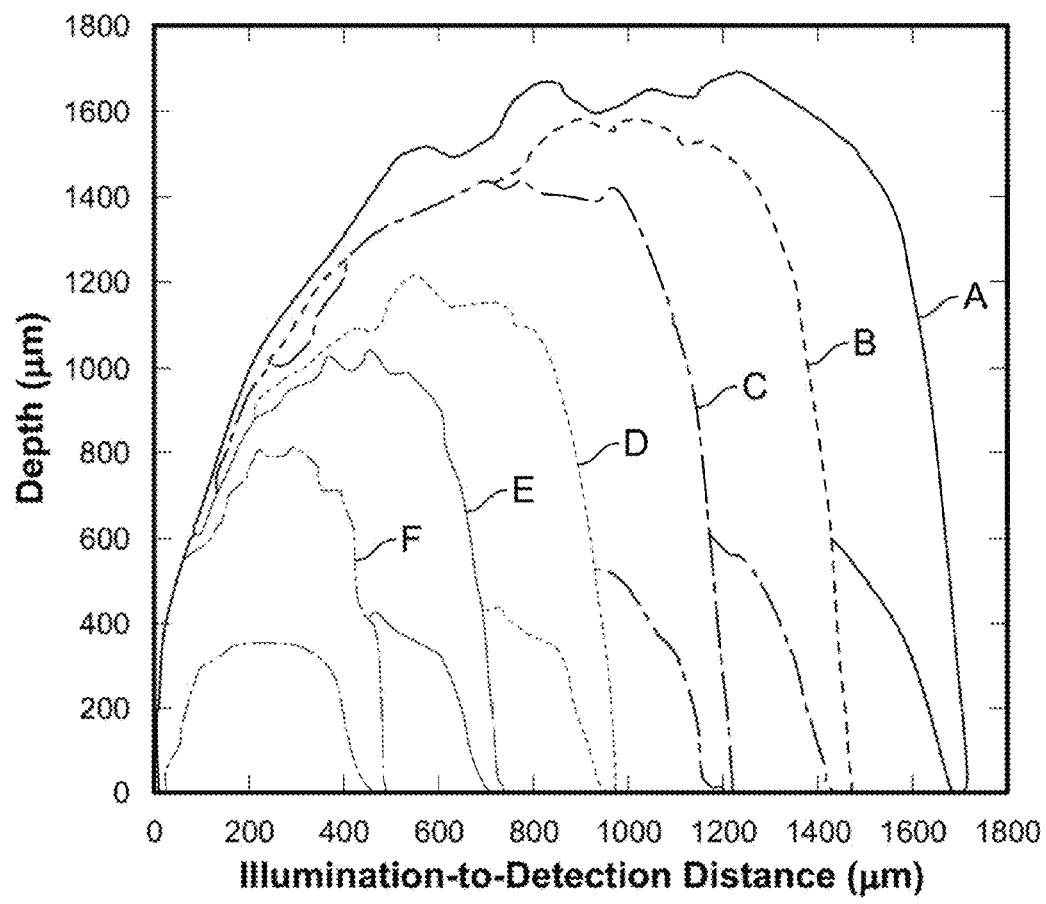
FIG. 88 shows the distribution of photons in tissue for varying source-detector distances.

Various embodiments for diffuse reflection, tomographic spectroscopic imaging (described below) utilize several photon travel path lengths and acquire NIR absorption spectra in different layers of skin tissue, as shown in FIGS. 87A and 87B, where the imaged layers have varying glucose concentrations. Spatial variation in the depths of tissue interrogated using different light path lengths (implemented by switching among different illuminator and detector distances) is shown in FIG. 88, with the associated mean paths shown in FIG. 89. FIG. 90 shows the differences between a subject with thin skin versus a subject with thick skin. Such embodiments of tomographic spectroscopic interrogation illumination system as described herein offers depth controllability below the skin surface as well as on the skin surface in x and y directions, thereby allowing a significantly improved subcutaneous tissue volume targeting.

As an example, there is a set of all $GL_{Fp}$ and $NO\text{-}GL_{Fq}$, features, where $p=1, \ldots, P$ and $q=1, \ldots, Q$, represent the total number of GL and NO-GL features as described above, extracted from spectroscopic acquisitions, and associated with subcutaneous tissue volumes of the simplified three layered skin tissue model of FIG. 87A (as shown in FIG. 68 or FIG. 70). Let this set be given by $EV_a(GL_p, NO\text{-}GL_{Fq})$, $DV_b(GL_{Fp}, NO\text{-}GL_{Fq})$, and, $SV_c(GL_{Fp}, NO\text{-}GL_{Fq})$, where epidermal (EV), dermal (DV) and subcutaneous tissue (SV) layers denote subsurface regions. These tissue regions interrogated during a tomographic sequence of illuminations are implemented in some embodiments via a fiber optical probe with a central detection system and rings of illuminators.

Let the rings Rt: $t=1, \ldots, T$ such that $T=A+B+C$ and $a=1, \ldots, A$, $b=1, \ldots, B$, $c=1, \ldots C$, represent the dominant photon travel paths through the epidermal, dermal and subcutaneous tissue layers respectively. Also, tissue volumes within EV, DV and SV may be further comprised of multiple volumes $EV_{a1}, EV_{a2}, \ldots, EV_{ax}$; $DV_{b1}, DV_{b2}, \ldots DV_{by}$; and, $SV_{c1}, SV_{c2}, \ldots SV_{cz}$, respectively (i.e., sub-layers), where each tissue layer is targeted by more than one illumination source and detection receiver combination or multiple rings targeting the same layer in the skin tissue. The total ring illuminations are then given by $T=X*A+Y*B+Z*C$. In such tomographic imaging, our computed differential energy absorption for an individual dermal volume compartment represented as:

$$DVb1(GLp, NO\text{-}GLq) | \forall \ EVa1(GLp, NO\text{-}GLq),$$
$$EVa2, \ldots, EVax(GLp, NO\text{-}GLq), \forall p,q \cup DVb2$$
$$(GLp, NO\text{-}GLq) | \forall \ EVa1(GLp, NO\text{-}GLq),$$
$$EVa2, \ldots, EVax(GLp, NO\text{-}GLq), \forall p, q$$
$$\cup DVby(GLp, NO\text{-}GLq) | \forall EVa1(GLp,$$
$$NO\text{-}GLq), EVa2, \ldots, EVax(GLp, NO\text{-}GLq),$$
$$\forall p,q \quad (27)$$

This expression represents an example estimator of glucose, as demonstrated in the glucose estimation results presented below, where the MARD value for a group of subjects was numerically less than 15%. The above expression is a representation of the net, renormalized spectral energy estimated through the collision process for different feature pairs in different rings. Given a design of the tomographic probe, this expression generally represents the total result set from all features over all illuminations. Computation of the net, renormalized spectral energy gain due to the analyte across different rings can be described by the above expression.

Figure 91:
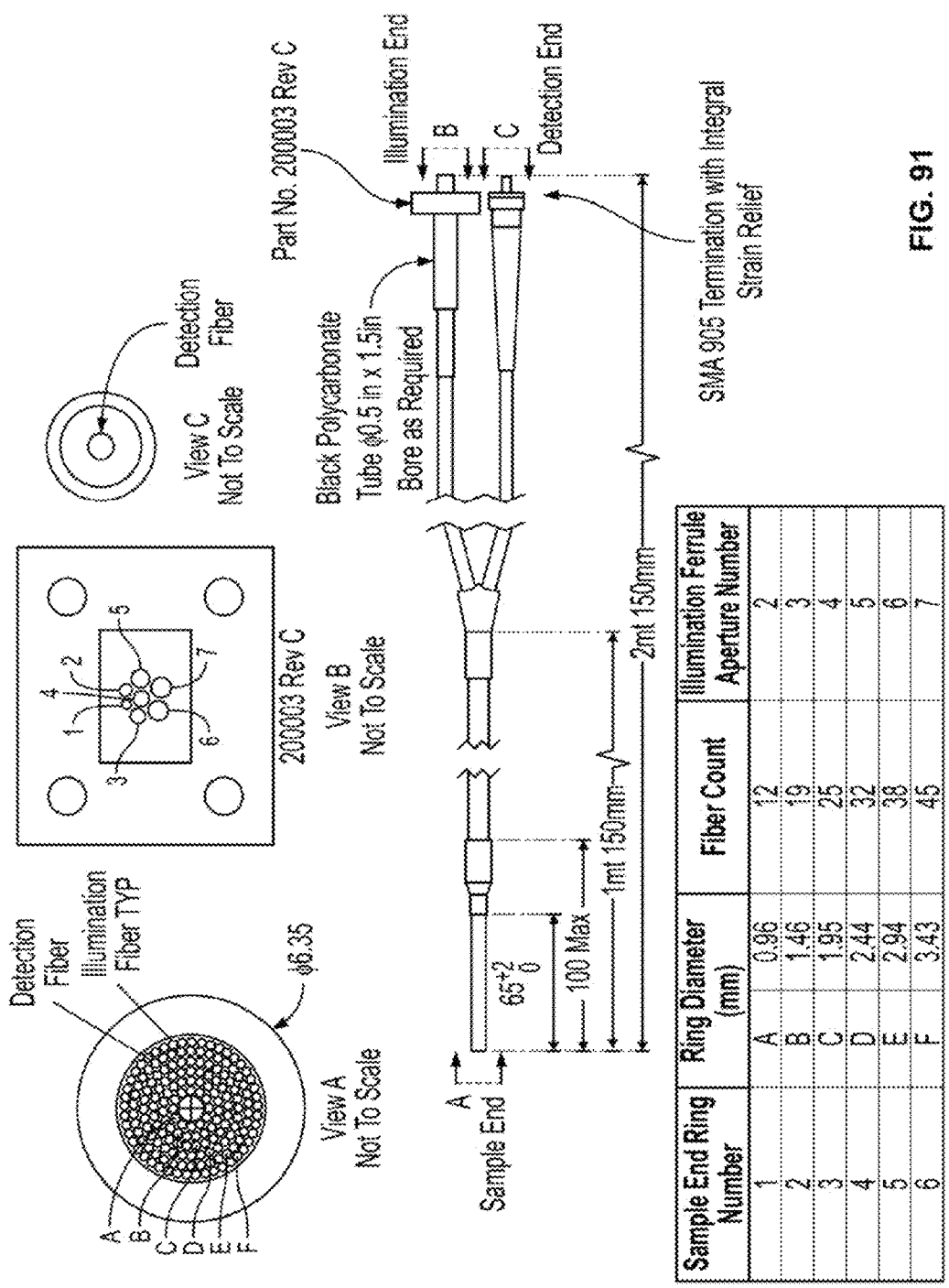
FIG. 91 shows a diagram of a probe with six illumination rings.
Figure 92:
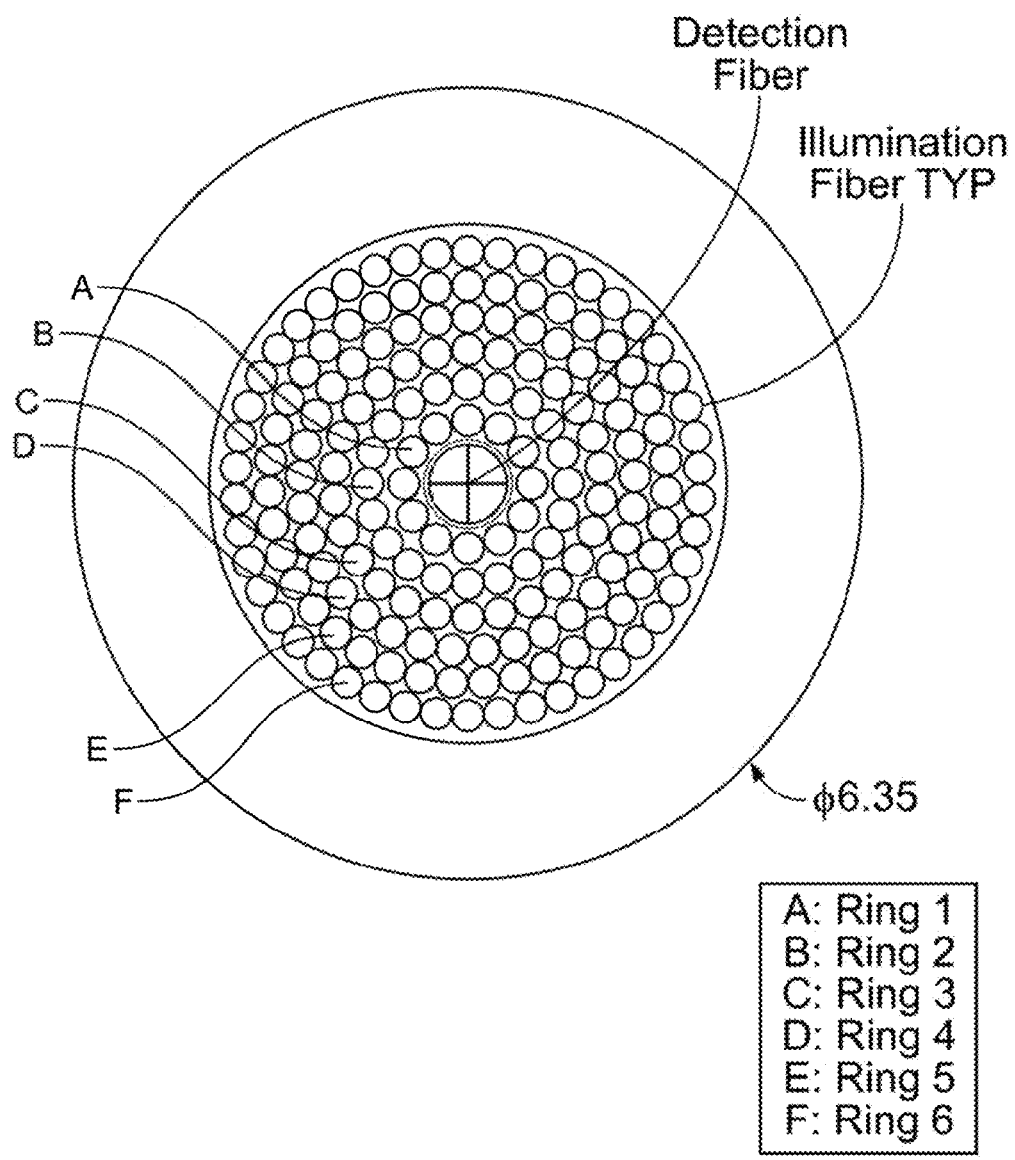
FIG. 92 shows an enlarged version of the probe from FIG. 91.
Figure 93:
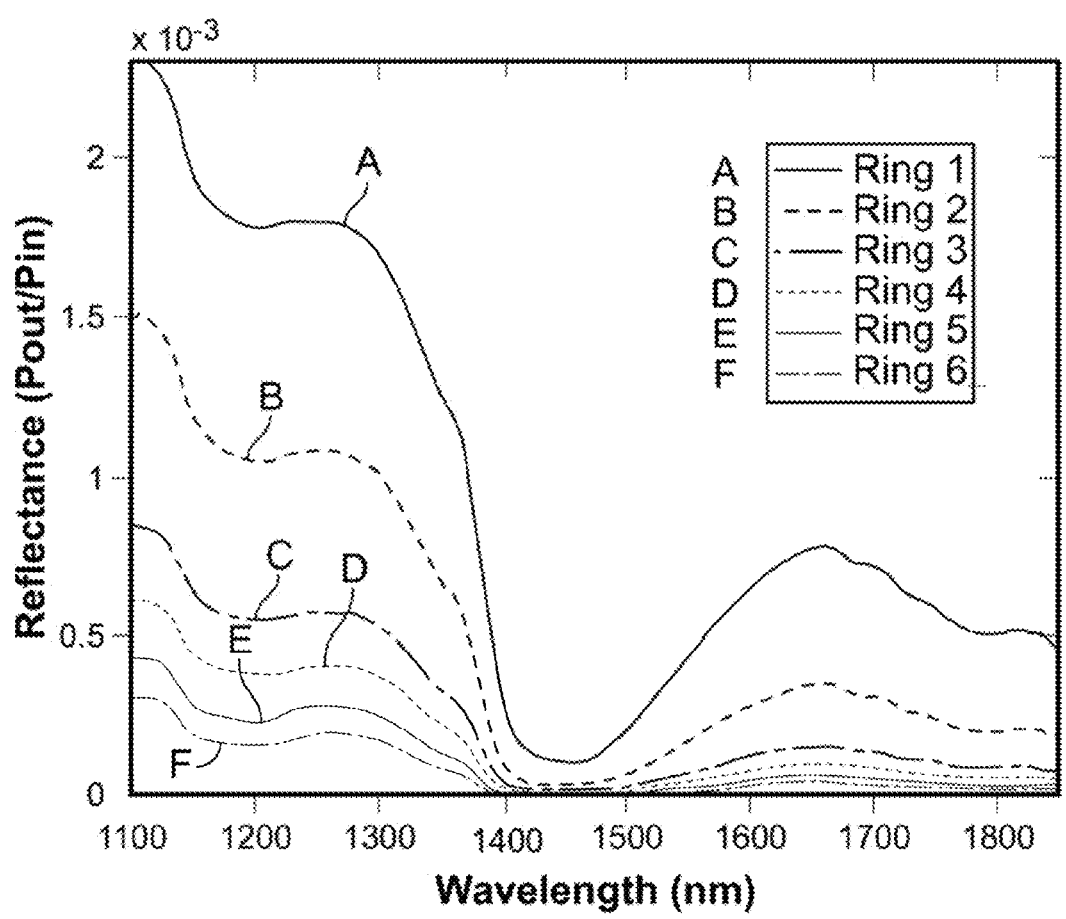
FIG. 93 shows spectra obtained for various rings of the probe in FIGS. 91-92.

The probe of FIG. 91, as detailed in FIG. 92, is designed such that targeting of different skin tissue layers by tomographic sequences $EV_{a1}, EV_{a2}, \ldots, EV_{ax}$; $DV_{b1}, DV_{b2}, \ldots DV_{by}$; and, $SV_{c1}, SV_{c2}, \ldots SV_{cz}$ can be verified based on examination of acquired spectra based on absorption of spectral bands known to be associated with biochemical compounds other than the analyte of interest, (such as by examination of intensity and absorbance amplitude profiles of the fat, protein and collagen bands as shown in FIG. 93 for different ring illuminations). Profiles of absorption gradients leading to the assessment of acceptable feature pairs is a function of the tomographic sequence and the results of the above expression, based on an anatomical and physiological understanding of skin tissue. The use of multiple illumination-detection pairs to target the same layer in the skin tissue, as described above (that is by increasing the tomographic states), can expand the glucose measurement capability and increase the ability of the system to compensate for male and female subjects with varying skin thickness, surface texture, and changes due to aging, gender, and/or ethnic differences.

Estimation and accumulation of the net analyte (i.e., glucose) spectrum (NAS) signal, $$\Delta \vec{e}_{(GL_{F_p}, NO-GL_{F_q}, Z_r, R_t)},$$

associated with a specific ring targeting some region of EV, DV or SV, through one or more repeated collisions between appropriately conditioned features (extracted from the spectroscopic data acquired during a multiple illumination tomographic sequence) and the Zyoton waveforms, combined with a renormalization step can offset and compensate for interference due to clutter and scattering losses during the propagation of light injected into the skin during each tomographic illumination. Varying tissue volume targeting through the tomographic spectroscopic imaging process described above allows the collision-computed energy change values, given by the expression t,? , to represent a robust estimator (an information measure) for the net analyte signal (NAS) contribution due to glucose, or an analyte, in general. Even though it is extremely difficult to replicate the sampling conditions during estimation to be the same as the sampling conditions during collection of calibration data, especially as the skin location and composition can change each time contact is made, tomographic imaging and collision-computing measurement of the NAS allows for universal calibration.

The process of Absorption Gradient (AG) normalization described with reference to FIG. 82 to compute NAG for the purposes of selecting an individual mapped projector curve, and the associated computation of NAG, can enhance the accuracy of non-invasive estimations on uncharacterized human subjects by compensating for physiological and tissue differences from the calibration subjects. This is achieved, at least in part, by weighting the differential absorption from each acceptable feature pair drawn from different regions of the acquired spectrum during a tomographic spectroscopic sequence of measurements that compensate for variations in subject- and site-specific physiological and biochemical composition.

While it is an important step for delivering universal calibration in an embodiment using collision computing with multiple features, the computation of $\overline{NAG^*}$ is not required for embodiments using only a single feature. Normalization of the absorption gradient provides a more robust mechanism for aggregating NAS estimates from different parts of the spectrum as different subjects present tissues with different levels of confounders, which can degrade the SCR to unacceptable levels. Computation of $\overline{NAG^*}$ can reduce uncertainty if SCR is degraded, and provide a more robust estimation of glucose.

The Projection process described with reference to FIG. 78, by referencing an estimate of NAS obtained through the collision computing processes on data acquired using tomographic spectroscopy, to the glucose energy absorption measured by synthetic tissue-phantoms prepared using known concentration of glucose, allows for universal calibration, such that estimates with a MARD accuracy below 15%, even in the case of measurement of uncharacterized subjects who were not part of any training or calibration set, can be obtained. The equivalence of the net, renormalized spectral energy gain due to glucose in skin tissue of any individual subject, by creating equivalence of the same level of energy absorbed due to glucose presence in a tissue phantom, also helps to filter variations in human subject measurements.

Tomographic spectroscopy using a number of illumination and detection elements and optional repeat sequences, followed by collision-computing processes with renormalization of post-collision results to obtain a glucose NAS signal estimate, then followed by a projection process, can achieve universal calibration in human non-invasive glucose measurement in various embodiments.

Figure 94:
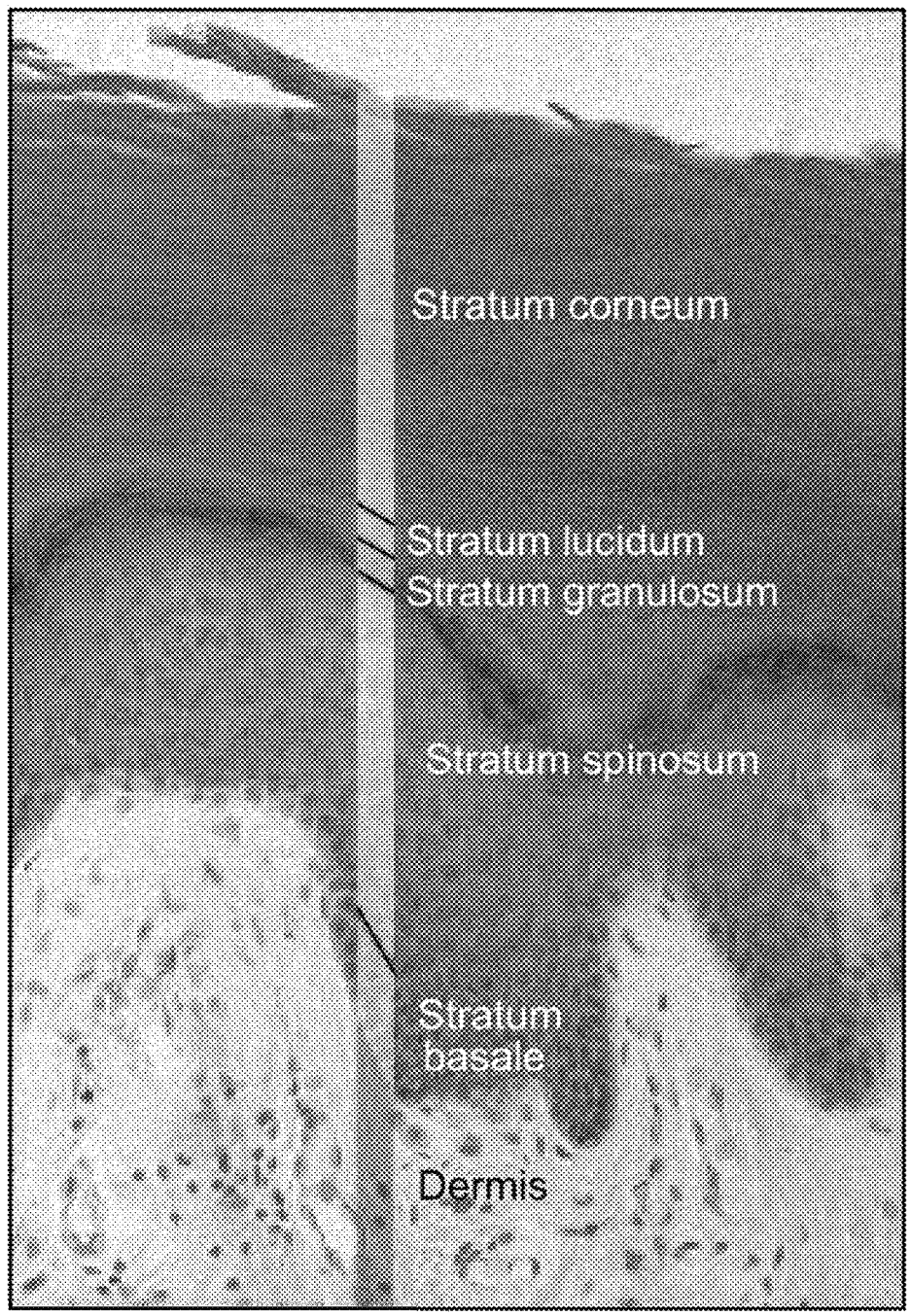
FIG. 94 is a detailed zoom-in into sublayers of the epidermis.

In some embodiments, for the detection and/or quantitation of analytes that are primarily present in what may be called "sublayers" of tissue (as shown in FIG. 94), a detector geometry with resolution of source-detector distances finer than the detector geometry shown for a glucose embodiment in FIG. 69, can be used to differentially interrogate those sublayers. Some examples include: detection of the presence of cross-linked collagen or other proteins that accumulate in tissue as the result of glycation of the proteins from hyperglycemia in diabetes, or in estimation of increase in lactate concentration that is a marker for detecting onset or progression of sepsis, or in monitoring the occurrence or progression of melanomas or other skin lesions. Materials related to these conditions are generally known to be present in varying amounts in different sublayers of the epidermis known as the stratum corneum, stratum lucidum, stratum spinosum, stratum granulosum, and stratum basale, as shown in the section in FIG. 94. Their concentration can be determined using the collision computing methods described here.

In various embodiments, optically targeting specific tissue regions using tomographic analysis is accomplished by optimizing the illumination and detection dimensions for the sublayer tissue volume of interest. For example, to target various layers of the stratum corneum and epidermis, the illumination-to-detection distance are optimally smaller than approximately 0.5 mm and the separation of adjacent illumination-to-detection distances are optimally less than 100 µm. In addition, due to skin layer thickness and composition differences between measurement locations and individuals, it is beneficial to have a number of distinct illumination-to-detection distances that enable adaptation to anatomical variations of skin.

Figure 95:
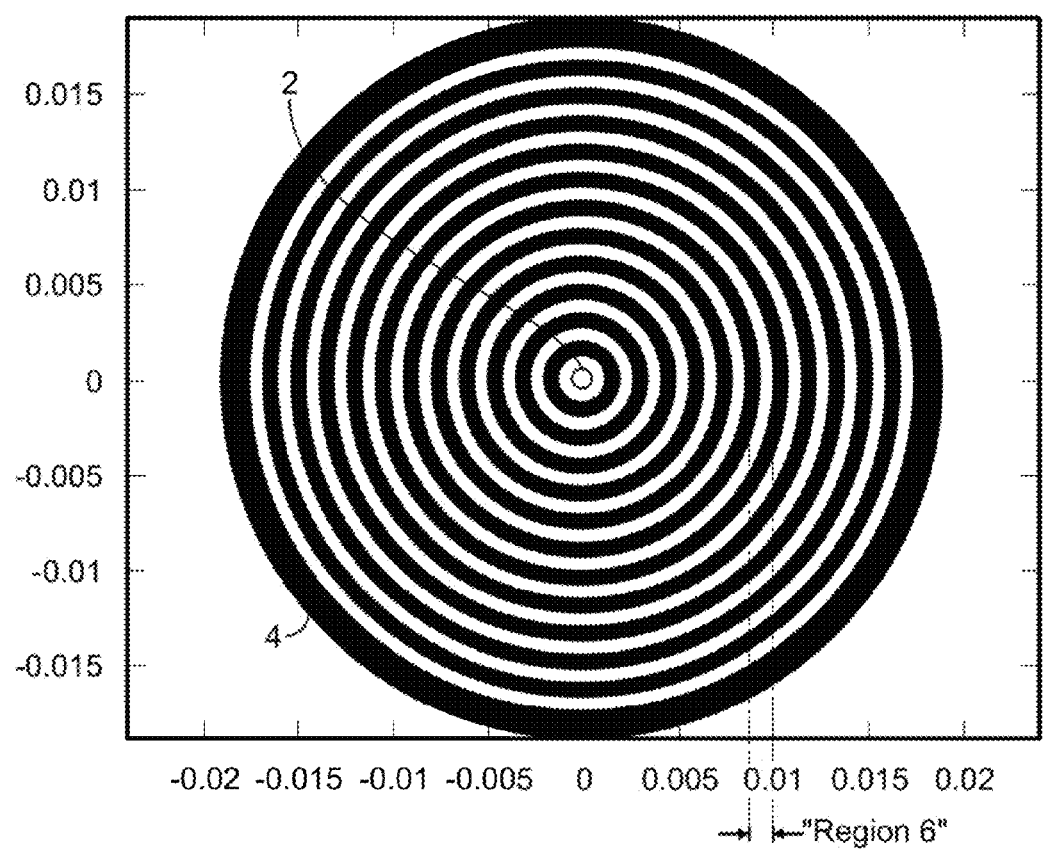
FIG. 95 shows a concentric ring based tomographic detector for sub-skin targeting.

For example, FIG. 95 represents a two-dimensional optical skin illumination and detection interface with a single 10-µm diameter illumination area, 2, and twelve annular collection regions, 4, each approximately 10 µm in width. The detection regions are separated from each other by a minimum of 5 µm and the angle of collected light is limited to ±45 degrees by the collection optics. The narrow illumination and collection widths support volume targeting by limiting the distribution of illumination-to-detection distances to a maximum range of ±20 µm, and the close proximity of the detection regions to the illumination area enables collection of relatively shallow penetrating light.

The use of twelve different annular detection rings, in the tomographic detector shown in FIG. 95, allows the optical probe to apply to a wide range of skin types and characteristics, and that the region of interest can be optically sampled in a number of measurements. The embodiments for glucose measurements described above generally require monotonicity over a set of three rings for all samples, but other embodiments may optionally use different combinations of rings to establish monotonicity. Fewer or more than 12 rings can be used in different embodiments.

Figure 96:
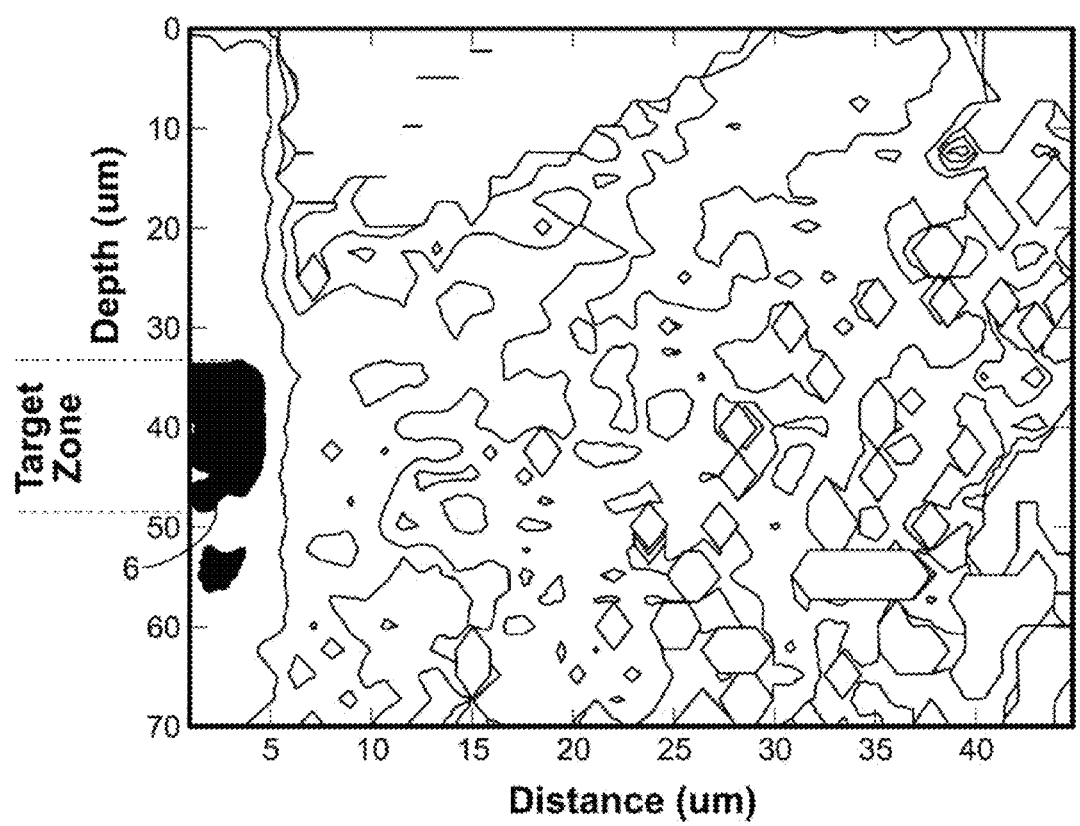
FIG. 96 illustrates targeting a 20μ thickness section sublayer between 35μ and 55μ depths.

A Monte Carlo simulation of skin tissue was performed with the optical probe shown in FIG. 95. A plot of the absorbance versus tissue depth and distance from the point of illumination for the first annular ring is provided in FIG. 96. In FIG. 95, light is launched downward into the skin within a circle 2 at the origin (the center of the illumination area) and diffusely reflected light is collected from the sixth circular ring from the center, delineated as "region 6" in FIG. 95, and spanning the distance 90-100 µm from the center. The darker regions of the plot in FIG. 96 represent higher levels of light absorption and indicate that a very specific volume of tissue is predominantly interrogated between 35 and 50 µm below the surface of the skin. The light absorption in the darker target zone 6 in FIG. 96 is 61.4% per unit volume higher than in the surrounding tissue.

Figure 97:
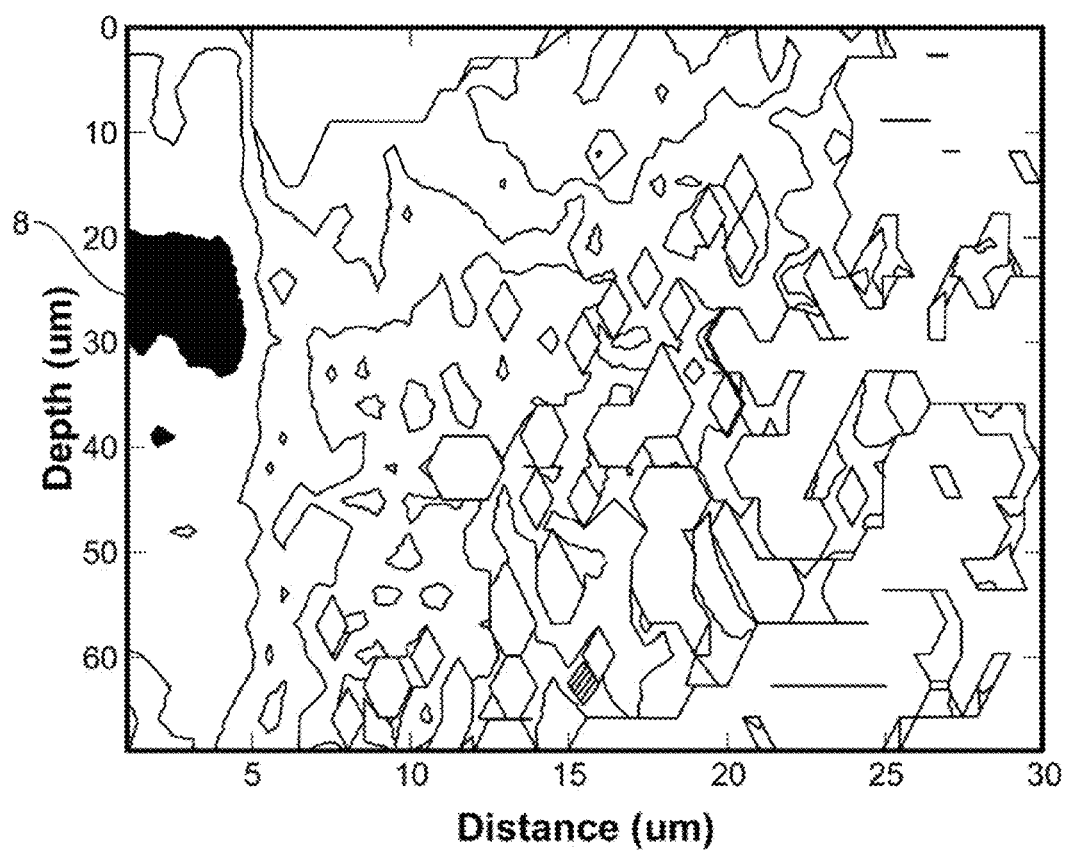
FIG. 97 illustrates targeting a 10μ thickness section sublayer between 20μ and 30μ depths.
Figure 98:
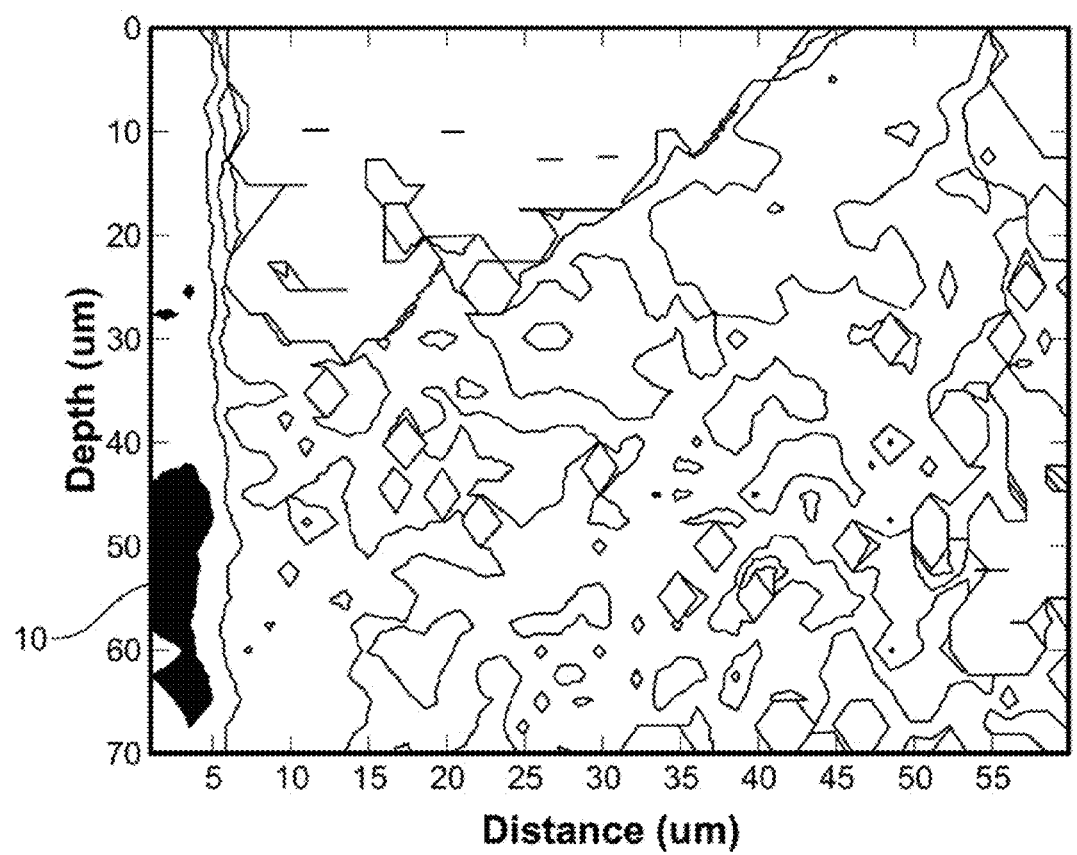
FIG. 98 illustrates targeting a 25μ thickness sublayer section between 45μ and 70μ depths.

Similarly, FIG. 97 shows the distribution of photonic absorption for the second annular ring with depth of the sampled tissue volume 8 being between 20-30 µm, and the light absorption in the darker target zone of FIG. 97 is 49.3% per unit volume higher than in the surrounding tissue. A final example is provided in FIG. 98 and indicates that the third annular ring is predominately sampling a tissue volume 10 between 45 and 70 µm below the skin surface. The light absorption in the darker target zone in FIG. 98 is 37.8% per unit volume higher than in the surrounding tissue.

Thus, a particular ring or a group of rings can target a specific sublayer of the skin, to facilitate quantitation of an analyte expected to be present in that sublayer. In some embodiments, such quantitation may require computation of absorption gradient(s) across a number of sublayers, e.g., sublayers above and/or below the particular sublayer in which the analyte is expected to be present. The additional sublayer(s) across which the absorption gradient is computed can be but need not be adjacent to each other and to the particular sublayer in which the analyte is expected to be present. Thus, absorption gradient may be computed across two or more sublayers where at least one intervening sublayer that is not used in the computation of the absorption gradient may be present between a pair of sublayers that are used in such computation. To facilitate such computation, more than one illuminator/detector rings can be illuminated according to a selected sequence, generally called an illumination sequence. As used herein, illumination sequence may represent either or both: a sequence according to which the illumination rings are illuminated, and a sequence according to which the detector rings are activated for detection.

Other specific tissue regions, for instance, separation of the papillary dermis from the reticular dermis for detection or measurement of other analytes, may be optically sampled by further adjusting the widths of the annular rings or restricting the illumination launch angle or the range of collection angles. In the example of the epidermis, targeting a shallow tissue volume, the detection angle may be restricted to between 22.5 and 67.5 degrees relative to and facing the area of illumination via an optical lens.

In summary, tomographic spectroscopy in conjunction with a non-linear collision computing processes is used to compensate for variations among individuals (and in a single individual over time) of the major variables in tissue glucose measurement (skin thickness, skin color, and most variations in subsurface anatomy and physiology). Calibration techniques for glucose measurement established with the process described herein, and with analyte concentrations determined using different embodiments of the projection system described above, rather than being specific for an individual, apply universally to almost all people with different, age, gender, and ethnicity. Thus, for essentially everyone, accurate glucose (and other analyte) measurements can be obtained without the need for a personalized calibration procedure or the periodic recalibration that has been needed for many other known or suggested noninvasive techniques.

Glucose Results Using Universal Calibration

Figure 99A:
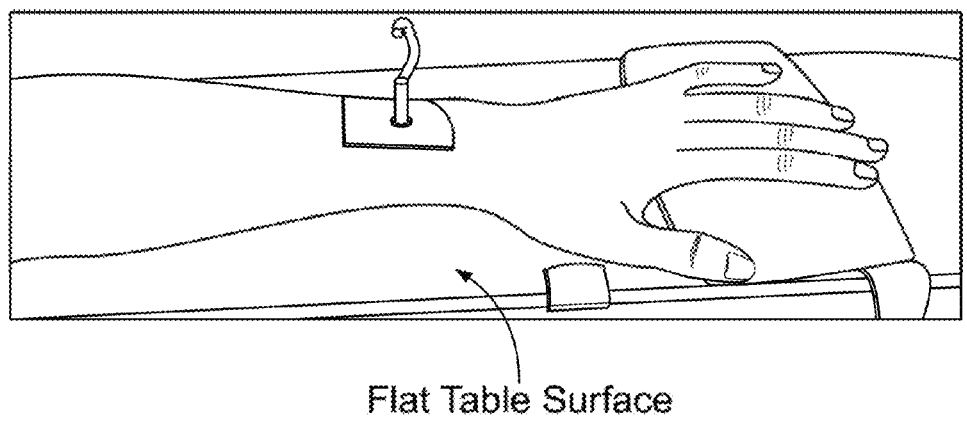
FIGS. 99A and 99B show two portions of the patient interface to a measurement probe.
Figure 99B:
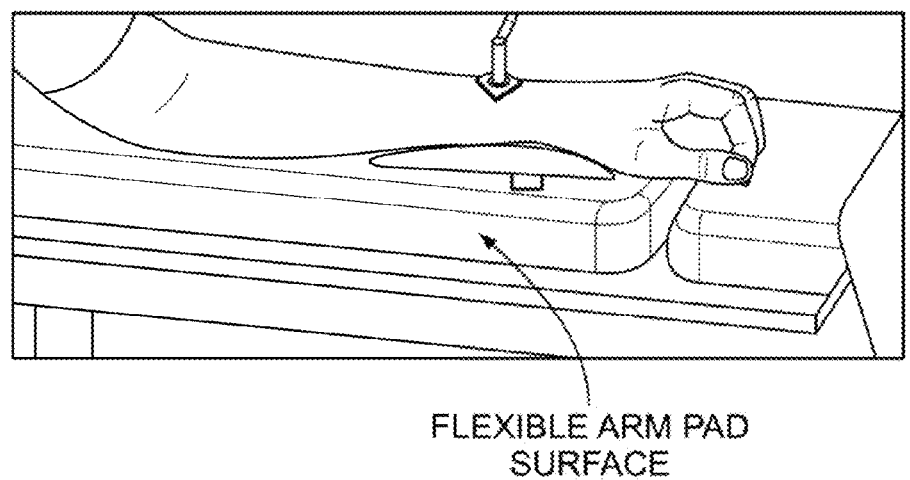

In some examples, a universal calibration was initially established with tissue phantoms having known glucose concentrations, as described above, and three human subjects with measured reference glucose values. The results shown with reference to FIGS. 100 through 103 were obtained (as shown in FIGS. 99A-B) using this calibration for 9 subjects (whose measurements and data were not included in the calibration process), with no adjustments or variations in the calibration for any of the subjects. The agreement shown for the 9 subjects indicates that the universal calibration developed produced acceptable agreement with reference measurements for all the subjects.

In various embodiments, the concentration of the analyte and, optionally, other results derived from data-analytic processes, may be displayed on a display device and/or may be stored in a database for subsequent communication to a user, and/or further processing. For example, the estimated glucose values may be used for personalized insulin dosing decision, insulin bolus optimization, insulin sensitivity, insulin resistance, glycemic resistance, glycemic response determination, hypo- and hyperglycemia monitoring, and metabolic health assessment. These use-cases are relevant to people with Type 1, Type 2, or gestational diabetes; people with prediabetes, and consumers interested in wellness measurements.

To summarize the entire projection process, calibration projector curves, (as detailed above) which are used to translate the estimated collision-computing changes derived from the resulting waveform due to a quantity of the analyte, are generated or obtained in step 16 of FIG. 13. For example, in the case of a non-invasive glucose measurement, calibration data is generated in two steps. In the first step, a series of in-vitro experiments are performed whereby different, known concentrations of the analyte of interest are provided in tissue phantoms which are spectrally imaged using the same hardware and process as used for analyzing the analyte in human subjects. The spectra from these tissue phantom samples are processed by the collision computing process to show that the resulting, computed spectral energies are monotonic to the concentration of the analyte. When monotonicity is achieved by refinements of the components of the collision computing process, a projector curve set is generated representing concentration (as the independent variable) and spectral energy (as the dependent variable).

In another data set, a series of measurements are made on one or more human subjects, where tissue spectra are acquired along with measured reference glucose values. Noninvasively measured energy change values are then computed which correspond to the reference glucose measurements. The conditioning and collision processing for non-invasively acquired spectra is the same as that used for processing spectral data from tissue phantoms. If monotonicity of the computed net, renormalized spectral energy gain values in relation to the reference concentration values is not achieved, the processing of the spectral data is further refined by one or more of modification of Zyotons, carrier kernels, collision-computing parameters, number of collision iterations, selection of frequency components in the spectral energy computation, and changes to the collision operator between collision iterations. One or more of the entities and/or parameters are revised to achieve a monotonic relationship between spectral energy and analyte concentration. Once monotonicity has been achieved, the human tissue spectral energy levels are projected or recast in terms of energy absorptions levels observed from the synthetic medium (e.g., tissue phantom), as described above.

Spectra Acquisition

Figure 104A:
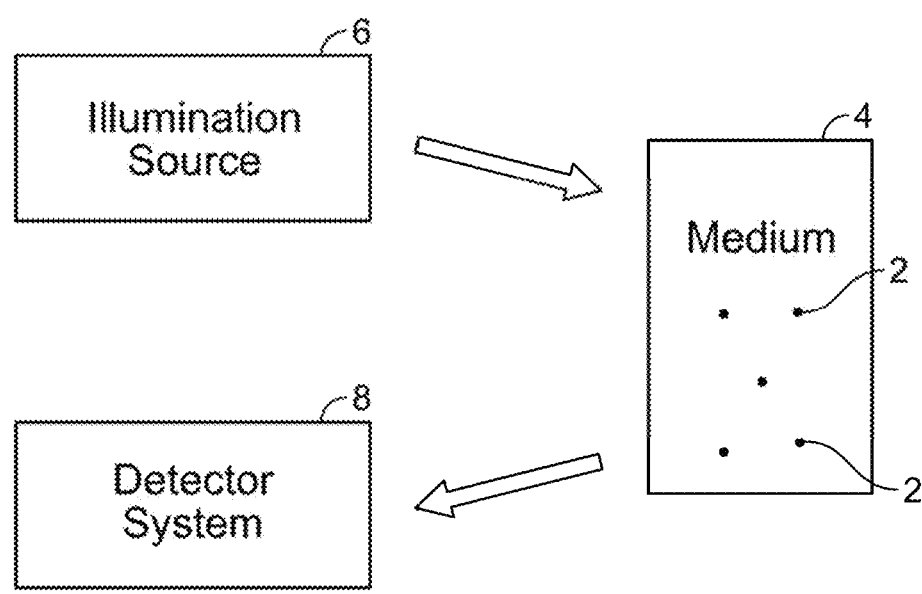
FIG. 104A schematically depicts an illumination/detection system for directing radiation to a medium and receiving radiation reflected therefrom, for analyte detection/quantification, according to one embodiment.
Figure 104B:
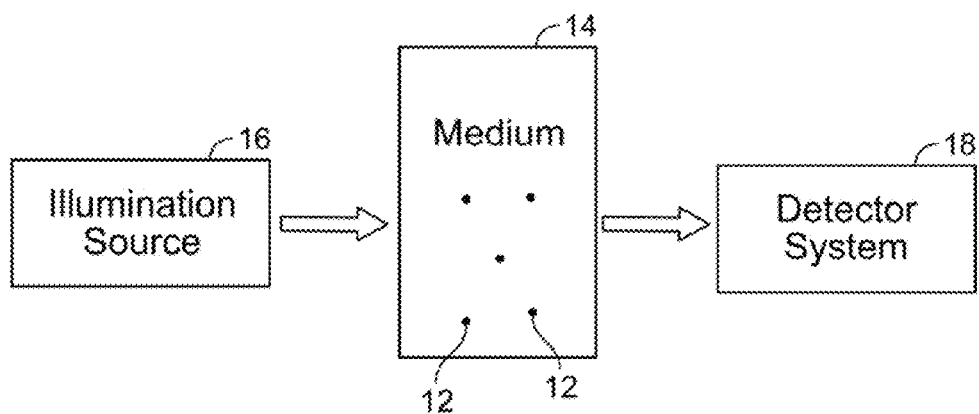
FIG. 104B schematically depicts an illumination/detection system for directing radiation to a medium and receiving radiation transmitted therethrough, for analyte detection/quantification, according to one embodiment.

With reference to FIG. 104A, a spectrum acquisition system used for the detection and/or measurement of an analyte of interest 2 in an in-vivo or an in-vitro medium 4 typically includes an illumination source 6 for illuminating the medium 4 with NIR. The system also includes a photodetector 8 for detecting the attenuated reflected photons, FIG. 104A, or the transmitted photons, FIG. 104B. An MIS may be employed by the illumination source 6 to acquire a set of spectra reflected from varying depths of the medium 4 to estimate the analyte of interest 2. In one embodiment, NIR radiation in the wavelength range from about 1,000 nm to about 1,700 nm is used to illuminate the medium 4.

The output of the spectral acquisition process is a series of NIR diffuse reflectance spectra represented as intensity vectors on a wavelength axis spanning the spectral bandwidth of the acquisition system. A reference intensity measurement is acquired for each illumination in the MIS using a diffuse reflectance standard, and these reference measurements are also represented as intensity spectra on the same wavelength axis as the reflectance spectra obtained from the medium 4. National Institute of Standards and Technology (NIST) certified Diffuse Reflectance Standards are used in some embodiments to calibrate the reflectance measurement of the system. These standards are chemically inert, with typical reflectance values ranging from 2% to 99%, and are spectrally flat over the NIR spectrum to +/−4%. A specific example of a standard used is a Spectralon® Diffuse Reflectance Standard—which is highly Lambertian, with Spectralon® SRM-99 reflectance material being a good Lambertian reflector for use over the wavelength range from 250-2500 nm.

Some embodiments utilize a Fourier transform near-infrared (FTNIR) spectrometer (an interferometer) as a processor of spectral NIR radiation to illuminate skin. In near-infrared spectroscopy, NIR radiation is passed into a sample. Some of the radiation is absorbed by the sample and some of it is either reflected (reflectance, FIG. 105B) or passed through (transmittance, FIG. 105A). The resulting spectrum represents the ensemble molecular absorption or transmission, creating an overall molecular fingerprint of the sample if the sample is a pure material. In an FTNIR implemented using a Michelson interferometer (FIGS. 105A-105B), light from the polychromatic near-infrared source, such as a halogen lamp, is collimated and directed to the interferometer. Interferometers typically employ a beam splitter which takes the incoming infrared beam and divides it into two optical beams. One beam reflects off of a flat mirror which is fixed in place. The other beam reflects off of a flat mirror which is attached to a mechanism which allows it to move a very short distance (typically a few millimeters) toward and away from the beam splitter. The two beams reflect off of their respective mirrors and are recombined when they meet back at the beam splitter. Because the path that one beam travels is a fixed length and the other is constantly changing as its mirror moves, the signal which exits the interferometer is the result of these two beams "interfering" with each other as the mirror moves. The resulting signal is called an interferogram (2 in FIG. 106) which represents the Fourier transform of a spectrum.

Figure 106:
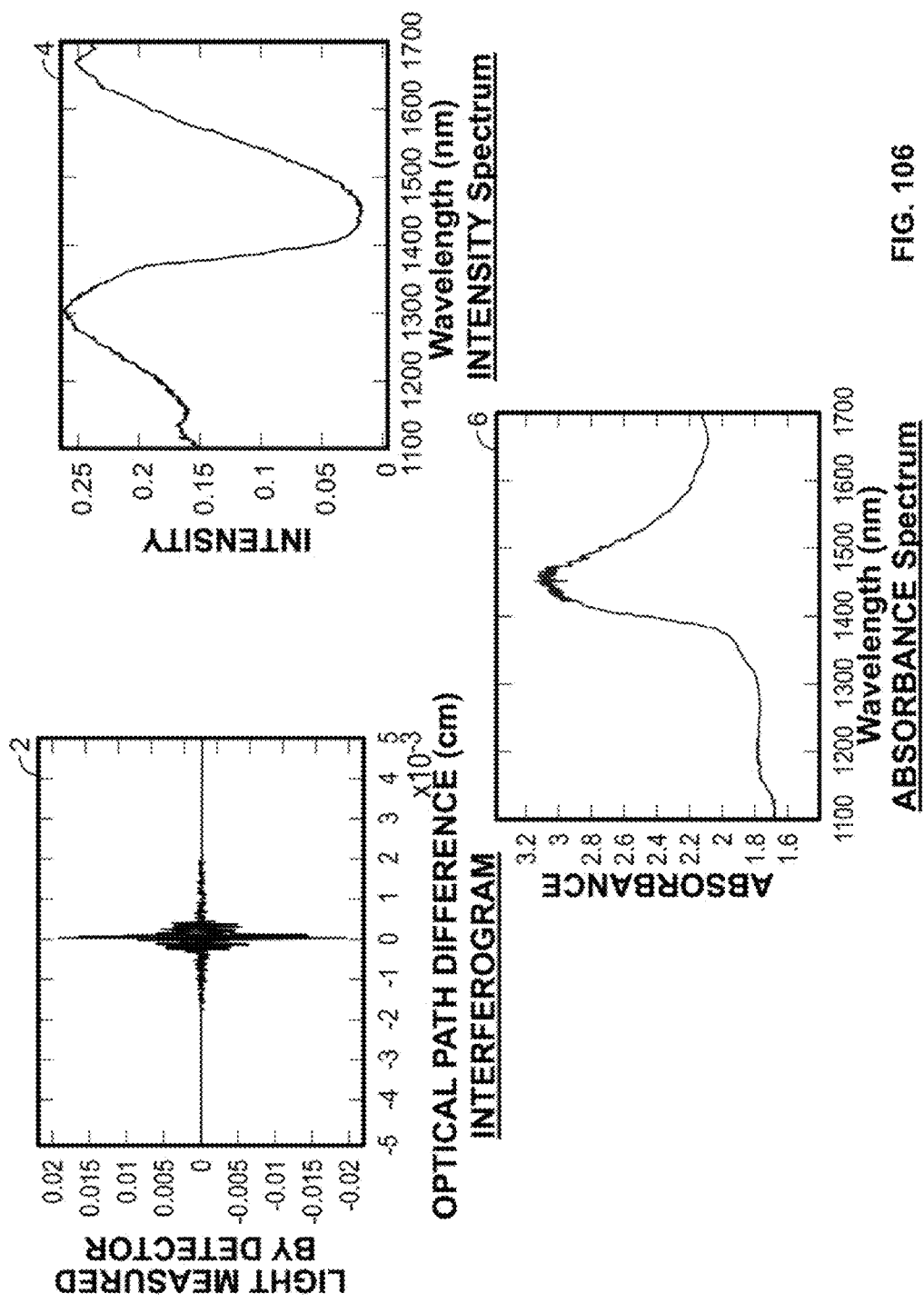
FIG. 106 depicts an example of an interferogram obtained from one embodiment of an illumination/detection system, a corresponding intensity spectrum, and a corresponding absorbance spectrum, for use in analyte detection/quantification.

About 50% of the light may be directed towards the fixed mirror and about 50% may be transmitted towards the moving mirror. Light is reflected from the two mirrors back to the beam splitter and passes into the sample compartment. There, the light is focused on the sample. The difference in optical path length between the two arms to the interferometer is commonly known as the retardation. An interferogram is obtained by varying the retardation and recording the signal from the detector for various values of the retardation. The form of the interferogram when no sample is present depends on factors such as the variation of source intensity and the splitter efficiency with wavelength. This results in a maximum at zero retardation, when there is constructive interference at all wavelengths, followed by series of wiggles, as shown in FIG. 106. When a sample is present, the background interferogram is modulated by the absorption bands in the sample.

Figures 105A, 105B:
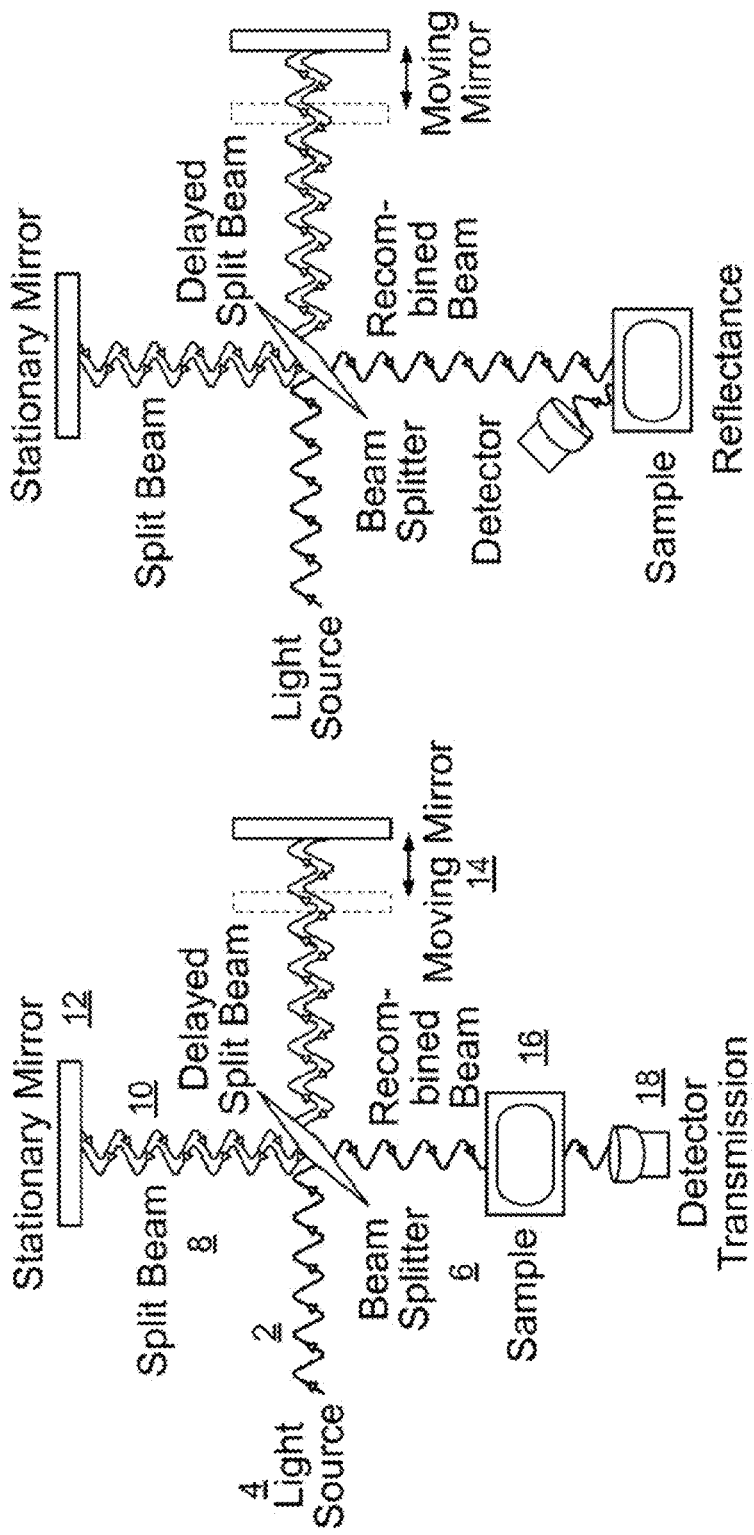
FIGS. 105A and 105B depict Michelson-type interferometers used, respectively, for transmission and reflectance measurements.

FIG. 106 depicts a typical interferogram 2 that may be acquired using a Fourier transform near-infrared spectrometer (such as of FIG. 105B). The waveform 4 represents the corresponding intensity spectrum along the wavelength axis after taking the inverse Fourier transform of the interferogram, and the waveform 6 represents the corresponding absorbance spectrum along the wavelength axis after dividing the intensity spectrum by the appropriate reference or background spectrum. In some embodiments, in order to extract the desired spectral features (step 4 of FIG. 37), each acquired intensity spectrum on the wavelength axis is transformed to a corresponding spectrum on a wavenumber axis.

Wavenumber units can be denoted by $(wn_s(k), k: 1,2 \ldots N_s)$ and wavelength units by $(wn_r(k), k: 1,2 \ldots N_r)$. The units can be interconverted using the relations:

$$wn_r(k) = \frac{10^7}{\text{wave}_r(k)} \forall k \tag{28}$$

$$wn_s(k) = \frac{10^7}{\text{wave}_s(k)} \forall k \tag{29}$$

The absorbance spectra may be displayed on the wavelength axis or the wavenumber axis. Several features are extracted from the each of the acquired absorbance spectra acquired during an MIS.

Feature Standardization, Deconstruction, and Conditioning

The preparation of spectral data acquired during an MIS for downstream analysis using collision computing entails two sub-processes, each with several steps. The two sub-processes in some embodiments are: (i) Feature Standardization, Extraction and Complementary Pairing; and, (ii) Feature Conditioning. In various embodiments, feature standardization, extraction and complementary pairing involves the following five processing steps:

Step (i) Spectrum standardization is performed prior to extraction of spectral features, and applied to the entire spectrum in the intensity space. The standardization computation depends on the dynamic range of the spectral sensor. Analog-to-digital converter (ADC) dynamic range and gain coefficients may be set such that when the maximum available radiation is directed to the medium, the detected peak intensities over the spectral bandwidth (wavelength range) are adjusted to be 80% of the full dynamic range. The illumination source 6 in FIG. 104A includes a number of emitters arranged in concentric rings (as shown in FIG. 69), and the emitters in one or more rings can be turned ON selectively. In some embodiments, maximum radiation can be directed to the medium by turning ON all rings simultaneously.

Step (ii) The intensities detected in response to other, less than maximum illuminations (e.g., illumination of one or more but not all rings in the illumination source example described above), are then normalized with respect to the intensity detected when maximum radiation is directed to the medium. Applied gain settings may be adjusted using a software interface. The sensor firmware gains are set such that the signal-to-noise ratio is maximized, as estimated near the mid-point of the bandwidth, e.g., at 1,350 nm. In some embodiments, an additional standardization step involves checking for the wavelength (or x-axis) consistency. This can be implemented by using a rare-earth oxide or other known material as a reference, using a peak in its absorbance spectrum to align the wavelength axis.

Step (iii) Background correction generally involves subtraction of dark current response, both from the spectra acquired during illumination of the medium to be tested and the reference spectrum for each illuminated sequence in the MIS. The dark current over the sensor bandwidth can be determined by measuring the detector output when it is not actively experiencing radiation—i.e., when the NIR illumination source is turned off.

Step (iv) In the absorbance computation step, the absorbance of the detected spectrum for each illumination in the MIS is computed using the reference spectrum associated with that illumination. In one embodiment, if any element of the intensity vector (i.e., a point of the intensity spectrum) obtained by illuminating the medium to be analyzed is substantially zero (e.g., the intensity value is less than $10^{-5}$), that element is set to a specified minimum value (e.g. $10^{-5}$). Using this modified intensity spectrum for the medium, the absorbance spectrum can be computed, element by element, e.g., as the negative of the log to the base 10 of the ratio of the intensity value of an element in the modified intensity spectrum for the medium to the intensity value of the corresponding element in the associated reference intensity spectrum.

In some embodiments, outlier spectra may be rejected using further computations, if certain conditions are satisfied. For example, in some cases, the minimum minus maximum absorbance in a specified region of the spectrum should be less than a specified threshold, e.g., 0.6. In some cases, the average absorbance over a specified range of wavenumbers is compared with the average absorbance over a different range of wavenumbers. If the difference between the two averages is greater than a specified threshold, the entire absorbance spectrum is considered an outlier and may be discarded.

Figure 107:
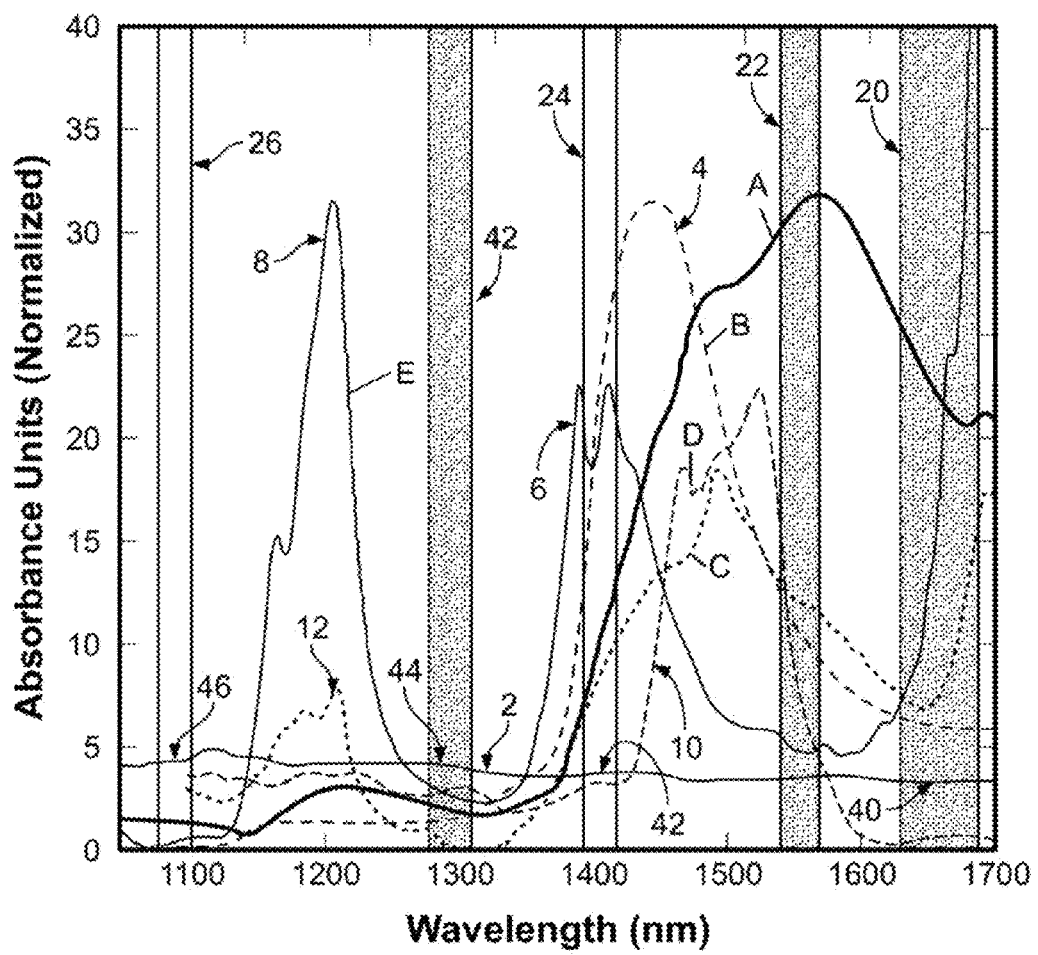
FIG. 107 depicts features of an example absorbance spectrum of glucose and several confounders, according to one embodiment.

Step (v) Features are then extracted from the various absorbance spectra. To this end, FIG. 107 shows pure component spectra A-E for selected analytes and confounders (e.g., water, collagen, glucose, urea, and fat). A pure component spectrum is an absorbance spectrum for a substance (e.g., an analyte or confounder) and can be acquired by either using the pure material or dissolving the substance in distilled water, and measuring a solvent-corrected absorbance spectrum for the substance. In the case of a mixture of substances, pure component spectra for each of the substances are determined and compared, and wavelength regions (termed "features") containing concentration information for the substances can be determined by inspecting the spectra. For example, the feature bands 20-26 and 42 are selected to represent concentration information for the analyte and confounding substances.

In various embodiments, the features are divided into (a) features that cover the spectral region(s) in which the analyte of interest substantially absorbs incident radiation described as Con_AN features, (called "GL" features in the embodiments for glucose measurements); and (b) those that do not cover the spectral regions in which the analyte substantially absorbs radiation, though one or more confounders may absorb, even strongly, called NegCon_AN (designated as "NO-GL" features in the embodiments for glucose measurement). It is to be understood that both Con_An/GL and NegCon/NO-GL features generally include energy absorbed by one or more confounders, as well as energy lost to noise from variations in the concentrations of these confounders and from scattering.

In the embodiment for glucose measurement, the GL and NO-GL features are selectively paired. This pairing is complementary, in that net differential loss in spectral energy in a feature from a region in which the analyte absorbs energy can be paired with a feature extracted from the same spectrum in a region in which the analyte only minimally absorbs energy, and these wavelength regions pairs can be used to estimate the net energy specifically absorbed by the analyte, as described above.

A seven-step process is used in some embodiments for the selection of features for analyte determination using collision computing. Step 1—An initial minimum feature length of 4 (i.e., len=4) is chosen and a sliding window interval of 4 index positions is chosen (i.e., shift=4). The start of first feature ($F_0$) is set to the first vector index $s_0$ position, i.e., i.e., the lowest wavelength or highest wavenumber, of the individual spectrum acquired in the sequence, i.e., $F_i=\{s_j, \ldots, s_{j+len}\}$, where $F_i$ is the i-th feature with start position of j; and $F_{i+1}=\{s_{k+shift}, \ldots, s_{k+len+shift}\}$ with k as the start position of the previous feature. $F_0=\{s_0, s_1, s_2, s_3\}$; Also, the boundaries of analyte absorbance (i.e., glucose absorbance) from the absorbance spectrum are established for regions corresponding to the first, second, or any other spectral harmonics of the analyte (known as "overtone regions") known to be covered by the spectrum (e.g.,., 1050 nm and 1700 nm). Denote $\Lambda_1=\{\xi_{l1}, \xi_{u1}; \Lambda_{l2}=\xi_{u2}\}$ where $\Lambda_1, \Lambda_2, \ldots$ denote the regions covered by the first overtone (the second spectral harmonic), the second overtone, and any higher-order overtones of fundamental glucose absorbances that appear in the NIR spectrum, with lower and upper spectral boundaries given by $\xi_{l1}$ and $\xi_{u1}$ and so on.

Step 2—A set of features is generated by sliding the feature start position by the sliding window interval. The process is repeated till the entire spectrum is spanned and selection of the next feature would exceed the last vector index of spectrum. Let the total set of features be denoted by $\{F_0, F_1, \ldots, F_n\}$. Step 3—Spectral energy of each feature in $\{F_0, F_1, \ldots, F_n\}$ is computed for the entire feature vector. Let the set of spectral energies be denoted by $\{E_0, E_1, \ldots, E_n\}$.

Step 4—The features are partitioned into two sets: "GL" features, which represent spectral regions of relatively high glucose absorbance, and "NO-GL" features, representing spectral regions where glucose absorbs minimally (these two sets correspond to the PosCon_AN and NegCon_AN sets described above, in general), and correspond to features that are generally within the boundaries of known glucose overtone region absorption wavelengths (e.g., 1500-1700 nm and 1050-1180 nm) and those that are generally outside the boundaries of glucose overtone region absorption wavelengths. Features with analyte spectral energies in the upper quartile, in the set associated with glucose overtones, are kept and the rest are discarded. Features with analyte spectral energies in the lower quartile, in the set not associated with glucose overtones, are preserved and the rest are discarded.

Step 5—Following the optional precursor frequency modulation of the feature, e.g., with 16.5 Hz, the remaining features (in both the GL and NO-GL sets) are conditioned by using them to modulate a carrier kernel to develop the conditioned feature waveforms. The co-dependency condition is checked to ensure that it is preserved for each conditioned feature waveform and the Zyoton, i.e., post-collision dispersal velocity is within a selected threshold limit κ. If the co-dependency condition is violated for any feature, that feature is discarded. Feature pairings are formed by coupling a feature (drawn from the GL-set with the highest glucose spectral energy of the modulated feature waveform ((based on the analyte-information representing, e.g., the first 3, 6, 10, etc., frequency components))) with a feature drawn from the NO-GL set with the lowest glucose spectral energy of the conditioned feature waveforms. Generally, the GL features are paired with all remaining NO-GL features in the set.

As described above, the term $$\Delta \vec{e}_{(GL_{F_p}, NO-GL_{F_q}, Z_r, R_t)},$$

which represents the relative renormalized spectral energy gain of the zyoton waveform ($Z_r$) resulting from collisions (with a collision iteration count of $\mathbb{N}$) with a feature extracted from the analyte-absorbing region of the acquired spectrum (e.g., $GL_{F_p}$) vis-á-vis the renormalized spectral energy gain of the same zyoton waveform, ($Z_r$), resulting from collisions with a different feature extracted from a region known to be minimally absorbing (i.e., NO-$GL_{F_q}$), for each illumination state (i.e., for each illumination state $R_t$, where t=1, 2, 3, ALL is as defined above) is computed, and the values of $$\Delta \vec{e}_{(GL_{F_p}, NO-GL_{F_q}, Z_r, R_t)}$$

are arranged in an ordered sequence with increasing energies. In some embodiments, Step 5 may be repeated for two tissue spectra taken from a subject calibration set of spectra (when ALL RINGS were illuminated) where glucose values are separated by 60 mg/dl.

In one example, a spectrum with a reference glucose value of 80 mg/dl and another with a reference value of 140 mg/dl from the same randomly chosen subject in the calibration set were used. Let the set of net normalized spectral energy gains of feature pairs generated using non-invasively acquired ALL-RING samples with a reference concentration of 80 mg/dl and 140 mg/dl respectively be denoted by $\{L_{p1}, L_{p2}, \ldots, L_{pm}\}$ and $\{U_{p1}, U_{p2}, \ldots, U_{pm}\}$. Any feature pairs where $U_{pk}$ is less than $L_{pk}$, both $U_{pk}$ and $L_{pk}$ were discarded.

This generally describes a Regeneration Process. If there are fewer than 4 surviving feature pairs, Steps 1 through Step 5 may be repeated by doubling the feature length. This is continued until the feature length becomes 64 cm$^{-1}$ for a measuring system resolution of 4 cm$^{-1}$ (longer lengths may be allowed if the system resolution is lower i.e., numerically greater than 4 cm$^{-1}$). Lower sensor resolution typically yields longer feature lengths. If again there are fewer than 4 surviving features and the maximum length of 64 cm$^{-1}$ has been reached, the process may be repeated with a an increase in the feature length of 4 cm$^{-1}$. Thus feature length values of 4, 6, 8, . . . up to 64 cm$^{-1}$ can be used to check that the surviving set has more than four features.

Step 6—Features in the surviving set are then introduced to the collision computer. Post-collision spectral energies from the first e.g., six frequency components are computed. The same check as in Step 5 is performed. In some embodiments, all of the features need to meet the condition after collision that also met it in Step 5 before collision. If all of the surviving features of Step 5 do not meet the condition after collision then the Regeneration Process of Step 5 may be repeated.

Step 7—Features that survive in Step 6 are then applied to the entire calibration set to check for the monotonicity condition over the concentration range tested in the calibration set. A minimum of 8 features were used in some embodiments (with the highest spectral energy ratios computed in Step 6) in Step 7. If the monotonicity condition fails, then the feature set is augmented by two additional features. This process may be repeated until the number of features in the monotonicity check reaches a preset threshold, e.g., 30, 50, 64, 80, etc.

Sets with more than 64 features were not used in some examples, as they failed to give sufficient performance in the NIR spectral band of interest (i.e., between 1000 nm and 1700 nm). It has been found that here are a limited number of spectral regions, in this spectral band with 2 cm$^{-1}$ resolution, where the gradient of the Fisher vector computed using the Fisher information matrix constructed using examples of pure component glucose spectra, was spatially separated from the gradient of Fisher vector computed using Fisher information matrix constructed using examples of pure component spectra of known confounders (obtained either through experiments or digitization of published spectra). This number can be higher or lower if a different spectral band and resolution were considered. Also, there is an upper bound on the number of features that can be effectively used, as determined using empirical methods in information theory such as the use of the gradient of the Fisher vector of the Fisher information matrix described in this example.

In some embodiments for noninvasive glucose measurement, 22 feature pairs, each with a length of 60 cm$^{-1}$ was used. The pairing of features can be performed based on measured spectra of the analyte and confounders in a selected band of wavelengths. This complementary pairing can support robust subsequent analysis using collision computing. In some embodiments, a tomographic spectroscopic illumination approach, referred to as spectroscopic tomography, in which different depths of tissue are sequentially or simultaneously interrogated can be used to advantage, based on knowledge of the concentrations of different analyte and/or confounder molecules at different depths.

As shown in FIG. 87A, skin tissue is a heterogeneous multi-layered media with optical absorption and scattering properties that vary with respect to wavelength, composition, physiological condition, and anatomical dimensions.

Consequently, even within a single individual, the optical properties may differ over time and by measurement position, and as a result of the physical and optical interaction between the measurement system and the sampled tissue site. When light, i.e., an ensemble of photons, is launched into the skin tissue, multiple scattering and absorption events occur as the applied photons encounter cells, cell subcomponents, fibrous protein structures, fluids, and vascular elements. Therefore, the scattering and absorption properties of each layer result from a wide range of individual components, their geometry and composition.

In some embodiments of the non-invasive measurement system using a fiber optic probe, photons are launched through one or more illumination fibers to a portion of the skin and collected by one or more detection fibers that are separated from the area of illumination by a distance, as shown in FIGS. 68-70. During transit from the area of illumination (or photon ingress) on the skin tissue, to the area of collection (or photon egress), several different types of events are possible. First, a fraction of the incident radiation may be specularly reflected from the skin surface due to the change in refractive index between the tissue and the air, optical fiber or optical coupling material. Second, penetrating optical radiation or photons may be absorbed by either the analyte or confounders, generally after a series of scattering events, and converted to heat or re-emitted. Third, generally following numerous scattering events, the photons may be diffusely reflected to the area of collection where they are subsequently transmitted via the fiber optic to a detector element. Other photons may also exit the skin outside the area of collection of the collection fiber(s) and be lost.

FIG. 87B shows the differential paths taken by exemplary NIR photons as they are launched from a light source and captured by a detector element as they emerge from the tissue. Detector positions A and B show the absorption due to notionally different distributions of molecules present in the skin at different depths.

Figure 108A:
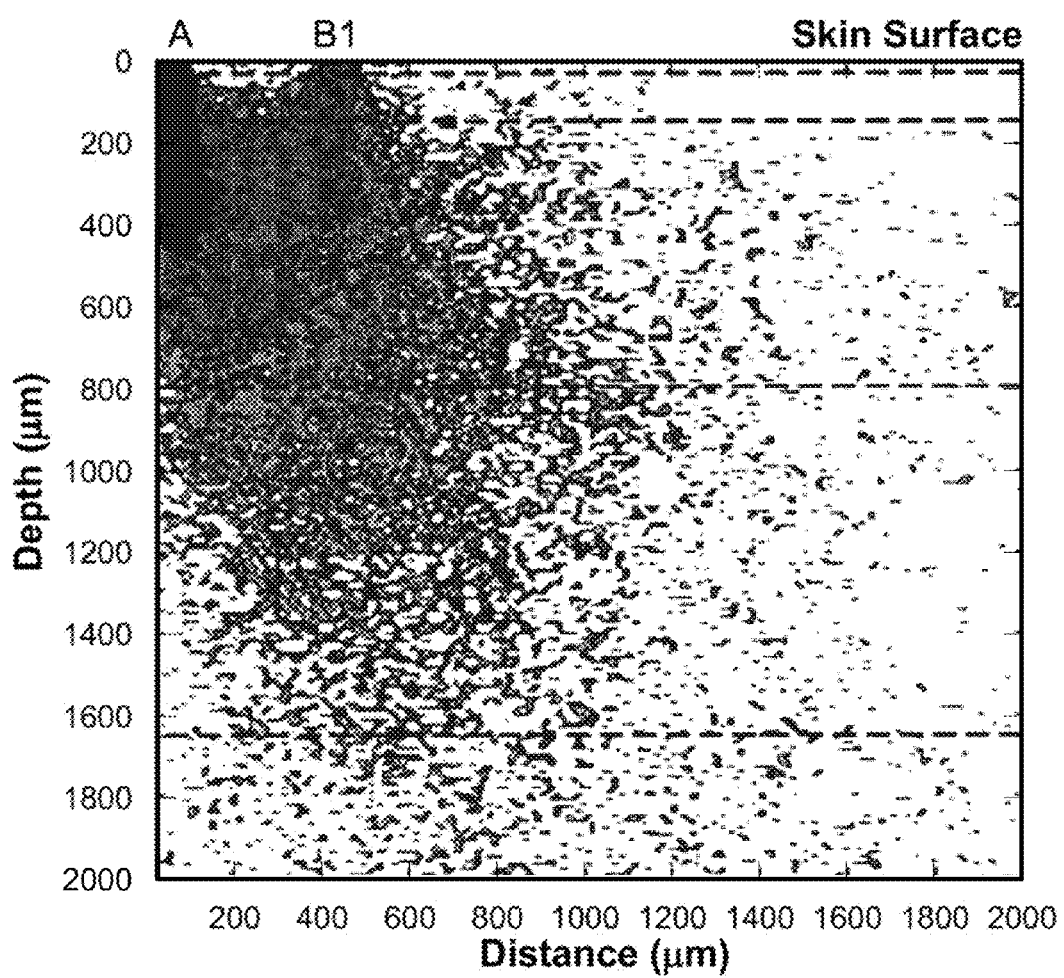
FIGS. 108A and 108B show the depth of penetration of photons under varying conditions.
Figure 108B:
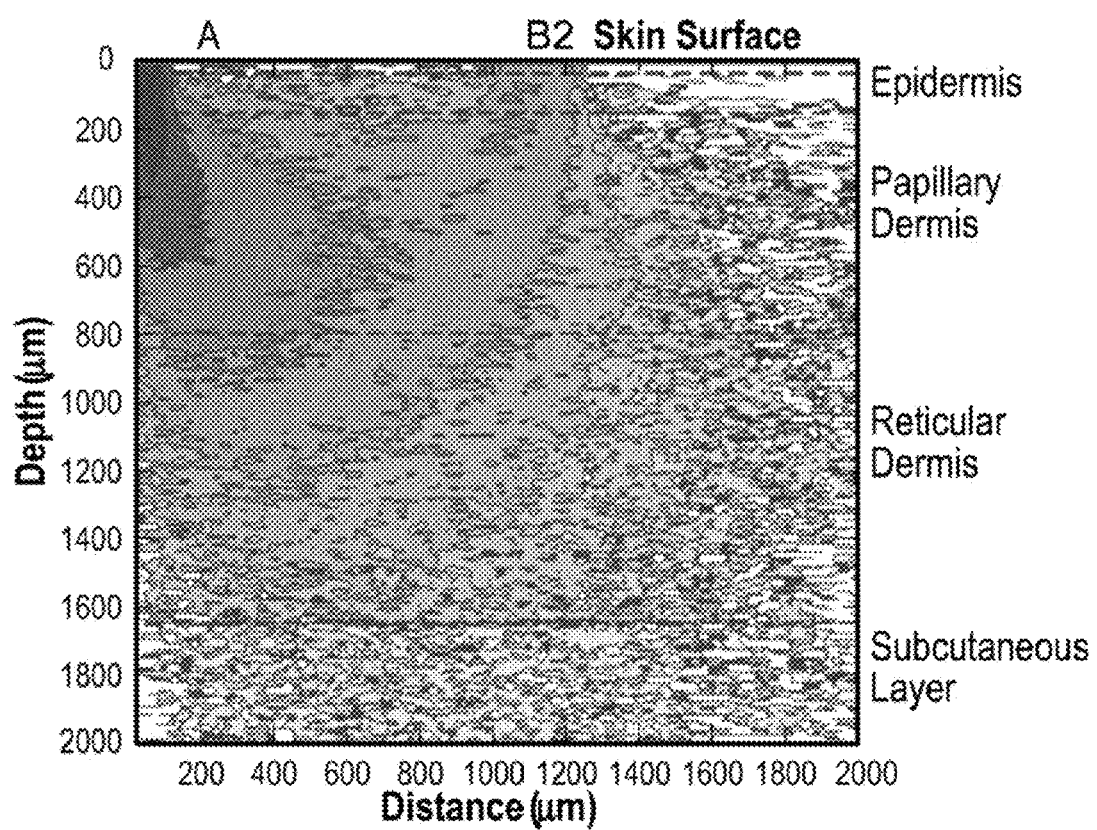
Figure 109:
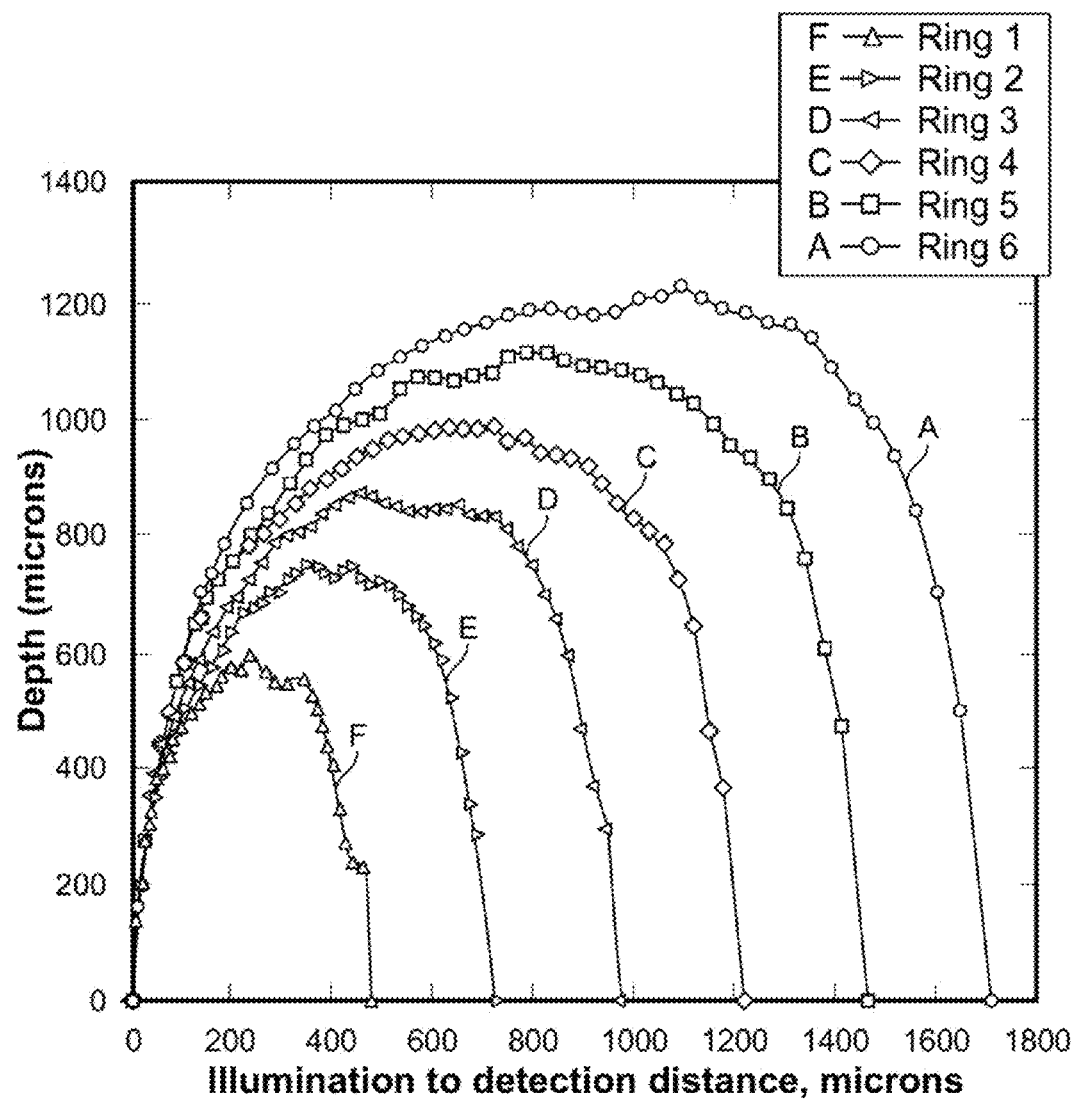
Figure 110:
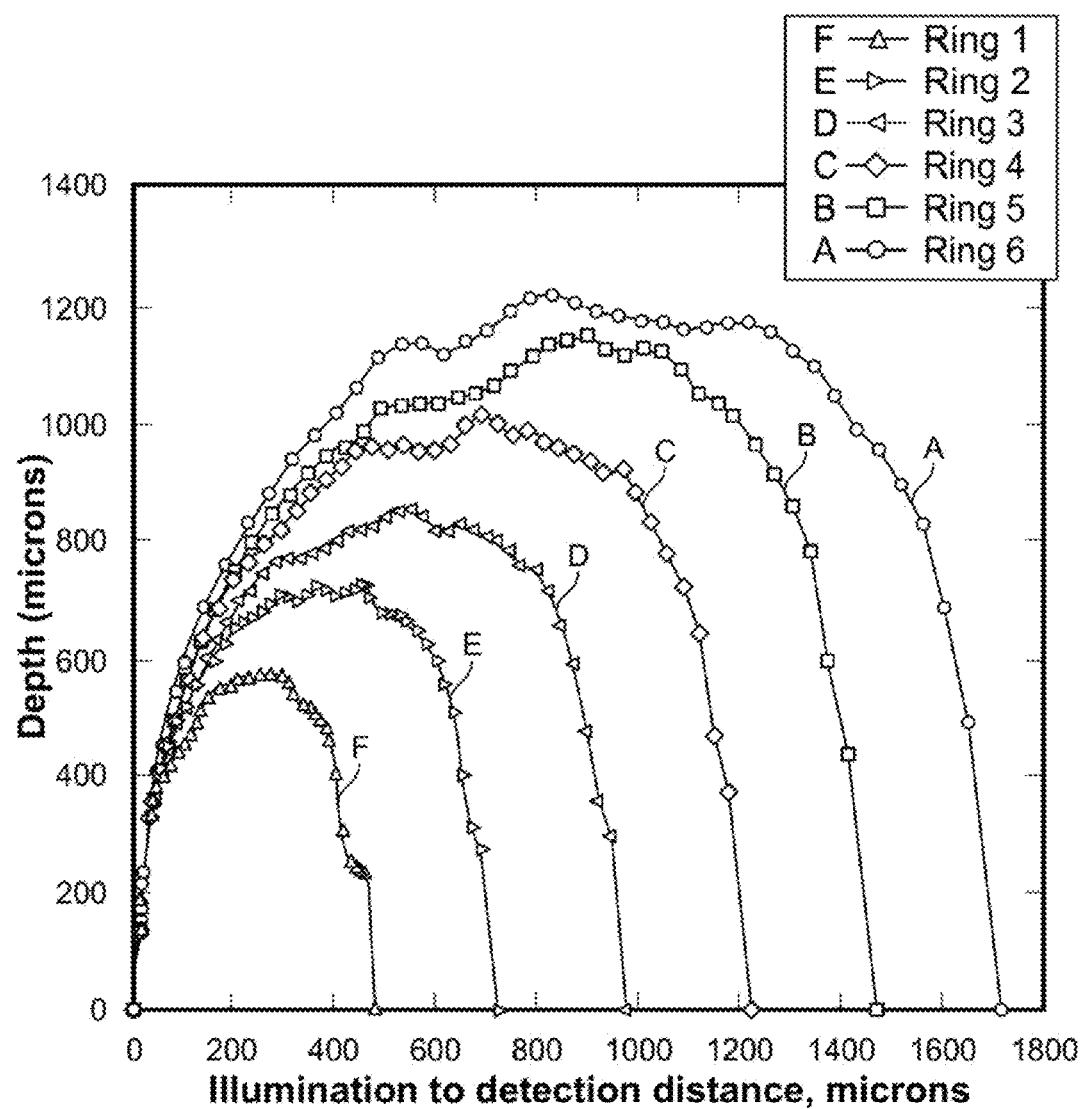
Figure 111:
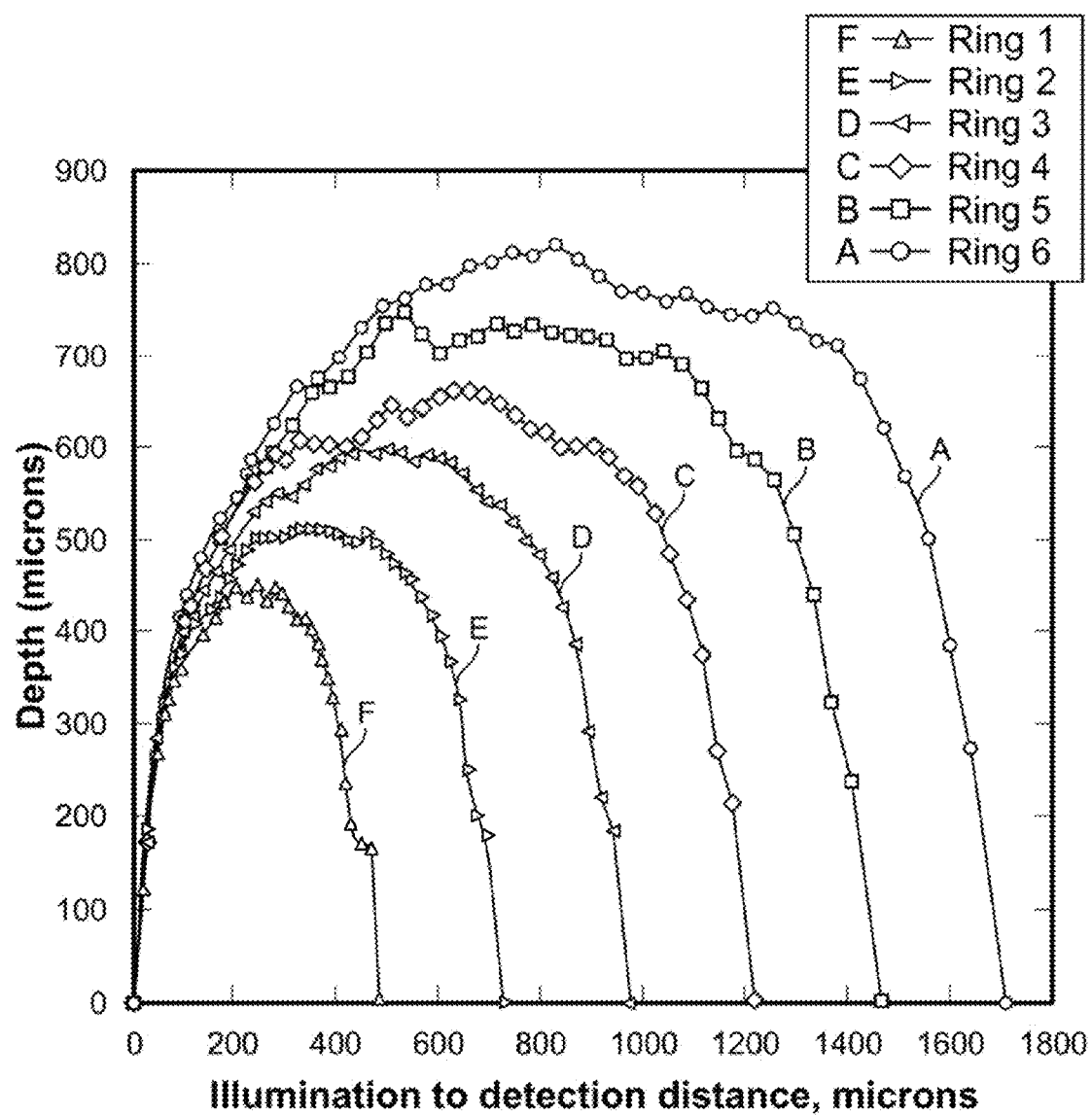
Figure 112:
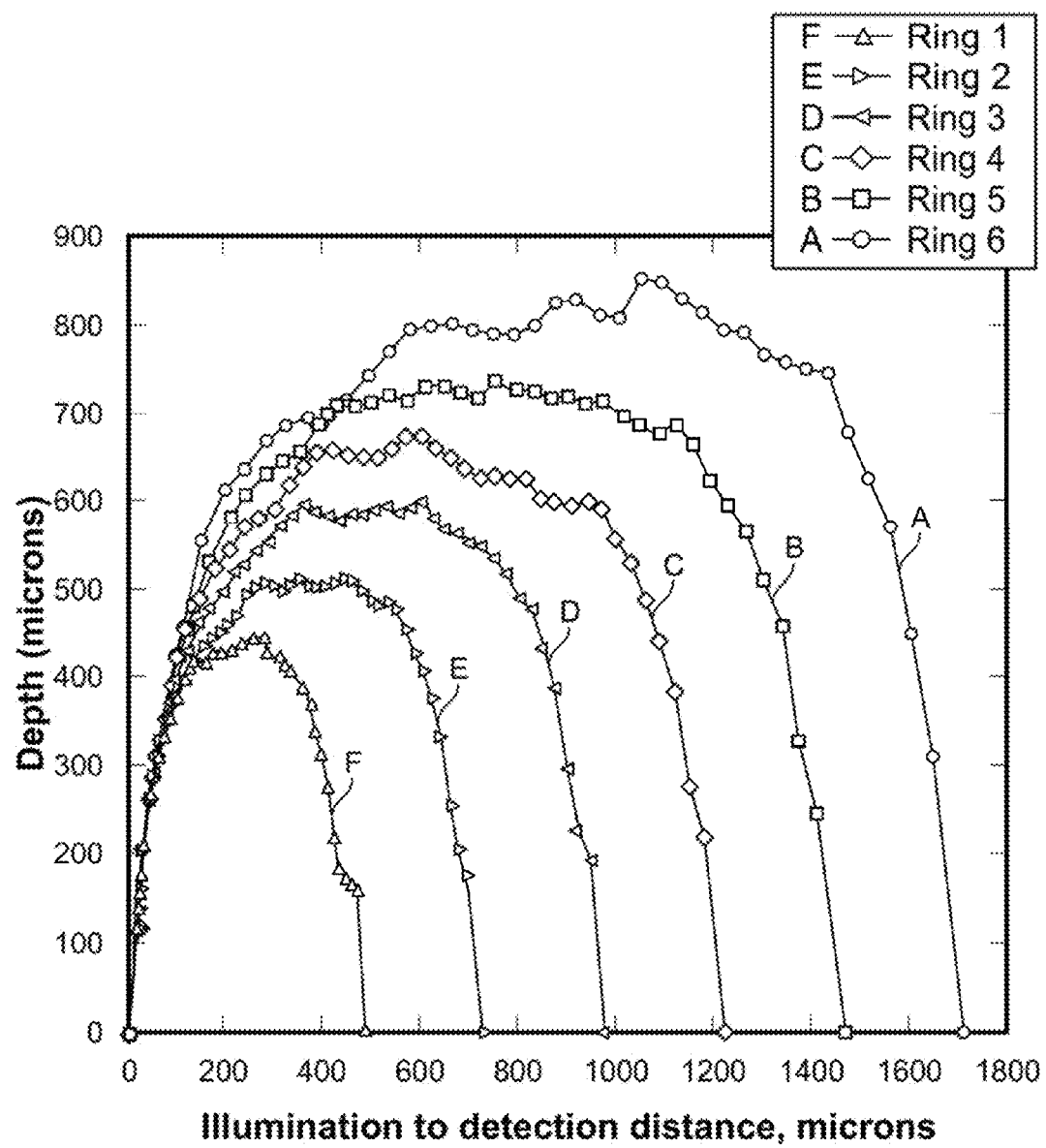

Due to scattering of the applied light, the tissue volume that is optically sampled includes a relatively large volume that increases with the distance between the illumination and detection areas. As an example, a Monte Carlo simulation of light transport in tissue was used to examine the distribution of photons in a three layer model of skin tissue. FIGS. 108A and 108B provide two plots of a cross section of the estimated volume-based distribution of photon absorbance by depth and radial distance from the point of illumination, given specific areas of illumination (A) and detection (B1 and B2). The shaded areas of the plots represent the level of light absorbance, with darker regions indicating higher levels of photon absorbance. The X- and Y-axes represent the distance from the point of illumination to detection and the depth from the skin surface, respectively.

In one embodiment, detection region B1 is about 282-482 µm from the area of illumination, A, while B2 is about 1022-1222 µm away. Due to the close proximity between regions A and B1, the tissue volume affecting the light collected at B1 (or the interrogated tissue volume) is relatively small and shallow compared to that collected at B2. Consequently, the contribution of the upper epidermis layer to the total optical signal collected in region B1 is significantly greater than that of B2. Conversely, the signal collected by B2 is more heavily dominated by light traversing the lower dermis layer.

Thus, it was determined that greater separation of the illumination and detection areas leads to deeper penetration of light, lower numbers of collected photons due to scattering, higher levels of absorption, and a larger optically-sampled tissue volume. This is further illustrated in FIG. 88, a plot of a simulation of the first to third quartile range of the optical path of detected photons at six specific illumination-to-detection distances. As the distance between illumination and detection regions is increased, the depth of photon penetration into tissue also increases and the interrogated three-dimensional tissue volume grows.

Consequently, knowledge of the relationship between the optically sampled tissue volume and the illumination-to-detection distance provides a basis for a spectroscopic tomographic optical probe design capable of discriminating specific analytes that are resident within known layers of the skin. For example, for noninvasive optical glucose measurement, given the anatomical and optical properties of the tissue volume under consideration, the probing optic is optimized when a number of channels, each representing a different illumination-to- detection distance, are spaced to appropriately interrogate the tissue.

However, the optically interrogated tissue volume for a fixed illumination-to-detection arrangement generally differs (i) between subjects; (ii) from site-to-site (within one subject); and, (iii) through time due to the dynamic nature of skin tissue and physiology. To illustrate this point, consider the mean path of detected photons as the average of the large ensemble of complex photon trajectories traversing the given distance. The path represents the central trajectory of light and the median of the optically sampled tissue volume.

Figure 89:
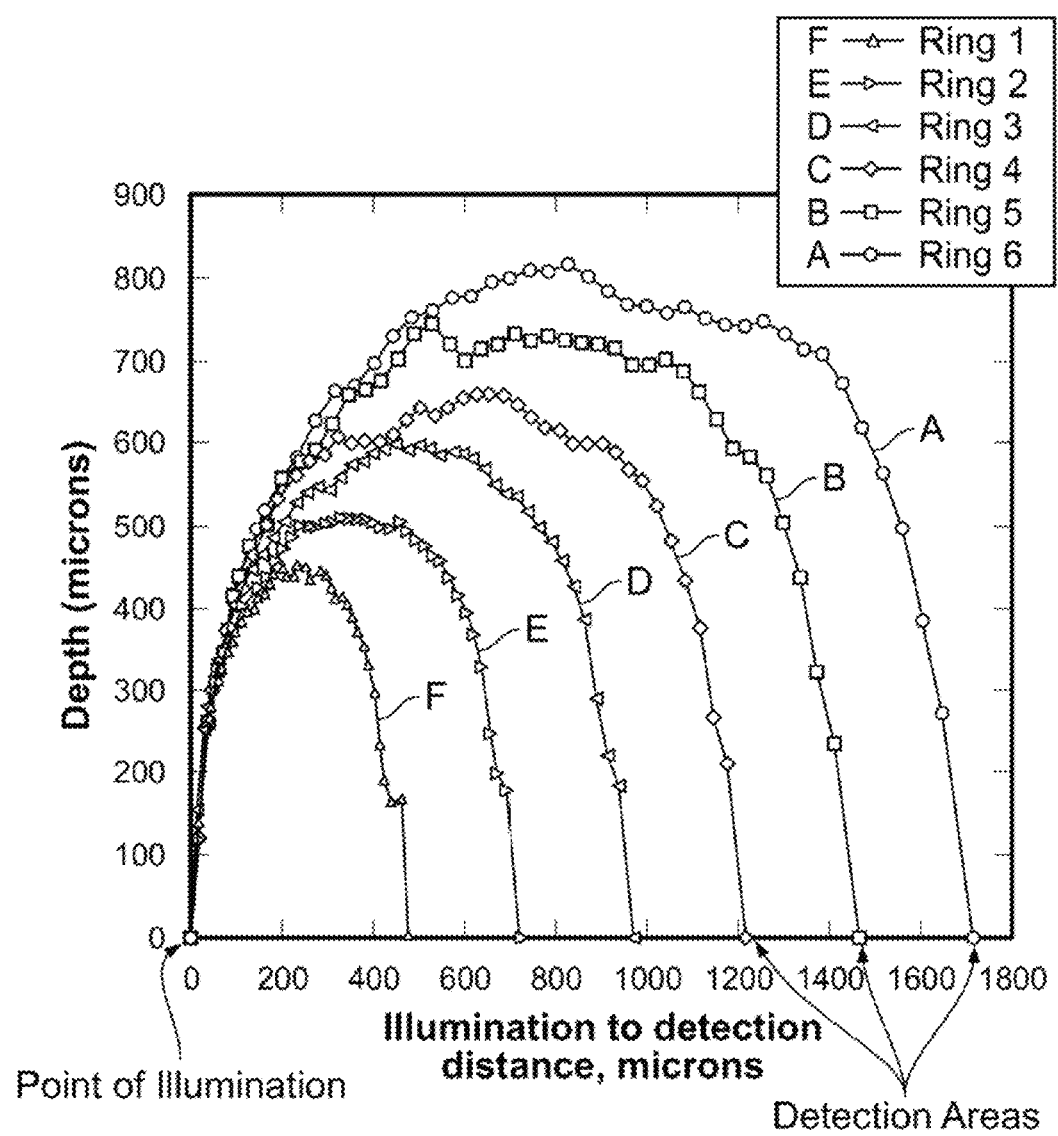
FIG. 89 shows the mean photon path for varying source-detector distances.
Figure 90:
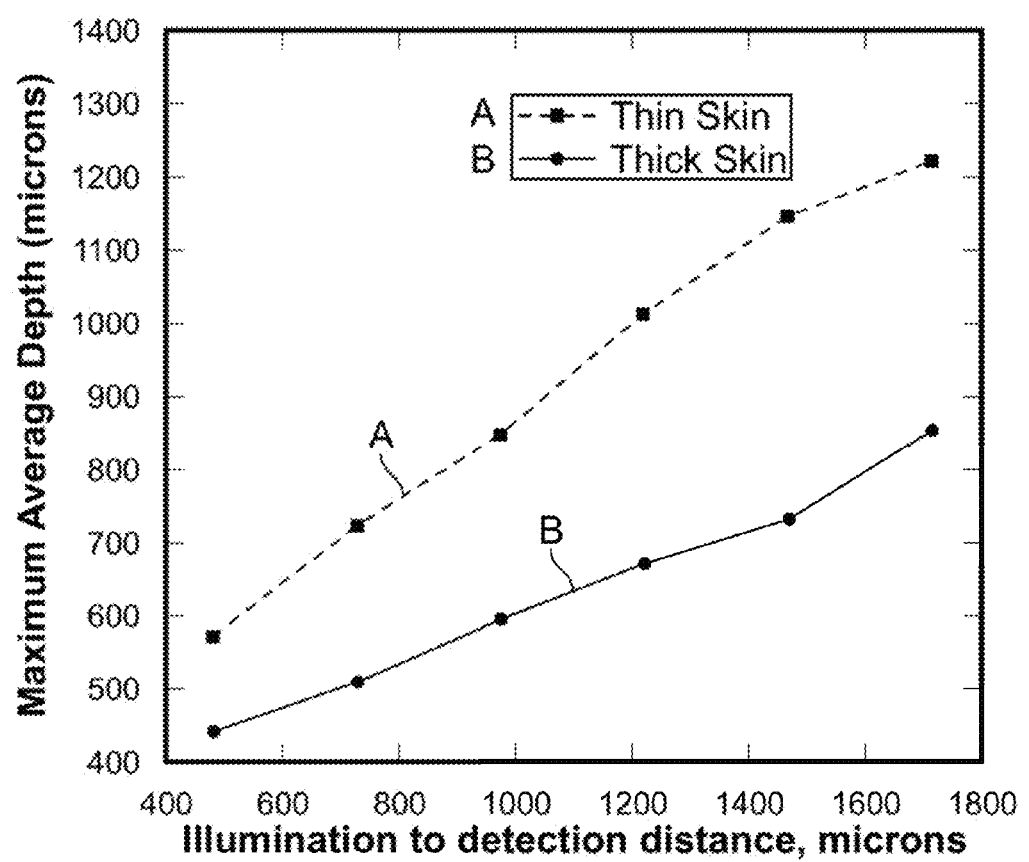
FIG. 90 shows the difference in average depth of penetration of photons for skin of different thicknesses.

Referring to FIG. 89, a plot of the simulated mean path or trajectory from six different illumination-to-detection areas is shown for a wavelength of 1550 nm. In this embodiment, each distance represents a ring of illumination fibers surrounding a single detection fiber. Although the mean path between illumination and detection areas is representative of the changing trajectory of photons with respect to distance, the cumulative set of photon trajectories is much larger and more complex.

FIGS. 109-112 show graphical plots of the simulated weighted mean path or trajectory from illumination-to-detection at a wavelength of 1550 nm for four different simulated skin tissue samples differing in thickness and glucose concentration. In all simulations, a fixed tomographic optical probe was used with six different illumination-to-detection distances, each representing a ring of illumination fibers surrounding a single detection fiber. The plots in FIGS. 109 and 110 were derived from a skin tissue model with a thin dermis (500 µm) and glucose concentrations of 80 mg/dl and 300 mg/dL respectively. A representative 1.5 mm dermis thickness was used in the simulations leading to FIGS. 111 and 112 and the associated glucose concentration of the plots were 80 and 300 mg/dl, respectively. Comparing FIG. 109 versus FIG. 110 and FIG. 111 versus FIG. 112, there is an imperceptible difference in the photon paths with more than a three-fold change in glucose concentration.

However, there is a profound difference between the trajectories associated with thin (FIGS. 109 and 110) versus thick skin (FIGS. 111 and 112) that is visibly much greater than the change due to glucose concentration. The change in trajectories with respect to skin thickness is a consequence of the varying composition and scattering between skin layers and, in particular, between the dermis and the subcutaneous layer. The dermis is approximately 75% water while the subcutaneous layer is 80% triglycerides (or fat). At the simulated wavelength of 1550 nm, it generally known that the absorption coefficient of water is many times that of fat.

Consequently, photons are absorbed at a significantly higher rate in the dermis (at 1550 nm) than in the subcutaneous layer. In the case of a 1500 μm dermis (FIGS. 111 and 112), the maximum point of the mean trajectories is approximately 800 μm. Consequently, the majority path of light in all trajectories in the dermis which is approximately 75% water. In the simulated case in which the dermis is only 500 μm thick (FIGS. 109 and 110), photon trajectories penetrate through the dermis into the subcutaneous layer to a mean depth of about 1200 μm where, due to the lower rate of absorption, longer pathlengths occur without reducing the probability of photons still reaching the detector. Since skin thickness varies between and within individuals, a change in this one parameter contributes greater pathlength variation than that due to physiologically possible changes in glucose.

Figure 113:
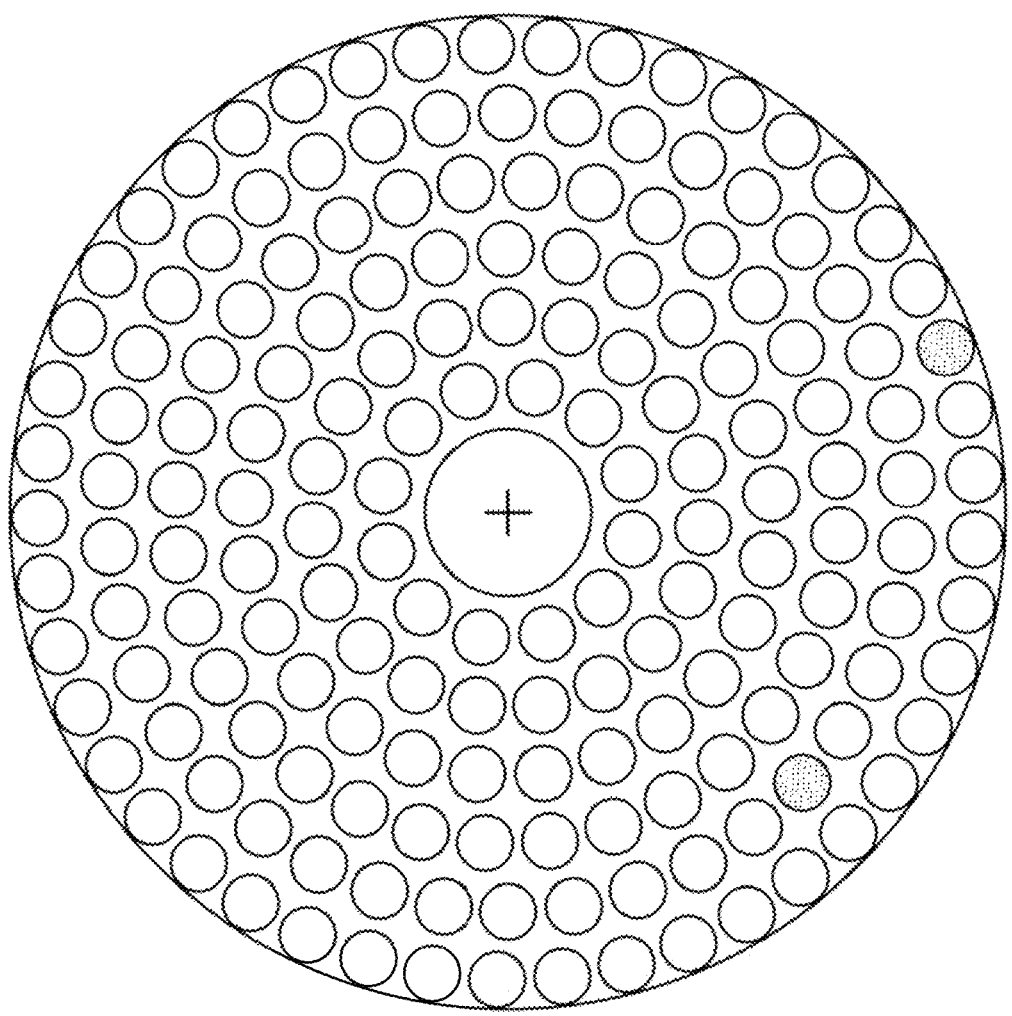

It follows that the maximum average depth of penetrating light into thin skin (due to the lower absorbing subcutaneous tissue) is significantly greater than that of thick skin, as shown in FIG. 90. Further, the optimal distance for glucose detection, measured on the basis of percent dermal absorbance, will vary significantly between individuals and be shorter for thin skin and longer for thick skin. An exemplary tomographic probe, capable of supporting glucose measurement on a variety of skin types, is shown in FIGS. 91-92, and 113. FIG. 91 illustrates aspects of the bifurcated fiber bundle including the sample side of the probe (View A), the illumination end (View B) and the detection end (View C).

FIG. 92 describes the design of the sample interface portion of the fiber bundle while FIG. 91 is a diagram of the constructed probe. The sample end of the tomographic probe has six distinct rings of 200 μm diameter core multi-mode ultra-low-OH fibers that are used for illumination and a single central 600 μpm diameter core detection multi-mode ultra-low-OH fiber that is used for detection. The illumination fibers have an approximate numerical aperture (NA) of 0.22 while the detection fiber has an NA of 0.37. By altering the illumination sequence, the tomographic probe can provide spatial and volumetric discrimination of the optically interrogated tissue sample.

In various embodiments, this arrangement provides a balance between the number of distinct illumination-to-detection distances, the illumination packing fraction of optical fibers, the percent dermis that is optically sampled and the signal strength of the collected light. However, numerous other arrangements support varying topographical measurements. For example, an alternate embodiment with similar beneficial characteristics (FIG. 70) has a single central illumination fiber with a plurality of surrounding rings of detection fibers where each fiber, ring of fibers, or spatially separated groups of fibers are used to supply light to a detection element.

Figure 114:
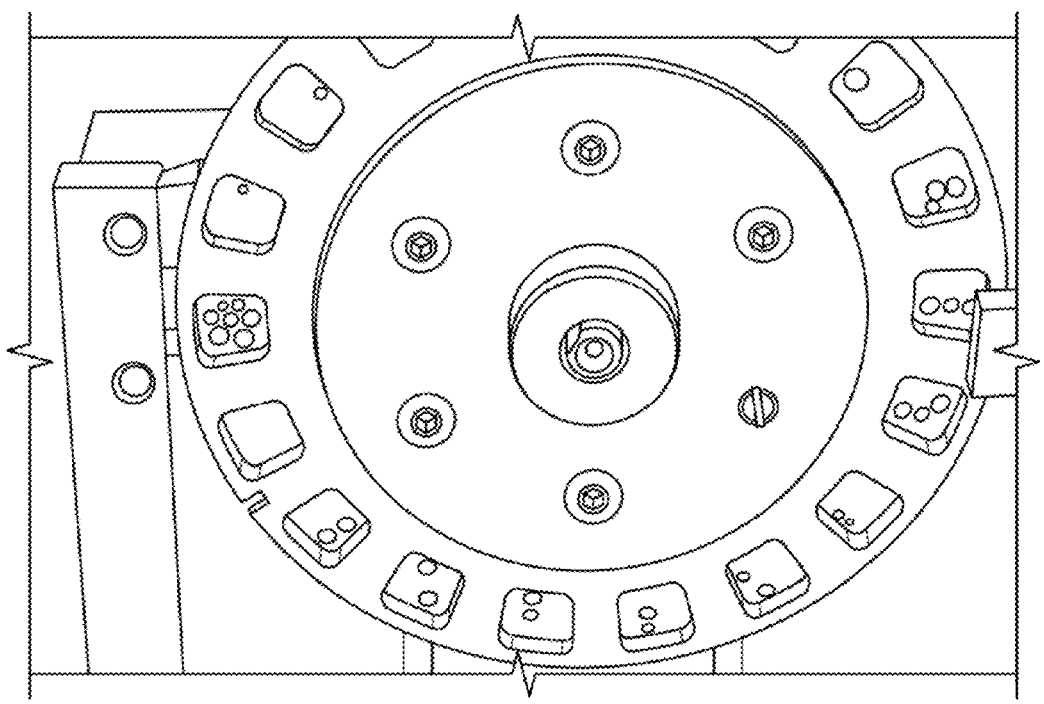

In some embodiments, individual rings of the tomographic probe (FIG. 91) are selectively illuminated by imaging a source filament through a wheel containing several selective mask positions on to the illumination end of the probe (FIG. 91). FIG. 114 is a diagram of a fabricated mask wheel with multiple rectangular regions, each of which contains an optical mask that passes light associated with one or more rings to the illumination ferrule that is illustrated in FIG. 91. By mechanically rotating the mask in front of the illumination ferrule, the fibers associated with individual rings or combinations of rings are selectively illuminated. Other embodiments utilize adaptive optics, individual sources, or modulated light to either alter the illuminating ring over time or to discriminate the originating ring of detected light.

The characteristics of the tomographic optical probe were evaluated via the previously described simulations and through in-vivo reflectance measurements. Reflectance was computed as the ratio of the photons collected by the detection fiber to the photons launched from the illumination fibers (as determined by the use of a standard material of known diffuse reflectance) and was determined by dividing the intensity (or power) of the detected light by the intensity (or power) of the illuminating light. Consequently, the reflectance depends on both the optical properties of skin tissue within the interrogated volume and the geometry and optical characteristics of the fiber optic probe.

The ring-by-ring reflectance of the probe while in contact with an in-vivo skin sample was measured using a Thermo Scientific Nicolet 6700 FTIR spectrometer. The collected intensity spectrum of each ring of fibers was ratioed to a background air spectrum (via a diffuse reflectance standard) and adjusted according to power measurements and simulation to produce the reflectance spectra as plotted versus wavelength in FIG. 93. As indicated in FIG. 93, the vast majority of light (i.e., greater than 99.9% at 1550 nm, where the reflectance is less than $1\times10^{-3}$) is absorbed prior to detection, particularly by water in the wavelength region near 1450 nm.

For illustrative purposes, the specific values for reflectance and absorbance at 1550 nm as well as the associated illumination-to-detection center-to-center distances for each ring, using a selected human subject measurement, are provided in Table 14 below. The reduction in detected light with distance is a function of the increasing pathlength, depth of penetration and optically illuminated tissue volume.

TABLE 14

Typical Reflectance Measurements of Skin Tissue using the Tomographic Optical Probe

| Illumination State | Ring Rt (as in example embodiment) | Center-to-Center Distance (microns) | Reflectance (1550 nm) |
|---|---|---|---|
| R1 | | 382 | 4.24E−04 |
| R2 | 1 | 629 | 1.55E−04 |
| R3 | 2 | 875 | 5.70E−05 |
| R4 | 3 | 1122 | 2.90E−05 |
| R5 | | 1368 | 1.50E−05 |
| R6 | | 1615 | 7.00E−06 |
| ALL Rings | R4 = {1,2,3} all ON simultaneously | | |

Figure 115A:
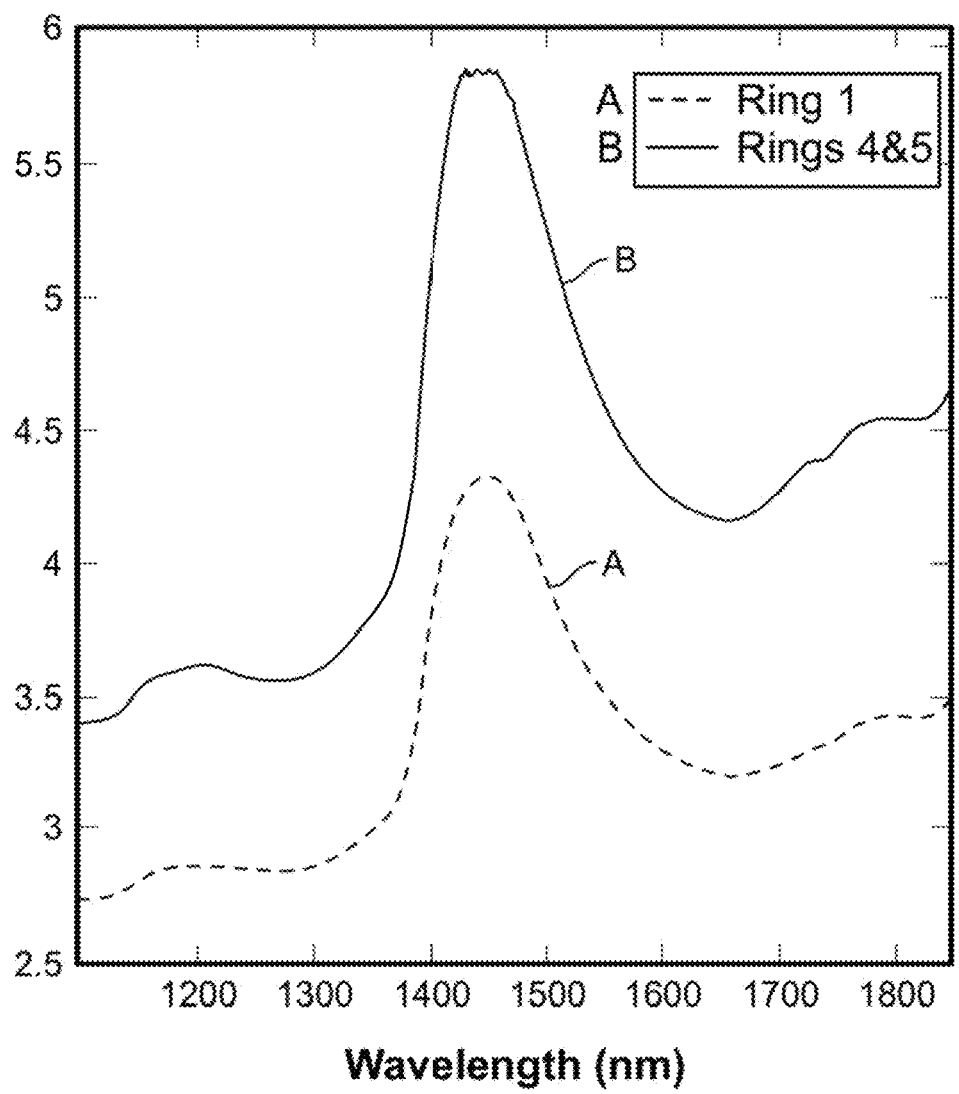

Volume-based sampling through the tomographic probe can be illustrated through a comparison of Ring 1 to Ring 4 and Ring 5 spectra absorbance of skin tissue, as provided in FIG. 115A. In addition to the significant increase in absorbance, the Ring 4 and Ring 5 spectrum includes unique features throughout the spectrum that are significantly larger than those of the Ring 1 spectrum. Specific absorbance bands appear larger in the Ring 4 spectrum at 1210, 1710, 1725 and 1760 nm and the shape of the 1650-1850 nm spectral region appears to change due to a significant increase in optical sampling of the subcutaneous layer.

Figure 115B:
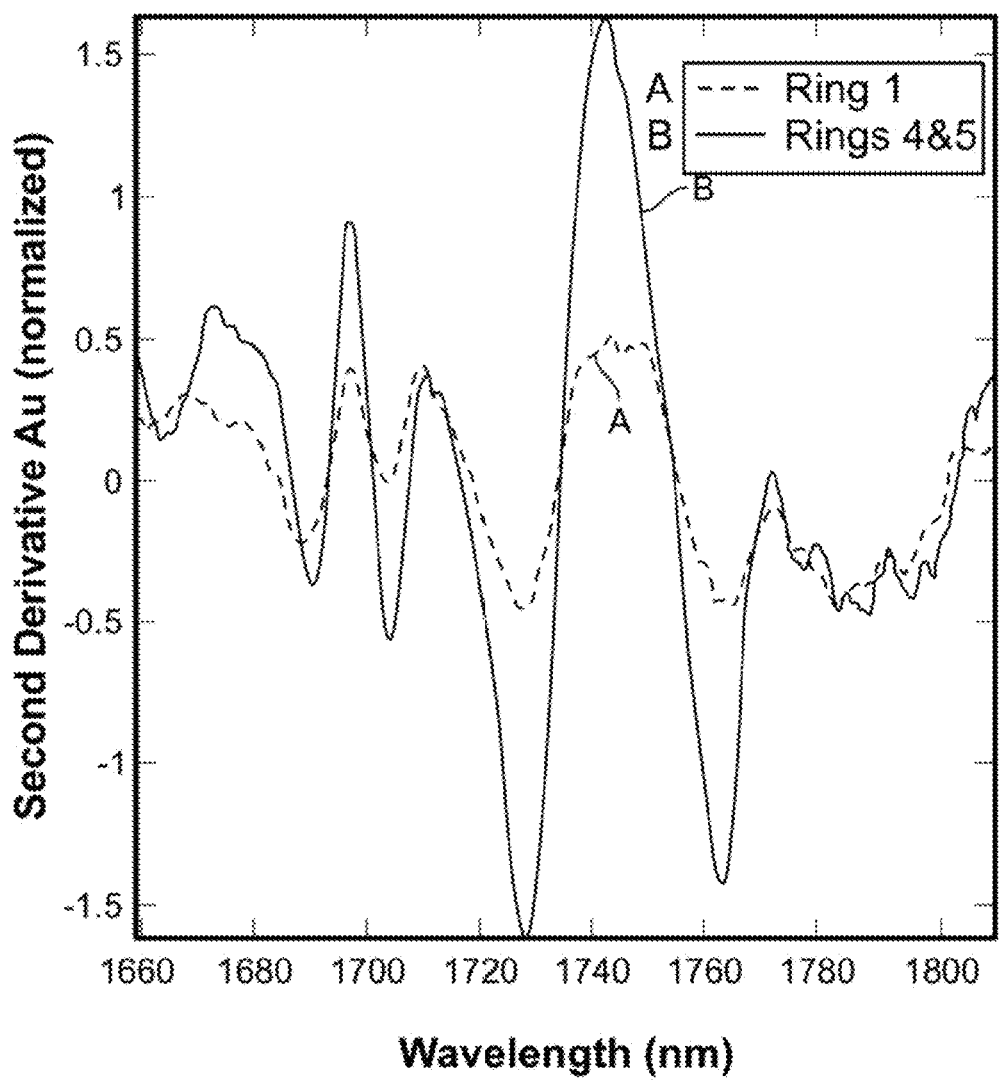
Figure 115C:
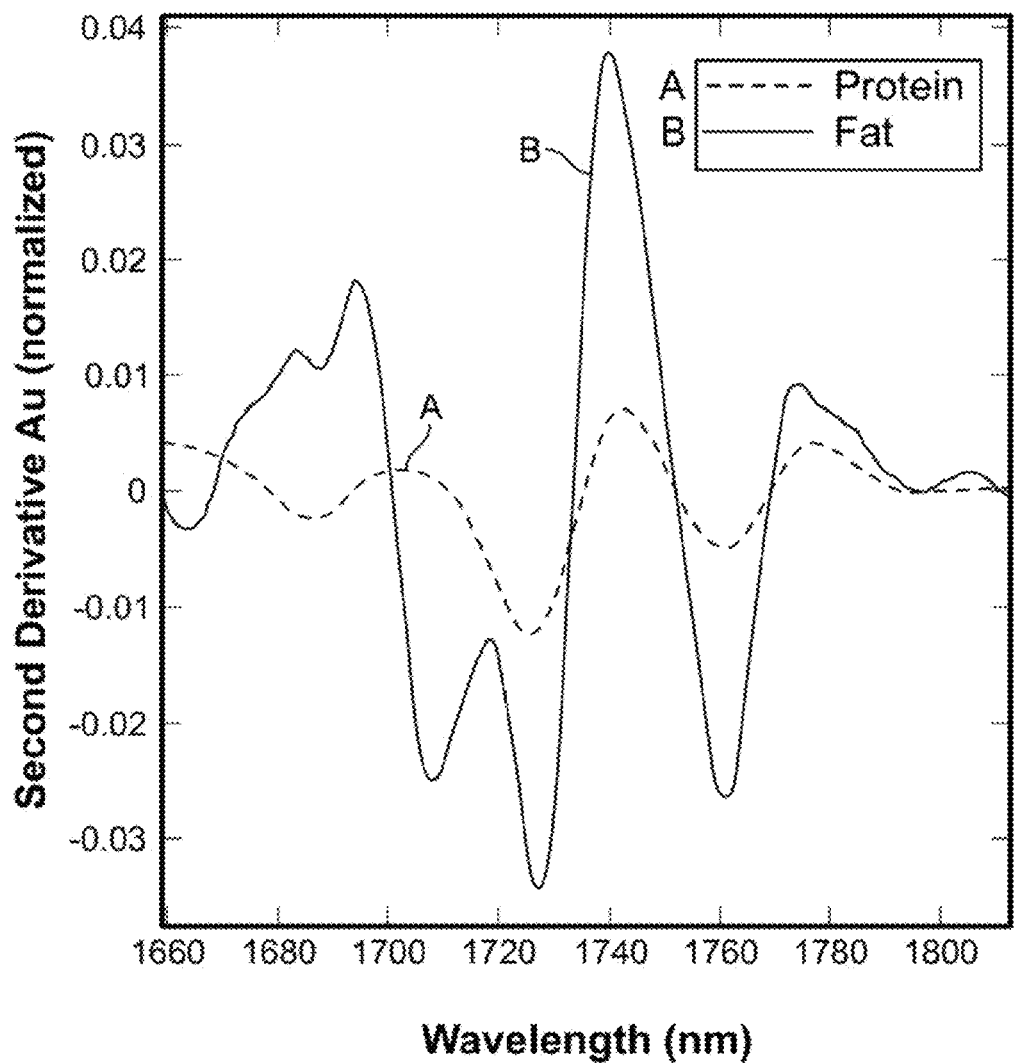

To accentuate the differences, the second derivative of each spectrum was calculated and is shown in FIG. 115B. The Ring 1 second derivative spectrum more closely represents the second derivative spectrum of protein (e.g., collagen and elastin) as represented in FIG. 115C which indicates that the epidermis is the primary skin layer that is optically sampled. However, the Ring 4 second derivative spectrum is dominated by the same absorbance pattern as that of fat which is plotted in FIG. 115C. Since fat is present primarily in subcutaneous tissue, the signal detected when Ring 4 and Ring 5 are illuminated represents a different volumetric compartment. Utilization of all six tomographic channels provides further discrimination of the tissue volume under consideration.

Since each optical measurement of the skin generally samples a different tissue volume (particularly between skin tissue sites on the body and among different individuals), the information represented in the various tomographic channels may change. This requires a measurement-by-measurement change in the optimized combination of channels and differential measurements. Determination of the absorbance, $\alpha_{ring,\lambda}$, of the optical signal acquired at each ring position is performed via the following equation:

$$a_{ring,\lambda} = -\log_{10}\left(\frac{x_{ring,\lambda}}{r_{,\lambda}} \frac{12}{N_{ring}} \times p_{ring} \times \Delta\right) \quad (30)$$

where $\lambda$ is the wavelength, $x_{ring,\lambda}$ is the measured sample intensity, $r_\lambda$ is the intensity of a 99% diffuse reflectance standard collected on only Ring 1, $N_{ring}$ is the number of fibers is the ring associated with the sample spectrum (FIG. 91), and $\Delta$ represents the combined attenuation due to (1) the distance between the reflectance standard and the probe and (2) the efficiency of the optical coupling between the detection fibers and detection element. Since $\Delta$ does not change, it is measured once after device fabrication.

The average relative illumination power between the fibers of Ring 1 and the ring associated with the sample spectrum is $p_{ring}$. The ratio is present due to non-uniform distribution of the lamp filament across the various ring bundles on the illumination end (FIG. 91) of the fiber bundle. Compensation with this ratio through time is necessary due to (1) differences in the average power delivered by the fibers in each ring, (2) changes in the lamp illumination ring intensity through time, and (3) differences in the distribution of optical power when a lamp is changed.

To illustrate this requirement, power measurements collected at the beginning ($T_0$) of a clinical study. at 180 days later, and 270 days later were compared to determine how the average power delivered by the optical fibers of Rings 1-4 changed through time. In Table 15 below, $T_0$ represents the starting point while the two subsequent measurement times, 180 days and 270 days, are used to show the percent changes through time. Each of the four rings experienced a change in delivered power although Ring 2 showed the highest (22.3%).

TABLE 15

Percent change through time of the average power delivered by Rings 1-4 of the Tomographic Optical Probe System

| Ring | $T_0$ | $\Delta$, 180 days | $\Delta$, 270 days |
|---|---|---|---|
| 1 | 100% | 5.2% | −5.3% |
| 2 | 100% | 6.2% | 22.3% |
| 3 | 100% | 1.7% | 0.8% |
| 4 | 100% | 4.6% | 4.6% |

Based on Table 15 above, it is expected that the average power delivered each ring is likely to change and may be distributed differently given the spatial placement of each ring's associated bundle within the illumination ferrule (FIG. 91) relative to the optical source and filament image. Table 16 below provides an example of average relative power delivered by the optical fibers of each ring through time. Ring 1, for example, delivered 16.4% more power than the average at $T_0$ while Ring 3 delivered 132% more light (by design). In addition to this uneven distribution of light by ring, the relative power changed through time in a manner that was different for each ring.

TABLE 16

Change through time in the relative illumination power of Rings 1-4 of a tomographic optical probe

| Ring | To | 180 days | 270 days |
|---|---|---|---|
| 1 | −16.4% | −24.2% | −7.2% |
| 2 | −17.6% | −11.3% | −2.0% |
| 3 | 132.2% | 139.4% | 127.7% |
| 4 | −1.4% | −4.6% | −0.3% |

Dynamically Controlled Illumination States

As scattering dominates light propagation in thick turbid media such as human skin tissue, it restricts both resolution and penetration depth within that tissue. As NIR photons propagate through the diffusive regime starting at approximately 1 mm below a human skin surface, their trajectories change from ballistic to diffusive due to an increased number of scattering events, which makes it difficult to identify, much less track, photon paths. However, steering such NIR photons (i.e., without using implanted devices such as fluorescent beads) to control their below-skin path of travel and to minimize random scattering, is complex and challenging. Consequently, dynamic focusing of light through dynamic control of illumination states or dynamic variation, illuminator-detector distances or other methods such as described below, may be used in some optical spectroscopy embodiments to offset the variability due to the variations interactions of light with tissue, and in conjunction with collision computing to analyze glucose and other analytes in tissue. Dynamic focusing is achieved in some embodiments using controlled light delivery.

In some embodiments, such dynamic focusing is achieved in a variety of ways that include: opto-mechanically or electro-optically varying source-detector spacing; opto-mechanically or electro-mechanically varying the size of illumination or detection area on the skin; using photorefractive materials such as phase-conjugate mirrors for control of optical focusing, or the use of an electrically or RF-modulated dynamic lens capable of changing focus, such as those fabricated with liquid crystals sandwiched between two pieces of glass. Techniques that do not require use of implanted waveguides (such as fluorescent beads or nanoparticles) are classified as noninvasive.

Noninvasive techniques for dynamic focusing include tuning the scattered light in phase to maximize the spatial or spatio-temporal density at a specific location below the skin, or time-reversing (by phase-conjugating monochromatic light) the scattered NIR photons back to their origin, such as time-reversed adapted-perturbation (TRAP) optical focusing through exploitation of intrinsic permittivity variations in the tissue. Use of TRAP focusing is summarized in Ma C et al., "Time Reversed adapted perturbation (TRAP) optical focusing onto dynamic objects inside scattering media," Nature Photonics, 2014, 8(12), pages 931-936.

Additionally, dynamic control or dynamic focusing helps offset changing SCR due to time-varying changes of confounder concentrations in the tissue responsible for changes in scattering properties (due to physiology changes, exercise, dehydration, metabolic stress, post-pharmacokinetic response, infection and other reasons) or due to rapidly changing analyte concentration (after a meal or after injection of insulin).

The net impact of employing dynamic control of illumination light or a dynamic focusing strategy, using the apparatus listed above or variants thereof, is the introduction of new and different illumination states in a tomographic sequence processed with collision computing. Dynamic control of light is a generalization of the tomographic illumination sequence detailed above.

Figure 116:
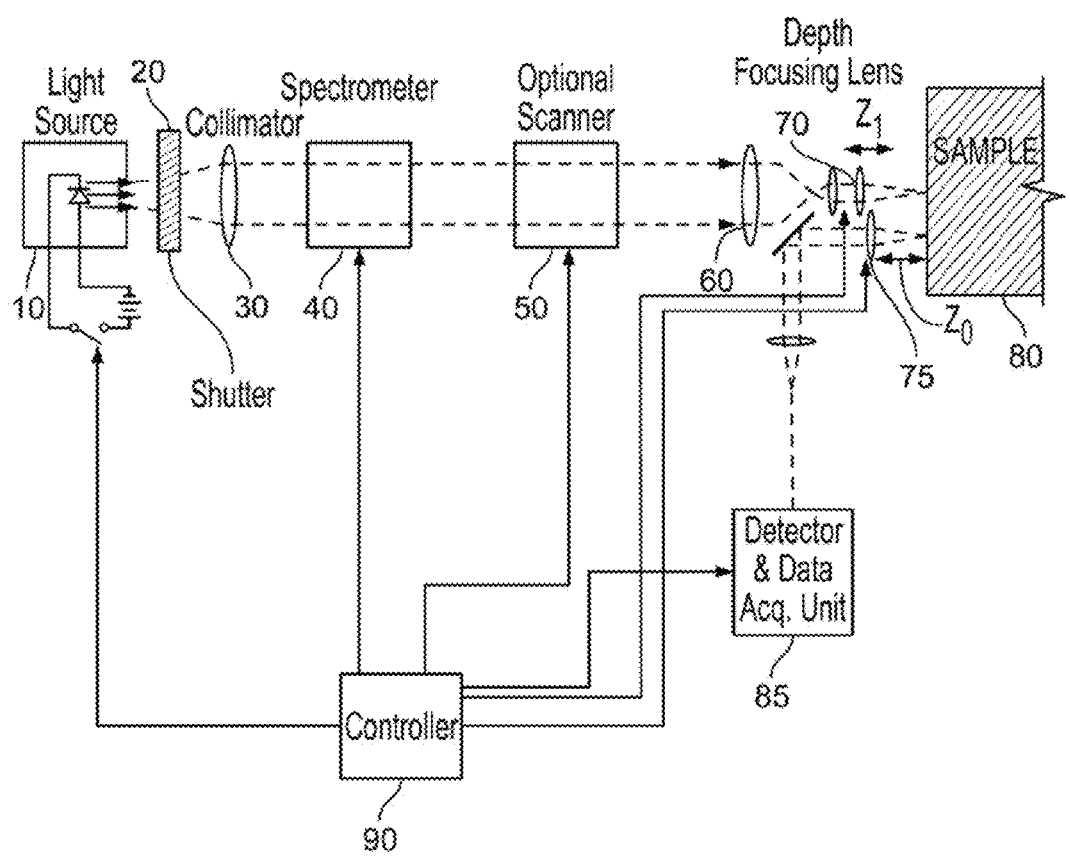

An embodiment of an apparatus for an optical engine embodiment that implements dynamically controlled illumination is illustrated in FIG. 116 for the detection of glucose and other biochemical and biological analytes, based on quantitative measurements of optical absorption of these species as a function of spatial position in three dimensions, i.e., as a function x, y and z where z is in the direction normal to the surface of the skin or sample. This embodiment is configured to acquire spectral and spatial optical absorbance data on short time scales, in effect capturing the spectral dynamics of the analyte and other biochemical species of interest. Overall, data are acquired in five dimensions—three spatial directions x, y, and z, and as a function of time and wavelength.

The shutter with controllable aperture 20, in front of a radiation element, such as a tungsten halogen lamp and/or a light-emitting diode 10, is used to throttle the number of emitted photons by varying the aperture width. The Controller 90 can also control the power to the light source and thereby modulate the number of emitted photons and their wavelength coverage. The photons allowed through the shutter 20 are collimated at 30 and focused onto the entrance aperture of the spectrometer 40. The output of the spectrometer is directed to an optional one-dimensional (1-D) or two-dimensional (2-D) scanner 50 that can steer the NIR photon beam onto the depth focusing lens or microlens 70. The scanner 50 can be of a deflecting-mirror type driven electrostatically or electromagnetically, or an acousto-optic scanner if one-dimensional scanning is desired.

The electrostatic and electromagnetic mirror scanners can be of a one- or two-dimensional type. A second microlens may be optionally inserted in the beam path to improve either the light efficiency or the throughput of this optical design and to focus the light into the sample and collect the light diffusely reflected from the sample. An additional microlens 75 may be used to modulate the reflected photon collection area. The reflected photons are directed to the detector and acquisition unit 85 which then outputs the spectra to the processing unit. Dynamic focusing and the quantity of launched photons are managed by Controller 90, which may optionally vary shutter aperture, depth of focus, scan rate, and/or scanning position. In some embodiments, lens 70 may be implemented as a microlens array with a different lens for each different incident angle of light directed to the skin. Optionally, electronically or acoustically tuned photorefractive material may be place between the depth focusing microlens 70 and the sample to improve optical coupling, eliminate optical crosstalk, minimize specular reflection, and control the angle of incidence to the skin.

Figure 117:
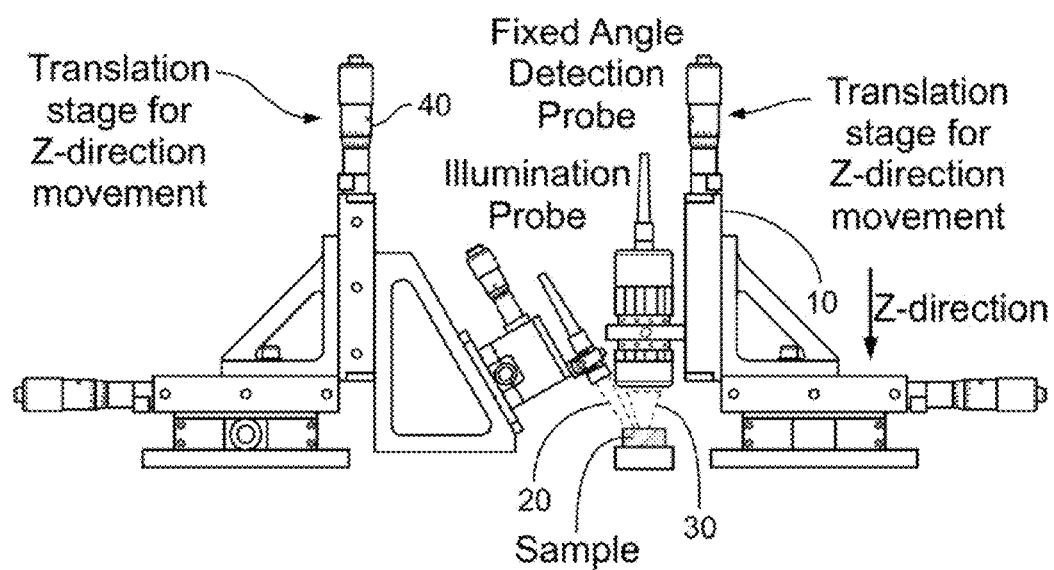

FIG. 117 shows an apparatus 10, 40 to dynamically vary depth of focus in the sample for spectroscopic tomography, and thereby change the size of the illumination and/or detection spot on the skin. In order to provide sampling at different depths, the incoming light is brought into the lens 10 that is attached to the translator that moves in z direction ($z_i$) and can focus the incoming light beam 30 into different depth from the sample surface. The diffusely reflected light from the sample is collected by another detection lens attached 40 that can also be positioned in z direction ($z_o$) normal to the sample surface.

The different z positions of this translated detection lens enable sampling into different depths and provide different paths of light traveling from the illumination path 30 to the detection path 20. The illumination lens and detection lens can be translated independently or together, depending on the desired depth sampling or optical path sampling. Light can be delivered either through free space or via fibers. The translators suited for this application can be electromagnetic actuators such as voice coils used in optical recording drives, compact drives or DVD's. The size of the illumination spot and detection spot can be independently changed by moving the attachments.

FIG. 118A shows spatial coverage in the x and y directions using the apparatus of FIG. 117. A fixed illumination spot on the tissue and a moving detection spot are shown in the figure. Optionally, by moving the translational stages in FIG. 117, the position of the illumination spot can be varied in both x and y directions; or alternately the position of both illumination and detection spot can be varied in either x or y or simultaneously in both directions.

FIG. 118B shows how depth focusing can be used to image different tissue volumes below skin in the z direction. This is achieved by varying the position of the depth lens 70 in the apparatus of FIG. 116. In some embodiments, the center of the illumination spots can be varied in the x and y directions in increments as small as 2 microns and in 5-micron increments in the z direction.

FIG. 119A shows an actuator 20 set to position a fiber probe that directs light to the skin at an angle of 30 degrees from the surface normal. The angle of incidence can be controlled in fine increments down to 2 degrees. FIG. 119B shows an embodiment built to inject light onto the skin surface at pre-set angles to the surface normal. By using two separate lens assemblies used for illumination and detection, a significant reduction of specularly reflected light from rough skin surfaces is observed, with an additional benefit of flexibility in selecting large numbers of sub-skin volumes (as in FIG. 118A-118B). The 2D scanning mirror used for x-y mapping of sample yields continuous, automated fast scanning, where the depth focusing with z translation (using a voice coil) enables both stand-off and contact acquisition. Such time-separated pulsed acquisition of data instead of steady state data reduces the complexity of mechanical coupling between the illumination and detection fibers required to implement ringed or fixed illumination states.

A benefit of embodiments employing dynamic controllability of light is that, as resolution is only diffraction limited, the illumination/detection diameter (as in FIG. 118A) depends only on the wavelength of light used, the focal length and size of the lens. For example, for X, Y scanning range of 10mm, a beam diameter <10 micron was achieved at 2500 nm wavelength and beam diameter of 4 micron was achieved at 1000 nm, with thousands of sub-volumes that size (as in FIG. 118B) that could be scanned. The achieved resolution can exceed what is achievable by fiber-based systems.

As described above, an illumination state is implemented in various embodiments by turning on and off multiple illumination sources such as concentric rings around a detector in an example embodiment. Also, the simultaneous turn-on condition of one or more illuminators (e.g., individual illuminators in a ring; groups of illuminators in one or more rings; all the illuminators in a ring; or all illuminators in multiple rings), corresponds to an "illumination state," denoted $R_t$ in various embodiments. Furthermore, an illumination sequence was designated as $I^1$, $I^2$, and $I^3$, where each $I^n$, i.e., an illumination state, can be achieved through a combination of simultaneous turn-on of one or more rings, and post-collision NRSEG $\Delta e_j^i$ correspond to the $i^{th}$ illumination state for the $j^{th}$ feature. The collision-computing framework specified above extends to embodiments with dynamic control of light and/or dynamic focusing.

In such dynamic focusing embodiments, let each illumination state ($I^n$), that results from any variations, over time a finite time interval $\Delta t > 0$, in one or more of the following:

Variation of (i) the source-detector spacing as a function of time, i.e., $|\Delta_{spacing}(t)| > 0$ (as in the example shown in FIG. 118A using the apparatus in FIG. 116).

Variation (ii) of the number of emitted NIR photons changes as a function of time, i.e., $|\Delta_{emitted\ photons}(t)| > 0$ as achieved by varying the exposed emitter surface or varying input power to the light source or other mechanism (as obtained by varying the shutter aperture 10 in FIG. 116).

Variation (iii) of the duration of photon launch or collection time or detection time window as a function of time, i.e., $|\Delta_{emitted\ photons}(t)| > 0$ (as obtained by varying the duration of shutter 10 opening time window in FIG. 116). Variation (iv) of the launch angle of emitted NIR photons as a function of time where $|\Delta_{launch\ angle}(t)| > 0$ and where launch angle $[-\pi, +\pi]$ (as obtained by varying the adjustable angle of illumination of fiber probe 20 in FIG. 119A). Variation (v) of the NIR photon detector/collector or photodetector gain over time where $|\Delta_{photodetector\ gain}(t)| > 0$, and where such gain is varied over one or more detectors (as obtained by varying the photodetector gain in 85 in FIG. 116). Variation (vi) of the NIR photon detector/collector area over time, where $\Delta_{photodetector\ area}(t) > 0$, and where such area is simultaneously varied over one or more detectors (as obtained by varying the focusing depth Zi in 70 in FIG. 116 or varying the focal length Zo in 75 in FIG. 116. Varying focusing depth of illumination beam or focusing lens 75 results in variable spot sizes as obtained at the tip of the light beams as in FIG. 117).

Variation (vii) of the focal length of focusing optics used to focus NIR photons onto the skin where $|\Delta_{focal\ length}(t)| > 0$ (as obtained by varying the focusing depth Zi 70 in FIG. 116 or varying the focal length Zo-75 in FIG. 116). Variation (viii) of the spectral bandwidth of the NIR photons launched into the skin or detected after reflectance where the bandwidth varies from illumination to illumination and does not exclude one or more spectral features impacting the pairing of GL and NO-GL features used in NRSEG determination (as obtained by changing the scan rate and scan parameters for the spectrometer 40 in FIG. 116).

Variation (ix) of the amount of light delivered to the skin surface where $|\Delta_{light\ delivered\ to\ skin}(t)| > 0$ (as obtained by varying the voltage 12 driving the light source 10, or by changing the shutter aperture 20 or by changing the settings of the spectrometer 40; and Variation (x), application of any skin tissue perfusion assist, such as through application of an optical coupling or gel, topical rubefacient, mechanical, RF, or electrical stimulation that varies the water content of the skin tissue or alters blood flow to the skin tissue.

In some embodiments, an optical diffuse reflectance spectrum collected during such dynamically varying illumination states is then (i) deconstructed into features, (ii) conditioned using a carrier kernel, then (iii) collided with a corresponding Zyoton waveform to obtain the NRSEG values, which (iv) which are then projected to obtain analyte concentration using the process described above. The repeats and replicate sequences, as described above for an embodiment using a fiber-optic ring illuminator system (which is an example of a fixed illumination system with several illumination states), also apply to various embodiments employing dynamic illumination and/or with focusing (called "dynamically varying illumination system with several illumination states). Thus, averaging of NRSEG in processing spectra from dynamically varying illumination system with several illumination states can be performed in a similar manner as for repeats and replicate spectra obtained using a fixed illumination system with several illumination states. In various embodiments, analytes may be found in higher concentrations in, for example, in specific depths, layers, or regions of the medium. In some embodiments for noninvasively determining glucose in tissue, glucose is found in a higher concentration in the dermis layer than it is in either the epidermis layer above or the subcutaneous layer below.

An optional refinement of the use of dynamically controlled light is through an optical interface to the tissue that allows alteration of the illumination or detection angle by angling optical fibers of a ring-based annular probe relative to the perpendicular, to accomplish a greater resolution of interrogated tissue volumes than just the variations in illumination-to-detection distances used in various optical systems described above. Modification of the illumination angle refers to a change in the angle of launched light from the perpendicular and leads to a change in the distribution of photons inserted into the skin. Hence, modification of the illumination angle can be used to target a specific tissue volume given the tissue state and structure (e.g., thickness, collagen density, scattering, hydration, etc.).

Modification of the detection angle refers to a change in the distribution of optical collection angles. For example, with a fiber optic in contact with, and perpendicular to, the skin, having a numerical aperture (NA) of 0.37, the collection volume can be a cone with an acceptance angle of approximately 22.5 degrees about the line perpendicular to the skin as illustrated in FIG. 120. A change in the detection angle refers to a modification of the central collection angle from the perpendicular.

FIG. 121 illustrates an optical interface that uses one central detection fiber (e.g., 500 µm ultra-low-OH silica fiber) and a series of annular rings made from angled 200 µm illumination fibers, with a single fiber from each ring shown. This exemplary optical interface lay-out may be employed for launching light into the skin at an angle that varies with the illumination-to-detection separation. The minimum illumination-to-detection distance can be, e.g., approximately 120 µm from the edge of the detection fiber to the edge of the closest illumination fiber, and, the illumination angle increases from approximately 0 degrees to greater than 45 degrees as the illumination-to-detection distance is increased, for example, from 150 µm to approximately 2 mm.

As depicted in FIGS. 121-123, the illumination angle (from the perpendicular) can be modified according to the interaction of light with the tissue at varying distances from the central detection fiber, to detect the maximum amount of light from a desired tissue volume. Specific designs may also be defined for optimizing the measurement of specific target analytes. Additional design parameters utilize measurements of the mean or median pathlengths of light in various layers, as determined from simulations of light interactions with tissue.

In some embodiments for non-invasive glucose measurement, design configurations include variations based on parameters that optimize one or more of the following characteristics: (1) Percentage of the total pathlength of light that is within the dermis; (2) The amount of reflectance; (3)

Product of characteristics (1) and (2); (4) The product of reflectance and the median dermal pathlength, minus the product of reflectance and the median epidermal pathlength, and also minus the product of reflectance with the median subcutaneous tissue pathlength, and; (5) The product of the square root of the reflectance and the median dermal pathlength, minus the product of the square root of the reflectance and the median epidermal pathlength, and also minus the product of the square root of the reflectance and the median subcutaneous tissue pathlength. The fifth characteristic is related to the signal-to-noise ratio of the absorption due to glucose in the dermis layer.

FIG. 122 shows an optical interface layout for preferentially detecting light at an acceptance angle that depends on the illumination-to-detection separation, where the angle of illumination is varied. This optical interface uses one central illumination fiber (e.g., 300, 350, 500 or 600 µm ultra-low-OH silica fiber) and a series of annular rings of 200 µm detection fibers. The minimum illumination-to-detection distance is, for example, approximately 120 µm from the edge of the illumination fiber to the edge of the closest detection fiber. In FIG. 123, the two prior concepts are combined and both the illumination and detection angles may be modified. This interface can both deliver light to the skin at different angles and collect light from the skin at different angles.

As described above, modification of the illumination (or detection) angles provides a means to target particular tissue volumes. As an example, using a Monte Carlo simulation, the change of the optically interrogated tissue volume when the illumination angle is changed from the perpendicular to 45 degrees is illustrated in FIGS. 124A-124B through plots of the distribution of light deposition into tissue, using an illumination-to-detection distance of 1.6 mm. The y-axis represents the depth of penetration of light into the skin with the zero point representing the skin surface. The x-axis represents the distance from the point of illumination, where the region of detection is centered at a distance of 1.6 mm and has a width of 0.2 mm.

When light is launched perpendicular to the skin, the distribution of locations where light is deposited into subcutaneous tissue varies widely. By launching light at a 45 degree angle, the distribution of deposited light is tighter, does not penetrate as far into subcutaneous tissue, where glucose concentration is lower than in the dermis, and preferentially targets the dermal region. FIG. 124A illustrates a comparison the interrogated tissue volume between a perpendicular photon launch, compared to a 45-degree photon launch in FIG. 124B.

An additional Monte Carlo simulation analysis was performed to determine the optimal illumination angle versus the distance between the point of illumination and the point of detection for three different skin types (thin, normal and thick). The simulation models of tissue involved five skin layers with characteristics described in Table 17 below.

The simulated detection area was studied using a 600 µm-diameter fiber with a NA of 0.37, and the illumination area was set as 200 µm. For each simulation (for each skin type and illumination-to-detection distance), the optimal illumination angle was determined by the product of median dermal pathlength and the square root of the reflectance minus the product of the square root of reflectance and the median epidermal pathlength and also minus the product of the square root of reflectance and the subcutaneous tissue pathlength.

The results of the illumination angle vs. the illumination-to-detection distance variations are shown in FIG. 125. In the plot, the launch angle is expressed in degrees from parallel with the skin such that a perpendicular launch angle is 90 degrees. Using the calculations described above, the results indicate that the optimal angle varies with respect to skin type (thick: >200 microns, thin: <100 microns, and normal: between 100 and 200 microns in thickness) and that measurement locations involving higher scattering or thicker dermal layers require lower illumination angles (i.e., less deviation from perpendicular light launch). On the other hand, optimal illumination of thin skin requires higher illumination angles (i.e., greater deviation from perpendicular). Simulations were performed to show the optimum illumination launch angle versus illumination-to-detection separation for three different skin types. In this case, the launch angle is expressed in degrees from parallel with the skin. As a result, the illumination angle shown here numerically increases as it varies from perpendicular toward parallel relative to the skin surface.

Depth and tissue volume targeting may also be optimized by control of the distribution of detected light according to angle. For example, FIG. 126A-126C illustrates the simulated distribution of light absorbance by layer for three different detection angles given a fixed 1 mm illumination-to-detection distance. An increase in the detection angle from 0 degrees to 40 degrees was found to decrease the percent of light absorbed in the subcutaneous tissue in preference to the epidermis and dermis. Additionally, the relative reflectance increased by factors of 1.7 and 2.3 times when the detection angle was increased from 0 degrees to 20 degrees and from 0 degrees to 40 degrees respectively. Consequently, modification of the angle of detection was found to enable improved targeting of the dermis and to increase the total amount of collected light measured as relative reflectance. For analytes such as glucose that are preferably detected in the dermal compartment, limiting light collection to specific angles can provide a significant improvement in glucose signal strength.

However, the optimal angle of collection generally varies with respect to (1) the illumination-to-detection distance, (2) the wavelength under consideration and (3) the physical and optical properties of the tissue under interrogation, such as the skin thickness and a tissue optical parameter called the scattering coefficient. Determination of the optimal angle

TABLE 17

Summary of optical properties used for the illumination-angle simulation

| Skin Type | Stratum Corneum Thickness (µm) | Epidermal Thickness (µm) | Papillary Dermal Thickness (µm) | Recticular Dermal Thickness (µm) | Subcutaneous Layer Thickness (mm) | Relative Scattering Magnitude (relative to normal skin thickness) |
|---|---|---|---|---|---|---|
| Normal | 20 | 100 | 400 | 600 | 1 | 1 |
| Thin | 20 | 100 | 250 | 250 | 1 | 0.7 |
| Thick | 20 | 100 | 500 | 1000 | 1 | 1.3 | across these three variables can be performed using Monte Carlo simulations and may be applied directly to a particular tissue type with measured optical properties.

As shown in FIG. 127A-127C, the optimal detection angle for a glucose embodiment was determined, through Monte Carlo simulation of a five-layer tissue model, on the basis of the percent of the total pathlength that is within the dermis and the reflectance, for two different skin types with different optical properties, six different illumination-to-detection distances, and over the wavelength range 1100-1800 nm. FIGS. 127A-127C provide plots of the percent increase in reflectance vs wavelength for detection angles ranging between 10 and 40 degrees from vertical, and at different illumination-to-detection distances. FIGS. 127A-127C show the percent increase in reflectance relative to that at zero degrees as a function of wavelength for an illumination-to-detection distance of 722 μm; FIG. 127B shows the percent increase in reflectance versus wavelength for an illumination-to-detection distance of 975 μm, and FIG. 127C shows the percent increase in reflectance versus wavelength for an illumination-to-detection distance of 1228 μm.

These results indicate that the amount of light collected generally increases with increasing detection angle but is also a function of wavelength and the illumination-to-detection distance. Consequently, an increase in the detection angle (or illumination angle) will result in a higher intensity signal. However, the increase in detected light does not necessarily correspond to an increase in the analytical signal of interest (e.g., the absorption of glucose). Instead, a combination of the percent pathlength of detected light passing through the dermis, in addition to the reflectance, provides a parameter that is related to the SNR of the analyte signal.

To illustrate the dependency of the optimal angle on skin type, the set of simulations was repeated with a thick skin tissue model and the results are summarized below in Table 2.

TABLE 18

Average optimal collection angle at six illumination-to-detection distances for skin with normal (100 μm) and thick epidermis (300 μm) skin

| Illumination-to-Detection Distance (μm) | Normal Skin Optimal Angle | Thick Epidermis Optimal Angle |
| --- | --- | --- |
| 470 | 8 | 0 |
| 722 | 10 | 1.5 |
| 975 | 20 | 2.5 |
| 1128 | 35 | 10 |
| 1480 | 40 | 18 |
| 1732 | 42 | 23 |

In summary, the illumination and/or detection angles can be used to change the optically interrogated tissue volume. Based upon the total detected light and the percent of light traversing the dermal layer, the optimal angle varies with respect to wavelength, illumination-to-detection distance and tissue type. Tissue measurements made on thinner skin are optimized by setting the illumination (or detection angles) significantly greater (further from perpendicular) than thicker or higher scattering skin. The optimal angle increases with illumination-to-detection distance.

As described herein, a pairing of NIR illumination and detection centers on skin can create numerous path lengths where different photon travel paths induce differential scattering and absorption. Both the fixed illumination system with multiple illumination states, and the dynamically varying illumination system with multiple illumination states provide a flexible skin surface scanning mechanism with ability to change optical path length. The resulting spectra may then be deconstructed into features, conditioned, collided with Zyotons, and their energy values projected to calculate concentrations of glucose and/or other analytes.

In some embodiments, pure component analyte spectra, acquired with the same instrumentation as that used to measure the analyte, are used as a reference for selecting features in regions of stronger and weaker analyte absorbance. As shown in the feature pairing table in FIG. 49, with reference to FIG. 107, two or more features in the region in which the analyte (glucose, in this example) more strongly absorbs energy are paired with features in a more weakly-absorbing region, to compensate for high levels of spectral energy absorption due to an unknown, uncharacterized number of confounders also absorbing in the same region(s) as the analyte. The number of pairings used may depend on the degree of confounder interference.

FIG. 83 shows the set of features used in a non-invasive glucose monitoring instrument, and an embodiment yielding a MARD numerically less than 15% was achieved in a daily-lifestyle clinical study conducted primarily with insulin-using subjects with Type 1 diabetes. MARD, as described above, is used as a measure of the degree of clinical accuracy of a new measurement technique when compared to reference measurements. As shown in FIG. 68, the embodiment comprises fiber optic illumination fibers arranged in a ring geometry with a central detection fiber. The probe is detailed in FIG. 69. A total of 34 features was used in this embodiment, some focusing on wavelengths where glucose is known to be more strongly absorbing and others in regions where glucose is more weakly absorbing. Wavelength coverage of features for glucose and some confounders is shown in FIG. 107. The number of features and length of each individual feature is directly related to one or more of the following factors, which provide the design rules.

Factor (a) The number of tomographic spectral scans (where each scan entails illumination through a particular ring or combination of rings); depth penetration of NIR photons in each scan; and the mean path model of propagation for NIR photons as a function of distance between the illuminator and detector (FIGS. 68 and 69). The propagation mean path, in three dimensions, generally specifies the volume of tissue interrogated by the radiation in each illumination. For a medium with a given coefficient of scattering, the number of illumination states and number of features generally describe the observability model for the measurement and the underlying confidence of observing the tissue volume.

Factor (b) The assumed clutter model and anticipated interference from confounders influence the number of features and length. As a design rule, more features are required if the anticipated interference is high. Also, a longer feature length is required if scattering is anticipated to dominate the total energy attenuation. Factor (c) The prediction performance requirements for accuracy and precision, with feature length proportional to high demand for accuracy and precision. Factor (d) A greater relative ratio of absorbance of glucose in a region where it strongly absorbs to the absorbance of a region of lower glucose absorbance requires a longer feature length.

Factor (e) Sensor resolution. If sensor resolution were numerically greater than 2 $cm^{-1}$, feature lengths less than 6 $cm^{-1}$ may lead to numerical instabilities and should be generally avoided. Depending on the resolution, the feature lengths can be as long as 256 wavenumbers. In one embodiment used for the study that achieved a MARD of less than 15%, the feature length was 60 cm$^{-1}$. Factor (f) The Zyoton waveform properties that provide separated glucose results from tissue phantoms with differing glucose concentrations. Factor (g) An anticipated large variation in optical properties of imaged skin over the population mandates use of a larger number of features compared to a scenario anticipating smaller variation.

In various embodiments, paired features which amplify and quantify differential energy absorption using the collision computing process are used to determine the energy absorbed by the analyte at various wavelengths. As the signal of interest, i.e., the net energy absorption due to the analyte, is very weak (e.g., less than 0.01% of the total energy attenuation in a tissue glucose embodiment), simple differencing (subtraction, linear scaling or ratioing operations) of estimated energy absorbed in paired combinations of Con_AN and NegCon_AN features generally does not yield robust analyte concentrations. In fact, a simple differencing can yield errors in excess of 100% of true analyte concentration in non-invasive measurements. To minimize such errors, various embodiments employ a non-linear, non-invertible collision computation process to estimate energy absorption represented by Con_AN and NegCon_AN features. Differential energy absorption due to an analyte is estimated by combining the energy absorption within the spectral regions identified by the Con_AN and its paired NegCon_AN features, and the result is used to compensate for variations in the medium in which the analyte is measured.

In some embodiments, the NegCon_AN features serve as a proxy for background estimation. Complementary pairing can be used to compensate for sampling variation from illumination to illumination of the same or different media. This can mitigate the effects of instrument or sensor drift, ambient changes in temperature and humidity and sensor orientation relative to the medium or the degree of sensor contact therewith. It is important that, in the tissue glucose embodiment, the same NO-GL features are paired with different Zyotons, thereby indicating that they are re-used in multiple independent computational collisions. One advantage of reusing NO-GL features is a reduction of the needed detector bandwidth for glucose detection. Glucose absorption is broadband and seen, to some extent, in most of the wavelength region between 1000 and 1700 nm. Measurements outside that wavelength window can increase detector cost and complexity substantially due to the need for more expensive materials.

The computed spectral absorbances (based on the reflectance values in Table 14) in the acquired spectra generally correspond to 2 to 5 absorbance units, meaning that between 0.001% to 1% of the amount of light input to the tissue is detected. The bio-optical simulation described above has shown the net absorbance due to glucose (as an example of an analyte of interest) in optical spectra acquired by sampling the skin tissue to be on the order of $10^{-8}$ to $10^{-6}$ absorbance units. As this net absorbance is well below the background noise level in the spectra, selective amplification of the net energy absorption changes due to glucose is essential.

Collision computing is used here to amplify the estimated net energy absorbed by the analyte over a range of absorbance of up to twelve orders of magnitude to achieve a MARD in estimated versus reference glucose values numerically less than 15%. To achieve this level of accuracy over the range of possible concentration values of glucose in blood or tissue from 20 mg/dl to as high as 1,000 mg/dl, can require the post-collision dynamic range of the measured spectral energy increase from collision computing to be six to eight orders of magnitude to accurately measure the actual glucose concentration.

Zyotons are thus selected to provide the needed signal amplification of six to eight orders of magnitude, and as many as a few hundred thousand repeated collision iterations may be required to yield a SCR increase of this magnitude, i.e., the expected required SCR. The Zyoton frequency bandwidth, the number of collisions, and the carrier kernel are strongly interrelated to achieve the expected SCR increase required to achieve the target accuracy. The expected interference due to concomitant NIR energy attenuation from scattering or spectroscopic confounders present in the medium sampled by the NIR sensor in the same spectral regions as the analyte of interest in a particular spectral band (e.g., the 1000 nm to 1700 nm spectral band), the sensor SNR, the specified level of accuracy, precision in the estimated analyte concentration, and the sensor sensitivity, stability, and resolution are used to guide the selection and configuration of the Zyotons, the collision-computing parameters, and the carrier kernel parameters used to measure tissue glucose using a tomographic spectroscopy platform, as described above.

The measurement of blood glucose concentration without requiring an invasive procedure can benefit a large population all over the world. To this end, human tissue can be viewed as a medium which contains glucose—the analyte of interest. Several confounders such as water, fat, collagen, and urea, are also present in the human tissue. Various embodiments of the illumination/detection system (e.g., described above with reference to FIGS. 68-70) to direct NIR light to human tissue (e.g., a portion of skin on the arm), to receive radiation reflected from or transmitted through the tissue, and associated embodiments of a collision computer directed to the measurement of blood glucose using the received radiation, are described below.

Illumination and Detection Systems for Measurement of Glucose

In various embodiments, a spectrometer can make non-invasive optical measurements of glucose in a patient's tissue using near-infrared light. In an embodiment that is suitable for use in a laboratory setting, the illumination/sensor system may include a near-infrared spectrometer, a fiber-optic probe, and an attached computer. The near-infrared spectrometer can be a table mounted Fourier transform infrared (FT-IR) such as a laboratory grade research instrument (Thermo Fisher 6700 FT-IR spectrometer), or a miniaturized system of much smaller dimensions. In some embodiments, all electrical and optical components, including, for example, the interferometer, a He—Ne laser used for wavelength calibration, a tungsten-halogen source, and optical filters and mirrors, are separated from the patient using an insulated mechanical encasement that also provides thermal and optical isolation. In some embodiments, the optical system of the spectrometer can block the light from the source except for wavelengths in the 1000 to 1700 nm range prior to coupling the light to a fiber optic bundle through an encased mechanical stage. As a result, only a small fraction of the bulb's energy may be applied to the patient's arm (e.g., less than 5 mW/mm$^2$).

Light can be delivered and collected through a fiber-optic cable, which may be up to 6 feet (or longer) in length. The fiber-optic bundle may include illumination fibers that distribute the delivered energy in a predetermined pattern on the skin surface and detection fiber(s) that collect the reflected light and deliver it back to the spectrometer system for analysis. In some instances, the fiber bundle has an approximately 1 cm² flat tip or probe that comes into close proximity to the patient's arm, either with or without an intervening inert and bio-compatible fluid (e.g., Fomblin grease, FC-40 or FC-70 fluorocarbon oil manufactured by 3M). The probe can be mounted on a stand above the dorsal aspect of the patient's arm, which may be resting on a flat surface (FIG. 99A) or on a cushioned foam pad, such as an arm cradle manufactured using sponge foam with a leather housing (FIG. 99B). The probe stand may optionally include a linear actuator which moves the fiber optic probe close to the patient's arm prior to the start of data collection.

In some instances, data collection events are initiated by commands from a computer that is attached to the spectrometer, to a linear actuator, and to an encased mechanical stage. The computer may receive the non-invasive near-infrared measurements from the spectrometer and may record the collected data for subsequent glucose measurement using collision computing.

An optical imaging source and detector system as depicted in FIG. 68 can be used to acquire spectral data from a person's skin and may include a fiber optic probe as depicted in FIG. 69. The fiber-optic probe is coupled to the light source and the detection system in the spectrometer. The probe includes a central detection fiber to capture diffuse reflected NIR light that traverses through and is reflected out of the skin. As shown in FIGS. 68 and 69, a portion of the skin depth can be illuminated by one or more NIR source arrangements ($S_1$ through $S_K$) that are disposed at different distances from the central detector fiber e.g., in concentric rings around the central detector. The radiation may traverse through different layers in varying depths of the skin, and may be absorbed by the molecules of glucose and any confounders located in those layers, depicted schematically by the various geometric symbols in FIG. 68.

FIG. 70 shows an alternative design, where the probe has a central illuminator and a number of detector fibers arranged in rings. While the probe shown in FIG. 69 may be easier to construct, the probe shown/used in FIG. 70 can offer greater photon collection efficiency and light throughput. The collision-computing processes described above are applicable to both designs.

Referring to FIGS. 68 and 69, the probe includes a central detection fiber made from a 600 micron diameter multi-modal optical fiber, and six concentric rings (R1, R2, R3, R4, R5, R6) of tightly nested illumination optical fibers made from 200 micron fibers. FIG. 68 shows the notional light path for the launched photons through the skin when a transverse section is examined, with rings of greater diameter providing photons which reach the detector fiber after generally traversing successively greater depths. Different rings can be illuminated in different sequences.

An example of one illumination sequence is S1, S2, S3, S2, S5, S6 wherein the rings R1, R2, R3, R2, R5 and R6 are sequentially illuminated. In one embodiment, the path lengths, that is, the distances from the center of the detector fiber to the center of source ring in for the probe are: (S1) 200 μm, (S2) 400 μm, (S3) 600 μm, (S4) 800 μm, (S5) 1000 μm, and (S6) 1200 μm. One or more rings may be used to construct an MIS. Also, multiple rings may be simultaneously illuminated. The duration of each illumination is one second, although shorter or longer durations can be used. One embodiment of an MIS for non-invasive measurement of glucose is S45, S2, S2, S3, S3, S4, S4, ALL where rings 4 and 5 are illuminated simultaneously, followed by ring 2, followed by ring 2, followed by ring 3, followed by ring 3, followed by ring 4, followed by ring 4, followed by illuminating ALL rings in the probe simultaneously. Each illumination generally yields a spectrum in the 1000 nm to 1700 nm range.

It should be understood that the number of rings used here, and the designation of rings or ring combinations to particular illumination states is illustrative only. Different numbers of rings, e.g., 4, 10, 12, 15, etc., and different designations of rings and/or ring combinations of two or more rings are contemplated. It should also be understood that a ring generally represents a particular set of sources of light such as fiber-optic bundles, light emitting diodes, or laser diodes or alternatively, a set of detectors. This set can be circular, elliptical, square-shaped, rectangular, triangular, hexagonal, etc. The set can also be one or more segments or an arc of the shapes described above. The shape of a ring can be selected according to the size and other properties of the medium to be analyzed and the nature of distribution of the analyte and/or one or more confounders therein.

Figure 129A:
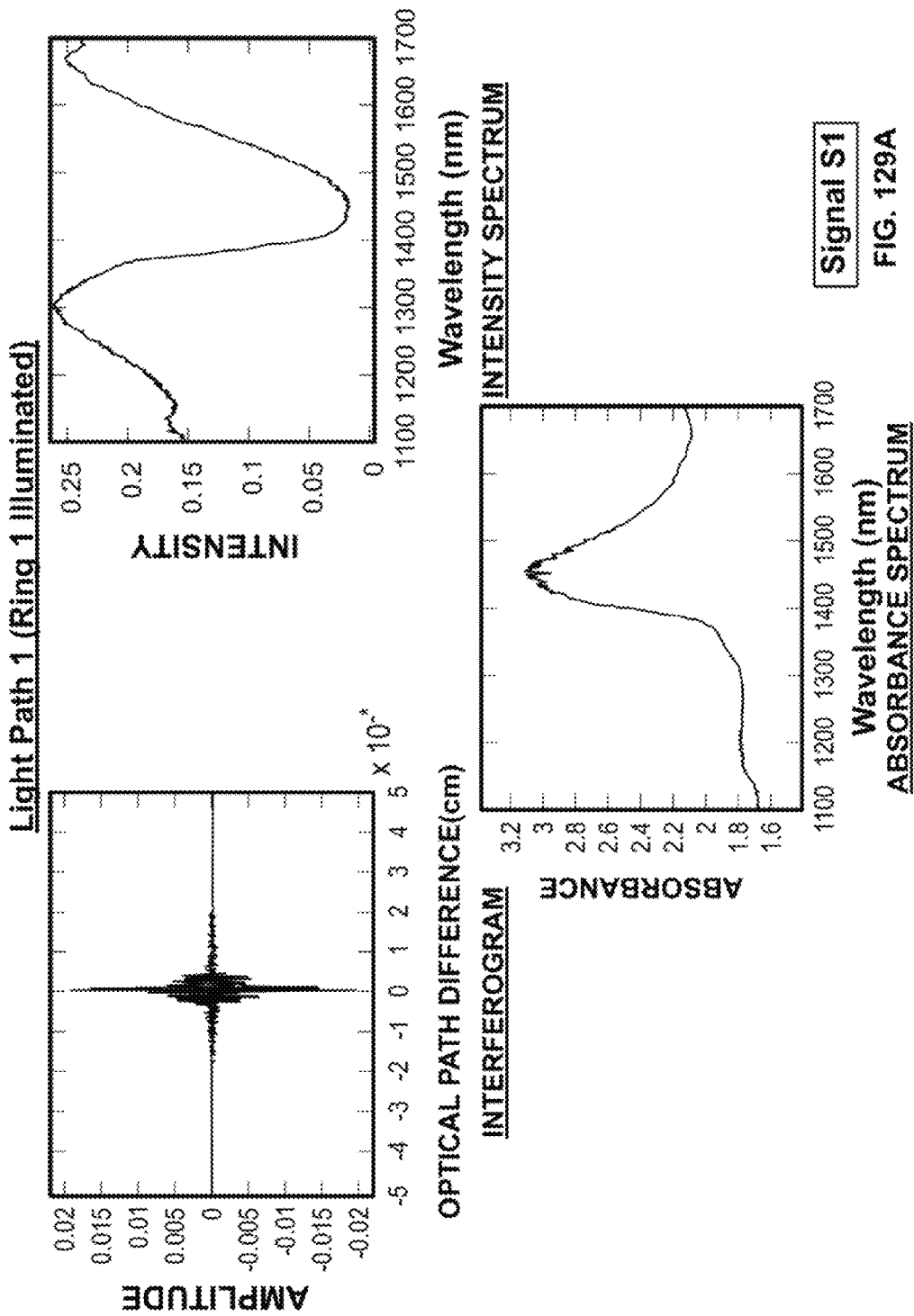
Figure 129B:
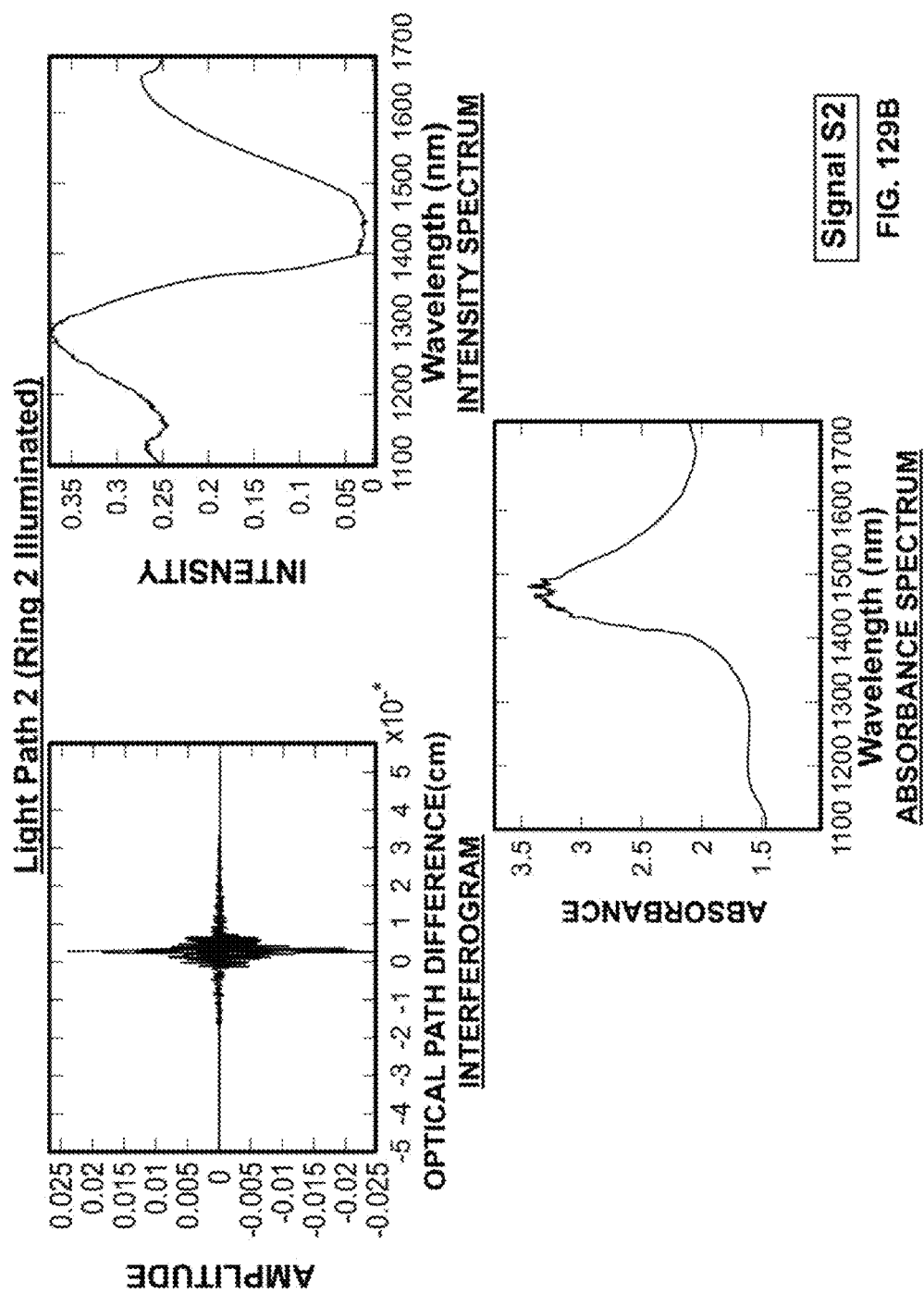
Figure 129C:
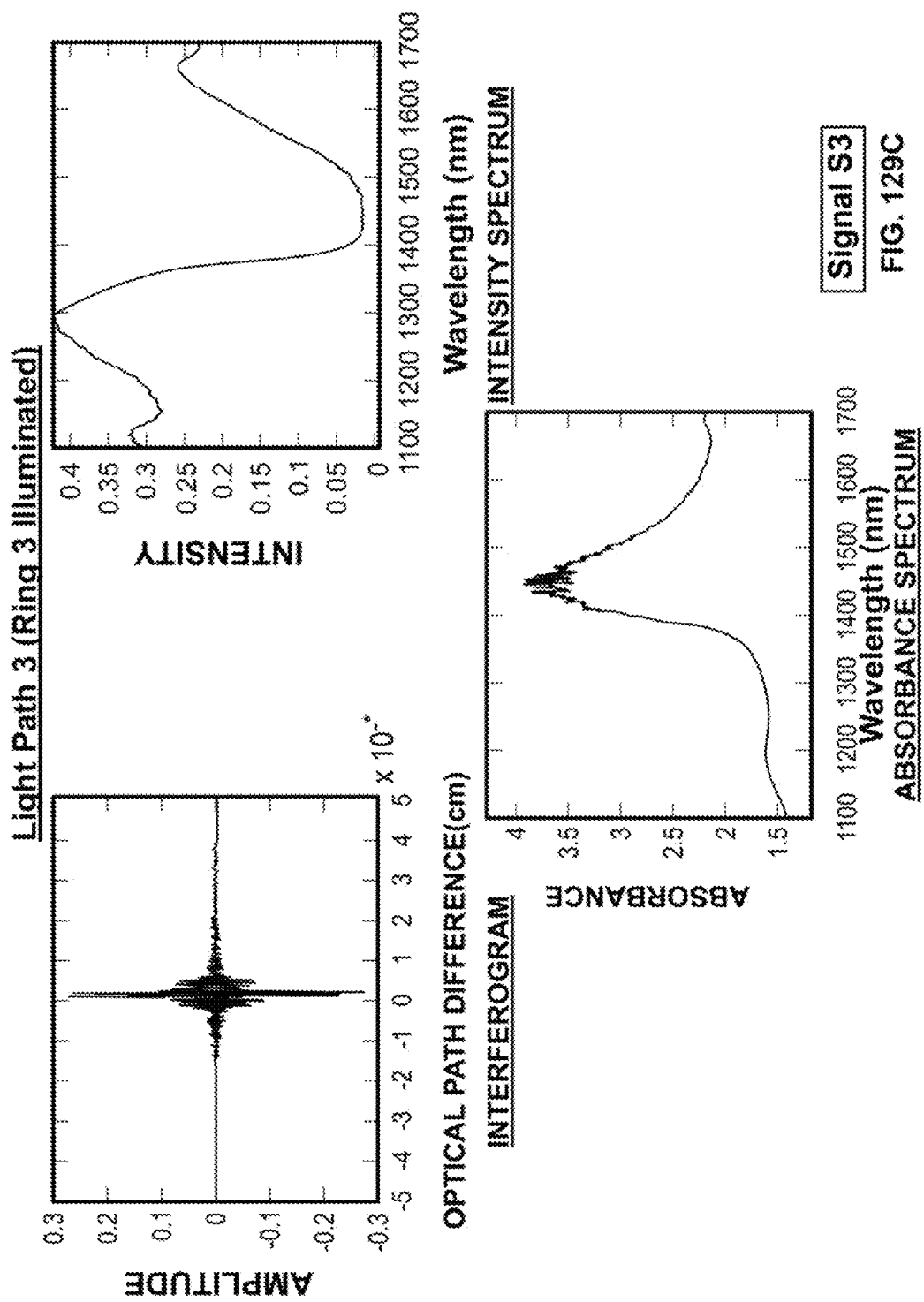
Figure 129D:
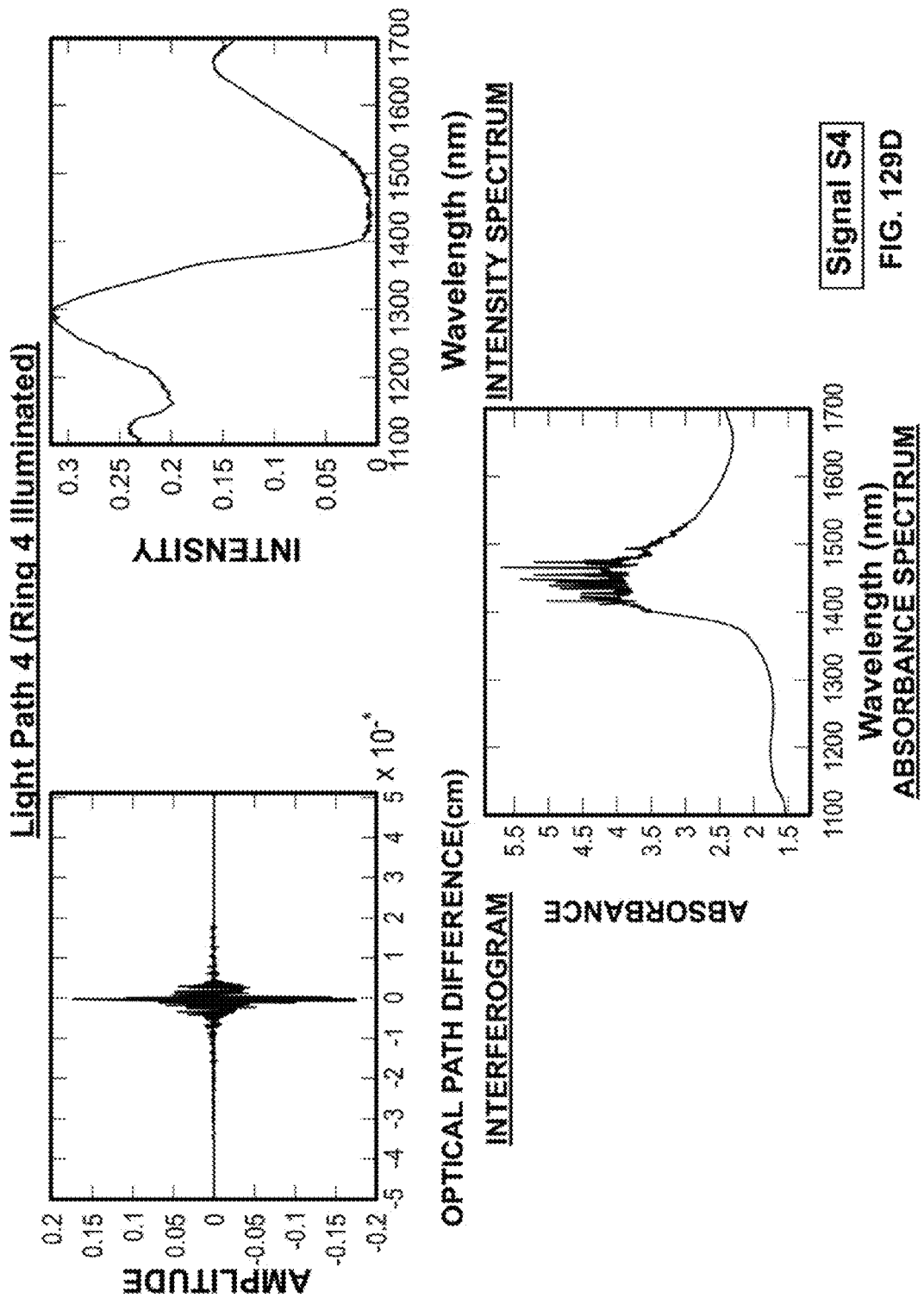
Figure 129E:
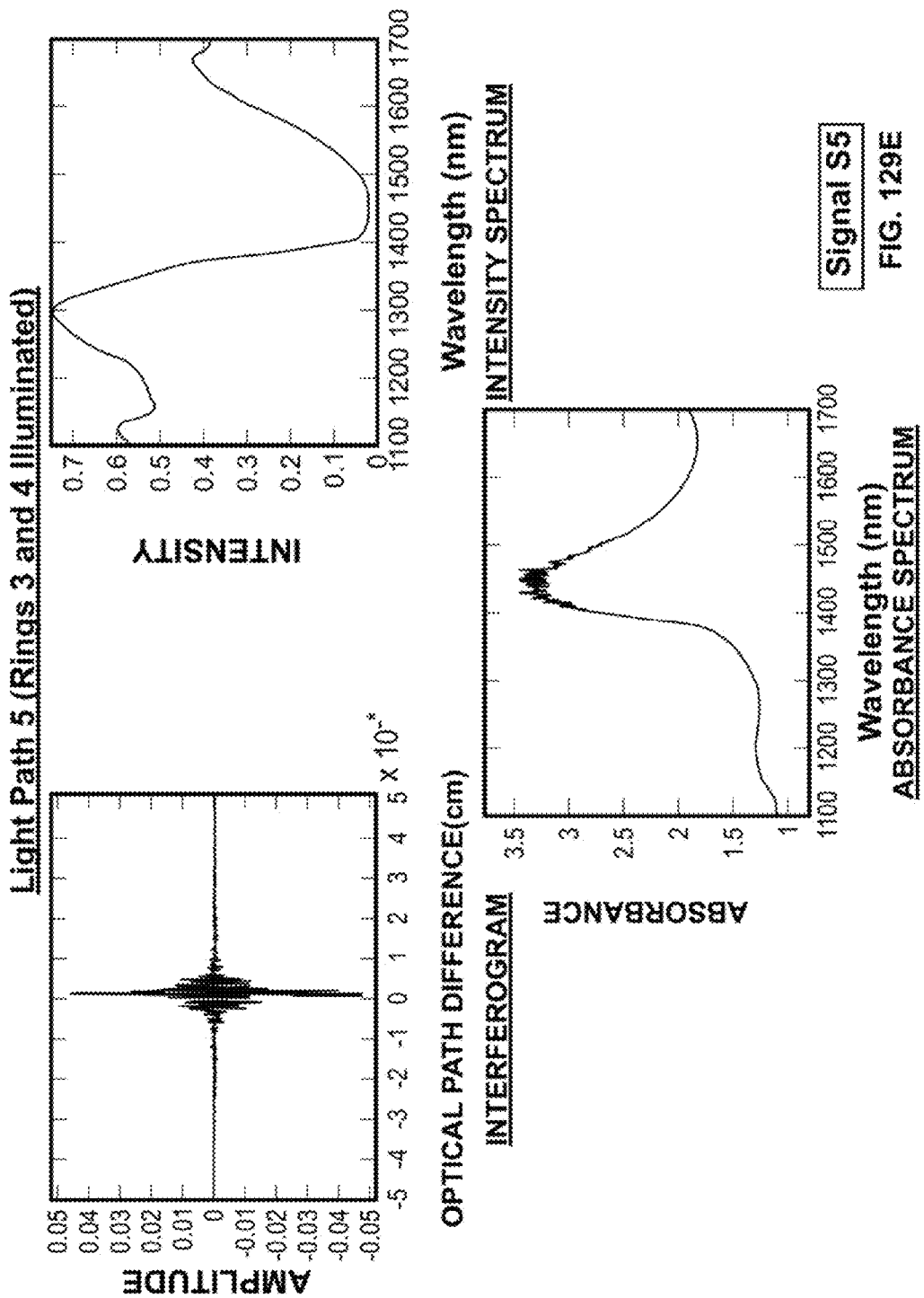
Figure 129F:
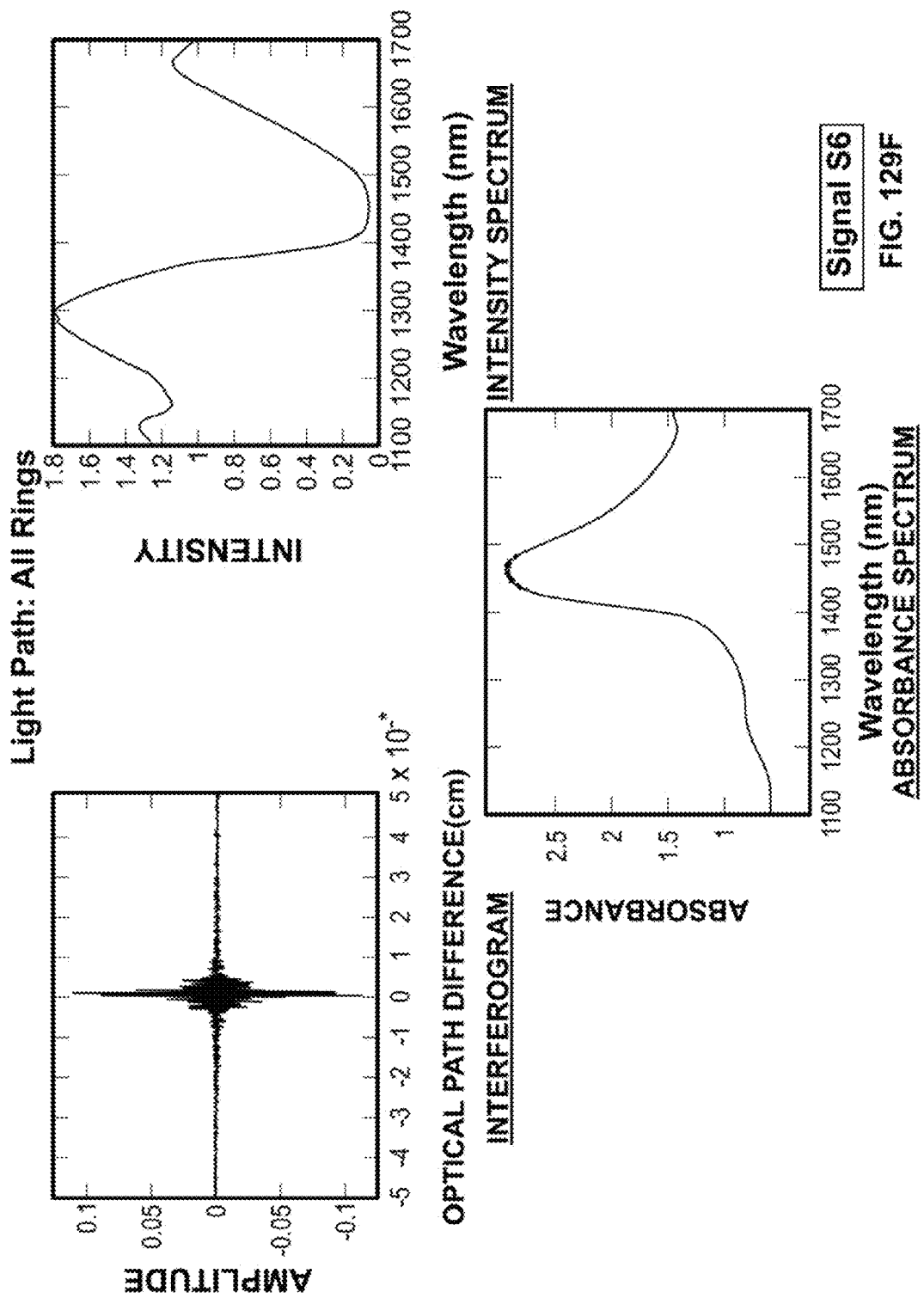

In various embodiments, the interferograms obtained according to the MIS described above are converted into intensity spectra corresponding to the signal reflected from a medium, i.e., the skin, as described above. Parameters, such as the bandwidth and the process employed for this purpose may be optimized to improve the SNR and data quality for non-invasive analyte detection/measurement. FIGS. 128A-128B depict different intensity spectra collected when the sample is illuminated in a collection sequence. Specifically, FIGS. 128A-128B show two examples: a high noise example and a desirable low noise example with minimal tissue optical transients. The entire set of signals may be collected in each acquisition. FIG. 129A shows the intensity spectrum generated from illumination of ring $S_1$ shown in FIG. 68. Similarly, FIGS. 129B through 129F show the intensity spectra generated as different rings are illuminated, including the combination of two rings (3 and 4 in FIG. 129E) and all rings illuminated simultaneously in FIG. 129F.

The light rings may be denoted by a position ID associated with them. In some instances the system collects data in a particular sequence based on position ID. For example p (45-5-5-4-4-3-3-All Rings) where the IDs 5, 4, 3, 45 refer to the ring number or combination of rings in the illumination sequence. The system can then acquire an intensity spectra associated with each sequence entry: $x_{p,rp,rep}(k)$, k: 1,2, ... $N_s$ where p∈[positions] is the ordinal ranking of illumination, i.e., rings 4 and 5 are simultaneously illuminated first and ring 5 is illuminated second in the above sequence; rp is the position (or ring) repeat—for example there are two illuminations of ring 5, two of ring 4 in the above example p; and rep is the sample replicate—i.e., the entire sequence performed twice or thrice in succession in the same spectral acquisition.

The total spectral acquisition time is typically a function of the number of different illuminations and can use hardware that involves movable parts for directing light to the skin. The number of repeats of the same illumination position is influenced by instrument drift and illumination source stability over time. Unstable or drifting systems require more repeats. The total number of intensity spectra in the data packet is P. In one embodiment, full sequence repetitions can be two minutes apart, and can be used to determine a rate of change in glucose concentration. Immediate repeats can be averaged to improve accuracy.

An intensity spectrum/vector can be converted into an absorbance spectrum using a corresponding reference spectrum, as described above. In one embodiment, if any element of $x'_{p,rp,rep}$ is equal to zero, it is set to $10^{-5}$. Thereafter, an absorbance spectrum/vector is computed as:

$$x'_{p,rp,rep}(k) = \max(x'_{p,rp,rep}(k), 10^5), \forall k, p, rp, rep \quad (31)$$

$$a_{p,rp,rep} = -\log_{10}\left(\frac{|x'_{p,rp,rep}/x_r|}{1}\right), \forall p, rp, rep \quad (32)$$

Bars in the Equation above represent absolute values of sampled intensities.

FIG. 129A shows an example of how the absorbance spectrum (on the wavelength axis) is generated using the illumination from ring $S_1$ shown in FIG. 68 and the above described computation, followed by division by the background spectrum to generate the absorbance spectrum. Similarly FIGS. 129B through 129F show how spectra are generated when different rings are illuminated, including a combination of two rings (3 and 4) in FIG. 129E and all rings illuminated simultaneously in FIG. 129F. In various embodiments, collision computing for glucose concentration is conducted using absorbance spectra on the wavenumber axis. A rare earth oxide standard may be used to calibrate the wavelength axis.

Outlier Rejection in Glucose Spectra

For each intensity spectrum in a data packet used for tissue glucose measurement, a step can include determining the degree of contact, which may include using the following equations:

$$v_{p,rp,rep} = 1/L\Sigma_k x'_{p,rp,rep}(k), \forall k \text{ such that } 6873 \text{ cm}^{-1} < wn_r(k) < 6920 \text{ cm}^{-1} \quad (33)$$

and L is the number of elements in $wn_r$ between 6873 and 6920 cm$^{-1}$ (1455 and 1445 nm). If $v_{p,rp,rep}$ associated with any spectrum is greater than the threshold, T, the sample may be flagged as being a contact outlier. FIGS. 128B-128A show example spectral profiles when acceptable patient contact is made and when no-contact is made, respectively. The quality of contact is amplified in the water absorption band around 1450 nm.

In instances in which all rings are illuminated simultaneously, the method may include checking for spectral outliers. In some cases, the minimum minus maximum absorbance in the wavenumber region of 8000-8700 cm$^{-1}$ should be less than −0.6. In some cases, this step can include the following steps using the following equations: The average absorbance between the wavenumbers 6873 and 6920 cm$^{-1}$ is calculated as:

$$h_{p,rp,rep} = 1/L\Sigma_k a_{p,rp,rep}(k), \forall k \text{ such that } 6873 \text{ cm}^{-1} < wn_r(k) < 6920 \text{ cm}^{-1} \quad (34)$$

where L is the number of elements in $wn_r$ between 6873 and 6920 cm$^{-1}$ (1455 and 1445 nm). The average absorbance is calculated between the wavenumbers 7600 and 7800 cm$^{-1}$ as:

$$q_{p,rp,rep} = 1/L\Sigma_k a_{p,rp,rep}(k), \forall k \text{ such that } 6006 \text{ cm}^{-1} < wn_r(k) < 6061 \text{ cm}^{-1} \quad (35)$$

where L is the number of elements in $wn_r$ between 7600 and 7800 cm$^{-1}$ (1316 and 1282 nm). In some embodiments, if $q_{p,rp,rep} - h_{p,rp,rep} > -0.6$ the entire sample is flagged as a spectral outlier. In different embodiments, different wavenumber regions and/or thresholds may be used according to the properties of the radiation generation and detection hardware and/or the properties of the medium to be analyzed.

Glucose Features

FIG. 107 shows, the features in more and less strongly glucose absorbing regions, and the features that may be used in a collision computing, for example, in conjunction with a radiation/detection subsystem that uses an Indium Gallium Arsenide (InGaAs) detector configured to operate in the 1000 nm to 1700 nm range. In one embodiment, each individual feature, conditioned to provide a corresponding conditioned feature waveform, is collided with its corresponding Zyoton. A spectrum obtained from each illumination state is deconstructed into 34 features, listed in the Table in FIG. 83, and the overall data package from illumination sequence of rings #4+#5, #2, #2, #3, #3, #4, #4, #ALL rings produces 272 features that may be collided with corresponding Zyotons. FIG. 130 shows an expanded wavelength illustration of one group of features.

Pairing of Glucose and Non-Glucose Features and Zyotons

The pairing used in one embodiment for non-invasive glucose measurement is shown in the table in FIG. 49. The table shows how 22 features covering regions in which glucose more strongly absorbs NIR radiation are paired with 11 complementary features covering regions in which glucose more minimally absorbs NIR radiation, and also with different Zyotons for collisions. The example mapping of features and Zyotons can is shown in the table in FIG. 49.

Each glucose feature (PosCon_GL or "GL") is paired with a complementary NegCon_GL ("NO-GL") feature. Each NegCon_GL ("NO-GL") and PosCon_GL ("GL") pair is associated with a specific Zyoton—also specific to a particular illumination state. Some NO-GL features are paired with several different GL features and, depending on the Zyoton pairing, collide with different Zyotons. In some embodiments, the table is loaded into the collision computer as a master control sequence for collisions for each sample (e.g., including several spectra) from the noninvasive tomographic acquisition sequences. Although the table in FIG. 49 list only 33 feature pairings, more or fewer features and corresponding feature and Zyoton pairing are possible.

Based on the table in FIG. 49, some examples of collisions for rows 1 and 10 of the table in FIG. 49 are shown in Table 19:

TABLE 19

| | |
|---|---|
| NO-GL-1 ⊗ Z_kernel_E1; | GL-1 ⊗ Z_kernel_E1 |
| NO-GL-1 ⊗ Z_kernel_D1; | GL-1 ⊗ Z_kernel_D1 |
| NO-GL-1 ⊗ Z_kernel_S1; | GL-1 ⊗ Z_kernel_S1 |
| NO-GL-1 ⊗ Z_kernel_MM1; | GL-1 ⊗ Z_kernel_MM1 |
| NO-GL-4 ⊗ Z_kernel_E2; | GL-10 ⊗ Z_kernel_E2 |
| NO-GL-4 ⊗ Z_kernel_D2; | GL-10 ⊗ Z_kernel_D2 |
| NO-GL-4 ⊗ Z_kernel_S2; | GL-10 ⊗ Z_kernel_S2 |
| NO-GL-4 ⊗ Z_kernel_MM2; | GL-10 ⊗ Z_kernel_MM2 |

Different features generally represent different levels of spectral energies associated with their corresponding modulated waveforms (the conditioned feature waveforms) which are also a function of absorbance due to glucose concentration. Using these features from uncharacterized samples with vastly differing analyte spectral energies (spanning 2 to 5 orders of magnitude in absorbance space), the post-collision energy change on a feature-by-feature basis can be quite different. Also, as shown in Table 11 above, amount of the incident NIR light entering the skin in a spectroscopic tomographic illumination sequence that yields the spectral dataset can be quite different, depending on the illuminated ring or combination of rings illuminated simultaneously.

Thus, a single Zyoton is often insufficient for colliding with all the different conditioned features generated from different features that may be extracted from different spectra acquired during a multiple illumination sequence. Different Zyotons (with different frequency components and/or amplitude profiles) are generally required to amplify spectral energy absorption due to glucose when analyzing the detected absorbance data from different rings. In some embodiments, illuminated rings R2, R3, R4 and ALL Rings, in an illumination sequence, yield four different absorbance profiles.

To balance the post-collision changes, to compensate for differences in incident light intensity (depending on the illumination sequence state), and to ensure that co-dependency condition on post-collision dispersion velocities and waveform divergence are met, 16 different Zyotons with different spectral energies were used in one embodiment for glucose measurement. Zyoton kernels E, D, S and MM represent 4 families of Zyoton kernels, i.e., waveform families and/or frequency generators used in Zyoton synthesis, as shown above in Table 19.

Different spectral energies are associated with the diffuse reflectance detected during different ring illuminations. Given the radial distance between a single illumination ring and central detection fiber in some embodiments, the mean path of NIR radiation below the skin is typically limited to the epidermis, dermis or subcutaneous regions. When all the rings are illuminated, the light spans all the below-skin layers to an approximate depth of 2 mm. Different skin layers represent different biochemical composition with varying levels of glucose, fat, protein, water, and other compound concentrations. Biochemical models provide guidance for the relative concentrations of tissue glucose in these regions vis-á-vis each other, and their associated absorbance. Empirical experiments of calibration data from human subjects in a controlled clinical study with reference samples was used to build different absorbance models for different layers.

These absorbance models indicate that different Zyotons are needed for analyzing feature data from different illuminations. Also, the features from each illumination state were further grouped into 4 classes in some embodiments. Each of the classes represented different levels of glucose absorbance. This resulted in an overall system of 16 Zyotons as shown with the Zyoton feature mapping shown in the table in FIG. 49 and the pairing relationship shown above.

As described above, Zyoton kernels E, D, S and MM represent four different families of kernels with different spectral energies, but when paired with the appropriate conditioned feature, the co-dependency condition was met in the case of each feature. Using the examples given above, the total number of feature pairings for each sample analysis is 4×22+4×22=(176) using the 16 distinct Zyotons. If the tomographic sequence includes several identical replicates, then the total number of pairings M is given by the following equation: M=#replicates*2* (# distinct GL & NO-GL feature pairings).

If a collision iteration count of $\mathbb{N}$ is implemented, then the total number of collisions, at the feature level, is given by M*$\mathbb{N}$. Typical values of $\mathbb{N}$ can range from the low tens to 100,000 or more, and numerous collision iterations are performed in various embodiments, as described above. In one embodiment, $\mathbb{N}$ for the non-invasive detection of glucose measurement in human subjects was set to be 20,000. As another example, $\mathbb{N}$ of 100,000 was used for analyzing glucose in a synthetic tissue phantom.

In general, the number of collision iterations may be determined according to one or more of the following four factors: Factor (i) The dynamic range of the spectral energy change required between the lowest expected concentration of the analyte and the highest expected concentration of the analyte. Higher dynamic range requires more collision iterations (also called collisions). As described above, spectral energy changes in each collision iteration are accretive. Thus the total spectral energy change is typically proportional to the number of collisions.

Factor (ii) The expected signal-to-clutter increase required: A higher SCR increase requires more collisions, as do more confounders with absorption in the same spectral band (e.g., NIR region for glucose). Different analytes may require a more even distribution of peak energies in lower and higher amplitude frequency components of the feature waveform for all concentrations of the analyte of interest. More collisions are often required to separate and amplify absorption energy changes from scattering-induced losses.

Factor (iii) The target accuracy and precision in the estimated analyte concentration: higher precision and accuracy both require more collisions, as a higher accuracy requirement translates into a finer gradation of the target dynamic range; and Factor (iv) The sensor resolution. Lower sensor resolution generally leads to a requirement for higher collision counts. Collision count is typically very sensitive to sensor resolution. This factor imposes an inverse relationship between collision count and sensor resolution. During a collision computer configuration, a collision count of 20,000 may be set for a sensor with 0.5 nm resolution for glucose detection, assuming a SCR of 0.0001.

Calibration

For glucose concentration measurement using spectra obtained by NIR illumination of skin, using some embodiments of the non-invasive systems described herein, the net energy loss due to glucose absorption in the tissue was turned into a glucose concentration using mapped projector curves developed from the measurement of subjects and tissue phantoms with known glucose concentrations, as described above. As a single composite projector curve for glucose concentration using this technique was found to be nonlinear over the dynamic range needed for human tissue ranging from 20 mg/dl to 1000 mg/dl, several overlapping individual curves, as described above, were used to properly cover the range.

In one embodiment, a collision iteration count of 20,000 was used to accommodate SCR <0.0001; 0.5 nm sensor resolution, a dynamic range of spectral energy change of $10^7$, and a MARD goal of under 15%. The tomographic spectroscopy platform and collision computing method described above was implemented and evaluated in an institutional review board-approved (IRB) prospective, single-sample correlational design clinical study with primarily insulin-dosing subjects with Type 1 diabetes, without controls. The purpose of the study was to evaluate the performance of the non-invasive glucose monitor described above against invasive home-use blood glucose monitors.

The system was trained and calibrated using data collected during three (3) single-day visits by different subjects without diabetes. Readings were recorded at 15 to 20-minute intervals. At each 20-minute interval, a non-invasive tissue spectral dataset ("sample") was acquired using the system described above and a blood glucose reading was taken from the finger and from an alternate-site (AS) dorsal side of the subject arm at locations within 2 to 3 inches from the fiber optical probe placement location on the arm. An Abbott Freestyle™ blood glucose meter was used as a reference system for this study. The estimates of noninvasively measured glucose concentrations were subsequently calculated using this calibration for all 9 subjects with the same measurement parameters.

To test the predictability of the system outside the training envelope (e.g., the instrument parameters originally used), several changes were made in the hardware configuration from the calibration setup when concentration calculations were made with this calibration set for a group of subjects called the "prediction set." For example, the acquisition time for a calibration set for the entire tomographic sample was around 4.5 minutes compared to 30 seconds for the prediction set. Also, the instrument used a 2.4µ bandwidth InGaAs detector during calibration, versus a 1.9µ bandwidth InGaAs detector at the time of prediction visits. Also, the calibration data was averaged over 16 scans (with a resolution of 4 $cm^{-1}$) versus one scan at the same resolution for prediction visits.

The prediction set included a total of 526 data samples acquired over 8-to-10 hour, 18-single day visits from the 9 different subjects, with 25 to 35 samples per day. The visits were on two consecutive days. Immediately after acquiring the spectrum, alternate-site capillary blood glucose and finger-stick reference blood glucose concentrations were measured. The alternate site location sampled was always on the same arm as the spectral measurement, and finger stick measurements alternated fingers. Throughout the study, the reference values were not provided to study personnel who calculated the predicted values until the final correlations were performed.

Demographic breakdown of the subjects is shown in the Table 20 below. Subjects in the prediction set were not part of the calibration set. Subject SUB-6 was reported to have type 2 diabetes, but was totally insulin-dependent and treated with an insulin pump and a continuous glucose monitoring system. This subject exhibited minimal c-peptide levels more typical of type 1 diabetes.

TABLE 20

Demographic Breakdown

| PATIENT ID | GENDER | AGE | DIABETES TYPE |
|---|---|---|---|
| SUB-1 | Male | 12 | Type 1 |
| SUB-2 | Female | 17 | Type 1 |
| SUB-3 | Male | 13 | Type 1 |
| SUB-4 | Male | 16 | Type 1 |
| SUB-5 | Male | 59 | Type 1 |
| SUB-6 | Male | 27 | Type 2* (c-peptide -) |
| SUB-7 | Male | 17 | Type 1 |
| SUB-8 | Female | 17 | Type 1 |
| SUB-9 | Male | 44 | Type 1 |

This was a non-significant risk (NSR) daily life-simulation study in which no control was placed on meals, subject activity or insulin administration, or insulin dosing time. Subjects took two meals per day that included breakfast and lunch. The estimation results from the collision-computing based measurement are summarized in FIGS. 100-103, 131A-131B, 132A-132B.

Clarke Error Grid Analysis can provide a framework to quantify the clinical accuracy of blood glucose measurements obtained using experimental measurements as compared to the blood glucose values obtained using a reference measurement (such as YSI, a LifeScan One Touch™ blood glucose meter, or an Abbott Freestyle™ blood glucose meter, etc.). The Clark Error Grid has become accepted as one of the "gold standards" for estimating the accuracy of new devices for measuring blood or tissue glucose. The Clark Error Grid breaks down a correlation scatterplot for a reference glucose measurement and an evaluated glucose monitoring system into five regions: Region A are those values within 20% of the reference sensor; Region B contains points that are outside of 20% but would not lead to inappropriate treatment; Region C are those points leading to unnecessary treatment; Region D are those points indicating a potentially dangerous failure to detect hypoglycemia or hyperglycemia; and, Region E are those points that would represent a significant danger by confusing treatment of hypoglycemia for hyperglycemia and vice-versa.

Figure 100:
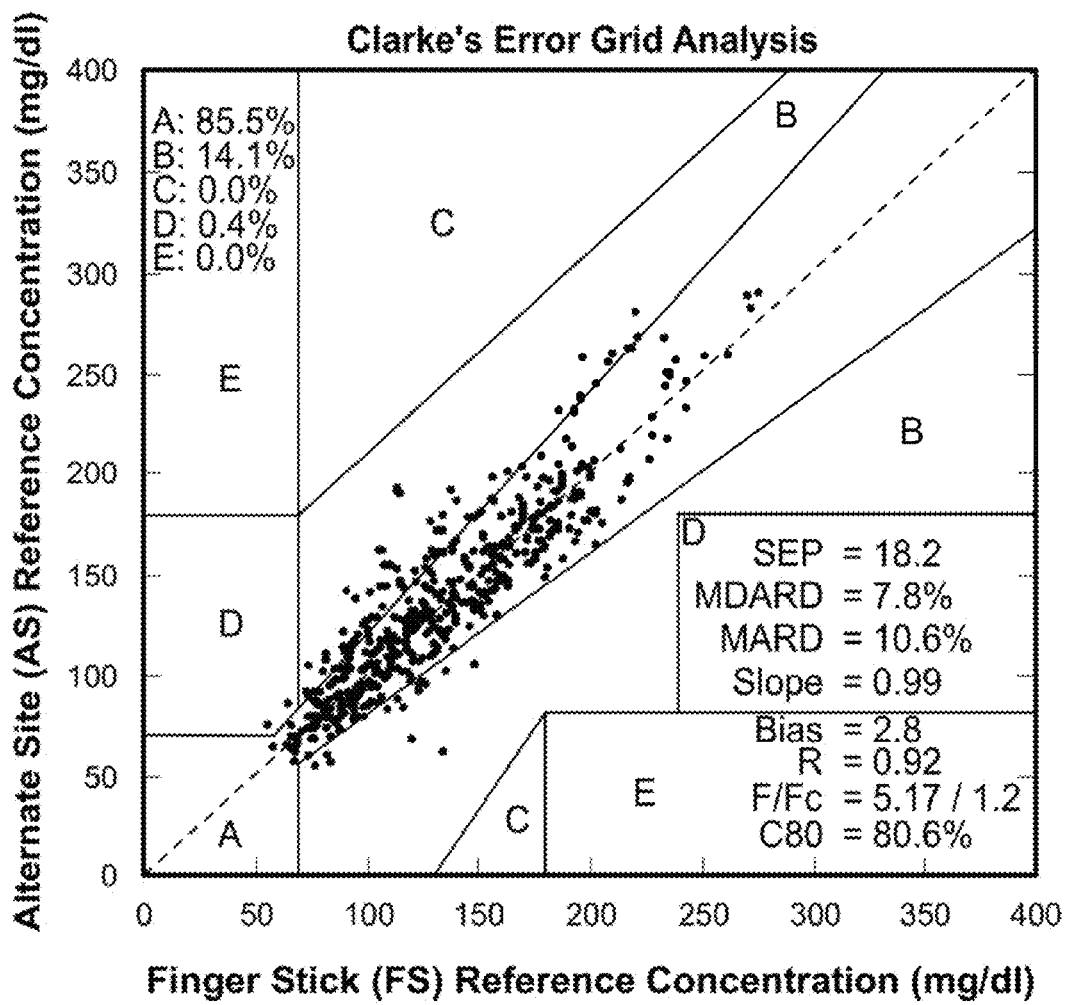
FIG. 100 shows a Clarke Error Grid plot of comparison of a glucose results obtained from the arm with glucose results obtained from the fingertip.

FIG. 100 shows a Clarke Error Grid comparison of a reference system used to measure blood glucose from the finger, with the same reference system used to measure blood glucose from an alternate site, i.e., the arm, illustrating that the two reference measurements agree in accuracy with a MARD of 10.6% and an R value of 0.92.

Figure 101:
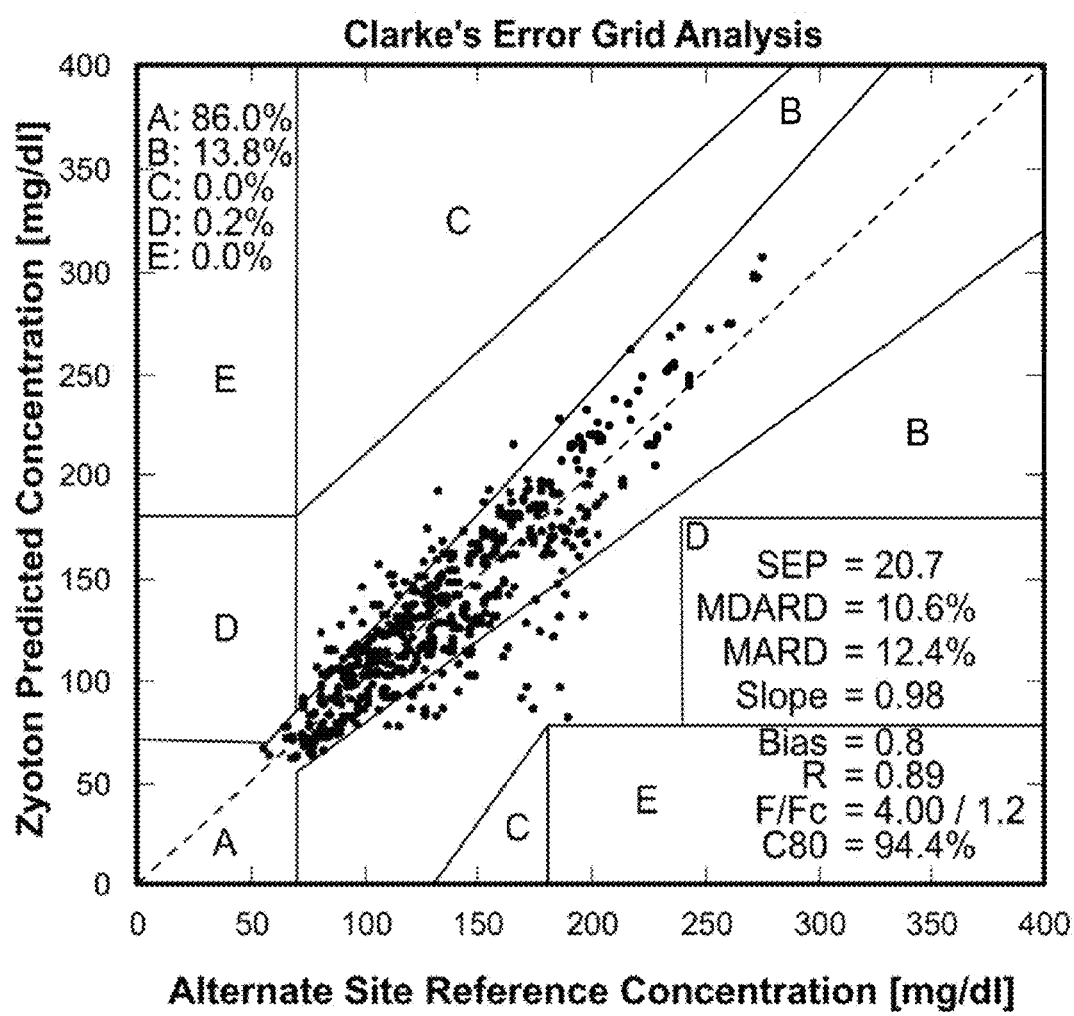
FIG. 101 shows a Clarke Error Grid plot of comparison of a glucose monitoring system utilizing collision computing and a reference system used to measure blood glucose from an alternate site.

FIG. 101 shows a Clarke Error Grid comparison of a glucose monitoring system utilizing collision computing with a reference system used to measure blood glucose from the arm ("alternate site"), illustrating that accuracy with a MARD of 12.4% and an R value of 0.89 were obtained. True noninvasive glucose measurements with this level of precision have not been reliably reported with any previously employed system.

As the results in FIG. 101 indicate, using collision computing in conjunction with the projection process detailed herein also yielded a value of "C80 Accuracy," (a term generally representing the percentage of glucose levels calculated as below 80 mg/dl that are within ±15 mg/dl of the reference value, and referred to in FIG. 101 as "C80"), of over 90% (94.4% in the results shown in of FIG. 101) when the non-invasive tissue measurements were compared to invasive blood glucose measurements from an alternate site.

Figure 102:
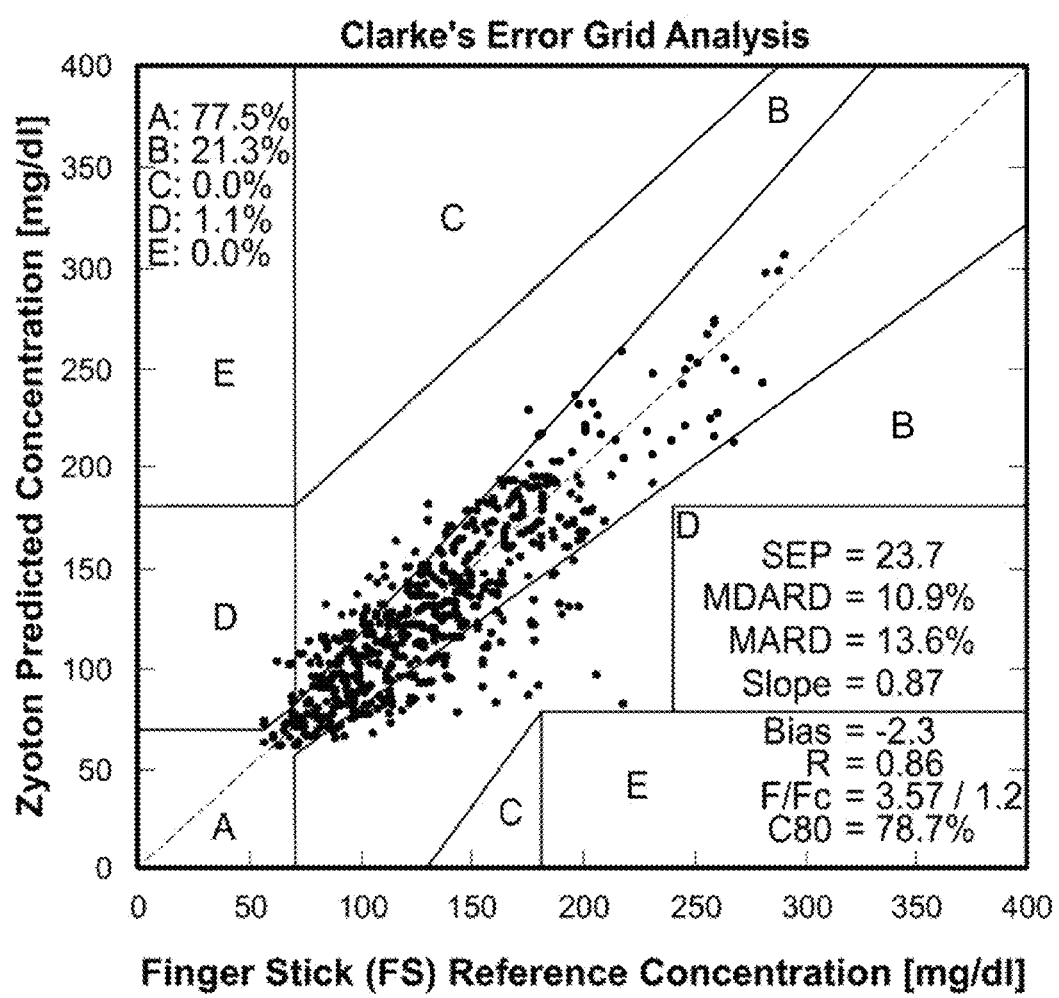
FIG. 102 shows a Clarke Error Grid plot of comparison of a glucose monitoring system utilizing collision computing and a reference system used to measure blood glucose from the fingertip.

FIG. 102 shows a Clarke Error Grid comparison of a glucose monitoring system utilizing collision computing with a reference system used to measure blood glucose from the fingertip, illustrating that accuracy with a MARD of 13.6% and an R value of 0.86 was obtained. In this case, the "C80 Accuracy" figure was over 75% (78.7% in the results shown in FIG. 102) when the non-invasive tissue measurements were compared to invasive blood glucose measurements from the finger.

Figure 103:
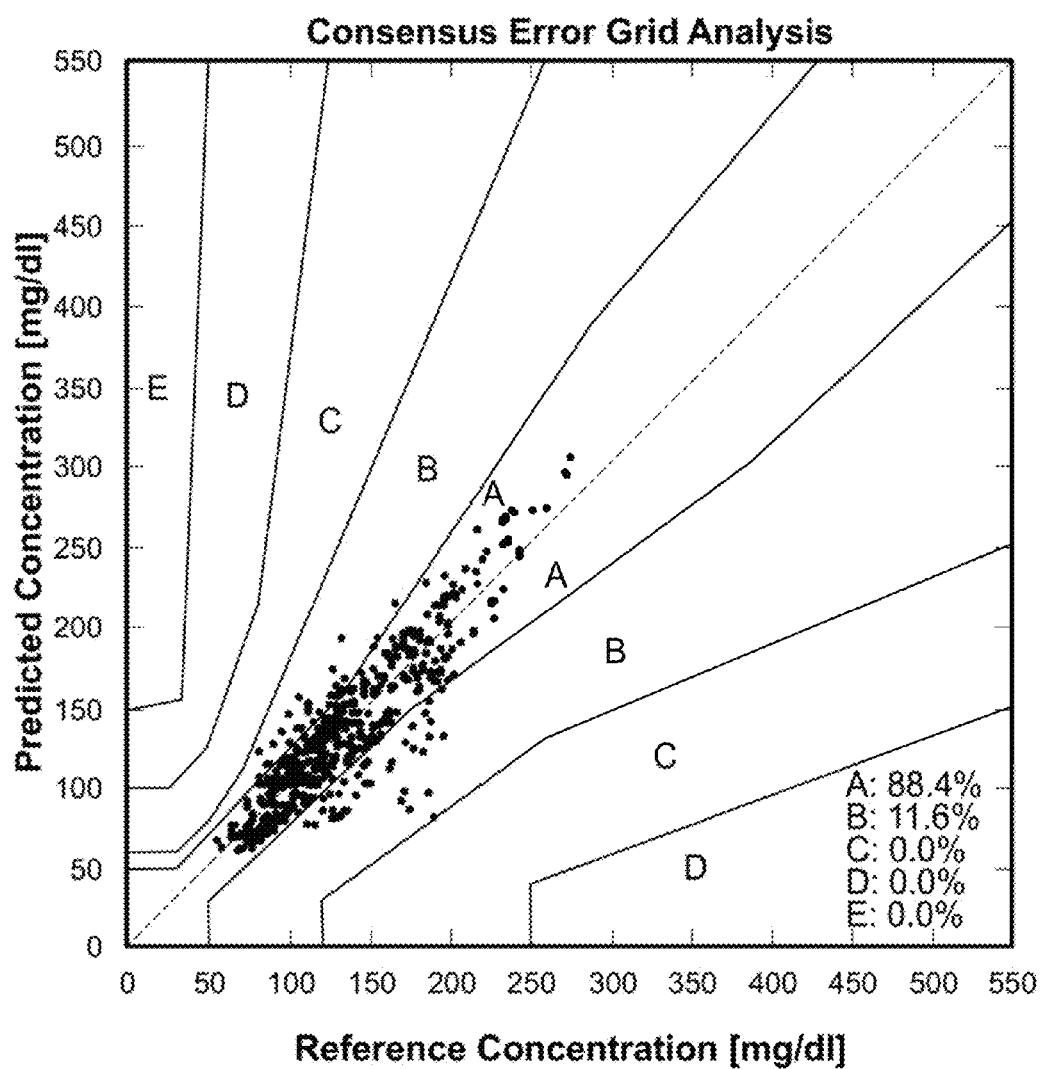
FIG. 103 shows the same results as FIG. 101, using a Consensus Error Grid.

FIG. 103 shows a similar comparison of results as in FIG. 102, but comparing the performance of collision computing based glucose estimation on a Consensus Error Grid (or Parkes Error Grid analysis) adopted by some clinicians. Consensus error grid assumptions are formed on the basis of five risk levels, which are labeled and described as follows: A: predicted blood glucose (BG) 20% difference from reference BG or both predicted and reference B below 70 mg/dl; region B: difference from reference BG within 20% but leads to no treatment or benign treatment; region C: overcorrection of acceptable BG levels; region D: dangerous failure to detect and treat BG errors; and E: erroneous treatment (i.e., treatment contradictory to that actually required). All, i.e., 100% of the estimated blood glucose results from collision computing were in the A or B region as seen in FIG. 103.

FIG. 131A shows a tracking curve of estimated glucose values obtained using collision computing compared to alternate site reference measurements. A correlation R of 0.96 was achieved for that visit for Subject 8. FIG. 131B shows the tracking curve of estimated glucose values obtained using collision computing compared to finger stick reference measurements. FIG. 132A shows the tracking curve of estimated glucose values obtained using collision computing for Subject 2 compared to the alternate site reference measurements. A correlation of 0.94 was achieved for that visit for Subject 2. FIG. 132B shows the tracking curve of estimated glucose values obtained using collision computing compared the finger stick reference measurements for Subject 2, with an R of 0.97.

After the glucose concentration has been determined, in various embodiments it can be provided to a user, and may also be used in analytics that include non-invasively predicted hypo/hyperglycemic alarms; determination of insulin sensitivity, insulin response, glycemic response, HbA1C, exercise response, wellness information, and fasting glucose levels.

Analysis of Other Types of Data

In addition to the use of spectroscopic measurement data for analysis of biochemical analytes in tissue, data from many other spectral, imaging, and other data sources can be analyzed with the collision-computing process described herein. The collision-computing and projection processes can be extended to other types of data where the information sought can be the equivalent of an analyte. Detection and/or measurement of an analyte in this context can be the detection or identification and/or measurement of any material, property, magnitude, event, anomaly, or condition using or from data acquired from a source. Such data is considered to be acquired form a "data-collection domain."

Figure 67:
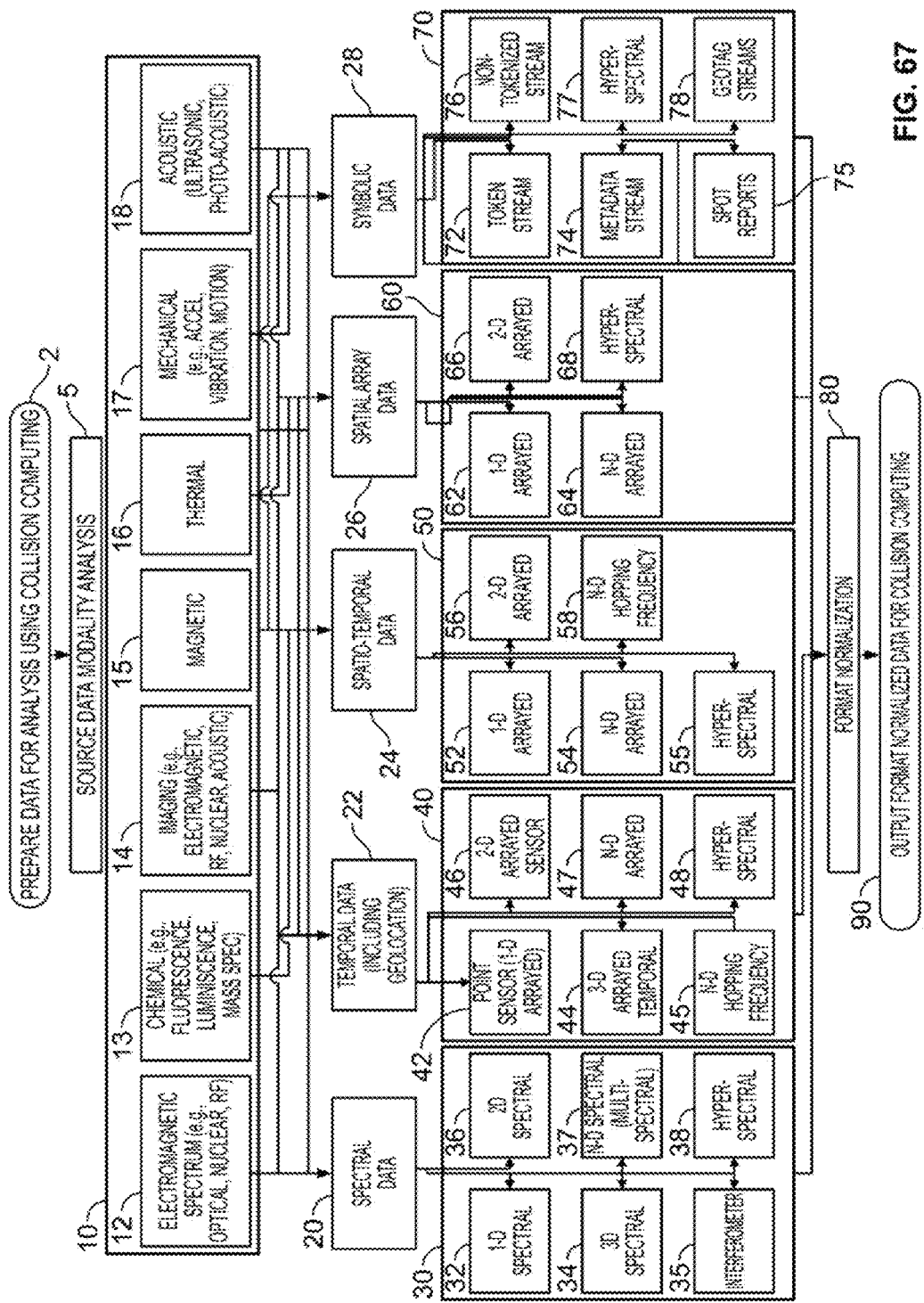
FIG. 67 illustrates other data forms that can be analyzed by collision computing, according to various embodiments.

FIG. 67 includes examples that indicate the diversity of the sources of other data and data types that may be subjected to the collision-computing process. In order to process these data using a collision-computing process described in various embodiments, the acquired data can first be transformed to the same data formats as those used in the noninvasive glucose example discussed above. Thus, after the transformation, one or more feature vectors can be represented as $\overline{x}_w(1:L)$ of some finite length L>0 and 0>w>W, where W is the number of features, L is feature length, and each element of the $w^{th}$ feature vector, at position i, given by $x_i$, is associated with a numerical amplitude value. In its most generalized form, a spectrum can be represented as a one-dimensional (1-D) amplitude vector where the spectral intensities represent the vector amplitudes, and the vector indices, e.g., i=1 to 384 correspond to the 1050 nm to 1700 nm NIR region with a 4-wavenumber instrument resolution, to provide a "semantic vector." Once data from different sensor types and data streams are transformed to an analogous representation that includes an amplitude vector and an associated semantic vector, the collision computing process can be applied.

Features containing amounts of energy corresponding to the information sought may be extracted from the source data in the same fashion as wavelength region features are extracted for glucose analysis using a spectroscopic tomography system with a number illumination states. These features can selectively represent the property sought, the absence of the property sought, and/or the presence and/or quantities of any confounders, and such features can be paired with one or more Zyotons designed to correspond to the different features.

As FIG. 67 illustrates, there are many data types or forms, data-collection domains, in general, of physical sensor data, imaging and video data, and computer data objects or tokenized data streams, which can be subjected to the collision computing process. A tokenized data stream refers to a human or machine processed, ordered collection of symbols (numerical, text, or alphanumeric character sets) that have been used to replace structured or unstructured data including text (articles, reports, messages, spreadsheets), images, video, audio data, and other sensor data, or any combination of these data types. Many of these data modalities involve the measurement of physiologically important substances or conditions, while others can relate to forms of physical data generated by a wide variety of sensors and data sources.

An example that shows the breadth of this approach is the use of optical, non-invasive photoplethysmography (PPG) data, which can be processed to measure heart rate, heart rate variability (HRV), heart rate recovery (HRR), and pulse transit time (PTT) for blood pressure, respiration rate, oxygen saturation, blood pressure and cardiac output assessments, neurologically induced skin perfusion changes, brain asymmetry, and also for detecting peripheral vascular disease. The example below describes an embodiment for the determination of heart rate.

As described above, one technique of applying collision computing to other data forms is to apply transformations that reformulate such data and the desired outputs to the data forms and process described above for non-invasive glucose measurements. This can be achieved by applying the process 2 in FIG. 67 that prepares data for analysis using collision computing. This can be achieved, at least in part, by establishing parallels between data structures (such as features), and the calibration and projection systems employed in the glucose example. This way, rather than establishing entirely new collision computing paradigms for each type of data, only a conversion of the other data types into the spectroscopic data used in non-invasive glucose determination may be performed, together with refinements of the calibration and projection process as required by the different data formats and the required results.

The initial step 5 of source data modality analysis determines the syntactic transformations and semantic normalization required to re-cast and format different datatypes into a "Normalized Data Format" for use in collisions. Specific syntactic transformations can be different for different data forms such as spectral (e.g., radio frequency, "RF"), thermal or other image data, and magnetic dipole moment (e.g., gradiometer) data, because the syntax and semantics of data involved in different modalities in Unit 10 can be different. For example, electromagnetic data 12, acquired from optical, electromagnetic, RF, nuclear, or mechanical sensors can be spectral data 20, temporal data 22, (e.g. from LIDAR), spatio-temporal data 24 (e.g. from radar), spatial data 26 (e.g., from a laser scanner), or symbolic data 28 (e.g., from a Doppler radar).

Similarly, data from chemical sensors 13, imaging sensors 14, magnetic sensors 15, thermal sensors 16, mechanical sensors 17, or acoustic sensors 18, can be acquired as spectral data 20, temporal data 22, spatio-temporal data 24, spatial data 26, or symbolic data 28. Location or geolocation data format can be treated as spatial data or as spatio-temporal data if the geolocation data is also associated with a capture or event timestamp. Collectively, the terms spectral, spatial, spatio-temporal, symbolic, and temporal data are referred to as syntactic modalities. Sensor data collection attributes for a specific syntactic modality, including the sensor dynamic range, sensor spatial/temporal resolution, sensor SNR, data collection time window, number of collection repeats/replicates can be used to perform source data modality analysis in step 5 to determine the computational transformations to generate feature data in a normalized data format. The set of applicable computation transformations represented as 30, 40, 50, 60 or 70 are related to the syntactic modalities 20, 22, 24, 26 and 28.

For example, if the spectral data are acquired from a single element spectrometer (e.g., a UV-visible spectrometer, an NMR (nuclear magnetic resonance sensor), or an atomic spectrometer) and is in the form of a 1-D spectral dataset 32, it can be disassembled into features in a process analogous to the glucose example described above. If the spectral data are acquired from a several-detector device such as a two-dimensional (2D) dispersive spectrometer, a 2-D NMR, or a 2-D-mass spectrometer such as MALDI, all of which yield a 2-D spectral dataset 36, the data can be disassembled into a number of 1D vector representations. Similarly, a 3-D mass spectrometer dataset 34 can be disassembled into a number of 1-D vectors for subsequent disassembly.

Some multi-spectral sensors, e.g., ultrasonic RF sensors for structural analysis, that yield n-dimensional spectral data 37, can be referred to as producing N-D spectral data, which can then be transformed into a collection of 1-D spectral representations. Optionally, some sensors such as a FTIR spectrometer 35, yield interferograms for each acquisition cycle, which can be first Fourier-transformed to obtain 1-D spectra 32 which may be processed further as described above.

Another sensor class, e.g., hyperspectral optical or electro-optical sensors 38, such as those used in target identification and classification, provide a 1-D spectrum for each pixel. In such cases, the process of transforming the data to a 1-D spectral representation is similar to that used for glucose, and may entail two steps to obtain features in some embodiments. The first step applies a pixel segmentation process to identify and group pixels that are assessed to have imaged the same object, followed by feature generation from the 1-D spectral data from all pixels associated with a segmented group of pixels. Pixels associated with different groups of segments may be processed in groups. If the target of interest is not known to be associated with any pixel of a hyperspectral sensor, then all the 1-D spectral vectors associated with all pixels may need to be transformed to a collection of multiple 1-D spectral vectors, and each vector may then be disassembled into features as in the case of glucose example, and then processed further using collision computing.

Temporal data 22 may include geolocation tracks (location of an entity over time) as the form of geolocation positions or amplitude vectors, $x(t)$ over $t=1, \ldots, T$. In the case of geolocation data, it may be optionally first transformed into distances from a fixed reference location in the same coordinate system as the geolocation data. If the temporal data is from a point sensor 42, such as a single element current, force, or flow-rate sensor that yields observation with intensity $x(t)$ as a function of time, then the intensity vector may be treated in the same manner as 1-D spectral data 32 and features may be developed by selecting groups of intensities $x(t_i), \ldots, x(t_{i+p})$ over different time intervals of length p, starting at a different position i.

A number of sensing elements may be combined to form a 2-D array 46, such as a force or capacitive film sensor. Data from such 2-D sensors 42 can be processed as multiple 1-D temporal streams. Similarly, 3-D arrayed temporal sensor data 44, such as data from a 3-axis rate gyro or 3-D geophone, may be processed as a collection of multiple 1-D temporal data streams as in 42. This process may be extended to the case of an N-D arrayed temporal sensor 47, such as a 9-axis multicomponent geophone used in seismic imaging, which is used to sense the directionally of p-wave and s-wave acoustic energy returns when optionally used in conjunction with a directional multicomponent energy source. Data from such N-D temporal sensor may be transformed into N 1-D temporal streams which may then be individually used for the selection of features.

Some RF sensing systems, such as RF receivers, are used to detect, collect and analyze RF energy in fixed energy bands corresponding to different frequencies, 45, over time, but the frequencies of such RF-detection systems can shift or hop over time. In such cases, the data may be 1-D or 2-D, but with different semantics of the frequency dimension. Data from such sensors can be treated as multiple 1-D temporal data streams, each of which may be transformed into features, and processed using the collision computing techniques described herein.

Some 2-D electro-optical imagers yield hyperspectral system data 48 that changes over time, where a 2-D group of pixels are associated with a 1-D spectrum. Such temporal data streams 36 can be treated as 2-D spectra, with each hyperspectral image processed at each instant of time. This can effectively reduce a 3-D temporal data stream, where each pixel is a vector, to specific wavelengths whose intensity value is changing over time.

Spatial data 26 can be 1-D, for example, a fiber optic strain gauge 62 where different locations of the fiber yield a strain measurement. Such data, in the form of a 1-D strain intensity vector over time, can be processed in a similar manner 42. 2-D arrayed spatial data 66 from CCD, thermal, or ultra-wideband (UWB) imagers may be transformed to concatenated 1-D spatial data from which features can be extracted. 3-D sensors such as wave gratings 54 used in imaging may be turned into a collection of multiple 1-D data 52 and processed as 1-D spatial data to generate features. Hyperspectral imaging sensors 68 may be used to develop features in a manner analogous to the hyperspectral temporal sensors 48.

Sensor data acquired from spatio-temporal modality sensors 50, where one or more sensor elements are used to collect data over time, may be processed in a manner analogous to the ways temporal or spatial data are analyzed. A distinction for this modality is optionally fixing the spatial or temporal dimension and then using the other (variable) dimension to generate 1-D vectors from which features may be developed. Examples of 1-D arrayed spatio-temporal sensors 52 include a group of one-axis accelerometers mounted on a system such as a smart phone, or a collection of microphones in a directional antenna. Visible or thermal video 56 is an example of 2-D arrayed spatio-temporal data. N-D arrayed systems 54 and N-D hopping frequency arrayed spatio-temporal sensors are seen in RF detectors used in RF sensors and directional C-band, microwave, X-band receiver arrays used in surveillance applications. Electro-optical hyperspectral visible video cameras 55 can yield spatio-temporal data streams in multiple dimensions.

The symbolic data modality 28 is a fundamentally different modality from 20, 22, 24 and 26. For example, a symbolic data stream may be generated, for example, from a text stream, document, audio-stream, video-stream, messages, chat, email, observations of events, or activities. Such a stream may be parsed and turned into a token stream where symbols are used to represent the presence of words, concepts (as in text or audio data), activities (as in video), or sightings (as in spot reports), using an underlying lexicon of tokens $TK_1, \ldots, TK_2$. The entire data stream may then be represented as a temporal stream of tokens TKi as a function of time TKi(t) 72, which may then be treated as the 1-D arrayed temporal data 42, and may be referred to as the token stream by assigning different numerical values to each token.

In processing symbolic data, the lexicon is maintained as a semantic data attribute to retain context, but features may be developed from the transformed 1-D token stream. If the occurrence or frequency of tokens is more important, then the occurrence or presence of tokens may be turned into a frequency histogram. The frequency histogram then becomes the proxy for the token data stream and may be used to generate features. In some applications, such as word spotting (i.e., analysis of an audio stream) to detect specific word occurrences, the audio stream may be directly turned into a frequency histogram 76 and analyzed as a non-tokenized stream. Speech recognition and speech understanding are examples of applications of data modalities 72 and 76. Spot reports 75 are human or machine-generated reports produced by completing pre-designed forms. Completion of pre-designed forms is analogous to confirming the presence of absence of tokens. Completed reports may then be transformed into tokenized or non-tokenized streams of data and transformed into features. Metadata 74 is analogous to spot reports in that the presence or absence of attributes may be used to develop token streams 72, which can then be processed.

In big-data applications, data sources may be large database tables, survey forms, audio or video captures (individually referred to as single-source) or a combination of all of these (multi-source). In such cases, two preprocessing steps may be used to turn these into a hyperspectral dataset which can then be used for selection of features using the steps 38, 48, 55, or 68, depending on how the dataset is produced. The two preprocessing steps may include tokenization of single-source or multiple-source data using a single-source lexicon or multi-source lexicon; followed by conversion to a numerical transformation 72 of tokens. Geotag streams 78 (such as GPS sightings of multiple receivers within a preset geofence or area) may be treated as analogous to token streams, wherein each received data point is treated as a token and each sighting treated as an occurrence of a token.

Once the data has been transformed into feature data for the encountered modality of a datatype of interest, i.e., format normalization 80, is completed, feature data may be generated. This is analogous to features extracted from time-domain spectra acquired as in the case of the noninvasive glucose example. Data 90 may then be output for further processing by collision computing. Once the entire collision-computing process is completed, the semantics of transformation into features may be used to project the results back to the data-collection domain. An example is provided below for the analysis of PPG data (an example of an optical 2-D temporal data modality 46), using the process and methods described above.

As an example, the transformation of PPG data to the spectral data representation used for non-invasive glucose can be performed in some embodiments as follows. In the art, PPG is a non-invasive, low-power, biophotonic modality for detection of perfusion or localized blood volumetric changes in subcutaneous vessels through skin surface measurements. Blood volumetric changes are inferred by analyzing the time-resolved Visible-NIR absorption differential between blood and the surrounding tissue bed that manifest as pulsations with each heartbeat. Exploitation of this phenomenon in PPG modality has found strong utility in clinical physiological monitoring, vascular assessment and autonomic function; specifically the use of a reflectance PPG signal in heart rate monitoring, With the increase in attention to wearable health and fitness monitoring systems, many investigators have tried to extract reliable information from the PPG waveform, but have been stymied by poor signal-to-noise ratio, noise and motion artifacts, and the lack of generally available sites on the body that generate reliable PPG signals.

In some embodiments, to make PPG measurements, the tissue is illuminated with visible and/or NIR light from a light-emitting diode (LED) source and the resultant scattered or transmitted light is measured with a photodiode. As described in Allen J (Physiological Measurement, March 2007;28(3);R1-39) and review by Tamura et al, "Wearable Photoplethysmographic Sensors—Past and present", Electronics 2104, 3, 282-302, in FIG. 133, the PPG waveform comprises of a pulsatile ("AC") physiological waveform attributed to cardiac-synchronous changes in the blood volume with each heartbeat, and is superimposed on a slowly varying ("DC") baseline with various lower frequency components attributed to respiration, sympathetic nervous system activity and thermoregulation.

As the tissue is highly perfused, it is relatively easy to detect the pulsatile component of the cardiac cycle. The DC component of the signal is attributable to the bulk absorption of the skin tissue, while the AC component is directly attributable to variation in blood volume in the tissue caused by the pressure pulse of the cardiac cycle as each cardiac cycle of the heart pumps blood to the limbs. Even though this pressure pulse is somewhat damped by the time it reaches the skin, it is enough to distend the arteries and arterioles in the subcutaneous tissue. The cardiac cycle refers to a complete heartbeat from its generation to the beginning of the next beat, and so includes the diastole, the systole, and the intervening pause. The frequency of the cardiac cycle is described by the heart rate, which is typically expressed as beats per minute.

Each cardiac cycle appears as a peak in the signal, as seen in FIG. 134. Because blood flow to the skin can be modulated by multiple other physiological systems, the PPG can also be used to monitor breathing, hypovolemia, and other circulatory conditions. Additionally, the shape of the PPG waveform differs from subject to subject, and varies with the location and manner in which the sensor is attached.

PPG generally operates on the principle that volumetric blood changes in the limb or digit result in changes in the optical density through and just beneath the skin over a vascular region. Apparatus having a light source (e.g., high intensity green light emitting diodes (LEDs) or Red or NIR LEDs) illuminates a small area of the tissue to which a transducer is applied. Light traveling through tissue can be absorbed by different substances, including pigments in skin, bone and arterial and venous blood. Most changes in blood flow occur mainly in the arteries and arterioles, compared to the veins. For example, arteries contain more blood volume during the systolic phase of the cardiac cycle than during the diastolic phase. PPG sensors optically detect changes in the blood flow volume (i.e., changes in the detected light intensity) in the microvascular bed of tissue via reflection from or transmission through the tissue.

Light scattered and transmitted through the capillaries of the region is detected by the photodiode, which is shielded from all other light. As the capillaries fill with blood, the blood density increases, thereby reducing the amount of light reaching the photodiode. The result causes resistance changes in the photodiode that can be measured and recorded. The two common modes of PPG include a transmissive mode where PPG devices can be worn on finger, toes, or clamps on ear lobe; and, a reflective mode where measurements are made on the cheek, forehead, or in the form of wearables such as watch, bracelet, on arm, legs, etc. In both modes, the received signal is assumed to be a measure of volume changes due to localized blood flow. Transmission mode occurs when the LED source is transmitted through the skin and detection occurs on the other side of the skin. This method can only be done through areas of the body thin enough for the photodetector to read a measurable signal.

The second mode, reflection, occurs when both the LED and photodetector are on the same side of the skin. As the LED emits light, the backscattered optical radiation from the blood pulsations is detected and measured. Whether the two components are placed across from each other across the skin or in parallel to each other on the same side of the skin, the photodetector measures the variations in blood pulsations and outputs a current that is formatted as a voltage for further analysis. Typical implementation of transmissive and reflectance mode is shown in FIGS. 135A-135B with error rates ranging from 2 bpm to 5 bpm during the resting state (when compared with HR derived from ECG), to 10 bpm to 30 bpm during low intensity exercise to 20 bpm to 50 bpm during high intensity exercise. Error rates using collision computing can be reduced to under 3 bpm during resting stage and low intensity exercise and under 10 bpm during high intensity exercise.

A heart cycle includes two states, i.e., systole and diastole, and the absorbance is different during these states. Specifically, the intensity of the attenuated light is highest during diastole when the diameter of the arterial vessels and hence the absorbance due to the blood volume is minimal, thus showing as a peak in the detected waveform. In contrast, the optical path length in the arteries increases during the systole period until the amount of absorbance reaches a maximum, which corresponds to the lower part of the curve in FIG. 133. Hence, the instantaneous heart rate can be extracted from the time interval of two successive peaks/feet which correspond to the local maximum/minimum point of the waveform.

In general, if there exists a $\lambda>0$ such that where $\Phi(t_i)>\Phi(t)$, where $|t-t_i|<\lambda$, the value at the point $t_i$ is the local maximum point, and $\Phi(t)$ is a function that represents the time-varying nature of the PPG waveform as shown in FIG. 134. Consequently we can obtain the time interval of two successive peaks: $\Delta t_i = t_{i+1} - t_i$, the inverse of which is the instantaneous heart rate. The average heart rate for a sequence of n heart cycles can therefore be calculated as:

$$HR = \sum_{i=1}^{n} \frac{1}{\Delta t_i} \quad (36)$$

Here the value of $\lambda$ is important since it can determine the local range for the maximum detection. For example, if it is greater than a heart cycle; only one peak is detected yielding a missing peak, thereby miscalculating the heart rate. FIG. 134 shows a typical PPG waveform and the local maxima $\Phi(t_i)$ with respect to the interval $\lambda$. In a practical setting, the local maximum/minimum points could be obtained via zero-crossing calculation methods through calculating the differences between adjacent elements of the original signal.

As shown in FIG. 136A, some embodiments use one or more green LED lights paired with light sensitive photodiodes to detect the amount of blood flowing through the wrist at any given moment. When the heart beats, the blood flow in the wrist and green light absorption is greater; between beats it is less. By flashing the LEDs at a rate of 100 Hz or greater, one can calculate the number of beats in each minute. FIG. 136B schematically shows a PPG monitor.

FIG. 137 shows the general principle of PPG waveform processing used in the prior art. Steps included collecting digitized waveform samples over a time window, followed by removal of the DC component and SNR estimation. Analog to digital gain scaling is applied to increase SNR as desired, followed by averaging to remove noise. When 3 to 5 peaks are detected, the heart rate is computed by taking the reciprocal of peaks over the time window. Often, the peak detection reduces to determining the start and end of a peak in the time domain or frequency domain.

In practical monitoring, the obtained plethysmographic signals might be influenced by various noises, e.g., motion artifacts, quantization effect, and electrical noise. PPG signal is highly susceptible to motion-induced signal corruption. Irregular movements, such as tennis or boxing, exacerbate the problem. So the key challenges in PPG processing are cancelling the effects of ambient light, accommodating different skin conditions and colors, and dealing with physical motion artifacts. Additionally, PPG with traditional measurement techniques can only be used on parts of the body that have a high concentration of blood vessels (for example, it can be difficult to get a good PPG signal from the wrist). Many additional factors, such as Skin perfusion, can affect the performance of PPG based heart rate sensor. Skin perfusion or the flow of blood in capillaries to the surrounding tissue bed, varies significantly from person to person and can also be impacted by the environment. For example, in colder temperatures, the skin perfusion may be too low for a PPG-based HR sensor to get a reading. Permanent or temporary changes to the skin, such as presence of tattoos, lesions, or scars, can also impact heart rate sensor performance.

FIGS. 138A and 138B show the distortion to the PPG waveform during a standstill state and with motion. The transition from standstill to motion state can typically represent a 20× reduction in SNR of the PPG waveform in the time domain and 10× in the frequency domain (based on periodogram distortion for the fundamental frequency). As motion becomes irregular, or there are large changes in the perfusion, the PPG waveform SNR can degrade to below 1:1 or 1:10. In such cases, peak determination based on local waveform amplitude or zero crossings is no longer viable.

Collision-computing presents a fundamentally different approach to PPG waveform processing, e.g., for determination of: heart-rate, heart rate variability (HRV), heart rate recovery (HRR), pulse transit time (PTT), oxygen saturation by measuring respiration rate measuring, blood pressure, etc., especially where the SNR is low, e.g., ranges from 1:100 to >1:1.

General Principles of PPG Data Analysis Using Collision Computing

In keeping with the principle described above of conversion of other data types to mimic spectroscopic data used in non-invasive glucose analysis, the PPG analysis process begins with an evaluation of the fundamental differences in data package acquired from a PPG data acquisition system to that used for glucose. While NIR tissue spectra for glucose determination are collected as discrete snapshots corresponding to different illuminations over time (a few milliseconds apart), they are analyzed in a time-invariant fashion; that is, spectral data are "static" and there is generally no consideration of time in the tissue spectral measurement. PPG data contains time-based information, and the temporal variability is of value in determining the "analyte" of interest, which is measurement of heart rate regardless of physical activity levels, postural position, or environment. In general, the term analyte represents a substance of interest that is present in a medium. In the glucose example, blood or tissue is the medium and glucose is the substance therein that is of interest, i.e., the analyte in the conventional sense. In the context of PPG however, one analyte is heart rate. Due to the significance of temporal variation in a PPG signal, rather than selecting discrete portions of a spectrum, time slices of the PPG signal can be used as "features" for collision computing.

In some embodiments, a PPG system includes L LEDs and P photodiodes operating in transmittance or reflectance mode as in FIG. 135A and 135B respectively. In some embodiments, L=P (i.e., each LED is paired with a corresponding photodiode), while in others L>P (i.e., at least one photodiode captures the response from one or multiple LEDs illuminated simultaneously), or L<P (i.e., at least one photodiode captures reflected optical signal from more than one LEDS). Let $\Phi(t,p)$ represent the time-varying nature of the PPG waveform as shown in FIG. 134, and detected by the $p^{th}$ LED, for p=1,, P and t≥0.

Similar to glucose spectral data, as discussed above, PPG data are subject to environmental effects, physiological variations due to activity levels, electronic noise sources, and large confounding effects that are grouped together into the term "clutter." The signal-to-clutter ratio ("SCR") is generally higher than in the case of glucose, but there is a similar intent to increase it to allow measurement within established clinical and general health monitoring needs. Where the figure of merit for accuracy in glucose was in one case described as concentration measurements within 15% of the "true" or reference value, one example of a comparable criterion in heart rate measurement is an error of under three beats per minute (bpm) as measured in each five-to-ten heartbeat periods in resting condition (sitting, standing, sleeping) and under 5 bpm during intensive exercise such as jogging, running, swimming or cycling, as compared to a reference system such as chest band (e.g. Polar V800 with chest strap) or compared to the heart rate derived from ECG measurements.

The basic separation of PPG signals into features equivalent to spectral features used in analysis of glucose begins with the identification of a PPG signal waveform feature related to each pulse cycle of the heart. When the beat is regular and the signal is strong, as in FIG. 134, any number of signal-processing approaches can be used to determine when a cycle begins. Current signal processing techniques for PPG processing, specifically waveform characterization for Min-Max, peak-to-peak interval, or pulse shape analysis include digital filtering, stochastic filtering, auto-regression, empirical mode decomposition, Kalman filters, wavelet decomposition, matched filters, neural network and fuzzy logic.

These approaches can determine beat events. Also, more recently 1-axis or 3 axis accelerometer data has been used to identify mode (such as walking, sleeping, running) and then combine with more traditional signal processing methods to better estimate HR. A key challenge with all conventional techniques is severe reduction in efficacy as signal to noise ratio decreases for any reason, which results in over- or under-counting peaks associated with the heart rate events. Since both the interval between cycles and the time of appearance, intensity, and duration of intermediate signals are of interest, care must be taken to use adaptive criteria, especially when signals are noisy, as shown in FIGS. 139A-139B.

When a selected traditional signal-processing technique indicates the start of a cycle, data can be acquired in varying lengths up to and beyond the inter-cycle timing period expected from observations of previous cycles. The time periods range from about two seconds for the lowest heart rate usually encountered to less than 200 milliseconds for heart rates up to 300 beats per minute, but in each case, the interval can be "sliced" into shorter subintervals that contain (or encode) the information of interest. One such piece of information is the location and depth of the "dichrotic notch" 4 that occurs between the two primary peaks of the pulse cycle, as shown in FIG. 134. Other information, such as heart function and blood pressure measurements, rely on the comparison of time of appearance, duration, and amplitude of observed shapes occurring during the pulse cycle.

By conditioning the time features extracted from a PPG signal with a carrier kernel (one designed for this embodiment to incorporate the specific frequency-domain components sought for amplification), each feature can be converted to a conditioned feature similar to that done for glucose. The conditioned feature can then be repetitively collided with a single or different Zyotons, also specifically designed for the frequency components intended to be amplified. A priori knowledge of the influences exerted by known conditions (such as due to malfunction of the heart including arrhythmia, coronary artery disease (CAD), angina, and cardiomyopathy) to be determined are used to guide the selection process for the features, the carrier kernel, and the Zyoton. After a sufficient number of collision iterations (generally less than in noninvasive glucose measurements owing to higher SNR and SCR of these data), the NRSEG for each feature is combined by a process similar to that used for glucose, in order to produce an equivalent net analyte signal (NAS) for the "analyte," i.e., heart rate, desired to be extracted from the PPG data.

Using a projection system similar to that of glucose, where PPG data acquired from subjects with known degrees of known conditions are used to create the projector curves as in glucose measurement, the quantity or degree of the analyte can be determined with the desired degree of accuracy. In the example of heart rate determination, the human calibration set may include subjects measured at rest and in various levels of exercise, with the reference heart rate measured by an ECG signal detector. Similarly, absorption gradients using NRSEG, the concept of the Normalized Absorption Gradient, and the projection to actual values for subject samples can be performed using projection structures equivalent to those employed in the glucose embodiment above.

Example of Heart Rate Data

The general appearance of a PPG waveform is shown in FIG. 140, with time on the horizontal axis, and a form of intensity on the Y-axis. The intensity can correspond to transmitted light, reflected light, or other optical signal intensity. FIG. 141 summarizes the process for computing a heart rate from a PPG sensor using the collision computing apparatus described in this invention. The process can be used to analyze the PPG pulse waveform, $\Phi(t,p)$ from some sensor, say the $p^{th}$ photodiode in an measurement system having one or more photodiodes for recording the reflected or transmitted light from an LED source.

The system can be operated in continuous-pulsed mode (where LEDs illuminate the skin at a preset on-off frequency) or in an episodic mode where LEDS are switched on-off for some interval, say for 15 seconds (the "episodic window") every 10 minutes (the "episodic gap" or "episodic displacement interval"); or for 5 seconds every minute; or even for 60 seconds every hour. The on-off frequency may range from 5 HZ to 256 Hz, while an episodic window could range from 3 seconds to 30 seconds), and an episodic displacement interval could range from 1 minute (during intensive exercise or a cardio workout such as aerobics) to 6 hours. The LED on-off frequency, episodic window, and episodic displacement interval can be explicitly configured by a user and/or may be configured using software, based on a user announcement (such as start of workout such as running, walking, cycling, swimming), or may be configured automatically using sensors such as 3-axis or angular accelerometers that determine type, intensity and duration of activity.

With reference to FIG. 141, in one embodiment for heart-rate determination, the logic for establishing on-off frequency ($\Omega$ in Hz), episodic window (EW in seconds), and episodic displacement interval (ED in seconds) for heart rate computations is received in step 5. Heart rate processing initiates when a start trigger input is received at step 10, and a PPG waveform is recorded. The digitized PPG waveform amplitudes $\Phi(t,p)$ where $t=1, \ldots, T$ where $T=\Omega*EW$, and p corresponds to the p-th photodiode source generating the PPG waveform data stream in the time domain are extracted at step 15. Depending on the subject's activity, HR may vary over the EW, but each beat duration is typically some multiple of $1/\Omega$ seconds. In one embodiment, T is set to 2i where i is an integer greater than 1 and T is greater than the expected beat duration (in seconds).

A multi-resolution time-slicing is performed at step 20 for preconditioning PPG data to be used as an input into collisions. The multi-resolution time slicing is implemented in some embodiments via windowing data into length WL=256 ms that is sufficient to capture the fastest beat rate expected where the PPG waveform sampling time is 16 ms (a fraction of $1/\Omega$), or other time that is generally different from the primary power line period. As shown in FIG. 142, the incoming data is simultaneously windowed into lengths 2WL (i.e. 512 ms), 4WL (i.e., 1024 ms) up to 8WL (i.e., 2048 ms), allowing capture of heart beats ranging from 300 bpm to 30 bpm.

Let such data streams be denoted by $\Phi(t,p,Wno)$ where Wno=1, 2, 3, and 4 to corresponds to lengths WL, 2WL, 4WL and 8WL, respectively. Also, $\Phi(t,p,1)$ is subsumed within $\Phi(t,p,2)$, $\Phi(t,p,2)$ is subsumed within $\Phi(t,p,3)$, and so on. An assumption is made that at least one beat occurs in the interval indicated by one of the windows Wno. If the bpm rate is close to the high end of the human bpm dynamic range then beats will be present in all time-windows. If, on the other hand, the bpm rate is close to the low end of human dynamic range, it will be present in the largest window corresponding to Wno=4. Also, per the Nyquist sampling theorem, the sampling frequency is set to be equal to at least twice the expected beat frequency. In various embodiments, the sampling frequency is set to be significantly greater than the Nyquist frequency. For example, in one embodiment, the sampling rate is set to be 16 times the highest expected beat frequency.

FIG. 143A illustrates this windowing of the PPG waveform 10 for a normal heart rate of 60 bpm, with the interval between beats of 1.0 seconds, 15. Window lengths of W, 2W, 4W, and 8W, are 20, 25, 30, and 40 respectively. An expanded display of window 50, corresponding to WL 20, shows the sampling intervals of every 16 milliseconds as vertical lines. FIG. 143B illustrates the PPG waveform 10 for a heart rate of 30 bpm, with the interval between beats of 2.0 seconds shown at 55, with the same windowing and sampling interval indications as in FIG. 143A. FIG. 143C, illustrates the PPG waveform 10 for a heart rate of 120 bpm, with the interval between beats of 0.5 seconds shown at 65, with the same windowing and sampling interval indications as in FIG. 143A.

It is further assumed that the beat event waveform shown in FIGS. 143A-143C can change in shape, amplitude, phase, and width. Let each data structure corresponding to the window $\Phi(t,p,Wno)$ be denoted as a feature. Data is collected for window of size WL and that is called Feature F(1,1). Data collection continues, and when window size 2WL is reached, all of that data is called Feature F(2,1), and so on for F(3,1), F(4,1) onwards.

Thus feature F(1,1) corresponds to data from time t=0 (or start of event trigger) to t=255 ms for Wno=1; feature F(1,2) corresponds to data from time t=256 ms to t=511 ms for Wno=1. Similarly, F(2,1) corresponds to data from t=0 to t=51 1ms; Thus total feature set can be represented as F={F(1,1),F(1,2), . . . ,F(1,8),F(2,1),F(2,2), . . . ,F(2,4),F(3,1),F(3,2),F(4,1)}, 15 members. The total episodic window is covered by EW/2048 ms spans of the largest window size. However, the windows {Wno=1, Wno=2, . . . , Wno=4} are moved by t=64 ms or length{Wno=1}/4 ms during the duration of episodic window. Hereafter, the processing is performed on all features in the set F.

From a logical view, PPG data is collected and sliced into time windows to generate features, i.e., data is collected for a window of size 8WL and then sliced into a smaller window. As described above, in one embodiment, the implementation follows a reverse procedure whereby data is collected for a window of size WL, then 2WL and so on.

FIG. 144 details conditioning of windowed PPG feature data, i.e., step 20 shown in FIG. 141. Feature data from each time-window $\Phi(t,p,Wno)$ is up-sampled by interpolation to 4096 points at step 22. A Fourier transform is performed on all features at step 24, followed by an optional amplitude modulation at step 26 to increase signal-to-noise ratio. At step 28, the features are used to modulate a carrier kernel CK that includes frequency components k, j, and m, (28) where, as an example, k=3, m=3 and j=4089. Spectral energy collision computations are intended to amplify the k-components.

With reference to FIGS. 145 and 141, the conditioned feature data is then entered into the collision engine 30. In the case of PPG, a single Zyoton Z is used. The Zyoton Z may be derived from the soliton families described above. Also, all the features associated with the set F are simultaneously introduced in the multiplexed collision engines 32, at step 30 (FIG. 141). For example, feature F1 collides with Zyoton Z in Collision Engine 1, feature F2 collides with Zyoton Z in Collision Engine 3, and so on. In some embodiments several different features are pipelined through a series of collision engines, each corresponding to data from a window with different accumulation length. A collision count as low as 16 may be used in the collision engine, assuming an SNR as low as to 1:100, with window length of 64 data points. Renormalization of the modified zyoton between collisions determines the spectral energy gain, computed as described above, but using k=3 components.

After completing the collisions NRSEG values associated with each of the features are computed in step 35 (FIG. 141). In one embodiment, each step through step 30 yields 15 NRSEG values corresponding to different conditioned features. The NRSEG values obtained from features with identical window sizes are averaged and reduced to 4 levels. As an example F(1,1),F(1,2), . . . F(1,8) are averaged to NRSEG_F1. F(2,1),F(2,2), . . . ,F(2,4) are averaged to NRSEG_F2, and so on.

Beat event localization is performed in step 40. A test of monotonicity is performed by regressing NRSEG_F1, . . . , NRSEG_F4 against window length. The presence of a beat implies an increase over a threshold value (e.g., 25% in one embodiment) in NRSEG numerical values. Also, presence of a beat in the smallest length window implies that the beat will be seen a number times in all other longer length windows. Thus NRSEG_F4>NRSEG_F3>NRSEG_F2> NRSEG_F1. Also, NRSEG_F4 is some multiple of NRSEG_F3, which is some multiple of NRSEG_F2, and so on. This multiple relationship provides an estimate of the number of beats detected in the window interval corresponding to Wno=4. It is possible that an event does not occur in some windows F(1,1),F(1,2),. . . F(1,8). Once an NRSEG change is detected in the averaged value corresponding to a window_size, then individual values are examined to check the presence of beats.

Projection includes the process whereby post-collision NRSEG values are used to determine the size of the smallest window size in which the beat can be detected. Once a beat is detected and localized in time (based on the window in which it was detected), it is added to a running count for the current episodic window. The time window is then incremented by the length of Wno/2, and the steps 22-28 in FIG. 144 is repeated. Only when a beat is detected in a new, later window where the beat start time is greater than the start time of the previous beat, the beat counter is updated at step 50. This is to allow for beats that are longer than the sliding interval and show up in multiple sliding time-slices.

Once the entire episodic interval has been covered, the accumulated beat rate is output to provide the heart rate. If the episodic interval is set to 10 seconds, the accumulated beat rate can be multiplied by 6 to get the heart rate per minute, in this example 60 bpm.

Sequences of numbers and waveforms are generally considered to be mathematical concepts and natural phenomena, respectively. Manipulation of a waveform, however, can be a limited, particular, useful application of the waveforms. For example, when amplitude modulation was invented decades ago, it described a particular manner in which one waveform, typically called a source waveform, could be used to modify another waveform, typically called a carrier waveform, so that a modulated waveform resulting from the modulation can be transmitted over long distances of up to hundreds or even thousands of miles. Frequency modulation describes another particular manner of manipulating a carrier waveform using a source waveform, that allowed for improvements in signal-to-noise ratio of the modulated waveform. Such techniques are generally not considered to be mathematical concepts or natural phenomena, but rather are highly useful methods of achieving beneficial technical results.

Collision computing, according to various embodiments described herein, is also a limited, particular manner of manipulating waveforms to achieve highly beneficial results. The collision operation is not a modulation technique, at least because modulation is an invertible operation, i.e., the source waveform can be regenerated from a modulated waveform via the process of demodulation. Collision operation, in general is non-invertible, however. This results from, at least in part, the bracketing and conditional interactions described above. These specific operations, that distinguish the collision operation from various modulation techniques and from other known waveform manipulation techniques, also make the methods and systems for collision computing limited and specialized techniques of waveform processing.

Unlike any generic operations such as data transmission and reception, unlike usual computer functions such as storage and access of information, and unlike any mathematical or mental processes such as comparing and categorizing information, the unconventional operations described herein are specifically orchestrated for selectively amplifying information represented within the frequency components of a signal. For example, some of the operations involve comparing frequencies of waveform components where a permissible difference between the frequencies is selected according to the nature of the waveform components in terms of the kind of information those components represent. Additional operations such as scaling, delay shifting, and phase rotation, are also particularly developed, non-generic operations.

Moreover, the waveforms used in the collision process are themselves of a limited, particular kind. Specifically, these waveforms are co-dependent in terms of their respective velocities, and in terms of a change that one waveform generally causes in another during a collision therebetween. The process of creating such waveforms, though it may start from various functions and/or number sequences, involves a careful selection of a number of frequencies associated with several waveform components. Unlike generic computer and database operations and typical mathematical or mental processes, this selection is based on, at least in part, the spectral properties of the analyte signals to be detected and/or measured, or an event or anomaly to be detected and/or characterized, as described above. As such, the methods and systems for synthesizing these co-dependent waveforms also involve unconventional, limited, and particularized operations generally involving analysis of spectral properties of signals.

While glucose (and other analytes) occur naturally in many living things including humans, accurate knowledge of the presence, absence, quantity, and/or concentration of these analytes is neither a natural phenomenon nor can such knowledge be obtained by mere mental processing. Typically, physical samples (e.g., blood) and/or signals (e.g., reflected or transmitted radiation, electromagnetic pulses, etc.) are obtained. This information is then processed and analyzed to determine the presence, absence, quantity, and/or concentration of the analyte. These information processing techniques, however, are generally not considered to be mental processes and/or natural phenomena. Collision computing described herein and implemented in various embodiments is a new, specialized technique to that end.

It is clear that there are many ways to configure the device and/or system components, interfaces, communication links, and methods described herein. The disclosed methods, devices, and systems can be deployed on convenient processor platforms, including network servers, personal and portable computers, and/or other processing platforms. Other platforms can be contemplated as processing capabilities improve, including personal digital assistants, computerized watches, cellular phones and/or other portable devices. The disclosed methods and systems can be integrated with known network management systems and methods. The disclosed methods and systems can operate as an SNMP agent, and can be configured with the IP address of a remote machine running a conformant management platform. Therefore, the scope of the disclosed methods and systems are not limited by the examples given herein, but can include the full scope of the claims and their legal equivalents.

The methods, devices, and systems described herein are not limited to a particular hardware or software configuration, and may find applicability in many computing or processing environments. The methods, devices, and systems can be implemented in hardware or software, or a combination of hardware and software. The methods, devices, and systems can be implemented in one or more computer programs, where a computer program can be understood to include one or more processor executable instructions. The computer program(s) can execute on one or more programmable processing elements or machines, and can be stored on one or more storage medium readable by the processor (including volatile and non-volatile memory and/or storage elements), one or more input devices, and/or one or more output devices. The processing elements/machines thus can access one or more input devices to obtain input data, and can access one or more output devices to communicate output data. The input and/or output devices can include one or more of the following: Random Access Memory (RAM), Redundant Array of Independent Disks (RAID), floppy drive, CD, DVD, magnetic disk, internal hard drive, external hard drive, memory stick, or other storage device capable of being accessed by a processing element as provided herein, where such aforementioned examples are not exhaustive, and are for illustration and not limitation.

The computer program(s) can be implemented using one or more high level procedural or object-oriented programming languages to communicate with a computer system; however, the program(s) can be implemented in assembly or machine language, if desired. The language can be compiled or interpreted.

As provided herein, the processor(s) and/or processing elements can thus be embedded in one or more devices that can be operated independently or together in a networked environment, where the network can include, for example, a Local Area Network (LAN), wide area network (WAN), and/or can include an intranet and/or the Internet and/or another network. The network(s) can be wired or wireless or a combination thereof and can use one or more communication protocols to facilitate communication between the different processors/processing elements. The processors can be configured for distributed processing and can utilize, in some embodiments, a client-server model as needed. Accordingly, the methods, devices, and systems can utilize multiple processors and/or processor devices, and the processor/processing element instructions can be divided amongst such single or multiple processor/devices/ processing elements.

The device(s) or computer systems that integrate with the processor(s)/processing element(s) can include, for example, a personal computer(s), workstation (e.g., Dell, HP), personal digital assistant (PDA), handheld device such as cellular telephone, laptop, handheld, or another device capable of being integrated with a processor(s) that can operate as provided herein. Accordingly, the devices provided herein are not exhaustive and are provided for illustration and not limitation.

References to "a processor", or "a processing element," "the processor," and "the processing element" can be understood to include one or more microprocessors that can communicate in a stand-alone and/or a distributed environment(s), and can thus can be configured to communicate via wired or wireless communication with other processors, where such one or more processor can be configured to operate on one or more processor/processing elements-controlled devices that can be similar or different devices. Use of such "microprocessor," "processor," or "processing element" terminology can thus also be understood to include a central processing unit, an arithmetic logic unit, an application-specific integrated circuit (IC), and/or a task engine, with such examples provided for illustration and not limitation.

Furthermore, references to memory, unless otherwise specified, can include one or more processor-readable and accessible memory elements and/or components that can be internal to the processor-controlled device, external to the processor-controlled device, and/or can be accessed via a wired or wireless network using a variety of communication protocols, and unless otherwise specified, can be arranged to include a combination of external and internal memory devices, where such memory can be contiguous and/or partitioned based on the application. For example, the memory can be a flash drive, a computer disc, CD/DVD, distributed memory, etc. References to structures include links, queues, graphs, trees, and such structures are provided for illustration and not limitation. References herein to instructions or executable instructions, in accordance with the above, can be understood to include programmable hardware.

Although the methods and systems have been described relative to specific embodiments thereof, they are not so limited. As such, many modifications and variations may become apparent in light of the above teachings. Many additional changes in the details, materials, and arrangement of parts, herein described and illustrated, can be made by those skilled in the art. Accordingly, it will be understood that the methods, devices, and systems provided herein are not to be limited to the embodiments disclosed herein, can include practices otherwise than specifically described, and are to be interpreted as broadly as allowed under the law.

What is claimed is:

1. A method for facilitating analysis of a medium, the method comprising the steps of: directing illumination to a medium; controlling a parameter of the illumination; collecting a first radiation fragment from the medium; and determining, via a collision computer, a first renormalized spectral energy change associated with at least a portion of the first radiation fragment.

2. The method of claim 1, wherein the medium comprises a tissue.

3. The method of claim 1, wherein controlling the parameter comprises selecting a value of the parameter based on, at least in part, a specified target volume within the medium.

4. The method of claim 1, wherein the first renormalized spectral energy change corresponds to a quantity of an analyte present within the medium.

5. The method of claim 1, further comprising:
collecting a second radiation fragment from the medium, at least one of: (i) a time of collection of the second fragment being different from a time of collection of the first fragment, and (ii) a spatial characteristic of the second fragment being different from a corresponding spatial characteristic of the first fragment; and determining, via collision computing, a second renormalized spectral energy change associated with at least a portion of the second radiation fragment, wherein one of:

(a1) the first renormalized spectral energy change comprises a first renormalized spectral energy gain and the second renormalized spectral energy change comprises a second renormalized spectral energy gain; and (b1) controlling the parameter comprises adjusting the parameter to a value at which the second renormalized spectral energy gain is not less than the first renormalized spectral energy gain; and (a2) the first renormalized spectral energy change comprises a first renormalized spectral energy loss and the second renormalized spectral energy change comprises a second renormalized spectral energy loss; and (b2) controlling the parameter comprises adjusting the parameter to a value at which the second renormalized spectral energy loss is not less than the first renormalized spectral energy loss.

6. The method of claim 5, wherein the parameter comprises at least one of: (i) an amplitude of the illumination, comprising at least one of an intensity of the illumination and a duration of the illumination, (ii) a focal length of the illumination, (iii) a focal point of the illumination, (iv) a location of a target region to be illuminated by the illumination, (v) a size of the target region to be illuminated by the illumination, (vi) an angle of incidence of the illumination upon the medium, and (vii) a spectral characteristic, comprising at least one of a wavelength and a bandwidth, of the illumination.

7. The method of claim 1, wherein controlling the parameter comprises adjusting a focal length of the illumination.

8. The method of claim 7, wherein adjusting the focal length comprises at least one of: (i) electronic tuning of a photorefractive material, (ii) acoustic tuning of a photorefractive material, (iii) electrical modulation of a dynamic lens, and (iv) radio frequency (RF) modulation of a dynamic lens.

9. The method of claim 1, wherein controlling the parameter comprises adjusting an amplitude of the illumination by adjusting at least one of: (i) an area of exposed emitter surface, (ii) a shutter aperture size, (iii) a voltage of the illumination source, and (iv) a number of illumination sources that are tuned ON.

10. The method of claim 1, wherein controlling the parameter comprises adjusting a spatial parameter associated with a target of the illumination.

11. The method of claim 10, wherein adjusting the spatial parameter comprises varying a spacing between the illumination target and an area of detection used for collecting the first radiation fragment, varying the spacing comprising at least one of opto-mechanically varying the spacing and electro-optically varying the spacing.

12. The method of claim 10, wherein adjusting the spatial parameter comprises varying an illuminated area of the illumination target, varying the illuminated area comprising at least one of opto-mechanically varying the illuminated area and electro-optically varying the illuminated area by adjusting at least one of a standoff and a focal length of an illumination source.

13. The method of claim 10, wherein adjusting the spatial parameter comprises at least one of opto-mechanically varying a location of the illumination target and electro-optically varying the location of the illumination target.

14. The method of claim 1, wherein controlling the parameter comprises adjusting a duration of the illumination by at least one of: (i) turning at least one illumination source ON and OFF, and (ii) adjusting a duration for which a shutter remains open.

15. The method of claim 1, wherein controlling the parameter comprises adjusting an angle at which the illumination is incident upon a surface of the medium.

16. The method of claim 1, wherein controlling the parameter comprises adjusting at least one of: (i) a wavelength of the illumination and (ii) a bandwidth of the illumination.

17. A system for facilitating analysis of a medium, comprising:

an adjustable illumination subsystem for directing illumination to a medium;

a collector for collecting a radiation fragment from the medium; and a collision computer programmed to compute a first renormalized spectral energy change associated with at least a portion of the radiation fragment.

18. The system of claim 17, wherein the adjustable illumination subsystem is adapted to adjust at least one of: (i) an amplitude of the illumination, comprising at least one of an intensity of the illumination and a duration of the illumination, (ii) a focal length of the illumination, (iii) a focal point of the illumination, (iv) a location of a target region to be illuminated by the illumination, (v) a size of the target region to be illuminated by the illumination, (vi) an angle of incidence of the illumination upon the medium, and (vii) a spectral characteristic, comprising at least one of a wavelength and a bandwidth, of the illumination.

19. The system of claim 17, wherein the adjustable illumination subsystem comprises a device having an adjustable focus, for adjusting a focal length of the illumination.

20. The method of claim 19, wherein the device comprises at least one of: (i) electronically tunable photorefractive element, (ii) acoustically tunable photorefractive element, (iii) an electrically modulated dynamic lens, and (iv) a radio frequency (RF) modulated dynamic lens.

21. The system of claim 20, wherein the photorefractive element comprises a phase-conjugate mirror.

22. The system of claim 17, wherein the adjustable illumination subsystem comprises at least one of: (i) an emitter having an adjustable exposed surface area, (ii) a shutter having an adjustable aperture, at least one of a size of the aperture and a duration for which the aperture is open being adjustable, (iii) an illumination source having adjustable voltage, and (iv) a plurality of illumination sources, at least one of which is selectively switchable ON and OFF, for adjusting an amplitude of the illumination.

23. The system of claim 22, wherein a duration for which at least one of the illumination sources is selectively switched ON is adjustable.

24. The system of claim 17, wherein the adjustable illumination subsystem comprises a translator adapted to spatially adjust at least one of: (i) a focal point of the illumination relative to a surface of the medium and (ii) a location of a target area of the illumination.

25. The system of claim 24, wherein the translator is adapted to adjust at least one of: (i) a focal length of the illumination, and (ii) a standoff between a component of the illumination subsystem and the surface of the medium.

26. The system of claim 24, wherein the translator comprises at least one of an opto-mechanical translator and an electro-optical translator.

27. The system of claim 24, wherein the translator comprises at least one of a scanning mirror and a voice coil.

28. The system of claim 17, wherein the adjustable illumination subsystem comprises an optical component for directing the illumination to the medium at a specified angle of incidence upon a surface of the medium.

29. The system of claim 28, wherein the optical component comprises a plurality of optical fibers each being oriented at a different angle relative to a normal axis.

30. The system of claim 17, wherein the adjustable illumination subsystem comprises an illumination source having at least one of: (i) an adjustable wavelength, and (ii) an adjustable bandwidth.

* * * * *

UNITED STATES PATENT AND TRADEMARK OFFICE
CERTIFICATE OF CORRECTION

PATENT NO.        : 9,453,794 B2
APPLICATION NO.   : 15/081430
DATED             : September 27, 2016
INVENTOR(S)       : Sandeep Gulati et al.

It is certified that error appears in the above-identified patent and that said Letters Patent is hereby corrected as shown below:

On the Title Page

Item (54), and in the Specification, Column 1, Replace "SYSTEMS AND METHODS FOR BLOOD GLUCOSE AND OTHER ANALYTE DETECTION AND MEASUREMENT USING COLLISION COMPUTING" with -- SYSTEMS AND METHODS FOR CONTROL OF ILLUMINATION FOR BLOOD GLUCOSE AND OTHER ANALYTE DETECTION AND MEASUREMENT USING COLLISION COMPUTING --.

In the Claims

In Claim 20, Column 226, Line 41, replace "(i) electronically" with -- (i) an electronically --.

In Claim 20, Column 226, Line 42, replace "(ii) acoustically" with -- (ii) an acoustically --.

Signed and Sealed this
Twenty-seventh Day of December, 2016

Michelle K. Lee
*Director of the United States Patent and Trademark Office*